United States Patent [19]

DeHoff et al.

[11] Patent Number: 5,876,991

[45] Date of Patent: Mar. 2, 1999

[54] POLYKETIDE SYNTHASE GENES

[75] Inventors: Bradley S. DeHoff; Stuart A. Kuhstoss; Paul R. Rosteck, Jr., all of Indianapolis; Kimberly L. Sutton, New Palestine, all of Ind.

[73] Assignee: Eli Lilly and Company, Indianapolis, Ind.

[21] Appl. No.: 804,227

[22] Filed: Feb. 21, 1997

Related U.S. Application Data

[60] Provisional application No. 60/012,078, filed Feb. 22, 1996.
[51] Int. Cl.$^6$ .............................. C12N 9/00; C12N 15/52; C12N 15/62; C12N 15/76
[52] U.S. Cl. .................... 435/183; 435/697; 435/752.35; 435/320.1; 435/471; 435/486; 536/23.2; 536/23.4; 935/10; 935/14; 935/29; 935/75
[58] Field of Search ...................................... 435/183, 189, 435/193, 195, 69.1, 69.7, 252.3, 252.35, 320.1, 471, 486; 536/23.2, 23.4

[56] References Cited

U.S. PATENT DOCUMENTS

| | | | |
|---|---|---|---|
| 4,366,247 | 12/1982 | Baltz et al. | 435/124 |
| 5,063,155 | 11/1991 | Cox et al. | 435/76 |
| 5,098,837 | 3/1992 | Beckmann et al. | 435/172.3 |
| 5,149,638 | 9/1992 | Beckmann et al. | 435/76 |
| 5,168,052 | 12/1992 | Cox | 435/72 |
| 5,252,474 | 10/1993 | Gewain et al. | 435/477 |
| 5,672,491 | 9/1997 | Cox | 435/320.1 |
| 5,716,849 | 2/1998 | Ligon et al. | 435/419 |
| 5,744,350 | 4/1998 | Vinci et al. | 435/254.11 |

FOREIGN PATENT DOCUMENTS

| | | |
|---|---|---|
| 0463707 | 1/1992 | European Pat. Off. . |
| WO 87/03907 | 7/1987 | WIPO . |
| WO 93/13663 | 7/1993 | WIPO . |

OTHER PUBLICATIONS

David A. Hopwood and David H. Sherman, "Molecular Genetics of Polyketides and its Comparison to Faty Acid Biosynthesis," *Annu. Rev. Genet.*, 24:37–66 (1990).
Stefano Donadio and Leonard Katz, "Organization of the enzymatic domains in the multifunctional polyketide synthase involved in erythromycin formation in *Saccharopolyspora erythrea*," *Gene*, 111:51–60 (1992).
Jesus Cortes, et al., "Repositioning of a Domain in a Modular Polyketide Synthase to Promote Specific Chain Cleavage," *Science*, 268:1487–1489 (1995).
Stefano Donadio, et al., "Modular Organization of Genes Required for Complex Polyketide Biosynthesis," *Science*, 252:675–679 (1991).
M. A. Richardson, et al., "Cloning of Spiromycin Biosynthetic Genes and Their Use in Constructing *Streptomyces ambofaciens* Mutants Defective in Spiramycin Biosynthesis," *Journal of Bacteriology*, vol. 172, No. 7, 3790–3798 (1990).

Robert J. Beckman, Karen Cox, and Eugene T. Seno, "A Cluster of Tylosin Biosynthetic Genes Is Interuppted by Structurally Unstable Segment Containing Four Repeated Sequences," *Genetics and Molecular Biology of Industrial Microorganisms*, 176–186 (1989).
Leonard Katz and Stefano Donadio, "Polyketide Synthesis: Prospects for Hybrid Antibiotics," *Annu. Rev. Microbiol.*, 47:875–912 (1993).
Stefano Donadio, et al., "Biosynthesis of the erythromycin macorlactone and a rational approach for producing hybrid macrolides," *Gene*, 115:97–103 (1992).
Douglas J. MacNeil, et al., "Complex organization of the *Streptomyces avermitilis* genes encoding the avermectin polyketide synthase," *Gene*, 115:119–125 (1992).
Douglas J. MacNeil, et al., "Correlation of the Avermectin Polyketide Synthase Genes to the Avermectin Structure," *Annals New York Academy of Sciences*, 721:123–132 (1994).
C. Richard Hutchinson, "Durg Synthesis by Genetically Engineered Microorganisms," *Bio/Technology*, 12:375–380 (1994).
Huber, M.L.B., et al., Anitmicrobial Agents and Chemotherapy, vol. 34, "Branched–chain fatty acids produced by mutants of *Streptomyces fradiae*, putative precursors of the lactone ring of tylosin", pp. 1535–1541, 1990.
Rezanka, T., et al., FEMS Microbiology Letters, vol. 84, "Isobutyrate as a precursor of n–butyrate in the biosynthesis of tylosine and fatty acids", pp. 33–36, 1991.
Geistlich, M., et al., Molecular Micorbiology, vol. 6, "Characterization of a novel regulatory gene governing the expression of a polyketide synthase gene in *Streptomyces ambofaciens*", pp. 2019–2029, 1992.
DeHoff, B. S., et al., Abstracts of the General Meeting of the American Society for Microbiology, vol. 92, "Sequencing and characterization of the putative tylactone synthase genes of *Streptomyces fradiae*", Abstract No. H–220, p. 219, 1992.
Kirst, H. A., Progress in Medicinal Chemistry, vol. 31, "5 Semi–synthetic derivative of 16–membered macrolide antibiotics", pp. 265–295, 1994.
Swan, D. G.., et al., Molecular and General Genetics, vol. 242, "Characterization of a *Streptomyces antibioticus* gene encoding a thepe I Polyketide synthase which has an unusual coding sequence", pp. 358–362, 1994.
Katz, L., et al., in Genetics and Biochemistry of Antibiotic Production, vining, L. C., et al., Eds., "Macrolides", pp. 385–420, Butterworth–Heineman, Pubs., Boston, 1995.
Aigle, B., et al., Microbiology, vol. 142, "An amplifiable and deletable locus of *Streptomyces ambofaciens* RP18110 contains a very large gene homologous to polyketide synthase genes", pp. 2815–2824, 1996.

*Primary Examiner*—Robert A. Wax
*Assistant Examiner*—William W. Moore
*Attorney, Agent, or Firm*—Thomas G. Plant; Paul R. Cantrell

[57] ABSTRACT

A DNA molecule isolated from *Streptomyces fradiae* encodes the multi-functional proteins which direct the synthesis of the polyketide tylactone.

23 Claims, 6 Drawing Sheets

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 43280 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 816..14234

( i x ) FEATURE:
        ( A ) NAME/KEY: CDS
        ( B ) LOCATION: 14351..19945

( i x ) FEATURE:
        ( A ) NAME/KEY: CDS
        ( B ) LOCATION: 20010..31199

( i x ) FEATURE:
        ( A ) NAME/KEY: CDS
        ( B ) LOCATION: 31232..36067

( i x ) FEATURE:
        ( A ) NAME/KEY: CDS
        ( B ) LOCATION: 36249..41774

( x i ) SEQUENCE DESCRIPTION: SEQ ID NO:1:

```
GAATTCGCGG   TCCGCTCGGG   TTCCGGTCCG   TTTTCTGCTT   CGAGCGTCTG   TGTCGTCATC        60

TCGGCTCTCT   CATCGGGCTG   GTGCGGGAAG   GCATCCCGGT   GCGGGGAGAC   ATCCTGCTGC       120

GGGAAGGAAT   CCTGGTGCGG   GAAGGCAACG   ACTGCGGGAC   GCGGGAGAAA   GGGGAATCGG       180

CGGGAATTTC   CCCCGCGCGG   CGGGGACGGT   GCCGGAGAAC   AACGGCGGGG   AAACAGCCCG       240

CGGTCCGTGA   CGACAACGGA   AACTATGGTC   CGCTTCCTCC   GTCCACAAGG   CGGAACCTGA       300

CATAGTCCCC   GCCCACGCGG   AAATCCCGCA   CGGCGGCCCG   CCGGCCGCCG   CACCGGACCT       360

GACATAGCCT   CGCCGGACCG   CTCCGGTGCG   GCCACCCCGT   TGGTGTTGGG   TGATGAGGTA       420

CCGGATCAGA   GGAGAAAGCA   CCATGCCCCG   CCCCTCGGCC   AGCGAACCGC   GCGGGACCAC       480

CCGTTCGGCG   ACCGCGCTGG   CGCGCCGCCG   TGGACCGGGC   CGTAACTCCC   CTGCGCCATC       540

GAATACTTCG   CCCCTCGAAT   CCCTCACCGG   GCGAGTTCCA   GGACCGCCCC   TCGCTCTCGC       600

CATACCGGAG   AACGAACCCG   AACGGCACGG   CGGAAAGCCC   GTCCGCAATG   CCCGGGACAT       660

TCCTGTGACC   CGACAACACG   GTTTGCCGAC   ACGGTTCGCC   GCAACGCTTG   TTGGCAGGCT       720

CACCGGCACG   GCCCGCTGAC   ACAGCTCGGT   GACACGGCAG   CCTGACGGGA   AACCGCCGAA       780

GCCTCTGGAG   TCCTCGCACA   TTCCGGAGAG   AACAG GTG TCT TCC GCG CTG CGG              833
                                            Met Ser Ser Ala Leu Arg
                                             1               5

CGC GCG GTG CAA TCC AAC TGT GGC TAC GGA GAC CTC ATG ACC TCG AAC                   881
Arg Ala Val Gln Ser Asn Cys Gly Tyr Gly Asp Leu Met Thr Ser Asn
        10                   15                        20

ACC GCT GCA CAG AAC ACC GGC GAC CAG GAA GAC GTC GAC GGT CCC GAC                   929
Thr Ala Ala Gln Asn Thr Gly Asp Gln Glu Asp Val Asp Gly Pro Asp
            25                      30                     35

AGC ACA CAC GGT GGG GAG ATC GCC GTC GTG GGA ATG TCG TGC CGT CTG                   977
Ser Thr His Gly Gly Glu Ile Ala Val Val Gly Met Ser Cys Arg Leu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 40  |     |     |     |     | 45  |     |     |     |     | 50  |     |     |      |
| CCG | GGC | GCG | GCC | GGT | GTC | GAG | GAA | TTC | TGG | GAA | CTG | CTG | CGC | AGC | GGA | 1025 |
| Pro | Gly | Ala | Ala | Gly | Val | Glu | Glu | Phe | Trp | Glu | Leu | Leu | Arg | Ser | Gly |      |
| 55  |     |     |     |     | 60  |     |     |     |     | 65  |     |     |     |     | 70  |      |
| CGC | GGT | ATG | CCC | ACC | CGT | CAG | GAC | GAC | GGC | ACC | TGG | CGG | GCC | GCC | CTG | 1073 |
| Arg | Gly | Met | Pro | Thr | Arg | Gln | Asp | Asp | Gly | Thr | Trp | Arg | Ala | Ala | Leu |      |
|     |     |     |     | 75  |     |     |     |     | 80  |     |     |     |     | 85  |     |      |
| GAG | GAC | CAC | GCC | GGC | TTC | GAC | GCC | GGG | TTC | TTC | GGC | ATG | AAC | GCC | CGG | 1121 |
| Glu | Asp | His | Ala | Gly | Phe | Asp | Ala | Gly | Phe | Phe | Gly | Met | Asn | Ala | Arg |      |
|     |     |     | 90  |     |     |     |     | 95  |     |     |     |     | 100 |     |     |      |
| CAG | GCC | GCC | GCC | ACC | GAC | CCG | CAG | CAC | CGA | CTG | ATG | CTG | GAA | CTC | GGA | 1169 |
| Gln | Ala | Ala | Ala | Thr | Asp | Pro | Gln | His | Arg | Leu | Met | Leu | Glu | Leu | Gly |      |
|     |     |     | 105 |     |     |     |     | 110 |     |     |     |     | 115 |     |     |      |
| TGG | GAG | GCA | CTG | GAG | GAC | GCG | GGC | ATC | GTC | CCC | GGC | GAT | CTC | ACC | GGC | 1217 |
| Trp | Glu | Ala | Leu | Glu | Asp | Ala | Gly | Ile | Val | Pro | Gly | Asp | Leu | Thr | Gly |      |
|     | 120 |     |     |     |     | 125 |     |     |     |     | 130 |     |     |     |     |      |
| ACC | GAC | ACC | GGA | GTC | TTC | GCC | GGC | GTG | GCG | TCC | GAC | GAC | TAT | GCC | GTT | 1265 |
| Thr | Asp | Thr | Gly | Val | Phe | Ala | Gly | Val | Ala | Ser | Asp | Asp | Tyr | Ala | Val |      |
| 135 |     |     |     |     | 140 |     |     |     |     | 145 |     |     |     |     | 150 |      |
| CTC | ACC | CGC | CGT | TCC | GCC | GTC | TCC | GCC | GGG | GGA | TAC | ACC | GCC | ACG | GGG | 1313 |
| Leu | Thr | Arg | Arg | Ser | Ala | Val | Ser | Ala | Gly | Gly | Tyr | Thr | Ala | Thr | Gly |      |
|     |     |     |     | 155 |     |     |     |     | 160 |     |     |     |     | 165 |     |      |
| CTG | CAC | CGC | GCC | CTG | GCC | GCC | AAC | CGC | CTC | TCC | CAC | TTC | CTG | GGC | CTG | 1361 |
| Leu | His | Arg | Ala | Leu | Ala | Ala | Asn | Arg | Leu | Ser | His | Phe | Leu | Gly | Leu |      |
|     |     |     | 170 |     |     |     |     | 175 |     |     |     |     | 180 |     |     |      |
| CGC | GGC | CCC | AGC | CTG | GTC | GTC | GAC | TCG | GCC | CAG | TCC | GCC | TCA | CTG | GTG | 1409 |
| Arg | Gly | Pro | Ser | Leu | Val | Val | Asp | Ser | Ala | Gln | Ser | Ala | Ser | Leu | Val |      |
|     |     |     | 185 |     |     |     |     | 190 |     |     |     |     | 195 |     |     |      |
| GCC | GTC | CAG | CTC | GCC | TGC | GAG | AGT | CTG | CGC | CGG | GGT | GAG | ACG | TCG | CTC | 1457 |
| Ala | Val | Gln | Leu | Ala | Cys | Glu | Ser | Leu | Arg | Arg | Gly | Glu | Thr | Ser | Leu |      |
| 200 |     |     |     |     | 205 |     |     |     |     | 210 |     |     |     |     |     |      |
| GCC | GTC | GCG | GGC | GGT | GTC | AAC | CTC | ATC | CTC | ACC | GAG | GAG | AGC | ACC | ACC | 1505 |
| Ala | Val | Ala | Gly | Gly | Val | Asn | Leu | Ile | Leu | Thr | Glu | Glu | Ser | Thr | Thr |      |
| 215 |     |     |     |     | 220 |     |     |     |     | 225 |     |     |     |     | 230 |      |
| GTC | ATG | GAG | CGT | ATG | GGA | GCG | CTC | TCA | CCC | GAC | GGC | CGC | TGC | CAC | ACC | 1553 |
| Val | Met | Glu | Arg | Met | Gly | Ala | Leu | Ser | Pro | Asp | Gly | Arg | Cys | His | Thr |      |
|     |     |     |     | 235 |     |     |     |     | 240 |     |     |     |     | 245 |     |      |
| TTC | GAC | GCC | CGC | GCC | AAC | GGC | TAC | GTA | CGC | GGC | GAG | GGC | GGC | GGA | GCC | 1601 |
| Phe | Asp | Ala | Arg | Ala | Asn | Gly | Tyr | Val | Arg | Gly | Glu | Gly | Gly | Gly | Ala |      |
|     |     |     | 250 |     |     |     |     | 255 |     |     |     |     | 260 |     |     |      |
| GTC | GTG | CTC | AAG | CCA | CTG | GAC | GCC | GCA | CTC | GCC | GAC | GGC | GAC | CGC | GTG | 1649 |
| Val | Val | Leu | Lys | Pro | Leu | Asp | Ala | Ala | Leu | Ala | Asp | Gly | Asp | Arg | Val |      |
|     |     |     | 265 |     |     |     |     | 270 |     |     |     |     | 275 |     |     |      |
| TAC | TGC | GTC | ATC | AAG | GGA | GGT | GCC | GTC | AAC | AAC | GAC | GGC | GGC | GGC | GCG | 1697 |
| Tyr | Cys | Val | Ile | Lys | Gly | Gly | Ala | Val | Asn | Asn | Asp | Gly | Gly | Gly | Ala |      |
|     |     |     | 280 |     |     |     |     | 285 |     |     |     |     | 290 |     |     |      |
| AGC | CTC | ACC | ACT | CCC | GAC | CGG | GAG | GCG | CAG | GAA | GCT | GTG | CTG | CGC | CAG | 1745 |
| Ser | Leu | Thr | Thr | Pro | Asp | Arg | Glu | Ala | Gln | Glu | Ala | Val | Leu | Arg | Gln |      |
| 295 |     |     |     |     | 300 |     |     |     |     | 305 |     |     |     |     | 310 |      |
| GCC | TAC | CGG | CGG | GCG | GGC | GTC | AGC | ACC | GGC | GCC | GTC | CGC | TAC | GTC | GAG | 1793 |
| Ala | Tyr | Arg | Arg | Ala | Gly | Val | Ser | Thr | Gly | Ala | Val | Arg | Tyr | Val | Glu |      |
|     |     |     |     | 315 |     |     |     |     | 320 |     |     |     |     | 325 |     |      |
| CTG | CAC | GGG | ACC | GGC | ACC | CGG | GCC | GGC | GAC | CCC | GTC | GAG | GCG | GCC | GCA | 1841 |
| Leu | His | Gly | Thr | Gly | Thr | Arg | Ala | Gly | Asp | Pro | Val | Glu | Ala | Ala | Ala |      |
|     |     |     | 330 |     |     |     |     | 335 |     |     |     |     | 340 |     |     |      |
| CTG | GGC | GCC | GTG | CTC | GGG | GCG | GGG | GCG | GAC | AGC | GGC | CGC | AGC | ACG | CCG | 1889 |
| Leu | Gly | Ala | Val | Leu | Gly | Ala | Gly | Ala | Asp | Ser | Gly | Arg | Ser | Thr | Pro |      |
|     |     |     | 345 |     |     |     |     | 350 |     |     |     |     | 355 |     |     |      |
| CTC | GCC | GTC | GGC | TCG | GTG | AAG | ACC | AAC | GTC | GGC | CAT | CTG | GAG | GGC | GCG | 1937 |
| Leu | Ala | Val | Gly | Ser | Val | Lys | Thr | Asn | Val | Gly | His | Leu | Glu | Gly | Ala |      |

-continued

```
            360                                    365                                    370
GCG  GGC  ATC  GTC  GGA  CTG  ATC  AAG  GCC  ACG  CTG  TGC  GTA  CGG  AAG  GGC        1985
Ala  Gly  Ile  Val  Gly  Leu  Ile  Lys  Ala  Thr  Leu  Cys  Val  Arg  Lys  Gly
375                 380                            385                            390

GAA  CTC  GTC  CCC  AGC  CTC  AAC  TTC  AGC  ACG  CCG  AAC  CCT  GAC  ATC  CCC        2033
Glu  Leu  Val  Pro  Ser  Leu  Asn  Phe  Ser  Thr  Pro  Asn  Pro  Asp  Ile  Pro
                         395                      400                      405

CTC  GAC  GAC  CTG  CGG  CTG  CGC  GTC  CAG  ACC  GAA  CGG  CAG  GAG  TGG  AAC        2081
Leu  Asp  Asp  Leu  Arg  Leu  Arg  Val  Gln  Thr  Glu  Arg  Gln  Glu  Trp  Asn
                    410                           415                      420

GAG  GAG  GAC  GAC  CGG  CCG  CGC  GTG  GCC  GGC  GTC  TCC  TCC  TTC  GGT  ATG        2129
Glu  Glu  Asp  Asp  Arg  Pro  Arg  Val  Ala  Gly  Val  Ser  Ser  Phe  Gly  Met
              425                      430                      435

GGC  GGA  ACC  AAT  GTC  CAC  CTC  GTG  ATC  GCG  GAG  GCT  CCG  GCC  GCG  GCG        2177
Gly  Gly  Thr  Asn  Val  His  Leu  Val  Ile  Ala  Glu  Ala  Pro  Ala  Ala  Ala
440                      445                      450

GGG  TCC  TCC  GGG  GCG  GGG  GGT  TCG  GGC  GCT  GGT  TCC  GGT  GCC  GGT  ATC        2225
Gly  Ser  Ser  Gly  Ala  Gly  Gly  Ser  Gly  Ala  Gly  Ser  Gly  Ala  Gly  Ile
455                      460                      465                           470

AGC  GCT  GTT  TCT  GGT  GTG  GTG  CCG  GTG  GTG  GTT  TCG  GGG  CGT  TCG  CGG        2273
Ser  Ala  Val  Ser  Gly  Val  Val  Pro  Val  Val  Val  Ser  Gly  Arg  Ser  Arg
                         475                      480                      485

GTG  GTG  GTG  CGG  GAG  GCT  GCG  GGC  CGG  TTG  GCG  GAG  GTG  GTG  GAG  GCC        2321
Val  Val  Val  Arg  Glu  Ala  Ala  Gly  Arg  Leu  Ala  Glu  Val  Val  Glu  Ala
                    490                           495                 500

GGT  GGT  GTG  GGG  CTG  GCG  GAT  GTG  GCG  GTG  ACG  ATG  GCG  GAC  CGG  TCG        2369
Gly  Gly  Val  Gly  Leu  Ala  Asp  Val  Ala  Val  Thr  Met  Ala  Asp  Arg  Ser
              505                      510                      515

CGG  TTT  GGG  TAT  CGG  GCG  GTT  GTG  CTG  GCT  CGG  GGT  GAG  GCT  GAG  CTT        2417
Arg  Phe  Gly  Tyr  Arg  Ala  Val  Val  Leu  Ala  Arg  Gly  Glu  Ala  Glu  Leu
     520                      525                      530

GCC  GGG  CGT  TTG  CGG  GCG  TTG  GCG  GGG  GGT  GAT  CCG  GAC  GCG  GGT  GTG        2465
Ala  Gly  Arg  Leu  Arg  Ala  Leu  Ala  Gly  Gly  Asp  Pro  Asp  Ala  Gly  Val
535                      540                      545                           550

GTC  ACC  GGT  GCG  GTT  CTC  GAC  GGT  GGT  GTG  GTT  GTC  GGT  GCT  GCC  CCC        2513
Val  Thr  Gly  Ala  Val  Leu  Asp  Gly  Gly  Val  Val  Val  Gly  Ala  Ala  Pro
                         555                      560                      565

GGC  GGT  GCC  GGT  GCT  GCC  GGT  GGT  GCC  GGT  GCT  GCC  GGT  GGT  GCC  GGT        2561
Gly  Gly  Ala  Gly  Ala  Ala  Gly  Gly  Ala  Gly  Ala  Ala  Gly  Gly  Ala  Gly
              570                      575                      580

GGT  GGG  GGC  GTG  GTG  TTG  GTT  TTC  CCT  GGT  CAG  GGG  ACG  CAG  TGG  GTG        2609
Gly  Gly  Gly  Val  Val  Leu  Val  Phe  Pro  Gly  Gln  Gly  Thr  Gln  Trp  Val
              585                      590                      595

GGG  ATG  GGT  GCG  GGG  CTG  CTG  GGG  TCT  TCG  GAG  GTG  TTT  GCG  GCG  TCG        2657
Gly  Met  Gly  Ala  Gly  Leu  Leu  Gly  Ser  Ser  Glu  Val  Phe  Ala  Ala  Ser
     600                      605                      610

ATG  CGG  GAG  TGT  GCG  CGG  GCG  CTG  AGT  GTT  CAT  GTG  GGG  TGG  GAT  TTG        2705
Met  Arg  Glu  Cys  Ala  Arg  Ala  Leu  Ser  Val  His  Val  Gly  Trp  Asp  Leu
615                      620                      625                           630

CTG  GAG  GTG  GTG  TCG  GGC  GGG  GCC  GGG  TTG  GAG  CGG  GTG  GAT  GTG  GTG        2753
Leu  Glu  Val  Val  Ser  Gly  Gly  Ala  Gly  Leu  Glu  Arg  Val  Asp  Val  Val
                    635                      640                      645

CAG  CCG  GTG  ACG  TGG  GCG  GTG  ATG  GTG  TCG  CTG  GCC  CGG  TAC  TGG  CAG        2801
Gln  Pro  Val  Thr  Trp  Ala  Val  Met  Val  Ser  Leu  Ala  Arg  Tyr  Trp  Gln
               650                      655                      660

GCG  ATG  GGT  GTG  GAC  GTG  GCT  GCG  GTG  GTG  GGT  CAT  TCC  CAG  GGG  GAG        2849
Ala  Met  Gly  Val  Asp  Val  Ala  Ala  Val  Val  Gly  His  Ser  Gln  Gly  Glu
          665                      670                      675

ATC  GCC  GCT  GCC  ACG  GTG  GCG  GGG  GCG  TTG  TCG  CTG  GAG  GAT  GCG  GCG        2897
Ile  Ala  Ala  Ala  Thr  Val  Ala  Gly  Ala  Leu  Ser  Leu  Glu  Asp  Ala  Ala
```

|     |     |     |     |     | 680 |     |     |     |     | 685 |     |     |     |     | 690 |      |
|-----|-----|-----|-----|-----|-----|-----|-----|-----|-----|-----|-----|-----|-----|-----|-----|------|
| GCT | GTG | GTC | GCT | CTG | CGG | GCG | GGG | TTG | ATT | GGC | CGG | TAT | CTG | GCG | GGT | 2945 |
| Ala | Val | Val | Ala | Leu | Arg | Ala | Gly | Leu | Ile | Gly | Arg | Tyr | Leu | Ala | Gly |      |
| 695 |     |     |     |     | 700 |     |     |     |     | 705 |     |     |     |     | 710 |      |

| CGT | GGT | GCG | ATG | GCG | GCT | GTT | CCG | CTG | CCT | GCC | GGC | GAG | GTC | GAG | GCC | 2993 |
|-----|-----|-----|-----|-----|-----|-----|-----|-----|-----|-----|-----|-----|-----|-----|-----|------|
| Arg | Gly | Ala | Met | Ala | Ala | Val | Pro | Leu | Pro | Ala | Gly | Glu | Val | Glu | Ala |      |
|     |     |     |     | 715 |     |     |     |     | 720 |     |     |     |     | 725 |     |      |

| GGG | CTG | GCG | AAG | TGG | CCG | GGT | GTG | GAG | GTC | GCG | GCG | GTC | AAC | GGT | CCG | 3041 |
|-----|-----|-----|-----|-----|-----|-----|-----|-----|-----|-----|-----|-----|-----|-----|-----|------|
| Gly | Leu | Ala | Lys | Trp | Pro | Gly | Val | Glu | Val | Ala | Ala | Val | Asn | Gly | Pro |      |
|     |     |     | 730 |     |     |     |     | 735 |     |     |     |     | 740 |     |     |      |

| GCG | TCT | ACG | GTG | GTT | TCC | GGG | GAT | CGG | CGG | GCG | GTG | GCC | GGT | TAT | GTG | 3089 |
|-----|-----|-----|-----|-----|-----|-----|-----|-----|-----|-----|-----|-----|-----|-----|-----|------|
| Ala | Ser | Thr | Val | Val | Ser | Gly | Asp | Arg | Arg | Ala | Val | Ala | Gly | Tyr | Val |      |
|     |     | 745 |     |     |     |     | 750 |     |     |     |     | 755 |     |     |     |      |

| GCC | GTC | TGT | CAG | GCG | GAG | GGT | GTG | CAG | GCC | CGG | TTG | ATA | CCG | GTG | GAC | 3137 |
|-----|-----|-----|-----|-----|-----|-----|-----|-----|-----|-----|-----|-----|-----|-----|-----|------|
| Ala | Val | Cys | Gln | Ala | Glu | Gly | Val | Gln | Ala | Arg | Leu | Ile | Pro | Val | Asp |      |
| 760 |     |     |     |     | 765 |     |     |     |     | 770 |     |     |     |     |     |      |

| TAC | GCC | TCT | CAC | TCC | CGC | CAT | GTG | GAG | GAC | CTG | AAG | GGC | GAG | TTG | GAG | 3185 |
|-----|-----|-----|-----|-----|-----|-----|-----|-----|-----|-----|-----|-----|-----|-----|-----|------|
| Tyr | Ala | Ser | His | Ser | Arg | His | Val | Glu | Asp | Leu | Lys | Gly | Glu | Leu | Glu |      |
| 775 |     |     |     |     | 780 |     |     |     |     | 785 |     |     |     |     | 790 |      |

| CGG | GTG | CTG | TCC | GGT | ATC | CGC | CCC | CGC | AGT | CCG | CGG | GTG | CCG | GTG | TGT | 3233 |
|-----|-----|-----|-----|-----|-----|-----|-----|-----|-----|-----|-----|-----|-----|-----|-----|------|
| Arg | Val | Leu | Ser | Gly | Ile | Arg | Pro | Arg | Ser | Pro | Arg | Val | Pro | Val | Cys |      |
|     |     |     |     | 795 |     |     |     |     | 800 |     |     |     |     | 805 |     |      |

| TCC | ACC | GTC | GCC | GGA | GAG | CAG | CCG | GGC | GAG | CCG | GTT | TTC | GAT | GCG | GGG | 3281 |
|-----|-----|-----|-----|-----|-----|-----|-----|-----|-----|-----|-----|-----|-----|-----|-----|------|
| Ser | Thr | Val | Ala | Gly | Glu | Gln | Pro | Gly | Glu | Pro | Val | Phe | Asp | Ala | Gly |      |
|     |     |     |     | 810 |     |     |     |     | 815 |     |     |     |     | 820 |     |      |

| TAT | TGG | TTC | CGT | AAT | CTG | CGG | AAC | CGG | GTT | GAG | TTC | TCC | GCG | GTG | GTC | 3329 |
|-----|-----|-----|-----|-----|-----|-----|-----|-----|-----|-----|-----|-----|-----|-----|-----|------|
| Tyr | Trp | Phe | Arg | Asn | Leu | Arg | Asn | Arg | Val | Glu | Phe | Ser | Ala | Val | Val |      |
|     |     |     | 825 |     |     |     |     | 830 |     |     |     |     | 835 |     |     |      |

| GGT | GGT | TTG | TTG | GAG | GAG | GGC | CAC | CGT | CGG | TTC | ATC | GAG | GTC | AGT | GCC | 3377 |
|-----|-----|-----|-----|-----|-----|-----|-----|-----|-----|-----|-----|-----|-----|-----|-----|------|
| Gly | Gly | Leu | Leu | Glu | Glu | Gly | His | Arg | Arg | Phe | Ile | Glu | Val | Ser | Ala |      |
| 840 |     |     |     |     | 845 |     |     |     |     | 850 |     |     |     |     |     |      |

| CAC | CCG | GTA | CTC | GTC | CAT | GCG | ATC | GAG | CAG | ACG | GCC | GAG | GCC | GCG | GAC | 3425 |
|-----|-----|-----|-----|-----|-----|-----|-----|-----|-----|-----|-----|-----|-----|-----|-----|------|
| His | Pro | Val | Leu | Val | His | Ala | Ile | Glu | Gln | Thr | Ala | Glu | Ala | Ala | Asp |      |
| 855 |     |     |     |     | 860 |     |     |     |     | 865 |     |     |     |     | 870 |      |

| CGG | AGT | GTC | CAT | GCC | ACC | GGG | ACC | CTG | CGC | CGC | CAG | GAC | GAC | AGC | CCG | 3473 |
|-----|-----|-----|-----|-----|-----|-----|-----|-----|-----|-----|-----|-----|-----|-----|-----|------|
| Arg | Ser | Val | His | Ala | Thr | Gly | Thr | Leu | Arg | Arg | Gln | Asp | Asp | Ser | Pro |      |
|     |     |     |     | 875 |     |     |     |     | 880 |     |     |     |     | 885 |     |      |

| CAC | CGC | CTG | CTG | ACC | TCC | ACC | GCC | GAG | GCC | TGG | GCC | CAC | GGC | GCC | ACC | 3521 |
|-----|-----|-----|-----|-----|-----|-----|-----|-----|-----|-----|-----|-----|-----|-----|-----|------|
| His | Arg | Leu | Leu | Thr | Ser | Thr | Ala | Glu | Ala | Trp | Ala | His | Gly | Ala | Thr |      |
|     |     |     | 890 |     |     |     |     | 895 |     |     |     |     | 900 |     |     |      |

| CTC | ACC | TGG | GAC | CCC | GCC | CTG | CCC | CCA | GGC | CAC | CTC | ACC | ACC | CTC | CCC | 3569 |
|-----|-----|-----|-----|-----|-----|-----|-----|-----|-----|-----|-----|-----|-----|-----|-----|------|
| Leu | Thr | Trp | Asp | Pro | Ala | Leu | Pro | Pro | Gly | His | Leu | Thr | Thr | Leu | Pro |      |
|     |     | 905 |     |     |     |     | 910 |     |     |     |     | 915 |     |     |     |      |

| ACC | TAC | CCC | TTC | AAC | CAC | CAC | CAC | TAC | TGG | CTC | GAC | ACC | ATT | GAC | GGG | 3617 |
|-----|-----|-----|-----|-----|-----|-----|-----|-----|-----|-----|-----|-----|-----|-----|-----|------|
| Thr | Tyr | Pro | Phe | Asn | His | His | His | Tyr | Trp | Leu | Asp | Thr | Ile | Asp | Gly |      |
|     | 920 |     |     |     |     | 925 |     |     |     |     | 930 |     |     |     |     |      |

| GGC | GGA | GGG | GAC | GAC | GCG | ACC | CAG | GAG | AAG | GAG | AGC | GGC | CCT | CTG | ACG | 3665 |
|-----|-----|-----|-----|-----|-----|-----|-----|-----|-----|-----|-----|-----|-----|-----|-----|------|
| Gly | Gly | Gly | Asp | Asp | Ala | Thr | Gln | Glu | Lys | Glu | Ser | Gly | Pro | Leu | Thr |      |
| 935 |     |     |     |     | 940 |     |     |     |     | 945 |     |     |     |     | 950 |      |

| CGG | GAA | CTG | CGT | GGG | CTG | CCG | TCC | TCT | CAG | AAG | CAA | CTG | GGT | TTC | CTG | 3713 |
|-----|-----|-----|-----|-----|-----|-----|-----|-----|-----|-----|-----|-----|-----|-----|-----|------|
| Arg | Glu | Leu | Arg | Gly | Leu | Pro | Ser | Ser | Gln | Lys | Gln | Leu | Gly | Phe | Leu |      |
|     |     |     |     | 955 |     |     |     |     | 960 |     |     |     |     | 965 |     |      |

| CTC | GAT | CTG | GTG | TGC | CGG | CAC | ACG | GCC | GTC | GTA | CTC | GGC | CTG | GAC | ACG | 3761 |
|-----|-----|-----|-----|-----|-----|-----|-----|-----|-----|-----|-----|-----|-----|-----|-----|------|
| Leu | Asp | Leu | Val | Cys | Arg | His | Thr | Ala | Val | Val | Leu | Gly | Leu | Asp | Thr |      |
|     |     |     | 970 |     |     |     |     | 975 |     |     |     |     | 980 |     |     |      |

| GCC | GCC | GAG | GTG | GAC | CCG | GAC | CTG | TCC | TTC | AAG | AAG | CAG | GGC | ATC | CAG | 3809 |
|-----|-----|-----|-----|-----|-----|-----|-----|-----|-----|-----|-----|-----|-----|-----|-----|------|
| Ala | Ala | Glu | Val | Asp | Pro | Asp | Leu | Ser | Phe | Lys | Lys | Gln | Gly | Ile | Gln |      |
|     |     | 985 |     |     |     |     | 990 |     |     |     |     | 995 |     |     |     |      |

| TCC | ATG | ACC | GGC | GTC | GAG | CTG | CGC | AAC | AGG | CTG | CTG | ACC | GAG | ACC | GGC | 3857 |
|-----|-----|-----|-----|-----|-----|-----|-----|-----|-----|-----|-----|-----|-----|-----|-----|------|
| Ser | Met | Thr | Gly | Val | Glu | Leu | Arg | Asn | Arg | Leu | Leu | Thr | Glu | Thr | Gly |      |

```
              1000                    1005                      1010

CTG  GCA  TTG  CCC  ACC  ACC  CTC  GTC  TAC  GAC  CGG  CCC  ACC  CCT  CGC  GCC        3905
Leu  Ala  Leu  Pro  Thr  Thr  Leu  Val  Tyr  Asp  Arg  Pro  Thr  Pro  Arg  Ala
1015                1020                     1025                     1030

CTG  GCG  CAG  TTC  CTC  CAC  ACC  GAG  TTG  CTC  GAC  GGC  TCC  CCC  TCG  GGC        3953
Leu  Ala  Gln  Phe  Leu  His  Thr  Glu  Leu  Leu  Asp  Gly  Ser  Pro  Ser  Gly
                         1035                     1040                     1045

TCC  GTC  CTC  GCA  CCG  GCG  CAG  AAG  AGC  TTC  GAA  GCC  CAG  GAG  CCG  ATC        4001
Ser  Val  Leu  Ala  Pro  Ala  Gln  Lys  Ser  Phe  Glu  Ala  Gln  Glu  Pro  Ile
               1050                     1055                     1060

GCG  GTG  GTG  GGT  ATG  GGG  TGC  CGG  TTC  CCC  GGT  GGG  GTG  GGT  TCG  CCG        4049
Ala  Val  Val  Gly  Met  Gly  Cys  Arg  Phe  Pro  Gly  Gly  Val  Gly  Ser  Pro
                         1065                     1070                     1075

GAG  GCG  TTG  TGG  CGG  TTG  GTG  GTG  GAG  GGG  GTG  GAC  GCG  GTT  TCC  CCG        4097
Glu  Ala  Leu  Trp  Arg  Leu  Val  Val  Glu  Gly  Val  Asp  Ala  Val  Ser  Pro
1080                     1085                     1090

TTT  CCC  GGT  GAT  CGT  GGC  TGG  GAT  GTG  GAG  GGG  TTG  TAC  GAC  CCG  GAG        4145
Phe  Pro  Gly  Asp  Arg  Gly  Trp  Asp  Val  Glu  Gly  Leu  Tyr  Asp  Pro  Glu
1095                     1100                     1105                     1110

CCG  GGT  GTG  GCG  GGG  AAG  TCG  TAT  GTG  CGG  GAG  GGG  GGT  TTT  CTG  CAT        4193
Pro  Gly  Val  Ala  Gly  Lys  Ser  Tyr  Val  Arg  Glu  Gly  Gly  Phe  Leu  His
                              1115                     1120                     1125

GAT  GCG  GCG  GAG  TTC  GAT  GCG  GAG  TTC  TTC  GGG  ATT  TCG  CCG  CGT  GAG        4241
Asp  Ala  Ala  Glu  Phe  Asp  Ala  Glu  Phe  Phe  Gly  Ile  Ser  Pro  Arg  Glu
                         1130                     1135                     1140

GCG  GTG  GCG  ATG  GAT  CCG  CAG  CAG  CGG  CTG  TTG  CTG  GAG  ACC  TCC  TGG        4289
Ala  Val  Ala  Met  Asp  Pro  Gln  Gln  Arg  Leu  Leu  Leu  Glu  Thr  Ser  Trp
                         1145                     1150                     1155

GAG  GCG  ATC  GAG  CGG  GCG  GGT  ATC  GAC  CCG  CAC  TCG  CTG  CAC  GGC  AGC        4337
Glu  Ala  Ile  Glu  Arg  Ala  Gly  Ile  Asp  Pro  His  Ser  Leu  His  Gly  Ser
1160                     1165                     1170

CGC  ACC  GGC  GTC  TAC  GCC  GGC  GTG  ATG  CCG  CAG  GAA  TAC  GGA  CCT  CGG        4385
Arg  Thr  Gly  Val  Tyr  Ala  Gly  Val  Met  Pro  Gln  Glu  Tyr  Gly  Pro  Arg
1175                     1180                     1185                     1190

CTC  GCC  GAA  GGA  GCG  GAA  GGC  AGC  GAC  GGC  TAC  CTC  CTC  ACC  GGT  ACG        4433
Leu  Ala  Glu  Gly  Ala  Glu  Gly  Ser  Asp  Gly  Tyr  Leu  Leu  Thr  Gly  Thr
                              1195                     1200                     1205

TCG  GGG  AGT  GTG  GTG  TCG  GGG  CGT  GTG  GCC  TAC  ACG  CTG  GGG  CTG  GAG        4481
Ser  Gly  Ser  Val  Val  Ser  Gly  Arg  Val  Ala  Tyr  Thr  Leu  Gly  Leu  Glu
                         1210                     1215                     1220

GGT  CCG  GCC  GTG  ACC  GTG  GAT  ACG  GCG  TGT  TCG  TCG  TCG  TTG  GTG  GCG        4529
Gly  Pro  Ala  Val  Thr  Val  Asp  Thr  Ala  Cys  Ser  Ser  Ser  Leu  Val  Ala
                    1225                     1230                     1235

TTG  CAT  CTG  GCG  GTG  CAG  GCG  TTG  CGG  GGT  GGC  GAG  TGT  GAC  ATG  GCG        4577
Leu  His  Leu  Ala  Val  Gln  Ala  Leu  Arg  Gly  Gly  Glu  Cys  Asp  Met  Ala
1240                     1245                     1250

TTG  GCC  GGT  GGT  GTG  ACG  GTG  ATG  GCC  GGG  CCG  GGG  ATG  TTC  GTG  GAG        4625
Leu  Ala  Gly  Gly  Val  Thr  Val  Met  Ala  Gly  Pro  Gly  Met  Phe  Val  Glu
1255                     1260                     1265                     1270

TTT  TCG  CGG  CAG  CGG  GGG  TTG  GCG  GCC  GAT  GGG  CGG  TGC  AAG  GCG  TTC        4673
Phe  Ser  Arg  Gln  Arg  Gly  Leu  Ala  Ala  Asp  Gly  Arg  Cys  Lys  Ala  Phe
                    1275                     1280                     1285

GCG  GAT  GGG  GCG  GAT  GGG  ACC  GCT  TGG  GCC  GAG  GGT  GCG  GGG  GTG  GTG        4721
Ala  Asp  Gly  Ala  Asp  Gly  Thr  Ala  Trp  Ala  Glu  Gly  Ala  Gly  Val  Val
                    1290                     1295                     1300

CTG  GTG  GAG  CGG  TTG  TCG  GAT  GCC  CGG  CGG  TTG  GGG  CAT  CCG  GTG  TTG        4769
Leu  Val  Glu  Arg  Leu  Ser  Asp  Ala  Arg  Arg  Leu  Gly  His  Pro  Val  Leu
               1305                     1310                     1315

GCG  GTG  GTG  TGT  GGG  TCG  GCG  GTG  AAT  CAG  GAC  GGT  GCG  TCG  AAT  GGT        4817
Ala  Val  Val  Cys  Gly  Ser  Ala  Val  Asn  Gln  Asp  Gly  Ala  Ser  Asn  Gly
```

-continued

```
        1320                    1325                         1330
TTG ACG GCG CCG AGT GGT CCG TCG CAG GAG CGG GTG ATT CGT CAG GCG    4865
Leu Thr Ala Pro Ser Gly Pro Ser Gln Glu Arg Val Ile Arg Gln Ala
1335                1340                1345                1350

TTG GGG AAT GCG CGG TTG ACG GTG GCG GAT GTG GAT GTG GTG GAG GCG    4913
Leu Gly Asn Ala Arg Leu Thr Val Ala Asp Val Asp Val Val Glu Ala
            1355                1360                    1365

CAT GGG ACG GGG ACG CGG CTG GGT GAT CCG ATC GAG GCG CAG GCG TTG    4961
His Gly Thr Gly Thr Arg Leu Gly Asp Pro Ile Glu Ala Gln Ala Leu
        1370                1375                    1380

CTG GGG ACG TAT GGG CGG GAT CGT GAT GGT GGG CGT CCG GTG TGG TTG    5009
Leu Gly Thr Tyr Gly Arg Asp Arg Asp Gly Gly Arg Pro Val Trp Leu
    1385                1390                1395

GGG TCG TTG AAG TCG AAT ATT GGT CAT GCT CAG GCG GCT GCG GGG GTG    5057
Gly Ser Leu Lys Ser Asn Ile Gly His Ala Gln Ala Ala Ala Gly Val
1400                    1405                1410

GCT GGT GTG ATC AAG ATG GTG TTG GCG ATG CGG TAT GGG TGG TTG CCG    5105
Ala Gly Val Ile Lys Met Val Leu Ala Met Arg Tyr Gly Trp Leu Pro
1415                1420                1425                1430

CGG ACG TTG CAT GTG GAT GAG CCG AGC CGG CAT GTG GAC TGG TCG GCT    5153
Arg Thr Leu His Val Asp Glu Pro Ser Arg His Val Asp Trp Ser Ala
            1435                1440                1445

GGT GGT GTG TGG TTG CTG ACC GAG GCG CGG GAG TGG CCG GGG GTG GAC    5201
Gly Gly Val Trp Leu Leu Thr Glu Ala Arg Glu Trp Pro Gly Val Asp
                1450                1455                1460

CGG CCG CGT CGG GCG GCG GTC TCC GCC TTT GGT GTC AGT GGT ACC AAC    5249
Arg Pro Arg Arg Ala Ala Val Ser Ala Phe Gly Val Ser Gly Thr Asn
            1465                1470                1475

GCC CAT CTG ATC CTC GAA GCC CCC GAC ACC GCC GAG GCG GAG AGC GCC    5297
Ala His Leu Ile Leu Glu Ala Pro Asp Thr Ala Glu Ala Glu Ser Ala
        1480                1485                1490

ACG ACC CCG GTC CGC TCT GAG GTG TCG GAG TCT GCT GCG GTC CTC GAT    5345
Thr Thr Pro Val Arg Ser Glu Val Ser Glu Ser Ala Ala Val Leu Asp
1495                1500                1505                1510

GCC CGC AGT GGT GTG GTG CCG GTG GTG GTT TCG GGG CGT TCG CGG GTG    5393
Ala Arg Ser Gly Val Val Pro Val Val Val Ser Gly Arg Ser Arg Val
                1515                1520                1525

GTG GTG CGG GAG GCT GCG GGC CGG TTG GCG GAG GTG GTG GAG GCC GGT    5441
Val Val Arg Glu Ala Ala Gly Arg Leu Ala Glu Val Val Glu Ala Gly
            1530                1535                1540

GGT GTG GGG CTG GCG GAT GTG GCG GTG ACG ATG GCG GGC CGG TCG CGG    5489
Gly Val Gly Leu Ala Asp Val Ala Val Thr Met Ala Gly Arg Ser Arg
        1545                1550                1555

TTT GGG TAT CGG GCG GTT GTG CTG GCT CGG GGT GAG GCT GAG CTT GCC    5537
Phe Gly Tyr Arg Ala Val Val Leu Ala Arg Gly Glu Ala Glu Leu Ala
1560                1565                1570

GGG CGT TTG CGG GCG TTG GCG GGG GGT GAT CCG GAC GCG GGT GTG GTC    5585
Gly Arg Leu Arg Ala Leu Ala Gly Gly Asp Pro Asp Ala Gly Val Val
1575                1580                1585                1590

ACC GGT GCG GTG GTG GAC CCG GAG ACG GGT TCC GGT GGT GGG GGC GTG    5633
Thr Gly Ala Val Val Asp Pro Glu Thr Gly Ser Gly Gly Gly Gly Val
            1595                1600                1605

GTG TTG GTT TTC CCT GGT CAG GGG ACG CAG TGG GTG GGG ATG GGT GCG    5681
Val Leu Val Phe Pro Gly Gln Gly Thr Gln Trp Val Gly Met Gly Ala
                1610                1615                1620

GGG CTG CTG GGG TCT TCG GAG GTG TTT GCG GCG TCG ATG CGG GAG TGT    5729
Gly Leu Leu Gly Ser Ser Glu Val Phe Ala Ala Ser Met Arg Glu Cys
            1625                1630                1635

GCG CGG GCG CTG AGT GTT CAT GTG GAG TGG GAT TTG CTG GAG GTG GTG    5777
Ala Arg Ala Leu Ser Val His Val Glu Trp Asp Leu Leu Glu Val Val
```

-continued

```
                1640                            1645                           1650
TCG  GGC  GGG  GCC  GGG  TTG  GAG  CGG  GTG  GAT  GTG  GTG  CAG  CCC  GTG  ACG         5825
Ser  Gly  Gly  Ala  Gly  Leu  Glu  Arg  Val  Asp  Val  Val  Gln  Pro  Val  Thr
1655                      1660                     1665                     1670

TGG  GCG  GTG  ATG  GTG  TCG  CTG  GCC  CGG  TAC  TGG  CAG  GCG  ATG  GGT  GTG         5873
Trp  Ala  Val  Met  Val  Ser  Leu  Ala  Arg  Tyr  Trp  Gln  Ala  Met  Gly  Val
                    1675                     1680                     1685

GAC  GTG  GCT  GCG  GTG  GTG  GGT  CAT  TCC  CAG  GGG  GAG  ATC  GCT  GCT  GCC         5921
Asp  Val  Ala  Ala  Val  Val  Gly  His  Ser  Gln  Gly  Glu  Ile  Ala  Ala  Ala
               1690                     1695                     1700

ACG  GTG  GCG  GGG  GCG  TTG  TCG  CTG  GAG  GAT  GCG  GCG  GCT  GTG  GTC  GCT         5969
Thr  Val  Ala  Gly  Ala  Leu  Ser  Leu  Glu  Asp  Ala  Ala  Ala  Val  Val  Ala
          1705                     1710                     1715

CTG  CGG  GCG  GGG  TTG  ATT  GGC  CGG  TAT  CTG  GCG  GGT  CGT  GGT  GCG  ATG         6017
Leu  Arg  Ala  Gly  Leu  Ile  Gly  Arg  Tyr  Leu  Ala  Gly  Arg  Gly  Ala  Met
     1720                     1725                     1730

GCG  GCT  GTT  CCG  CTG  CCT  GCC  GGC  GAG  GTC  GAG  GCC  GGG  CTG  GCG  AAG         6065
Ala  Ala  Val  Pro  Leu  Pro  Ala  Gly  Glu  Val  Glu  Ala  Gly  Leu  Ala  Lys
1735                     1740                     1745                     1750

TGG  CCG  GGT  GTG  GAG  GTC  GCG  GCG  GTC  AAC  GGT  CCG  GCG  TCC  ACG  GTG         6113
Trp  Pro  Gly  Val  Glu  Val  Ala  Ala  Val  Asn  Gly  Pro  Ala  Ser  Thr  Val
                    1755                     1760                     1765

GTT  TCC  GGG  GAT  CGG  CGG  GCG  GTG  GCC  GGT  TAT  GTG  GCC  GTC  TGT  CAG         6161
Val  Ser  Gly  Asp  Arg  Arg  Ala  Val  Ala  Gly  Tyr  Val  Ala  Val  Cys  Gln
               1770                     1775                     1780

GCG  GAG  GGT  GTG  CAG  GCT  CGG  TTG  ATA  CCG  GTG  GAC  TAC  GCC  TCT  CAC         6209
Ala  Glu  Gly  Val  Gln  Ala  Arg  Leu  Ile  Pro  Val  Asp  Tyr  Ala  Ser  His
          1785                     1790                     1795

TCC  CGC  CAT  GTG  GAG  GAC  CTG  AAG  GGC  GAG  TTG  GAG  CGG  GTG  CTG  TCC         6257
Ser  Arg  His  Val  Glu  Asp  Leu  Lys  Gly  Glu  Leu  Glu  Arg  Val  Leu  Ser
     1800                     1805                     1810

GGT  ATC  CGC  CCC  CGC  AGT  CCG  CGG  GTG  CCG  GTG  TGT  TCC  ACC  GTC  GCC         6305
Gly  Ile  Arg  Pro  Arg  Ser  Pro  Arg  Val  Pro  Val  Cys  Ser  Thr  Val  Ala
1815                     1820                     1825                     1830

GGA  GAG  CAG  CCG  GGC  GAG  CCG  GTT  TTC  GAT  GCG  GGG  TAT  TGG  TTC  CGT         6353
Gly  Glu  Gln  Pro  Gly  Glu  Pro  Val  Phe  Asp  Ala  Gly  Tyr  Trp  Phe  Arg
                    1835                     1840                     1845

AAT  CTG  CGG  AAC  CGG  GTT  GAG  TTC  TCC  GCG  GTG  GTC  GGT  GGT  TTG  TTG         6401
Asn  Leu  Arg  Asn  Arg  Val  Glu  Phe  Ser  Ala  Val  Val  Gly  Gly  Leu  Leu
               1850                     1855                     1860

GAG  GAG  GGC  CAC  CGT  CGG  TTC  ATC  GAG  GTC  AGT  GCC  CAC  CCG  GTA  CTC         6449
Glu  Glu  Gly  His  Arg  Arg  Phe  Ile  Glu  Val  Ser  Ala  His  Pro  Val  Leu
          1865                     1870                     1875

GTC  CAT  GCG  ATC  GAG  CAG  ACG  GCC  GAG  GCC  GCG  GAC  CGG  AGT  GTC  CAT         6497
Val  His  Ala  Ile  Glu  Gln  Thr  Ala  Glu  Ala  Ala  Asp  Arg  Ser  Val  His
1880                     1885                     1890

GCC  ACC  GGG  ACC  CTG  CGC  CGC  CAG  GAC  GAC  AGC  CCG  CAC  CGC  CTG  CTG         6545
Ala  Thr  Gly  Thr  Leu  Arg  Arg  Gln  Asp  Asp  Ser  Pro  His  Arg  Leu  Leu
1895                     1900                     1905                     1910

ACC  TCC  ACC  GCC  GAG  GCC  TGG  GCC  CAC  GGC  GCC  ACC  CTC  ACC  TGG  GAC         6593
Thr  Ser  Thr  Ala  Glu  Ala  Trp  Ala  His  Gly  Ala  Thr  Leu  Thr  Trp  Asp
                    1915                     1920                     1925

CCC  GCC  CTG  CCC  CCA  GGC  CAC  CTC  ACC  ACC  CTC  CCC  ACC  TAC  CCC  TTC         6641
Pro  Ala  Leu  Pro  Pro  Gly  His  Leu  Thr  Thr  Leu  Pro  Thr  Tyr  Pro  Phe
               1930                     1935                     1940

AAC  CAC  CAC  CAC  TAC  TGG  CTC  GAC  ACC  ACC  CCC  ACC  ACC  CCC  GCG  ACG         6689
Asn  His  His  His  Tyr  Trp  Leu  Asp  Thr  Thr  Pro  Thr  Thr  Pro  Ala  Thr
          1945                     1950                     1955

ACC  ACC  CAG  AGC  CCC  ACC  GAT  GCC  TGG  CGC  TAC  CGC  GTC  ACC  TGG  AAA         6737
Thr  Thr  Gln  Ser  Pro  Thr  Asp  Ala  Trp  Arg  Tyr  Arg  Val  Thr  Trp  Lys
```

-continued

```
       1960                        1965                         1970
GCC   CTG   ACC   GAA   TCC   TCC   CCC   GTC   CGC   CCT   CAC   TCC   ATC   GGT   CGC   TGC      6785
Ala   Leu   Thr   Glu   Ser   Ser   Pro   Val   Arg   Pro   His   Ser   Ile   Gly   Arg   Cys
1975                    1980                          1985                           1990

CTC   CTC   GTT   GCA   CCC   CCG   ACC   ACC   GAC   GGC   GAG   CTC   CTC   GAC   GGA   CTG      6833
Leu   Leu   Val   Ala   Pro   Pro   Thr   Thr   Asp   Gly   Glu   Leu   Leu   Asp   Gly   Leu
                        1995                          2000                           2005

ACA   ACG   GTG   TTG   TCC   GAG   CGC   GGT   GCC   TCC   GTC   GCC   CGC   CTT   GAG   GTG      6881
Thr   Thr   Val   Leu   Ser   Glu   Arg   Gly   Ala   Ser   Val   Ala   Arg   Leu   Glu   Val
                  2010                          2015                          2020

CCC   ATC   GGC   GCG   CGG   CGT   GCC   GAG   GTC   GCC   GAA   CTG   CTC   AAG   CCC   TCC      6929
Pro   Ile   Gly   Ala   Arg   Arg   Ala   Glu   Val   Ala   Glu   Leu   Leu   Lys   Pro   Ser
            2025                          2030                          2035

ATG   GAG   TCA   GCG   GGG   GAG   GAG   AAC   ACC   ACC   GTC   GTC   TCG   CTT   CTC   GGT      6977
Met   Glu   Ser   Ala   Gly   Glu   Glu   Asn   Thr   Thr   Val   Val   Ser   Leu   Leu   Gly
2040                          2045                          2050

CTG   GTG   CCC   TCC   ACG   GAC   GCG   GTC   AGG   ACG   TCG   ATA   GCG   CTC   CTC   CAG      7025
Leu   Val   Pro   Ser   Thr   Asp   Ala   Val   Arg   Thr   Ser   Ile   Ala   Leu   Leu   Gln
2055                    2060                          2065                           2070

GCG   GTC   TCC   GAC   ATC   GGC   GTC   CCG   GCC   GCC   AGG   GTC   TGG   GCG   CTG   ACG      7073
Ala   Val   Ser   Asp   Ile   Gly   Val   Pro   Ala   Ala   Arg   Val   Trp   Ala   Leu   Thr
                        2075                          2080                    2085

CGG   AGG   GCC   GTG   GCC   GTG   GTT   CCC   GGG   GAG   ACG   CCG   CAG   GAC   GCG   GGG      7121
Arg   Arg   Ala   Val   Ala   Val   Val   Pro   Gly   Glu   Thr   Pro   Gln   Asp   Ala   Gly
                  2090                          2095                          2100

GCC   CAG   TTG   TGG   GGC   TTC   GGA   CGA   GTG   GCG   GCC   CTT   GAA   CTC   CCG   GAT      7169
Ala   Gln   Leu   Trp   Gly   Phe   Gly   Arg   Val   Ala   Ala   Leu   Glu   Leu   Pro   Asp
                  2105                          2110                    2115

ATC   TGG   GGC   GGC   TTG   ATC   GAT   CTG   CCG   GAG   ACA   GCG   GAG   CTG   ACG   CGG      7217
Ile   Trp   Gly   Gly   Leu   Ile   Asp   Leu   Pro   Glu   Thr   Ala   Glu   Leu   Thr   Arg
            2120                          2125                          2130

ACG   CCG   GAG   ACC   TCA   CAG   CCC   CCA   CAG   ACC   CCG   GAG   AGG   CTG   CCG   CAG      7265
Thr   Pro   Glu   Thr   Ser   Gln   Pro   Pro   Gln   Thr   Pro   Glu   Arg   Leu   Pro   Gln
2135                          2140                          2145                           2150

ACT   CCG   AAC   CGA   CGC   GCC   CTT   GAG   CTT   GCT   GCC   GCC   GTC   CTC   GCC   GGC      7313
Thr   Pro   Asn   Arg   Arg   Ala   Leu   Glu   Leu   Ala   Ala   Ala   Val   Leu   Ala   Gly
                  2155                          2160                          2165

CGC   GAC   GGC   GAG   GAC   CAG   GTC   GCC   GTG   CGC   GCC   TCG   GGG   ATC   TAC   GGG      7361
Arg   Asp   Gly   Glu   Asp   Gln   Val   Ala   Val   Arg   Ala   Ser   Gly   Ile   Tyr   Gly
                        2170                          2175                          2180

CGG   CGG   GTG   TCG   CGG   GCC   GCG   GCA   GCG   GGG   GCC   GCC   TCC   TGG   CAG   CCG      7409
Arg   Arg   Val   Ser   Arg   Ala   Ala   Ala   Ala   Gly   Ala   Ala   Ser   Trp   Gln   Pro
                  2185                          2190                          2195

TCC   GGC   ACG   GTG   CTG   ATC   ACC   GGC   GGC   ATG   GGT   GCC   ATC   GGC   AGG   CGG      7457
Ser   Gly   Thr   Val   Leu   Ile   Thr   Gly   Gly   Met   Gly   Ala   Ile   Gly   Arg   Arg
      2200                          2205                          2210

CTC   GCC   CGC   AGG   CTG   GCG   GCC   GAG   GGA   GCC   GAA   CGC   CTG   GTC   CTC   ACC      7505
Leu   Ala   Arg   Arg   Leu   Ala   Ala   Glu   Gly   Ala   Glu   Arg   Leu   Val   Leu   Thr
2215                          2220                          2225                           2230

AGC   CGT   CGC   GGA   CCG   GAG   GCG   CCG   GGC   GCC   GCC   GAA   CTC   GCC   GAG   GAA      7553
Ser   Arg   Arg   Gly   Pro   Glu   Ala   Pro   Gly   Ala   Ala   Glu   Leu   Ala   Glu   Glu
                        2235                          2240                          2245

CTG   CGA   GGA   CAT   GGC   TGC   GAG   GTC   GTG   CAC   GCG   GCC   TGT   GAC   GTG   GCC      7601
Leu   Arg   Gly   His   Gly   Cys   Glu   Val   Val   His   Ala   Ala   Cys   Asp   Val   Ala
                  2250                          2255                          2260

GAG   CGT   GAT   GCG   CTC   GCC   GCG   CTC   GTC   ACC   GCG   TAT   CCG   CCG   AAC   GCC      7649
Glu   Arg   Asp   Ala   Leu   Ala   Ala   Leu   Val   Thr   Ala   Tyr   Pro   Pro   Asn   Ala
            2265                          2270                          2275

GTC   TTC   CAC   ACC   GCC   GGG   ATT   CTG   GAC   GAC   GCG   GTG   ATC   GAC   ACG   CTG      7697
Val   Phe   His   Thr   Ala   Gly   Ile   Leu   Asp   Asp   Ala   Val   Ile   Asp   Thr   Leu
```

-continued

```
                  2280                              2285                              2290
TCA  CCG  GAG  AGC  TTC  GAG  ACC  GTC  CGC  GGG  GCG  AAG  GTG  TGC  GGC  GCG       7745
Ser  Pro  Glu  Ser  Phe  Glu  Thr  Val  Arg  Gly  Ala  Lys  Val  Cys  Gly  Ala
2295            2300                              2305                         2310

GAG  CTG  CTG  CAC  CAA  CTG  ACT  GCG  GAC  ATA  AAA  GGG  TTG  GAC  GCC  TTC       7793
Glu  Leu  Leu  His  Gln  Leu  Thr  Ala  Asp  Ile  Lys  Gly  Leu  Asp  Ala  Phe
                    2315                         2320                         2325

GTC  CTC  TTC  TCC  TCC  GTC  ACC  GGC  ACA  TGG  GGC  AAC  GCC  GGC  CAG  GGT       7841
Val  Leu  Phe  Ser  Ser  Val  Thr  Gly  Thr  Trp  Gly  Asn  Ala  Gly  Gln  Gly
               2330                         2335                              2340

GCG  TAC  GCC  GCC  GCC  AAC  GCC  GCG  CTC  GAC  GCC  CTC  GCC  GAG  CGT  CGC       7889
Ala  Tyr  Ala  Ala  Ala  Asn  Ala  Ala  Leu  Asp  Ala  Leu  Ala  Glu  Arg  Arg
          2345                         2350                         2355

CGT  GCC  GCC  GGA  CTG  CCC  GCG  ACC  TCC  GTC  GCC  TGG  GGC  CTT  TGG  GGC       7937
Arg  Ala  Ala  Gly  Leu  Pro  Ala  Thr  Ser  Val  Ala  Trp  Gly  Leu  Trp  Gly
     2360                         2365                         2370

GGG  GGA  GGC  ATG  GCG  GCG  GGT  GCG  GGC  GAG  GAG  AGT  CTG  TCG  CGG  CGA       7985
Gly  Gly  Gly  Met  Ala  Ala  Gly  Ala  Gly  Glu  Glu  Ser  Leu  Ser  Arg  Arg
2375                    2380                         2385                         2390

GGG  CTG  CGG  GCC  ATG  GAC  CCC  GAC  GCG  GCC  GTC  GAC  GCG  CTC  CTG  GGC       8033
Gly  Leu  Arg  Ala  Met  Asp  Pro  Asp  Ala  Ala  Val  Asp  Ala  Leu  Leu  Gly
                         2395                         2400                    2405

GCC  ATG  GGC  AGG  AAC  GAC  GTG  TGC  GTC  ACT  GTC  GTC  GAC  GTC  GAC  TGG       8081
Ala  Met  Gly  Arg  Asn  Asp  Val  Cys  Val  Thr  Val  Val  Asp  Val  Asp  Trp
               2410                         2415                         2420

GAG  CGT  TTC  GCG  CCC  GCG  ACG  AAC  GCC  ATC  CGT  CCC  GGG  CGG  CTG  TTC       8129
Glu  Arg  Phe  Ala  Pro  Ala  Thr  Asn  Ala  Ile  Arg  Pro  Gly  Arg  Leu  Phe
          2425                         2430                         2435

GAC  ACC  GTG  CCG  GAG  GCG  CGG  GAG  GCC  CTG  ACG  GCA  GCC  GGC  ACC  ACG       8177
Asp  Thr  Val  Pro  Glu  Ala  Arg  Glu  Ala  Leu  Thr  Ala  Ala  Gly  Thr  Thr
     2440                         2445                         2450

TCC  GCG  ACG  CCG  GAC  GGC  GCG  CCC  GAG  CTG  GCG  CGG  CGG  TTG  TCC  ATG       8225
Ser  Ala  Thr  Pro  Asp  Gly  Ala  Pro  Glu  Leu  Ala  Arg  Arg  Leu  Ser  Met
2455                    2460                         2465                         2470

CTG  AAC  GAG  ACC  GAA  CGC  CTG  CGG  AAG  CTG  GTC  GAA  CTC  GTC  CGT  ACC       8273
Leu  Asn  Glu  Thr  Glu  Arg  Leu  Arg  Lys  Leu  Val  Glu  Leu  Val  Arg  Thr
                    2475                         2480                         2485

GAG  GCG  GCC  TTT  GTG  CTG  CGG  CAT  CCG  AAC  ACG  GAC  GCC  ATC  GGC  GCC       8321
Glu  Ala  Ala  Phe  Val  Leu  Arg  His  Pro  Asn  Thr  Asp  Ala  Ile  Gly  Ala
               2490                         2495                         2500

GAA  CGC  CCG  TTC  AAG  TCG  GCC  GGT  TTC  GAC  TCC  CTG  ACC  TCC  CTG  GAA       8369
Glu  Arg  Pro  Phe  Lys  Ser  Ala  Gly  Phe  Asp  Ser  Leu  Thr  Ser  Leu  Glu
          2505                         2510                         2515

CTC  CGC  AAC  CGC  CTC  AAT  GCC  GGC  ACA  GGC  CTG  AAG  CTA  CCC  GCC  ACC       8417
Leu  Arg  Asn  Arg  Leu  Asn  Ala  Gly  Thr  Gly  Leu  Lys  Leu  Pro  Ala  Thr
2520                    2525                         2530

GTC  ATC  TTC  GAC  CAC  CCC  AGC  CCG  ACC  GCC  CTG  GCC  AGA  CTG  CTG  CTC       8465
Val  Ile  Phe  Asp  His  Pro  Ser  Pro  Thr  Ala  Leu  Ala  Arg  Leu  Leu  Leu
2535                    2540                         2545                         2550

GAC  CGG  CTG  ACC  GGC  GCC  GGA  GCC  CCC  GCG  CCC  GCC  GCC  GAT  GAG  CCG       8513
Asp  Arg  Leu  Thr  Gly  Ala  Gly  Ala  Pro  Ala  Pro  Ala  Ala  Asp  Glu  Pro
                         2555                         2560                    2565

CCA  CTG  CCC  GTC  GCC  GTG  GCC  GAC  GAC  GAC  CCG  GTG  GTC  ATC  GTC  GGC       8561
Pro  Leu  Pro  Val  Ala  Val  Ala  Asp  Asp  Asp  Pro  Val  Val  Ile  Val  Gly
               2570                         2575                         2580

ATG  GCG  TGC  CGT  TTC  CCC  GGT  GGG  GCG  GGC  ACC  CCT  GAG  GCG  CTG  TGG       8609
Met  Ala  Cys  Arg  Phe  Pro  Gly  Gly  Ala  Gly  Thr  Pro  Glu  Ala  Leu  Trp
          2585                         2590                         2595

AAG  CTG  GTG  ACC  GAG  GAG  CGT  GAC  GTC  ATA  GGC  GCC  GCG  CCC  ACC  GAC       8657
Lys  Leu  Val  Thr  Glu  Glu  Arg  Asp  Val  Ile  Gly  Ala  Ala  Pro  Thr  Asp
```

```
                   2600                     2605                        2610
CGG  GGC  TGG  GAC  CTG  GAT  TCC  GTC  TAC  GAC  CCG  GAG  CCG  GGT  GTG  GCG      8705
Arg  Gly  Trp  Asp  Leu  Asp  Ser  Val  Tyr  Asp  Pro  Glu  Pro  Gly  Val  Ala
2615                2620                     2625                       2630

GGG  AAG  ACA  TAT  GTG  CGG  GAG  GGG  GGT  TTT  CTC  CAC  GAC  GCG  GCG  GAG      8753
Gly  Lys  Thr  Tyr  Val  Arg  Glu  Gly  Gly  Phe  Leu  His  Asp  Ala  Ala  Glu
                    2635                     2640                       2645

TTC  GAC  GCG  GAG  TTC  TTC  GGG  ATT  TCG  CCG  CGT  GAG  GCG  GTG  GCG  ATG      8801
Phe  Asp  Ala  Glu  Phe  Phe  Gly  Ile  Ser  Pro  Arg  Glu  Ala  Val  Ala  Met
                    2650                     2655                       2660

GAT  CCG  CAG  CAG  CGG  CTG  TTG  CTG  GAG  ACC  TCC  TGG  GAG  GCG  ATC  GAG      8849
Asp  Pro  Gln  Gln  Arg  Leu  Leu  Leu  Glu  Thr  Ser  Trp  Glu  Ala  Ile  Glu
                    2665                     2670                       2675

CGG  GCG  GGT  ATC  GAC  CCG  CAC  TCG  CTG  CAC  GGC  AGC  CGC  ACC  GGG  GTA      8897
Arg  Ala  Gly  Ile  Asp  Pro  His  Ser  Leu  His  Gly  Ser  Arg  Thr  Gly  Val
2680                2685                     2690

TAC  GTC  GGG  CTG  ACC  CAT  CAG  GAG  TAC  GCC  TCC  CGG  CTG  CAC  GAG  GCC      8945
Tyr  Val  Gly  Leu  Thr  His  Gln  Glu  Tyr  Ala  Ser  Arg  Leu  His  Glu  Ala
2695                     2700                     2705                  2710

CCG  GAG  GAG  TAC  GAA  GGC  TAT  CTG  CTC  ACC  GGC  AAG  TCG  GCG  AGC  GTC      8993
Pro  Glu  Glu  Tyr  Glu  Gly  Tyr  Leu  Leu  Thr  Gly  Lys  Ser  Ala  Ser  Val
                    2715                     2720                       2725

GTC  TCC  GGC  CGC  ATC  TCG  TAC  ACG  CTG  GGG  CTG  GAG  GGT  CCT  TCG  CTC      9041
Val  Ser  Gly  Arg  Ile  Ser  Tyr  Thr  Leu  Gly  Leu  Glu  Gly  Pro  Ser  Leu
                    2730                     2735                       2740

TCC  ATC  GAC  ACC  GCG  TGT  TCG  TCG  TCG  CTG  GTC  GCC  CTG  CAC  AAC  GCG      9089
Ser  Ile  Asp  Thr  Ala  Cys  Ser  Ser  Ser  Leu  Val  Ala  Leu  His  Asn  Ala
                    2745                     2750                       2755

GCG  CAG  GCG  TTG  CGG  GGT  GGC  GAG  TGT  GAC  ATG  GCG  TTG  GCC  GGT  GGT      9137
Ala  Gln  Ala  Leu  Arg  Gly  Gly  Glu  Cys  Asp  Met  Ala  Leu  Ala  Gly  Gly
2760                     2765                     2770

GTG  ACG  GTG  ATG  GCG  GCA  CCC  GGA  TTG  TTC  GTG  GAG  TTT  TCG  CGG  CAG      9185
Val  Thr  Val  Met  Ala  Ala  Pro  Gly  Leu  Phe  Val  Glu  Phe  Ser  Arg  Gln
2775                     2780                     2785                  2790

CGG  GGG  TTG  GCG  GCC  GAT  GGG  CGG  TGC  AAG  GCG  TTC  GCG  GAT  GGG  GCG      9233
Arg  Gly  Leu  Ala  Ala  Asp  Gly  Arg  Cys  Lys  Ala  Phe  Ala  Asp  Gly  Ala
                    2795                     2800                       2805

GAT  GGG  ACC  GCT  TGG  GCC  GAG  GGT  GCG  GGG  GTG  GTG  CTG  GTG  GAG  CGG      9281
Asp  Gly  Thr  Ala  Trp  Ala  Glu  Gly  Ala  Gly  Val  Val  Leu  Val  Glu  Arg
                    2810                     2815                       2820

TTG  TCG  GAT  GCC  CGG  CGG  TTG  GGG  CAT  CCG  GTG  TTG  GCG  GTG  GTG  TGT      9329
Leu  Ser  Asp  Ala  Arg  Arg  Leu  Gly  His  Pro  Val  Leu  Ala  Val  Val  Cys
                    2825                     2830                       2835

GGG  TCG  GCG  GTG  AAT  CAG  GAC  GGT  GCG  TCG  AAT  GGT  TTG  ACG  GCG  CCG      9377
Gly  Ser  Ala  Val  Asn  Gln  Asp  Gly  Ala  Ser  Asn  Gly  Leu  Thr  Ala  Pro
2840                     2845                     2850

AGT  GGT  CCG  TCG  CAG  GAG  CGG  GTG  ATT  CGT  CAG  GCG  TTG  GCG  AAT  GCG      9425
Ser  Gly  Pro  Ser  Gln  Glu  Arg  Val  Ile  Arg  Gln  Ala  Leu  Ala  Asn  Ala
2855                     2860                     2865                  2870

CGG  TTG  ACG  GTG  GCG  GAT  GTG  GAT  GTG  GTG  GAG  GCG  CAT  GGG  ACG  GGG      9473
Arg  Leu  Thr  Val  Ala  Asp  Val  Asp  Val  Val  Glu  Ala  His  Gly  Thr  Gly
                    2875                     2880                       2885

ACG  CGG  CTG  GGT  GAT  CCG  ATC  GAG  GCG  CAG  GCG  TTG  CTG  GGG  ACG  TAT      9521
Thr  Arg  Leu  Gly  Asp  Pro  Ile  Glu  Ala  Gln  Ala  Leu  Leu  Gly  Thr  Tyr
                    2890                     2895                       2900

GGG  CGG  GAT  CGT  GAT  GCT  GAG  TGT  CCG  GTG  TGG  TTG  GGG  TCG  TTG  AAG      9569
Gly  Arg  Asp  Arg  Asp  Ala  Glu  Cys  Pro  Val  Trp  Leu  Gly  Ser  Leu  Lys
                    2905                     2910                       2915

TCG  AAT  ATT  GGT  CAT  GCT  CAG  GCG  GCT  GCG  GGG  GTG  GCT  GGT  GTG  ATC      9617
Ser  Asn  Ile  Gly  His  Ala  Gln  Ala  Ala  Ala  Gly  Val  Ala  Gly  Val  Ile
```

```
                2920                            2925                            2930
AAG  ATG  GTG  TTG  GCG  ATG  CGG  TAT  GGG  TGG  TTG  CCG  CGG  ACG  TTG  CAT      9665
Lys  Met  Val  Leu  Ala  Met  Arg  Tyr  Gly  Trp  Leu  Pro  Arg  Thr  Leu  His
2935                      2940                          2945                     2950

GTG  GAT  GAG  CCG  AGC  CGG  CAT  GTG  GAC  TGG  TCG  GCT  GGT  GGT  GTG  CGG      9713
Val  Asp  Glu  Pro  Ser  Arg  His  Val  Asp  Trp  Ser  Ala  Gly  Gly  Val  Arg
                          2955                          2960                     2965

TTG  CTG  ACC  GAG  GCG  CGG  GAG  TGG  CCG  GGG  GTG  GAC  CGG  CCG  CGT  CGG      9761
Leu  Leu  Thr  Glu  Ala  Arg  Glu  Trp  Pro  Gly  Val  Asp  Arg  Pro  Arg  Arg
               2970                          2975                     2980

GCG  GCG  GTC  TCC  GCC  TTC  GGT  GTC  AGT  GGT  ACC  AAC  GCC  CAT  CTG  ATC      9809
Ala  Ala  Val  Ser  Ala  Phe  Gly  Val  Ser  Gly  Thr  Asn  Ala  His  Leu  Ile
          2985                          2990                     2995

CTC  GAA  GCC  CCC  GAA  GCC  CTC  GAA  GCC  CTC  GAA  GCC  ACC  GAC  GCC  CCC      9857
Leu  Glu  Ala  Pro  Glu  Ala  Leu  Glu  Ala  Leu  Glu  Ala  Thr  Asp  Ala  Pro
     3000                          3005                          3010

GAA  GCC  CCC  GAA  GCC  CCC  GAA  GCC  CCC  GAC  GTC  ACC  GAC  GTC  ACC  GAA      9905
Glu  Ala  Pro  Glu  Ala  Pro  Glu  Ala  Pro  Asp  Val  Thr  Asp  Val  Thr  Glu
3015                     3020                     3025                     3030

GCC  CTC  GAA  GCC  CCC  GAC  GCC  ACC  GAG  GCG  GAG  GGT  GCG  AAG  GCT  CCT      9953
Ala  Leu  Glu  Ala  Pro  Asp  Ala  Thr  Glu  Ala  Glu  Gly  Ala  Lys  Ala  Pro
                    3035                          3040                     3045

GGC  AGT  CCC  GAA  GAG  GCA  CAG  CCT  GCT  GTG  GGT  GTG  GTG  CCG  GTG  GTG      10001
Gly  Ser  Pro  Glu  Glu  Ala  Gln  Pro  Ala  Val  Gly  Val  Val  Pro  Val  Val
               3050                          3055                     3060

GTT  TCG  GGG  CGT  TCG  CGG  GTG  GTG  GTG  CGG  GAG  GCT  GCG  GGC  CGG  TTG      10049
Val  Ser  Gly  Arg  Ser  Arg  Val  Val  Val  Arg  Glu  Ala  Ala  Gly  Arg  Leu
          3065                          3070                     3075

GCG  GAG  GTG  GTG  GAG  GCC  GGT  GGT  GTG  GGG  CTG  GCG  GAT  GTG  GCG  GTG      10097
Ala  Glu  Val  Val  Glu  Ala  Gly  Gly  Val  Gly  Leu  Ala  Asp  Val  Ala  Val
3080                          3085                          3090

ACG  ATG  GCG  GGC  CGG  TCG  CGG  TTT  GGG  TAT  CGG  GCG  GTT  GTG  CTG  GCT      10145
Thr  Met  Ala  Gly  Arg  Ser  Arg  Phe  Gly  Tyr  Arg  Ala  Val  Val  Leu  Ala
3095                     3100                          3105                3110

CGG  GGT  GAG  GCT  GAG  CTT  GCC  GGG  CGT  TTG  CGG  GCG  TTG  GCG  GGG  GGT      10193
Arg  Gly  Glu  Ala  Glu  Leu  Ala  Gly  Arg  Leu  Arg  Ala  Leu  Ala  Gly  Gly
                         3115                     3120                     3125

GAT  CCG  GAC  GCG  GGT  GTG  GTC  ACC  GGT  GCG  GTG  GTG  GAC  CCG  GAG  ACG      10241
Asp  Pro  Asp  Ala  Gly  Val  Val  Thr  Gly  Ala  Val  Val  Asp  Pro  Glu  Thr
               3130                          3135                     3140

GGG  TCC  GGT  GGT  GGG  GGC  GTG  GTG  TTG  GTT  TTC  CCT  GGT  CAG  GGG  ACG      10289
Gly  Ser  Gly  Gly  Gly  Gly  Val  Val  Leu  Val  Phe  Pro  Gly  Gln  Gly  Thr
          3145                          3150                     3155

CAG  TGG  GTG  GGG  ATG  GGT  GCG  GGG  CTG  CTG  GGG  TCT  TCG  GAG  GTG  TTT      10337
Gln  Trp  Val  Gly  Met  Gly  Ala  Gly  Leu  Leu  Gly  Ser  Ser  Glu  Val  Phe
3160                          3165                          3170

GCG  GCG  TCG  ATG  CGG  GAG  TGT  GCG  CGG  GCG  CTG  AGT  GTT  CAT  GTG  GAG      10385
Ala  Ala  Ser  Met  Arg  Glu  Cys  Ala  Arg  Ala  Leu  Ser  Val  His  Val  Glu
3175                     3180                          3185                3190

TGG  GAT  TTG  CTG  GAG  GTG  GTG  TCG  GGC  GGG  GCC  GGG  TTG  GAG  CGG  GTG      10433
Trp  Asp  Leu  Leu  Glu  Val  Val  Ser  Gly  Gly  Ala  Gly  Leu  Glu  Arg  Val
                    3195                          3200                     3205

GAT  GTG  GTG  CAG  CCC  GTG  ACG  TGG  GCG  GTG  ATG  GTG  TCG  CTG  GCC  CGG      10481
Asp  Val  Val  Gln  Pro  Val  Thr  Trp  Ala  Val  Met  Val  Ser  Leu  Ala  Arg
               3210                          3215                     3220

TAC  TGG  CAG  GCG  ATG  GGT  GTG  GAC  GTG  GCT  GCG  GTG  GTG  GGT  CAT  TCC      10529
Tyr  Trp  Gln  Ala  Met  Gly  Val  Asp  Val  Ala  Ala  Val  Val  Gly  His  Ser
          3225                          3230                     3235

CAG  GGG  GAG  ATC  GCT  GCT  GCC  ACG  GTG  GCG  GGG  GCG  TTG  TCG  CTG  GAG      10577
Gln  Gly  Glu  Ile  Ala  Ala  Ala  Thr  Val  Ala  Gly  Ala  Leu  Ser  Leu  Glu
```

-continued

|     |     |     |     |     |     |     |     |     |     |     |     |     |     |     |     |       |
|-----|-----|-----|-----|-----|-----|-----|-----|-----|-----|-----|-----|-----|-----|-----|-----|-------|
|     |     |     |3240 |     |     |     |     |3245 |     |     |     |     |3250 |     |     |       |
| GAT | GCG | GCG | GCT | GTG | GTC | GCT | CTG | CGG | GCG | GGG | TTG | ATT | GGC | CGG | TAT | 10625 |
| Asp | Ala | Ala | Ala | Val | Val | Ala | Leu | Arg | Ala | Gly | Leu | Ile | Gly | Arg | Tyr |       |
| 3255 |    |     |     |     |3260 |     |     |     |     |3265 |     |     |     |     |3270 |       |
| CTG | GCG | GGT | CGT | GGT | GCG | ATG | GCG | GCT | GTT | CCG | CTG | CCT | GCC | GGC | GAG | 10673 |
| Leu | Ala | Gly | Arg | Gly | Ala | Met | Ala | Ala | Val | Pro | Leu | Pro | Ala | Gly | Glu |       |
|     |     |     |     |3275 |     |     |     |     |3280 |     |     |     |     |3285 |     |       |
| GTC | GAG | GCC | GGG | CTG | GCG | AAG | TGG | CCC | GGA | GTA | CAG | GTA | GCC | GCG | GTC | 10721 |
| Val | Glu | Ala | Gly | Leu | Ala | Lys | Trp | Pro | Gly | Val | Gln | Val | Ala | Ala | Val |       |
|     |     |     |3290 |     |     |     |     |3295 |     |     |     |     |3300 |     |     |       |
| AAC | GGT | CCG | GCG | TCC | ACG | GTG | GTT | TCC | GGG | GAT | CGG | CGG | GCG | GTG | GCC | 10769 |
| Asn | Gly | Pro | Ala | Ser | Thr | Val | Val | Ser | Gly | Asp | Arg | Arg | Ala | Val | Ala |       |
|     |     |3305 |     |     |     |     |3310 |     |     |     |     |3315 |     |     |     |       |
| GGT | TAT | GTG | GCC | GTC | TGT | CAG | GCG | GAG | GGT | GTG | CAG | GCT | CGG | TTG | ATA | 10817 |
| Gly | Tyr | Val | Ala | Val | Cys | Gln | Ala | Glu | Gly | Val | Gln | Ala | Arg | Leu | Ile |       |
|     |3320 |    |     |     |     |3325 |     |     |     |     |3330 |     |     |     |     |       |
| CCG | GTG | GAC | TAC | GCC | TCT | CAC | TCC | CGC | CAT | GTG | GAG | GAC | CTG | AAG | GGC | 10865 |
| Pro | Val | Asp | Tyr | Ala | Ser | His | Ser | Arg | His | Val | Glu | Asp | Leu | Lys | Gly |       |
| 3335 |    |     |     |     |3340 |     |     |     |     |3345 |     |     |     |     |3350 |       |
| GAG | TTG | GAG | CGG | GTG | CTG | TCC | GGT | ATC | CGC | CCC | CGC | AGT | CCG | CGG | GTG | 10913 |
| Glu | Leu | Glu | Arg | Val | Leu | Ser | Gly | Ile | Arg | Pro | Arg | Ser | Pro | Arg | Val |       |
|     |     |     |     |3355 |     |     |     |     |3360 |     |     |     |     |3365 |     |       |
| CCG | GTG | TGT | TCC | ACC | GTC | GCC | GGA | GAG | CAG | CCG | GGC | GAG | CCG | GTT | TTC | 10961 |
| Pro | Val | Cys | Ser | Thr | Val | Ala | Gly | Glu | Gln | Pro | Gly | Glu | Pro | Val | Phe |       |
|     |     |     |3370 |     |     |     |     |3375 |     |     |     |     |3380 |     |     |       |
| GAT | GCG | GGG | TAT | TGG | TTC | CGT | AAT | CTG | CGG | AAC | CGG | GTT | GAG | TTC | TCC | 11009 |
| Asp | Ala | Gly | Tyr | Trp | Phe | Arg | Asn | Leu | Arg | Asn | Arg | Val | Glu | Phe | Ser |       |
|     |     |     |     |3385 |     |     |     |     |3390 |     |     |     |     |3395 |     |       |
| GCG | GTG | GTC | GGT | GGT | TTG | TTG | GAG | CAG | GGC | CAC | CGT | CGG | TTC | ATC | GAG | 11057 |
| Ala | Val | Val | Gly | Gly | Leu | Leu | Glu | Gln | Gly | His | Arg | Arg | Phe | Ile | Glu |       |
| 3400 |    |     |     |     |3405 |     |     |     |     |3410 |     |     |     |     |     |       |
| GTC | AGT | GCC | CAC | CCG | GTA | CTC | GTC | CAT | GCC | ATT | GAG | CAG | ACG | GCC | GAG | 11105 |
| Val | Ser | Ala | His | Pro | Val | Leu | Val | His | Ala | Ile | Glu | Gln | Thr | Ala | Glu |       |
| 3415 |    |     |     |     |3420 |     |     |     |     |3425 |     |     |     |     |3430 |       |
| GCC | GCG | GAC | CGG | AGT | GTC | CAT | GCC | ACC | GGA | ACC | CTG | CGC | CGC | CAG | GAC | 11153 |
| Ala | Ala | Asp | Arg | Ser | Val | His | Ala | Thr | Gly | Thr | Leu | Arg | Arg | Gln | Asp |       |
|     |     |     |     |3435 |     |     |     |     |3440 |     |     |     |     |3445 |     |       |
| GAC | AGC | CCG | CAC | CGC | CTG | CTG | ACC | TCC | ACC | GCC | GAG | GCC | TGG | GCC | CAC | 11201 |
| Asp | Ser | Pro | His | Arg | Leu | Leu | Thr | Ser | Thr | Ala | Glu | Ala | Trp | Ala | His |       |
|     |     |     |3450 |     |     |     |     |3455 |     |     |     |     |3460 |     |     |       |
| GGC | GCC | ACC | CTC | ACC | TGG | GAC | CCC | GCC | CTG | CCC | CCA | GGT | CAC | CTC | ACC | 11249 |
| Gly | Ala | Thr | Leu | Thr | Trp | Asp | Pro | Ala | Leu | Pro | Pro | Gly | His | Leu | Thr |       |
|     |     |     |3465 |     |     |     |     |3470 |     |     |     |     |3475 |     |     |       |
| ACC | CTC | CCC | ACC | TAC | CCC | TTC | AAC | CAC | CAC | CAC | TAC | TGG | GCC | GTG | ACA | 11297 |
| Thr | Leu | Pro | Thr | Tyr | Pro | Phe | Asn | His | His | His | Tyr | Trp | Ala | Val | Thr |       |
| 3480 |    |     |     |     |3485 |     |     |     |     |3490 |     |     |     |     |     |       |
| TCC | CCC | GCC | GGA | GTC | GGC | GAC | GCG | GCT | GCG | GGC | CGG | TTC | GGT | ATG | ACC | 11345 |
| Ser | Pro | Ala | Gly | Val | Gly | Asp | Ala | Ala | Ala | Gly | Arg | Phe | Gly | Met | Thr |       |
| 3495 |    |     |     |     |3500 |     |     |     |     |3505 |     |     |     |     |3510 |       |
| TGG | GAG | GAC | CAC | CCC | TTC | CTC | CGT | GGC | GGG | TTA | CCC | CTG | GCC | GAC | TCC | 11393 |
| Trp | Glu | Asp | His | Pro | Phe | Leu | Arg | Gly | Gly | Leu | Pro | Leu | Ala | Asp | Ser |       |
|     |     |     |     |3515 |     |     |     |     |3520 |     |     |     |     |3525 |     |       |
| GGT | GAG | CGG | GTG | TTC | GCC | GGG | CGG | CTG | GCG | GGC | TCC | GAG | CAC | GAC | TGG | 11441 |
| Gly | Glu | Arg | Val | Phe | Ala | Gly | Arg | Leu | Ala | Gly | Ser | Glu | His | Asp | Trp |       |
|     |     |     |3530 |     |     |     |     |3535 |     |     |     |     |3540 |     |     |       |
| CTG | ACG | GAC | CAT | GCC | GTG | TCC | GGG | GTG | ACG | TTG | CTG | CCG | GGT | ACG | GCC | 11489 |
| Leu | Thr | Asp | His | Ala | Val | Ser | Gly | Val | Thr | Leu | Leu | Pro | Gly | Thr | Ala |       |
|     |     |     |     |3545 |     |     |     |     |3550 |     |     |     |     |3555 |     |       |
| TTC | GTG | GAG | TTC | GCG | CTG | CAC | GCG | GGA | GCC | GCC | ACC | GGC | TGC | GGG | CGG | 11537 |
| Phe | Val | Glu | Phe | Ala | Leu | His | Ala | Gly | Ala | Ala | Thr | Gly | Cys | Gly | Arg |       |

```
                        3560                     3565                          3570
CTG  GAA  GAG  CTG  AGC  GTT  GAG  GCG  CCG  TTG  GTC  TTG  CCC  GCC  GCC  GGT     11585
Leu  Glu  Glu  Leu  Ser  Val  Glu  Ala  Pro  Leu  Val  Leu  Pro  Ala  Ala  Gly
3575                3580                     3585                          3590

GGT  GTG  CGG  GTG  CAG  ATG  AGG  GTG  TCG  GCC  GCC  GAC  GAG  TCG  GGA  CGG     11633
Gly  Val  Arg  Val  Gln  Met  Arg  Val  Ser  Ala  Ala  Asp  Glu  Ser  Gly  Arg
                         3595                     3600                     3605

CGG  AGG  GTC  GCC  ATC  CAC  TCG  GCC  CCG  GAA  GCC  GCC  GTC  CAC  TCG  GCC     11681
Arg  Arg  Val  Ala  Ile  His  Ser  Ala  Pro  Glu  Ala  Ala  Val  His  Ser  Ala
               3610                     3615                          3620

GCA  GAA  GGC  GGC  GAC  TCG  GCC  GGT  GTC  TGG  ACG  CGG  CAC  GGC  GAG  GGC     11729
Ala  Glu  Gly  Gly  Asp  Ser  Ala  Gly  Val  Trp  Thr  Arg  His  Gly  Glu  Gly
          3625                     3630                          3635

ACG  CTC  GTG  CCG  GAC  CCG  GAG  CCC  ACG  CCT  CCG  GAC  GCC  GAC  TGG  GCG     11777
Thr  Leu  Val  Pro  Asp  Pro  Glu  Pro  Thr  Pro  Pro  Asp  Ala  Asp  Trp  Ala
3640                     3645                                3650

CGG  GCC  TGG  CCG  CCC  GCC  GGG  GAA  CGC  GTC  GAA  CCG  GCC  GAG  CTC  TAC     11825
Arg  Ala  Trp  Pro  Pro  Ala  Gly  Glu  Arg  Val  Glu  Pro  Ala  Glu  Leu  Tyr
3655                          3660                     3665                     3670

GAA  CGG  TTC  GGG  GCC  CTG  GGC  TAC  GAG  TAC  GGT  GAG  GCG  TTC  GCG  GGC     11873
Glu  Arg  Phe  Gly  Ala  Leu  Gly  Tyr  Glu  Tyr  Gly  Glu  Ala  Phe  Ala  Gly
                         3675                     3680                     3685

GTG  CGC  GCC  GTA  TGG  CGG  CAG  CCG  GAC  GCG  CTG  CTC  GCC  GAG  GTG  CTC     11921
Val  Arg  Ala  Val  Trp  Arg  Gln  Pro  Asp  Ala  Leu  Leu  Ala  Glu  Val  Leu
                    3690                     3695                     3700

CTG  CCC  GAC  CGG  GCC  TCG  ACC  GGT  GCC  GGC  CGG  TTC  GGT  GTG  CAC  CCC     11969
Leu  Pro  Asp  Arg  Ala  Ser  Thr  Gly  Ala  Gly  Arg  Phe  Gly  Val  His  Pro
          3705                     3710                     3715

GCG  CTG  CTG  GAC  GCG  GCG  CTG  CAG  CCG  TGG  ATC  GCC  GGT  GGT  CTC  CTC     12017
Ala  Leu  Leu  Asp  Ala  Ala  Leu  Gln  Pro  Trp  Ile  Ala  Gly  Gly  Leu  Leu
          3720                     3725                     3730

GAA  GTG  CCG  GAG  GAC  GCA  GTG  CTG  CTG  CCC  TTC  GCC  TGG  CAG  GGA  GTG     12065
Glu  Val  Pro  Glu  Asp  Ala  Val  Leu  Leu  Pro  Phe  Ala  Trp  Gln  Gly  Val
3735                     3740                     3745                     3750

TCG  CTC  TAC  GCG  ACG  GGT  GCC  GGT  GCT  CTG  CGG  GTG  CGG  CTG  ACG  AAG     12113
Ser  Leu  Tyr  Ala  Thr  Gly  Ala  Gly  Ala  Leu  Arg  Val  Arg  Leu  Thr  Lys
                    3755                     3760                     3765

GCG  GGT  GAC  GGG  GCG  GTC  TCG  CTC  CAG  GCC  GCA  GAC  ACG  TCC  GGC  GCG     12161
Ala  Gly  Asp  Gly  Ala  Val  Ser  Leu  Gln  Ala  Ala  Asp  Thr  Ser  Gly  Ala
               3770                     3775                     3780

GCC  GTG  CTC  TCC  TTG  GGG  GCC  CTG  GTG  ATG  CGT  CCG  CTG  GCG  CGC  CGG     12209
Ala  Val  Leu  Ser  Leu  Gly  Ala  Leu  Val  Met  Arg  Pro  Leu  Ala  Arg  Arg
               3785                     3790                     3795

AAG  CTG  GAC  GTG  CTG  CTC  GGC  ACG  GAC  GCC  GGC  GAA  CGG  TCG  CTG  TAC     12257
Lys  Leu  Asp  Val  Leu  Leu  Gly  Thr  Asp  Ala  Gly  Glu  Arg  Ser  Leu  Tyr
3800                     3805                     3810

CGC  GTC  GAG  TGG  CAG  CCG  CGG  CTC  CTG  CCC  GCC  GGC  CCG  CCG  CGC  TCC     12305
Arg  Val  Glu  Trp  Gln  Pro  Arg  Leu  Leu  Pro  Ala  Gly  Pro  Pro  Arg  Ser
3815                     3820                     3825                     3830

TGG  GCG  GTG  CTC  GGC  CCC  GAC  GCG  GAC  CGG  CTC  GCC  GGG  ACG  CCG  GGC     12353
Trp  Ala  Val  Leu  Gly  Pro  Asp  Ala  Asp  Arg  Leu  Ala  Gly  Thr  Pro  Gly
                    3835                     3840                     3845

CTG  GGG  GAT  CAG  CCG  GAC  GGT  GGG  CCC  ACC  GCG  CTG  TAC  CCG  GAG  GTG     12401
Leu  Gly  Asp  Gln  Pro  Asp  Gly  Gly  Pro  Thr  Ala  Leu  Tyr  Pro  Glu  Val
               3850                     3855                     3860

CGG  GCG  CTG  CGG  AAG  GCG  CTG  GCG  GCG  GGC  GCG  CCG  CGG  CCG  GAA  GCG     12449
Arg  Ala  Leu  Arg  Lys  Ala  Leu  Ala  Ala  Gly  Ala  Pro  Arg  Pro  Glu  Ala
                    3865                     3870                     3875

GTC  GTA  CTG  CCG  GTG  CTC  TCC  GGG  GCC  GGG  GCC  ACT  CCG  GAG  TCG  GTG     12497
Val  Val  Leu  Pro  Val  Leu  Ser  Gly  Ala  Gly  Ala  Thr  Pro  Glu  Ser  Val
```

-continued

```
           3880                         3885                         3890
CGG   CAG   ACA   ACG   GAG   CGC   TGT   CTG   ACC   GCG   CTC   CAG   GAC   TGG   CTG   GAC        12545
Arg   Gln   Thr   Thr   Glu   Arg   Cys   Leu   Thr   Ala   Leu   Gln   Asp   Trp   Leu   Asp
3895                    3900                          3905                          3910

GCC   GAG   GAG   TTG   GTG   GAC   ACA   CCG   CTC   ATA   GTG   CTC   ACC   AGG   GGA   GCC        12593
Ala   Glu   Glu   Leu   Val   Asp   Thr   Pro   Leu   Ile   Val   Leu   Thr   Arg   Gly   Ala
                        3915                          3920                          3925

GTC   GCC   GCC   GTA   CCG   GGG   GAG   GAG   ATC   GGG   GAC   CTG   GCG   TGT   GCG   GGG        12641
Val   Ala   Ala   Val   Pro   Gly   Glu   Glu   Ile   Gly   Asp   Leu   Ala   Cys   Ala   Gly
            3930                          3935                          3940

GTG   TGG   GGC   CTG   GTG   AGG   TCC   GCG   CGG   TCC   GAG   CAC   CCG   GGC   CGC   TTC        12689
Val   Trp   Gly   Leu   Val   Arg   Ser   Ala   Arg   Ser   Glu   His   Pro   Gly   Arg   Phe
            3945                          3950                          3955

GCC   CTC   GTC   GAC   ACC   GAC   GGG   CAT   CCG   GAC   GAC   CGC   ACC   GCG   CTG   CCC        12737
Ala   Leu   Val   Asp   Thr   Asp   Gly   His   Pro   Asp   Asp   Arg   Thr   Ala   Leu   Pro
3960                                3965                          3970

CTC   GCG   CTG   CGC   GCG   GTC   CTC   GAC   GGC   GCC   GGC   CAG   CTC   TCC   CTG   CGG        12785
Leu   Ala   Leu   Arg   Ala   Val   Leu   Asp   Gly   Ala   Gly   Gln   Leu   Ser   Leu   Arg
3975                    3980                          3985                          3990

GCC   GGC   ACC   GCC   CGG   ACC   CCG   GTC   CTC   CTC   CGG   GCC   GGG   ACC   CCG   GAG        12833
Ala   Gly   Thr   Ala   Arg   Thr   Pro   Val   Leu   Leu   Arg   Ala   Gly   Thr   Pro   Glu
                        3995                          4000                          4005

GAG   CAG   CGG   GGT   CCG   GCA   TTC   GAC   CCG   GCG   GGC   ACG   GTC   CTG   GTG   ACG        12881
Glu   Gln   Arg   Gly   Pro   Ala   Phe   Asp   Pro   Ala   Gly   Thr   Val   Leu   Val   Thr
            4010                          4015                          4020

GGC   GCG   ACC   GGC   ACG   CTC   GGG   CGG   CTG   CTG   GCC   CGG   CAT   CTG   GCC   GCC        12929
Gly   Ala   Thr   Gly   Thr   Leu   Gly   Arg   Leu   Leu   Ala   Arg   His   Leu   Ala   Ala
            4025                          4030                          4035

GAG   CAC   GGT   GTG   CGC   CAT   CTG   CTG   CTG   CTG   AGC   CGC   GGC   GGC   CGG   GCT        12977
Glu   His   Gly   Val   Arg   His   Leu   Leu   Leu   Leu   Ser   Arg   Gly   Gly   Arg   Ala
            4040                          4045                          4050

GCC   GAA   GGC   GCG   GAC   GAA   CTC   GCC   GCG   GAA   CTG   GCC   GGG   TTG   GAA   GCC        13025
Ala   Glu   Gly   Ala   Asp   Glu   Leu   Ala   Ala   Glu   Leu   Ala   Gly   Leu   Glu   Ala
4055                          4060                          4065                          4070

GAG   CCG   TGC   TTC   GCG   GCC   TGT   GAC   GCG   GCG   GAC   CGC   GAG   GCC   CTG   GCA        13073
Glu   Pro   Cys   Phe   Ala   Ala   Cys   Asp   Ala   Ala   Asp   Arg   Glu   Ala   Leu   Ala
                        4075                          4080                          4085

CGG   GTG   CTG   GCG   GAG   GTG   CCG   GCC   GAC   CGG   CCG   CTG   ACC   GGA   GTG   ATC        13121
Arg   Val   Leu   Ala   Glu   Val   Pro   Ala   Asp   Arg   Pro   Leu   Thr   Gly   Val   Ile
            4090                          4095                          4100

CAC   GCG   GCC   GGG   GTG   CTC   GAC   GAC   GGC   ACA   CTC   GAC   GCG   CTG   ACC   CCG        13169
His   Ala   Ala   Gly   Val   Leu   Asp   Asp   Gly   Thr   Leu   Asp   Ala   Leu   Thr   Pro
            4105                          4110                          4115

GAA   CGG   ATC   GGT   ACC   GTC   ATG   CGG   CCG   AAG   GCG   GAC   GCG   GCG   CTG   AAC        13217
Glu   Arg   Ile   Gly   Thr   Val   Met   Arg   Pro   Lys   Ala   Asp   Ala   Ala   Leu   Asn
4120                          4125                          4130

CTG   CAC   GAA   CTG   ACC   CGG   ACC   AGC   CCG   CTG   TCG   GTG   TTC   GCG   GTC   TTC        13265
Leu   His   Glu   Leu   Thr   Arg   Thr   Ser   Pro   Leu   Ser   Val   Phe   Ala   Val   Phe
4135                    4140                          4145                          4150

TCG   GGC   GCT   GCC   GGC   ATC   CTG   GGC   CGC   CCC   GGA   CAG   GCC   AAC   TAC   GCC        13313
Ser   Gly   Ala   Ala   Gly   Ile   Leu   Gly   Arg   Pro   Gly   Gln   Ala   Asn   Tyr   Ala
                        4155                          4160                          4165

GCC   GCC   AAC   ACC   TTC   CTC   GAC   GCG   CTC   GCG   CAG   CAC   CGC   CGC   GCC   CAC        13361
Ala   Ala   Asn   Thr   Phe   Leu   Asp   Ala   Leu   Ala   Gln   His   Arg   Arg   Ala   His
                        4170                          4175                          4180

GGC   CTC   CCC   GCC   GTG   TCG   CTG   GCC   TGG   GGG   CTG   TGG   GGC   GGG   GCG   ACC        13409
Gly   Leu   Pro   Ala   Val   Ser   Leu   Ala   Trp   Gly   Leu   Trp   Gly   Gly   Ala   Thr
            4185                          4190                          4195

GGC   ATG   ACC   GGC   CAT   CTG   TCC   GGC   ACC   GAT   CTG   CGC   CGG   ATG   CGC   AGG        13457
Gly   Met   Thr   Gly   His   Leu   Ser   Gly   Thr   Asp   Leu   Arg   Arg   Met   Arg   Arg
```

|     |     |     |     |     |     |     |     |     |     |     |     |     |     |     |     |       |
|-----|-----|-----|-----|-----|-----|-----|-----|-----|-----|-----|-----|-----|-----|-----|-----|-------|
|     |     | 4200|     |     |     |     | 4205|     |     |     |     |     | 4210|     |     |       |
| TCC | GGT | ATC | GCG | CCG | ATG | ACC | CAC | GAC | CAG | GGG | CTC | GCC | CTG | TTC | GAC | 13505 |
| Ser | Gly | Ile | Ala | Pro | Met | Thr | His | Asp | Gln | Gly | Leu | Ala | Leu | Phe | Asp |       |
| 4215|     |     |     | 4220|     |     |     |     | 4225|     |     |     |     | 4230|     |       |
| CGA | GCG | CTC | GCC | GCC | TCG | GCC | GAG | GAC | CCG | CTG | CTC | GTA | CCG | ATG | CGG | 13553 |
| Arg | Ala | Leu | Ala | Ala | Ser | Ala | Glu | Asp | Pro | Leu | Leu | Val | Pro | Met | Arg |       |
|     |     |     |     | 4235|     |     |     |     | 4240|     |     |     |     | 4245|     |       |
| CTG | GAC | CTG | GCC | GCC | CTC | GTC | CGG | GAG | CGG | GCC | GAG | CAC | GGG | CCG | GAC | 13601 |
| Leu | Asp | Leu | Ala | Ala | Leu | Val | Arg | Glu | Arg | Ala | Glu | His | Gly | Pro | Asp |       |
|     |     |     | 4250|     |     |     |     | 4255|     |     |     |     | 4260|     |     |       |
| GCG | GTG | CCC | GGA | CCG | CTG | CTC | GGG | CTG | CTG | CCC | GCC | CGG | GCC | GCG | GTG | 13649 |
| Ala | Val | Pro | Gly | Pro | Leu | Leu | Gly | Leu | Leu | Pro | Ala | Arg | Ala | Ala | Val |       |
|     |     | 4265|     |     |     |     | 4270|     |     |     |     | 4275|     |     |     |       |
| CGG | CAG | GCG | GCG | GCA | CCG | GTA | CGC | GGC | GGA | GCC | CCC | GCC | CCC | GCC | GGC | 13697 |
| Arg | Gln | Ala | Ala | Ala | Pro | Val | Arg | Gly | Gly | Ala | Pro | Ala | Pro | Ala | Gly |       |
|     | 4280|     |     |     |     | 4285|     |     |     |     | 4290|     |     |     |     |       |
| GGC | GAG | GGG | ACG | GCC | GAG | CGG | CTG | GCC | GGG | CTC | GGG | GAG | GAG | GCC | AGG | 13745 |
| Gly | Glu | Gly | Thr | Ala | Glu | Arg | Leu | Ala | Gly | Leu | Gly | Glu | Glu | Ala | Arg |       |
| 4295|     |     |     | 4300|     |     |     |     | 4305|     |     |     |     | 4310|     |       |
| CTG | CGC | GAG | CTG | GTG | AGG | CTG | GTC | CGC | GCC | GAG | GTG | TCG | GGC | GTG | CTG | 13793 |
| Leu | Arg | Glu | Leu | Val | Arg | Leu | Val | Arg | Ala | Glu | Val | Ser | Gly | Val | Leu |       |
|     |     |     |     | 4315|     |     |     |     | 4320|     |     |     |     | 4325|     |       |
| GGC | TAC | TCG | GGC | CCG | GAC | GCG | GTG | GAG | CCC | GGG | CGC | CCG | TTC | AAG | GAT | 13841 |
| Gly | Tyr | Ser | Gly | Pro | Asp | Ala | Val | Glu | Pro | Gly | Arg | Pro | Phe | Lys | Asp |       |
|     |     |     | 4330|     |     |     |     | 4335|     |     |     |     | 4340|     |     |       |
| CTC | GGC | TTC | GAC | TCG | CTG | ACC | GCC | GTG | GAG | CTG | CGC | AAC | CGC | CTC | GGC | 13889 |
| Leu | Gly | Phe | Asp | Ser | Leu | Thr | Ala | Val | Glu | Leu | Arg | Asn | Arg | Leu | Gly |       |
|     |     |     |     | 4345|     |     |     |     | 4350|     |     |     |     | 4355|     |       |
| GCC | GCC | ACC | GGG | CTG | CGG | CTG | CCG | ACC | GCG | CTG | GTC | TTC | GAC | CGC | CCG | 13937 |
| Ala | Ala | Thr | Gly | Leu | Arg | Leu | Pro | Thr | Ala | Leu | Val | Phe | Asp | Arg | Pro |       |
|     |     |     | 4360|     |     |     |     | 4365|     |     |     |     | 4370|     |     |       |
| ACG | TCC | CAG | GCA | GTG | GCC | GAG | TAC | CTC | GCT | GCC | GAA | CTG | GCC | GGA | CCG | 13985 |
| Thr | Ser | Gln | Ala | Val | Ala | Glu | Tyr | Leu | Ala | Ala | Glu | Leu | Ala | Gly | Pro |       |
| 4375|     |     |     | 4380|     |     |     |     | 4385|     |     |     |     | 4390|     |       |
| CGG | GAC | GGC | GGC | GAC | ACC | GCG | GCC | GCC | GCG | TTC | GAG | GGC | CTG | GAG | GCG | 14033 |
| Arg | Asp | Gly | Gly | Asp | Thr | Ala | Ala | Ala | Ala | Phe | Glu | Gly | Leu | Glu | Ala |       |
|     |     |     |     | 4395|     |     |     |     | 4400|     |     |     |     | 4405|     |       |
| CTG | GCC | GCG | GCG | GTG | GGC | GCG | CTG | GCC | GAG | GAC | GAT | CTG | CGG | CGC | GAC | 14081 |
| Leu | Ala | Ala | Ala | Val | Gly | Ala | Leu | Ala | Glu | Asp | Asp | Leu | Arg | Arg | Asp |       |
|     |     |     | 4410|     |     |     |     | 4415|     |     |     |     | 4420|     |     |       |
| GTG | CTC | CGG | CGG | CGA | CTG | ACC | GAA | CTG | GCC | GCC | GCG | CTC | ACC | CCG | CAG | 14129 |
| Val | Leu | Arg | Arg | Arg | Leu | Thr | Glu | Leu | Ala | Ala | Ala | Leu | Thr | Pro | Gln |       |
|     |     | 4425|     |     |     |     | 4430|     |     |     |     | 4435|     |     |     |       |
| GGC | CGG | AAC | CCC | TCC | GCG | CCC | GCA | CCC | GCC | CCG | TCC | GAT | CTG | GAC | GAG | 14177 |
| Gly | Arg | Asn | Pro | Ser | Ala | Pro | Ala | Pro | Ala | Pro | Ser | Asp | Leu | Asp | Glu |       |
|     | 4440|     |     |     |     | 4445|     |     |     |     | 4450|     |     |     |     |       |
| CGG | CTG | GAC | TCC | GCG | AAC | GAC | GAC | GAC | CTC | TTC | GCC | TTC | ATC | GAG | GAG | 14225 |
| Arg | Leu | Asp | Ser | Ala | Asn | Asp | Asp | Asp | Leu | Phe | Ala | Phe | Ile | Glu | Glu |       |
| 4455|     |     |     | 4460|     |     |     |     | 4465|     |     |     |     | 4470|     |       |
| CAG | CTT | TGA | GCAGCGAGAA | CGACAGCAGC | GAGAACGACG | GCGACGACAC |     |     |     |     |     |     |     |     |     | 14274 |
| Gln | Leu |     |            |            |            |            |     |     |     |     |     |     |     |     |     |       |
| GGCCGGGGCA | GCTCCGGGGA | CGGCTCCGGG | GGCCTCCCCC | CGGCAGGACG | ACCGGGTCAG |     |     |     |     |     |     |     |     |     |     | 14334 |
| GGAGTATCTG | AAGCGG | GTG | ACC | GCC | GAA | CTG | GTC | GCC | ACC | CGC | AAG | CGG |     |     |     | 14383 |
|            |        | Met | Thr | Ala | Glu | Leu | Val | Ala | Thr | Arg | Lys | Arg |     |     |     |       |
|            |        | 1   |     |     | 5   |     |     |     |     |     | 10  |     |     |     |     |       |
| CTC | GGC | GCG | CTG | GAG | GAG | CGG | GCC | CGC | GAA | CCG | ATC | GCC | GTC | GTC | GCG | 14431 |
| Leu | Gly | Ala | Leu | Glu | Glu | Arg | Ala | Arg | Glu | Pro | Ile | Ala | Val | Val | Ala |       |
|     |     |     |     | 15  |     |     |     |     | 20  |     |     |     |     | 25  |     |       |
| ATG | AGC | TGC | CGC | TAC | CCG | GGC | GGG | GTG | ACG | ACC | CCC | GAG | GAC | CTG | TGG | 14479 |
| Met | Ser | Cys | Arg | Tyr | Pro | Gly | Gly | Val | Thr | Thr | Pro | Glu | Asp | Leu | Trp |       |

|  |  |  | 30 |  |  |  |  | 35 |  |  |  |  | 40 |  |  |  |
|---|---|---|---|---|---|---|---|---|---|---|---|---|---|---|---|---|
| CGG | CTT | CTC | GCG | GAC | GAA | CGC | GAC | GCC | GTA | TCC | GGA | CTT | CCC | CGG | GAC | 14527 |
| Arg | Leu | Leu | Ala | Asp | Glu | Arg | Asp | Ala | Val | Ser | Gly | Leu | Pro | Arg | Asp |  |
|  |  |  | 45 |  |  |  | 50 |  |  |  |  | 55 |  |  |  |  |
| CGC | GGC | TGG | GAC | CTG | GAC | GCC | CTC | TAC | GAC | CCC | GAC | GGC | GGC | CCC | GGC | 14575 |
| Arg | Gly | Trp | Asp | Leu | Asp | Ala | Leu | Tyr | Asp | Pro | Asp | Gly | Gly | Pro | Gly |  |
| 60 |  |  |  |  | 65 |  |  |  |  | 70 |  |  |  |  | 75 |  |
| ACC | AGC | TAC | GCC | CGC | GAA | GGC | GGC | TTC | CTG | AGC | CAC | TGC | GCC | GGA | TTC | 14623 |
| Thr | Ser | Tyr | Ala | Arg | Glu | Gly | Gly | Phe | Leu | Ser | His | Cys | Ala | Gly | Phe |  |
|  |  |  |  | 80 |  |  |  |  | 85 |  |  |  |  | 90 |  |  |
| GAC | GCG | GAG | TTC | TTC | GGC | ATC | TCC | CCG | CGC | GAG | GCG | CTG | GCG | ATG | GAC | 14671 |
| Asp | Ala | Glu | Phe | Phe | Gly | Ile | Ser | Pro | Arg | Glu | Ala | Leu | Ala | Met | Asp |  |
|  |  |  | 95 |  |  |  |  | 100 |  |  |  |  | 105 |  |  |  |
| CCG | CAG | CAG | CGG | CTG | CTG | CTG | GAG | ACC | TCC | TGG | GAG | GCC | CTG | GAA | CGC | 14719 |
| Pro | Gln | Gln | Arg | Leu | Leu | Leu | Glu | Thr | Ser | Trp | Glu | Ala | Leu | Glu | Arg |  |
|  |  | 110 |  |  |  |  | 115 |  |  |  |  | 120 |  |  |  |  |
| GCC | GGA | GTC | ACC | GCC | GAC | CGC | GCC | CGG | GGC | AGC | CGG | ACG | GGC | GTG | TAC | 14767 |
| Ala | Gly | Val | Thr | Ala | Asp | Arg | Ala | Arg | Gly | Ser | Arg | Thr | Gly | Val | Tyr |  |
|  | 125 |  |  |  |  | 130 |  |  |  |  | 135 |  |  |  |  |  |
| GCG | GGC | GTC | ATG | TAC | GAC | GAC | TAC | GGC | GCC | CGG | GTG | CTG | TAC | GGC | GCC | 14815 |
| Ala | Gly | Val | Met | Tyr | Asp | Asp | Tyr | Gly | Ala | Arg | Val | Leu | Tyr | Gly | Ala |  |
| 140 |  |  |  |  | 145 |  |  |  |  | 150 |  |  |  |  | 155 |  |
| GGC | GCC | GGC | CCG | CCC | GAG | GAC | CTG | GAG | GGT | TAT | CTC | GTC | AAC | GGC | AGC | 14863 |
| Gly | Ala | Gly | Pro | Pro | Glu | Asp | Leu | Glu | Gly | Tyr | Leu | Val | Asn | Gly | Ser |  |
|  |  |  |  | 160 |  |  |  |  | 165 |  |  |  |  | 170 |  |  |
| GCG | GGC | AGC | ATC | GCC | TCC | GGC | CGT | GTC | TCC | TAC | ACG | TTC | GGG | CTG | CGC | 14911 |
| Ala | Gly | Ser | Ile | Ala | Ser | Gly | Arg | Val | Ser | Tyr | Thr | Phe | Gly | Leu | Arg |  |
|  |  |  | 175 |  |  |  |  | 180 |  |  |  |  | 185 |  |  |  |
| GGC | CCC | GCG | GTC | ACC | GTC | AAT | ACG | GCC | TGT | TCG | TCG | TCA | CTG | GTG | TCG | 14959 |
| Gly | Pro | Ala | Val | Thr | Val | Asn | Thr | Ala | Cys | Ser | Ser | Ser | Leu | Val | Ser |  |
|  |  | 190 |  |  |  |  | 195 |  |  |  |  | 200 |  |  |  |  |
| CTC | CAT | CTG | GCG | GTG | CGT | GCC | CTG | CGG | AAC | GGC | GAG | TGC | GAC | ATG | GCA | 15007 |
| Leu | His | Leu | Ala | Val | Arg | Ala | Leu | Arg | Asn | Gly | Glu | Cys | Asp | Met | Ala |  |
| 205 |  |  |  |  | 210 |  |  |  |  | 215 |  |  |  |  |  |  |
| CTG | GCC | GGC | GGG | GCG | ACG | GTG | CTG | TCC | ACC | CCC | ACC | GTG | CTC | GTG | GAC | 15055 |
| Leu | Ala | Gly | Gly | Ala | Thr | Val | Leu | Ser | Thr | Pro | Thr | Val | Leu | Val | Asp |  |
| 220 |  |  |  |  | 225 |  |  |  |  | 230 |  |  |  |  | 235 |  |
| TTC | TCC | CGC | CAG | CGC | GGT | CTG | GCC | CCC | GAC | GGC | CGC | TGC | AAG | GCG | TTC | 15103 |
| Phe | Ser | Arg | Gln | Arg | Gly | Leu | Ala | Pro | Asp | Gly | Arg | Cys | Lys | Ala | Phe |  |
|  |  |  |  | 240 |  |  |  |  | 245 |  |  |  |  | 250 |  |  |
| GCC | GAC | TCC | GCC | GAC | GGC | ACC | TCC | TGG | GCC | GAG | GGC | GCC | GGA | ATG | CTG | 15151 |
| Ala | Asp | Ser | Ala | Asp | Gly | Thr | Ser | Trp | Ala | Glu | Gly | Ala | Gly | Met | Leu |  |
|  |  |  | 255 |  |  |  |  | 260 |  |  |  |  | 265 |  |  |  |
| CTG | CTC | CAG | CGG | CTG | TCC | GAC | GCC | CGC | CGC | GAG | GGG | CGC | CCC | GTG | CTG | 15199 |
| Leu | Leu | Gln | Arg | Leu | Ser | Asp | Ala | Arg | Arg | Glu | Gly | Arg | Pro | Val | Leu |  |
|  |  | 270 |  |  |  |  | 275 |  |  |  |  | 280 |  |  |  |  |
| GCC | GTC | ATT | CGC | GGC | TCG | GCC | GTC | AAC | CAG | GAC | GGC | GCC | AGC | AAC | GGA | 15247 |
| Ala | Val | Ile | Arg | Gly | Ser | Ala | Val | Asn | Gln | Asp | Gly | Ala | Ser | Asn | Gly |  |
|  | 285 |  |  |  |  | 290 |  |  |  |  | 295 |  |  |  |  |  |
| CTG | ACC | GCC | CCC | AAC | GGG | CGG | GCG | CAG | CGG | CAG | GTC | ATC | GAG | GAC | GCG | 15295 |
| Leu | Thr | Ala | Pro | Asn | Gly | Arg | Ala | Gln | Arg | Gln | Val | Ile | Glu | Asp | Ala |  |
| 300 |  |  |  |  | 305 |  |  |  |  | 310 |  |  |  |  | 315 |  |
| CTG | CGC | GAC | GCC | GGG | GTC | GGC | CCC | GAC | CAG | GTG | GAC | GCG | GTC | GAG | GCG | 15343 |
| Leu | Arg | Asp | Ala | Gly | Val | Gly | Pro | Asp | Gln | Val | Asp | Ala | Val | Glu | Ala |  |
|  |  |  |  | 320 |  |  |  |  | 325 |  |  |  |  | 330 |  |  |
| CAT | GGC | ACC | GGT | ACC | GAG | CTG | GGC | GAC | CCC | ATC | GAG | GCC | GGG | GCG | CTG | 15391 |
| His | Gly | Thr | Gly | Thr | Glu | Leu | Gly | Asp | Pro | Ile | Glu | Ala | Gly | Ala | Leu |  |
|  |  |  | 335 |  |  |  |  | 340 |  |  |  |  | 345 |  |  |  |
| CTC | GCC | ACC | TAT | GGA | ACG | GCC | CGT | ACG | GCG | GAG | CGC | CCG | CTG | TGG | CTC | 15439 |
| Leu | Ala | Thr | Tyr | Gly | Thr | Ala | Arg | Thr | Ala | Glu | Arg | Pro | Leu | Trp | Leu |  |

-continued

|   |   |   | 350 |   |   |   |   | 355 |   |   |   |   | 360 |   |   |       |
|---|---|---|---|---|---|---|---|---|---|---|---|---|---|---|---|---|
| GGC | TCC | CTG | AAG | TCC | AAC | ATC | GGG | CAC | ACC | CAG | GCC | GCC | GCC | GGT | GTT | 15487 |
| Gly | Ser | Leu | Lys | Ser | Asn | Ile | Gly | His | Thr | Gln | Ala | Ala | Ala | Gly | Val |  |
|  | 365 |  |  |  |  | 370 |  |  |  |  | 375 |  |  |  |  |  |
| GCG | GGC | GTC | ATC | AAG | ATG | GTG | CTG | GCG | ATG | CGG | CAC | GGC | CGG | CTG | CCC | 15535 |
| Ala | Gly | Val | Ile | Lys | Met | Val | Leu | Ala | Met | Arg | His | Gly | Arg | Leu | Pro |  |
| 380 |  |  |  |  | 385 |  |  |  |  | 390 |  |  |  |  | 395 |  |
| CGC | ACC | CTG | CAC | GTG | GAC | CGG | CCC | ACC | ACC | CGG | GTG | GAC | TGG | GAG | AAG | 15583 |
| Arg | Thr | Leu | His | Val | Asp | Arg | Pro | Thr | Thr | Arg | Val | Asp | Trp | Glu | Lys |  |
|  |  |  |  | 400 |  |  |  |  | 405 |  |  |  |  |  | 410 |  |
| GGC | GGG | GTG | CGG | CTC | CTC | ACG | GAG | CCG | GTG | CCA | TGG | CCG | GGG | GAA | GCG | 15631 |
| Gly | Gly | Val | Arg | Leu | Leu | Thr | Glu | Pro | Val | Pro | Trp | Pro | Gly | Glu | Ala |  |
|  |  |  | 415 |  |  |  |  | 420 |  |  |  |  | 425 |  |  |  |
| GGG | GAG | CCG | CGT | CGC | GCG | GGC | GTG | TCC | TCC | TTC | GGC | GCG | AGC | GGC | ACG | 15679 |
| Gly | Glu | Pro | Arg | Arg | Ala | Gly | Val | Ser | Ser | Phe | Gly | Ala | Ser | Gly | Thr |  |
|  |  | 430 |  |  |  |  |  | 435 |  |  |  |  |  | 440 |  |  |
| AAC | GCG | CAT | GTG | GTG | CTG | GAG | AGC | GTC | CCG | GCC | GGT | GAA | CCG | CCC | GCC | 15727 |
| Asn | Ala | His | Val | Val | Leu | Glu | Ser | Val | Pro | Ala | Gly | Glu | Pro | Pro | Ala |  |
|  | 445 |  |  |  |  | 450 |  |  |  |  | 455 |  |  |  |  |  |
| GCC | GGG | CGG | CCG | GAG | GAC | ACA | GGC | GGC | GCC | TGG | ACG | GTC | AGC | GGC | CGC | 15775 |
| Ala | Gly | Arg | Pro | Glu | Asp | Thr | Gly | Gly | Ala | Trp | Thr | Val | Ser | Gly | Arg |  |
| 460 |  |  |  |  | 465 |  |  |  |  | 470 |  |  |  |  | 475 |  |
| GGC | CCG | GCG | GCC | CTG | CGC | GCC | CAG | GCC | GCC | CGG | CTG | TAC | GAC | GCG | CTC | 15823 |
| Gly | Pro | Ala | Ala | Leu | Arg | Ala | Gln | Ala | Ala | Arg | Leu | Tyr | Asp | Ala | Leu |  |
|  |  |  |  | 480 |  |  |  |  | 485 |  |  |  |  |  | 490 |  |
| ACC | GGC | ACC | GGC | ACC | GGC | ACC | GGA | CAG | GGC | GCC | GGA | CAG | GGC | GCC | GGA | 15871 |
| Thr | Gly | Thr | Gly | Thr | Gly | Thr | Gly | Gln | Gly | Ala | Gly | Gln | Gly | Ala | Gly |  |
|  |  |  |  | 495 |  |  |  |  | 500 |  |  |  |  | 505 |  |  |
| CCC | GGC | ACC | GCC | GAG | GTG | GCC | GGC | GCG | CTG | GCC | CAC | GCC | CGT | ACC | GCG | 15919 |
| Pro | Gly | Thr | Ala | Glu | Val | Ala | Gly | Ala | Leu | Ala | His | Ala | Arg | Thr | Ala |  |
|  |  | 510 |  |  |  |  |  | 515 |  |  |  |  | 520 |  |  |  |
| TTC | CGG | CAC | CGG | GCC | GTC | GTG | CTC | GGC | GGA | AAC | CGC | GCC | GAA | CTG | CTC | 15967 |
| Phe | Arg | His | Arg | Ala | Val | Val | Leu | Gly | Gly | Asn | Arg | Ala | Glu | Leu | Leu |  |
|  | 525 |  |  |  |  | 530 |  |  |  |  | 535 |  |  |  |  |  |
| GCG | GGG | CTG | CGC | GAG | CTG | GCG | GAG | GAG | GAG | CAT | CCC | GGA | CCC | CGC | GTG | 16015 |
| Ala | Gly | Leu | Arg | Glu | Leu | Ala | Glu | Glu | Glu | His | Pro | Gly | Pro | Arg | Val |  |
| 540 |  |  |  |  | 545 |  |  |  |  | 550 |  |  |  |  | 555 |  |
| GTC | ACA | GGG | ACC | GCC | CCG | GCC | ACC | GAG | CGG | CGG | ACG | GCC | TTC | CTC | TTC | 16063 |
| Val | Thr | Gly | Thr | Ala | Pro | Ala | Thr | Glu | Arg | Arg | Thr | Ala | Phe | Leu | Phe |  |
|  |  |  |  | 560 |  |  |  |  | 565 |  |  |  |  |  | 570 |  |
| TCC | GGG | CAG | GGC | AGC | CAG | CGG | GCC | GGC | TCC | GGC | CGG | GGC | CTG | TAC | CGC | 16111 |
| Ser | Gly | Gln | Gly | Ser | Gln | Arg | Ala | Gly | Ser | Gly | Arg | Gly | Leu | Tyr | Arg |  |
|  |  |  | 575 |  |  |  |  | 580 |  |  |  |  | 585 |  |  |  |
| CGC | CAC | CCG | GTC | TTC | GCC | CGC | GCC | CTC | GAC | GAG | GTG | TGC | GCC | GCG | CTC | 16159 |
| Arg | His | Pro | Val | Phe | Ala | Arg | Ala | Leu | Asp | Glu | Val | Cys | Ala | Ala | Leu |  |
|  |  | 590 |  |  |  |  |  | 595 |  |  |  |  | 600 |  |  |  |
| GAA | CCG | CAT | CTT | CAC | CGC | CCC | CTG | CGT | GAC | CTG | ATG | TTC | GCC | GAG | CCC | 16207 |
| Glu | Pro | His | Leu | His | Arg | Pro | Leu | Arg | Asp | Leu | Met | Phe | Ala | Glu | Pro |  |
|  | 605 |  |  |  |  | 610 |  |  |  |  | 615 |  |  |  |  |  |
| GGC | AGC | CCG | GAA | GCG | GAG | CCG | CTC | GAC | CGC | ACC | GAG | TTC | ACC | CAG | CCC | 16255 |
| Gly | Ser | Pro | Glu | Ala | Glu | Pro | Leu | Asp | Arg | Thr | Glu | Phe | Thr | Gln | Pro |  |
| 620 |  |  |  |  | 625 |  |  |  |  | 630 |  |  |  |  | 635 |  |
| GCG | CTG | TTC | GCG | CTC | CAG | ACC | GCC | CTG | TTC | CGG | CTG | GCC | GAG | CAC | CAC | 16303 |
| Ala | Leu | Phe | Ala | Leu | Gln | Thr | Ala | Leu | Phe | Arg | Leu | Ala | Glu | His | His |  |
|  |  |  |  | 640 |  |  |  |  | 645 |  |  |  |  |  | 650 |  |
| GGG | CTG | CGC | GCC | GAG | GCG | CTG | TGC | GGG | CAC | AGC | GTC | GGC | GAG | ATC | GCG | 16351 |
| Gly | Leu | Arg | Ala | Glu | Ala | Leu | Cys | Gly | His | Ser | Val | Gly | Glu | Ile | Ala |  |
|  |  |  |  | 655 |  |  |  |  | 660 |  |  |  |  | 665 |  |  |
| GCC | GCC | CAT | GCC | GCC | GGT | GTG | CTG | ACC | CTG | CCC | GAC | GCG | GCC | CGT | CTG | 16399 |
| Ala | Ala | His | Ala | Ala | Gly | Val | Leu | Thr | Leu | Pro | Asp | Ala | Ala | Arg | Leu |  |

```
                     670                        675                         680
GTG  GCC  GCC  CGG  GGA  CGG  CTG  ATG  CAG  GCC  CTG  CCG  GCC  GGC  GGT  GCC    16447
Val  Ala  Ala  Arg  Gly  Arg  Leu  Met  Gln  Ala  Leu  Pro  Ala  Gly  Gly  Ala
     685                      690                     695

ATG  GCC  GCG  CTG  CGC  GCC  ACC  GCC  GAG  GAG  ATC  GCA  CCA  CTG  CTG  GAG    16495
Met  Ala  Ala  Leu  Arg  Ala  Thr  Ala  Glu  Glu  Ile  Ala  Pro  Leu  Leu  Glu
700                      705                     710                         715

CGC  CGC  GCG  GGC  GAA  CTG  GCG  CTC  GCC  GCC  GTC  AAC  GGC  CCC  TCC  TCG    16543
Arg  Arg  Ala  Gly  Glu  Leu  Ala  Leu  Ala  Ala  Val  Asn  Gly  Pro  Ser  Ser
                         720                     725                    730

GTG  GTG  GTG  TCG  GGC  GAC  GAG  GCC  GCC  GTC  CTG  GAG  CTA  CTG  GAG  CAG    16591
Val  Val  Val  Ser  Gly  Asp  Glu  Ala  Ala  Val  Leu  Glu  Leu  Leu  Glu  Gln
               735                     740                     745

TGG  CGG  GCC  GAG  GGC  CGC  GAG  GCC  AGG  CGG  CTC  GCC  GTC  AGC  CAT  GCC    16639
Trp  Arg  Ala  Glu  Gly  Arg  Glu  Ala  Arg  Arg  Leu  Ala  Val  Ser  His  Ala
          750                      755                     760

TTC  CAT  TCA  CCG  CGG  ATG  GAC  GGA  ATG  TTG  ACA  CAG  TTC  GAC  CGG  GTC    16687
Phe  His  Ser  Pro  Arg  Met  Asp  Gly  Met  Leu  Thr  Gln  Phe  Asp  Arg  Val
     765                     770                      775

GCT  CGC  ACC  CTG  ACG  TTC  GCT  CCG  CCG  ACC  ATT  CCC  CTC  GTG  TCC  ACC    16735
Ala  Arg  Thr  Leu  Thr  Phe  Ala  Pro  Pro  Thr  Ile  Pro  Leu  Val  Ser  Thr
780                      785                     790                          795

CTC  ACC  GGT  ACG  CCC  GTC  ACC  GAG  GAA  ACC  CTG  TGC  ACC  GCG  GAC  CAC    16783
Leu  Thr  Gly  Thr  Pro  Val  Thr  Glu  Glu  Thr  Leu  Cys  Thr  Ala  Asp  His
                         800                     805                     810

TGG  GTC  CGC  CAG  GCG  CGC  GAG  CCG  GTG  CGC  TTC  CTG  GAC  GCC  ATG  CGG    16831
Trp  Val  Arg  Gln  Ala  Arg  Glu  Pro  Val  Arg  Phe  Leu  Asp  Ala  Met  Arg
               815                     820                      825

ACC  CTG  CGC  GCC  GAC  GGG  ATC  GAC  ACC  TTC  GTG  GAA  CTC  GGC  CCC  GAC    16879
Thr  Leu  Arg  Ala  Asp  Gly  Ile  Asp  Thr  Phe  Val  Glu  Leu  Gly  Pro  Asp
               830                     835                          840

GGC  GTG  CTG  TCC  GCC  ATG  GCC  CGC  GAC  TGC  GCG  GAC  GAC  CGG  CCC  GAT    16927
Gly  Val  Leu  Ser  Ala  Met  Ala  Arg  Asp  Cys  Ala  Asp  Asp  Arg  Pro  Asp
     845                     850                      855

GGC  GAC  ACA  ACC  GGG  GCC  GGG  GAC  GGG  GAG  ACC  CCC  GAT  CCG  CTG  CTC    16975
Gly  Asp  Thr  Thr  Gly  Ala  Gly  Asp  Gly  Glu  Thr  Pro  Asp  Pro  Leu  Leu
860                          865                     870                      875

ACC  CTC  CCG  CTG  CTG  CGC  CGC  TCC  GTG  CCC  GAG  ACC  GGC  GAC  GCC  GAA    17023
Thr  Leu  Pro  Leu  Leu  Arg  Arg  Ser  Val  Pro  Glu  Thr  Gly  Asp  Ala  Glu
                         880                     885                          890

CAC  CCC  GGC  GGC  TTC  GAA  CGG  GCC  CTG  GCC  ACC  GCC  TAC  GCA  CAC  GGC    17071
His  Pro  Gly  Gly  Phe  Glu  Arg  Ala  Leu  Ala  Thr  Ala  Tyr  Ala  His  Gly
                    895                          900                     905

GTC  CCC  CTG  CGG  CTC  GCG  CCC  GCC  CCC  GAC  GCC  GCG  TCC  CTC  GCC  GTG    17119
Val  Pro  Leu  Arg  Leu  Ala  Pro  Ala  Pro  Asp  Ala  Ala  Ser  Leu  Ala  Val
               910                     915                          920

GCC  GCC  GAA  CTG  CCC  ACC  TAC  GCC  TTC  CAG  CGC  ACC  CAC  TAC  TGG  CTC    17167
Ala  Ala  Glu  Leu  Pro  Thr  Tyr  Ala  Phe  Gln  Arg  Thr  His  Tyr  Trp  Leu
     925                     930                      935

GAC  GCG  CCC  GCC  GCC  CCC  GCC  GCC  CTC  CCC  GCC  GGG  CTC  GAC  GAC  GCC    17215
Asp  Ala  Pro  Ala  Ala  Pro  Ala  Ala  Leu  Pro  Ala  Gly  Leu  Asp  Asp  Ala
940                      945                      950                         955

GGT  CAC  CCG  CTG  CTC  TCC  GCG  GCC  CTC  GAC  CTG  CCC  GGC  GGA  CGC  GGA    17263
Gly  His  Pro  Leu  Leu  Ser  Ala  Ala  Leu  Asp  Leu  Pro  Gly  Gly  Arg  Gly
                         960                     965                     970

ACG  GTG  TGG  ACC  GGA  GCG  CTC  TCC  GCC  GCC  ACC  CTG  CCC  TGG  GCC  GCG    17311
Thr  Val  Trp  Thr  Gly  Ala  Leu  Ser  Ala  Ala  Thr  Leu  Pro  Trp  Ala  Ala
               975                     980                      985

GAC  CAC  AGC  GTG  CAC  GGC  CGC  ACC  GTC  CTG  CCG  GGC  ACC  GCC  CTG  CTC    17359
Asp  His  Ser  Val  His  Gly  Arg  Thr  Val  Leu  Pro  Gly  Thr  Ala  Leu  Leu
```

-continued

```
              990                           995                                  1000
GAC  CTG  GCG  CTC  CAC  GCC  GCC  CCG  CGC  GTC  GGC  GAG  TTG  ACC  TTC  GAG         17407
Asp  Leu  Ala  Leu  His  Ala  Ala  Pro  Arg  Val  Gly  Glu  Leu  Thr  Phe  Glu
               1005                          1010                      1015

GCG  CCG  CTG  GTG  CTG  CCG  GAG  GAC  GGA  GAG  GTC  CGG  CTG  CGC  GTC  GTA         17455
Ala  Pro  Leu  Val  Leu  Pro  Glu  Asp  Gly  Glu  Val  Arg  Leu  Arg  Val  Val
1020                          1025                      1030                      1035

CTC  GCT  GAA  CCG  GAC  GCG  AGC  GGA  GTA  CGC  GAA  CTG  TCT  GTC  CAC  TCC         17503
Leu  Ala  Glu  Pro  Asp  Ala  Ser  Gly  Val  Arg  Glu  Leu  Ser  Val  His  Ser
               1040                          1045                      1050

GCC  GGC  GAG  GAC  GGC  GGC  TGG  ACC  CGG  CAC  GCG  ACA  GCG  GTC  CTG  GAC         17551
Ala  Gly  Glu  Asp  Gly  Gly  Trp  Thr  Arg  His  Ala  Thr  Ala  Val  Leu  Asp
               1055                          1060                      1065

ACC  GGC  ACC  ACC  ACC  GCC  GGG  GAG  CCC  GCC  GGC  GCA  CCG  CCC  GCC  GCA         17599
Thr  Gly  Thr  Thr  Thr  Ala  Gly  Glu  Pro  Ala  Gly  Ala  Pro  Pro  Ala  Ala
               1070                          1075                      1080

TGG  CCG  CCC  GGG  GAC  GCC  GAA  CCC  CTC  GAC  CTT  GCC  GCC  GAG  TAC  GAG         17647
Trp  Pro  Pro  Gly  Asp  Ala  Glu  Pro  Leu  Asp  Leu  Ala  Ala  Glu  Tyr  Glu
               1085                          1090                      1095

CGC  TTC  GCC  GAC  GCC  GGC  ATC  GGA  TAC  GGC  CCC  GCC  TTC  CGC  GGA  CTG         17695
Arg  Phe  Ala  Asp  Ala  Gly  Ile  Gly  Tyr  Gly  Pro  Ala  Phe  Arg  Gly  Leu
1100                          1105                      1110                      1115

CGC  TCC  GCC  TGG  CGC  GAC  GGC  GAC  GCG  ATA  CTG  GCC  GAC  GTA  CGG  CTG         17743
Arg  Ser  Ala  Trp  Arg  Asp  Gly  Asp  Ala  Ile  Leu  Ala  Asp  Val  Arg  Leu
               1120                          1125                      1130

CCC  GGC  GAA  CTG  GCC  GGC  GAA  GCC  GAC  CGG  TAC  GGC  ATC  CAC  CCG  GCC         17791
Pro  Gly  Glu  Leu  Ala  Gly  Glu  Ala  Asp  Arg  Tyr  Gly  Ile  His  Pro  Ala
               1135                          1140                      1145

CTG  CTC  GAC  GCC  GCC  CTG  CAC  ACC  GCG  GCC  GCC  GCC  CTG  GGA  GGG  GCG         17839
Leu  Leu  Asp  Ala  Ala  Leu  His  Thr  Ala  Ala  Ala  Ala  Leu  Gly  Gly  Ala
               1150                          1155                      1160

CAC  GGG  ATG  CTG  CCG  TTC  ACG  TGG  AAC  GGC  GTC  ACC  CTC  CAC  GCC  CGC         17887
His  Gly  Met  Leu  Pro  Phe  Thr  Trp  Asn  Gly  Val  Thr  Leu  His  Ala  Arg
               1165                          1170                      1175

GGA  GCG  CAC  GCC  ATC  CGG  GTG  CGG  CTG  ACC  CCG  GCC  GGC  CCC  GAC  GCG         17935
Gly  Ala  His  Ala  Ile  Arg  Val  Arg  Leu  Thr  Pro  Ala  Gly  Pro  Asp  Ala
1180                          1185                      1190                      1195

GTC  GCG  GTC  ACC  GCC  GTG  GAC  CCG  GCG  GGG  CGC  CCC  GTG  TTC  ACG  GCC         17983
Val  Ala  Val  Thr  Ala  Val  Asp  Pro  Ala  Gly  Arg  Pro  Val  Phe  Thr  Ala
               1200                          1205                      1210

GCC  TCG  CTC  ACC  CTG  CGA  CCG  GTC  ACG  ACC  GGG  CAG  CTG  ACC  GCG  GCC         18031
Ala  Ser  Leu  Thr  Leu  Arg  Pro  Val  Thr  Thr  Gly  Gln  Leu  Thr  Ala  Ala
               1215                          1220                      1225

GAG  GCC  GCG  CGG  GCC  CCG  CTG  TAC  CGG  GTG  CGC  TGG  ACC  GGC  CTC  CCG         18079
Glu  Ala  Ala  Arg  Ala  Pro  Leu  Tyr  Arg  Val  Arg  Trp  Thr  Gly  Leu  Pro
               1230                          1235                      1240

GAC  ACC  GGA  ACC  GCC  CGG  GAC  CAC  ACC  TGG  GCG  GTG  GCC  GGC  GGC  CCG         18127
Asp  Thr  Gly  Thr  Ala  Arg  Asp  His  Thr  Trp  Ala  Val  Ala  Gly  Gly  Pro
               1245                          1250                      1255

GGC  GAC  CTG  TTA  CCC  GGG  GAG  ACC  CCG  CAC  CAC  CCC  GAC  CTC  GCC  TCC         18175
Gly  Asp  Leu  Leu  Pro  Gly  Glu  Thr  Pro  His  His  Pro  Asp  Leu  Ala  Ser
1260                          1265                      1270                      1275

GCG  CTC  GCC  GAC  ACC  GGC  ACC  GCC  CCC  TTC  CGC  GTA  CTG  GCG  GAT  CTG         18223
Ala  Leu  Ala  Asp  Thr  Gly  Thr  Ala  Pro  Phe  Arg  Val  Leu  Ala  Asp  Leu
               1280                          1285                      1290

CGC  GGA  TAC  GGC  ACC  GCC  ACC  CCC  CGG  GAA  CTC  GCC  TCC  CAG  GCG  CTC         18271
Arg  Gly  Tyr  Gly  Thr  Ala  Thr  Pro  Arg  Glu  Leu  Ala  Ser  Gln  Ala  Leu
               1295                          1300                      1305

GCC  CTC  GTC  CAG  CAG  TGG  GCC  GAC  GCG  GCC  GAG  GCC  GCC  GAA  GGC  AGG         18319
Ala  Leu  Val  Gln  Gln  Trp  Ala  Asp  Ala  Ala  Glu  Ala  Ala  Glu  Gly  Arg
```

```
              1310                         1315                           1320
CTC  GTC  CTG  GTG  ACA  CGC  CGG  GCC  GTC  GAC  ATC  GGT  GAC  GGC  GTC  ACG      18367
Leu  Val  Leu  Val  Thr  Arg  Arg  Ala  Val  Asp  Ile  Gly  Asp  Gly  Val  Thr
               1325                    1330                         1335

GAC  CCG  GCG  GCG  GCG  ACC  GTG  TGG  GGA  CTG  GTC  CGG  GCG  GCA  CAG  TCC      18415
Asp  Pro  Ala  Ala  Ala  Thr  Val  Trp  Gly  Leu  Val  Arg  Ala  Ala  Gln  Ser
1340                         1345                    1350                    1355

GAG  CAC  CCC  GGG  TGC  TTC  GCG  CTC  CTC  GAC  ACC  GAC  GAC  TCC  CCC  CGC      18463
Glu  His  Pro  Gly  Cys  Phe  Ala  Leu  Leu  Asp  Thr  Asp  Asp  Ser  Pro  Arg
                         1360                    1365                    1370

TCC  CGG  CAA  CTC  CTG  CCA  CGC  GTC  GCG  GGC  ACC  GCC  GAG  CAG  CTC  GCA      18511
Ser  Arg  Gln  Leu  Leu  Pro  Arg  Val  Ala  Gly  Thr  Ala  Glu  Gln  Leu  Ala
               1375                    1380                         1385

CTC  CGC  GAC  GGC  ACC  CTG  CTC  GCC  CCC  TCC  CTC  ACC  CGT  GCC  ACG  CTG      18559
Leu  Arg  Asp  Gly  Thr  Leu  Leu  Ala  Pro  Ser  Leu  Thr  Arg  Ala  Thr  Leu
               1390                    1395                         1400

CCC  GCC  GGC  GCC  CGG  CTG  CCC  GCA  CTC  GAC  GGC  ACC  GTC  CTG  ATC  ACT      18607
Pro  Ala  Gly  Ala  Arg  Leu  Pro  Ala  Leu  Asp  Gly  Thr  Val  Leu  Ile  Thr
               1405                    1410                         1415

GGG  GGC  ACC  GGC  AGC  CTC  GGC  GCG  GAG  GCG  GCC  CGC  CAT  CTG  GTC  ACC      18655
Gly  Gly  Thr  Gly  Ser  Leu  Gly  Ala  Glu  Ala  Ala  Arg  His  Leu  Val  Thr
1420                         1425                    1430                    1435

CGG  CAC  GGT  GCC  CGG  CGC  CTG  CTC  CTG  ACC  AGC  CGA  AGC  GGC  CCG  CAG      18703
Arg  His  Gly  Ala  Arg  Arg  Leu  Leu  Leu  Thr  Ser  Arg  Ser  Gly  Pro  Gln
                         1440                    1445                    1450

GCC  CCC  GGC  GCG  GCC  GAA  CTC  GTC  GCC  GAA  CTG  GCC  GCC  TTG  GGC  GCC      18751
Ala  Pro  Gly  Ala  Ala  Glu  Leu  Val  Ala  Glu  Leu  Ala  Ala  Leu  Gly  Ala
               1455                    1460                         1465

CAC  GCG  GAC  GTG  GCC  GCC  TGC  GAC  GTC  GCC  GAC  CGC  GCC  GCC  CTG  CGG      18799
His  Ala  Asp  Val  Ala  Ala  Cys  Asp  Val  Ala  Asp  Arg  Ala  Ala  Leu  Arg
               1470                    1475                         1480

GCC  CTG  CTC  GAC  CGC  GTA  CCC  GCC  GGC  CAC  CCG  CTG  ACC  GCG  GTC  CTG      18847
Ala  Leu  Leu  Asp  Arg  Val  Pro  Ala  Gly  His  Pro  Leu  Thr  Ala  Val  Leu
               1485                    1490                         1495

CAC  ACG  GCG  GGC  GTC  CTG  GAC  GAC  GGC  GTC  CTC  ACC  GCC  CAG  ACA  CCG      18895
His  Thr  Ala  Gly  Val  Leu  Asp  Asp  Gly  Val  Leu  Thr  Ala  Gln  Thr  Pro
1500                         1505                    1510                    1515

CAG  CGG  CTC  GCG  GCC  GTC  CTC  CGC  CCG  AAG  GCC  GAC  GCC  GTA  CGC  AAT      18943
Gln  Arg  Leu  Ala  Ala  Val  Leu  Arg  Pro  Lys  Ala  Asp  Ala  Val  Arg  Asn
               1520                    1525                         1530

CTG  CAC  GAA  CTC  ACC  CAG  GGG  CAC  GCC  CTG  TCG  GCG  TTC  ATC  CTC  TAC      18991
Leu  His  Glu  Leu  Thr  Gln  Gly  His  Ala  Leu  Ser  Ala  Phe  Ile  Leu  Tyr
                    1535                    1540                    1545

TCG  TCG  GCC  GCC  GGA  GTG  CTC  GGC  AGC  GCG  GGC  CAG  AGC  GGC  TAC  GCC      19039
Ser  Ser  Ala  Ala  Gly  Val  Leu  Gly  Ser  Ala  Gly  Gln  Ser  Gly  Tyr  Ala
               1550                    1555                         1560

GCC  GCC  AAC  GCC  TAC  CTG  GAC  TCC  TTC  GCC  GTC  TGG  CGG  CGG  AGC  CGG      19087
Ala  Ala  Asn  Ala  Tyr  Leu  Asp  Ser  Phe  Ala  Val  Trp  Arg  Arg  Ser  Arg
               1565                    1570                         1575

GGA  CTG  CCC  GCC  GTA  TCG  CTC  GGC  TGG  GGC  CCG  TGG  GAC  GGC  GGC  GGC      19135
Gly  Leu  Pro  Ala  Val  Ser  Leu  Gly  Trp  Gly  Pro  Trp  Asp  Gly  Gly  Gly
1580                         1585                    1590                    1595

ATG  GCG  AGC  GGA  CTC  GGC  GGA  ACC  GAC  ACG  GCC  CGG  CTG  CGG  CGC  AGC      19183
Met  Ala  Ser  Gly  Leu  Gly  Gly  Thr  Asp  Thr  Ala  Arg  Leu  Arg  Arg  Ser
                         1600                    1605                    1610

GGC  ATC  GCA  CCC  CTC  AGC  CGC  GCC  GAG  GGC  CTG  GCC  GCG  CTC  GAC  GCG      19231
Gly  Ile  Ala  Pro  Leu  Ser  Arg  Ala  Glu  Gly  Leu  Ala  Ala  Leu  Asp  Ala
               1615                    1620                         1625

GCG  CTC  GCG  GCC  GGC  GGC  GAC  GAC  ACC  GCG  CCG  GCC  CAC  CTG  CTG  CCG      19279
Ala  Leu  Ala  Ala  Gly  Gly  Asp  Asp  Thr  Ala  Pro  Ala  His  Leu  Leu  Pro
```

```
             1630                      1635                      1640
ATC  CGC  GTC  GAC  GCG  GTG  ACC  CTG  CGC  GGC  GCC  GAC  ACC  GTC  CCC  GCC    19327
Ile  Arg  Val  Asp  Ala  Val  Thr  Leu  Arg  Gly  Ala  Asp  Thr  Val  Pro  Ala
     1645                     1650                     1655

GTG  CTG  CGC  GAC  CTG  GCG  GGA  ACC  GCG  CCA  AGC  GCC  GCC  GAA  CGG  CCC    19375
Val  Leu  Arg  Asp  Leu  Ala  Gly  Thr  Ala  Pro  Ser  Ala  Ala  Glu  Arg  Pro
1660                     1665                     1670                     1675

CCC  GGG  ACA  CCG  GAG  GAC  ACG  AAC  GCG  CCC  CTG  GCG  GAC  GTC  ACC  CAA    19423
Pro  Gly  Thr  Pro  Glu  Asp  Thr  Asn  Ala  Pro  Leu  Ala  Asp  Val  Thr  Gln
               1680                     1685                     1690

CTG  CAC  GGC  CGG  GAA  CGG  AAG  GAG  GCA  CTG  ACC  GGC  TTC  GTA  CGC  GCC    19471
Leu  His  Gly  Arg  Glu  Arg  Lys  Glu  Ala  Leu  Thr  Gly  Phe  Val  Arg  Ala
          1695                     1700                     1705

CAG  GTG  GCC  GCG  GTG  CTC  GGC  CAC  CCC  ACG  TCC  GAC  ACG  ATC  GAC  GTC    19519
Gln  Val  Ala  Ala  Val  Leu  Gly  His  Pro  Thr  Ser  Asp  Thr  Ile  Asp  Val
     1710                     1715                     1720

CGC  CGG  AGC  TTC  AAG  GAA  GCG  GGC  TTC  GAC  TCC  CTC  ACC  GCC  GTC  GAA    19567
Arg  Arg  Ser  Phe  Lys  Glu  Ala  Gly  Phe  Asp  Ser  Leu  Thr  Ala  Val  Glu
1725                     1730                     1735

CTG  CGC  AAC  CGG  CTG  CGC  GCC  GCC  ACC  GGG  CTG  AAG  CTG  CCC  GCC  ACG    19615
Leu  Arg  Asn  Arg  Leu  Arg  Ala  Ala  Thr  Gly  Leu  Lys  Leu  Pro  Ala  Thr
1740                     1745                     1750                     1755

CTG  GTG  TTC  GAC  CAC  CCG  ACC  CCC  CTC  GCG  CTC  GCC  GGC  TTC  CTC  CAC    19663
Leu  Val  Phe  Asp  His  Pro  Thr  Pro  Leu  Ala  Leu  Ala  Gly  Phe  Leu  His
               1760                     1765                     1770

CGC  GAA  CTC  CCC  GGC  GCC  GAA  GCC  TCC  CTG  ATG  AGC  GCG  ATC  GAC  ACT    19711
Arg  Glu  Leu  Pro  Gly  Ala  Glu  Ala  Ser  Leu  Met  Ser  Ala  Ile  Asp  Thr
          1775                     1780                     1785

CTC  CGG  CAC  CGG  CTG  CGC  GAC  GCC  CTG  GCC  GAC  GAC  GCC  GCA  GAC  GAC    19759
Leu  Arg  His  Arg  Leu  Arg  Asp  Ala  Leu  Ala  Asp  Asp  Ala  Ala  Asp  Asp
     1790                     1795                     1800

GCC  CTG  CGC  GAC  CAG  ATC  ACC  CGA  CGA  CTC  GAG  ACC  CTG  CTG  GCC  GGC    19807
Ala  Leu  Arg  Asp  Gln  Ile  Thr  Arg  Arg  Leu  Glu  Thr  Leu  Leu  Ala  Gly
          1805                     1810                     1815

ATA  GCC  CGG  ACC  GAG  GAG  CCC  GCG  CCC  GCC  ACC  GCC  GCC  GCC  GAC  GAC    19855
Ile  Ala  Arg  Thr  Glu  Glu  Pro  Ala  Pro  Ala  Thr  Ala  Ala  Ala  Asp  Asp
1820                     1825                     1830                     1835

GGG  AGC  GGA  GCC  GGT  GAT  GTC  GCG  GAA  CGA  CTG  AGC  ACC  GCG  TCG  GAC    19903
Gly  Ser  Gly  Ala  Gly  Asp  Val  Ala  Glu  Arg  Leu  Ser  Thr  Ala  Ser  Asp
               1840                     1845                     1850

GAC  GAA  CTG  TTC  GAA  CTG  CTC  GAC  AGC  GGT  TTC  ACA  CCC  TGA  CCGGCCGGCG  19955
Asp  Glu  Leu  Phe  Glu  Leu  Leu  Asp  Ser  Gly  Phe  Thr  Pro
          1855                     1860

GACCGGCACC  ACGACATCGA  GGCGACCGCA  CCGAACACCC  CCAGGGGGAA  AGCT               20009

GTG  TCC  ACC  GAG  AAC  TCC  ACC  AAC  GTC  CCG  GCG  AGC  GAG                   20048
Met  Ser  Thr  Glu  Asn  Ser  Thr  Asn  Val  Pro  Ala  Ser  Glu
1                        5                        10

GAC  AAG  CTC  CGC  GCC  TAT  CTG  CGT  CGC  GCG  ATG  GCC  GAC  CTC  CAC  GAG    20096
Asp  Lys  Leu  Arg  Ala  Tyr  Leu  Arg  Arg  Ala  Met  Ala  Asp  Leu  His  Glu
     15                       20                       25

TCC  CGC  GAA  CGG  CTC  CGC  GCC  ACG  GAA  GCG  CGC  GCC  CAG  GAG  CCG  ATC    20144
Ser  Arg  Glu  Arg  Leu  Arg  Ala  Thr  Glu  Ala  Arg  Ala  Gln  Glu  Pro  Ile
30                       35                       40                       45

GCG  GTG  GTG  GGT  ATG  GGG  TGC  CGG  TTC  CCC  GGT  GGG  GTG  GGT  TCG  CCG    20192
Ala  Val  Val  Gly  Met  Gly  Cys  Arg  Phe  Pro  Gly  Gly  Val  Gly  Ser  Pro
               50                       55                       60

GAG  GCG  TTG  TGG  CGG  TTG  GTG  GTG  GAG  GGG  GTG  GAC  GCG  GTT  TCC  CCG    20240
Glu  Ala  Leu  Trp  Arg  Leu  Val  Val  Glu  Gly  Val  Asp  Ala  Val  Ser  Pro
          65                       70                       75
```

| | | | | | | | | | | | | | | | | |
|---|---|---|---|---|---|---|---|---|---|---|---|---|---|---|---|---|
| TTT | CCC | GGT | GAT | CGT | GGC | TGG | GAT | GTG | GAG | GGG | TTG | TAC | GAC | CCG | GAG | 20288 |
| Phe | Pro | Gly | Asp | Arg | Gly | Trp | Asp | Val | Glu | Gly | Leu | Tyr | Asp | Pro | Glu | |
| | | 80 | | | | 85 | | | | 90 | | | | | | |
| CCG | GGT | GTG | GCG | GGG | AAG | TCG | TAT | GTG | CGG | GAG | GGG | GGT | TTT | CTG | CAT | 20336 |
| Pro | Gly | Val | Ala | Gly | Lys | Ser | Tyr | Val | Arg | Glu | Gly | Gly | Phe | Leu | His | |
| | 95 | | | | | 100 | | | | 105 | | | | | | |
| GAT | GCG | GCG | GAG | TTC | GAT | GCG | GAG | TTC | TTC | GGG | ATT | TCG | CCG | CGT | GAG | 20384 |
| Asp | Ala | Ala | Glu | Phe | Asp | Ala | Glu | Phe | Phe | Gly | Ile | Ser | Pro | Arg | Glu | |
| 110 | | | | | 115 | | | | 120 | | | | | | 125 | |
| GCG | GTG | GCG | ATG | GAT | CCG | CAG | CAG | CGG | CTG | TTG | CTG | GAG | ACC | TCC | TGG | 20432 |
| Ala | Val | Ala | Met | Asp | Pro | Gln | Gln | Arg | Leu | Leu | Leu | Glu | Thr | Ser | Trp | |
| | | | | 130 | | | | | 135 | | | | | 140 | | |
| GAG | GCG | ATC | GAG | CGG | GCG | GGT | ATC | GAC | CCG | CAT | TCG | CTG | CAC | GGC | AGC | 20480 |
| Glu | Ala | Ile | Glu | Arg | Ala | Gly | Ile | Asp | Pro | His | Ser | Leu | His | Gly | Ser | |
| | | | 145 | | | | | 150 | | | | | 155 | | | |
| CGC | ACC | GGC | GTC | TAC | GCC | GGC | GTG | ATG | TAC | CAC | GAC | TAT | GGC | ACG | GGA | 20528 |
| Arg | Thr | Gly | Val | Tyr | Ala | Gly | Val | Met | Tyr | His | Asp | Tyr | Gly | Thr | Gly | |
| | | 160 | | | | | 165 | | | | | 170 | | | | |
| CAG | ACC | TCC | GCG | ACC | GAC | ACG | AGC | GGT | TAT | TCC | GGC | ACC | GGT | ACG | TCG | 20576 |
| Gln | Thr | Ser | Ala | Thr | Asp | Thr | Ser | Gly | Tyr | Ser | Gly | Thr | Gly | Thr | Ser | |
| | 175 | | | | | 180 | | | | | 185 | | | | | |
| GGG | AGT | GTG | GTG | TCG | GGG | CGT | GTG | GCC | TAC | ACG | CTG | GGG | CTG | GAG | GGT | 20624 |
| Gly | Ser | Val | Val | Ser | Gly | Arg | Val | Ala | Tyr | Thr | Leu | Gly | Leu | Glu | Gly | |
| 190 | | | | | 195 | | | | | 200 | | | | | 205 | |
| CCG | GCC | GTG | ACC | GTG | GAT | ACG | GCG | TGT | TCG | TCG | TCG | TTG | GTG | GCG | TTG | 20672 |
| Pro | Ala | Val | Thr | Val | Asp | Thr | Ala | Cys | Ser | Ser | Ser | Leu | Val | Ala | Leu | |
| | | | | 210 | | | | 215 | | | | | 220 | | | |
| CAT | CTG | GCG | GTG | CAG | GCG | TTG | CGG | GGT | GGC | GAG | TGT | GAC | ATG | GCG | TTG | 20720 |
| His | Leu | Ala | Val | Gln | Ala | Leu | Arg | Gly | Gly | Glu | Cys | Asp | Met | Ala | Leu | |
| | | | | 225 | | | | | 230 | | | | | 235 | | |
| GCC | GGT | GGT | GTG | ACG | GTG | ATG | GCC | GGG | CCG | GGG | ATG | TTC | GTG | GAG | TTT | 20768 |
| Ala | Gly | Gly | Val | Thr | Val | Met | Ala | Gly | Pro | Gly | Met | Phe | Val | Glu | Phe | |
| | | | 240 | | | | | 245 | | | | | 250 | | | |
| TCG | CGG | CAG | CGG | GGG | TTG | GCG | GCC | GAT | GGG | CGG | TGC | AAG | GCG | TTC | GCG | 20816 |
| Ser | Arg | Gln | Arg | Gly | Leu | Ala | Ala | Asp | Gly | Arg | Cys | Lys | Ala | Phe | Ala | |
| | 255 | | | | | 260 | | | | | 265 | | | | | |
| GAT | GGG | GCG | GAT | GGG | ACC | GCT | TGG | GCC | GAG | GGT | GCG | GGG | GTG | GTG | CTG | 20864 |
| Asp | Gly | Ala | Asp | Gly | Thr | Ala | Trp | Ala | Glu | Gly | Ala | Gly | Val | Val | Leu | |
| 270 | | | | | 275 | | | | | 280 | | | | | 285 | |
| GTG | GAG | CGG | TTG | TCG | GAT | GCC | CGG | CGG | TTG | GGG | CAT | CCG | GTG | TTG | GCG | 20912 |
| Val | Glu | Arg | Leu | Ser | Asp | Ala | Arg | Arg | Leu | Gly | His | Pro | Val | Leu | Ala | |
| | | | | 290 | | | | | 295 | | | | | 300 | | |
| GTG | GTG | TGT | GGG | TCG | GCG | GTG | AAT | CAG | GAC | GGT | GCG | TCG | AAT | GGT | TTG | 20960 |
| Val | Val | Cys | Gly | Ser | Ala | Val | Asn | Gln | Asp | Gly | Ala | Ser | Asn | Gly | Leu | |
| | | | 305 | | | | | 310 | | | | | 315 | | | |
| ACG | GCG | CCG | AGT | GGT | CCG | TCG | CAG | GAG | CGG | GTG | ATT | CGT | CAG | GCG | TTG | 21008 |
| Thr | Ala | Pro | Ser | Gly | Pro | Ser | Gln | Glu | Arg | Val | Ile | Arg | Gln | Ala | Leu | |
| | | 320 | | | | | 325 | | | | | 330 | | | | |
| GCG | AAT | GCG | CGG | TTG | ACG | GTG | GCG | GAT | GTG | GAT | GTG | GTG | GAG | GCG | CAT | 21056 |
| Ala | Asn | Ala | Arg | Leu | Thr | Val | Ala | Asp | Val | Asp | Val | Val | Glu | Ala | His | |
| | 335 | | | | | 340 | | | | | 345 | | | | | |
| GGG | ACG | GGG | ACG | CGG | CTG | GGT | GAT | CCG | ATC | GAG | GCG | CAG | GCG | TTG | CTG | 21104 |
| Gly | Thr | Gly | Thr | Arg | Leu | Gly | Asp | Pro | Ile | Glu | Ala | Gln | Ala | Leu | Leu | |
| 350 | | | | | 355 | | | | | 360 | | | | | 365 | |
| GGG | ACG | TAT | GGG | CGG | GAT | CGT | GAT | GGT | GGG | CGT | CCG | GTG | TGG | TTG | GGG | 21152 |
| Gly | Thr | Tyr | Gly | Arg | Asp | Arg | Asp | Gly | Gly | Arg | Pro | Val | Trp | Leu | Gly | |
| | | | | 370 | | | | | 375 | | | | | 380 | | |
| TCG | TTG | AAG | TCG | AAT | ATT | GGT | CAT | GCT | CAG | GCG | GCT | GCG | GGG | GTG | GCT | 21200 |
| Ser | Leu | Lys | Ser | Asn | Ile | Gly | His | Ala | Gln | Ala | Ala | Ala | Gly | Val | Ala | |
| | | | 385 | | | | | 390 | | | | | 395 | | | |

| | | | | | | | | | | | | | | | | |
|---|---|---|---|---|---|---|---|---|---|---|---|---|---|---|---|---|
| GGT | GTG | ATC | AAG | ATG | GTG | TTG | GCG | ATG | CGG | TAT | GGG | TGG | TTG | CCG | CGG | 21248 |
| Gly | Val | Ile | Lys | Met | Val | Leu | Ala | Met | Arg | Tyr | Gly | Trp | Leu | Pro | Arg | |
| | | 400 | | | 405 | | | | | 410 | | | | | | |
| ACG | TTG | CAT | GTG | GAT | GAG | CCG | AGC | CGG | CAT | GTG | GAC | TGG | TCG | GCT | GGT | 21296 |
| Thr | Leu | His | Val | Asp | Glu | Pro | Ser | Arg | His | Val | Asp | Trp | Ser | Ala | Gly | |
| | 415 | | | | 420 | | | | | 425 | | | | | | |
| GGT | GTG | TGG | TTG | CTG | ACC | GAG | GCG | CGG | GAG | TGG | CCG | GGG | GTG | GAC | CGG | 21344 |
| Gly | Val | Trp | Leu | Leu | Thr | Glu | Ala | Arg | Glu | Trp | Pro | Gly | Val | Asp | Arg | |
| 430 | | | | | 435 | | | | 440 | | | | | | 445 | |
| CCG | CGT | CGG | GCG | GCG | GTC | TCC | GCC | TTT | GGT | GTC | AGT | GGT | ACC | AAC | GCC | 21392 |
| Pro | Arg | Arg | Ala | Ala | Val | Ser | Ala | Phe | Gly | Val | Ser | Gly | Thr | Asn | Ala | |
| | | | | 450 | | | | | 455 | | | | | 460 | | |
| CAT | CTG | ATC | CTC | GAA | GCC | CCC | GAC | ACC | GCC | GAG | GCG | GAG | AGC | GCC | ACG | 21440 |
| His | Leu | Ile | Leu | Glu | Ala | Pro | Asp | Thr | Ala | Glu | Ala | Glu | Ser | Ala | Thr | |
| | | | 465 | | | | | 470 | | | | | 475 | | | |
| ACC | CCG | GTC | CGC | TCT | GAG | GTG | TCG | GAG | TCT | GCT | GCG | GTC | TTC | GAT | GCC | 21488 |
| Thr | Pro | Val | Arg | Ser | Glu | Val | Ser | Glu | Ser | Ala | Ala | Val | Phe | Asp | Ala | |
| | | 480 | | | | | 485 | | | | | 490 | | | | |
| CGC | AGT | GGT | GTG | GTG | CCG | GTG | GTG | GTT | TCG | GGG | CGT | TCG | CGG | GTG | GTG | 21536 |
| Arg | Ser | Gly | Val | Val | Pro | Val | Val | Val | Ser | Gly | Arg | Ser | Arg | Val | Val | |
| | 495 | | | | 500 | | | | | 505 | | | | | | |
| GTG | CGG | GAG | GCT | GCG | GGC | CGG | TTG | GCG | GAG | GTG | GTG | GAG | GCC | GGT | GGT | 21584 |
| Val | Arg | Glu | Ala | Ala | Gly | Arg | Leu | Ala | Glu | Val | Val | Glu | Ala | Gly | Gly | |
| 510 | | | | | 515 | | | | 520 | | | | | | 525 | |
| GTG | GGG | CTG | GCG | GAT | GTG | GCG | GTG | ACG | ATG | GCG | GGC | CGG | TCG | CGG | TTT | 21632 |
| Val | Gly | Leu | Ala | Asp | Val | Ala | Val | Thr | Met | Ala | Gly | Arg | Ser | Arg | Phe | |
| | | | | 530 | | | | | 535 | | | | | 540 | | |
| GGG | TAT | CGG | GCG | GTT | GTG | CTG | GCT | CGG | GGT | GAG | GCT | GAG | CTT | GCC | GGG | 21680 |
| Gly | Tyr | Arg | Ala | Val | Val | Leu | Ala | Arg | Gly | Glu | Ala | Glu | Leu | Ala | Gly | |
| | | | 545 | | | | | 550 | | | | | 555 | | | |
| CGT | TTG | CGG | GCG | TTG | GCG | GGG | GGT | GAT | CCG | GAC | GCG | GGT | GTG | GTC | ACG | 21728 |
| Arg | Leu | Arg | Ala | Leu | Ala | Gly | Gly | Asp | Pro | Asp | Ala | Gly | Val | Val | Thr | |
| | | 560 | | | | | 565 | | | | | 570 | | | | |
| GGT | GCG | GTG | GTG | GAC | CCG | GAG | ACG | GGG | TCC | GGT | GGT | GGG | GGG | GTG | GTG | 21776 |
| Gly | Ala | Val | Val | Asp | Pro | Glu | Thr | Gly | Ser | Gly | Gly | Gly | Gly | Val | Val | |
| | 575 | | | | | 580 | | | | | 585 | | | | | |
| TTG | GTT | TTC | CCT | GGT | CAG | GGG | ACG | CAG | TGG | GTG | GGG | ATG | GGT | GCG | GGG | 21824 |
| Leu | Val | Phe | Pro | Gly | Gln | Gly | Thr | Gln | Trp | Val | Gly | Met | Gly | Ala | Gly | |
| 590 | | | | | 595 | | | | 600 | | | | | | 605 | |
| CTG | CTG | GGG | TCT | TCG | GAG | GTG | TTT | GCG | GCG | TCG | ATG | CGG | GAG | TGT | GCG | 21872 |
| Leu | Leu | Gly | Ser | Ser | Glu | Val | Phe | Ala | Ala | Ser | Met | Arg | Glu | Cys | Ala | |
| | | | | 610 | | | | | 615 | | | | | 620 | | |
| CGG | GCG | CTG | AGT | GTT | CAT | GTG | GGG | TGG | GAT | TTG | CTG | GAG | GTG | GTG | TCG | 21920 |
| Arg | Ala | Leu | Ser | Val | His | Val | Gly | Trp | Asp | Leu | Leu | Glu | Val | Val | Ser | |
| | | | 625 | | | | | 630 | | | | | 635 | | | |
| GGC | GGG | GCC | GGG | TTG | GAG | CGG | GTG | GAT | GTG | GTG | CAG | CCG | GTG | ACG | TGG | 21968 |
| Gly | Gly | Ala | Gly | Leu | Glu | Arg | Val | Asp | Val | Val | Gln | Pro | Val | Thr | Trp | |
| | | 640 | | | | | 645 | | | | | 650 | | | | |
| GCG | GTG | ATG | GTG | TCG | CTG | GCC | CGG | TAC | TGG | CAG | GCG | ATG | GGT | GTG | GAC | 22016 |
| Ala | Val | Met | Val | Ser | Leu | Ala | Arg | Tyr | Trp | Gln | Ala | Met | Gly | Val | Asp | |
| | 655 | | | | | 660 | | | | | 665 | | | | | |
| GTG | GCT | GCG | GTG | GTG | GGT | CAT | TCC | CAG | GGG | GAG | ATC | GCT | GCT | GCC | ACG | 22064 |
| Val | Ala | Ala | Val | Val | Gly | His | Ser | Gln | Gly | Glu | Ile | Ala | Ala | Ala | Thr | |
| 670 | | | | | 675 | | | | 680 | | | | | | 685 | |
| GTG | GCG | GGG | GCG | TTG | TCG | CTG | GAG | GAT | GCG | GCG | GCT | GTG | GTC | GCT | CTG | 22112 |
| Val | Ala | Gly | Ala | Leu | Ser | Leu | Glu | Asp | Ala | Ala | Ala | Val | Val | Ala | Leu | |
| | | | | 690 | | | | | 695 | | | | | 700 | | |
| CGG | GCG | GGG | TTG | ATT | GGC | CGG | TAT | CTG | GCG | GGT | CGT | GGT | GCG | ATG | GCG | 22160 |
| Arg | Ala | Gly | Leu | Ile | Gly | Arg | Tyr | Leu | Ala | Gly | Arg | Gly | Ala | Met | Ala | |
| | | | 705 | | | | | 710 | | | | | 715 | | | |

| | | | | | | | | | | | | | | | | |
|---|---|---|---|---|---|---|---|---|---|---|---|---|---|---|---|---|
| GCT | GTT | CCG | CTG | CCT | GCC | GGC | GAG | GTC | GAG | GCC | GGG | CTG | GCG | AAG | TGG | 22208 |
| Ala | Val | Pro | Leu | Pro | Ala | Gly | Glu | Val | Glu | Ala | Gly | Leu | Ala | Lys | Trp | |
| | | 720 | | | | | 725 | | | | | 730 | | | | |
| CCG | GGT | GTG | GAG | GTC | GCG | GCG | GTC | AAC | GGT | CCG | GCG | TCT | ACG | GTG | GTT | 22256 |
| Pro | Gly | Val | Glu | Val | Ala | Ala | Val | Asn | Gly | Pro | Ala | Ser | Thr | Val | Val | |
| 735 | | | | | 740 | | | | | 745 | | | | | | |
| TCC | GGG | GAT | CGG | CGG | GCG | GTG | GCC | GGT | TAT | GTG | GCC | GTC | TGT | CAG | GCG | 22304 |
| Ser | Gly | Asp | Arg | Arg | Ala | Val | Ala | Gly | Tyr | Val | Ala | Val | Cys | Gln | Ala | |
| 750 | | | | 755 | | | | | 760 | | | | | | 765 | |
| GAG | GGT | GTG | CAG | GCT | CGG | TTG | ATA | CCG | GTG | GAC | TAC | GCC | TCT | CAC | TCC | 22352 |
| Glu | Gly | Val | Gln | Ala | Arg | Leu | Ile | Pro | Val | Asp | Tyr | Ala | Ser | His | Ser | |
| | | | | 770 | | | | | 775 | | | | | 780 | | |
| CGC | CAT | GTG | GAG | GAC | CTG | AAG | GGC | GAG | TTG | GAG | CGG | GTG | CTG | TCC | GGT | 22400 |
| Arg | His | Val | Glu | Asp | Leu | Lys | Gly | Glu | Leu | Glu | Arg | Val | Leu | Ser | Gly | |
| | | | 785 | | | | | 790 | | | | | 795 | | | |
| ATC | CGC | CCG | CGC | AGT | CCG | CGG | GTG | CCG | GTG | TGT | TCC | ACC | GTC | GCC | GGA | 22448 |
| Ile | Arg | Pro | Arg | Ser | Pro | Arg | Val | Pro | Val | Cys | Ser | Thr | Val | Ala | Gly | |
| | | 800 | | | | | 805 | | | | | 810 | | | | |
| GAG | CAG | CCG | GGC | GAG | CCG | GTT | TTC | GAT | GCG | GGG | TAT | TGG | TTC | CGT | AAT | 22496 |
| Glu | Gln | Pro | Gly | Glu | Pro | Val | Phe | Asp | Ala | Gly | Tyr | Trp | Phe | Arg | Asn | |
| 815 | | | | | 820 | | | | | 825 | | | | | | |
| CTG | CGG | AAC | CGG | GTT | GAG | TTC | TCC | GCG | GTG | GTC | GGT | GGT | TTG | TTG | GAG | 22544 |
| Leu | Arg | Asn | Arg | Val | Glu | Phe | Ser | Ala | Val | Val | Gly | Gly | Leu | Leu | Glu | |
| 830 | | | | | 835 | | | | | 840 | | | | | 845 | |
| GAG | GGC | CAC | CGT | CGG | TTC | ATC | GAG | GTC | AGT | GCC | CAC | CCG | GTA | CTC | GTT | 22592 |
| Glu | Gly | His | Arg | Arg | Phe | Ile | Glu | Val | Ser | Ala | His | Pro | Val | Leu | Val | |
| | | | | 850 | | | | | 855 | | | | | 860 | | |
| CAT | GCC | ATT | GAG | CAG | ACG | GCC | GAG | GCC | GCG | GAC | CGG | AGT | GTC | CAT | GCC | 22640 |
| His | Ala | Ile | Glu | Gln | Thr | Ala | Glu | Ala | Ala | Asp | Arg | Ser | Val | His | Ala | |
| | | | 865 | | | | | 870 | | | | | 875 | | | |
| ACC | GGG | ACC | CTG | CGC | CGC | CAG | GAC | GAC | AGC | CCG | CAC | CGC | CTG | CTG | ACC | 22688 |
| Thr | Gly | Thr | Leu | Arg | Arg | Gln | Asp | Asp | Ser | Pro | His | Arg | Leu | Leu | Thr | |
| | | 880 | | | | | 885 | | | | | 890 | | | | |
| TCC | ACC | GCC | GAG | GCC | TGG | GCC | CAC | GGC | GCC | ACC | CTC | ACC | TGG | GAC | CCC | 22736 |
| Ser | Thr | Ala | Glu | Ala | Trp | Ala | His | Gly | Ala | Thr | Leu | Thr | Trp | Asp | Pro | |
| | 895 | | | | | 900 | | | | | 905 | | | | | |
| GCC | CTG | CCC | CCA | GGC | CAC | CTC | ACC | ACC | CTC | CCC | ACC | TAC | CCC | TTC | AAC | 22784 |
| Ala | Leu | Pro | Pro | Gly | His | Leu | Thr | Thr | Leu | Pro | Thr | Tyr | Pro | Phe | Asn | |
| 910 | | | | | 915 | | | | | 920 | | | | | 925 | |
| CAC | CAC | CAC | TAC | TGG | CTC | GAC | ACC | ACC | CCC | ACC | ACC | CCC | GCG | ACG | ACC | 22832 |
| His | His | His | Tyr | Trp | Leu | Asp | Thr | Thr | Pro | Thr | Thr | Pro | Ala | Thr | Thr | |
| | | | | | 930 | | | | | 935 | | | | | 940 | |
| ACC | CAG | AGC | CCC | ACC | GAT | GCC | CAG | AAC | CCC | GCC | GAC | GCC | CTT | CCC | TAC | 22880 |
| Thr | Gln | Ser | Pro | Thr | Asp | Ala | Gln | Asn | Pro | Ala | Asp | Ala | Leu | Pro | Tyr | |
| | | | 945 | | | | | 950 | | | | | 955 | | | |
| AAG | GTG | AGT | TGG | AAG | CGG | TTG | CGG | GAC | CAG | GAC | AGC | TTG | ACC | GCG | CGC | 22928 |
| Lys | Val | Ser | Trp | Lys | Arg | Leu | Arg | Asp | Gln | Asp | Ser | Leu | Thr | Ala | Arg | |
| | | 960 | | | | | 965 | | | | | 970 | | | | |
| CTC | GAC | GGC | CGA | TGG | CTG | CTG | GTG | GTA | CCG | GAG | GCG | TCG | GCG | GAC | CCG | 22976 |
| Leu | Asp | Gly | Arg | Trp | Leu | Leu | Val | Val | Pro | Glu | Ala | Ser | Ala | Asp | Pro | |
| | 975 | | | | | 980 | | | | | 985 | | | | | |
| TCG | GTT | GCT | GAG | GGC | GTC | GCG | CGC | GAG | CTG | ACC | GCG | CGG | GGC | GCG | ACC | 23024 |
| Ser | Val | Ala | Glu | Gly | Val | Ala | Arg | Glu | Leu | Thr | Ala | Arg | Gly | Ala | Thr | |
| 990 | | | | | 995 | | | | | 1000 | | | | | 1005 | |
| GTG | GAG | TCG | CTG | ACG | GTC | GAG | CCG | GGC | GCC | GAC | CGT | TCG | CGG | CTG | CGC | 23072 |
| Val | Glu | Ser | Leu | Thr | Val | Glu | Pro | Gly | Ala | Asp | Arg | Ser | Arg | Leu | Arg | |
| | | | | 1010 | | | | | 1015 | | | | | 1020 | | |
| GGG | CTG | CTG | GTC | GAC | GCC | ACG | GAA | CGG | GAC | GAA | GCC | GGG | CCG | CTG | CGC | 23120 |
| Gly | Leu | Leu | Val | Asp | Ala | Thr | Glu | Arg | Asp | Glu | Ala | Gly | Pro | Leu | Arg | |
| | | | | 1025 | | | | | 1030 | | | | | 1035 | | |

```
GGG ATC GTC TCG CTG CTG GCG TTG GCC GGG GAC CAC GCC GGG GCC GAC    23168
Gly Ile Val Ser Leu Leu Ala Leu Ala Gly Asp His Ala Gly Ala Asp
        1040                1045                1050

GGG GCA CGC CCG GTG GTT CCG GCC GGC CTG GCA GCG TCA CTG GCG CTG    23216
Gly Ala Arg Pro Val Val Pro Ala Gly Leu Ala Ala Ser Leu Ala Leu
        1055                1060                1065

ATC CAG GCC GCG GGC GAC GCG GGC ACG GAG GCC GGG CTG TGG GCG GTG    23264
Ile Gln Ala Ala Gly Asp Ala Gly Thr Glu Ala Gly Leu Trp Ala Val
1070                1075                1080                1085

ACC CGC GGC GCC GTC GCG GCC GTG CCC GGT GAC GTA CCG GCG CCG TCG    23312
Thr Arg Gly Ala Val Ala Ala Val Pro Gly Asp Val Pro Ala Pro Ser
        1090                1095                1100

CAG GCG CTG CTC TGG GGA TTC GGC CGG GTG GCC GGG ATC GAG CTG CCG    23360
Gln Ala Leu Leu Trp Gly Phe Gly Arg Val Ala Gly Ile Glu Leu Pro
        1105                1110                1115

CAC TGC TGG GGC GGC CTG CTC GAC CTG CCG ACC GGG CCC GGC GAC TCC    23408
His Cys Trp Gly Gly Leu Leu Asp Leu Pro Thr Gly Pro Gly Asp Ser
        1120                1125                1130

GGG TTC CGG CAA CTG GCC GCG ACC CTG GCG GGC CGT CCC GCG GAG GAC    23456
Gly Phe Arg Gln Leu Ala Ala Thr Leu Ala Gly Arg Pro Ala Glu Asp
        1135                1140                1145

CAG GTG GCG CTG CGG GCT TCG GGC GCG TAC GGC CGC AGG CTG GTC CGG    23504
Gln Val Ala Leu Arg Ala Ser Gly Ala Tyr Gly Arg Arg Leu Val Arg
1150                1155                1160                1165

GCC TCC GCG GCG GGC GGC GCG GAC GGC TGG CGG CCG CGG GGA ACG GTG    23552
Ala Ser Ala Ala Gly Gly Ala Asp Gly Trp Arg Pro Arg Gly Thr Val
        1170                1175                1180

CTG GTG GTG GGC GAC ACC GCG GAG GTC GCC GGA CCG CTG GTG CGC TGG    23600
Leu Val Val Gly Asp Thr Ala Glu Val Ala Gly Pro Leu Val Arg Trp
        1185                1190                1195

CTG CTC GGC AAC GGC GCA CGG CGG GTG ACC CTG TCC GGA CTC TCC GGC    23648
Leu Leu Gly Asn Gly Ala Arg Arg Val Thr Leu Ser Gly Leu Ser Gly
        1200                1205                1210

CCG CTG CCG GAG GAA CTC GCC GAT GTG GCG GCA CGG GTG ACC GTG GCG    23696
Pro Leu Pro Glu Glu Leu Ala Asp Val Ala Ala Arg Val Thr Val Ala
        1215                1220                1225

CCC TGT GAT CCG GCC GAT CGC CCC GCC CTG CGG ACG CTG CTC GCC GAA    23744
Pro Cys Asp Pro Ala Asp Arg Pro Ala Leu Arg Thr Leu Leu Ala Glu
1230                1235                1240                1245

CAG GCG CCG ACC GCC GTG CTC GTG GCG CCC CCG GCC GTC CCG CCC ACG    23792
Gln Ala Pro Thr Ala Val Leu Val Ala Pro Pro Ala Val Pro Pro Thr
        1250                1255                1260

CCG CTC GCG GAG ATG ACC GCC GAG GCG TTA GCC ATC GCG CTG TCC GCG    23840
Pro Leu Ala Glu Met Thr Ala Glu Ala Leu Ala Ile Ala Leu Ser Ala
        1265                1270                1275

AAG ACC GGT CTG GTC GAC CGT CTG GAC TCG CTG CTC GAC GAG CCG GAC    23888
Lys Thr Gly Leu Val Asp Arg Leu Asp Ser Leu Leu Asp Glu Pro Asp
        1280                1285                1290

CCC CTG CTC GAG GAC GGG GAA CTC GAC GCG TTC GTC GTC TTC TCC TCC    23936
Pro Leu Leu Glu Asp Gly Glu Leu Asp Ala Phe Val Val Phe Ser Ser
        1295                1300                1305

GTG GCA GGG GTG TGG GGC GGC GCG GGA CAG GGT GGT TAC GCG GCC GGT    23984
Val Ala Gly Val Trp Gly Gly Ala Gly Gln Gly Gly Tyr Ala Ala Gly
1310                1315                1320                1325

ACC GCG TAC CTC GAC GCG CTC GCC GAA TGC CGG CGG GCC GGG GGG CTG    24032
Thr Ala Tyr Leu Asp Ala Leu Ala Glu Cys Arg Arg Ala Gly Gly Leu
        1330                1335                1340

CCG GTC ACC TCG GTG GCG TGG ACG CCG TGG CTC GGT ACG CCG GCG GCG    24080
Pro Val Thr Ser Val Ala Trp Thr Pro Trp Leu Gly Thr Pro Ala Ala
        1345                1350                1355
```

```
GAC TCC CTG GGC GAG CAG ATG AGC CGA GCT GGC ATC ACC CCC CTG GAT      24128
Asp Ser Leu Gly Glu Gln Met Ser Arg Ala Gly Ile Thr Pro Leu Asp
            1360                1365                1370

CCG GCG GCC TCG CTG GAT GCG CTC GCC CGT GCG GTG GGC CGG CGC GCG      24176
Pro Ala Ala Ser Leu Asp Ala Leu Ala Arg Ala Val Gly Arg Arg Ala
        1375                1380                1385

GGC TGT GTG ACG GTC GCC GAC ATC GAC TGG GAG CGG TTC GCC TCC GCG      24224
Gly Cys Val Thr Val Ala Asp Ile Asp Trp Glu Arg Phe Ala Ser Ala
1390                1395                1400                1405

TAC ACG GCC ACC CGT CCC ACG CCG ATG TTC GAC GAG GTG CCC GAG GTG      24272
Tyr Thr Ala Thr Arg Pro Thr Pro Met Phe Asp Glu Val Pro Glu Val
            1410                1415                1420

CGG CGG ATA CAG GCC GCG TGG GCG GAA GCG GAG GCC GAC GCC GCG CGC      24320
Arg Arg Ile Gln Ala Ala Trp Ala Glu Ala Glu Ala Asp Ala Ala Arg
        1425                1430                1435

AGC GGT GCC GGC GGC GAC TCG CAG CTG CTG CGC TCC CTC CGG GGC CGG      24368
Ser Gly Ala Gly Gly Asp Ser Gln Leu Leu Arg Ser Leu Arg Gly Arg
    1440                1445                1450

CCC GAG GAG GCC CAA CTG GCG GAG CTG CTG CGG CTG GTG CGC ACC CAT      24416
Pro Glu Glu Ala Gln Leu Ala Glu Leu Leu Arg Leu Val Arg Thr His
1455                1460                1465

GCC GCC GCG GTG CTC GGC CTG GGC TCG CCC GGC GCG GTG GAG GCG CGG      24464
Ala Ala Ala Val Leu Gly Leu Gly Ser Pro Gly Ala Val Glu Ala Arg
1470                1475                1480                1485

CGT TCG TTC AAG GAC CTG GGC TTC AAC TCG GTG ACG GCG GTG GAG CTG      24512
Arg Ser Phe Lys Asp Leu Gly Phe Asn Ser Val Thr Ala Val Glu Leu
            1490                1495                1500

CGG AAC CGG CTG AAG GAG GCG ACG GGA CTC CGG CTG GAG GTG TCC CTG      24560
Arg Asn Arg Leu Lys Glu Ala Thr Gly Leu Arg Leu Glu Val Ser Leu
        1505                1510                1515

GTC TTC GAC CAC CCG GAC CCG GCC TCC CTC GCC CGG CAT CTG CTG GAT      24608
Val Phe Asp His Pro Asp Pro Ala Ser Leu Ala Arg His Leu Leu Asp
    1520                1525                1530

CTC GCC CTC GGC CAG GAG CCG GAG GAG ACG CCG CGG GCG TTC GCG CTC      24656
Leu Ala Leu Gly Gln Glu Pro Glu Glu Thr Pro Arg Ala Phe Ala Leu
1535                1540                1545

GAA CCC GCG CCG AAC GGG GAG CCG ATC GCG ATC GTG TCC ATG GCC TGC      24704
Glu Pro Ala Pro Asn Gly Glu Pro Ile Ala Ile Val Ser Met Ala Cys
1550                1555                1560                1565

CGT ATG CCG GGG GGT GTC AGC ACG CCC GAG GAG CTG TGG CGG CTG CTG      24752
Arg Met Pro Gly Gly Val Ser Thr Pro Glu Glu Leu Trp Arg Leu Leu
            1570                1575                1580

CGG GAC GGC AAG GAC GCG ATC GGG CCG TTC CCC GCC AAC CGG GGC TGG      24800
Arg Asp Gly Lys Asp Ala Ile Gly Pro Phe Pro Ala Asn Arg Gly Trp
        1585                1590                1595

GAC CTG GAG AAC CTC TAC GAC CCC GAC CCG GAC GCC GAC GGC CGC ACC      24848
Asp Leu Glu Asn Leu Tyr Asp Pro Asp Pro Asp Ala Asp Gly Arg Thr
    1600                1605                1610

TAT GTG CGC GAG GGC GGA TTC CTC CAC GAG GCA CCG GAC TTC GAC CCC      24896
Tyr Val Arg Glu Gly Gly Phe Leu His Glu Ala Pro Asp Phe Asp Pro
1615                1620                1625

TCG TTC TTC GGC ATC TCG CCG CGC GAG GCG CTG GCG ATG GAC CCG CAG      24944
Ser Phe Phe Gly Ile Ser Pro Arg Glu Ala Leu Ala Met Asp Pro Gln
1630                1635                1640                1645

CAG CGG CTG CTG CTG GAG ACT TCC TGG GAG GCC TTG GAG CGC GCC GGC      24992
Gln Arg Leu Leu Leu Glu Thr Ser Trp Glu Ala Leu Glu Arg Ala Gly
            1650                1655                1660

ATC GAC CCG GCG AGG CTG CGC GGC AGC CGT ACC GGC GTC TTC GTC GGG      25040
Ile Asp Pro Ala Arg Leu Arg Gly Ser Arg Thr Gly Val Phe Val Gly
        1665                1670                1675
```

```
ACG AAC GGC CAG CAC TAC ATG CCG CTG CTC CAG AAC GGC GGG GAC AGC      25088
Thr Asn Gly Gln His Tyr Met Pro Leu Leu Gln Asn Gly Gly Asp Ser
        1680                1685                1690

TTC GAC GGC TAT CTG GGC ACC GGC AAC TCG GCG AGT GTG ATG TCG GGC      25136
Phe Asp Gly Tyr Leu Gly Thr Gly Asn Ser Ala Ser Val Met Ser Gly
        1695                1700                1705

CGG CTG TCG TAC GTG TTC GGC CTC GAA GGC CCC GCC GTG ACC GTG GAC      25184
Arg Leu Ser Tyr Val Phe Gly Leu Glu Gly Pro Ala Val Thr Val Asp
1710                1715                1720                1725

ACC GCC TGC TCG GCG TCC CTG GTG GCG CTG CAC CTG GCG GTG CAG GCG      25232
Thr Ala Cys Ser Ala Ser Leu Val Ala Leu His Leu Ala Val Gln Ala
                1730                1735                1740

ATG CGG CGC GGC GAG TGC GAC ATG GCG CTG GTC GGC GGC GCG ACG GTG      25280
Met Arg Arg Gly Glu Cys Asp Met Ala Leu Val Gly Gly Ala Thr Val
        1745                1750                1755

ATG TCG ACG CCC GAG ATG CTG GTG GAG TTC TCC CGG CAG CGG GTG ATC      25328
Met Ser Thr Pro Glu Met Leu Val Glu Phe Ser Arg Gln Arg Val Ile
        1760                1765                1770

TCC GCC AAC GGC CGG TCG AGG GCC TTC GCC GCC GGT GCC GAC GGT GTG      25376
Ser Ala Asn Gly Arg Ser Arg Ala Phe Ala Ala Gly Ala Asp Gly Val
        1775                1780                1785

GCG CTC GGC GAG GGC GTG GGC GTC CTG CTG GTG GAG CGG CTG TCG GAC      25424
Ala Leu Gly Glu Gly Val Gly Val Leu Leu Val Glu Arg Leu Ser Asp
1790                1795                1800                1805

GCC GAG CGC AAC GGC CAT CCG GTG CTG GCG GTG GTC CGC GGC TCG GCG      25472
Ala Glu Arg Asn Gly His Pro Val Leu Ala Val Val Arg Gly Ser Ala
                1810                1815                1820

GTC AAC CAG GAC GGC GCC TCC AAC GGG CTG ACG GCG CCC AAC GGG CCC      25520
Val Asn Gln Asp Gly Ala Ser Asn Gly Leu Thr Ala Pro Asn Gly Pro
                1825                1830                1835

TCC CAG CAG CGG GTG ATC CGG CAG GCG CTG GCG GAC GCC GGG CTG CGG      25568
Ser Gln Gln Arg Val Ile Arg Gln Ala Leu Ala Asp Ala Gly Leu Arg
        1840                1845                1850

CCC GAG GAC ATC GAC GCC GTC GAG GCG CAC GGC ACC GGC ACC GAG CTG      25616
Pro Glu Asp Ile Asp Ala Val Glu Ala His Gly Thr Gly Thr Glu Leu
        1855                1860                1865

GGC GAC CCC ATC GAG GCC GAG GCG CTG CTC GCC ACC TAT GGA AGG ACC      25664
Gly Asp Pro Ile Glu Ala Glu Ala Leu Leu Ala Thr Tyr Gly Arg Thr
1870                1875                1880                1885

CGT ACG GCG GAC CGC CCG CTG TGG CTC GGC TCC CTG AAG TCC AAC ATC      25712
Arg Thr Ala Asp Arg Pro Leu Trp Leu Gly Ser Leu Lys Ser Asn Ile
                1890                1895                1900

GGG CAC ACC CAG GCC GCC GCC GGC GTG GCG GGC GTC ATC AAG ATG GTG      25760
Gly His Thr Gln Ala Ala Ala Gly Val Ala Gly Val Ile Lys Met Val
                1905                1910                1915

CTC GCG CTG GGC AAC GAG ACA CTG CCG CGC ACC CTG CAC GTG GAT GAG      25808
Leu Ala Leu Gly Asn Glu Thr Leu Pro Arg Thr Leu His Val Asp Glu
        1920                1925                1930

CCC ACA CCG CGC GTG GAC TGG TCC TCT GGC GCG GTC TCC CTG CTC ACC      25856
Pro Thr Pro Arg Val Asp Trp Ser Ser Gly Ala Val Ser Leu Leu Thr
        1935                1940                1945

GAG CCG GTG GAC TGG CCC GCC GGC CCG TCC GCG CCG CGC CGT GCG GCC      25904
Glu Pro Val Asp Trp Pro Ala Gly Pro Ser Ala Pro Arg Arg Ala Ala
1950                1955                1960                1965

GTG TCC TCG TTC GGC ATC AGC GGC ACC AAC GCC CAC ACG ATC CTG GAG      25952
Val Ser Ser Phe Gly Ile Ser Gly Thr Asn Ala His Thr Ile Leu Glu
                1970                1975                1980

CAG GCC CCC GTC CCC GCG GAG TCC CGC CCC GGG ACG GAG CCG GCG GAC      26000
Gln Ala Pro Val Pro Ala Glu Ser Arg Pro Gly Thr Glu Pro Ala Asp
        1985                1990                1995
```

```
GGC ACG GGC GCG TGG GAG AAC GTG ACC GTT CCG CTG CTG CTG TCC GGC    26048
Gly Thr Gly Ala Trp Glu Asn Val Thr Val Pro Leu Leu Leu Ser Gly
2000                    2005                2010

CAC ACC GAG GCG GCG CTG CGC GAG CAG AGC ACG AGG CTG CTG AAC GAC    26096
His Thr Glu Ala Ala Leu Arg Glu Gln Ser Thr Arg Leu Leu Asn Asp
    2015                2020                2025

CTG CTG GAG CAC CCG GAC GAG CAC CCG GCC GAC GTC GGC TAC ACC CTG    26144
Leu Leu Glu His Pro Asp Glu His Pro Ala Asp Val Gly Tyr Thr Leu
2030                2035                2040                2045

ATC ACC GGC AGG GCC CAC TTC GGG CAC CGG GCC GCC GTG ATC GGC GAG    26192
Ile Thr Gly Arg Ala His Phe Gly His Arg Ala Ala Val Ile Gly Glu
                2050                2055                2060

AGC CGG GAA GAA CTG CTC GAC GCC CTG AAG GCT CTG GCC GAG GGC CGC    26240
Ser Arg Glu Glu Leu Leu Asp Ala Leu Lys Ala Leu Ala Glu Gly Arg
            2065                2070                2075

GAG CAC CAC ACC GTG GTA CGG GGC GAC GGG ACG GCC CAC CCG GAC CGG    26288
Glu His His Thr Val Val Arg Gly Asp Gly Thr Ala His Pro Asp Arg
        2080                2085                2090

CGC GTG GTC TTC GTC TTC CCC GGG CAG GGC TCG CAG TGG CCG TCG ATG    26336
Arg Val Val Phe Val Phe Pro Gly Gln Gly Ser Gln Trp Pro Ser Met
    2095                2100                2105

GCC CGG GAC CTG CTC GAC CGC GCG CCC GCC TTC CGC GAG ACG GCG AAG    26384
Ala Arg Asp Leu Leu Asp Arg Ala Pro Ala Phe Arg Glu Thr Ala Lys
2110                2115                2120                2125

GCC TGC GAC GCC GCG CTG AGC GTC CAT CTG GAC TGG TCC GTG CTC GAT    26432
Ala Cys Asp Ala Ala Leu Ser Val His Leu Asp Trp Ser Val Leu Asp
                2130                2135                2140

GTC CTC CAG GAG AAG CCG GAC GCG CCG CCG CTG AGC CGG GTC GAC GTG    26480
Val Leu Gln Glu Lys Pro Asp Ala Pro Pro Leu Ser Arg Val Asp Val
            2145                2150                2155

GTG CAG CCC GTG CTG TTC ACG ATG ATG CTG TCG CTC GCC GCC TGC TGG    26528
Val Gln Pro Val Leu Phe Thr Met Met Leu Ser Leu Ala Ala Cys Trp
        2160                2165                2170

CGG GAC CTC GGC GTC CAC CCG GCC GCC GTG GTG GGC CAC TCC CAG GGA    26576
Arg Asp Leu Gly Val His Pro Ala Ala Val Val Gly His Ser Gln Gly
    2175                2180                2185

GAG ATC GCG GCG GCC TGC GTG GCC GGC GCG CTC TCC CTG GAG GAC GCG    26624
Glu Ile Ala Ala Ala Cys Val Ala Gly Ala Leu Ser Leu Glu Asp Ala
2190                2195                2200                2205

GCG CGG ATC GTG GCG CTG CGC AGC CGG GCA TGG CTC ACA CTG GCC GGC    26672
Ala Arg Ile Val Ala Leu Arg Ser Arg Ala Trp Leu Thr Leu Ala Gly
                2210                2215                2220

AAG GGC GGC ATG GCC GCC GTC TCC CTG CCG GAA GCC CGG CTG CGC GAG    26720
Lys Gly Gly Met Ala Ala Val Ser Leu Pro Glu Ala Arg Leu Arg Glu
            2225                2230                2235

CGG ATC GAG CGG TTC GGG CAG CGG CTG TCG GTG GCC GCG GTG AAC AGC    26768
Arg Ile Glu Arg Phe Gly Gln Arg Leu Ser Val Ala Ala Val Asn Ser
        2240                2245                2250

CCG GGC ACG GCG GCG GTC GCC GGT GAC GTG GAC GCG CTG CGG GAA CTG    26816
Pro Gly Thr Ala Ala Val Ala Gly Asp Val Asp Ala Leu Arg Glu Leu
    2255                2260                2265

CTG GCG GAG CTG ACC GCG GAG GGC ATC CGG GCC AAG CCG ATC CCC GGC    26864
Leu Ala Glu Leu Thr Ala Glu Gly Ile Arg Ala Lys Pro Ile Pro Gly
2270                2275                2280                2285

GTG GAC ACG GCC GGC CAC TCC GCG CAG GTG GAC GGC CTG AAG GAG CAT    26912
Val Asp Thr Ala Gly His Ser Ala Gln Val Asp Gly Leu Lys Glu His
                2290                2295                2300

CTC TTC GAG GTG CTG GCG CCG GTC TCC CCG CGC TCC TCG GAC ATC CCG    26960
Leu Phe Glu Val Leu Ala Pro Val Ser Pro Arg Ser Ser Asp Ile Pro
            2305                2310                2315
```

-continued

| | | | | | | | | | | | | | | | | |
|---|---|---|---|---|---|---|---|---|---|---|---|---|---|---|---|---|
| TTC | TAC | TCG | ACG | GTG | ACG | GGC | GCG | CCG | CTG | GAC | ACC | GAG | CGG | CTG | GAC | 27008 |
| Phe | Tyr | Ser | Thr | Val | Thr | Gly | Ala | Pro | Leu | Asp | Thr | Glu | Arg | Leu | Asp | |
| | | | 2320 | | | | 2325 | | | | 2330 | | | | | |
| GCC | GGG | TAC | TGG | TAC | CGC | AAC | ATG | CGG | GAG | CCC | GTG | GAG | TTC | GAG | AAG | 27056 |
| Ala | Gly | Tyr | Trp | Tyr | Arg | Asn | Met | Arg | Glu | Pro | Val | Glu | Phe | Glu | Lys | |
| | | 2335 | | | | | 2340 | | | | | 2345 | | | | |
| GCC | GTC | AGG | GCA | CTG | ATC | GCC | GAC | GGC | TAC | GAC | CTG | TTC | CTG | GAG | TGC | 27104 |
| Ala | Val | Arg | Ala | Leu | Ile | Ala | Asp | Gly | Tyr | Asp | Leu | Phe | Leu | Glu | Cys | |
| 2350 | | | | | 2355 | | | | | 2360 | | | | | 2365 | |
| AAC | CCG | CAC | CCG | ATG | CTC | GCC | ATG | TCG | CTG | GAC | GAG | ACA | CTC | ACC | GAC | 27152 |
| Asn | Pro | His | Pro | Met | Leu | Ala | Met | Ser | Leu | Asp | Glu | Thr | Leu | Thr | Asp | |
| | | | | 2370 | | | | | 2375 | | | | | 2380 | | |
| AGC | GGC | GGC | CAC | GGC | ACC | GTG | ATG | CAC | ACC | CTC | CGC | CGG | CAG | AAG | GGC | 27200 |
| Ser | Gly | Gly | His | Gly | Thr | Val | Met | His | Thr | Leu | Arg | Arg | Gln | Lys | Gly | |
| | | | | 2385 | | | | | 2390 | | | | | 2395 | | |
| AGC | GCC | AAG | GAC | TTC | GGC | ATG | GCG | CTC | TGC | CTC | GCC | TAT | GTC | AAC | GGA | 27248 |
| Ser | Ala | Lys | Asp | Phe | Gly | Met | Ala | Leu | Cys | Leu | Ala | Tyr | Val | Asn | Gly | |
| | | | 2400 | | | | | 2405 | | | | | 2410 | | | |
| CTG | GAG | ATC | GAC | GGA | GAA | GCC | CTC | TTC | GGC | CCC | GAC | TCA | CGC | CGG | GTG | 27296 |
| Leu | Glu | Ile | Asp | Gly | Glu | Ala | Leu | Phe | Gly | Pro | Asp | Ser | Arg | Arg | Val | |
| | | 2415 | | | | | 2420 | | | | | 2425 | | | | |
| AAC | CCG | CCG | ACG | TAC | CCG | TTC | CAG | CGG | GAG | CGC | TAC | TGG | TAC | CAC | CCC | 27344 |
| Asn | Pro | Pro | Thr | Tyr | Pro | Phe | Gln | Arg | Glu | Arg | Tyr | Trp | Tyr | His | Pro | |
| 2430 | | | | | 2435 | | | | | 2440 | | | | | 2445 | |
| ACG | AGC | GGC | AGG | CGC | GGC | GAC | ATC | ACG | GCG | GCC | GGC | GTG | GCC | GAG | GCG | 27392 |
| Thr | Ser | Gly | Arg | Arg | Gly | Asp | Ile | Thr | Ala | Ala | Gly | Val | Ala | Glu | Ala | |
| | | | | 2450 | | | | | 2455 | | | | | 2460 | | |
| GAG | CAC | CCG | CTG | CTC | GGC | GCC | GGC | GTC | GAA | CTC | CCG | GAG | ACC | GGG | GGC | 27440 |
| Glu | His | Pro | Leu | Leu | Gly | Ala | Gly | Val | Glu | Leu | Pro | Glu | Thr | Gly | Gly | |
| | | | | 2465 | | | | | 2470 | | | | | 2475 | | |
| ACG | GTG | TAC | ACC | GCG | CGG | TTC | GGC | CCG | GAC | AGC | CGG | CCG | TGG | CTG | GCC | 27488 |
| Thr | Val | Tyr | Thr | Ala | Arg | Phe | Gly | Pro | Asp | Ser | Arg | Pro | Trp | Leu | Ala | |
| | | | 2480 | | | | | 2485 | | | | | 2490 | | | |
| GAC | CAC | GCG | CTG | CTG | GGC | ACC | GTG | CTG | CTG | CCC | GGC | ACG | GCA | ATC | CTG | 27536 |
| Asp | His | Ala | Leu | Leu | Gly | Thr | Val | Leu | Leu | Pro | Gly | Thr | Ala | Ile | Leu | |
| | | | 2495 | | | | | 2500 | | | | | 2505 | | | |
| GAC | CTG | GTG | CTG | TGG | GCG | GGC | GAA | CGC | TCC | GGC | TGC | GGC | CGC | GTC | GGT | 27584 |
| Asp | Leu | Val | Leu | Trp | Ala | Gly | Glu | Arg | Ser | Gly | Cys | Gly | Arg | Val | Gly | |
| 2510 | | | | | 2515 | | | | | 2520 | | | | | 2525 | |
| GAA | CTG | GCG | CTC | CAG | GCA | CCG | CTG | GTC | CTG | CCG | GAC | AGC | GGC | GAC | GTC | 27632 |
| Glu | Leu | Ala | Leu | Gln | Ala | Pro | Leu | Val | Leu | Pro | Asp | Ser | Gly | Asp | Val | |
| | | | | 2530 | | | | | 2535 | | | | | 2540 | | |
| GAA | CTG | CGG | CTG | CTG | GTC | GGC | GGC | CCG | GAC | GAG | GAG | AAA | CGG | CGC | ACC | 27680 |
| Glu | Leu | Arg | Leu | Leu | Val | Gly | Gly | Pro | Asp | Glu | Glu | Lys | Arg | Arg | Thr | |
| | | | 2545 | | | | | 2550 | | | | | 2555 | | | |
| GTC | ACC | GTG | CAC | GCG | CGG | CCC | GCG | GCG | GCC | GGC | GCG | GAG | GCG | CCG | TGG | 27728 |
| Val | Thr | Val | His | Ala | Arg | Pro | Ala | Ala | Ala | Gly | Ala | Glu | Ala | Pro | Trp | |
| | | | 2560 | | | | | 2565 | | | | | 2570 | | | |
| ACC | CGG | CAC | GCC | GAA | GCC | GTG | GTG | CTG | CCC | GCC | ACC | GGC | GAG | GAG | CCG | 27776 |
| Thr | Arg | His | Ala | Glu | Ala | Val | Val | Leu | Pro | Ala | Thr | Gly | Glu | Glu | Pro | |
| | | 2575 | | | | | 2580 | | | | | 2585 | | | | |
| ACC | CCC | GCC | CCG | CGC | CCC | GTC | CCC | GAG | CCG | GCG | GGC | ACC | ACG | GAC | CCC | 27824 |
| Thr | Pro | Ala | Pro | Arg | Pro | Val | Pro | Glu | Pro | Ala | Gly | Thr | Thr | Asp | Pro | |
| 2590 | | | | | 2595 | | | | | 2600 | | | | | 2605 | |
| GCC | GCG | TTC | TAC | GCG | GAG | TTC | GCC | GAG | CGC | GGC | TAC | GAC | TAC | GGC | CCG | 27872 |
| Ala | Ala | Phe | Tyr | Ala | Glu | Phe | Ala | Glu | Arg | Gly | Tyr | Asp | Tyr | Gly | Pro | |
| | | | | 2610 | | | | | 2615 | | | | | 2620 | | |
| GCC | TTC | CAG | GGC | TTC | ACC | GCC | GGA | GCG | CGC | CAC | GGC | GAG | GAC | GTC | GTC | 27920 |
| Ala | Phe | Gln | Gly | Phe | Thr | Ala | Gly | Ala | Arg | His | Gly | Glu | Asp | Val | Val | |
| | | | 2625 | | | | | 2630 | | | | | 2635 | | | |

```
GCC GAG GTG GCG CTG CCC AGC GGC CTG GTG GCG GAC GCC CGT CAC CAC    27968
Ala Glu Val Ala Leu Pro Ser Gly Leu Val Ala Asp Ala Arg His His
        2640                2645                2650

CGG CTG CAC CCG GCG CTG CTC GAC GCC GCG CTC CAG GCG ATG ATC CTC    28016
Arg Leu His Pro Ala Leu Leu Asp Ala Ala Leu Gln Ala Met Ile Leu
    2655                2660                2665

GGC ACG TTC TTT GCC GAC GAC GGC CGC GCC CGG ATG CCG TTC GCG GTG    28064
Gly Thr Phe Phe Ala Asp Asp Gly Arg Ala Arg Met Pro Phe Ala Val
2670                2675                2680                2685

CGC GGA GTA CGG CTG CAC ACG GCC GGC GCC GAC CGG CTG CGC GTC CTG    28112
Arg Gly Val Arg Leu His Thr Ala Gly Ala Asp Arg Leu Arg Val Leu
                2690                2695                2700

ATC TCC CCG GCG GGC GAC GAG ACC GTA CGG CTG CTC TGC ACC GAC CTC    28160
Ile Ser Pro Ala Gly Asp Glu Thr Val Arg Leu Leu Cys Thr Asp Leu
            2705                2710                2715

GCG ACC GGC GCC CCC GTG CTG GAG ATC GAC GAA CTG GTC GTC CGC CCG    28208
Ala Thr Gly Ala Pro Val Leu Glu Ile Asp Glu Leu Val Val Arg Pro
    2720                2725                2730

GTG TCC GGC GAG CAG TTG GCG GCC GGC GCC CCG GGC CGC AAC GGC GGC    28256
Val Ser Gly Glu Gln Leu Ala Ala Gly Ala Pro Gly Arg Asn Gly Gly
        2735                2740                2745

GAG CTG TAC CGG GTC GAC TGG ACG GTG CTG CCG GAG CCC GCC GAG GTG    28304
Glu Leu Tyr Arg Val Asp Trp Thr Val Leu Pro Glu Pro Ala Glu Val
2750                2755                2760                2765

CCC GCG CCG CGC TGG GCC CTC CTC GGC GAG GAC CAC GCC GGC CTG GCC    28352
Pro Ala Pro Arg Trp Ala Leu Leu Gly Glu Asp His Ala Gly Leu Ala
                2770                2775                2780

GAT GTG CTC GGA GGG ACG GGC GGC TGC GAG CGG TAC GAC ACC CTC        28400
Asp Val Leu Gly Gly Thr Gly Gly Cys Glu Arg Tyr Asp Thr Leu
            2785                2790                2795

ACC GGC CTG CTG GAG GCC ACC ACC CGG TCG GCC GGC GGA ATC CTG CCC    28448
Thr Gly Leu Leu Glu Ala Thr Thr Arg Ser Ala Gly Gly Ile Leu Pro
    2800                2805                2810

GAC ATC GTC GCG CTC TCC TTG CCC ACC GCC CCG GAG CCC GGC CCC CAG    28496
Asp Ile Val Ala Leu Ser Leu Pro Thr Ala Pro Glu Pro Gly Pro Gln
        2815                2820                2825

GCG GTG CGC GAG GTG CTG TCC CAG GCG CTC GAC GCC GCC CAG GCG TGG    28544
Ala Val Arg Glu Val Leu Ser Gln Ala Leu Asp Ala Ala Gln Ala Trp
2830                2835                2840                2845

CTG GCC GCC GGC GCC GAG ACC GCC TCC GCC CGG CTG GTG TTC GTC ACC    28592
Leu Ala Ala Gly Ala Glu Thr Ala Ser Ala Arg Leu Val Phe Val Thr
                2850                2855                2860

GGC GGC GCG GTG GCC ACC ACG GCC GAC GAA ACC GTG CGC GAC ATC GCG    28640
Gly Gly Ala Val Ala Thr Thr Ala Asp Glu Thr Val Arg Asp Ile Ala
            2865                2870                2875

GCG GCC GCC GTC TGG GGC CTG GTC CGC TCG GCG CAG TCC GAG GAA CCC    28688
Ala Ala Ala Val Trp Gly Leu Val Arg Ser Ala Gln Ser Glu Glu Pro
    2880                2885                2890

GAC CGC ATG GTC CTG CTC GAC CTG GAC GGC GAG CGG CCC ACC GCG CGG    28736
Asp Arg Met Val Leu Leu Asp Leu Asp Gly Glu Arg Pro Thr Ala Arg
        2895                2900                2905

ACG CTG GCG GCG GCG CTC GCG TCC GGC GAA CCG CAA CTC GCC GTG CGC    28784
Thr Leu Ala Ala Ala Leu Ala Ser Gly Glu Pro Gln Leu Ala Val Arg
2910                2915                2920                2925

GGC TCC ACG GTG GCC GCT CCC CGG CTG GCC CCG GCC GGG CCC GGC CCG    28832
Gly Ser Thr Val Ala Ala Pro Arg Leu Ala Pro Ala Gly Pro Gly Pro
                2930                2935                2940

GAG GAC CTC GTA CCG CCC GCC GGC ACC ACC GCC TGG CGG CTC ACC CCC    28880
Glu Asp Leu Val Pro Pro Ala Gly Thr Thr Ala Trp Arg Leu Thr Pro
            2945                2950                2955
```

```
GGC GGG GGG ACG CTG GAG GAA CTG TCG CTC GCG CCC GCC CCC GAC GCG      28928
Gly Gly Gly Thr Leu Glu Glu Leu Ser Leu Ala Pro Ala Pro Asp Ala
            2960            2965                2970

GAG GAA CCA CTG GCA CCG GGC CAG GTA CGC ATC GCC GTC CGC GCG GCG      28976
Glu Glu Pro Leu Ala Pro Gly Gln Val Arg Ile Ala Val Arg Ala Ala
        2975            2980                2985

GGC GTG AAC TTC CGC GAC GCC CTG ATC GCC CTC GGC ATG TAC CCG GGC      29024
Gly Val Asn Phe Arg Asp Ala Leu Ile Ala Leu Gly Met Tyr Pro Gly
2990            2995                3000                    3005

AAG GGA ACC ATG GGC GCC GAG GGA GCC GGC GTC GTC GTC GAG ACC GCC      29072
Lys Gly Thr Met Gly Ala Glu Gly Ala Gly Val Val Val Glu Thr Ala
            3010                3015                3020

CCC GAT GTC ACC GGC CTC TCC GCC GGA GAC CGC GTG CTC GGC ATG TGG      29120
Pro Asp Val Thr Gly Leu Ser Ala Gly Asp Arg Val Leu Gly Met Trp
        3025                3030                3035

AAC GGC GGC TTC GGG CCC CTC GTG GTG GCC GAC CAC CGC ATG GTG GCC      29168
Asn Gly Gly Phe Gly Pro Leu Val Val Ala Asp His Arg Met Val Ala
            3040                3045                3050

CCG ATC CCC CAC GGC TGG TCG TAC GCC GAG GCG GCC TCC GTG CCC GCC      29216
Pro Ile Pro His Gly Trp Ser Tyr Ala Glu Ala Ala Ser Val Pro Ala
        3055                3060                3065

GTG CTC CTC ACC TCC TAC TAC GCG CTG ACC CGG CTG GCC CGG GCC CGC      29264
Val Leu Leu Thr Ser Tyr Tyr Ala Leu Thr Arg Leu Ala Arg Ala Arg
3070            3075                3080                    3085

ACC GGA CAG ACC GTC CTC GTC CAC GCC GCC GCC GGC GGT GTC GGC ATG      29312
Thr Gly Gln Thr Val Leu Val His Ala Ala Ala Gly Gly Val Gly Met
            3090                3095                3100

GCG ACC CTC CAA CTC GCC CGC CAC CTC GGC CTG GAG GTG TAC GCC ACC      29360
Ala Thr Leu Gln Leu Ala Arg His Leu Gly Leu Glu Val Tyr Ala Thr
        3105                3110                3115

GCG AGC ACC GGC AAA TGG GAC GCC CTG CAG AAG CAC GGC ATC CCC GAC      29408
Ala Ser Thr Gly Lys Trp Asp Ala Leu Gln Lys His Gly Ile Pro Asp
        3120                3125                3130

GAC CGC ATC GCC GAC TCC CGC ACC CTG GAC TTC GCC GAG CGC TTC CTG      29456
Asp Arg Ile Ala Asp Ser Arg Thr Leu Asp Phe Ala Glu Arg Phe Leu
        3135                3140                3145

TCC CGG ACG GGC GGC CGG GGT GTC GAC ATC GTG CTG AAC TCC CTG GCC      29504
Ser Arg Thr Gly Gly Arg Gly Val Asp Ile Val Leu Asn Ser Leu Ala
3150            3155                3160                    3165

GGC GAG TTC GTC GAC GCC TCA CTG CGG CTG CTG CCG CGC GGC GGG CAC      29552
Gly Glu Phe Val Asp Ala Ser Leu Arg Leu Leu Pro Arg Gly Gly His
        3170                3175                3180

TTC CTG GAA CTC GGC AAG GCC GAC GTC CGC GAC CCC CGG CGG ATC GCC      29600
Phe Leu Glu Leu Gly Lys Ala Asp Val Arg Asp Pro Arg Arg Ile Ala
            3185                3190                3195

GCC GCC CAT CCG GGC ACC GAC TAC CGG GCG TTC GAC CTG GTG CAG GCC      29648
Ala Ala His Pro Gly Thr Asp Tyr Arg Ala Phe Asp Leu Val Gln Ala
        3200                3205                3210

GGT CCC GAC ACC GTC GGG GAG ATG CTC GGG GAA CTG CTG GAA CTG TTC      29696
Gly Pro Asp Thr Val Gly Glu Met Leu Gly Glu Leu Leu Glu Leu Phe
        3215                3220                3225

GCG GCC GGA GCG CTG CGC CCG CTG CCG CTC ACC GCC TAC GGC ATA CGC      29744
Ala Ala Gly Ala Leu Arg Pro Leu Pro Leu Thr Ala Tyr Gly Ile Arg
3230            3235                3240                    3245

GAC GCC CGC ACC GCC TTG CGC ACC CTC AGC CAG GCC CGG CAC ACC GGC      29792
Asp Ala Arg Thr Ala Leu Arg Thr Leu Ser Gln Ala Arg His Thr Gly
        3250                3255                3260

AAG CTC GTG CTG ACG GTG CCT GCC GGA TTC GAC ACC CAC CGC ACG GTG      29840
Lys Leu Val Leu Thr Val Pro Ala Gly Phe Asp Thr His Arg Thr Val
            3265                3270                3275
```

| | | | | | | | | | | | | | | | | |
|---|---|---|---|---|---|---|---|---|---|---|---|---|---|---|---|---|
| CTC | CTC | ACC | GGC | GGC | ACG | GGC | ACG | CTC | GGC | CAG | ACA | CTC | GCC | CGC | CAT | 29888 |
| Leu | Leu | Thr | Gly | Gly | Thr | Gly | Thr | Leu | Gly | Gln | Thr | Leu | Ala | Arg | His | |
| | | 3280 | | | | 3285 | | | | | | 3290 | | | | |
| CTG | GTC | AAC | CGC | CAC | GGC | GTA | CGG | CAC | CTG | CTG | CTC | GCC | GGC | CGC | ACC | 29936 |
| Leu | Val | Asn | Arg | His | Gly | Val | Arg | His | Leu | Leu | Leu | Ala | Gly | Arg | Thr | |
| | | 3295 | | | | 3300 | | | | | | 3305 | | | | |
| GGC | GCG | GCG | GCC | GAG | GGC | GTC | GCG | GAA | CTG | ATT | GGT | GAA | CTG | GGC | GAG | 29984 |
| Gly | Ala | Ala | Ala | Glu | Gly | Val | Ala | Glu | Leu | Ile | Gly | Glu | Leu | Gly | Glu | |
| 3310 | | | | | 3315 | | | | 3320 | | | | | | 3325 | |
| TTG | GGC | GCC | GAG | GTC | CGG | GTC | GCG | GCC | TGC | GAC | GCG | GCC | GAC | CGG | CAG | 30032 |
| Leu | Gly | Ala | Glu | Val | Arg | Val | Ala | Ala | Cys | Asp | Ala | Ala | Asp | Arg | Gln | |
| | | | | 3330 | | | | 3335 | | | | | 3340 | | | |
| CGG | CTC | ACC | GAA | CTC | CTC | GCC | GGA | ATC | CCC | GTC | GAG | CAC | CCG | CTC | GGC | 30080 |
| Arg | Leu | Thr | Glu | Leu | Leu | Ala | Gly | Ile | Pro | Val | Glu | His | Pro | Leu | Gly | |
| | | | 3345 | | | | 3350 | | | | | 3355 | | | | |
| GCC | GTC | GTC | CAC | GCC | GCG | GGC | ACC | CTC | GAC | GAC | GGC | ACC | ATC | CCC | TCA | 30128 |
| Ala | Val | Val | His | Ala | Ala | Gly | Thr | Leu | Asp | Asp | Gly | Thr | Ile | Pro | Ser | |
| | | 3360 | | | | 3365 | | | | | | 3370 | | | | |
| CTG | ACC | GGC | GAG | AAC | ATC | GAC | AAC | GTG | CTG | CGG | CCC | AAG | GCC | GAC | GCC | 30176 |
| Leu | Thr | Gly | Glu | Asn | Ile | Asp | Asn | Val | Leu | Arg | Pro | Lys | Ala | Asp | Ala | |
| | | 3375 | | | | 3380 | | | | | | 3385 | | | | |
| GTG | CTC | AAC | CTG | CAC | GAG | CTG | ACC | CGC | GAC | GCC | GAC | CTC | TCG | GCG | TTC | 30224 |
| Val | Leu | Asn | Leu | His | Glu | Leu | Thr | Arg | Asp | Ala | Asp | Leu | Ser | Ala | Phe | |
| 3390 | | | | | 3395 | | | | 3400 | | | | | | 3405 | |
| GTC | CTC | TAC | TCG | TCC | TCC | TCG | GCG | CTG | CTC | GGC | AGC | CCC | GGC | CAG | GGC | 30272 |
| Val | Leu | Tyr | Ser | Ser | Ser | Ser | Ala | Leu | Leu | Gly | Ser | Pro | Gly | Gln | Gly | |
| | | | | 3410 | | | | 3415 | | | | | 3420 | | | |
| GCC | TAC | GCC | GCG | GCC | AAC | GCC | TTC | CTG | GAC | GGC | TTC | GCC | CGA | TAC | CGC | 30320 |
| Ala | Tyr | Ala | Ala | Ala | Asn | Ala | Phe | Leu | Asp | Gly | Phe | Ala | Arg | Tyr | Arg | |
| | | | | 3425 | | | | 3430 | | | | | 3435 | | | |
| AAG | GGC | CTC | GGG | CTG | CCG | GCG | CTC | TCG | CTG | GCC | TGG | GGA | CTG | TGG | GGC | 30368 |
| Lys | Gly | Leu | Gly | Leu | Pro | Ala | Leu | Ser | Leu | Ala | Trp | Gly | Leu | Trp | Gly | |
| | | | 3440 | | | | 3445 | | | | | 3450 | | | | |
| AGC | AAC | AGC | CGC | ATG | GCG | GGC | CAC | CTC | GAC | CAG | TCG | GGC | ATG | CAA | CGG | 30416 |
| Ser | Asn | Ser | Arg | Met | Ala | Gly | His | Leu | Asp | Gln | Ser | Gly | Met | Gln | Arg | |
| | | | 3455 | | | | 3460 | | | | | 3465 | | | | |
| CGC | CTG | AAC | CGG | AGC | GGC | ATC | ATG | GCG | CTC | ACC | GAC | GCC | GAG | GGC | CTC | 30464 |
| Arg | Leu | Asn | Arg | Ser | Gly | Ile | Met | Ala | Leu | Thr | Asp | Ala | Glu | Gly | Leu | |
| 3470 | | | | | 3475 | | | | 3480 | | | | | | 3485 | |
| GCC | CTG | TTC | GAC | GCC | GCA | CAG | GAC | GGG | GGG | GAC | GCG | CTG | CTG | GTG | CCG | 30512 |
| Ala | Leu | Phe | Asp | Ala | Ala | Gln | Asp | Gly | Gly | Asp | Ala | Leu | Leu | Val | Pro | |
| | | | | 3490 | | | | 3495 | | | | | 3500 | | | |
| ATG | CGG | CTC | AAC | CGG | ACG | GCC | CTT | CGC | GCC | TCG | GGA | CGG | ATC | ACC | CCG | 30560 |
| Met | Arg | Leu | Asn | Arg | Thr | Ala | Leu | Arg | Ala | Ser | Gly | Arg | Ile | Thr | Pro | |
| | | | | 3505 | | | | 3510 | | | | | 3515 | | | |
| TTC | CTC | AGC | GGC | TTG | GCC | GGC | GGC | GGG | CCG | GCG | GCG | GGG | GAG | AGG | CGC | 30608 |
| Phe | Leu | Ser | Gly | Leu | Ala | Gly | Gly | Gly | Pro | Ala | Ala | Gly | Glu | Arg | Arg | |
| | | | 3520 | | | | 3525 | | | | | 3530 | | | | |
| CCC | GAG | GTG | GCA | GCC | GTA | TCC | GGG | ACA | CTC | GCG | GAA | CGG | CTG | ACC | GGG | 30656 |
| Pro | Glu | Val | Ala | Ala | Val | Ser | Gly | Thr | Leu | Ala | Glu | Arg | Leu | Thr | Gly | |
| | | | 3535 | | | | 3540 | | | | | 3545 | | | | |
| CTC | ACG | GCA | CAG | GAA | GGG | CAC | GCC | CTC | GTC | CTG | GCC | GAG | ATC | CGC | GCC | 30704 |
| Leu | Thr | Ala | Gln | Glu | Gly | His | Ala | Leu | Val | Leu | Ala | Glu | Ile | Arg | Ala | |
| 3550 | | | | | 3555 | | | | 3560 | | | | | | 3565 | |
| CAC | GCG | GCG | GCG | GTG | CTG | GGC | CAC | GGC | TCC | GAC | GAC | TCG | ATC | CCC | GAG | 30752 |
| His | Ala | Ala | Ala | Val | Leu | Gly | His | Gly | Ser | Asp | Asp | Ser | Ile | Pro | Glu | |
| | | | | 3570 | | | | 3575 | | | | | 3580 | | | |
| GAC | CGG | GCC | TTC | AAG | GAC | CTC | GGC | TTC | GAC | TCG | CTC | ACC | GCC | GTG | GAG | 30800 |
| Asp | Arg | Ala | Phe | Lys | Asp | Leu | Gly | Phe | Asp | Ser | Leu | Thr | Ala | Val | Glu | |
| | | | | 3585 | | | | 3590 | | | | | 3595 | | | |

| | | | | | | | | | | | | | | | | |
|---|---|---|---|---|---|---|---|---|---|---|---|---|---|---|---|---|
| ATG | CGC | AAC | CGG | CTG | AGC | GCG | GCC | ACC | GGC | CTC | CGG | CTG | CCC | GCC | ACC | 30848 |
| Met | Arg | Asn | Arg | Leu | Ser | Ala | Ala | Thr | Gly | Leu | Arg | Leu | Pro | Ala | Thr | |
| | | 3600 | | | | 3605 | | | | 3610 | | | | | | |
| CTC | GTC | TTC | GAC | CAC | CCG | ACC | CCG | GGC | GAG | CTG | GCC | GGC | CAC | CTG | AGT | 30896 |
| Leu | Val | Phe | Asp | His | Pro | Thr | Pro | Gly | Glu | Leu | Ala | Gly | His | Leu | Ser | |
| 3615 | | | | | 3620 | | | | | 3625 | | | | | | |
| GCT | GAA | CTG | TCC | GCC | GAC | GAT | GCC | CCG | GGC | AGC | GCC | TCC | CCG | CTT | ACC | 30944 |
| Ala | Glu | Leu | Ser | Ala | Asp | Asp | Ala | Pro | Gly | Ser | Ala | Ser | Pro | Leu | Thr | |
| 3630 | | | | | 3635 | | | | | 3640 | | | | | 3645 | |
| GAA | CTC | GAC | CGT | TTC | GAA | GCC | CTG | TTC | ACC | GCT | CTC | GCA | CCG | GGG | ACC | 30992 |
| Glu | Leu | Asp | Arg | Phe | Glu | Ala | Leu | Phe | Thr | Ala | Leu | Ala | Pro | Gly | Thr | |
| | | | | 3650 | | | | | 3655 | | | | | 3660 | | |
| ACC | AAG | GAC | ACC | CCG | GGC | GGG | GCC | GGG | GCA | CTG | ATG | ATC | GAC | GAG | GCC | 31040 |
| Thr | Lys | Asp | Thr | Pro | Gly | Gly | Ala | Gly | Ala | Leu | Met | Ile | Asp | Glu | Ala | |
| | | | 3665 | | | | | 3670 | | | | | 3675 | | | |
| GAG | CGC | CAA | GAG | ATC | GCC | GGG | CGG | CTC | GCG | GCG | CTG | GCC | GGT | CTG | TGG | 31088 |
| Glu | Arg | Gln | Glu | Ile | Ala | Gly | Arg | Leu | Ala | Ala | Leu | Ala | Gly | Leu | Trp | |
| | | 3680 | | | | | 3685 | | | | | 3690 | | | | |
| AAC | CGG | CTG | CAC | GGC | ACC | ACG | ACG | GCT | CCT | GAG | GAC | GGC | GAC | ACC | GTC | 31136 |
| Asn | Arg | Leu | His | Gly | Thr | Thr | Thr | Ala | Pro | Glu | Asp | Gly | Asp | Thr | Val | |
| | 3695 | | | | | 3700 | | | | | 3705 | | | | | |
| GCG | GAC | GCC | CTG | GAA | GCC | GCG | GAC | GAC | CAC | GAG | ATC | TTC | GCA | TTC | CTC | 31184 |
| Ala | Asp | Ala | Leu | Glu | Ala | Ala | Asp | Asp | His | Glu | Ile | Phe | Ala | Phe | Leu | |
| 3710 | | | | | 3715 | | | | | 3720 | | | | | 3725 | |
| GAC | GAG | CGG | TTC | TGA | GCCCGCCCCA | | GCGACAGCAC | | AGGTGAAAAC | | AC | ATG | GCC | | | 31237 |
| Asp | Glu | Arg | Phe | | | | | | | | | Met | Ala | | | |
| | | | | | | | | | | | | 1 | | | | |
| AAC | GCG | AAC | GAG | CAG | CAA | CTC | CGT | GCC | TAT | CTG | AAG | CGA | GCG | ACG | ACC | 31285 |
| Asn | Ala | Asn | Glu | Gln | Gln | Leu | Arg | Ala | Tyr | Leu | Lys | Arg | Ala | Thr | Thr | |
| | | 5 | | | | | 10 | | | | | 15 | | | | |
| GAA | CTC | CAC | CGT | ACC | TCC | GAA | CAA | CTG | AGG | GAG | GAG | CGG | GCA | CGG | GCC | 31333 |
| Glu | Leu | His | Arg | Thr | Ser | Glu | Gln | Leu | Arg | Glu | Glu | Arg | Ala | Arg | Ala | |
| | 20 | | | | | 25 | | | | | 30 | | | | | |
| CAC | GAG | CCG | ATC | GCC | GTC | GTC | GGC | ATG | GCC | TGC | CGC | TAC | CCC | GGA | GGC | 31381 |
| His | Glu | Pro | Ile | Ala | Val | Val | Gly | Met | Ala | Cys | Arg | Tyr | Pro | Gly | Gly | |
| 35 | | | | | 40 | | | | | 45 | | | | | 50 | |
| GCG | AAC | ACC | CCC | GAA | CAG | TTC | TGG | GAA | CTG | CTC | GAC | ACC | GGC | ACC | GAC | 31429 |
| Ala | Asn | Thr | Pro | Glu | Gln | Phe | Trp | Glu | Leu | Leu | Asp | Thr | Gly | Thr | Asp | |
| | | | | 55 | | | | | 60 | | | | | 65 | | |
| GCC | GCC | GCG | CCG | ATG | CCC | TCC | GAC | CGG | GGA | TGG | GAC | ACC | CAC | GGG | CTG | 31477 |
| Ala | Ala | Ala | Pro | Met | Pro | Ser | Asp | Arg | Gly | Trp | Asp | Thr | His | Gly | Leu | |
| | | | 70 | | | | | 75 | | | | | 80 | | | |
| TAC | GAC | CCC | GAC | CCG | GCG | GCA | GCG | GGG | CGC | ACC | TAC | TGC | CGG | GAG | GGC | 31525 |
| Tyr | Asp | Pro | Asp | Pro | Ala | Ala | Ala | Gly | Arg | Thr | Tyr | Cys | Arg | Glu | Gly | |
| | | 85 | | | | | 90 | | | | | 95 | | | | |
| GGC | TTC | CTC | CAC | GAC | GCG | GGC | GAC | TTC | GAC | GCG | GAC | TTC | TTC | GGG | ATT | 31573 |
| Gly | Phe | Leu | His | Asp | Ala | Gly | Asp | Phe | Asp | Ala | Asp | Phe | Phe | Gly | Ile | |
| | 100 | | | | | 105 | | | | | 110 | | | | | |
| TCG | CCG | CGT | GAG | GCG | GTG | GCG | ATG | GAT | CCG | CAG | CAG | CGG | CTG | TTG | CTG | 31621 |
| Ser | Pro | Arg | Glu | Ala | Val | Ala | Met | Asp | Pro | Gln | Gln | Arg | Leu | Leu | Leu | |
| 115 | | | | | 120 | | | | | 125 | | | | | 130 | |
| GAG | ACC | TCC | TGG | GAG | GCG | ATC | GAA | GCG | GCC | GGT | ATC | GAC | CCG | CGA | GGA | 31669 |
| Glu | Thr | Ser | Trp | Glu | Ala | Ile | Glu | Ala | Ala | Gly | Ile | Asp | Pro | Arg | Gly | |
| | | | | 135 | | | | | 140 | | | | | 145 | | |
| CTC | CGC | GGC | AGC | CGC | ACC | GGG | GTG | TAC | GTG | GGC | GCC | TGG | GAC | AGC | GGC | 31717 |
| Leu | Arg | Gly | Ser | Arg | Thr | Gly | Val | Tyr | Val | Gly | Ala | Trp | Asp | Ser | Gly | |
| | | | 150 | | | | | 155 | | | | | 160 | | | |
| TAC | ACC | GGC | CAG | GCG | CAC | GCG | CCC | TCG | GCC | GAG | TTG | GAG | GCC | GAC | CTG | 31765 |
| Tyr | Thr | Gly | Gln | Ala | His | Ala | Pro | Ser | Ala | Glu | Leu | Glu | Ala | Asp | Leu | |
| | | 165 | | | | | 170 | | | | | 175 | | | | |

| | | | | | | | | | | | | | | | | |
|---|---|---|---|---|---|---|---|---|---|---|---|---|---|---|---|---|
| CTG | ACC | GGC | GGC | GTC | GTC | AGC | TTC | ACC | TCC | GGC | CGT | ATC | GCC | TAC | ACG | 31813 |
| Leu | Thr | Gly | Gly | Val | Val | Ser | Phe | Thr | Ser | Gly | Arg | Ile | Ala | Tyr | Thr | |
| | 180 | | | | | 185 | | | | | 190 | | | | | |
| CTG | GGG | CTG | GAG | GGT | CCG | GCC | TTG | ACC | GTG | GAC | ACC | GCG | TGT | TCG | TCG | 31861 |
| Leu | Gly | Leu | Glu | Gly | Pro | Ala | Leu | Thr | Val | Asp | Thr | Ala | Cys | Ser | Ser | |
| 195 | | | | | 200 | | | | | 205 | | | | | 210 | |
| TCG | CTG | GTC | GCC | CTG | CAC | AAC | GCG | GCG | CAG | GCG | CTG | CGG | CGC | GGC | GAA | 31909 |
| Ser | Leu | Val | Ala | Leu | His | Asn | Ala | Ala | Gln | Ala | Leu | Arg | Arg | Gly | Glu | |
| | | | | 215 | | | | | 220 | | | | | 225 | | |
| TGC | GAC | CTG | GCG | TTG | GCC | GGT | GGT | GTG | ACG | GTG | ATG | GCG | ACC | CCG | GCG | 31957 |
| Cys | Asp | Leu | Ala | Leu | Ala | Gly | Gly | Val | Thr | Val | Met | Ala | Thr | Pro | Ala | |
| | | | 230 | | | | | 235 | | | | | 240 | | | |
| GTG | TTC | GTC | CAG | TTC | GCC | CGG | CAG | CGA | GGG | CTG | GCG | CCG | GAC | GGC | CGC | 32005 |
| Val | Phe | Val | Gln | Phe | Ala | Arg | Gln | Arg | Gly | Leu | Ala | Pro | Asp | Gly | Arg | |
| | | 245 | | | | | 250 | | | | | 255 | | | | |
| TGC | AAG | GCG | TTC | GCC | GAC | GCC | GCC | GAC | GGC | TTC | GGC | CCC | GCC | GAG | GGT | 32053 |
| Cys | Lys | Ala | Phe | Ala | Asp | Ala | Ala | Asp | Gly | Phe | Gly | Pro | Ala | Glu | Gly | |
| | 260 | | | | | 265 | | | | | 270 | | | | | |
| GTG | GGG | ATG | GTG | CTG | GTG | GAG | CGG | TTG | TCG | GAT | GCC | CGG | CGG | TTG | GGG | 32101 |
| Val | Gly | Met | Val | Leu | Val | Glu | Arg | Leu | Ser | Asp | Ala | Arg | Arg | Leu | Gly | |
| 275 | | | | | 280 | | | | | 285 | | | | | 290 | |
| CAT | CCG | GTG | TTG | GCG | GTG | GTG | TGT | GGG | TCG | GCG | GTG | AAT | CAG | GAC | GGT | 32149 |
| His | Pro | Val | Leu | Ala | Val | Val | Cys | Gly | Ser | Ala | Val | Asn | Gln | Asp | Gly | |
| | | | | 295 | | | | | 300 | | | | | 305 | | |
| GCG | TCG | AAT | GGT | TTG | ACG | GCG | CCG | AGT | GGT | CCG | TCG | CAG | GAG | CGG | GTG | 32197 |
| Ala | Ser | Asn | Gly | Leu | Thr | Ala | Pro | Ser | Gly | Pro | Ser | Gln | Glu | Arg | Val | |
| | | | 310 | | | | | 315 | | | | | 320 | | | |
| ATT | CGT | CAG | GCG | TTG | GGG | AAT | GCG | CGG | TTG | ACG | GTG | GCG | GAT | GTG | GAT | 32245 |
| Ile | Arg | Gln | Ala | Leu | Gly | Asn | Ala | Arg | Leu | Thr | Val | Ala | Asp | Val | Asp | |
| | | 325 | | | | | 330 | | | | | 335 | | | | |
| GTG | GTG | GAG | GCG | CAT | GGG | ACG | GGG | ACG | CGG | CTG | GGT | GAT | CCG | ATC | GAG | 32293 |
| Val | Val | Glu | Ala | His | Gly | Thr | Gly | Thr | Arg | Leu | Gly | Asp | Pro | Ile | Glu | |
| | 340 | | | | | 345 | | | | | 350 | | | | | |
| GCG | CAG | GCG | TTG | CTG | GGG | ACG | TAT | GGG | CGG | GAT | CGT | GAT | GGT | GGG | CGT | 32341 |
| Ala | Gln | Ala | Leu | Leu | Gly | Thr | Tyr | Gly | Arg | Asp | Arg | Asp | Gly | Gly | Arg | |
| 355 | | | | | 360 | | | | | 365 | | | | | 370 | |
| CCG | GTG | TGG | TTG | GGG | TCG | TTG | AAG | TCG | AAT | ATT | GGT | CAT | GCT | CAG | GCG | 32389 |
| Pro | Val | Trp | Leu | Gly | Ser | Leu | Lys | Ser | Asn | Ile | Gly | His | Ala | Gln | Ala | |
| | | | | 375 | | | | | 380 | | | | | 385 | | |
| GCT | GCG | GGG | GTG | GCT | GGT | GTG | ATC | AAG | ATG | GTG | TTG | GCG | ATG | CGG | TAT | 32437 |
| Ala | Ala | Gly | Val | Ala | Gly | Val | Ile | Lys | Met | Val | Leu | Ala | Met | Arg | Tyr | |
| | | | 390 | | | | | 395 | | | | | 400 | | | |
| GGG | TGG | TTG | CCG | CGG | ACG | TTG | CAT | GTG | GAT | GAG | CCG | AGC | CGG | CAT | GTG | 32485 |
| Gly | Trp | Leu | Pro | Arg | Thr | Leu | His | Val | Asp | Glu | Pro | Ser | Arg | His | Val | |
| | | 405 | | | | | 410 | | | | | 415 | | | | |
| GAC | TGG | TCG | GCT | GGT | GGT | GTG | CGG | TTG | CTG | ACC | GAG | GCG | CGG | GAG | TGG | 32533 |
| Asp | Trp | Ser | Ala | Gly | Gly | Val | Arg | Leu | Leu | Thr | Glu | Ala | Arg | Glu | Trp | |
| | 420 | | | | | 425 | | | | | 430 | | | | | |
| CCG | GGG | GTG | GAC | CGG | CCG | CGT | CGG | GCG | GCG | GTC | TCC | GCC | TTT | GGT | GTC | 32581 |
| Pro | Gly | Val | Asp | Arg | Pro | Arg | Arg | Ala | Ala | Val | Ser | Ala | Phe | Gly | Val | |
| 435 | | | | | 440 | | | | | 445 | | | | | 450 | |
| AGT | GGT | ACC | AAC | GCC | CAT | CTG | ATC | CTC | GAA | GCC | CCC | GAC | ACC | GCC | GAG | 32629 |
| Ser | Gly | Thr | Asn | Ala | His | Leu | Ile | Leu | Glu | Ala | Pro | Asp | Thr | Ala | Glu | |
| | | | | 455 | | | | | 460 | | | | | 465 | | |
| GCG | GAG | AGC | GCC | ACG | ACC | CCG | GTC | CGC | TCT | GAG | GTG | TCG | GAG | TCT | GCT | 32677 |
| Ala | Glu | Ser | Ala | Thr | Thr | Pro | Val | Arg | Ser | Glu | Val | Ser | Glu | Ser | Ala | |
| | | | 470 | | | | | 475 | | | | | 480 | | | |
| GCG | GTC | CTC | GAT | GCC | CGC | AGT | GGT | GTG | GTG | CCG | GTG | GTG | GTT | TCG | GGG | 32725 |
| Ala | Val | Leu | Asp | Ala | Arg | Ser | Gly | Val | Val | Pro | Val | Val | Val | Ser | Gly | |
| | | 485 | | | | | 490 | | | | | 495 | | | | |

| | | | | | | | | | | | | | | | | |
|---|---|---|---|---|---|---|---|---|---|---|---|---|---|---|---|---|
| CGT | TCG | CGG | GTG | GTG | GTG | CGG | GAG | GCT | GCG | GGC | CGG | TTG | GCG | GAG | GTG | 32773 |
| Arg | Ser | Arg | Val | Val | Val | Arg | Glu | Ala | Ala | Gly | Arg | Leu | Ala | Glu | Val | |
| | 500 | | | | 505 | | | | | 510 | | | | | | |
| GTG | GAG | GCC | GGT | GGT | GTG | GGG | CTG | GCG | GAT | GTG | GCG | GTG | ACG | ATG | GCG | 32821 |
| Val | Glu | Ala | Gly | Gly | Val | Gly | Leu | Ala | Asp | Val | Ala | Val | Thr | Met | Ala | |
| 515 | | | | | 520 | | | | | 525 | | | | | 530 | |
| GGC | CGG | TCG | CGG | TTT | GGG | TAT | CGG | GCG | GTT | GTG | CTG | GCT | CGG | GGT | GAG | 32869 |
| Gly | Arg | Ser | Arg | Phe | Gly | Tyr | Arg | Ala | Val | Val | Leu | Ala | Arg | Gly | Glu | |
| | | | | 535 | | | | | 540 | | | | | | 545 | |
| GCT | GAG | CTT | GCC | GGG | CGT | TTG | CGG | GCG | TTG | GCG | GGG | GGT | GAT | CCG | GAC | 32917 |
| Ala | Glu | Leu | Ala | Gly | Arg | Leu | Arg | Ala | Leu | Ala | Gly | Gly | Asp | Pro | Asp | |
| | | | 550 | | | | | 555 | | | | | 560 | | | |
| GCG | GGT | GTG | GTC | ACG | GGT | GCG | GTG | GTG | GAC | CCG | GAG | ACG | GGG | TCC | GGT | 32965 |
| Ala | Gly | Val | Val | Thr | Gly | Ala | Val | Val | Asp | Pro | Glu | Thr | Gly | Ser | Gly | |
| | | | 565 | | | | 570 | | | | | 575 | | | | |
| GGT | GGG | GGG | GTG | GTG | TTG | GTT | TTC | CCT | GGT | CAG | GGG | ACG | CAG | TGG | GTG | 33013 |
| Gly | Gly | Gly | Val | Val | Leu | Val | Phe | Pro | Gly | Gln | Gly | Thr | Gln | Trp | Val | |
| | 580 | | | | | 585 | | | | | 590 | | | | | |
| GGG | ATG | GGT | GCG | GGG | CTG | CTG | GGG | TCT | TCG | GAG | GTG | TTT | GCG | GCG | TCG | 33061 |
| Gly | Met | Gly | Ala | Gly | Leu | Leu | Gly | Ser | Ser | Glu | Val | Phe | Ala | Ala | Ser | |
| 595 | | | | | 600 | | | | | 605 | | | | | 610 | |
| ATG | CGG | GAG | TGT | GCG | CGG | GCG | CTG | AGT | GTT | CAT | GTG | GGG | TGG | GAT | TTG | 33109 |
| Met | Arg | Glu | Cys | Ala | Arg | Ala | Leu | Ser | Val | His | Val | Gly | Trp | Asp | Leu | |
| | | | | 615 | | | | | 620 | | | | | 625 | | |
| CTG | GAG | GTG | GTG | TCG | GGC | GGG | GCC | GGG | TTG | GAG | CGG | GTG | GAT | GTG | GTG | 33157 |
| Leu | Glu | Val | Val | Ser | Gly | Gly | Ala | Gly | Leu | Glu | Arg | Val | Asp | Val | Val | |
| | | | 630 | | | | | 635 | | | | | 640 | | | |
| CAG | CCG | GTG | ACG | TGG | GCG | GTG | ATG | GTG | TCG | CTG | GCC | CGG | TAC | TGG | CAG | 33205 |
| Gln | Pro | Val | Thr | Trp | Ala | Val | Met | Val | Ser | Leu | Ala | Arg | Tyr | Trp | Gln | |
| | | | 645 | | | | 650 | | | | | 655 | | | | |
| GCG | ATG | GGT | GTG | GAC | GTG | GCT | GCG | GTG | GTG | GGT | CAT | TCC | CAG | GGG | GAG | 33253 |
| Ala | Met | Gly | Val | Asp | Val | Ala | Ala | Val | Val | Gly | His | Ser | Gln | Gly | Glu | |
| | 660 | | | | | 665 | | | | | 670 | | | | | |
| ATC | GCT | GCT | GCC | ACG | GTG | GCG | GGG | GCG | TTG | TCG | CTG | GAG | GAT | GCG | GCG | 33301 |
| Ile | Ala | Ala | Ala | Thr | Val | Ala | Gly | Ala | Leu | Ser | Leu | Glu | Asp | Ala | Ala | |
| 675 | | | | | 680 | | | | | 685 | | | | | 690 | |
| GCT | GTG | GTC | GCT | CTG | CGG | GCG | GGG | TTG | ATT | GGC | CGG | TAT | CTG | GCG | GGT | 33349 |
| Ala | Val | Val | Ala | Leu | Arg | Ala | Gly | Leu | Ile | Gly | Arg | Tyr | Leu | Ala | Gly | |
| | | | | 695 | | | | | 700 | | | | | 705 | | |
| CGT | GGT | GCG | ATG | GCG | GCT | GTT | CCG | CTG | CCT | GCC | GGC | GAG | GTC | GAG | GCC | 33397 |
| Arg | Gly | Ala | Met | Ala | Ala | Val | Pro | Leu | Pro | Ala | Gly | Glu | Val | Glu | Ala | |
| | | | 710 | | | | | 715 | | | | | 720 | | | |
| GGG | CTG | GCG | AAG | TGG | CCG | GGT | GTG | GAG | GTC | GCG | GCG | GTC | AAC | GGT | CCG | 33445 |
| Gly | Leu | Ala | Lys | Trp | Pro | Gly | Val | Glu | Val | Ala | Ala | Val | Asn | Gly | Pro | |
| | | 725 | | | | | 730 | | | | | 735 | | | | |
| GCG | TCT | ACG | GTG | GTT | TCC | GGG | GAT | CGG | CGG | GCG | GTG | GCC | GGT | TAT | GTG | 33493 |
| Ala | Ser | Thr | Val | Val | Ser | Gly | Asp | Arg | Arg | Ala | Val | Ala | Gly | Tyr | Val | |
| | 740 | | | | | 745 | | | | | 750 | | | | | |
| GCC | GTC | TGT | CAG | GCG | GAG | GGT | GTG | CAG | GCT | CGG | TTG | ATA | CCG | GTG | GAC | 33541 |
| Ala | Val | Cys | Gln | Ala | Glu | Gly | Val | Gln | Ala | Arg | Leu | Ile | Pro | Val | Asp | |
| 755 | | | | | 760 | | | | | 765 | | | | | 770 | |
| TAC | GCC | TCT | CAC | TCC | CGC | CAT | GTG | GAG | GAC | CTG | AAG | GGC | GAG | TTG | GAG | 33589 |
| Tyr | Ala | Ser | His | Ser | Arg | His | Val | Glu | Asp | Leu | Lys | Gly | Glu | Leu | Glu | |
| | | | | 775 | | | | | 780 | | | | | 785 | | |
| CGG | GTG | CTG | TCC | GGT | ATC | CGC | CCC | CGC | AGT | CCG | CGG | GTG | CCG | GTG | TGT | 33637 |
| Arg | Val | Leu | Ser | Gly | Ile | Arg | Pro | Arg | Ser | Pro | Arg | Val | Pro | Val | Cys | |
| | | | 790 | | | | | 795 | | | | | 800 | | | |
| TCC | ACC | GTC | GCC | GGA | GAG | CAG | CCG | GGC | GAG | CCG | GTT | TTC | GAT | GCG | GGG | 33685 |
| Ser | Thr | Val | Ala | Gly | Glu | Gln | Pro | Gly | Glu | Pro | Val | Phe | Asp | Ala | Gly | |
| | | 805 | | | | | 810 | | | | | 815 | | | | |

| | | | | | | | | | | | | | | | | |
|---|---|---|---|---|---|---|---|---|---|---|---|---|---|---|---|---|
| TAT | TGG | TTC | CGT | AAT | CTG | CGG | AAC | CGG | GTT | GAG | TTC | TCC | GCG | GTG | GTC | 33733 |
| Tyr | Trp | Phe | Arg | Asn | Leu | Arg | Asn | Arg | Val | Glu | Phe | Ser | Ala | Val | Val | |
| | 820 | | | | 825 | | | | | 830 | | | | | | |
| GGT | GGT | TTG | TTG | GAG | GAG | GGC | CAC | CGT | CGG | TTC | ATC | GAG | GTC | AGT | GCC | 33781 |
| Gly | Gly | Leu | Leu | Glu | Glu | Gly | His | Arg | Arg | Phe | Ile | Glu | Val | Ser | Ala | |
| 835 | | | | | 840 | | | | | 845 | | | | | 850 | |
| CAC | CCG | GTA | CTC | GTC | CAT | GCC | ATT | GAG | CAG | ACG | GCC | GAG | GCC | GCG | GAC | 33829 |
| His | Pro | Val | Leu | Val | His | Ala | Ile | Glu | Gln | Thr | Ala | Glu | Ala | Ala | Asp | |
| | | | | 855 | | | | | 860 | | | | | 865 | | |
| CGG | AGT | GTC | CAT | GCC | ACC | GGG | ACC | CTG | CGC | CGC | CAG | GAC | GAC | AGC | CCG | 33877 |
| Arg | Ser | Val | His | Ala | Thr | Gly | Thr | Leu | Arg | Arg | Gln | Asp | Asp | Ser | Pro | |
| | | | 870 | | | | 875 | | | | | 880 | | | | |
| CAC | CGC | CTG | CTG | ACC | TCC | ACC | GCC | GAG | GCC | TGG | GCC | CAC | GGC | GCC | ACC | 33925 |
| His | Arg | Leu | Leu | Thr | Ser | Thr | Ala | Glu | Ala | Trp | Ala | His | Gly | Ala | Thr | |
| | | 885 | | | | | 890 | | | | | 895 | | | | |
| CTC | ACC | TGG | GAC | CCC | GCC | CTG | CCC | CCA | GGC | CAC | CTC | ACC | ACC | CTC | CCC | 33973 |
| Leu | Thr | Trp | Asp | Pro | Ala | Leu | Pro | Pro | Gly | His | Leu | Thr | Thr | Leu | Pro | |
| 900 | | | | | 905 | | | | | 910 | | | | | | |
| ACC | TAC | CCC | TTC | AAC | CAC | CAC | CAC | TAC | TGG | CTC | GAC | ACC | ACC | CCC | ACC | 34021 |
| Thr | Tyr | Pro | Phe | Asn | His | His | His | Tyr | Trp | Leu | Asp | Thr | Thr | Pro | Thr | |
| 915 | | | | | 920 | | | | | 925 | | | | | 930 | |
| ACC | CCC | GCG | ACG | ACC | ACC | CAG | AGC | CCC | ACC | GAT | GCC | TGG | CGC | TAC | CGC | 34069 |
| Thr | Pro | Ala | Thr | Thr | Thr | Gln | Ser | Pro | Thr | Asp | Ala | Trp | Arg | Tyr | Arg | |
| | | | | 935 | | | | | 940 | | | | | 945 | | |
| GTC | ACC | TGG | AAA | GCC | CTG | ACC | GAA | GAA | TCC | ACT | CCG | GCC | TCG | TCC | CCC | 34117 |
| Val | Thr | Trp | Lys | Ala | Leu | Thr | Glu | Glu | Ser | Thr | Pro | Ala | Ser | Ser | Pro | |
| | | | 950 | | | | | 955 | | | | | 960 | | | |
| TCC | GGT | CAC | TGG | CTC | CTC | GTC | ACA | CCC | CCG | ACC | CCC | GAA | GGC | CGC | ACG | 34165 |
| Ser | Gly | His | Trp | Leu | Leu | Val | Thr | Pro | Pro | Thr | Pro | Glu | Gly | Arg | Thr | |
| | | 965 | | | | | 970 | | | | | 975 | | | | |
| CTC | GGG | GAC | CGG | GCC | GCC | GGC | GCC | CTC | GCA | CGT | CAG | GGG | GCC | ACG | GTG | 34213 |
| Leu | Gly | Asp | Arg | Ala | Ala | Gly | Ala | Leu | Ala | Arg | Gln | Gly | Ala | Thr | Val | |
| | 980 | | | | | 985 | | | | | 990 | | | | | |
| GAA | CGG | CTG | GTG | GTC | GAT | CCG | GTC | GCC | GTC | GGA | CGC | GAC | GGG | CTC | GCG | 34261 |
| Glu | Arg | Leu | Val | Val | Asp | Pro | Val | Ala | Val | Gly | Arg | Asp | Gly | Leu | Ala | |
| 995 | | | | | 1000 | | | | | 1005 | | | | | 1010 | |
| GCG | CGC | CTG | GGC | GAA | CGG | TGG | GAC | GGT | GTG | CTG | TCC | CTG | CTC | GGC | GCC | 34309 |
| Ala | Arg | Leu | Gly | Glu | Arg | Trp | Asp | Gly | Val | Leu | Ser | Leu | Leu | Gly | Ala | |
| | | | | 1015 | | | | | 1020 | | | | | 1025 | | |
| GAC | GAG | CGT | CCG | CTC | CCA | CGG | CAT | CCC | GCC | CTC | AAC | CGC | GCC | GTC | ATG | 34357 |
| Asp | Glu | Arg | Pro | Leu | Pro | Arg | His | Pro | Ala | Leu | Asn | Arg | Ala | Val | Met | |
| | | | 1030 | | | | | 1035 | | | | | 1040 | | | |
| GGC | ACC | ACG | CTG | CTC | GCC | CAG | GCC | GCT | CTG | GAC | GCA | GGA | TGC | GAG | GCG | 34405 |
| Gly | Thr | Thr | Leu | Leu | Ala | Gln | Ala | Ala | Leu | Asp | Ala | Gly | Cys | Glu | Ala | |
| | | 1045 | | | | | 1050 | | | | | 1055 | | | | |
| CGG | ATA | TGG | GCC | GTG | ACG | CGG | GAG | GCC | GTC | GCC | GTC | TCC | CCG | AGC | GAG | 34453 |
| Arg | Ile | Trp | Ala | Val | Thr | Arg | Glu | Ala | Val | Ala | Val | Ser | Pro | Ser | Glu | |
| | 1060 | | | | | 1065 | | | | | 1070 | | | | | |
| GTG | CCG | CGG | GAC | GCC | GGC | GCG | CAG | CTC | TGG | GGG | CTC | GGG | CGG | GGC | ATC | 34501 |
| Val | Pro | Arg | Asp | Ala | Gly | Ala | Gln | Leu | Trp | Gly | Leu | Gly | Arg | Gly | Ile | |
| 1075 | | | | | 1080 | | | | | 1085 | | | | | 1090 | |
| GCG | CTG | GAA | CAC | CCC | TCC | CTC | TGG | GGC | GGA | TTG | ATC | GAT | CTG | CCC | GCC | 34549 |
| Ala | Leu | Glu | His | Pro | Ser | Leu | Trp | Gly | Gly | Leu | Ile | Asp | Leu | Pro | Ala | |
| | | | | 1095 | | | | | 1100 | | | | | 1105 | | |
| GTG | CCG | GAC | GAA | CGC | GCG | TGG | GCC | AGG | GCC | GTC | CGG | CGG | CTC | GTC | CCG | 34597 |
| Val | Pro | Asp | Glu | Arg | Ala | Trp | Ala | Arg | Ala | Val | Arg | Arg | Leu | Val | Pro | |
| | | | 1110 | | | | | 1115 | | | | | 1120 | | | |
| CAC | GGT | GAG | GAC | CAG | ATC | GCC | GCG | CGC | GCC | TCG | GGT | GCC | TAT | GGG | CGC | 34645 |
| His | Gly | Glu | Asp | Gln | Ile | Ala | Ala | Arg | Ala | Ser | Gly | Ala | Tyr | Gly | Arg | |
| | | 1125 | | | | | 1130 | | | | | 1135 | | | | |

```
AGG CTC CTG CCG GCT CCG CCG GCC GCG TCG CGC CGC ACC TGC ACA CCG    34693
Arg Leu Leu Pro Ala Pro Pro Ala Ala Ser Arg Arg Thr Cys Thr Pro
    1140            1145                1150

TCC GGC ACG GTG CTG GTC ACC GGC GGT ACG GGA GCG CTC GGC GGT CAT    34741
Ser Gly Thr Val Leu Val Thr Gly Gly Thr Gly Ala Leu Gly Gly His
1155            1160                1165                    1170

CTG GCC CGC CGT CTC GCA CGC GGC GGG ACC GGG CAT CTG GTG CTC ACC    34789
Leu Ala Arg Arg Leu Ala Arg Gly Gly Thr Gly His Leu Val Leu Thr
                1175                1180                1185

AGC CGT CGC GGC CCG GAC GCG CCG GGC GCC GGT GAA CTC GCC GGT GAA    34837
Ser Arg Arg Gly Pro Asp Ala Pro Gly Ala Gly Glu Leu Ala Gly Glu
            1190                1195                1200

CTC GCC TCC CTG GGC GCG AAG GTC ACG GTC GCC GCG TGC GAC ATG GCC    34885
Leu Ala Ser Leu Gly Ala Lys Val Thr Val Ala Ala Cys Asp Met Ala
        1205                1210                1215

GAC CGT GAA GCC GTG CGG GCG CTG CTC GAC GAG CAC CGG CCG ACC GCG    34933
Asp Arg Glu Ala Val Arg Ala Leu Leu Asp Glu His Arg Pro Thr Ala
    1220                1225                1230

GTG TTC CAC ACG GCG GGC ACG CCC CAC TCG GCG GAG TTC ACG GCG CTG    34981
Val Phe His Thr Ala Gly Thr Pro His Ser Ala Glu Phe Thr Ala Leu
1235            1240                1245                    1250

GAC GAG ACG ACG ACG GCC GGG GTG TAC GGC GGG AAG GTC CTG GGT GCC    35029
Asp Glu Thr Thr Thr Ala Gly Val Tyr Gly Gly Lys Val Leu Gly Ala
                1255                1260                1265

CGG CAT CTG GAC GAA CTG ACC CGG GAA CTC GGC ATC GGG CTG GAC GCG    35077
Arg His Leu Asp Glu Leu Thr Arg Glu Leu Gly Ile Gly Leu Asp Ala
            1270                1275                1280

TTC GTC CTC TTC TCC TCC GGC GCC GCG GTC TGG GGC AGC GGC GGC CAG    35125
Phe Val Leu Phe Ser Ser Gly Ala Ala Val Trp Gly Ser Gly Gly Gln
        1285                1290                1295

ACC GCT TAC GGG GCC GCG AAC GCC GCG CTG GAC GCC CTC GCC GAG CGG    35173
Thr Ala Tyr Gly Ala Ala Asn Ala Ala Leu Asp Ala Leu Ala Glu Arg
    1300                1305                1310

CGC CGT GCC GCC GGG CTG CCC GCG ACC TCC GTC GCC TGG GGC CTG TGG    35221
Arg Arg Ala Ala Gly Leu Pro Ala Thr Ser Val Ala Trp Gly Leu Trp
1315            1320                1325                    1330

GGC GGC GGA GGC ATG GGG GAG GGG GAC GGT GAG GAG TTC CTC AGC CGG    35269
Gly Gly Gly Gly Met Gly Glu Gly Asp Gly Glu Glu Phe Leu Ser Arg
                1335                1340                1345

CGC GGC CTC GGC GTG ATG CCG CCG GAG GAC GCG CTG GAA GCC CTG GAC    35317
Arg Gly Leu Gly Val Met Pro Pro Glu Asp Ala Leu Glu Ala Leu Asp
            1350                1355                1360

CGG GCC CTG GAC CGG GAG GAC ACC ACC GTC GTG GTG GCG GAT GTC GAC    35365
Arg Ala Leu Asp Arg Glu Asp Thr Thr Val Val Val Ala Asp Val Asp
        1365                1370                1375

TGG GAG CGG TTC GCC CCG GCC TTC ACC GCG TTC CGG CCC AGT GCG CTG    35413
Trp Glu Arg Phe Ala Pro Ala Phe Thr Ala Phe Arg Pro Ser Ala Leu
    1380                1385                1390

ATC TCC CGG CTG GTC TCG GAC GGC GGG GAG GCG GGG GGG CAG GAC GCC    35461
Ile Ser Arg Leu Val Ser Asp Gly Gly Glu Ala Gly Gly Gln Asp Ala
1395            1400                1405                    1410

CCG GAC GGC ACG CTG TTC GCC GCC GGG TTC GCG GCC GCC GGG CCA CTG    35509
Pro Asp Gly Thr Leu Phe Ala Ala Gly Phe Ala Ala Ala Gly Pro Leu
                1415                1420                1425

GAG CGG CAG GAG ATG CTG CTC GGC CTG GTG CGC CGG CAT GTG GCC GCC    35557
Glu Arg Gln Glu Met Leu Leu Gly Leu Val Arg Arg His Val Ala Ala
            1430                1435                1440

GTA CTC GGC CAC CCG GGG ACC GCG GAC ATC GGT CCC GAC CGT GCT TTC    35605
Val Leu Gly His Pro Gly Thr Ala Asp Ile Gly Pro Asp Arg Ala Phe
        1445                1450                1455
```

-continued

| | | | | | | | | | | | | | | | | |
|---|---|---|---|---|---|---|---|---|---|---|---|---|---|---|---|---|
| AAG | GAG | CTG | GGG | TTC | AGT | TCG | GTC | ACC | GCC | GTC | GAG | CTG | GCC | GGG | CGG | 35653 |
| Lys | Glu | Leu | Gly | Phe | Ser | Ser | Val | Thr | Ala | Val | Glu | Leu | Ala | Gly | Arg | |
| | 1460 | | | | 1465 | | | | | 1470 | | | | | | |
| CTG | GGC | CGG | GAG | TGC | GGA | CGG | AAG | CTG | CCG | CCG | ACG | CTG | GTC | TTC | GAC | 35701 |
| Leu | Gly | Arg | Glu | Cys | Gly | Arg | Lys | Leu | Pro | Pro | Thr | Leu | Val | Phe | Asp | |
| 1475 | | | | | 1480 | | | | 1485 | | | | | | 1490 | |
| CAT | CCG | ACT | GCC | GCG | GCG | GCC | GTC | GAA | CAC | CTG | GCG | GAG | CTG | CTG | ACA | 35749 |
| His | Pro | Thr | Ala | Ala | Ala | Ala | Val | Glu | His | Leu | Ala | Glu | Leu | Leu | Thr | |
| | | | | 1495 | | | | | 1500 | | | | | 1505 | | |
| CCG | CCC | GCC | GGT | CCC | GCC | GCC | GGT | CCC | CGG | GAG | GAG | GAG | GCG | CGG | GCC | 35797 |
| Pro | Pro | Ala | Gly | Pro | Ala | Ala | Gly | Pro | Arg | Glu | Glu | Glu | Ala | Arg | Ala | |
| | | | 1510 | | | | | 1515 | | | | | 1520 | | | |
| GCC | CTG | GCG | CGC | GTG | CCG | CTC | GAA | CGG | CTG | AGG | GAA | GCC | GGC | CTG | CTG | 35845 |
| Ala | Leu | Ala | Arg | Val | Pro | Leu | Glu | Arg | Leu | Arg | Glu | Ala | Gly | Leu | Leu | |
| | | 1525 | | | | | 1530 | | | | | 1535 | | | | |
| GAC | GCA | CTG | CTG | CGG | CTC | GCC | GCG | GAC | GAA | TCC | GGG | GCG | ACA | ACC | CCC | 35893 |
| Asp | Ala | Leu | Leu | Arg | Leu | Ala | Ala | Asp | Glu | Ser | Gly | Ala | Thr | Thr | Pro | |
| | 1540 | | | | | 1545 | | | | | 1550 | | | | | |
| CGT | ACG | TCT | GCC | GCG | TCC | GGC | GCA | CCC | CGC | GGC | CGG | GAG | GAG | CCG | GAC | 35941 |
| Arg | Thr | Ser | Ala | Ala | Ser | Gly | Ala | Pro | Arg | Gly | Arg | Glu | Glu | Pro | Asp | |
| 1555 | | | | | 1560 | | | | | 1565 | | | | | 1570 | |
| GGC | CGC | GGC | GAG | CCG | GAC | GGC | TCG | GGA | CAC | CGC | GAA | AGC | CCG | GAC | GCG | 35989 |
| Gly | Arg | Gly | Glu | Pro | Asp | Gly | Ser | Gly | His | Arg | Glu | Ser | Pro | Asp | Ala | |
| | | | | 1575 | | | | | 1580 | | | | | 1585 | | |
| GCC | GGC | GGG | TCG | GAC | GCC | CTG | GAC | GAT | CTC | GAC | GGG | GAC | GCC | CTG | GTG | 36037 |
| Ala | Gly | Gly | Ser | Asp | Ala | Leu | Asp | Asp | Leu | Asp | Gly | Asp | Ala | Leu | Val | |
| | | | 1590 | | | | | 1595 | | | | | 1600 | | | |
| CGG | CTC | GCC | CTC | GGG | GAA | CCG | GGC | GAG | TGA | CCGGCCGGCG | | | GAGCACACCC | | | 36087 |
| Arg | Leu | Ala | Leu | Gly | Glu | Pro | Gly | Glu | | | | | | | | |
| | | 1605 | | | | | 1610 | | | | | | | | | |

| | | | | | |
|---|---|---|---|---|---|
| GGCCGTCTCC | GGCCCGGCCG | CGGCCGGGCC | GGAAGCCATC | CGCCGCCCAC | CCGGTACCGA | 36147 |
| CCCCTCAAGC | CCTTCAAGCC | CTTCGACCCG | TCCGATCAGT | CAGTCCGGCG | GTCCTCCACG | 36207 |

| | | | | | | | | | | | | | | | | |
|---|---|---|---|---|---|---|---|---|---|---|---|---|---|---|---|---|
| ACCGGTCCGG | | | AATCGCCCCC | | | ACACGAGTCA | | | GGAAGCACAC | | | C | ATG | GCC | ATG | TCC | 36260 |
| | | | | | | | | | | | | | Met | Ala | Met | Ser |
| | | | | | | | | | | | | | 1 | | | |
| GCC | GAG | AGG | CTG | ACG | GAG | GCG | CTG | CGG | ACC | TCG | CTC | AAG | GAG | GCC | GAG | 36308 |
| Ala | Glu | Arg | Leu | Thr | Glu | Ala | Leu | Arg | Thr | Ser | Leu | Lys | Glu | Ala | Glu | |
| 5 | | | | 10 | | | | | 15 | | | | | | 20 | |
| CGG | CTC | CGG | CGG | CAG | AAC | CGC | GAA | CTG | AGG | GCC | GCG | CGG | GAC | GCG | GCG | 36356 |
| Arg | Leu | Arg | Arg | Gln | Asn | Arg | Glu | Leu | Arg | Ala | Ala | Arg | Asp | Ala | Ala | |
| | | | | 25 | | | | | 30 | | | | | 35 | | |
| CGG | GAG | CCG | ATC | GCC | GTC | GTC | GGC | ATG | GCC | TGC | CGC | TAC | CCG | GGC | GGT | 36404 |
| Arg | Glu | Pro | Ile | Ala | Val | Val | Gly | Met | Ala | Cys | Arg | Tyr | Pro | Gly | Gly | |
| | | | 40 | | | | | 45 | | | | | 50 | | | |
| GTC | ACC | GGC | CCC | GAG | GAG | CTG | TGG | GAG | CTG | GTG | GCC | GGA | GGC | CGG | GAC | 36452 |
| Val | Thr | Gly | Pro | Glu | Glu | Leu | Trp | Glu | Leu | Val | Ala | Gly | Gly | Arg | Asp | |
| | | 55 | | | | | 60 | | | | | 65 | | | | |
| GCG | ATC | GGG | CCG | TTC | CCC | GTG | GAC | CGG | GGC | TGG | GAC | GTG | GCG | TCG | GTG | 36500 |
| Ala | Ile | Gly | Pro | Phe | Pro | Val | Asp | Arg | Gly | Trp | Asp | Val | Ala | Ser | Val | |
| | | 70 | | | | 75 | | | | | 80 | | | | | |
| TAC | GAC | CCG | GAT | CCC | GAG | TCG | AAG | GGC | ACC | ACG | TAC | TGC | CGG | GAG | GGC | 36548 |
| Tyr | Asp | Pro | Asp | Pro | Glu | Ser | Lys | Gly | Thr | Thr | Tyr | Cys | Arg | Glu | Gly | |
| 85 | | | | | 90 | | | | | 95 | | | | | 100 | |
| GGG | TTC | CTG | GAA | GGC | GCC | GGT | GAC | TTC | GAC | GCC | GCC | TTC | TTC | GGC | ATC | 36596 |
| Gly | Phe | Leu | Glu | Gly | Ala | Gly | Asp | Phe | Asp | Ala | Ala | Phe | Phe | Gly | Ile | |
| | | | | 105 | | | | | 110 | | | | | 115 | | |
| TCG | CCG | CGC | GAG | GCC | CTG | GTG | ATG | GAC | CCG | CAG | CAG | CGG | CTG | CTG | CTG | 36644 |
| Ser | Pro | Arg | Glu | Ala | Leu | Val | Met | Asp | Pro | Gln | Gln | Arg | Leu | Leu | Leu | |
| | | | 120 | | | | | 125 | | | | | 130 | | | |

-continued

| | | | | | | | | | | | | | | | | |
|---|---|---|---|---|---|---|---|---|---|---|---|---|---|---|---|---|
| GAG | GTG | TCC | TGG | GAG | GCG | CTG | GAA | CGC | GCG | GGC | ATC | GAC | CCG | TCC | TCG | 36692 |
| Glu | Val | Ser | Trp | Glu | Ala | Leu | Glu | Arg | Ala | Gly | Ile | Asp | Pro | Ser | Ser | |
| | | 135 | | | 140 | | | | | 145 | | | | | | |
| CTG | CGC | GGC | AGC | CGC | GGT | GGT | GTC | TAC | GTG | GGC | GCC | GCG | CAC | GGC | TCG | 36740 |
| Leu | Arg | Gly | Ser | Arg | Gly | Gly | Val | Tyr | Val | Gly | Ala | Ala | His | Gly | Ser | |
| | 150 | | | | | 155 | | | | | 160 | | | | | |
| TAC | GCC | TCC | GAT | CCC | CGG | CTG | GTG | CCC | GAG | GGC | TCG | GAG | GGC | TAT | CTG | 36788 |
| Tyr | Ala | Ser | Asp | Pro | Arg | Leu | Val | Pro | Glu | Gly | Ser | Glu | Gly | Tyr | Leu | |
| 165 | | | | | 170 | | | | | 175 | | | | | 180 | |
| CTG | ACC | GGC | AGC | GCC | GAC | GCG | GTG | ATG | TCC | GGC | CGC | ATC | TCC | TAC | GCG | 36836 |
| Leu | Thr | Gly | Ser | Ala | Asp | Ala | Val | Met | Ser | Gly | Arg | Ile | Ser | Tyr | Ala | |
| | | | | 185 | | | | | 190 | | | | | 195 | | |
| CTC | GGT | CTC | GAA | GGA | CCG | TCC | ATG | ACG | GTG | GAG | ACG | GCC | TGC | TCC | TCC | 36884 |
| Leu | Gly | Leu | Glu | Gly | Pro | Ser | Met | Thr | Val | Glu | Thr | Ala | Cys | Ser | Ser | |
| | | | 200 | | | | | 205 | | | | | 210 | | | |
| TCG | CTG | GTG | GCG | CTG | CAT | CTG | GCG | GTA | CGG | GCG | CTG | CGG | CAC | GGC | GAG | 36932 |
| Ser | Leu | Val | Ala | Leu | His | Leu | Ala | Val | Arg | Ala | Leu | Arg | His | Gly | Glu | |
| | | 215 | | | | | 220 | | | | | 225 | | | | |
| TGC | GGG | CTC | GCG | CTG | GCG | GGC | GGG | GTG | GCG | GTG | ATG | GCC | GAT | CCG | GCG | 36980 |
| Cys | Gly | Leu | Ala | Leu | Ala | Gly | Gly | Val | Ala | Val | Met | Ala | Asp | Pro | Ala | |
| | 230 | | | | | 235 | | | | | 240 | | | | | |
| GCG | TTC | GTG | GAG | TTC | TCC | CGG | CAG | AAG | GGG | CTG | GCC | GCC | GAC | GGC | CGC | 37028 |
| Ala | Phe | Val | Glu | Phe | Ser | Arg | Gln | Lys | Gly | Leu | Ala | Ala | Asp | Gly | Arg | |
| 245 | | | | | 250 | | | | | 255 | | | | | 260 | |
| TGC | AAG | GCG | TTC | TCG | GCC | GCC | GCC | GAC | GGC | ACC | GGC | TGG | GCC | GAG | GGC | 37076 |
| Cys | Lys | Ala | Phe | Ser | Ala | Ala | Ala | Asp | Gly | Thr | Gly | Trp | Ala | Glu | Gly | |
| | | | | 265 | | | | | 270 | | | | | 275 | | |
| GTC | GGC | GTG | CTC | GTC | CTG | GAG | CGG | CTG | TCG | GAC | GCG | CGC | GCG | GGG | | 37124 |
| Val | Gly | Val | Leu | Val | Leu | Glu | Arg | Leu | Ser | Asp | Ala | Arg | Ala | Gly | | |
| | | | 280 | | | | | 285 | | | | | 290 | | | |
| CAC | ACG | GTC | CTC | GGC | CTG | GTC | ACC | GGC | ACC | GCG | GTC | AAC | CAG | GAC | GGT | 37172 |
| His | Thr | Val | Leu | Gly | Leu | Val | Thr | Gly | Thr | Ala | Val | Asn | Gln | Asp | Gly | |
| | | 295 | | | | | 300 | | | | | 305 | | | | |
| GCC | TCC | AAC | GGG | CTG | ACC | GCG | CCC | AAC | GGC | CCA | GCC | CAG | CAA | CGC | GTC | 37220 |
| Ala | Ser | Asn | Gly | Leu | Thr | Ala | Pro | Asn | Gly | Pro | Ala | Gln | Gln | Arg | Val | |
| | | 310 | | | | | 315 | | | | | 320 | | | | |
| ATC | GCC | GAG | GCG | CTC | GCC | GAC | GCC | GGG | CTG | TCC | CCG | GAG | GAC | GTG | GAC | 37268 |
| Ile | Ala | Glu | Ala | Leu | Ala | Asp | Ala | Gly | Leu | Ser | Pro | Glu | Asp | Val | Asp | |
| 325 | | | | | 330 | | | | | 335 | | | | | 340 | |
| GCG | GTC | GAG | GCG | CAC | GGC | ACC | GGC | ACC | CGG | CTC | GGC | GAC | CCC | ATC | GAG | 37316 |
| Ala | Val | Glu | Ala | His | Gly | Thr | Gly | Thr | Arg | Leu | Gly | Asp | Pro | Ile | Glu | |
| | | | | 345 | | | | | 350 | | | | | 355 | | |
| GCC | GGG | GCG | CTG | CTC | GCC | GCC | TCC | GGA | CGG | AAC | CGT | TCC | GGC | GAC | CAC | 37364 |
| Ala | Gly | Ala | Leu | Leu | Ala | Ala | Ser | Gly | Arg | Asn | Arg | Ser | Gly | Asp | His | |
| | | | 360 | | | | | 365 | | | | | 370 | | | |
| CCG | CTG | TGG | CTC | GGC | TCG | CTG | AAG | TCC | AAC | ATC | GGG | CAT | GCC | CAG | GCC | 37412 |
| Pro | Leu | Trp | Leu | Gly | Ser | Leu | Lys | Ser | Asn | Ile | Gly | His | Ala | Gln | Ala | |
| | | 375 | | | | | 380 | | | | | 385 | | | | |
| GCC | GCC | GGT | GTC | GGC | GGC | GTC | ATC | AAG | ATG | CTC | CAG | GCG | CTG | CGG | CAC | 37460 |
| Ala | Ala | Gly | Val | Gly | Gly | Val | Ile | Lys | Met | Leu | Gln | Ala | Leu | Arg | His | |
| | | 390 | | | | | 395 | | | | | 400 | | | | |
| GGC | TTG | CTG | CCC | CGC | ACC | CTC | CAC | GCC | GAC | GAG | CCG | ACC | CCG | CAT | GCC | 37508 |
| Gly | Leu | Leu | Pro | Arg | Thr | Leu | His | Ala | Asp | Glu | Pro | Thr | Pro | His | Ala | |
| 405 | | | | | 410 | | | | | 415 | | | | | 420 | |
| GAC | TGG | AGC | TCC | GGC | CGG | GTA | CGG | CTG | CTC | ACC | TCC | GAG | GTG | CCG | TGG | 37556 |
| Asp | Trp | Ser | Ser | Gly | Arg | Val | Arg | Leu | Leu | Thr | Ser | Glu | Val | Pro | Trp | |
| | | | | 425 | | | | | 430 | | | | | 435 | | |
| CAG | CGG | ACC | GGC | CGG | CCC | CGG | CGG | ACC | GGG | GTG | TCC | GCC | TTC | GGC | GTC | 37604 |
| Gln | Arg | Thr | Gly | Arg | Pro | Arg | Arg | Thr | Gly | Val | Ser | Ala | Phe | Gly | Val | |
| | | | 440 | | | | | 445 | | | | | 450 | | | |

| | | | | | | | | | | | | | | | | |
|---|---|---|---|---|---|---|---|---|---|---|---|---|---|---|---|---|
| GGC | GGC | ACC | AAT | GCC | CAT | GTC | GTC | CTC | GAA | GAG | GCA | CCC | GCC | CCG | CCC | 37652 |
| Gly | Gly | Thr<br>455 | Asn | Ala | His | Val<br>460 | Val | Leu | Glu | Glu | Ala<br>465 | Pro | Ala | Pro | Pro | |
| GCG | CCG | GAA | CCG | GCC | GGG | GAG | GCC | CCC | GGC | GGC | TCC | CGC | GCC | GCA | GAA | 37700 |
| Ala | Pro<br>470 | Glu | Pro | Ala | Gly<br>475 | Glu | Ala | Pro | Gly | Gly<br>480 | Ser | Arg | Ala | Ala | Glu | |
| GGG | GCG | GAA | GGG | CCC | CTG | GCC | TGG | GTG | GTC | TCC | GGA | CGC | GAC | GAG | CCG | 37748 |
| Gly<br>485 | Ala | Glu | Gly | Pro<br>490 | Leu | Ala | Trp | Val | Val<br>495 | Ser | Gly | Arg | Asp | Glu | Pro<br>500 | |
| GCC | CTG | CGG | TCC | CAG | GCC | CGG | CGG | CTC | CGC | GAC | CAC | CTC | TCC | CGC | ACC | 37796 |
| Ala | Leu | Arg | Ser | Gln<br>505 | Ala | Arg | Arg | Leu | Arg<br>510 | Asp | His | Leu | Ser | Arg<br>515 | Thr | |
| CCC | GGG | GCC | CGC | CCG | CGT | GAC | ATC | GCC | TTC | TCC | CTC | GCC | GCC | ACG | CGC | 37844 |
| Pro | Gly | Ala | Arg<br>520 | Pro | Arg | Asp | Ile | Ala<br>525 | Phe | Ser | Leu | Ala | Ala<br>530 | Thr | Arg | |
| GCA | GCC | TTT | GAC | CAC | CGC | GCC | GTG | CTG | ATC | GGC | TCG | GAC | GGG | GCC | GAA | 37892 |
| Ala | Ala | Phe<br>535 | Asp | His | Arg | Ala | Val<br>540 | Leu | Ile | Gly | Ser | Asp<br>545 | Gly | Ala | Glu | |
| CTC | GCC | GCC | GCC | CTG | GAC | GCG | TTG | GCC | GAA | GGA | CGC | GAC | GGT | CCG | GCG | 37940 |
| Leu | Ala<br>550 | Ala | Ala | Leu | Asp<br>555 | Ala | Leu | Ala | Glu | Gly<br>560 | Arg | Asp | Gly | Pro | Ala | |
| GTG | GTG | CGC | GGA | GTC | CGC | GAC | CGG | GAC | GGC | AGG | ATG | GCC | TTC | CTC | TTC | 37988 |
| Val<br>565 | Val | Arg | Gly | Val<br>570 | Arg | Asp | Arg | Asp | Gly<br>575 | Arg | Met | Ala | Phe | Leu<br>580 | Phe | |
| ACC | GGG | CAG | GGC | AGC | CAG | CGC | GCC | GGG | ATG | GCC | CAC | GAC | CTG | CAT | GCC | 38036 |
| Thr | Gly | Gln | Gly | Ser<br>585 | Gln | Arg | Ala | Gly | Met<br>590 | Ala | His | Asp | Leu | His<br>595 | Ala | |
| GCC | CAT | ACC | TTC | TTC | GCG | TCC | GCC | CTC | GAC | GAG | GTG | ACG | GAC | CGT | CTC | 38084 |
| Ala | His | Thr | Phe<br>600 | Phe | Ala | Ser | Ala | Leu<br>605 | Asp | Glu | Val | Thr | Asp<br>610 | Arg | Leu | |
| GAC | CCG | CTG | CTC | GGC | CGG | CCG | CTC | GGC | GCG | CTG | CTG | GAC | GCC | CGA | CCC | 38132 |
| Asp | Pro | Leu<br>615 | Leu | Gly | Arg | Pro | Leu<br>620 | Gly | Ala | Leu | Leu | Asp<br>625 | Ala | Arg | Pro | |
| GGC | TCG | CCC | GAA | GCG | GCA | CTC | CTG | GAC | CGG | ACC | GAG | TAC | ACC | CAG | CCG | 38180 |
| Gly | Ser<br>630 | Pro | Glu | Ala | Ala<br>635 | Leu | Leu | Asp | Arg | Thr<br>640 | Glu | Tyr | Thr | Gln | Pro | |
| GCG | CTC | TTC | GCC | GTC | GAG | GTG | GCG | CTC | CAC | CGG | CTG | CTG | GAG | CAC | TGG | 38228 |
| Ala | Leu<br>645 | Phe | Ala | Val | Glu<br>650 | Val | Ala | Leu | His | Arg<br>655 | Leu | Leu | Glu | His | Trp<br>660 | |
| GGG | ATG | CGC | CCC | GAC | CTG | CTG | CTG | GGG | CAC | TCG | GTG | GGC | GAA | CTG | GCG | 38276 |
| Gly | Met | Arg | Pro | Asp<br>665 | Leu | Leu | Leu | Gly | His<br>670 | Ser | Val | Gly | Glu | Leu<br>675 | Ala | |
| GCC | GCC | CAC | GTC | GCG | GGT | GTG | CTC | GAT | CTC | GAC | GAC | GCC | TGC | GCG | CTG | 38324 |
| Ala | Ala | His | Val<br>680 | Ala | Gly | Val | Leu<br>685 | Asp | Leu | Asp | Asp | Ala<br>690 | Cys | Ala | Leu | |
| GTG | GCC | GCC | CGC | GGC | AGG | CTG | ATG | CAG | CGC | CTG | CCG | CCC | GGC | GGC | GCG | 38372 |
| Val | Ala | Ala<br>695 | Arg | Gly | Arg | Leu | Met<br>700 | Gln | Arg | Leu | Pro | Pro<br>705 | Gly | Gly | Ala | |
| ATG | GTC | TCC | GTG | CGG | GCC | GGC | GAG | GAC | GAG | GTC | CGC | GCA | CTG | CTG | GCC | 38420 |
| Met | Val | Ser<br>710 | Val | Arg | Ala | Gly<br>715 | Glu | Asp | Glu | Val | Arg<br>720 | Ala | Leu | Leu | Ala | |
| GGC | CGC | GAG | GAC | GCC | GTC | TGC | GTC | GCC | GCG | GTG | AAC | GGC | CCC | CGG | TCG | 38468 |
| Gly | Arg<br>725 | Glu | Asp | Ala | Val<br>730 | Cys | Val | Ala | Ala<br>735 | Val | Asn | Gly | Pro | Arg<br>740 | Ser | |
| GTG | GTG | ATC | TCC | GGC | GCG | GAG | GAA | GCG | GTG | GCC | GAG | GCG | GCG | GCG | CAG | 38516 |
| Val | Val | Ile | Ser | Gly<br>745 | Ala | Glu | Glu | Ala<br>750 | Val | Ala | Glu | Ala | Ala<br>755 | Ala | Gln | |
| CTC | GCC | GGA | CGA | GGC | CGC | CGC | ACC | AGG | CGG | CTC | CGC | GTC | GCG | CAC | GCC | 38564 |
| Leu | Ala | Gly | Arg<br>760 | Gly | Arg | Arg | Thr | Arg<br>765 | Arg | Leu | Arg | Val | Ala<br>770 | His | Ala | |

| | | | | | | | | | | | | | | | | |
|---|---|---|---|---|---|---|---|---|---|---|---|---|---|---|---|---|
| TTC | CAC | TCA | CCC | CTG | ATG | GAC | GGC | ATG | CTC | GCC | GGA | TTC | CGG | GAG | GTC | 38612 |
| Phe | His | Ser 775 | Pro | Leu | Met | Asp | Gly 780 | Met | Leu | Ala | Gly | Phe 785 | Arg | Glu | Val | |
| GCC | GCC | GGC | CTG | CGC | TAC | CGG | GAA | CCG | GAG | CTG | ACG | GTC | GTC | TCC | ACG | 38660 |
| Ala | Ala 790 | Gly | Leu | Arg | Tyr | Arg 795 | Glu | Pro | Glu | Leu | Thr 800 | Val | Val | Ser | Thr | |
| GTC | ACG | GGG | CGG | CCC | GCC | CGC | CCC | GGT | GAA | CTC | ACC | GGC | CCC | GAC | TAC | 38708 |
| Val 805 | Thr | Gly | Arg | Pro | Ala 810 | Arg | Pro | Gly | Glu | Leu 815 | Thr | Gly | Pro | Asp | Tyr 820 | |
| TGG | GTG | GCC | CAG | GTC | CGT | GAG | CCC | GTG | CGC | TTC | GCG | GAC | GCG | GTC | CGC | 38756 |
| Trp | Val | Ala | Gln | Val 825 | Arg | Glu | Pro | Val | Arg 830 | Phe | Ala | Asp | Ala | Val | Arg 835 | |
| ACG | GCA | CAC | CGC | CTC | GGA | GCC | CGC | ACC | TTC | CTG | GAG | ACC | GGC | CCG | GAC | 38804 |
| Thr | Ala | His | Arg 840 | Leu | Gly | Ala | Arg | Thr 845 | Phe | Leu | Glu | Thr | Gly 850 | Pro | Asp | |
| GGC | GTG | CTG | TGC | GGC | ATG | GCA | GAG | GAG | TGC | CTG | GAG | GAC | GAC | ACC | GTG | 38852 |
| Gly | Val | Leu 855 | Cys | Gly | Met | Ala | Glu 860 | Glu | Cys | Leu | Glu | Asp 865 | Asp | Thr | Val | |
| GCC | CTG | CTG | CCG | GCG | ATC | CAC | AAG | CCC | GGC | ACC | GCG | CCG | CAC | GGT | CCG | 38900 |
| Ala | Leu | Leu 870 | Pro | Ala | Ile | His | Lys 875 | Pro | Gly | Thr | Ala | Pro 880 | His | Gly | Pro | |
| GCG | GCT | CCC | GGC | GCG | CTG | CGG | GCG | GCC | GCC | GCC | GCG | TAC | GGC | CGG | GGC | 38948 |
| Ala 885 | Ala | Pro | Gly | Ala | Leu 890 | Arg | Ala | Ala | Ala | Ala 895 | Ala | Tyr | Gly | Arg | Gly 900 | |
| GCC | CGG | GTG | GAC | TGG | GCC | GGG | ATG | CAC | GCC | GAC | GGC | CCC | GAG | GGG | CCG | 38996 |
| Ala | Arg | Val | Asp | Trp 905 | Ala | Gly | Met | His | Ala 910 | Asp | Gly | Pro | Glu | Gly 915 | Pro | |
| GCC | CGC | CGC | GTC | GAA | CTG | CCC | GTC | CAC | GCC | TTC | CGG | CAC | CGC | CGC | TAC | 39044 |
| Ala | Arg | Arg | Val 920 | Glu | Leu | Pro | Val | His 925 | Ala | Phe | Arg | His | Arg 930 | Arg | Tyr | |
| TGG | CTC | GCC | CCG | GGC | CGC | GCG | GCG | GAC | ACC | GAC | GAC | TGG | ATG | TAC | CGG | 39092 |
| Trp | Leu | Ala | Pro 935 | Gly | Arg | Ala | Ala | Asp 940 | Thr | Asp | Asp | Trp | Met 945 | Tyr | Arg | |
| ATC | GGC | TGG | GAC | CGG | CTG | CCG | GCT | GTG | ACC | GGC | GGG | GCC | CGG | ACC | GCC | 39140 |
| Ile | Gly | Trp | Asp 950 | Arg | Leu | Pro | Ala | Val 955 | Thr | Gly | Gly | Ala | Arg 960 | Thr | Ala | |
| GGC | CGC | TGG | CTG | GTG | ATC | CAC | CCC | GAC | AGC | CCG | CGC | TGC | CGG | GAG | CTG | 39188 |
| Gly 965 | Arg | Trp | Leu | Val | Ile 970 | His | Pro | Asp | Ser | Pro 975 | Arg | Cys | Arg | Glu | Leu 980 | |
| TCC | GGC | CAC | GCC | GAA | CGC | GCG | CTG | CGC | GCC | GCG | GGC | GCG | AGC | CCC | GTA | 39236 |
| Ser | Gly | His | Ala | Glu 985 | Arg | Ala | Leu | Arg | Ala 990 | Ala | Gly | Ala | Ser | Pro 995 | Val | |
| CCG | CTG | CCC | GTG | GAC | GCT | CCG | GCC | GCC | GAC | CGG | GCG | TCC | TTC | GCG | GCA | 39284 |
| Pro | Leu | Pro | Val 1000 | Asp | Ala | Pro | Ala | Ala 1005 | Asp | Arg | Ala | Ser | Phe 1010 | Ala | Ala | |
| CTG | CTG | CGC | TCC | GCC | ACC | GGA | CCT | GAC | ACA | CGA | GGT | GAC | ACA | GCC | GCG | 39332 |
| Leu | Leu | Arg | Ser 1015 | Ala | Thr | Gly | Pro | Asp 1020 | Thr | Arg | Gly | Asp | Thr 1025 | Ala | Ala | |
| CCC | GTG | GCC | GGT | GTG | CTG | TCG | CTG | CTG | TCC | GAG | GAG | GAT | CGG | CCC | CAT | 39380 |
| Pro | Val | Ala 1030 | Gly | Val | Leu | Ser | Leu 1035 | Leu | Ser | Glu | Glu | Asp 1040 | Arg | Pro | His | |
| CGC | CAG | CAC | GCC | CCG | GTA | CCC | GCC | GGG | GTC | CTG | GCG | ACG | CTG | TCC | CTG | 39428 |
| Arg | Gln | His | Ala 1045 | Pro | Val | Pro 1050 | Ala | Gly | Val | Leu 1055 | Ala | Thr | Leu | Ser | Leu 1060 | |
| ATG | CAG | GCT | ATG | GAG | GAG | GAG | GCG | GTG | GAG | GCT | CGC | GTG | TGG | TGC | GTC | 39476 |
| Met | Gln | Ala | Met | Glu 1065 | Glu | Glu | Ala | Val | Glu 1070 | Ala | Arg | Val | Trp | Cys 1075 | Val | |
| TCC | CGC | GCC | GCG | GTC | GCC | GCC | GCC | GAC | CGG | GAA | CGG | CCC | GTC | GGC | GCG | 39524 |
| Ser | Arg | Ala | Ala | Val 1080 | Ala | Ala | Ala | Asp | Arg 1085 | Glu | Arg | Pro | Val | Gly 1090 | Ala | |

```
GGC GCC GCC CTG TGG GGG CTG GGG CGG GTG GCC GCC CTG GAA CGC CCC   39572
Gly Ala Ala Leu Trp Gly Leu Gly Arg Val Ala Ala Leu Glu Arg Pro
        1095                1100               1105

ACC CGG TGG GGC GGT CTC GTG GAC CTG CCC GCC TCG CCC GGT GCG GCG   39620
Thr Arg Trp Gly Gly Leu Val Asp Leu Pro Ala Ser Pro Gly Ala Ala
        1110                1115               1120

CAC TGG GCG GCC GCC GTG GAA CGG CTC GCC GGT CCC GAG GAC CAG ATC   39668
His Trp Ala Ala Ala Val Glu Arg Leu Ala Gly Pro Glu Asp Gln Ile
1125                1130               1135                1140

GCC GTG CGC GCG TCC GGC AGT TGG GGC CGG CGC CTC ACC AGG CTG CCG   39716
Ala Val Arg Ala Ser Gly Ser Trp Gly Arg Arg Leu Thr Arg Leu Pro
        1145                1150               1155

CGC GAC GGC GGC GGC CGG ACG GCC GCA CCC GCG TAC CGG CCG CGC GGC   39764
Arg Asp Gly Gly Gly Arg Thr Ala Ala Pro Ala Tyr Arg Pro Arg Gly
        1160                1165               1170

ACG GTG CTC GTC ACC GGT GGC ACC GGT GCG CTC GGC GGG CAT CTC GCC   39812
Thr Val Leu Val Thr Gly Gly Thr Gly Ala Leu Gly Gly His Leu Ala
        1175                1180               1185

CGC TGG CTC GCC GCG GCG GGC GCC GAA CAC CTG GCG CTC ACC AGC CGC   39860
Arg Trp Leu Ala Ala Ala Gly Ala Glu His Leu Ala Leu Thr Ser Arg
        1190                1195               1200

CGG GGC CCG GAC GCG CCC GGC GCC GCC GGA CTC GAG GCC GAA CTC CTC   39908
Arg Gly Pro Asp Ala Pro Gly Ala Ala Gly Leu Glu Ala Glu Leu Leu
1205                1210               1215                1220

CTC CTG GGC GCC AAG GTG ACG TTC GCC GCC TGC GAC ACC GCC GAC CGC   39956
Leu Leu Gly Ala Lys Val Thr Phe Ala Ala Cys Asp Thr Ala Asp Arg
        1225                1230               1235

GAC GGC CTC GCC CGG GTC CTG CGG GCG ATA CCG GAG GAC ACC CCG CTC   40004
Asp Gly Leu Ala Arg Val Leu Arg Ala Ile Pro Glu Asp Thr Pro Leu
        1240                1245               1250

ACC GCG GTG TTC CAC GCC GCG GGC GTA CCG CAG GTC ACG CCG CTG TCC   40052
Thr Ala Val Phe His Ala Ala Gly Val Pro Gln Val Thr Pro Leu Ser
        1255                1260               1265

CGT ACC TCG CCC GAG CAC TTC GCC GAC GTG TAC GCG GGC AAG GCG GCG   40100
Arg Thr Ser Pro Glu His Phe Ala Asp Val Tyr Ala Gly Lys Ala Ala
        1270                1275               1280

GGC GCC GCG CAC CTG GAC GAA CTG ACC CGC GAA CTC GGC GCC GGA CTC   40148
Gly Ala Ala His Leu Asp Glu Leu Thr Arg Glu Leu Gly Ala Gly Leu
1285                1290               1295                1300

GAC GCG TTC GTC CTC TAC TCC TCC GGC GCC GGC GTC TGG GGC AGC GCC   40196
Asp Ala Phe Val Leu Tyr Ser Ser Gly Ala Gly Val Trp Gly Ser Ala
        1305                1310               1315

GGC CAG GGT GCC TAC GCC GCC GCC AAC GCC GCC CTG GAC GCG CTC GCC   40244
Gly Gln Gly Ala Tyr Ala Ala Ala Asn Ala Ala Leu Asp Ala Leu Ala
        1320                1325               1330

CGG CGC CGT GCG GCG GAC GGA CTC CCC GCC ACC TCC ATC GCC TGG GGC   40292
Arg Arg Arg Ala Ala Asp Gly Leu Pro Ala Thr Ser Ile Ala Trp Gly
        1335                1340               1345

GTG TGG GGC GGC GGT ATG GGG GCC GAC GAG GCG GGC GCG GAG TAT        40340
Val Trp Gly Gly Gly Gly Met Gly Ala Asp Glu Ala Gly Ala Glu Tyr
        1350                1355               1360

CTG GGC CGG CGC GGT ATG CGC CCC ATG GCA CCG GTC TCC GCG CTC CGG   40388
Leu Gly Arg Arg Gly Met Arg Pro Met Ala Pro Val Ser Ala Leu Arg
1365                1370               1375                1380

GCG ATG GCC ACC GCC ATC GCC TCC GGG GAA CCC TGC CCC ACC GTC ACC   40436
Ala Met Ala Thr Ala Ile Ala Ser Gly Glu Pro Cys Pro Thr Val Thr
        1385                1390               1395

CAC ACC GAC TGG GAG CGC TTC GGC GAG GGC TTC ACC GCC TTC CGG CCC   40484
His Thr Asp Trp Glu Arg Phe Gly Glu Gly Phe Thr Ala Phe Arg Pro
        1400                1405               1410
```

```
AGC CCT CTG ATC GCG GGG CTC GGC ACG CCG GGC GGC GGC CGG GCG GCG     40532
Ser Pro Leu Ile Ala Gly Leu Gly Thr Pro Gly Gly Gly Arg Ala Ala
    1415                1420                1425

GAG ACC CCC GAG GAG GGG AAC GCC ACC GCT GCG GCG GAC CTC ACC GCC     40580
Glu Thr Pro Glu Glu Gly Asn Ala Thr Ala Ala Ala Asp Leu Thr Ala
1430                1435                1440

CTG CCG CCC GCC GAA CTC CGC ACC GCG CTG CGC GAG CTG GTG CGA GCC     40628
Leu Pro Pro Ala Glu Leu Arg Thr Ala Leu Arg Glu Leu Val Arg Ala
1445                1450                1455                1460

CGG ACC GCC GCG GCG CTC GGC CTC GAC GAC CCG GCC GAG GTC GCC GAG     40676
Arg Thr Ala Ala Ala Leu Gly Leu Asp Asp Pro Ala Glu Val Ala Glu
                1465                1470                1475

GGC GAA CGG TTC CCC GCC ATG GGC TTC GAC TCC CTG GCC ACC GTA CGG     40724
Gly Glu Arg Phe Pro Ala Met Gly Phe Asp Ser Leu Ala Thr Val Arg
            1480                1485                1490

CTG CGC CGC GGA CTC GCC TCG GCC ACG GGC CTC GAC CTG CCC CCC GAT     40772
Leu Arg Arg Gly Leu Ala Ser Ala Thr Gly Leu Asp Leu Pro Pro Asp
        1495                1500                1505

CTG CTC TTC GAC CGG GAC ACC CCG GCC GCG CTC GCC GCC CAC CTG GCC     40820
Leu Leu Phe Asp Arg Asp Thr Pro Ala Ala Leu Ala Ala His Leu Ala
    1510                1515                1520

GAA CTG CTC GCC ACC GCA CGG GAC CAC GGA CCC GGC GGC CCC GGG ACC     40868
Glu Leu Leu Ala Thr Ala Arg Asp His Gly Pro Gly Gly Pro Gly Thr
1525                1530                1535                1540

GGT GCC GCG CCG GCC GAT GCC GGA AGC GGC CTG CCG GCC CTC TAC CGG     40916
Gly Ala Ala Pro Ala Asp Ala Gly Ser Gly Leu Pro Ala Leu Tyr Arg
                1545                1550                1555

GAG GCC GTC CGC ACC GGC CGG GCC GCG GAA ATG GCC GAA CTG CTC GCC     40964
Glu Ala Val Arg Thr Gly Arg Ala Ala Glu Met Ala Glu Leu Leu Ala
            1560                1565                1570

GCC GCT TCC CGG TTC CGC CCC GCC TTC GGG ACG GCG GAC CGG CAG CCG     41012
Ala Ala Ser Arg Phe Arg Pro Ala Phe Gly Thr Ala Asp Arg Gln Pro
        1575                1580                1585

GTG GCC CTC GTG CCG CTG GCC GAC GGC GCG GAG GAC ACC GGG CTC CCG     41060
Val Ala Leu Val Pro Leu Ala Asp Gly Ala Glu Asp Thr Gly Leu Pro
    1590                1595                1600

CTG CTC GTG GGC TGC GCC GGG ACG GCG GTG GCC TCC GGC CCG GTG GAG     41108
Leu Leu Val Gly Cys Ala Gly Thr Ala Val Ala Ser Gly Pro Val Glu
1605                1610                1615                1620

TTC ACC GCC TTC GCC GGA GCG CTG GCG GAC CTC CCG GCG GCG GCC CCG     41156
Phe Thr Ala Phe Ala Gly Ala Leu Ala Asp Leu Pro Ala Ala Ala Pro
                1625                1630                1635

ATG GCC GCG CTG CCG CAG CCC GGC TTT CTG CCG GGA GAA CGA GTC CCG     41204
Met Ala Ala Leu Pro Gln Pro Gly Phe Leu Pro Gly Glu Arg Val Pro
            1640                1645                1650

GCC ACC CCG GAG GCA TTG TTC GAG GCC CAG GCG GAA GCG CTG CTG CGC     41252
Ala Thr Pro Glu Ala Leu Phe Glu Ala Gln Ala Glu Ala Leu Leu Arg
        1655                1660                1665

TAC GCG GCC GGC CGG CCC TTC GTG CTG CTG GGG CAC TCC GCC GGC GCC     41300
Tyr Ala Ala Gly Arg Pro Phe Val Leu Leu Gly His Ser Ala Gly Ala
    1670                1675                1680

AAC ATG GCC CAC GCC CTG ACC CGT CAT CTG GAG GCG AAC GGT GGC GGC     41348
Asn Met Ala His Ala Leu Thr Arg His Leu Glu Ala Asn Gly Gly Gly
1685                1690                1695                1700

CCC GCA GGG CTG GTG CTC ATG GAC ATC TAC ACC CCC GCC GAC CCC GGC     41396
Pro Ala Gly Leu Val Leu Met Asp Ile Tyr Thr Pro Ala Asp Pro Gly
                1705                1710                1715

GCG ATG GGC GTC TGG CGG AAC GAC ATG TTC CAG TGG GTC TGG CGG CGC     41444
Ala Met Gly Val Trp Arg Asn Asp Met Phe Gln Trp Val Trp Arg Arg
            1720                1725                1730
```

```
TCG GAC ATC CCC CCG GAC GAC CAC CGC CTC ACG GCC ATG GGC GCC TAC       41492
Ser Asp Ile Pro Pro Asp Asp His Arg Leu Thr Ala Met Gly Ala Tyr
        1735                1740                1745

CAC CGG CTG CTT CTC GAC TGG TCG CCC ACC CCC GTC CGC GCC CCC GTA       41540
His Arg Leu Leu Leu Asp Trp Ser Pro Thr Pro Val Arg Ala Pro Val
1750                    1755                1760

CTG CAT CTG CGC GCC GCG GAA CCC ATG GGC GAC TGG CCA CCC GGG GAC       41588
Leu His Leu Arg Ala Ala Glu Pro Met Gly Asp Trp Pro Pro Gly Asp
1765                1770                1775                1780

ACC GGC TGG CAG TCC CAC TGG GAC GGC GCG CAC ACC ACC GCC GGC ATC       41636
Thr Gly Trp Gln Ser His Trp Asp Gly Ala His Thr Thr Ala Gly Ile
                1785                1790                1795

CCC GGA AAC CAC TTC ACG ATG ATG ACC GAA CAC GCC TCC GCC GCC GCC       41684
Pro Gly Asn His Phe Thr Met Met Thr Glu His Ala Ser Ala Ala Ala
            1800                1805                1810

CGG CTC GTG CAC GGC TGG CTC GCG GAA CGG ACC CCG TCC GGG CAG GGC       41732
Arg Leu Val His Gly Trp Leu Ala Glu Arg Thr Pro Ser Gly Gln Gly
        1815                1820                1825

GGG TCA CCG TCC CGC GCG GCG GGG AGA GAG GAG AGG CCG TGA               41774
Gly Ser Pro Ser Arg Ala Ala Gly Arg Glu Glu Arg Pro
    1830                1835                1840

ACACGGCAGC CGGCCCGACC GGCACCGCCG CCGGCGGCAC CACCGCCCCG GCGGCGGCAC     41834
ACGACCTGTC CCGCGCCGGA CGCAGGCTCC AACTCACCCG GCCGCACAG  TGGTTCGCCG     41894
GCAACCAGGG AGACCCCTAC GGGATGATCC TGCGCGCCGG CACCGCCGAC CCGGCACCGT     41954
ACGAGGAAGA GATCCGTGAG CGGGGGCCGC TGTTCCACAG CGAACTCCTC GGCGCCTGGG     42014
TGACCGGCAG CCGCCATGTC GCCGACGCCG TGACGGCCGA CGACGCGTTC GGCGCCCTCA     42074
CCGCGGACGG TGCACGGCCA GGAGTCCGCG AACTGCCGCT CTCCGGCAGC GCCCTCGACG     42134
CCGCCCACGG GAACCCCGGC GGCCCGCCCC TCCCCGGAGG GTGGCCGCAC CGGCCCCCGG     42194
ACAGGGAGGA GCGAGACGAC CCGGACCGGC ACGCGGCGGA CCTGCTGAAC GCCGCCGGCC     42254
CGGGGCAGGT CCTCGACCTC GTCCCGTTCG CCCGGCGGCT GGCGGCCCGG ACGGCCGGCG     42314
CGTGGCTGGG CGTCCCGGCG GAACGGCTGC CGCGCTTCGA CGGCACTC   ACCGGCTGCC     42374
GCCGCGCCCT CGACGCCCTG CTCTGCCCCC AGCTCCTGGC CGACGCGCGG GCCGGACTGG     42434
CCGCCGAGGA GGCCCTGCGC GCCGTGCTCG GCGAGACCCC GGAGGCACGC GGACGTCCGC     42494
CCGGCGCGGT CGAGGCGGCC CGCGCGCACG CCGTCAGCGC GGCGGAGCCC ATCGCCGTCC     42554
TGCTGTGCAA CGCGGTGCGG GAACTGATGG AACGGCCGGC CCAGTGGCGG CGCTCACCG     42614
CCGACCCCGG CCTGGCGGGC GCCGCGATCA CCGAAACACT GCTCTGGGCA CCGCCGGTGC     42674
GCCTGGAGAG CAGGGTGGCA CGCGAGACGG CCGTACTCGC CGGGCGGACG CTGCCCGCTG     42734
GAACCCATCT CGTCGTCCTC GCCGCCGCCG CCAACCGCGA CGCCTGCCGG AACGCCGGTC     42794
CGGCCGTCAC CGGCTTCGAC GTCCTCCGCC GCGCCTCGGA CGGCGGCCCC CAGCCCCACG     42854
GACTCCCGGA GGACCTGCAC TTCCGTCTCT CGGGCCCGCT CGTCCGGCGG ACCGCCGAGG     42914
CCGGTCTGAG GGCGCTCGCC GAACGCTTCC CCGGCTGCGC CCGGCCGGCC CCGCAGTCCG     42974
AGTCCGCCGG TCACCGGTGC TCCGCGGTCT CGGCCGGCTG CCCGTCGCCC CGTATGTCCC     43034
CGAGTGAGAA GGGCACTGGA TGACCGCCGC CGAGGACCGC ACGGACCGGA AGGGAAACCG     43094
CCGATGCGCG TACTGCTGAC CTGTATCGCG CACAACACCC ACTACTACAA CCTGGTGCCG     43154
GTCGCCTGGG CCCTGAGAGC GGCCGGACAC GAGGTGCGGG TGGCCGCGCA GCCCGCCCTC     43214
ACCGACACGA TCACCGCCTC CGGACTGACC GCCGTGCCGG TCGGCGGCAA CGAGTCCGTG     43274
CTCGAG                                                                43280
```

5,876,991

-continued ( 2 ) INFORMATION FOR SEQ ID NO:2:

( i ) SEQUENCE CHARACTERISTICS:
        ( A ) LENGTH: 4472 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

```
Met Ser Ser Ala Leu Arg Arg Ala Val Gln Ser Asn Cys Gly Tyr Gly
 1               5                  10                  15

Asp Leu Met Thr Ser Asn Thr Ala Ala Gln Asn Thr Gly Asp Gln Glu
             20                  25                  30

Asp Val Asp Gly Pro Asp Ser Thr His Gly Gly Glu Ile Ala Val Val
         35                  40                  45

Gly Met Ser Cys Arg Leu Pro Gly Ala Ala Gly Val Glu Glu Phe Trp
     50                  55                  60

Glu Leu Leu Arg Ser Gly Arg Gly Met Pro Thr Arg Gln Asp Asp Gly
 65                  70                  75                  80

Thr Trp Arg Ala Ala Leu Glu Asp His Ala Gly Phe Asp Ala Gly Phe
                 85                  90                  95

Phe Gly Met Asn Ala Arg Gln Ala Ala Ala Thr Asp Pro Gln His Arg
                100                 105                 110

Leu Met Leu Glu Leu Gly Trp Glu Ala Leu Glu Asp Ala Gly Ile Val
            115                 120                 125

Pro Gly Asp Leu Thr Gly Thr Asp Thr Gly Val Phe Ala Gly Val Ala
        130                 135                 140

Ser Asp Asp Tyr Ala Val Leu Thr Arg Arg Ser Ala Val Ser Ala Gly
145                 150                 155                 160

Gly Tyr Thr Ala Thr Gly Leu His Arg Ala Leu Ala Ala Asn Arg Leu
                165                 170                 175

Ser His Phe Leu Gly Leu Arg Gly Pro Ser Leu Val Val Asp Ser Ala
                180                 185                 190

Gln Ser Ala Ser Leu Val Ala Val Gln Leu Ala Cys Glu Ser Leu Arg
            195                 200                 205

Arg Gly Glu Thr Ser Leu Ala Val Ala Gly Gly Val Asn Leu Ile Leu
        210                 215                 220

Thr Glu Glu Ser Thr Thr Val Met Glu Arg Met Gly Ala Leu Ser Pro
225                 230                 235                 240

Asp Gly Arg Cys His Thr Phe Asp Ala Arg Ala Asn Gly Tyr Val Arg
                245                 250                 255

Gly Glu Gly Gly Gly Ala Val Val Leu Lys Pro Leu Asp Ala Ala Leu
                260                 265                 270

Ala Asp Gly Asp Arg Val Tyr Cys Val Ile Lys Gly Gly Ala Val Asn
            275                 280                 285

Asn Asp Gly Gly Gly Ala Ser Leu Thr Thr Pro Asp Arg Glu Ala Gln
290                 295                 300

Glu Ala Val Leu Arg Gln Ala Tyr Arg Arg Ala Gly Val Ser Thr Gly
305                 310                 315                 320

Ala Val Arg Tyr Val Glu Leu His Gly Thr Gly Thr Arg Ala Gly Asp
                325                 330                 335

Pro Val Glu Ala Ala Ala Leu Gly Ala Val Leu Gly Ala Gly Ala Asp
            340                 345                 350

Ser Gly Arg Ser Thr Pro Leu Ala Val Gly Ser Val Lys Thr Asn Val
        355                 360                 365
```

```
Gly His Leu Glu Gly Ala Ala Gly Ile Val Gly Leu Ile Lys Ala Thr
    370             375             380
Leu Cys Val Arg Lys Gly Glu Leu Val Pro Ser Leu Asn Phe Ser Thr
385             390             395             400
Pro Asn Pro Asp Ile Pro Leu Asp Asp Leu Arg Leu Arg Val Gln Thr
                405             410             415
Glu Arg Gln Glu Trp Asn Glu Glu Asp Asp Arg Pro Arg Val Ala Gly
            420             425             430
Val Ser Ser Phe Gly Met Gly Gly Thr Asn Val His Leu Val Ile Ala
        435             440             445
Glu Ala Pro Ala Ala Ala Gly Ser Ser Gly Ala Gly Gly Ser Gly Ala
    450             455             460
Gly Ser Gly Ala Gly Ile Ser Ala Val Ser Gly Val Val Pro Val Val
465             470             475             480
Val Ser Gly Arg Ser Arg Val Val Val Arg Glu Ala Ala Gly Arg Leu
            485             490             495
Ala Glu Val Val Glu Ala Gly Gly Val Gly Leu Ala Asp Val Ala Val
        500             505             510
Thr Met Ala Asp Arg Ser Arg Phe Gly Tyr Arg Ala Val Val Leu Ala
    515             520             525
Arg Gly Glu Ala Glu Leu Ala Gly Arg Leu Arg Ala Leu Ala Gly Gly
    530             535             540
Asp Pro Asp Ala Gly Val Val Thr Gly Ala Val Leu Asp Gly Gly Val
545             550             555             560
Val Val Gly Ala Ala Pro Gly Gly Ala Gly Ala Ala Gly Gly Ala Gly
            565             570             575
Ala Ala Gly Gly Ala Gly Gly Gly Gly Val Val Leu Val Phe Pro Gly
        580             585             590
Gln Gly Thr Gln Trp Val Gly Met Gly Ala Gly Leu Leu Gly Ser Ser
        595             600             605
Glu Val Phe Ala Ala Ser Met Arg Glu Cys Ala Arg Ala Leu Ser Val
610             615             620
His Val Gly Trp Asp Leu Leu Glu Val Val Ser Gly Gly Ala Gly Leu
625             630             635             640
Glu Arg Val Asp Val Val Gln Pro Val Thr Trp Ala Val Met Val Ser
            645             650             655
Leu Ala Arg Tyr Trp Gln Ala Met Gly Val Asp Val Ala Ala Val Val
            660             665             670
Gly His Ser Gln Gly Glu Ile Ala Ala Ala Thr Val Ala Gly Ala Leu
        675             680             685
Ser Leu Glu Asp Ala Ala Ala Val Val Ala Leu Arg Ala Gly Leu Ile
    690             695             700
Gly Arg Tyr Leu Ala Gly Arg Gly Ala Met Ala Ala Val Pro Leu Pro
705             710             715             720
Ala Gly Glu Val Glu Ala Gly Leu Ala Lys Trp Pro Gly Val Glu Val
            725             730             735
Ala Ala Val Asn Gly Pro Ala Ser Thr Val Val Ser Gly Asp Arg Arg
            740             745             750
Ala Val Ala Gly Tyr Val Ala Val Cys Gln Ala Glu Gly Val Gln Ala
        755             760             765
Arg Leu Ile Pro Val Asp Tyr Ala Ser His Ser Arg His Val Glu Asp
    770             775             780
Leu Lys Gly Glu Leu Glu Arg Val Leu Ser Gly Ile Arg Pro Arg Ser
```

-continued

```
               785                      790                     795                     800
Pro  Arg  Val  Pro  Val  Cys  Ser  Thr  Val  Ala  Gly  Glu  Gln  Pro  Gly  Glu
                    805                      810                     815

Pro  Val  Phe  Asp  Ala  Gly  Tyr  Trp  Phe  Arg  Asn  Leu  Arg  Asn  Arg  Val
                    820                      825                     830

Glu  Phe  Ser  Ala  Val  Val  Gly  Gly  Leu  Leu  Glu  Glu  Gly  His  Arg  Arg
                    835                      840                     845

Phe  Ile  Glu  Val  Ser  Ala  His  Pro  Val  Leu  Val  His  Ala  Ile  Glu  Gln
850                           855                          860

Thr  Ala  Glu  Ala  Ala  Asp  Arg  Ser  Val  His  Ala  Thr  Gly  Thr  Leu  Arg
865                      870                      875                          880

Arg  Gln  Asp  Asp  Ser  Pro  His  Arg  Leu  Leu  Thr  Ser  Thr  Ala  Glu  Ala
                    885                      890                     895

Trp  Ala  His  Gly  Ala  Thr  Leu  Thr  Trp  Asp  Pro  Ala  Leu  Pro  Pro  Gly
                    900                      905                     910

His  Leu  Thr  Thr  Leu  Pro  Thr  Tyr  Pro  Phe  Asn  His  His  His  Tyr  Trp
               915                      920                     925

Leu  Asp  Thr  Ile  Asp  Gly  Gly  Gly  Asp  Asp  Ala  Thr  Gln  Glu  Lys
     930                      935                      940

Glu  Ser  Gly  Pro  Leu  Thr  Arg  Glu  Leu  Arg  Gly  Leu  Pro  Ser  Ser  Gln
945                      950                      955                          960

Lys  Gln  Leu  Gly  Phe  Leu  Leu  Asp  Leu  Val  Cys  Arg  His  Thr  Ala  Val
                    965                      970                     975

Val  Leu  Gly  Leu  Asp  Thr  Ala  Ala  Glu  Val  Asp  Pro  Asp  Leu  Ser  Phe
                    980                      985                     990

Lys  Lys  Gln  Gly  Ile  Gln  Ser  Met  Thr  Gly  Val  Glu  Leu  Arg  Asn  Arg
                    995                      1000                    1005

Leu  Leu  Thr  Glu  Thr  Gly  Leu  Ala  Leu  Pro  Thr  Thr  Leu  Val  Tyr  Asp
     1010                     1015                     1020

Arg  Pro  Thr  Pro  Arg  Ala  Leu  Ala  Gln  Phe  Leu  His  Thr  Glu  Leu  Leu
1025                     1030                     1035                         1040

Asp  Gly  Ser  Pro  Ser  Gly  Ser  Val  Leu  Ala  Pro  Ala  Gln  Lys  Ser  Phe
                    1045                     1050                    1055

Glu  Ala  Gln  Glu  Pro  Ile  Ala  Val  Val  Gly  Met  Gly  Cys  Arg  Phe  Pro
                    1060                     1065                    1070

Gly  Gly  Val  Gly  Ser  Pro  Glu  Ala  Leu  Trp  Arg  Leu  Val  Val  Glu  Gly
                    1075                     1080                    1085

Val  Asp  Ala  Val  Ser  Pro  Phe  Pro  Gly  Asp  Arg  Gly  Trp  Asp  Val  Glu
                    1090                     1095                    1100

Gly  Leu  Tyr  Asp  Pro  Glu  Pro  Gly  Val  Ala  Gly  Lys  Ser  Tyr  Val  Arg
1105                     1110                     1115                         1120

Glu  Gly  Gly  Phe  Leu  His  Asp  Ala  Ala  Glu  Phe  Asp  Ala  Glu  Phe  Phe
                    1125                     1130                    1135

Gly  Ile  Ser  Pro  Arg  Glu  Ala  Val  Ala  Met  Asp  Pro  Gln  Gln  Arg  Leu
                    1140                     1145                    1150

Leu  Leu  Glu  Thr  Ser  Trp  Glu  Ala  Ile  Glu  Arg  Ala  Gly  Ile  Asp  Pro
                    1155                     1160                    1165

His  Ser  Leu  His  Gly  Ser  Arg  Thr  Gly  Val  Tyr  Ala  Gly  Val  Met  Pro
                    1170                     1175                    1180

Gln  Glu  Tyr  Gly  Pro  Arg  Leu  Ala  Glu  Gly  Ala  Glu  Gly  Ser  Asp  Gly
1185                     1190                     1195                         1200

Tyr  Leu  Leu  Thr  Gly  Thr  Ser  Gly  Ser  Val  Val  Ser  Gly  Arg  Val  Ala
                    1205                     1210                    1215
```

-continued

```
Tyr  Thr  Leu  Gly  Leu  Glu  Gly  Pro  Ala  Val  Thr  Val  Asp  Thr  Ala  Cys
               1220                    1225                    1230

Ser  Ser  Ser  Leu  Val  Ala  Leu  His  Leu  Ala  Val  Gln  Ala  Leu  Arg  Gly
               1235                    1240                    1245

Gly  Glu  Cys  Asp  Met  Ala  Leu  Ala  Gly  Gly  Val  Thr  Val  Met  Ala  Gly
     1250                    1255                    1260

Pro  Gly  Met  Phe  Val  Glu  Phe  Ser  Arg  Gln  Arg  Gly  Leu  Ala  Ala  Asp
1265                    1270                    1275                    1280

Gly  Arg  Cys  Lys  Ala  Phe  Ala  Asp  Gly  Ala  Asp  Gly  Thr  Ala  Trp  Ala
                    1285                    1290                    1295

Glu  Gly  Ala  Gly  Val  Val  Leu  Val  Glu  Arg  Leu  Ser  Asp  Ala  Arg  Arg
               1300                    1305                    1310

Leu  Gly  His  Pro  Val  Leu  Ala  Val  Val  Cys  Gly  Ser  Ala  Val  Asn  Gln
               1315                    1320                    1325

Asp  Gly  Ala  Ser  Asn  Gly  Leu  Thr  Ala  Pro  Ser  Gly  Pro  Ser  Gln  Glu
          1330                    1335                    1340

Arg  Val  Ile  Arg  Gln  Ala  Leu  Gly  Asn  Ala  Arg  Leu  Thr  Val  Ala  Asp
1345                    1350                    1355                    1360

Val  Asp  Val  Val  Glu  Ala  His  Gly  Thr  Gly  Thr  Arg  Leu  Gly  Asp  Pro
               1365                    1370                    1375

Ile  Glu  Ala  Gln  Ala  Leu  Leu  Gly  Thr  Tyr  Gly  Arg  Asp  Arg  Asp  Gly
               1380                    1385                    1390

Gly  Arg  Pro  Val  Trp  Leu  Gly  Ser  Leu  Lys  Ser  Asn  Ile  Gly  His  Ala
               1395                    1400                    1405

Gln  Ala  Ala  Ala  Gly  Val  Ala  Gly  Val  Ile  Lys  Met  Val  Leu  Ala  Met
     1410                    1415                    1420

Arg  Tyr  Gly  Trp  Leu  Pro  Arg  Thr  Leu  His  Val  Asp  Glu  Pro  Ser  Arg
1425                    1430                    1435                    1440

His  Val  Asp  Trp  Ser  Ala  Gly  Gly  Val  Trp  Leu  Leu  Thr  Glu  Ala  Arg
               1445                    1450                    1455

Glu  Trp  Pro  Gly  Val  Asp  Arg  Pro  Arg  Arg  Ala  Ala  Val  Ser  Ala  Phe
               1460                    1465                    1470

Gly  Val  Ser  Gly  Thr  Asn  Ala  His  Leu  Ile  Leu  Glu  Ala  Pro  Asp  Thr
               1475                    1480                    1485

Ala  Glu  Ala  Glu  Ser  Ala  Thr  Thr  Pro  Val  Arg  Ser  Glu  Val  Ser  Glu
     1490                    1495                    1500

Ser  Ala  Ala  Val  Leu  Asp  Ala  Arg  Ser  Gly  Val  Val  Pro  Val  Val  Val
1505                    1510                    1515                    1520

Ser  Gly  Arg  Ser  Arg  Val  Val  Arg  Glu  Ala  Ala  Gly  Arg  Leu  Ala
                    1525                    1530                    1535

Glu  Val  Val  Glu  Ala  Gly  Gly  Val  Gly  Leu  Ala  Asp  Val  Ala  Val  Thr
          1540                    1545                    1550

Met  Ala  Gly  Arg  Ser  Arg  Phe  Gly  Tyr  Arg  Ala  Val  Val  Leu  Ala  Arg
               1555                    1560                    1565

Gly  Glu  Ala  Glu  Leu  Ala  Gly  Arg  Leu  Arg  Ala  Leu  Ala  Gly  Gly  Asp
               1570                    1575                    1580

Pro  Asp  Ala  Gly  Val  Val  Thr  Gly  Ala  Val  Val  Asp  Pro  Glu  Thr  Gly
1585                    1590                    1595                    1600

Ser  Gly  Gly  Gly  Gly  Val  Val  Leu  Val  Phe  Pro  Gly  Gln  Gly  Thr  Gln
                    1605                    1610                    1615

Trp  Val  Gly  Met  Gly  Ala  Gly  Leu  Leu  Gly  Ser  Ser  Glu  Val  Phe  Ala
               1620                    1625                    1630

Ala  Ser  Met  Arg  Glu  Cys  Ala  Arg  Ala  Leu  Ser  Val  His  Val  Glu  Trp
               1635                    1640                    1645
```

```
Asp Leu Leu Glu Val Val Ser Gly Gly Ala Gly Leu Glu Arg Val Asp
    1650                1655                1660
Val Val Gln Pro Val Thr Trp Ala Val Met Val Ser Leu Ala Arg Tyr
1665                1670                1675                1680
Trp Gln Ala Met Gly Val Asp Val Ala Ala Val Val Gly His Ser Gln
                1685                1690                1695
Gly Glu Ile Ala Ala Ala Thr Val Ala Gly Ala Leu Ser Leu Glu Asp
            1700                1705                1710
Ala Ala Ala Val Val Ala Leu Arg Ala Gly Leu Ile Gly Arg Tyr Leu
        1715                1720                1725
Ala Gly Arg Gly Ala Met Ala Ala Val Pro Leu Pro Ala Gly Glu Val
        1730                1735                1740
Glu Ala Gly Leu Ala Lys Trp Pro Gly Val Glu Val Ala Ala Val Asn
1745                1750                1755                1760
Gly Pro Ala Ser Thr Val Val Ser Gly Asp Arg Arg Ala Val Ala Gly
                1765                1770                1775
Tyr Val Ala Val Cys Gln Ala Glu Gly Val Gln Ala Arg Leu Ile Pro
                1780                1785                1790
Val Asp Tyr Ala Ser His Ser Arg His Val Glu Asp Leu Lys Gly Glu
                1795                1800                1805
Leu Glu Arg Val Leu Ser Gly Ile Arg Pro Arg Ser Pro Arg Val Pro
    1810                1815                1820
Val Cys Ser Thr Val Ala Gly Glu Gln Pro Gly Glu Pro Val Phe Asp
1825                1830                1835                1840
Ala Gly Tyr Trp Phe Arg Asn Leu Arg Asn Arg Val Glu Phe Ser Ala
                1845                1850                1855
Val Val Gly Gly Leu Leu Glu Glu Gly His Arg Arg Phe Ile Glu Val
                1860                1865                1870
Ser Ala His Pro Val Leu Val His Ala Ile Glu Gln Thr Ala Glu Ala
        1875                1880                1885
Ala Asp Arg Ser Val His Ala Thr Gly Thr Leu Arg Arg Gln Asp Asp
1890                1895                1900
Ser Pro His Arg Leu Leu Thr Ser Thr Ala Glu Ala Trp Ala His Gly
1905                1910                1915                1920
Ala Thr Leu Thr Trp Asp Pro Ala Leu Pro Pro Gly His Leu Thr Thr
                1925                1930                1935
Leu Pro Thr Tyr Pro Phe Asn His His His Tyr Trp Leu Asp Thr Thr
                1940                1945                1950
Pro Thr Thr Pro Ala Thr Thr Thr Gln Ser Pro Thr Asp Ala Trp Arg
            1955                1960                1965
Tyr Arg Val Thr Trp Lys Ala Leu Thr Glu Ser Ser Pro Val Arg Pro
    1970                1975                1980
His Ser Ile Gly Arg Cys Leu Leu Val Ala Pro Pro Thr Thr Asp Gly
1985                1990                1995                2000
Glu Leu Leu Asp Gly Leu Thr Thr Val Leu Ser Glu Arg Gly Ala Ser
                2005                2010                2015
Val Ala Arg Leu Glu Val Pro Ile Gly Ala Arg Arg Ala Glu Val Ala
                2020                2025                2030
Glu Leu Leu Lys Pro Ser Met Glu Ser Ala Gly Glu Glu Asn Thr Thr
                2035                2040                2045
Val Val Ser Leu Leu Gly Leu Val Pro Ser Thr Asp Ala Val Arg Thr
2050                2055                2060
Ser Ile Ala Leu Leu Gln Ala Val Ser Asp Ile Gly Val Pro Ala Ala
```

```
2065                 2070                 2075                 2080
Arg Val Trp Ala Leu Thr Arg Arg Ala Val Ala Val Val Pro Gly Glu
                2085                2090                2095
Thr Pro Gln Asp Ala Gly Ala Gln Leu Trp Gly Phe Gly Arg Val Ala
                2100                2105                2110
Ala Leu Glu Leu Pro Asp Ile Trp Gly Gly Leu Ile Asp Leu Pro Glu
                2115                2120                2125
Thr Ala Glu Leu Thr Arg Thr Pro Glu Thr Ser Gln Pro Pro Gln Thr
 2130                2135                2140
Pro Glu Arg Leu Pro Gln Thr Pro Asn Arg Arg Ala Leu Glu Leu Ala
 2145                2150                2155                2160
Ala Ala Val Leu Ala Gly Arg Asp Gly Glu Asp Gln Val Ala Val Arg
                2165                2170                2175
Ala Ser Gly Ile Tyr Gly Arg Arg Val Ser Arg Ala Ala Ala Ala Gly
                2180                2185                2190
Ala Ala Ser Trp Gln Pro Ser Gly Thr Val Leu Ile Thr Gly Gly Met
                2195                2200                2205
Gly Ala Ile Gly Arg Arg Leu Ala Arg Arg Leu Ala Ala Glu Gly Ala
                2210                2215                2220
Glu Arg Leu Val Leu Thr Ser Arg Arg Gly Pro Glu Ala Pro Gly Ala
 2225                2230                2235                2240
Ala Glu Leu Ala Glu Glu Leu Arg Gly His Gly Cys Glu Val Val His
                2245                2250                2255
Ala Ala Cys Asp Val Ala Glu Arg Asp Ala Leu Ala Ala Leu Val Thr
                2260                2265                2270
Ala Tyr Pro Pro Asn Ala Val Phe His Thr Ala Gly Ile Leu Asp Asp
                2275                2280                2285
Ala Val Ile Asp Thr Leu Ser Pro Glu Ser Phe Glu Thr Val Arg Gly
 2290                2295                2300
Ala Lys Val Cys Gly Ala Glu Leu Leu His Gln Leu Thr Ala Asp Ile
 2305                2310                2315                2320
Lys Gly Leu Asp Ala Phe Val Leu Phe Ser Ser Val Thr Gly Thr Trp
                2325                2330                2335
Gly Asn Ala Gly Gln Gly Ala Tyr Ala Ala Ala Asn Ala Ala Leu Asp
                2340                2345                2350
Ala Leu Ala Glu Arg Arg Arg Ala Ala Gly Leu Pro Ala Thr Ser Val
                2355                2360                2365
Ala Trp Gly Leu Trp Gly Gly Gly Gly Met Ala Ala Gly Ala Gly Glu
                2370                2375                2380
Glu Ser Leu Ser Arg Arg Gly Leu Arg Ala Met Asp Pro Asp Ala Ala
 2385                2390                2395                2400
Val Asp Ala Leu Leu Gly Ala Met Gly Arg Asn Asp Val Cys Val Thr
                2405                2410                2415
Val Val Asp Val Asp Trp Glu Arg Phe Ala Pro Ala Thr Asn Ala Ile
                2420                2425                2430
Arg Pro Gly Arg Leu Phe Asp Thr Val Pro Glu Ala Arg Glu Ala Leu
                2435                2440                2445
Thr Ala Ala Gly Thr Thr Ser Ala Thr Pro Asp Gly Ala Pro Glu Leu
                2450                2455                2460
Ala Arg Arg Leu Ser Met Leu Asn Glu Thr Glu Arg Leu Arg Lys Leu
 2465                2470                2475                2480
Val Glu Leu Val Arg Thr Glu Ala Ala Phe Val Leu Arg His Pro Asn
                2485                2490                2495
```

```
Thr  Asp  Ala  Ile  Gly  Ala  Glu  Arg  Pro  Phe  Lys  Ser  Ala  Gly  Phe  Asp
               2500                2505                    2510

Ser  Leu  Thr  Ser  Leu  Glu  Leu  Arg  Asn  Arg  Leu  Asn  Ala  Gly  Thr  Gly
               2515                2520                    2525

Leu  Lys  Leu  Pro  Ala  Thr  Val  Ile  Phe  Asp  His  Pro  Ser  Pro  Thr  Ala
          2530                2535                    2540

Leu  Ala  Arg  Leu  Leu  Leu  Asp  Arg  Leu  Thr  Gly  Ala  Gly  Ala  Pro  Ala
2545                2550                    2555                         2560

Pro  Ala  Ala  Asp  Glu  Pro  Pro  Leu  Pro  Val  Ala  Val  Ala  Asp  Asp
               2565                2570                    2575

Pro  Val  Val  Ile  Val  Gly  Met  Ala  Cys  Arg  Phe  Pro  Gly  Gly  Ala  Gly
               2580                2585                    2590

Thr  Pro  Glu  Ala  Leu  Trp  Lys  Leu  Val  Thr  Glu  Glu  Arg  Asp  Val  Ile
          2595                2600                    2605

Gly  Ala  Ala  Pro  Thr  Asp  Arg  Gly  Trp  Asp  Leu  Asp  Ser  Val  Tyr  Asp
          2610                2615                    2620

Pro  Glu  Pro  Gly  Val  Ala  Gly  Lys  Thr  Tyr  Val  Arg  Glu  Gly  Gly  Phe
2625                2630                    2635                         2640

Leu  His  Asp  Ala  Ala  Glu  Phe  Asp  Ala  Glu  Phe  Phe  Gly  Ile  Ser  Pro
               2645                2650                    2655

Arg  Glu  Ala  Val  Ala  Met  Asp  Pro  Gln  Gln  Arg  Leu  Leu  Leu  Glu  Thr
               2660                2665                    2670

Ser  Trp  Glu  Ala  Ile  Glu  Arg  Ala  Gly  Ile  Asp  Pro  His  Ser  Leu  His
               2675                2680                    2685

Gly  Ser  Arg  Thr  Gly  Val  Tyr  Val  Gly  Leu  Thr  His  Gln  Glu  Tyr  Ala
          2690                2695                    2700

Ser  Arg  Leu  His  Glu  Ala  Pro  Glu  Glu  Tyr  Glu  Gly  Tyr  Leu  Leu  Thr
2705                2710                    2715                         2720

Gly  Lys  Ser  Ala  Ser  Val  Val  Ser  Gly  Arg  Ile  Ser  Tyr  Thr  Leu  Gly
               2725                2730                    2735

Leu  Glu  Gly  Pro  Ser  Leu  Ser  Ile  Asp  Thr  Ala  Cys  Ser  Ser  Ser  Leu
               2740                2745                    2750

Val  Ala  Leu  His  Asn  Ala  Ala  Gln  Ala  Leu  Arg  Gly  Gly  Glu  Cys  Asp
               2755                2760                    2765

Met  Ala  Leu  Ala  Gly  Gly  Val  Thr  Val  Met  Ala  Ala  Pro  Gly  Leu  Phe
     2770                2775                    2780

Val  Glu  Phe  Ser  Arg  Gln  Arg  Gly  Leu  Ala  Ala  Asp  Gly  Arg  Cys  Lys
2785                2790                    2795                         2800

Ala  Phe  Ala  Asp  Gly  Ala  Asp  Gly  Thr  Ala  Trp  Ala  Glu  Gly  Ala  Gly
               2805                2810                    2815

Val  Val  Leu  Val  Glu  Arg  Leu  Ser  Asp  Ala  Arg  Arg  Leu  Gly  His  Pro
               2820                2825                    2830

Val  Leu  Ala  Val  Val  Cys  Gly  Ser  Ala  Val  Asn  Gln  Asp  Gly  Ala  Ser
          2835                2840                    2845

Asn  Gly  Leu  Thr  Ala  Pro  Ser  Gly  Pro  Ser  Gln  Glu  Arg  Val  Ile  Arg
          2850                2855                    2860

Gln  Ala  Leu  Ala  Asn  Ala  Arg  Leu  Thr  Val  Ala  Asp  Val  Asp  Val  Val
2865                2870                    2875                         2880

Glu  Ala  His  Gly  Thr  Gly  Thr  Arg  Leu  Gly  Asp  Pro  Ile  Glu  Ala  Gln
               2885                2890                    2895

Ala  Leu  Leu  Gly  Thr  Tyr  Gly  Arg  Asp  Arg  Asp  Ala  Glu  Cys  Pro  Val
               2900                2905                    2910

Trp  Leu  Gly  Ser  Leu  Lys  Ser  Asn  Ile  Gly  His  Ala  Gln  Ala  Ala  Ala
               2915                2920                    2925
```

```
Gly Val Ala Gly Val Ile Lys Met Val Leu Ala Met Arg Tyr Gly Trp
         2930                2935                 2940

Leu Pro Arg Thr Leu His Val Asp Glu Pro Ser Arg His Val Asp Trp
2945                2950                2955                 2960

Ser Ala Gly Gly Val Arg Leu Leu Thr Glu Ala Arg Glu Trp Pro Gly
                2965                2970                2975

Val Asp Arg Pro Arg Arg Ala Ala Val Ser Ala Phe Gly Val Ser Gly
            2980                2985                 2990

Thr Asn Ala His Leu Ile Leu Glu Ala Pro Glu Ala Leu Glu Ala Leu
            2995                 3000                3005

Glu Ala Thr Asp Ala Pro Glu Ala Pro Glu Ala Pro Glu Ala Pro Asp
3010                3015                 3020

Val Thr Asp Val Thr Glu Ala Leu Glu Ala Pro Asp Ala Thr Glu Ala
3025                3030                 3035                3040

Glu Gly Ala Lys Ala Pro Gly Ser Pro Glu Glu Ala Gln Pro Ala Val
            3045                3050                 3055

Gly Val Val Pro Val Val Val Ser Gly Arg Ser Arg Val Val Arg
            3060                3065                 3070

Glu Ala Ala Gly Arg Leu Ala Glu Val Val Glu Ala Gly Gly Val Gly
        3075                3080                 3085

Leu Ala Asp Val Ala Val Thr Met Ala Gly Arg Ser Arg Phe Gly Tyr
            3090                3095                 3100

Arg Ala Val Val Leu Ala Arg Gly Glu Ala Glu Leu Ala Gly Arg Leu
3105                3110                 3115                3120

Arg Ala Leu Ala Gly Gly Asp Pro Asp Ala Gly Val Val Thr Gly Ala
                3125                3130                 3135

Val Val Asp Pro Glu Thr Gly Ser Gly Gly Gly Gly Val Val Leu Val
            3140                3145                 3150

Phe Pro Gly Gln Gly Thr Gln Trp Val Gly Met Gly Ala Gly Leu Leu
            3155                3160                 3165

Gly Ser Ser Glu Val Phe Ala Ala Ser Met Arg Glu Cys Ala Arg Ala
            3170                3175                 3180

Leu Ser Val His Val Glu Trp Asp Leu Leu Glu Val Val Ser Gly Gly
3185                3190                 3195                3200

Ala Gly Leu Glu Arg Val Asp Val Val Gln Pro Val Thr Trp Ala Val
                3205                3210                 3215

Met Val Ser Leu Ala Arg Tyr Trp Gln Ala Met Gly Val Asp Val Ala
                3220                3225                 3230

Ala Val Val Gly His Ser Gln Gly Glu Ile Ala Ala Ala Thr Val Ala
            3235                3240                 3245

Gly Ala Leu Ser Leu Glu Asp Ala Ala Ala Val Val Ala Leu Arg Ala
3250                3255                 3260

Gly Leu Ile Gly Arg Tyr Leu Ala Gly Arg Gly Ala Met Ala Ala Val
3265                3270                 3275                3280

Pro Leu Pro Ala Gly Glu Val Glu Ala Gly Leu Ala Lys Trp Pro Gly
                3285                3290                 3295

Val Gln Val Ala Ala Val Asn Gly Pro Ala Ser Thr Val Val Ser Gly
            3300                3305                 3310

Asp Arg Arg Ala Val Ala Gly Tyr Val Ala Val Cys Gln Ala Glu Gly
            3315                3320                 3325

Val Gln Ala Arg Leu Ile Pro Val Asp Tyr Ala Ser His Ser Arg His
3330                3335                 3340

Val Glu Asp Leu Lys Gly Glu Leu Glu Arg Val Leu Ser Gly Ile Arg
```

|  |  |  |  |
| --- | --- | --- | --- |
| 3345 | 3350 | 3355 | 3360 |

Pro Arg Ser Pro Arg Val Pro Val Cys Ser Thr Val Ala Gly Glu Gln
                    3365                    3370                    3375

Pro Gly Glu Pro Val Phe Asp Ala Gly Tyr Trp Phe Arg Asn Leu Arg
                    3380                    3385                    3390

Asn Arg Val Glu Phe Ser Ala Val Val Gly Gly Leu Leu Glu Gln Gly
                    3395                    3400                    3405

His Arg Arg Phe Ile Glu Val Ser Ala His Pro Val Leu Val His Ala
        3410                    3415                    3420

Ile Glu Gln Thr Ala Glu Ala Ala Asp Arg Ser Val His Ala Thr Gly
3425                    3430                    3435                    3440

Thr Leu Arg Arg Gln Asp Asp Ser Pro His Arg Leu Leu Thr Ser Thr
                    3445                    3450                    3455

Ala Glu Ala Trp Ala His Gly Ala Thr Leu Thr Trp Asp Pro Ala Leu
                    3460                    3465                    3470

Pro Pro Gly His Leu Thr Thr Leu Pro Thr Tyr Pro Phe Asn His His
        3475                    3480                    3485

His Tyr Trp Ala Val Thr Ser Pro Ala Gly Val Gly Asp Ala Ala Ala
        3490                    3495                    3500

Gly Arg Phe Gly Met Thr Trp Glu Asp His Pro Phe Leu Arg Gly Gly
3505                    3510                    3515                    3520

Leu Pro Leu Ala Asp Ser Gly Glu Arg Val Phe Ala Gly Arg Leu Ala
                    3525                    3530                    3535

Gly Ser Glu His Asp Trp Leu Thr Asp His Ala Val Ser Gly Val Thr
                    3540                    3545                    3550

Leu Leu Pro Gly Thr Ala Phe Val Glu Phe Ala Leu His Ala Gly Ala
        3555                    3560                    3565

Ala Thr Gly Cys Gly Arg Leu Glu Glu Leu Ser Val Glu Ala Pro Leu
3570                    3575                    3580

Val Leu Pro Ala Ala Gly Gly Val Arg Val Gln Met Arg Val Ser Ala
3585                    3590                    3595                    3600

Ala Asp Glu Ser Gly Arg Arg Arg Val Ala Ile His Ser Ala Pro Glu
                    3605                    3610                    3615

Ala Ala Val His Ser Ala Ala Glu Gly Gly Asp Ser Ala Gly Val Trp
        3620                    3625                    3630

Thr Arg His Gly Glu Gly Thr Leu Val Pro Asp Pro Glu Pro Thr Pro
        3635                    3640                    3645

Pro Asp Ala Asp Trp Ala Arg Ala Trp Pro Pro Ala Gly Glu Arg Val
        3650                    3655                    3660

Glu Pro Ala Glu Leu Tyr Glu Arg Phe Gly Ala Leu Gly Tyr Glu Tyr
3665                    3670                    3675                    3680

Gly Glu Ala Phe Ala Gly Val Arg Ala Val Trp Arg Gln Pro Asp Ala
                    3685                    3690                    3695

Leu Leu Ala Glu Val Leu Leu Pro Asp Arg Ala Ser Thr Gly Ala Gly
                    3700                    3705                    3710

Arg Phe Gly Val His Pro Ala Leu Leu Asp Ala Ala Leu Gln Pro Trp
        3715                    3720                    3725

Ile Ala Gly Gly Leu Leu Glu Val Pro Glu Asp Ala Val Leu Leu Pro
3730                    3735                    3740

Phe Ala Trp Gln Gly Val Ser Leu Tyr Ala Thr Gly Ala Gly Ala Leu
3745                    3750                    3755                    3760

Arg Val Arg Leu Thr Lys Ala Gly Asp Gly Ala Val Ser Leu Gln Ala
                    3765                    3770                    3775

```
Ala  Asp  Thr  Ser  Gly  Ala  Ala  Val  Leu  Ser  Leu  Gly  Ala  Leu  Val  Met
               3780                3785                     3790

Arg  Pro  Leu  Ala  Arg  Arg  Lys  Leu  Asp  Val  Leu  Leu  Gly  Thr  Asp  Ala
               3795                3800                     3805

Gly  Glu  Arg  Ser  Leu  Tyr  Arg  Val  Glu  Trp  Gln  Pro  Arg  Leu  Leu  Pro
               3810                3815                     3820

Ala  Gly  Pro  Pro  Arg  Ser  Trp  Ala  Val  Leu  Gly  Pro  Asp  Ala  Asp  Arg
3825                3830                3835                              3840

Leu  Ala  Gly  Thr  Pro  Gly  Leu  Gly  Asp  Gln  Pro  Asp  Gly  Gly  Pro  Thr
               3845                3850                     3855

Ala  Leu  Tyr  Pro  Glu  Val  Arg  Ala  Leu  Arg  Lys  Ala  Leu  Ala  Ala  Gly
               3860                3865                     3870

Ala  Pro  Arg  Pro  Glu  Ala  Val  Val  Leu  Pro  Val  Leu  Ser  Gly  Ala  Gly
               3875                3880                     3885

Ala  Thr  Pro  Glu  Ser  Val  Arg  Gln  Thr  Thr  Glu  Arg  Cys  Leu  Thr  Ala
               3890                3895                     3900

Leu  Gln  Asp  Trp  Leu  Asp  Ala  Glu  Glu  Leu  Val  Asp  Thr  Pro  Leu  Ile
3905                3910                3915                              3920

Val  Leu  Thr  Arg  Gly  Ala  Val  Ala  Ala  Val  Pro  Gly  Glu  Glu  Ile  Gly
               3925                3930                     3935

Asp  Leu  Ala  Cys  Ala  Gly  Val  Trp  Gly  Leu  Val  Arg  Ser  Ala  Arg  Ser
               3940                3945                     3950

Glu  His  Pro  Gly  Arg  Phe  Ala  Leu  Val  Asp  Thr  Asp  Gly  His  Pro  Asp
               3955                3960                     3965

Asp  Arg  Thr  Ala  Leu  Pro  Leu  Ala  Leu  Arg  Ala  Val  Leu  Asp  Gly  Ala
               3970                3975                     3980

Gly  Gln  Leu  Ser  Leu  Arg  Ala  Gly  Thr  Ala  Arg  Thr  Pro  Val  Leu  Leu
3985                3990                3995                              4000

Arg  Ala  Gly  Thr  Pro  Glu  Glu  Gln  Arg  Gly  Pro  Ala  Phe  Asp  Pro  Ala
               4005                4010                     4015

Gly  Thr  Val  Leu  Val  Thr  Gly  Ala  Thr  Gly  Thr  Leu  Gly  Arg  Leu  Leu
               4020                4025                     4030

Ala  Arg  His  Leu  Ala  Ala  Glu  His  Gly  Val  Arg  His  Leu  Leu  Leu  Leu
               4035                4040                     4045

Ser  Arg  Gly  Gly  Arg  Ala  Ala  Glu  Gly  Ala  Asp  Glu  Leu  Ala  Ala  Glu
4050                4055                4060

Leu  Ala  Gly  Leu  Glu  Ala  Glu  Pro  Cys  Phe  Ala  Ala  Cys  Asp  Ala  Ala
4065                4070                4075                              4080

Asp  Arg  Glu  Ala  Leu  Ala  Arg  Val  Leu  Ala  Glu  Val  Pro  Ala  Asp  Arg
               4085                4090                     4095

Pro  Leu  Thr  Gly  Val  Ile  His  Ala  Ala  Gly  Val  Leu  Asp  Asp  Gly  Thr
               4100                4105                     4110

Leu  Asp  Ala  Leu  Thr  Pro  Glu  Arg  Ile  Gly  Thr  Val  Met  Arg  Pro  Lys
               4115                4120                     4125

Ala  Asp  Ala  Ala  Leu  Asn  Leu  His  Glu  Leu  Thr  Arg  Thr  Ser  Pro  Leu
               4130                4135                     4140

Ser  Val  Phe  Ala  Val  Phe  Ser  Gly  Ala  Ala  Gly  Ile  Leu  Gly  Arg  Pro
4145                4150                4155                              4160

Gly  Gln  Ala  Asn  Tyr  Ala  Ala  Ala  Asn  Thr  Phe  Leu  Asp  Ala  Leu  Ala
               4165                4170                     4175

Gln  His  Arg  Arg  Ala  His  Gly  Leu  Pro  Ala  Val  Ser  Leu  Ala  Trp  Gly
               4180                4185                     4190

Leu  Trp  Gly  Gly  Ala  Thr  Gly  Met  Thr  Gly  His  Leu  Ser  Gly  Thr  Asp
               4195                4200                     4205
```

| | | | | | | | | | | | | | | |
|---|---|---|---|---|---|---|---|---|---|---|---|---|---|---|
|Leu|Arg|Arg|Met|Arg|Arg|Ser|Gly|Ile|Ala|Pro|Met|Thr|His|Asp|Gln|
| |4210| | | |4215| | | |4220| | | | | |
|Gly|Leu|Ala|Leu|Phe|Asp|Arg|Ala|Leu|Ala|Ala|Ser|Ala|Glu|Asp|Pro|
|4225| | | | |4230| | | |4235| | | | |4240| |
|Leu|Leu|Val|Pro|Met|Arg|Leu|Asp|Leu|Ala|Ala|Leu|Val|Arg|Glu|Arg|
| | | | |4245| | | |4250| | | | |4255| | |
|Ala|Glu|His|Gly|Pro|Asp|Ala|Val|Pro|Gly|Pro|Leu|Leu|Gly|Leu|Leu|
| | | |4260| | | | |4265| | | | |4270| | |
|Pro|Ala|Arg|Ala|Ala|Val|Arg|Gln|Ala|Ala|Ala|Pro|Val|Arg|Gly|Gly|
| | |4275| | | | |4280| | | | |4285| | | |
|Ala|Pro|Ala|Pro|Ala|Gly|Gly|Glu|Gly|Thr|Ala|Glu|Arg|Leu|Ala|Gly|
| | |4290| | | | |4295| | | | |4300| | | |
|Leu|Gly|Glu|Glu|Ala|Arg|Leu|Arg|Glu|Leu|Val|Arg|Leu|Val|Arg|Ala|
|4305| | | | |4310| | | | |4315| | | | |4320|
|Glu|Val|Ser|Gly|Val|Leu|Gly|Tyr|Ser|Gly|Pro|Asp|Ala|Val|Glu|Pro|
| | | | |4325| | | | |4330| | | | |4335| |
|Gly|Arg|Pro|Phe|Lys|Asp|Leu|Gly|Phe|Asp|Ser|Leu|Thr|Ala|Val|Glu|
| | | | |4340| | | | |4345| | | | |4350| |
|Leu|Arg|Asn|Arg|Leu|Gly|Ala|Ala|Thr|Gly|Leu|Arg|Leu|Pro|Thr|Ala|
| | | |4355| | | | |4360| | | | |4365| | |
|Leu|Val|Phe|Asp|Arg|Pro|Thr|Ser|Gln|Ala|Val|Ala|Glu|Tyr|Leu|Ala|
| | | |4370| | | | |4375| | | | |4380| | |
|Ala|Glu|Leu|Ala|Gly|Pro|Arg|Asp|Gly|Gly|Asp|Thr|Ala|Ala|Ala|Ala|
|4385| | | | |4390| | | | |4395| | | | |4400|
|Phe|Glu|Gly|Leu|Glu|Ala|Leu|Ala|Ala|Ala|Val|Gly|Ala|Leu|Ala|Glu|
| | | | |4405| | | | |4410| | | | |4415| |
|Asp|Asp|Leu|Arg|Arg|Asp|Val|Leu|Arg|Arg|Arg|Leu|Thr|Glu|Leu|Ala|
| | | |4420| | | | |4425| | | | |4430| | |
|Ala|Ala|Leu|Thr|Pro|Gln|Gly|Arg|Asn|Pro|Ser|Ala|Pro|Ala|Pro|Ala|
| | |4435| | | | |4440| | | | |4445| | | |
|Pro|Ser|Asp|Leu|Asp|Glu|Arg|Leu|Asp|Ser|Ala|Asn|Asp|Asp|Asp|Leu|
| | |4450| | | | |4455| | | | |4460| | | |
|Phe|Ala|Phe|Ile|Glu|Glu|Gln|Leu| | | | | | | | |
|4465| | | | |4470| | | | | | | | | | |

( 2 ) INFORMATION FOR SEQ ID NO:3:

( i ) SEQUENCE CHARACTERISTICS:
        ( A ) LENGTH: 1864 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|---|
|Met|Thr|Ala|Glu|Leu|Val|Ala|Thr|Arg|Lys|Arg|Leu|Gly|Ala|Leu|Glu|
|1| | | |5| | | | |10| | | | |15| |
|Glu|Arg|Ala|Arg|Glu|Pro|Ile|Ala|Val|Val|Ala|Met|Ser|Cys|Arg|Tyr|
| | | | |20| | | | |25| | | | |30| |
|Pro|Gly|Gly|Val|Thr|Thr|Pro|Glu|Asp|Leu|Trp|Arg|Leu|Leu|Ala|Asp|
| | | |35| | | | |40| | | | |45| | |
|Glu|Arg|Asp|Ala|Val|Ser|Gly|Leu|Pro|Arg|Asp|Gly|Trp|Asp|Leu| |
| |50| | | | |55| | | | |60| | | | |
|Asp|Ala|Leu|Tyr|Asp|Pro|Asp|Gly|Pro|Gly|Thr|Ser|Tyr|Ala|Arg| |
|65| | | | |70| | | | |75| | | | |80| |
|Glu|Gly|Gly|Phe|Leu|Ser|His|Cys|Ala|Gly|Phe|Asp|Ala|Glu|Phe|Phe|

|   |   |   | 85 |   |   |   | 90 |   |   |   | 95 |   |   |
|---|---|---|---|---|---|---|---|---|---|---|---|---|---|
| Gly | Ile | Ser | Pro<br>100 | Arg | Glu | Ala | Leu<br>105 | Ala | Met | Asp | Pro | Gln<br>110 | Gln | Arg | Leu |
| Leu | Leu | Glu<br>115 | Thr | Ser | Trp | Glu<br>120 | Ala | Leu | Glu | Arg | Ala<br>125 | Gly | Val | Thr | Ala |
| Asp | Arg<br>130 | Ala | Arg | Gly | Ser<br>135 | Arg | Thr | Gly | Val | Tyr<br>140 | Ala | Gly | Val | Met | Tyr |
| Asp<br>145 | Asp | Tyr | Gly | Ala | Arg<br>150 | Val | Leu | Tyr | Gly | Ala<br>155 | Gly | Ala | Gly | Pro | Pro<br>160 |
| Glu | Asp | Leu | Glu | Gly<br>165 | Tyr | Leu | Val | Asn | Gly<br>170 | Ser | Ala | Gly | Ser<br>175 | Ile | Ala |
| Ser | Gly | Arg | Val<br>180 | Ser | Tyr | Thr | Phe<br>185 | Gly | Leu | Arg | Gly | Pro<br>190 | Ala | Val | Thr |
| Val | Asn | Thr<br>195 | Ala | Cys | Ser | Ser<br>200 | Ser | Leu | Val | Ser | Leu<br>205 | His | Leu | Ala | Val |
| Arg | Ala<br>210 | Leu | Arg | Asn | Gly | Glu<br>215 | Cys | Asp | Met | Ala | Leu<br>220 | Ala | Gly | Gly | Ala |
| Thr<br>225 | Val | Leu | Ser | Thr | Pro<br>230 | Thr | Val | Leu | Val | Asp<br>235 | Phe | Ser | Arg | Gln | Arg<br>240 |
| Gly | Leu | Ala | Pro | Asp<br>245 | Gly | Arg | Cys | Lys | Ala<br>250 | Phe | Ala | Asp | Ser | Ala<br>255 | Asp |
| Gly | Thr | Ser | Trp<br>260 | Ala | Glu | Gly | Ala<br>265 | Gly | Met | Leu | Leu | Leu<br>270 | Gln | Arg | Leu |
| Ser | Asp | Ala<br>275 | Arg | Arg | Glu | Gly<br>280 | Arg | Pro | Val | Leu | Ala<br>285 | Val | Ile | Arg | Gly |
| Ser | Ala<br>290 | Val | Asn | Gln | Asp<br>295 | Gly | Ala | Ser | Asn | Gly<br>300 | Leu | Thr | Ala | Pro | Asn |
| Gly<br>305 | Arg | Ala | Gln | Arg | Gln<br>310 | Val | Ile | Glu | Asp | Ala<br>315 | Leu | Arg | Asp | Ala | Gly<br>320 |
| Val | Gly | Pro | Asp | Gln<br>325 | Val | Asp | Ala | Val | Glu<br>330 | Ala | His | Gly | Thr | Gly<br>335 | Thr |
| Glu | Leu | Gly | Asp<br>340 | Pro | Ile | Glu | Ala | Gly<br>345 | Ala | Leu | Leu | Ala | Thr<br>350 | Tyr | Gly |
| Thr | Ala | Arg<br>355 | Thr | Ala | Glu | Arg<br>360 | Pro | Leu | Trp | Leu | Gly<br>365 | Ser | Leu | Lys | Ser |
| Asn | Ile<br>370 | Gly | His | Thr | Gln<br>375 | Ala | Ala | Ala | Gly | Val<br>380 | Ala | Gly | Val | Ile | Lys |
| Met<br>385 | Val | Leu | Ala | Met | Arg<br>390 | His | Gly | Arg | Leu | Pro<br>395 | Arg | Thr | Leu | His | Val<br>400 |
| Asp | Arg | Pro | Thr | Thr<br>405 | Arg | Val | Asp | Trp | Glu<br>410 | Lys | Gly | Gly | Val | Arg<br>415 | Leu |
| Leu | Thr | Glu | Pro<br>420 | Val | Pro | Trp | Pro<br>425 | Gly | Glu | Ala | Gly | Glu<br>430 | Pro | Arg | Arg |
| Ala | Gly | Val<br>435 | Ser | Ser | Phe | Gly<br>440 | Ala | Ser | Gly | Thr | Asn<br>445 | Ala | His | Val | Val |
| Leu | Glu<br>450 | Ser | Val | Pro | Ala<br>455 | Gly | Glu | Pro | Ala | Ala<br>460 | Gly | Arg | Pro | Glu |
| Asp<br>465 | Thr | Gly | Gly | Ala | Trp<br>470 | Thr | Val | Ser | Gly | Arg<br>475 | Gly | Pro | Ala | Ala | Leu<br>480 |
| Arg | Ala | Gln | Ala | Ala<br>485 | Arg | Leu | Tyr | Asp | Ala<br>490 | Leu | Thr | Gly | Thr | Gly<br>495 | Thr |
| Gly | Thr | Gly | Gln<br>500 | Gly | Ala | Gly | Gln<br>505 | Gly | Ala | Gly | Pro | Gly<br>510 | Thr | Ala | Glu |

-continued

```
Val Ala Gly Ala Leu Ala His Ala Arg Thr Ala Phe Arg His Arg Ala
            515                 520                 525
Val Val Leu Gly Gly Asn Arg Ala Glu Leu Leu Ala Gly Leu Arg Glu
            530                 535                 540
Leu Ala Glu Glu Glu His Pro Gly Pro Arg Val Thr Gly Thr Ala
545                         550                 555                 560
Pro Ala Thr Glu Arg Arg Thr Ala Phe Leu Phe Ser Gly Gln Gly Ser
                    565                 570                 575
Gln Arg Ala Gly Ser Gly Arg Gly Leu Tyr Arg Arg His Pro Val Phe
                580                 585                 590
Ala Arg Ala Leu Asp Glu Val Cys Ala Ala Leu Glu Pro His Leu His
            595                 600                 605
Arg Pro Leu Arg Asp Leu Met Phe Ala Glu Pro Gly Ser Pro Glu Ala
        610                 615                 620
Glu Pro Leu Asp Arg Thr Glu Phe Thr Gln Pro Ala Leu Phe Ala Leu
625                 630                 635                 640
Gln Thr Ala Leu Phe Arg Leu Ala Glu His His Gly Leu Arg Ala Glu
                645                 650                 655
Ala Leu Cys Gly His Ser Val Gly Glu Ile Ala Ala Ala His Ala Ala
            660                 665                 670
Gly Val Leu Thr Leu Pro Asp Ala Ala Arg Leu Val Ala Ala Arg Gly
        675                 680                 685
Arg Leu Met Gln Ala Leu Pro Ala Gly Gly Ala Met Ala Ala Leu Arg
    690                 695                 700
Ala Thr Ala Glu Glu Ile Ala Pro Leu Leu Glu Arg Arg Ala Gly Glu
705                 710                 715                 720
Leu Ala Leu Ala Ala Val Asn Gly Pro Ser Ser Val Val Val Ser Gly
                725                 730                 735
Asp Glu Ala Ala Val Leu Glu Leu Leu Glu Gln Trp Arg Ala Glu Gly
            740                 745                 750
Arg Glu Ala Arg Arg Leu Ala Val Ser His Ala Phe His Ser Pro Arg
        755                 760                 765
Met Asp Gly Met Leu Thr Gln Phe Asp Arg Val Ala Arg Thr Leu Thr
    770                 775                 780
Phe Ala Pro Pro Thr Ile Pro Leu Val Ser Thr Leu Thr Gly Thr Pro
785                 790                 795                 800
Val Thr Glu Glu Thr Leu Cys Thr Ala Asp His Trp Val Arg Gln Ala
                805                 810                 815
Arg Glu Pro Val Arg Phe Leu Asp Ala Met Arg Thr Leu Arg Ala Asp
            820                 825                 830
Gly Ile Asp Thr Phe Val Glu Leu Gly Pro Asp Gly Val Leu Ser Ala
        835                 840                 845
Met Ala Arg Asp Cys Ala Asp Asp Arg Pro Asp Gly Asp Thr Thr Gly
    850                 855                 860
Ala Gly Asp Gly Glu Thr Pro Asp Pro Leu Leu Thr Leu Pro Leu Leu
865                 870                 875                 880
Arg Arg Ser Val Pro Glu Thr Gly Asp Ala Glu His Pro Gly Gly Phe
                885                 890                 895
Glu Arg Ala Leu Ala Thr Ala Tyr Ala His Gly Val Pro Leu Arg Leu
            900                 905                 910
Ala Pro Ala Pro Asp Ala Ala Ser Leu Ala Val Ala Ala Glu Leu Pro
        915                 920                 925
Thr Tyr Ala Phe Gln Arg Thr His Tyr Trp Leu Asp Ala Pro Ala Ala
    930                 935                 940
```

```
Pro Ala Ala Leu Pro Ala Gly Leu Asp Asp Ala Gly His Pro Leu Leu
945                 950                 955                 960

Ser Ala Ala Leu Asp Leu Pro Gly Gly Arg Gly Thr Val Trp Thr Gly
                965                 970                 975

Ala Leu Ser Ala Ala Thr Leu Pro Trp Ala Ala Asp His Ser Val His
            980                 985                 990

Gly Arg Thr Val Leu Pro Gly Thr Ala Leu Leu Asp Leu Ala Leu His
        995                 1000                1005

Ala Ala Pro Arg Val Gly Glu Leu Thr Phe Glu Ala Pro Leu Val Leu
    1010                1015                1020

Pro Glu Asp Gly Glu Val Arg Leu Arg Val Val Leu Ala Glu Pro Asp
1025                1030                1035                1040

Ala Ser Gly Val Arg Glu Leu Ser Val His Ser Ala Gly Glu Asp Gly
                1045                1050                1055

Gly Trp Thr Arg His Ala Thr Ala Val Leu Asp Thr Gly Thr Thr Thr
                1060                1065                1070

Ala Gly Glu Pro Ala Gly Ala Pro Pro Ala Ala Trp Pro Pro Gly Asp
            1075                1080                1085

Ala Glu Pro Leu Asp Leu Ala Ala Glu Tyr Glu Arg Phe Ala Asp Ala
            1090                1095                1100

Gly Ile Gly Tyr Gly Pro Ala Phe Arg Gly Leu Arg Ser Ala Trp Arg
1105                1110                1115                1120

Asp Gly Asp Ala Ile Leu Ala Asp Val Arg Leu Pro Gly Glu Leu Ala
                1125                1130                1135

Gly Glu Ala Asp Arg Tyr Gly Ile His Pro Ala Leu Leu Asp Ala Ala
                1140                1145                1150

Leu His Thr Ala Ala Ala Ala Leu Gly Gly Ala His Gly Met Leu Pro
            1155                1160                1165

Phe Thr Trp Asn Gly Val Thr Leu His Ala Arg Gly Ala His Ala Ile
            1170                1175                1180

Arg Val Arg Leu Thr Pro Ala Gly Pro Asp Ala Val Ala Val Thr Ala
1185                1190                1195                1200

Val Asp Pro Ala Gly Arg Pro Val Phe Thr Ala Ala Ser Leu Thr Leu
                1205                1210                1215

Arg Pro Val Thr Thr Gly Gln Leu Thr Ala Ala Glu Ala Ala Arg Ala
            1220                1225                1230

Pro Leu Tyr Arg Val Arg Trp Thr Gly Leu Pro Asp Thr Gly Thr Ala
            1235                1240                1245

Arg Asp His Thr Trp Ala Val Ala Gly Gly Pro Gly Asp Leu Leu Pro
            1250                1255                1260

Gly Glu Thr Pro His His Pro Asp Leu Ala Ser Ala Leu Ala Asp Thr
1265                1270                1275                1280

Gly Thr Ala Pro Phe Arg Val Leu Ala Asp Leu Arg Gly Tyr Gly Thr
                1285                1290                1295

Ala Thr Pro Arg Glu Leu Ala Ser Gln Ala Leu Ala Leu Val Gln Gln
            1300                1305                1310

Trp Ala Asp Ala Ala Glu Ala Ala Glu Gly Arg Leu Val Leu Val Thr
            1315                1320                1325

Arg Arg Ala Val Asp Ile Gly Asp Gly Val Thr Asp Pro Ala Ala Ala
1330                1335                1340

Thr Val Trp Gly Leu Val Arg Ala Ala Gln Ser Glu His Pro Gly Cys
1345                1350                1355                1360

Phe Ala Leu Leu Asp Thr Asp Asp Ser Pro Arg Ser Arg Gln Leu Leu
```

-continued

```
                         1365                      1370                          1375
Pro  Arg  Val  Ala  Gly  Thr  Ala  Glu  Gln  Leu  Ala  Leu  Arg  Asp  Gly  Thr
               1380                     1385                         1390
Leu  Leu  Ala  Pro  Ser  Leu  Thr  Arg  Ala  Thr  Leu  Pro  Ala  Gly  Ala  Arg
               1395                     1400                         1405
Leu  Pro  Ala  Leu  Asp  Gly  Thr  Val  Leu  Ile  Thr  Gly  Gly  Thr  Gly  Ser
               1410                     1415                         1420
Leu  Gly  Ala  Glu  Ala  Ala  Arg  His  Leu  Val  Thr  Arg  His  Gly  Ala  Arg
1425                     1430                          1435                    1440
Arg  Leu  Leu  Leu  Thr  Ser  Arg  Ser  Gly  Pro  Gln  Ala  Pro  Gly  Ala  Ala
               1445                     1450                         1455
Glu  Leu  Val  Ala  Glu  Leu  Ala  Ala  Leu  Gly  Ala  His  Ala  Asp  Val  Ala
               1460                     1465                         1470
Ala  Cys  Asp  Val  Ala  Asp  Arg  Ala  Ala  Leu  Arg  Ala  Leu  Leu  Asp  Arg
               1475                     1480                         1485
Val  Pro  Ala  Gly  His  Pro  Leu  Thr  Ala  Val  Leu  His  Thr  Ala  Gly  Val
               1490                     1495                         1500
Leu  Asp  Asp  Gly  Val  Leu  Thr  Ala  Gln  Thr  Pro  Gln  Arg  Leu  Ala  Ala
1505                     1510                          1515                    1520
Val  Leu  Arg  Pro  Lys  Ala  Asp  Ala  Val  Arg  Asn  Leu  His  Glu  Leu  Thr
               1525                     1530                         1535
Gln  Gly  His  Ala  Leu  Ser  Ala  Phe  Ile  Leu  Tyr  Ser  Ser  Ala  Ala  Gly
               1540                     1545                         1550
Val  Leu  Gly  Ser  Ala  Gly  Gln  Ser  Gly  Tyr  Ala  Ala  Ala  Asn  Ala  Tyr
               1555                     1560                         1565
Leu  Asp  Ser  Phe  Ala  Val  Trp  Arg  Arg  Ser  Arg  Gly  Leu  Pro  Ala  Val
               1570                     1575                         1580
Ser  Leu  Gly  Trp  Gly  Pro  Trp  Asp  Gly  Gly  Met  Ala  Ser  Gly  Leu
1585                     1590                          1595                    1600
Gly  Gly  Thr  Asp  Thr  Ala  Arg  Leu  Arg  Arg  Ser  Gly  Ile  Ala  Pro  Leu
               1605                     1610                         1615
Ser  Arg  Ala  Glu  Gly  Leu  Ala  Ala  Leu  Asp  Ala  Ala  Leu  Ala  Ala  Gly
               1620                     1625                         1630
Gly  Asp  Asp  Thr  Ala  Pro  Ala  His  Leu  Leu  Pro  Ile  Arg  Val  Asp  Ala
               1635                     1640                         1645
Val  Thr  Leu  Arg  Gly  Ala  Asp  Thr  Val  Pro  Ala  Val  Leu  Arg  Asp  Leu
               1650                     1655                         1660
Ala  Gly  Thr  Ala  Pro  Ser  Ala  Ala  Glu  Arg  Pro  Pro  Gly  Thr  Pro  Glu
1665                     1670                          1675                    1680
Asp  Thr  Asn  Ala  Pro  Leu  Ala  Asp  Val  Thr  Gln  Leu  His  Gly  Arg  Glu
               1685                     1690                         1695
Arg  Lys  Glu  Ala  Leu  Thr  Gly  Phe  Val  Arg  Ala  Gln  Val  Ala  Ala  Val
               1700                     1705                         1710
Leu  Gly  His  Pro  Thr  Ser  Asp  Thr  Ile  Asp  Val  Arg  Arg  Ser  Phe  Lys
               1715                     1720                         1725
Glu  Ala  Gly  Phe  Asp  Ser  Leu  Thr  Ala  Val  Glu  Leu  Arg  Asn  Arg  Leu
               1730                     1735                         1740
Arg  Ala  Ala  Thr  Gly  Leu  Lys  Leu  Pro  Ala  Thr  Leu  Val  Phe  Asp  His
1745                     1750                          1755                    1760
Pro  Thr  Pro  Leu  Ala  Leu  Ala  Gly  Phe  Leu  His  Arg  Glu  Leu  Pro  Gly
               1765                     1770                         1775
Ala  Glu  Ala  Ser  Leu  Met  Ser  Ala  Ile  Asp  Thr  Leu  Arg  His  Arg  Leu
               1780                     1785                         1790
```

```
Arg  Asp  Ala  Leu  Ala  Asp  Asp  Ala  Ala  Asp  Asp  Ala  Leu  Arg  Asp  Gln
          1795                    1800                    1805

Ile  Thr  Arg  Arg  Leu  Glu  Thr  Leu  Leu  Ala  Gly  Ile  Ala  Arg  Thr  Glu
     1810                    1815                    1820

Glu  Pro  Ala  Pro  Ala  Thr  Ala  Ala  Ala  Asp  Asp  Gly  Ser  Gly  Ala  Gly
1825                    1830                    1835                         1840

Asp  Val  Ala  Glu  Arg  Leu  Ser  Thr  Ala  Ser  Asp  Asp  Glu  Leu  Phe  Glu
               1845                    1850                    1855

Leu  Leu  Asp  Ser  Gly  Phe  Thr  Pro
               1860
```

( 2 ) INFORMATION FOR SEQ ID NO:4:

( i ) SEQUENCE CHARACTERISTICS:
    ( A ) LENGTH: 3729 amino acids
    ( B ) TYPE: amino acid
    ( D ) TOPOLOGY: unknown ( i i ) MOLECULE TYPE: protein ( x i ) SEQUENCE DESCRIPTION: SEQ ID NO:4:

```
Met  Ser  Thr  Glu  Asn  Ser  Thr  Asn  Val  Pro  Ala  Ser  Glu  Asp  Lys  Leu
1                   5                    10                        15

Arg  Ala  Tyr  Leu  Arg  Arg  Ala  Met  Ala  Asp  Leu  His  Glu  Ser  Arg  Glu
               20                    25                        30

Arg  Leu  Arg  Ala  Thr  Glu  Ala  Arg  Ala  Gln  Glu  Pro  Ile  Ala  Val  Val
               35                    40                        45

Gly  Met  Gly  Cys  Arg  Phe  Pro  Gly  Gly  Val  Gly  Ser  Pro  Glu  Ala  Leu
     50                    55                         60

Trp  Arg  Leu  Val  Val  Glu  Gly  Val  Asp  Ala  Val  Ser  Pro  Phe  Pro  Gly
65                        70                    75                         80

Asp  Arg  Gly  Trp  Asp  Val  Glu  Gly  Leu  Tyr  Asp  Pro  Glu  Pro  Gly  Val
                    85                    90                         95

Ala  Gly  Lys  Ser  Tyr  Val  Arg  Glu  Gly  Gly  Phe  Leu  His  Asp  Ala  Ala
               100                   105                       110

Glu  Phe  Asp  Ala  Glu  Phe  Phe  Gly  Ile  Ser  Pro  Arg  Glu  Ala  Val  Ala
          115                   120                       125

Met  Asp  Pro  Gln  Gln  Arg  Leu  Leu  Leu  Glu  Thr  Ser  Trp  Glu  Ala  Ile
     130                   135                       140

Glu  Arg  Ala  Gly  Ile  Asp  Pro  His  Ser  Leu  His  Gly  Ser  Arg  Thr  Gly
145                        150                       155                   160

Val  Tyr  Ala  Gly  Val  Met  Tyr  His  Asp  Tyr  Gly  Thr  Gly  Gln  Thr  Ser
                    165                   170                       175

Ala  Thr  Asp  Thr  Ser  Gly  Tyr  Ser  Gly  Thr  Gly  Thr  Ser  Gly  Ser  Val
               180                   185                       190

Val  Ser  Gly  Arg  Val  Ala  Tyr  Thr  Leu  Gly  Leu  Glu  Gly  Pro  Ala  Val
          195                   200                       205

Thr  Val  Asp  Thr  Ala  Cys  Ser  Ser  Ser  Leu  Val  Ala  Leu  His  Leu  Ala
     210                   215                       220

Val  Gln  Ala  Leu  Arg  Gly  Gly  Glu  Cys  Asp  Met  Ala  Leu  Ala  Gly  Gly
225                   230                       235                        240

Val  Thr  Val  Met  Ala  Gly  Pro  Gly  Met  Phe  Val  Glu  Phe  Ser  Arg  Gln
                    245                   250                       255

Arg  Gly  Leu  Ala  Ala  Asp  Gly  Arg  Cys  Lys  Ala  Phe  Ala  Asp  Gly  Ala
               260                   265                       270

Asp  Gly  Thr  Ala  Trp  Ala  Glu  Gly  Ala  Gly  Val  Val  Leu  Val  Glu  Arg
          275                   280                       285
```

```
Leu  Ser  Asp  Ala  Arg  Arg  Leu  Gly  His  Pro  Val  Leu  Ala  Val  Val  Cys
     290                 295                 300

Gly  Ser  Ala  Val  Asn  Gln  Asp  Gly  Ala  Ser  Asn  Gly  Leu  Thr  Ala  Pro
305                      310                 315                      320

Ser  Gly  Pro  Ser  Gln  Glu  Arg  Val  Ile  Arg  Gln  Ala  Leu  Ala  Asn  Ala
                    325                 330                           335

Arg  Leu  Thr  Val  Ala  Asp  Val  Asp  Val  Glu  Ala  His  Gly  Thr  Gly
               340                 345                 350

Thr  Arg  Leu  Gly  Asp  Pro  Ile  Glu  Ala  Gln  Ala  Leu  Leu  Gly  Thr  Tyr
               355                 360                      365

Gly  Arg  Asp  Arg  Asp  Gly  Gly  Arg  Pro  Val  Trp  Leu  Gly  Ser  Leu  Lys
     370                 375                 380

Ser  Asn  Ile  Gly  His  Ala  Gln  Ala  Ala  Ala  Gly  Val  Ala  Gly  Val  Ile
385                      390                 395                           400

Lys  Met  Val  Leu  Ala  Met  Arg  Tyr  Gly  Trp  Leu  Pro  Arg  Thr  Leu  His
                    405                 410                      415

Val  Asp  Glu  Pro  Ser  Arg  His  Val  Asp  Trp  Ser  Ala  Gly  Gly  Val  Trp
               420                 425                 430

Leu  Leu  Thr  Glu  Ala  Arg  Glu  Trp  Pro  Gly  Val  Asp  Arg  Pro  Arg  Arg
               435                 440                 445

Ala  Ala  Val  Ser  Ala  Phe  Val  Ser  Gly  Thr  Asn  Ala  His  Leu  Ile
     450                 455                 460

Leu  Glu  Ala  Pro  Asp  Thr  Ala  Glu  Ala  Glu  Ser  Ala  Thr  Thr  Pro  Val
465                      470                 475                           480

Arg  Ser  Glu  Val  Ser  Glu  Ser  Ala  Ala  Val  Phe  Asp  Ala  Arg  Ser  Gly
                    485                 490                      495

Val  Val  Pro  Val  Val  Val  Ser  Gly  Arg  Ser  Arg  Val  Val  Val  Arg  Glu
               500                 505                 510

Ala  Ala  Gly  Arg  Leu  Ala  Glu  Val  Val  Glu  Ala  Gly  Gly  Val  Gly  Leu
          515                 520                      525

Ala  Asp  Val  Ala  Val  Thr  Met  Ala  Gly  Arg  Ser  Arg  Phe  Gly  Tyr  Arg
     530                 535                 540

Ala  Val  Val  Leu  Ala  Arg  Gly  Glu  Ala  Glu  Leu  Ala  Gly  Arg  Leu  Arg
545                 550                 555                           560

Ala  Leu  Ala  Gly  Gly  Asp  Pro  Asp  Ala  Gly  Val  Val  Thr  Gly  Ala  Val
               565                 570                           575

Val  Asp  Pro  Glu  Thr  Gly  Ser  Gly  Gly  Gly  Val  Val  Leu  Val  Phe
               580                 585                      590

Pro  Gly  Gln  Gly  Thr  Gln  Trp  Val  Gly  Met  Gly  Ala  Gly  Leu  Leu  Gly
          595                 600                      605

Ser  Ser  Glu  Val  Phe  Ala  Ala  Ser  Met  Arg  Glu  Cys  Ala  Arg  Ala  Leu
610                      615                 620

Ser  Val  His  Val  Gly  Trp  Asp  Leu  Leu  Glu  Val  Val  Ser  Gly  Gly  Ala
625                      630                 635                           640

Gly  Leu  Glu  Arg  Val  Asp  Val  Val  Gln  Pro  Val  Thr  Trp  Ala  Val  Met
               645                 650                      655

Val  Ser  Leu  Ala  Arg  Tyr  Trp  Gln  Ala  Met  Gly  Val  Asp  Val  Ala  Ala
               660                 665                 670

Val  Val  Gly  His  Ser  Gln  Gly  Glu  Ile  Ala  Ala  Ala  Thr  Val  Ala  Gly
          675                 680                      685

Ala  Leu  Ser  Leu  Glu  Asp  Ala  Ala  Ala  Val  Val  Ala  Leu  Arg  Ala  Gly
     690                 695                 700

Leu  Ile  Gly  Arg  Tyr  Leu  Ala  Gly  Arg  Gly  Ala  Met  Ala  Ala  Val  Pro
```

-continued

```
        705                 710                 715                 720
Leu Pro Ala Gly Glu Val Glu Ala Gly Leu Ala Lys Trp Pro Gly Val
                725                 730                 735
Glu Val Ala Ala Val Asn Gly Pro Ala Ser Thr Val Val Ser Gly Asp
                740                 745                 750
Arg Arg Ala Val Ala Gly Tyr Val Ala Val Cys Gln Ala Glu Gly Val
                755                 760                 765
Gln Ala Arg Leu Ile Pro Val Asp Tyr Ala Ser His Ser Arg His Val
                770                 775                 780
Glu Asp Leu Lys Gly Glu Leu Glu Arg Val Leu Ser Gly Ile Arg Pro
785                 790                 795                 800
Arg Ser Pro Arg Val Pro Val Cys Ser Thr Val Ala Gly Glu Gln Pro
                805                 810                 815
Gly Glu Pro Val Phe Asp Ala Gly Tyr Trp Phe Arg Asn Leu Arg Asn
                820                 825                 830
Arg Val Glu Phe Ser Ala Val Val Gly Gly Leu Leu Glu Glu Gly His
                835                 840                 845
Arg Arg Phe Ile Glu Val Ser Ala His Pro Val Leu Val His Ala Ile
                850                 855                 860
Glu Gln Thr Ala Glu Ala Ala Asp Arg Ser Val His Ala Thr Gly Thr
865                 870                 875                 880
Leu Arg Arg Gln Asp Asp Ser Pro His Arg Leu Leu Thr Ser Thr Ala
                885                 890                 895
Glu Ala Trp Ala His Gly Ala Thr Leu Thr Trp Asp Pro Ala Leu Pro
                900                 905                 910
Pro Gly His Leu Thr Thr Leu Pro Thr Tyr Pro Phe Asn His His His
                915                 920                 925
Tyr Trp Leu Asp Thr Thr Pro Thr Thr Pro Ala Thr Thr Thr Gln Ser
930                 935                 940
Pro Thr Asp Ala Gln Asn Pro Ala Asp Ala Leu Pro Tyr Lys Val Ser
945                 950                 955                 960
Trp Lys Arg Leu Arg Asp Gln Asp Ser Leu Thr Ala Arg Leu Asp Gly
                965                 970                 975
Arg Trp Leu Leu Val Val Pro Glu Ala Ser Ala Asp Pro Ser Val Ala
                980                 985                 990
Glu Gly Val Ala Arg Glu Leu Thr Ala Arg Gly Ala Thr Val Glu Ser
                995                 1000                1005
Leu Thr Val Glu Pro Gly Ala Asp Arg Ser Arg Leu Arg Gly Leu Leu
                1010                1015                1020
Val Asp Ala Thr Glu Arg Asp Glu Ala Gly Pro Leu Arg Gly Ile Val
1025                1030                1035                1040
Ser Leu Leu Ala Leu Ala Gly Asp His Ala Gly Ala Asp Gly Ala Arg
                1045                1050                1055
Pro Val Val Pro Ala Gly Leu Ala Ala Ser Leu Ala Leu Ile Gln Ala
                1060                1065                1070
Ala Gly Asp Ala Gly Thr Glu Ala Gly Leu Trp Ala Val Thr Arg Gly
                1075                1080                1085
Ala Val Ala Ala Val Pro Gly Asp Val Pro Ala Pro Ser Gln Ala Leu
                1090                1095                1100
Leu Trp Gly Phe Gly Arg Val Ala Gly Ile Glu Leu Pro His Cys Trp
1105                1110                1115                1120
Gly Gly Leu Leu Asp Leu Pro Thr Gly Pro Gly Asp Ser Gly Phe Arg
                1125                1130                1135
```

```
Gln  Leu  Ala  Ala  Thr  Leu  Ala  Gly  Arg  Pro  Ala  Glu  Asp  Gln  Val  Ala
               1140                    1145                    1150

Leu  Arg  Ala  Ser  Gly  Ala  Tyr  Gly  Arg  Arg  Leu  Val  Arg  Ala  Ser  Ala
               1155                    1160                    1165

Ala  Gly  Gly  Ala  Asp  Gly  Trp  Arg  Pro  Arg  Gly  Thr  Val  Leu  Val  Val
          1170                    1175                    1180

Gly  Asp  Thr  Ala  Glu  Val  Ala  Gly  Pro  Leu  Val  Arg  Trp  Leu  Leu  Gly
1185                    1190                    1195                         1200

Asn  Gly  Ala  Arg  Arg  Val  Thr  Leu  Ser  Gly  Leu  Ser  Gly  Pro  Leu  Pro
               1205                    1210                    1215

Glu  Glu  Leu  Ala  Asp  Val  Ala  Ala  Arg  Val  Thr  Val  Ala  Pro  Cys  Asp
               1220                    1225                    1230

Pro  Ala  Asp  Arg  Pro  Ala  Leu  Arg  Thr  Leu  Leu  Ala  Glu  Gln  Ala  Pro
               1235                    1240                    1245

Thr  Ala  Val  Leu  Val  Ala  Pro  Pro  Ala  Val  Pro  Pro  Thr  Pro  Leu  Ala
               1250                    1255                    1260

Glu  Met  Thr  Ala  Glu  Ala  Leu  Ala  Ile  Ala  Leu  Ser  Ala  Lys  Thr  Gly
1265                    1270                    1275                         1280

Leu  Val  Asp  Arg  Leu  Asp  Ser  Leu  Leu  Asp  Glu  Pro  Asp  Pro  Leu  Leu
               1285                    1290                    1295

Glu  Asp  Gly  Glu  Leu  Asp  Ala  Phe  Val  Val  Phe  Ser  Ser  Val  Ala  Gly
               1300                    1305                    1310

Val  Trp  Gly  Gly  Ala  Gly  Gln  Gly  Gly  Tyr  Ala  Ala  Gly  Thr  Ala  Tyr
               1315                    1320                    1325

Leu  Asp  Ala  Leu  Ala  Glu  Cys  Arg  Arg  Ala  Gly  Gly  Leu  Pro  Val  Thr
               1330                    1335                    1340

Ser  Val  Ala  Trp  Thr  Pro  Trp  Leu  Gly  Thr  Pro  Ala  Ala  Asp  Ser  Leu
1345                    1350                    1355                         1360

Gly  Glu  Gln  Met  Ser  Arg  Ala  Gly  Ile  Thr  Pro  Leu  Asp  Pro  Ala  Ala
               1365                    1370                    1375

Ser  Leu  Asp  Ala  Leu  Ala  Arg  Ala  Val  Gly  Arg  Arg  Ala  Gly  Cys  Val
               1380                    1385                    1390

Thr  Val  Ala  Asp  Ile  Asp  Trp  Glu  Arg  Phe  Ala  Ser  Ala  Tyr  Thr  Ala
               1395                    1400                    1405

Thr  Arg  Pro  Thr  Pro  Met  Phe  Asp  Glu  Val  Pro  Glu  Val  Arg  Arg  Ile
               1410                    1415                    1420

Gln  Ala  Ala  Trp  Ala  Glu  Ala  Glu  Ala  Asp  Ala  Ala  Arg  Ser  Gly  Ala
1425                    1430                    1435                         1440

Gly  Gly  Asp  Ser  Gln  Leu  Leu  Arg  Ser  Leu  Arg  Gly  Arg  Pro  Glu  Glu
               1445                    1450                    1455

Ala  Gln  Leu  Ala  Glu  Leu  Leu  Arg  Leu  Val  Arg  Thr  His  Ala  Ala  Ala
               1460                    1465                    1470

Val  Leu  Gly  Leu  Gly  Ser  Pro  Gly  Ala  Val  Glu  Ala  Arg  Arg  Ser  Phe
               1475                    1480                    1485

Lys  Asp  Leu  Gly  Phe  Asn  Ser  Val  Thr  Ala  Val  Glu  Leu  Arg  Asn  Arg
               1490                    1495                    1500

Leu  Lys  Glu  Ala  Thr  Gly  Leu  Arg  Leu  Glu  Val  Ser  Leu  Val  Phe  Asp
1505                    1510                    1515                         1520

His  Pro  Asp  Pro  Ala  Ser  Leu  Ala  Arg  His  Leu  Leu  Asp  Leu  Ala  Leu
               1525                    1530                    1535

Gly  Gln  Glu  Pro  Glu  Glu  Thr  Pro  Arg  Ala  Phe  Ala  Leu  Glu  Pro  Ala
               1540                    1545                    1550

Pro  Asn  Gly  Glu  Pro  Ile  Ala  Ile  Val  Ser  Met  Ala  Cys  Arg  Met  Pro
               1555                    1560                    1565
```

```
Gly Gly Val Ser Thr Pro Glu Glu Leu Trp Arg Leu Leu Arg Asp Gly
     1570            1575                1580
Lys Asp Ala Ile Gly Pro Phe Pro Ala Asn Arg Gly Trp Asp Leu Glu
1585            1590            1595                1600
Asn Leu Tyr Asp Pro Asp Pro Asp Ala Asp Gly Arg Thr Tyr Val Arg
            1605            1610                1615
Glu Gly Gly Phe Leu His Glu Ala Pro Asp Phe Asp Pro Ser Phe Phe
        1620            1625                1630
Gly Ile Ser Pro Arg Glu Ala Leu Ala Met Asp Pro Gln Gln Arg Leu
    1635            1640                1645
Leu Leu Glu Thr Ser Trp Glu Ala Leu Glu Arg Ala Gly Ile Asp Pro
        1650            1655                1660
Ala Arg Leu Arg Gly Ser Arg Thr Gly Val Phe Val Gly Thr Asn Gly
1665            1670            1675                1680
Gln His Tyr Met Pro Leu Leu Gln Asn Gly Gly Asp Ser Phe Asp Gly
                1685            1690                1695
Tyr Leu Gly Thr Gly Asn Ser Ala Ser Val Met Ser Gly Arg Leu Ser
            1700            1705                1710
Tyr Val Phe Gly Leu Glu Gly Pro Ala Val Thr Val Asp Thr Ala Cys
        1715            1720                1725
Ser Ala Ser Leu Val Ala Leu His Leu Ala Val Gln Ala Met Arg Arg
    1730            1735                1740
Gly Glu Cys Asp Met Ala Leu Val Gly Gly Ala Thr Val Met Ser Thr
1745            1750            1755                1760
Pro Glu Met Leu Val Glu Phe Ser Arg Gln Arg Val Ile Ser Ala Asn
                1765            1770                1775
Gly Arg Ser Arg Ala Phe Ala Ala Gly Ala Asp Gly Val Ala Leu Gly
            1780            1785                1790
Glu Gly Val Gly Val Leu Leu Val Glu Arg Leu Ser Asp Ala Glu Arg
        1795            1800                1805
Asn Gly His Pro Val Leu Ala Val Val Arg Gly Ser Ala Val Asn Gln
    1810            1815                1820
Asp Gly Ala Ser Asn Gly Leu Thr Ala Pro Asn Gly Pro Ser Gln Gln
1825            1830            1835                1840
Arg Val Ile Arg Gln Ala Leu Ala Asp Ala Gly Leu Arg Pro Glu Asp
                1845            1850                1855
Ile Asp Ala Val Glu Ala His Gly Thr Gly Thr Glu Leu Gly Asp Pro
            1860            1865                1870
Ile Glu Ala Glu Ala Leu Leu Ala Thr Tyr Gly Arg Thr Arg Thr Ala
        1875            1880                1885
Asp Arg Pro Leu Trp Leu Gly Ser Leu Lys Ser Asn Ile Gly His Thr
    1890            1895                1900
Gln Ala Ala Ala Gly Val Ala Gly Val Ile Lys Met Val Leu Ala Leu
1905            1910            1915                1920
Gly Asn Glu Thr Leu Pro Arg Thr Leu His Val Asp Glu Pro Thr Pro
                1925            1930                1935
Arg Val Asp Trp Ser Ser Gly Ala Val Ser Leu Leu Thr Glu Pro Val
            1940            1945                1950
Asp Trp Pro Ala Gly Pro Ser Ala Pro Arg Arg Ala Ala Val Ser Ser
        1955            1960                1965
Phe Gly Ile Ser Gly Thr Asn Ala His Thr Ile Leu Glu Gln Ala Pro
    1970            1975                1980
Val Pro Ala Glu Ser Arg Pro Gly Thr Glu Pro Ala Asp Gly Thr Gly
```

-continued

```
            1985                    1990                    1995                    2000
Ala  Trp  Glu  Asn  Val  Thr  Val  Pro  Leu  Leu  Leu  Ser  Gly  His  Thr  Glu
                         2005                    2010                    2015
Ala  Ala  Leu  Arg  Glu  Gln  Ser  Thr  Arg  Leu  Leu  Asn  Asp  Leu  Leu  Glu
                         2020                    2025                    2030
His  Pro  Asp  Glu  His  Pro  Ala  Asp  Val  Gly  Tyr  Thr  Leu  Ile  Thr  Gly
                         2035                    2040                    2045
Arg  Ala  His  Phe  Gly  His  Arg  Ala  Ala  Val  Ile  Gly  Glu  Ser  Arg  Glu
                         2050                    2055                    2060
Glu  Leu  Leu  Asp  Ala  Leu  Lys  Ala  Leu  Ala  Glu  Gly  Arg  Glu  His  His
2065                     2070                    2075                    2080
Thr  Val  Val  Arg  Gly  Asp  Gly  Thr  Ala  His  Pro  Asp  Arg  Arg  Val  Val
                         2085                    2090                    2095
Phe  Val  Phe  Pro  Gly  Gln  Gly  Ser  Gln  Trp  Pro  Ser  Met  Ala  Arg  Asp
                         2100                    2105                    2110
Leu  Leu  Asp  Arg  Ala  Pro  Ala  Phe  Arg  Glu  Thr  Ala  Lys  Ala  Cys  Asp
                         2115                    2120                    2125
Ala  Ala  Leu  Ser  Val  His  Leu  Asp  Trp  Ser  Val  Leu  Asp  Val  Leu  Gln
                         2130                    2135                    2140
Glu  Lys  Pro  Asp  Ala  Pro  Pro  Leu  Ser  Arg  Val  Asp  Val  Val  Gln  Pro
2145                     2150                    2155                    2160
Val  Leu  Phe  Thr  Met  Met  Leu  Ser  Leu  Ala  Ala  Cys  Trp  Arg  Asp  Leu
                         2165                    2170                    2175
Gly  Val  His  Pro  Ala  Ala  Val  Val  Gly  His  Ser  Gln  Gly  Glu  Ile  Ala
                         2180                    2185                    2190
Ala  Ala  Cys  Val  Ala  Gly  Ala  Leu  Ser  Leu  Glu  Asp  Ala  Ala  Arg  Ile
                         2195                    2200                    2205
Val  Ala  Leu  Arg  Ser  Arg  Ala  Trp  Leu  Thr  Leu  Ala  Gly  Lys  Gly  Gly
                         2210                    2215                    2220
Met  Ala  Ala  Val  Ser  Leu  Pro  Glu  Ala  Arg  Leu  Arg  Glu  Arg  Ile  Glu
2225                     2230                    2235                    2240
Arg  Phe  Gly  Gln  Arg  Leu  Ser  Val  Ala  Ala  Val  Asn  Ser  Pro  Gly  Thr
                         2245                    2250                    2255
Ala  Ala  Val  Ala  Gly  Asp  Val  Asp  Ala  Leu  Arg  Glu  Leu  Leu  Ala  Glu
                         2260                    2265                    2270
Leu  Thr  Ala  Glu  Gly  Ile  Arg  Ala  Lys  Pro  Ile  Pro  Gly  Val  Asp  Thr
                         2275                    2280                    2285
Ala  Gly  His  Ser  Ala  Gln  Val  Asp  Gly  Leu  Lys  Glu  His  Leu  Phe  Glu
                         2290                    2295                    2300
Val  Leu  Ala  Pro  Val  Ser  Pro  Arg  Ser  Ser  Asp  Ile  Pro  Phe  Tyr  Ser
2305                     2310                    2315                    2320
Thr  Val  Thr  Gly  Ala  Pro  Leu  Asp  Thr  Glu  Arg  Leu  Asp  Ala  Gly  Tyr
                         2325                    2330                    2335
Trp  Tyr  Arg  Asn  Met  Arg  Glu  Pro  Val  Glu  Phe  Glu  Lys  Ala  Val  Arg
                         2340                    2345                    2350
Ala  Leu  Ile  Ala  Asp  Gly  Tyr  Asp  Leu  Phe  Leu  Glu  Cys  Asn  Pro  His
                         2355                    2360                    2365
Pro  Met  Leu  Ala  Met  Ser  Leu  Asp  Glu  Thr  Leu  Thr  Asp  Ser  Gly  Gly
                         2370                    2375                    2380
His  Gly  Thr  Val  Met  His  Thr  Leu  Arg  Arg  Gln  Lys  Gly  Ser  Ala  Lys
2385                     2390                    2395                    2400
Asp  Phe  Gly  Met  Ala  Leu  Cys  Leu  Ala  Tyr  Val  Asn  Gly  Leu  Glu  Ile
                         2405                    2410                    2415
```

```
Asp  Gly  Glu  Ala  Leu  Phe  Gly  Pro  Asp  Ser  Arg  Arg  Val  Asn  Pro  Pro
               2420                    2425                    2430

Thr  Tyr  Pro  Phe  Gln  Arg  Glu  Arg  Tyr  Trp  Tyr  His  Pro  Thr  Ser  Gly
               2435                    2440                    2445

Arg  Arg  Gly  Asp  Ile  Thr  Ala  Ala  Gly  Val  Ala  Ala  Glu  His  Pro
               2450                    2455                    2460

Leu  Leu  Gly  Ala  Gly  Val  Glu  Leu  Pro  Glu  Thr  Gly  Gly  Thr  Val  Tyr
2465                    2470                    2475                    2480

Thr  Ala  Arg  Phe  Gly  Pro  Asp  Ser  Arg  Pro  Trp  Leu  Ala  Asp  His  Ala
               2485                    2490                    2495

Leu  Leu  Gly  Thr  Val  Leu  Leu  Pro  Gly  Thr  Ala  Ile  Leu  Asp  Leu  Val
               2500                    2505                    2510

Leu  Trp  Ala  Gly  Glu  Arg  Ser  Gly  Cys  Gly  Arg  Val  Gly  Glu  Leu  Ala
               2515                    2520                    2525

Leu  Gln  Ala  Pro  Leu  Val  Leu  Pro  Asp  Ser  Gly  Asp  Val  Glu  Leu  Arg
               2530                    2535                    2540

Leu  Leu  Val  Gly  Gly  Pro  Asp  Glu  Glu  Lys  Arg  Arg  Thr  Val  Thr  Val
2545                    2550                    2555                    2560

His  Ala  Arg  Pro  Ala  Ala  Ala  Gly  Ala  Glu  Ala  Pro  Trp  Thr  Arg  His
               2565                    2570                    2575

Ala  Glu  Ala  Val  Val  Leu  Pro  Ala  Thr  Gly  Glu  Glu  Pro  Thr  Pro  Ala
               2580                    2585                    2590

Pro  Arg  Pro  Val  Pro  Glu  Pro  Ala  Gly  Thr  Thr  Asp  Pro  Ala  Ala  Phe
               2595                    2600                    2605

Tyr  Ala  Glu  Phe  Ala  Glu  Arg  Gly  Tyr  Asp  Tyr  Gly  Pro  Ala  Phe  Gln
               2610                    2615                    2620

Gly  Phe  Thr  Ala  Gly  Ala  Arg  His  Gly  Glu  Asp  Val  Val  Ala  Glu  Val
2625                    2630                    2635                    2640

Ala  Leu  Pro  Ser  Gly  Leu  Val  Ala  Asp  Ala  Arg  His  His  Arg  Leu  His
               2645                    2650                    2655

Pro  Ala  Leu  Leu  Asp  Ala  Ala  Leu  Gln  Ala  Met  Ile  Leu  Gly  Thr  Phe
               2660                    2665                    2670

Phe  Ala  Asp  Asp  Gly  Arg  Ala  Arg  Met  Pro  Phe  Ala  Val  Arg  Gly  Val
               2675                    2680                    2685

Arg  Leu  His  Thr  Ala  Gly  Ala  Asp  Arg  Leu  Arg  Val  Leu  Ile  Ser  Pro
               2690                    2695                    2700

Ala  Gly  Asp  Glu  Thr  Val  Arg  Leu  Leu  Cys  Thr  Asp  Leu  Ala  Thr  Gly
2705                    2710                    2715                    2720

Ala  Pro  Val  Leu  Glu  Ile  Asp  Glu  Leu  Val  Val  Arg  Pro  Val  Ser  Gly
               2725                    2730                    2735

Glu  Gln  Leu  Ala  Ala  Gly  Ala  Pro  Gly  Arg  Asn  Gly  Gly  Glu  Leu  Tyr
               2740                    2745                    2750

Arg  Val  Asp  Trp  Thr  Val  Leu  Pro  Glu  Pro  Ala  Glu  Val  Pro  Ala  Pro
               2755                    2760                    2765

Arg  Trp  Ala  Leu  Leu  Gly  Glu  Asp  His  Ala  Gly  Leu  Ala  Asp  Val  Leu
               2770                    2775                    2780

Gly  Gly  Thr  Gly  Gly  Gly  Cys  Glu  Arg  Tyr  Asp  Thr  Leu  Thr  Gly  Leu
2785                    2790                    2795                    2800

Leu  Glu  Ala  Thr  Thr  Arg  Ser  Ala  Gly  Gly  Ile  Leu  Pro  Asp  Ile  Val
               2805                    2810                    2815

Ala  Leu  Ser  Leu  Pro  Thr  Ala  Pro  Glu  Pro  Gly  Pro  Gln  Ala  Val  Arg
               2820                    2825                    2830

Glu  Val  Leu  Ser  Gln  Ala  Leu  Asp  Ala  Ala  Gln  Ala  Trp  Leu  Ala  Ala
               2835                    2840                    2845
```

```
Gly  Ala  Glu  Thr  Ala  Ser  Ala  Arg  Leu  Val  Phe  Val  Thr  Gly  Gly  Ala
2850                2855                     2860
Val  Ala  Thr  Thr  Ala  Asp  Glu  Thr  Val  Arg  Asp  Ile  Ala  Ala  Ala  Ala
2865                2870                     2875                          2880
Val  Trp  Gly  Leu  Val  Arg  Ser  Ala  Gln  Ser  Glu  Glu  Pro  Asp  Arg  Met
               2885                     2890                     2895
Val  Leu  Leu  Asp  Leu  Asp  Gly  Glu  Arg  Pro  Thr  Ala  Arg  Thr  Leu  Ala
          2900                     2905                          2910
Ala  Ala  Leu  Ala  Ser  Gly  Glu  Pro  Gln  Leu  Ala  Val  Arg  Gly  Ser  Thr
               2915                     2920                     2925
Val  Ala  Ala  Pro  Arg  Leu  Ala  Pro  Ala  Gly  Pro  Gly  Pro  Glu  Asp  Leu
          2930                     2935                     2940
Val  Pro  Pro  Ala  Gly  Thr  Thr  Ala  Trp  Arg  Leu  Thr  Pro  Gly  Gly  Gly
2945                2950                     2955                          2960
Thr  Leu  Glu  Glu  Leu  Ser  Leu  Ala  Pro  Ala  Pro  Asp  Ala  Glu  Glu  Pro
                    2965                     2970                     2975
Leu  Ala  Pro  Gly  Gln  Val  Arg  Ile  Ala  Val  Arg  Ala  Ala  Gly  Val  Asn
               2980                     2985                     2990
Phe  Arg  Asp  Ala  Leu  Ile  Ala  Leu  Gly  Met  Tyr  Pro  Gly  Lys  Gly  Thr
          2995                     3000                     3005
Met  Gly  Ala  Glu  Gly  Ala  Gly  Val  Val  Val  Glu  Thr  Ala  Pro  Asp  Val
     3010                     3015                     3020
Thr  Gly  Leu  Ser  Ala  Gly  Asp  Arg  Val  Leu  Gly  Met  Trp  Asn  Gly  Gly
3025                3030                     3035                          3040
Phe  Gly  Pro  Leu  Val  Val  Ala  Asp  His  Arg  Met  Val  Ala  Pro  Ile  Pro
                    3045                     3050                     3055
His  Gly  Trp  Ser  Tyr  Ala  Glu  Ala  Ala  Ser  Val  Pro  Ala  Val  Leu  Leu
               3060                     3065                     3070
Thr  Ser  Tyr  Tyr  Ala  Leu  Thr  Arg  Leu  Ala  Arg  Ala  Arg  Thr  Gly  Gln
          3075                     3080                     3085
Thr  Val  Leu  Val  His  Ala  Ala  Ala  Gly  Gly  Val  Gly  Met  Ala  Thr  Leu
     3090                     3095                     3100
Gln  Leu  Ala  Arg  His  Leu  Gly  Leu  Glu  Val  Tyr  Ala  Thr  Ala  Ser  Thr
3105                3110                     3115                          3120
Gly  Lys  Trp  Asp  Ala  Leu  Gln  Lys  His  Gly  Ile  Pro  Asp  Asp  Arg  Ile
               3125                     3130                     3135
Ala  Asp  Ser  Arg  Thr  Leu  Asp  Phe  Ala  Glu  Arg  Phe  Leu  Ser  Arg  Thr
               3140                     3145                     3150
Gly  Gly  Arg  Gly  Val  Asp  Ile  Val  Leu  Asn  Ser  Leu  Ala  Gly  Glu  Phe
          3155                     3160                     3165
Val  Asp  Ala  Ser  Leu  Arg  Leu  Leu  Pro  Arg  Gly  Gly  His  Phe  Leu  Glu
     3170                     3175                     3180
Leu  Gly  Lys  Ala  Asp  Val  Arg  Asp  Pro  Arg  Arg  Ile  Ala  Ala  Ala  His
3185                3190                     3195                          3200
Pro  Gly  Thr  Asp  Tyr  Arg  Ala  Phe  Asp  Leu  Val  Gln  Ala  Gly  Pro  Asp
               3205                     3210                     3215
Thr  Val  Gly  Glu  Met  Leu  Gly  Glu  Leu  Leu  Glu  Leu  Phe  Ala  Ala  Gly
               3220                     3225                     3230
Ala  Leu  Arg  Pro  Leu  Pro  Leu  Thr  Ala  Tyr  Gly  Ile  Arg  Asp  Ala  Arg
          3235                     3240                     3245
Thr  Ala  Leu  Arg  Thr  Leu  Ser  Gln  Ala  Arg  His  Thr  Gly  Lys  Leu  Val
     3250                     3255                     3260
Leu  Thr  Val  Pro  Ala  Gly  Phe  Asp  Thr  His  Arg  Thr  Val  Leu  Leu  Thr
```

-continued

```
                  3265                    3270                    3275                    3280
Gly  Gly  Thr  Gly  Thr  Leu  Gly  Gln  Thr  Leu  Ala  Arg  His  Leu  Val  Asn
                           3285                    3290                    3295
Arg  His  Gly  Val  Arg  His  Leu  Leu  Leu  Ala  Gly  Arg  Thr  Gly  Ala  Ala
         3300                    3305                    3310
Ala  Glu  Gly  Val  Ala  Glu  Leu  Ile  Gly  Glu  Leu  Gly  Glu  Leu  Gly  Ala
              3315                    3320                    3325
Glu  Val  Arg  Val  Ala  Ala  Cys  Asp  Ala  Ala  Asp  Arg  Gln  Arg  Leu  Thr
         3330                    3335                    3340
Glu  Leu  Leu  Ala  Gly  Ile  Pro  Val  Glu  His  Pro  Leu  Gly  Ala  Val  Val
3345                    3350                    3355                    3360
His  Ala  Ala  Gly  Thr  Leu  Asp  Asp  Gly  Thr  Ile  Pro  Ser  Leu  Thr  Gly
                   3365                    3370                    3375
Glu  Asn  Ile  Asp  Asn  Val  Leu  Arg  Pro  Lys  Ala  Asp  Ala  Val  Leu  Asn
                   3380                    3385                    3390
Leu  His  Glu  Leu  Thr  Arg  Asp  Ala  Asp  Leu  Ser  Ala  Phe  Val  Leu  Tyr
              3395                    3400                    3405
Ser  Ser  Ser  Ser  Ala  Leu  Leu  Gly  Ser  Pro  Gly  Gln  Gly  Ala  Tyr  Ala
              3410                    3415                    3420
Ala  Ala  Asn  Ala  Phe  Leu  Asp  Gly  Phe  Ala  Arg  Tyr  Arg  Lys  Gly  Leu
3425                    3430                    3435                    3440
Gly  Leu  Pro  Ala  Leu  Ser  Leu  Ala  Trp  Gly  Leu  Trp  Gly  Ser  Asn  Ser
                   3445                    3450                    3455
Arg  Met  Ala  Gly  His  Leu  Asp  Gln  Ser  Gly  Met  Gln  Arg  Arg  Leu  Asn
              3460                    3465                    3470
Arg  Ser  Gly  Ile  Met  Ala  Leu  Thr  Asp  Ala  Glu  Gly  Leu  Ala  Leu  Phe
         3475                    3480                    3485
Asp  Ala  Ala  Gln  Asp  Gly  Gly  Asp  Ala  Leu  Leu  Val  Pro  Met  Arg  Leu
         3490                    3495                    3500
Asn  Arg  Thr  Ala  Leu  Arg  Ala  Ser  Gly  Arg  Ile  Thr  Pro  Phe  Leu  Ser
3505                    3510                    3515                    3520
Gly  Leu  Ala  Gly  Gly  Gly  Pro  Ala  Ala  Gly  Glu  Arg  Arg  Pro  Glu  Val
                   3525                    3530                    3535
Ala  Ala  Val  Ser  Gly  Thr  Leu  Ala  Glu  Arg  Leu  Thr  Gly  Leu  Thr  Ala
                   3540                    3545                    3550
Gln  Glu  Gly  His  Ala  Leu  Val  Leu  Ala  Glu  Ile  Arg  Ala  His  Ala  Ala
              3555                    3560                    3565
Ala  Val  Leu  Gly  His  Gly  Ser  Asp  Asp  Ser  Ile  Pro  Glu  Asp  Arg  Ala
              3570                    3575                    3580
Phe  Lys  Asp  Leu  Gly  Phe  Asp  Ser  Leu  Thr  Ala  Val  Glu  Met  Arg  Asn
3585                    3590                    3595                    3600
Arg  Leu  Ser  Ala  Ala  Thr  Gly  Leu  Arg  Leu  Pro  Ala  Thr  Leu  Val  Phe
                   3605                    3610                    3615
Asp  His  Pro  Thr  Pro  Gly  Glu  Leu  Ala  Gly  His  Leu  Ser  Ala  Glu  Leu
                   3620                    3625                    3630
Ser  Ala  Asp  Asp  Ala  Pro  Gly  Ser  Ala  Ser  Pro  Leu  Thr  Glu  Leu  Asp
              3635                    3640                    3645
Arg  Phe  Glu  Ala  Leu  Phe  Thr  Ala  Leu  Ala  Pro  Gly  Thr  Thr  Lys  Asp
         3650                    3655                    3660
Thr  Pro  Gly  Gly  Ala  Gly  Ala  Leu  Met  Ile  Asp  Glu  Ala  Glu  Arg  Gln
3665                    3670                    3675                    3680
Glu  Ile  Ala  Gly  Arg  Leu  Ala  Ala  Leu  Ala  Gly  Leu  Trp  Asn  Arg  Leu
                   3685                    3690                    3695
```

His Gly Thr Thr Thr Ala Pro Glu Asp Gly Asp Thr Val Ala Asp Ala
            3700            3705            3710

Leu Glu Ala Ala Asp Asp His Glu Ile Phe Ala Phe Leu Asp Glu Arg
            3715            3720            3725

Phe ( 2 ) INFORMATION FOR SEQ ID NO:5:

( i ) SEQUENCE CHARACTERISTICS:
        ( A ) LENGTH: 1611 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:5:

Met Ala Asn Ala Asn Glu Gln Gln Leu Arg Ala Tyr Leu Lys Arg Ala
1               5                   10                  15

Thr Thr Glu Leu His Arg Thr Ser Gln Leu Arg Glu Gly Glu Arg Ala
            20              25                  30

Arg Ala His Glu Pro Ile Ala Val Val Gly Met Ala Cys Arg Tyr Pro
            35              40                  45

Gly Gly Ala Asn Thr Pro Glu Gln Phe Trp Glu Leu Leu Asp Thr Gly
    50              55                  60

Thr Asp Ala Ala Ala Pro Met Pro Ser Asp Arg Gly Trp Asp Thr His
65              70                  75                  80

Gly Leu Tyr Asp Pro Asp Pro Ala Ala Ala Gly Arg Thr Tyr Cys Arg
            85                  90                  95

Glu Gly Gly Phe Leu His Asp Ala Gly Asp Phe Asp Ala Asp Phe Phe
            100             105                 110

Gly Ile Ser Pro Arg Glu Ala Val Ala Met Asp Pro Gln Arg Leu
            115             120                 125

Leu Leu Glu Thr Ser Trp Glu Ala Ile Glu Ala Ala Gly Ile Asp Pro
            130             135                 140

Arg Gly Leu Arg Gly Ser Arg Thr Gly Val Tyr Val Gly Ala Trp Asp
145             150                 155                 160

Ser Gly Tyr Thr Gly Gln Ala His Ala Pro Ser Ala Glu Leu Glu Ala
            165             170                 175

Asp Leu Leu Thr Gly Gly Val Val Ser Phe Thr Ser Gly Arg Ile Ala
            180             185                 190

Tyr Thr Leu Gly Leu Glu Gly Pro Ala Leu Thr Val Asp Thr Ala Cys
            195             200                 205

Ser Ser Ser Leu Val Ala Leu His Asn Ala Ala Gln Ala Leu Arg Arg
210             215                 220

Gly Glu Cys Asp Leu Ala Leu Ala Gly Gly Val Thr Val Met Ala Thr
225             230                 235                 240

Pro Ala Val Phe Val Gln Phe Ala Arg Gln Arg Gly Leu Ala Pro Asp
            245             250                 255

Gly Arg Cys Lys Ala Phe Ala Asp Ala Ala Asp Gly Phe Gly Pro Ala
            260             265                 270

Glu Gly Val Gly Met Val Leu Val Glu Arg Leu Ser Asp Ala Arg Arg
            275             280                 285

Leu Gly His Pro Val Leu Ala Val Val Cys Gly Ser Ala Val Asn Gln
            290             295                 300

Asp Gly Ala Ser Asn Gly Leu Thr Ala Pro Ser Gly Pro Ser Gln Glu
305             310                 315                 320

| | | | | | | | | | | | | | | |
|---|---|---|---|---|---|---|---|---|---|---|---|---|---|---|
|Arg|Val|Ile|Arg|Gln|Ala|Leu|Gly|Asn|Ala|Arg|Leu|Thr|Val|Ala|Asp|
| | | |325| | | |330| | | | |335| | |
|Val|Asp|Val|Val|Glu|Ala|His|Gly|Thr|Gly|Thr|Arg|Leu|Gly|Asp|Pro|
| | | |340| | | |345| | | | |350| | |
|Ile|Glu|Ala|Gln|Ala|Leu|Leu|Thr|Tyr|Gly|Arg|Asp|Arg|Asp|Gly|
| | |355| | | |360| | | |365| | | |
|Gly|Arg|Pro|Val|Trp|Leu|Gly|Ser|Leu|Lys|Ser|Asn|Ile|Gly|His|Ala|
| |370| | | |375| | | |380| | | | | |
|Gln|Ala|Ala|Ala|Gly|Val|Ala|Gly|Val|Ile|Lys|Met|Val|Leu|Ala|Met|
|385| | | |390| | | |395| | | | |400|
|Arg|Tyr|Gly|Trp|Leu|Pro|Arg|Thr|Leu|His|Val|Asp|Glu|Pro|Ser|Arg|
| | | |405| | | |410| | | | |415| | |
|His|Val|Asp|Trp|Ser|Ala|Gly|Gly|Val|Arg|Leu|Leu|Thr|Glu|Ala|Arg|
| | |420| | | |425| | | |430| | | |
|Glu|Trp|Pro|Gly|Val|Asp|Arg|Pro|Arg|Arg|Ala|Ala|Val|Ser|Ala|Phe|
| | |435| | | |440| | | |445| | | |
|Gly|Val|Ser|Gly|Thr|Asn|Ala|His|Leu|Ile|Leu|Glu|Ala|Pro|Asp|Thr|
| |450| | | |455| | | |460| | | | | |
|Ala|Glu|Ala|Glu|Ser|Ala|Thr|Thr|Pro|Val|Arg|Ser|Glu|Val|Ser|Glu|
|465| | | |470| | | |475| | | | |480|
|Ser|Ala|Ala|Val|Leu|Asp|Ala|Arg|Ser|Gly|Val|Val|Pro|Val|Val|Val|
| | | |485| | | |490| | | | |495| | |
|Ser|Gly|Arg|Ser|Arg|Val|Val|Val|Arg|Glu|Ala|Ala|Gly|Arg|Leu|Ala|
| | |500| | | |505| | | |510| | | |
|Glu|Val|Val|Glu|Ala|Gly|Gly|Val|Gly|Leu|Ala|Asp|Val|Ala|Val|Thr|
| |515| | | |520| | | |525| | | | | |
|Met|Ala|Gly|Arg|Ser|Arg|Phe|Gly|Tyr|Arg|Ala|Val|Val|Leu|Ala|Arg|
| |530| | | |535| | | |540| | | | | |
|Gly|Glu|Ala|Glu|Leu|Ala|Gly|Arg|Leu|Arg|Ala|Leu|Ala|Gly|Gly|Asp|
|545| | | |550| | | |555| | | | |560|
|Pro|Asp|Ala|Gly|Val|Val|Thr|Gly|Ala|Val|Val|Asp|Pro|Glu|Thr|Gly|
| | | |565| | | |570| | | | |575| | |
|Ser|Gly|Gly|Gly|Gly|Val|Val|Leu|Val|Phe|Pro|Gly|Gln|Gly|Thr|Gln|
| | | |580| | | |585| | | | |590| | |
|Trp|Val|Gly|Met|Gly|Ala|Gly|Leu|Leu|Gly|Ser|Ser|Glu|Val|Phe|Ala|
| | |595| | | |600| | | | |605| | | |
|Ala|Ser|Met|Arg|Glu|Cys|Ala|Arg|Ala|Leu|Ser|Val|His|Val|Gly|Trp|
| |610| | | |615| | | |620| | | | | |
|Asp|Leu|Leu|Glu|Val|Val|Ser|Gly|Gly|Ala|Gly|Leu|Glu|Arg|Val|Asp|
|625| | | |630| | | |635| | | | |640|
|Val|Val|Gln|Pro|Val|Thr|Trp|Ala|Val|Met|Val|Ser|Leu|Ala|Arg|Tyr|
| | | |645| | | |650| | | | |655| | |
|Trp|Gln|Ala|Met|Gly|Val|Asp|Val|Ala|Ala|Val|Val|Gly|His|Ser|Gln|
| | |660| | | |665| | | | |670| | | |
|Gly|Glu|Ile|Ala|Ala|Ala|Thr|Val|Ala|Gly|Ala|Leu|Ser|Leu|Glu|Asp|
| | |675| | | |680| | | | |685| | | |
|Ala|Ala|Ala|Val|Val|Ala|Leu|Arg|Ala|Gly|Leu|Ile|Gly|Arg|Tyr|Leu|
| |690| | | |695| | | |700| | | | | |
|Ala|Gly|Arg|Gly|Ala|Met|Ala|Ala|Val|Pro|Leu|Pro|Ala|Gly|Glu|Val|
|705| | | |710| | | |715| | | | |720|
|Glu|Ala|Gly|Leu|Ala|Lys|Trp|Pro|Gly|Val|Glu|Val|Ala|Ala|Val|Asn|
| | | |725| | | |730| | | | |735| | |
|Gly|Pro|Ala|Ser|Thr|Val|Val|Ser|Gly|Asp|Arg|Arg|Ala|Val|Ala|Gly|
| | |740| | | |745| | | | |750| | | |

```
Tyr  Val  Ala  Val  Cys  Gln  Ala  Glu  Gly  Val  Gln  Ala  Arg  Leu  Ile  Pro
          755                 760                 765

Val  Asp  Tyr  Ala  Ser  His  Ser  Arg  His  Val  Glu  Asp  Leu  Lys  Gly  Glu
     770                 775                 780

Leu  Glu  Arg  Val  Leu  Ser  Gly  Ile  Arg  Pro  Arg  Ser  Pro  Arg  Val  Pro
785                      790                 795                           800

Val  Cys  Ser  Thr  Val  Ala  Gly  Glu  Gln  Pro  Gly  Glu  Pro  Val  Phe  Asp
               805                      810                           815

Ala  Gly  Tyr  Trp  Phe  Arg  Asn  Leu  Arg  Asn  Arg  Val  Glu  Phe  Ser  Ala
          820                      825                      830

Val  Val  Gly  Gly  Leu  Leu  Glu  Glu  Gly  His  Arg  Arg  Phe  Ile  Glu  Val
          835                      840                 845

Ser  Ala  His  Pro  Val  Leu  Val  His  Ala  Ile  Glu  Gln  Thr  Ala  Glu  Ala
     850                      855                 860

Ala  Asp  Arg  Ser  Val  His  Ala  Thr  Gly  Thr  Leu  Arg  Arg  Gln  Asp  Asp
865                      870                 875                           880

Ser  Pro  His  Arg  Leu  Leu  Thr  Ser  Thr  Ala  Glu  Ala  Trp  Ala  His  Gly
               885                      890                      895

Ala  Thr  Leu  Thr  Trp  Asp  Pro  Ala  Leu  Pro  Pro  Gly  His  Leu  Thr  Thr
               900                      905                      910

Leu  Pro  Thr  Tyr  Pro  Phe  Asn  His  His  Tyr  Trp  Leu  Asp  Thr  Thr
               915                      920                 925

Pro  Thr  Thr  Pro  Ala  Thr  Thr  Thr  Gln  Ser  Pro  Thr  Asp  Ala  Trp  Arg
     930                      935                 940

Tyr  Arg  Val  Thr  Trp  Lys  Ala  Leu  Thr  Glu  Glu  Ser  Thr  Pro  Ala  Ser
945                      950                 955                           960

Ser  Pro  Ser  Gly  His  Trp  Leu  Leu  Val  Thr  Pro  Pro  Thr  Pro  Glu  Gly
               965                      970                      975

Arg  Thr  Leu  Gly  Asp  Arg  Ala  Ala  Gly  Ala  Leu  Ala  Arg  Gln  Gly  Ala
               980                      985                 990

Thr  Val  Glu  Arg  Leu  Val  Val  Asp  Pro  Val  Ala  Val  Gly  Arg  Asp  Gly
               995                      1000                     1005

Leu  Ala  Ala  Arg  Leu  Gly  Glu  Arg  Trp  Asp  Gly  Val  Leu  Ser  Leu  Leu
     1010                     1015                     1020

Gly  Ala  Asp  Glu  Arg  Pro  Leu  Pro  Arg  His  Pro  Ala  Leu  Asn  Arg  Ala
1025                     1030                     1035                     1040

Val  Met  Gly  Thr  Thr  Leu  Leu  Ala  Gln  Ala  Ala  Leu  Asp  Ala  Gly  Cys
               1045                     1050                     1055

Glu  Ala  Arg  Ile  Trp  Ala  Val  Thr  Arg  Glu  Ala  Val  Ala  Val  Ser  Pro
               1060                     1065                     1070

Ser  Glu  Val  Pro  Arg  Asp  Ala  Gly  Ala  Gln  Leu  Trp  Gly  Leu  Gly  Arg
               1075                     1080                     1085

Gly  Ile  Ala  Leu  Glu  His  Pro  Ser  Leu  Trp  Gly  Leu  Ile  Asp  Leu
               1090                     1095                     1100

Pro  Ala  Val  Pro  Asp  Glu  Arg  Ala  Trp  Ala  Arg  Ala  Val  Arg  Arg  Leu
1105                     1110                     1115                     1120

Val  Pro  His  Gly  Glu  Asp  Gln  Ile  Ala  Ala  Arg  Ala  Ser  Gly  Ala  Tyr
               1125                     1130                     1135

Gly  Arg  Arg  Leu  Leu  Pro  Ala  Pro  Pro  Ala  Ala  Ser  Arg  Arg  Thr  Cys
               1140                     1145                     1150

Thr  Pro  Ser  Gly  Thr  Val  Leu  Val  Thr  Gly  Gly  Thr  Gly  Ala  Leu  Gly
               1155                     1160                     1165

Gly  His  Leu  Ala  Arg  Arg  Leu  Ala  Arg  Gly  Gly  Thr  Gly  His  Leu  Val
```

-continued

```
                  1170                      1175                        1180
Leu  Thr  Ser  Arg  Arg  Gly  Pro  Asp  Ala  Pro  Gly  Ala  Gly  Glu  Leu  Ala
1185                     1190                       1195                      1200

Gly  Glu  Leu  Ala  Ser  Leu  Gly  Ala  Lys  Val  Thr  Val  Ala  Ala  Cys  Asp
                    1205                      1210                       1215

Met  Ala  Asp  Arg  Glu  Ala  Val  Arg  Ala  Leu  Leu  Asp  Glu  His  Arg  Pro
               1220                      1225                       1230

Thr  Ala  Val  Phe  His  Thr  Ala  Gly  Thr  Pro  His  Ser  Ala  Glu  Phe  Thr
                    1235                      1240                       1245

Ala  Leu  Asp  Glu  Thr  Thr  Thr  Ala  Gly  Val  Tyr  Gly  Gly  Lys  Val  Leu
               1250                      1255                       1260

Gly  Ala  Arg  His  Leu  Asp  Glu  Leu  Thr  Arg  Glu  Leu  Gly  Ile  Gly  Leu
1265                     1270                       1275                      1280

Asp  Ala  Phe  Val  Leu  Phe  Ser  Ser  Gly  Ala  Ala  Val  Trp  Gly  Ser  Gly
                    1285                      1290                       1295

Gly  Gln  Thr  Ala  Tyr  Gly  Ala  Ala  Asn  Ala  Ala  Leu  Asp  Ala  Leu  Ala
               1300                      1305                       1310

Glu  Arg  Arg  Arg  Ala  Ala  Gly  Leu  Pro  Ala  Thr  Ser  Val  Ala  Trp  Gly
               1315                      1320                       1325

Leu  Trp  Gly  Gly  Gly  Gly  Met  Gly  Glu  Gly  Asp  Gly  Glu  Glu  Phe  Leu
1330                     1335                       1340

Ser  Arg  Arg  Gly  Leu  Gly  Val  Met  Pro  Pro  Glu  Asp  Ala  Leu  Glu  Ala
1345                     1350                       1355                      1360

Leu  Asp  Arg  Ala  Leu  Asp  Arg  Glu  Asp  Thr  Thr  Val  Val  Val  Ala  Asp
                    1365                      1370                       1375

Val  Asp  Trp  Glu  Arg  Phe  Ala  Pro  Ala  Phe  Thr  Ala  Phe  Arg  Pro  Ser
               1380                      1385                       1390

Ala  Leu  Ile  Ser  Arg  Leu  Val  Ser  Asp  Gly  Gly  Glu  Ala  Gly  Gly  Gln
               1395                      1400                       1405

Asp  Ala  Pro  Asp  Gly  Thr  Leu  Phe  Ala  Ala  Gly  Phe  Ala  Ala  Ala  Gly
               1410                      1415                       1420

Pro  Leu  Glu  Arg  Gln  Glu  Met  Leu  Leu  Gly  Leu  Val  Arg  Arg  His  Val
1425                     1430                       1435                      1440

Ala  Ala  Val  Leu  Gly  His  Pro  Gly  Thr  Ala  Asp  Ile  Gly  Pro  Asp  Arg
                    1445                      1450                       1455

Ala  Phe  Lys  Glu  Leu  Gly  Phe  Ser  Ser  Val  Thr  Ala  Val  Glu  Leu  Ala
               1460                      1465                       1470

Gly  Arg  Leu  Gly  Arg  Glu  Cys  Gly  Arg  Lys  Leu  Pro  Pro  Thr  Leu  Val
                    1475                      1480                       1485

Phe  Asp  His  Pro  Thr  Ala  Ala  Ala  Ala  Val  Glu  His  Leu  Ala  Glu  Leu
               1490                      1495                       1500

Leu  Thr  Pro  Pro  Ala  Gly  Pro  Ala  Ala  Gly  Pro  Arg  Glu  Glu  Glu  Ala
1505                     1510                       1515                      1520

Arg  Ala  Ala  Leu  Ala  Arg  Val  Pro  Leu  Glu  Arg  Leu  Arg  Glu  Ala  Gly
                    1525                      1530                       1535

Leu  Leu  Asp  Ala  Leu  Leu  Arg  Leu  Ala  Ala  Asp  Glu  Ser  Gly  Ala  Thr
               1540                      1545                       1550

Thr  Pro  Arg  Thr  Ser  Ala  Ala  Ser  Gly  Ala  Pro  Arg  Gly  Arg  Glu  Glu
               1555                      1560                       1565

Pro  Asp  Gly  Arg  Gly  Glu  Pro  Asp  Gly  Ser  Gly  His  Arg  Glu  Ser  Pro
               1570                      1575                       1580

Asp  Ala  Ala  Gly  Gly  Ser  Asp  Ala  Leu  Asp  Asp  Leu  Asp  Gly  Asp  Ala
1585                     1590                       1595                      1600
```

Leu Val Arg Leu Ala Leu Gly Glu Pro Gly Glu
            1605                1610

(2) INFORMATION FOR SEQ ID NO:6:

(i) SEQUENCE CHARACTERISTICS:
        (A) LENGTH: 1841 amino acids
        (B) TYPE: amino acid
        (D) TOPOLOGY: unknown (ii) MOLECULE TYPE: protein (xi) SEQUENCE DESCRIPTION: SEQ ID NO:6:

```
Met Ala Met Ser Ala Glu Arg Leu Thr Glu Ala Leu Arg Thr Ser Leu
 1               5                  10                 15

Lys Glu Ala Glu Arg Leu Arg Arg Gln Asn Arg Glu Leu Arg Ala Ala
             20                  25                 30

Arg Asp Ala Ala Arg Glu Pro Ile Ala Val Val Gly Met Ala Cys Arg
         35                  40                 45

Tyr Pro Gly Gly Val Thr Gly Pro Glu Glu Leu Trp Glu Leu Val Ala
     50                  55                 60

Gly Gly Arg Asp Ala Ile Gly Pro Phe Pro Val Asp Arg Gly Trp Asp
 65                  70                 75                 80

Val Ala Ser Val Tyr Asp Pro Asp Pro Glu Ser Lys Gly Thr Thr Tyr
                 85                  90                 95

Cys Arg Glu Gly Gly Phe Leu Glu Gly Ala Gly Asp Phe Asp Ala Ala
            100                 105                110

Phe Phe Gly Ile Ser Pro Arg Glu Ala Leu Val Met Asp Pro Gln Gln
            115                 120                125

Arg Leu Leu Leu Glu Val Ser Trp Glu Ala Leu Glu Arg Ala Gly Ile
        130                 135                 140

Asp Pro Ser Ser Leu Arg Gly Ser Arg Gly Gly Val Tyr Val Gly Ala
145                 150                 155                160

Ala His Gly Ser Tyr Ala Ser Asp Pro Arg Leu Val Pro Glu Gly Ser
                165                 170                 175

Glu Gly Tyr Leu Leu Thr Gly Ser Ala Asp Ala Val Met Ser Gly Arg
            180                 185                 190

Ile Ser Tyr Ala Leu Gly Leu Glu Gly Pro Ser Met Thr Val Glu Thr
        195                 200                 205

Ala Cys Ser Ser Ser Leu Val Ala Leu His Leu Ala Val Arg Ala Leu
    210                 215                 220

Arg His Gly Glu Cys Gly Leu Ala Leu Ala Gly Gly Val Ala Val Met
225                 230                 235                240

Ala Asp Pro Ala Ala Phe Val Glu Phe Ser Arg Gln Lys Gly Leu Ala
                245                 250                 255

Ala Asp Gly Arg Cys Lys Ala Phe Ser Ala Ala Ala Asp Gly Thr Gly
            260                 265                 270

Trp Ala Glu Gly Val Gly Val Leu Val Leu Glu Arg Leu Ser Asp Ala
        275                 280                 285

Arg Arg Ala Gly His Thr Val Leu Gly Leu Val Thr Gly Thr Ala Val
290                 295                 300

Asn Gln Asp Gly Ala Ser Asn Gly Leu Thr Ala Pro Asn Gly Pro Ala
305                 310                 315                320

Gln Gln Arg Val Ile Ala Glu Ala Leu Ala Asp Ala Gly Leu Ser Pro
                325                 330                 335

Glu Asp Val Asp Ala Val Glu Ala His Gly Thr Gly Thr Arg Leu Gly
            340                 345                 350
```

```
Asp Pro Ile Glu Ala Gly Ala Leu Leu Ala Ala Ser Gly Arg Asn Arg
        355                 360                 365

Ser Gly Asp His Pro Leu Trp Leu Gly Ser Leu Lys Ser Asn Ile Gly
    370                 375                 380

His Ala Gln Ala Ala Ala Gly Val Gly Gly Val Ile Lys Met Leu Gln
385                 390                 395                 400

Ala Leu Arg His Gly Leu Leu Pro Arg Thr Leu His Ala Asp Glu Pro
                405                 410                 415

Thr Pro His Ala Asp Trp Ser Ser Gly Arg Val Arg Leu Leu Thr Ser
                420                 425                 430

Glu Val Pro Trp Gln Arg Thr Gly Arg Pro Arg Arg Thr Gly Val Ser
            435                 440                 445

Ala Phe Gly Val Gly Gly Thr Asn Ala His Val Val Leu Glu Glu Ala
        450                 455                 460

Pro Ala Pro Pro Ala Pro Glu Pro Ala Gly Glu Ala Pro Gly Gly Ser
465                 470                 475                 480

Arg Ala Ala Glu Gly Ala Glu Gly Pro Leu Ala Trp Val Val Ser Gly
                485                 490                 495

Arg Asp Glu Pro Ala Leu Arg Ser Gln Ala Arg Arg Leu Arg Asp His
            500                 505                 510

Leu Ser Arg Thr Pro Gly Ala Arg Pro Arg Asp Ile Ala Phe Ser Leu
        515                 520                 525

Ala Ala Thr Arg Ala Ala Phe Asp His Arg Ala Val Leu Ile Gly Ser
    530                 535                 540

Asp Gly Ala Glu Leu Ala Ala Ala Leu Asp Ala Leu Ala Glu Gly Arg
545                 550                 555                 560

Asp Gly Pro Ala Val Val Arg Gly Val Arg Asp Arg Asp Gly Arg Met
                565                 570                 575

Ala Phe Leu Phe Thr Gly Gln Gly Ser Gln Arg Ala Gly Met Ala His
            580                 585                 590

Asp Leu His Ala Ala His Thr Phe Phe Ala Ser Ala Leu Asp Glu Val
        595                 600                 605

Thr Asp Arg Leu Asp Pro Leu Leu Gly Arg Pro Leu Gly Ala Leu Leu
    610                 615                 620

Asp Ala Arg Pro Gly Ser Pro Glu Ala Ala Leu Leu Asp Arg Thr Glu
625                 630                 635                 640

Tyr Thr Gln Pro Ala Leu Phe Ala Val Glu Val Ala Leu His Arg Leu
                645                 650                 655

Leu Glu His Trp Gly Met Arg Pro Asp Leu Leu Gly His Ser Val
            660                 665                 670

Gly Glu Leu Ala Ala Ala His Val Ala Gly Val Leu Asp Leu Asp Asp
        675                 680                 685

Ala Cys Ala Leu Val Ala Ala Arg Gly Arg Leu Met Gln Arg Leu Pro
    690                 695                 700

Pro Gly Gly Ala Met Val Ser Val Arg Ala Gly Glu Asp Glu Val Arg
705                 710                 715                 720

Ala Leu Leu Ala Gly Arg Glu Asp Ala Val Cys Val Ala Val Asn
                725                 730                 735

Gly Pro Arg Ser Val Val Ile Ser Gly Ala Glu Glu Ala Val Ala Glu
            740                 745                 750

Ala Ala Ala Gln Leu Ala Gly Arg Gly Arg Arg Thr Arg Arg Leu Arg
        755                 760                 765

Val Ala His Ala Phe His Ser Pro Leu Met Asp Gly Met Leu Ala Gly
```

|     |     |     | 770 |     |     |     | 775 |     |     |     | 780 |     |     |
| --- | --- | --- | --- | --- | --- | --- | --- | --- | --- | --- | --- | --- | --- |
| Phe | Arg | Glu | Val | Ala | Ala | Gly | Leu | Arg | Tyr | Arg | Glu | Pro | Glu | Leu | Thr |
| 785 |     |     |     |     | 790 |     |     |     |     | 795 |     |     |     |     | 800 |
| Val | Val | Ser | Thr | Val | Thr | Gly | Arg | Pro | Ala | Arg | Pro | Gly | Glu | Leu | Thr |
|     |     |     |     | 805 |     |     |     |     | 810 |     |     |     |     | 815 |     |
| Gly | Pro | Asp | Tyr | Trp | Val | Ala | Gln | Val | Arg | Glu | Pro | Val | Arg | Phe | Ala |
|     |     |     |     | 820 |     |     |     |     | 825 |     |     |     |     | 830 |     |
| Asp | Ala | Val | Arg | Thr | Ala | His | Arg | Leu | Gly | Ala | Arg | Thr | Phe | Leu | Glu |
|     |     |     | 835 |     |     |     |     | 840 |     |     |     |     | 845 |     |     |
| Thr | Gly | Pro | Asp | Gly | Val | Leu | Cys | Gly | Met | Ala | Glu | Glu | Cys | Leu | Glu |
|     |     | 850 |     |     |     |     | 855 |     |     |     |     | 860 |     |     |     |
| Asp | Asp | Thr | Val | Ala | Leu | Leu | Pro | Ala | Ile | His | Lys | Pro | Gly | Thr | Ala |
| 865 |     |     |     |     | 870 |     |     |     |     | 875 |     |     |     |     | 880 |
| Pro | His | Gly | Pro | Ala | Ala | Pro | Gly | Ala | Leu | Arg | Ala | Ala | Ala | Ala | Ala |
|     |     |     |     | 885 |     |     |     |     | 890 |     |     |     |     | 895 |     |
| Tyr | Gly | Arg | Gly | Ala | Arg | Val | Asp | Trp | Ala | Gly | Met | His | Ala | Asp | Gly |
|     |     |     |     | 900 |     |     |     |     | 905 |     |     |     |     | 910 |     |
| Pro | Glu | Gly | Pro | Ala | Arg | Arg | Val | Glu | Leu | Pro | Val | His | Ala | Phe | Arg |
|     |     |     | 915 |     |     |     |     | 920 |     |     |     |     | 925 |     |     |
| His | Arg | Arg | Tyr | Trp | Leu | Ala | Pro | Gly | Arg | Ala | Ala | Asp | Thr | Asp | Asp |
|     |     | 930 |     |     |     |     | 935 |     |     |     |     | 940 |     |     |     |
| Trp | Met | Tyr | Arg | Ile | Gly | Trp | Asp | Arg | Leu | Pro | Ala | Val | Thr | Gly | Gly |
| 945 |     |     |     |     | 950 |     |     |     |     | 955 |     |     |     |     | 960 |
| Ala | Arg | Thr | Ala | Gly | Arg | Trp | Leu | Val | Ile | His | Pro | Asp | Ser | Pro | Arg |
|     |     |     |     | 965 |     |     |     |     | 970 |     |     |     |     | 975 |     |
| Cys | Arg | Glu | Leu | Ser | Gly | His | Ala | Glu | Arg | Ala | Leu | Arg | Ala | Ala | Gly |
|     |     |     |     | 980 |     |     |     |     | 985 |     |     |     |     | 990 |     |
| Ala | Ser | Pro | Val | Pro | Leu | Pro | Val | Asp | Ala | Pro | Ala | Ala | Asp | Arg | Ala |
|     |     | 995 |     |     |     |     | 1000|     |     |     |     | 1005|     |     |     |
| Ser | Phe | Ala | Ala | Leu | Leu | Arg | Ser | Ala | Thr | Gly | Pro | Asp | Thr | Arg | Gly |
|     |     | 1010|     |     |     |     | 1015|     |     |     |     | 1020|     |     |     |
| Asp | Thr | Ala | Ala | Pro | Val | Ala | Gly | Val | Leu | Ser | Leu | Leu | Ser | Glu | Glu |
| 1025|     |     |     |     | 1030|     |     |     |     | 1035|     |     |     |     | 1040|
| Asp | Arg | Pro | His | Arg | Gln | His | Ala | Pro | Val | Pro | Ala | Gly | Val | Leu | Ala |
|     |     |     |     | 1045|     |     |     |     | 1050|     |     |     |     | 1055|     |
| Thr | Leu | Ser | Leu | Met | Gln | Ala | Met | Glu | Glu | Glu | Ala | Val | Glu | Ala | Arg |
|     |     |     |     | 1060|     |     |     |     | 1065|     |     |     |     | 1070|     |
| Val | Trp | Cys | Val | Ser | Arg | Ala | Ala | Val | Ala | Ala | Ala | Asp | Arg | Glu | Arg |
|     |     | 1075|     |     |     |     | 1080|     |     |     |     | 1085|     |     |     |
| Pro | Val | Gly | Ala | Gly | Ala | Ala | Leu | Trp | Gly | Leu | Gly | Arg | Val | Ala | Ala |
|     |     | 1090|     |     |     |     | 1095|     |     |     |     | 1100|     |     |     |
| Leu | Glu | Arg | Pro | Thr | Arg | Trp | Gly | Gly | Leu | Val | Asp | Leu | Pro | Ala | Ser |
| 1105|     |     |     |     | 1110|     |     |     |     | 1115|     |     |     |     | 1120|
| Pro | Gly | Ala | Ala | His | Trp | Ala | Ala | Ala | Val | Glu | Arg | Leu | Ala | Gly | Pro |
|     |     |     |     | 1125|     |     |     |     | 1130|     |     |     |     | 1135|     |
| Glu | Asp | Gln | Ile | Ala | Val | Arg | Ala | Ser | Gly | Ser | Trp | Gly | Arg | Arg | Leu |
|     |     |     |     | 1140|     |     |     |     | 1145|     |     |     |     | 1150|     |
| Thr | Arg | Leu | Pro | Arg | Asp | Gly | Gly | Gly | Arg | Thr | Ala | Ala | Pro | Ala | Tyr |
|     |     |     | 1155|     |     |     |     | 1160|     |     |     |     | 1165|     |     |
| Arg | Pro | Arg | Gly | Thr | Val | Leu | Val | Thr | Gly | Gly | Thr | Gly | Ala | Leu | Gly |
|     |     |     | 1170|     |     |     |     | 1175|     |     |     |     | 1180|     |     |
| Gly | His | Leu | Ala | Arg | Trp | Leu | Ala | Ala | Ala | Gly | Ala | Glu | His | Leu | Ala |
| 1185|     |     |     |     | 1190|     |     |     |     | 1195|     |     |     |     | 1200|

```
Leu Thr Ser Arg Arg Gly Pro Asp Ala Pro Gly Ala Ala Gly Leu Glu
                1205                1210                1215

Ala Glu Leu Leu Leu Leu Gly Ala Lys Val Thr Phe Ala Ala Cys Asp
                1220                1225                1230

Thr Ala Asp Arg Asp Gly Leu Ala Arg Val Leu Arg Ala Ile Pro Glu
                1235                1240                1245

Asp Thr Pro Leu Thr Ala Val Phe His Ala Ala Gly Val Pro Gln Val
                1250                1255                1260

Thr Pro Leu Ser Arg Thr Ser Pro Glu His Phe Ala Asp Val Tyr Ala
1265                1270                1275                1280

Gly Lys Ala Ala Gly Ala Ala His Leu Asp Glu Leu Thr Arg Glu Leu
                1285                1290                1295

Gly Ala Gly Leu Asp Ala Phe Val Leu Tyr Ser Ser Gly Ala Gly Val
                1300                1305                1310

Trp Gly Ser Ala Gly Gln Gly Ala Tyr Ala Ala Ala Asn Ala Ala Leu
                1315                1320                1325

Asp Ala Leu Ala Arg Arg Arg Ala Ala Asp Gly Leu Pro Ala Thr Ser
                1330                1335                1340

Ile Ala Trp Gly Val Trp Gly Gly Gly Gly Met Gly Ala Asp Glu Ala
1345                1350                1355                1360

Gly Ala Glu Tyr Leu Gly Arg Arg Gly Met Arg Pro Met Ala Pro Val
                1365                1370                1375

Ser Ala Leu Arg Ala Met Ala Thr Ala Ile Ala Ser Gly Glu Pro Cys
                1380                1385                1390

Pro Thr Val Thr His Thr Asp Trp Glu Arg Phe Gly Glu Gly Phe Thr
                1395                1400                1405

Ala Phe Arg Pro Ser Pro Leu Ile Ala Gly Leu Gly Thr Pro Gly Gly
                1410                1415                1420

Gly Arg Ala Ala Glu Thr Pro Glu Glu Gly Asn Ala Thr Ala Ala Ala
1425                1430                1435                1440

Asp Leu Thr Ala Leu Pro Pro Ala Glu Leu Arg Thr Ala Leu Arg Glu
                1445                1450                1455

Leu Val Arg Ala Arg Thr Ala Ala Ala Leu Gly Leu Asp Asp Pro Ala
                1460                1465                1470

Glu Val Ala Glu Gly Glu Arg Phe Pro Ala Met Gly Phe Asp Ser Leu
                1475                1480                1485

Ala Thr Val Arg Leu Arg Arg Gly Leu Ala Ser Ala Thr Gly Leu Asp
                1490                1495                1500

Leu Pro Pro Asp Leu Leu Phe Asp Arg Asp Thr Pro Ala Ala Leu Ala
1505                1510                1515                1520

Ala His Leu Ala Glu Leu Leu Ala Thr Ala Arg Asp His Gly Pro Gly
                1525                1530                1535

Gly Pro Gly Thr Gly Ala Ala Pro Ala Asp Ala Gly Ser Gly Leu Pro
                1540                1545                1550

Ala Leu Tyr Arg Glu Ala Val Arg Thr Gly Arg Ala Ala Glu Met Ala
                1555                1560                1565

Glu Leu Leu Ala Ala Ala Ser Arg Phe Arg Pro Ala Phe Gly Thr Ala
                1570                1575                1580

Asp Arg Gln Pro Val Ala Leu Val Pro Leu Ala Asp Gly Ala Glu Asp
1585                1590                1595                1600

Thr Gly Leu Pro Leu Leu Val Gly Cys Ala Gly Thr Ala Val Ala Ser
                1605                1610                1615

Gly Pro Val Glu Phe Thr Ala Phe Ala Gly Ala Leu Ala Asp Leu Pro
                1620                1625                1630
```

```
Ala  Ala  Ala  Pro  Met  Ala  Ala  Leu  Pro  Gln  Pro  Gly  Phe  Leu  Pro  Gly
               1635                1640                1645

Glu  Arg  Val  Pro  Ala  Thr  Pro  Glu  Ala  Leu  Phe  Glu  Ala  Gln  Ala  Glu
     1650                1655                1660

Ala  Leu  Leu  Arg  Tyr  Ala  Ala  Gly  Arg  Pro  Phe  Val  Leu  Leu  Gly  His
1665                1670                1675                          1680

Ser  Ala  Gly  Ala  Asn  Met  Ala  His  Ala  Leu  Thr  Arg  His  Leu  Glu  Ala
                    1685                1690                          1695

Asn  Gly  Gly  Gly  Pro  Ala  Gly  Leu  Val  Leu  Met  Asp  Ile  Tyr  Thr  Pro
               1700                1705                     1710

Ala  Asp  Pro  Gly  Ala  Met  Gly  Val  Trp  Arg  Asn  Asp  Met  Phe  Gln  Trp
               1715                1720                     1725

Val  Trp  Arg  Arg  Ser  Asp  Ile  Pro  Pro  Asp  Asp  His  Arg  Leu  Thr  Ala
     1730                1735                     1740

Met  Gly  Ala  Tyr  His  Arg  Leu  Leu  Leu  Asp  Trp  Ser  Pro  Thr  Pro  Val
1745                1750                     1755                          1760

Arg  Ala  Pro  Val  Leu  His  Leu  Arg  Ala  Ala  Glu  Pro  Met  Gly  Asp  Trp
                    1765                1770                          1775

Pro  Pro  Gly  Asp  Thr  Gly  Trp  Gln  Ser  His  Trp  Asp  Gly  Ala  His  Thr
               1780                1785                          1790

Thr  Ala  Gly  Ile  Pro  Gly  Asn  His  Phe  Thr  Met  Met  Thr  Glu  His  Ala
          1795                1800                     1805

Ser  Ala  Ala  Ala  Arg  Leu  Val  His  Gly  Trp  Leu  Ala  Glu  Arg  Thr  Pro
          1810                1815                1820

Ser  Gly  Gln  Gly  Gly  Ser  Pro  Ser  Arg  Ala  Ala  Gly  Arg  Glu  Glu  Arg
1825                1830                1835                          1840

Pro
```

( 2 ) INFORMATION FOR SEQ ID NO:7:

( i ) SEQUENCE CHARACTERISTICS:
  ( A ) LENGTH: 44377 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 350..14002

( i x ) FEATURE:
  ( A ) NAME/KEY: CDS
  ( B ) LOCATION: 14046..20036

( i x ) FEATURE:
  ( A ) NAME/KEY: CDS
  ( B ) LOCATION: 20110..31284

( i x ) FEATURE:
  ( A ) NAME/KEY: CDS
  ( B ) LOCATION: 31329..36071

( i x ) FEATURE:
  ( A ) NAME/KEY: CDS
  ( B ) LOCATION: 36155..41830

( x i ) SEQUENCE DESCRIPTION: SEQ ID NO:7:

```
GACCGCTCGG  GGAGACCTGA  CATATTCGTC  GCGAAGTGGT  TGTCCGCGCC  GCGAGGTACT        60

GAAATCTTCT  CCGCTCGCCC  AGGACTCCGC  GTGCAGGTCA  CCGGAGTGCG  CGACCGGCCG       120

GGACGTCGGA  GCGCCGACCC  TGCGGACCTG  GTGCGATGCC  GTGTGGTCCC  GCATGATCCC       180
```

-continued

```
GCGCCGTCTC CGGTGACGAG AATCGGTGGA CAATCTCCGA ACTTGACACA ATTGATTGTC      240
GTTCACCGGC CGTTCCTGTC GCCCGGCAGT TCGCCCGCTG TACGCTCGGG AAGATCAAGA      300
AAAGGCAGAA AAGCCACGGC GTGGTACGGC GAACATATGA GGGATGCAGG TGTCTGGAGA      360
ACTCGCGATT TCCCGCAGTG ACGACCGGTC CGACGCCGTT GCCGTGGTCG GAATGGCGTG      420
CCGGTTTCCC GGCGCCCCGG GAATTGCCGA ATTCTGGAAA CTGCTGACCG ACGGAAGGGA      480
CGCGATCGGC CGGGACGCCG ACGGCCGCCG GCGCGGCATG ATCGAGGCGC CCGGCGACTT      540
CGACGCCGCC TTCTTCGGCA TGTCACCCCG CGAGGCCGCC GAGACCGACC CCAGCAGCG       600
CCTGATGCTC GAACTCGGCT GGGAGGCTCT GGAGGACGCC GGCATCGTCC CCGGCTCCCT      660
GCGCGGCGAG GCGGTCGGCG TCTTCGTCGG GGCCATGCAC GACGACTACG CCACCCTGCT      720
CCACCGCGCC GGCGCGCCGG TCGGCCCCCA CACCGCCACC GGCCTCCAGC GCGCCATGCT      780
CGCCAACCGG CTCTCCTACG TCCTGGGGAC GCGCGGCCCC AGCCTCGCGG TCGACACCGC      840
CCAGTCGTCC TCCCTGGTCG CCGTGGCCCT CGCCGTCGAG AGCCTGCGGG CCGGCACCTC      900
CCGCGTCGCC GTCGCCGGGG GCGTCAACCT GGTCCTCGCC GACGAGGGAA CGGCCGCCAT      960
GGAACGCCTC GGCGCGCTGT CACCCGACGG CCGCTGCCAC ACCTTCGACG CCCGTGCCAA     1020
CGGCTATGTC CGCGGTGAGG GCGGCGCCGC CGTCGTCCTG AAGCCCCTCG CCGACGCCCT     1080
GGCCGACGGG GACCCCGTGT ACTGCGTGGT GCGTGGCGTC GCCGTCGGCA ACGACGGCGG     1140
CGGCCCCGGG CTGACCGCTC CCGACCGCGA GGGACAGGAG GCGGTGCTCC GGGCCGCCTG     1200
CGCCCAGGCC CGGGTCGACC CCGCCGAGGT GCGTTTCGTC GAACTGCACG GCACGGGAAC     1260
CCCGGTGGGC GACCCGGTCG AGGCACACGC CCTCGGCGCG GTGCACGGCT CCGGTCGGCC     1320
GGCCGACGAC CCCCTGCTGG TGGGGTCGGT GAAGACCAAC ATCGGCCACC TGGAGGGCGC     1380
CGCCGGCATC GCGGGCCTGG TCAAGGCCGC ACTGTGCCTG CGGGAACGCA CCCTTCCCGG     1440
CTCGCTGAAC TTCGCCACCC CCTCTCCGGC CATCCCGCTG GACCAGCTCC GGCTGAAGGT     1500
GCAGACCGCT GCCGCCGAGC TGCCGCTCGC CCCGGGCGGC GCACCCCTGC TGGCGGGTGT     1560
CAGTTCGTTC GGCATCGGTG GCACCAACTG CCATGTGGTC CTGGAACACC TGCCCTCCCG     1620
GCCCACCCCG GCCGTCTCCG TCGCCGCCTC GCTTCCGGAC GTCCCGCCGC TGTTGTTGTC     1680
CGCGCGGTCG GAGGGGGCGT TGCGGGCGCA GGCGGTGCGG TTGGGTGAGT ACGTGGAGCG     1740
GGTGGGCGCG GATCCGCGGG ATGTGGCTTA TTCGCTGGCT TCGACGCGGA CTCTTTTCGA     1800
GCACCGTGCG GTGGTGCCGT GTGGTGGGCG TGGGGAGCTC GTCGCTGCTC TTGGTGGGTT     1860
TGCTGCCGGG AGGGTGTCTG GGGGTGTGCG GTCCGGGCGG GCTGTGCCGG GTGGGGTGGG     1920
GGTGTTGTTC ACGGGTCAGG GTGCGCAGTG GGTTGGTATG GGGCGTGGGT TGTATGCGGG     1980
GGGTGGGGTG TTTGCGGAGG TGCTGGATGA GGTGTTGTCG ATGGTGGGGG AGGTGGATGG     2040
TCGGTCGTTG CGGGATGTGA TGTTCGGCGA CGTCGACGTG GACGCGGGTG CCGGGGCTGA     2100
TGCGGGTGCC GGTGCGGGTG CTGGGGTCGG TTCTGGTTCC GGTTCTGTGG GTGGGTTGTT     2160
GGGTCGGACG GAGTTTGCTC AGCCTGCGTT GTTTGCGTTG GAGGTGGCGT TGTTCCGGGC     2220
GTTGGAGGCT CGGGGTGTGG AGGTGTCGGT GGTGTTGGGT CATTCGGTGG GGAGGTGGC     2280
TGCTGCGTAT GTGGCGGGGG TGTTGTCGTT GGGTGATGCG GTGCGGTTGG TGGTGGCGCG     2340
GGGTGGGTTG ATGGGTGGGT TGCCGGTGGG TGGGGGATG TGGTCGGTGG GGGCGTCGGA     2400
GTCGGTGGTG CGGGGGGTTG TTGAGGGGTT GGGGGAGTGG GTGTCGGTTG CGGCGGTGAA     2460
TGGGCCGCGG TCGGTGGTGT TGTCGGGTGA TGTGGGTGTG CTGGAGTCGG TGGTTGCCTC     2520
GCTGATGGGG GATGGGGTGG AGTGCCGGCG GTTGGATGTG TCGCATGGGT TTCATTCGGT     2580
```

-continued

| | | | | | | |
|---|---|---|---|---|---|---|
| GTTGATGGAG | CCGGTGTTGG | GGGAGTTCCG | GGGGGTTGTG | GAGTCGTTGG | AGTTCGGTCG | 2640 |
| GGTGCGGCCG | GGTGTGGTGG | TGGTGTCGGG | TGTGTCGGGT | GGGGTGGTGG | GTTCGGGGGA | 2700 |
| GTTGGGGGAT | CCGGGGTATT | GGGTGCGTCA | TGCGCGGGAG | GCGGTGCGTT | TCGCGGATGG | 2760 |
| GGTGGGGGTG | GTGCGTGGTC | TGGGTGTGGG | GACGTTGGTG | GAGGTGGGTC | CGCATGGGGT | 2820 |
| GCTGACGGGG | ATGGCGGGTG | AGTGCCTGGG | GGCCGGTGAT | GATGTGGTGG | TGGTGCCGGC | 2880 |
| GATGCGGCGG | GGCCGTGCGG | AGCGGGAGGT | GTTCGAGGCG | GCGCTGGCGA | CGGTGTTCAC | 2940 |
| CCGGGACGCC | GGCCTGGACG | CCACGGCACT | CCACACCGGG | AGCACCGGCC | GGCGCATCGA | 3000 |
| CCTCCCCACC | TACCCCTTCC | AACGCCGTAC | CCACTGGTCG | CCCGCGCTGA | GCCGGCCGGT | 3060 |
| CACGGCCGAC | GCCGGGGCGG | GTGTGACCGC | CACCGATGCC | GTGGGGCACA | GCGTCTCCCC | 3120 |
| GGACCCGGAG | AGCACCGAGG | GGACGTCCCA | CAGGGACACG | GACGACGAGG | CGGACTCGGC | 3180 |
| GTCACCGGAG | CCGATGTCCC | CCGAGGATGC | CGTCCGCCTG | GTCCGCGAGA | GCACCGCGGC | 3240 |
| CGTCCTGGGC | CACGACGATC | CCGGCGAGGT | CGCGCTCGAC | CGCACCTTCA | CCTCCCAGGG | 3300 |
| CATGGACTCG | GTGACCGCGG | TCGAGCTGTG | CGACCTGCTG | AAGGGCGCCT | CGGGGCTCCC | 3360 |
| CCTCGCCGCC | ACGCTGGTCT | ACGACCTGCC | CACCCCGCGT | GCCGTCGCCG | AGCACATCGT | 3420 |
| GGAAGCCGCG | GGCGGGCCGA | AGGACTCGGT | TGCCGGTGGG | CCCGGAGTGC | TCTCGTCGGC | 3480 |
| CGCGGTAGGG | GTGTCGGACG | CCCGGGGCGG | CAGCCGGGAC | GACGACGACC | CGATCGCCAT | 3540 |
| CGTGGGTGTC | GGCTGCCGGC | TCCCCGGCGG | CGTCGACTCG | CGCGCCGCTC | TCTGGGAGCT | 3600 |
| GCTGGAGTCC | GGCGCCGACG | CCATCTCGTC | CTTCCCCACC | GACCGCGGCT | GGGACCTCGA | 3660 |
| CGGGCTGTAC | GACCCCGAGC | CCGGGACGCC | CGGCAAGACC | TATGTGCGGG | AGGGCGGGTT | 3720 |
| CCTGCACTCG | GCGGCCGAGT | TCGACGCGGA | GTTCTTCGGG | ATATCGCCGC | GCGAGGCCAC | 3780 |
| GGCCATGGAC | CCGCAGCAGC | GCTTGCTGCT | GGAAGCGTCG | TGGGAGGCCC | TCAGGACGC | 3840 |
| CGGAGTGCTC | CCCGAGTCAC | TGCGCGGCGG | CGACGCCGGA | GTGTTCGTCG | GCGCCACCGC | 3900 |
| ACCGGAGTAC | GGGCCGAGGC | TTCACGAGGG | AGCGGACGGA | TACGAGGGGT | ACCTGCTCAC | 3960 |
| CGGCACCACC | GCGAGCGTGG | CCTCCGGCCG | GATCGCCTAC | ACCCTCGGCA | CCGGCGGACC | 4020 |
| GGCGCTCACC | GTCGACACCG | CGTGCTCCTC | GTCCCTGGTG | GCGCTGCACC | TGGCCGTGCA | 4080 |
| GGCGCTGCGC | CGGGGCGAGT | GCGGGCTGGC | TCTGGCGGGC | GGCGCCACGG | TGATGTCGGG | 4140 |
| GCCCGGCATG | TTCGTGGAGT | TCTCGCGGCA | GCGCGGGCTC | GCCCCCGACG | GCCGCTGCAT | 4200 |
| GCCGTTCTCC | GCCGATGCCG | ACGGTACGGC | CTGGTCCGAG | GGTGTCGCCG | TACTGGCACT | 4260 |
| GGAGCGGCTC | TCCGACGCCC | GGCGTGCGGG | ACACCGGGTG | CTGGGCGTGG | TGCGGGGCAG | 4320 |
| TGCGGTCAAC | CAGGACGGTG | CCAGCAACGG | CCTGACCGCT | CCCAACCGCT | CCGCGCAGGA | 4380 |
| GGGCGTCATC | CGAGCTGCCC | TGGCCGACGC | CGGCCTCGCG | CCGGGTGACG | TGGACGCGGT | 4440 |
| GGAGGCGCAC | GGTACGGGGA | CGGCGCTGGG | CGATCCGATC | GAGGCGAGCG | CGCTGCTGGC | 4500 |
| CACGTACGGG | CGTGAGCGGG | TGGGCGACCC | CTTGTGGCTC | GGGTCGCTGA | AGTCCAACGT | 4560 |
| CGGTCACACC | CAGGCCGCCG | CGGGGGCCGC | GGGTGTGGTC | AAGATGCTGC | TTGCCCTGGA | 4620 |
| GCACGGCACG | CTGCCGCGGA | CACTTCACGC | GGACCGGCCC | AGCACGCACG | TCGACTGGTC | 4680 |
| GTCGGGCACC | GTCGCCCTGC | TGGCAGAGGC | GCGCCGGTGG | CCCCGGCGGT | CGGACCGCCC | 4740 |
| GCGCCGGGCG | GCTGTGTCGT | CGTTCGGGAT | CAGTGGGACG | AACGCGCATC | TGATCATCGA | 4800 |
| GGAGGCGCCG | GAGTGGGTCG | AGGACATCGA | CGGCGTCGCT | GCTCCTGACC | GCGGTACCGC | 4860 |
| GGACGCGGCT | GCTCCGTCGC | CGCTGTTGTT | GTCCGCGCGG | TCGGAGGGGG | CGTTGCGGGC | 4920 |
| GCAGGCGGTG | CGGTTGGGTG | AGTACGTGGA | GCGGGTGGGT | GCGGATCCGC | GGGATGTGGC | 4980 |

-continued

| | | | | | | |
|---|---|---|---|---|---|---|
| TTATTCGCTG | GCTTCGACGC | GGACTCTTTT | CGAGCACCGT | GCGGTGGTGC | CGTGTGGTGG | 5040 |
| GCGTGGGGAG | CTCGTCGCTG | CTCTTGGTGG | GTTTGCTGCC | GGGAGGGTGT | CTGGGGGTGT | 5100 |
| GCGGTCCGGG | CGGGCTGTGC | CGGGTGGGGT | GGGGGTGTTG | TTCACGGGTC | AGGGTGCGCA | 5160 |
| GTGGGTTGGT | ATGGGGCGTG | GGTTGTATGC | GGGGGGTGGG | GTGTTTGCGG | AGGTGCTGGA | 5220 |
| TGAGGTGTTG | TCGATGGTGG | GGGAGGTGGA | TGGTCGGTCG | TTGCGGGATG | TGATGTTCGG | 5280 |
| CGACGTCGAC | GTGGACGCGG | GTGCCGGGGC | TGATGCGGGT | GCCGGTGCGG | GTGCTGGGGT | 5340 |
| CGGTTCTGGT | TCCGGTTCTG | TGGGTGGGTT | GTTGGGTCGG | ACGGAGTTTG | CTCAGCCTGC | 5400 |
| GCTGTTTGCG | TTGGAGGTGG | CGTTGTTCCG | GGCGTTGGAG | GCTCGGGGTG | TGGAGGTGTC | 5460 |
| GGTGGTGTTG | GGTCATTCGG | TGGGGGAGGT | GGCTGCTGCG | TATGTGGCGG | GGGTGTTGTC | 5520 |
| GTTGGGTGAT | GCGGTGCGGT | TGGTGGTGGC | GCGGGGTGGG | TTGATGGGTG | GGTTGCCGGT | 5580 |
| GGGTGGGGGG | ATGTGGTCGG | TGGGGGCGTC | GGAGTCGGTG | GTGCGGGGGG | TTGTTGAGGG | 5640 |
| GTTGGGGGAG | TGGGTGTCGG | TTGCGGCGGT | GAATGGGCCG | CGGTCGGTGG | TGTTGTCGGG | 5700 |
| TGATGTGGGT | GTGCTGGAGT | CGGTGGTTGC | CTCGCTGATG | GGGGATGGGG | TGGAGTGCCG | 5760 |
| GCGGTTGGAT | GTGTCGCATG | GGTTTCATTC | GGTGTTGATG | GAGCCGGTGT | TGGGGGAGTT | 5820 |
| CCGGGGGGTT | GTGGAGTCGT | TGGAGTTCGG | TCGGGTGCGG | CCGGGTGTGG | TGGTGGTGTC | 5880 |
| GGGTGTGTCG | GGTGGGGTGG | TGGGTTCGGG | GGAGTTGGGG | GATCCGGGGT | ATTGGGTGCG | 5940 |
| TCATGCGCGG | GAGGCGGTGC | GTTTCGCGGA | TGGGGTGGGG | GTGGTGCGTG | GTCTGGGTGT | 6000 |
| GGGGACGTTG | GTGGAGGTGG | GTCCGCATGG | GGTGCTGACG | GGGATGGCGG | GTGAGTGCCT | 6060 |
| GGGGGCCGGT | GATGATGTGG | TGGTGGTGCC | GGCGATGCGG | CGGGGCCGTG | CGGAGCGGGA | 6120 |
| GGTGTTCGAG | GCGGCGCTGG | CGACGGTGTT | CACCCGGGAC | GCCGGCCTGG | ACGCCACGGC | 6180 |
| ACTCCACACC | GGGAGCACCG | GCCGGCGCAT | CGACCTCCCC | ACCTACCCCT | TCCAACGCGA | 6240 |
| CCGCTACTGG | CTGGACCCCG | TTCGCACCGC | CGTGACCGGC | GTCGAGCCCG | CCGGCTCGCC | 6300 |
| GGCGGACGCT | CGGGCCACTG | AGCGGGGACG | GTCGACGACG | GCCGGGATCC | GCTACCGCGT | 6360 |
| CGCTTGGCAG | CCGGCCGTCG | TCGACCGCGG | CAACCCCGGG | CCTGCCGGTC | ATGTGCTGCT | 6420 |
| TCTGGCCCCG | GACGAGGACA | CGGCCGACTC | CGGACTCGCC | CCCGCGATCG | CACGTGAACT | 6480 |
| CGCCGTGCGC | GGGGCCGAGG | TCCACACCGT | CGCCGTGCCG | GTCGGTACAG | GCCGGGAGGC | 6540 |
| AGCCGGGGAC | CTGTTGCGGG | CCGCCGGTGA | CGGTGCCGCC | CGCAGCACCC | GAGTTCTGTG | 6600 |
| GCTCGCCCCG | GCCGAGCCGG | ACGCGGCCGA | CGCCGTCGCC | CTCGTCCAGG | CGCTGGGCGA | 6660 |
| GGCGGTACCC | GAAGCCCCGC | TCTGGATCAC | CACCCGTGAG | GCGGCGGCCG | TGCGGCCGGA | 6720 |
| CGAGACCCCT | TCCGTCGGGG | GCGCTCAGCT | GTGGGGACTC | GGACAGGTCG | CCGCGCTCGA | 6780 |
| ACTGGGGCGG | CGCTGGGGCG | GCTTGGCGGA | CCTGCCCGGG | AGTGCGTCGC | CCGCGGTGCT | 6840 |
| CCGTACGTTC | GTCGGGGCGC | TGCTCGCCGG | GGGAGAGAAC | CAGTTCGCGG | TACGGCCCTC | 6900 |
| CGGCGTCCAT | GTCCGCCGTG | TGGTTCCCGC | GCCCGTCCCC | GTCCCGGCCT | CCGCTCGCAC | 6960 |
| CGTCACCACG | GCCCCCGCCA | CCGCCGTCGG | CGAGGACGCA | CGGAACGACA | CCTCGGACGT | 7020 |
| GGTCGTGCCG | GACGACCGGT | GGTCCTCCGG | CACCGTACTG | ATCACCGGGG | GCACCGGTGC | 7080 |
| CCTGGGTGCG | CAGGTCGCCC | GCAGGCTCGC | CCGGTCGGGC | GCCGCGCGTC | TGCTCCTGGT | 7140 |
| GGGCCGGCGC | GGCGCGGCCG | GCCCCGGAGT | GGGCGAACTC | GTCGAGGAGC | TGACGGCGCT | 7200 |
| CGGTTCCGAA | GTGGCCGTCG | AGGCCTGCGA | CGTCGCCGAC | CGGGACGCAC | TGGCCGCGCT | 7260 |
| CCTCGCGGGC | CTCCCCGAGG | AGCGGCCCCT | CGTCGCCGTA | CTGCACGCGG | CAGGTGTGCT | 7320 |
| CGACGACGGT | GTGCTCGACT | CGCTCACCTC | CGACCGGGTG | GACGCCGTAC | TGCGGGACAA | 7380 |

```
GGTCACCGCC GCCCGTCACC TGGACGAGCT GACCGCGGAC CTTCCGCTCG ACGCCTTCGT      7440
GCTCTTCTCC TCCATCGTCG GCGTGTGGGG CAACGGAGGG CAGGCCGTCT ACGCGGCCGC      7500
CAACGCCGCG CTCGACGCCC TGGCGCAGCG GCGCCGGGCC AGGGGAGCCC GTGCCGCCTC      7560
GATCGCCTGG GGGCCGTGGG CCGGTGCCGG AATGGCCTCC GGAACGGCGG CGAAGTCCTT      7620
CGAACGGGAC GGCGTCACGG CCCTGGACCC CGAGCGCGCG CTCGACGTCC TCGACGACGT      7680
GGTGGGCGCC GGCGGGACCT CTGCCGCAGG GACGCACGCG GCCGGCGAGA GCTCCCTGCT      7740
CGTCGCCGAC GTGGACTGGG AGACCTTCGT CGGGCGTTCG GTCACCCGCC GTACCTGGTC      7800
GCTCTTCGAC GGCGTCTCCG CCGCCCGTTC GGCGCGTGCC GGCCATGCCG CGGACGACCG      7860
TGCCGCTCTC ACCCCAGGGA CGCGGCCGGG CGACGGCGCA CCGGGCGGGA GCGGACAGGA      7920
CGGGGGCGAG GGCCGGCCGT GGCTCTCCGT CGGCCCCTCG CCGGCGGAAC GCCGTCGTGC      7980
TCTGCTCACG CTTGTGCGCT CGGAGGCCGC CGGGATCCTG CGCCACGCCT CGGCCGACGC      8040
GGTCGACCCG GAGCTGGCCT TCCGGTCCGC CGGGTTCGAC TCCCTCACCG TTCTCGAACT      8100
GCGTAACCGC CTGACCGCTG CCACCGGCCT GAACCTGCCG AACACGCTGC TCTTCGACCA      8160
CCCGACCCCC CTCTCGCTCG CCTCCCACCT GCACGACGAA CTGTTCGGTC CGACAGCGA      8220
GGCGGAGCCG GCAGCGGCCG CCCCCACGCC GGTCATGGCC GACGAGCGTG AGCCGATCGC      8280
GATCGTGGGC ATGGCGTGCC GTTACCCGGG CGGTGTGGCG TCGCCGGACG ACCTGTGGGA      8340
CCTGGTGGCC GGTGACGGGC ACACGCTCTC CCCGTTCCCG GCCGACCGTG GCTGGGACGT      8400
CGAGGGGCTG TACGACCCGG AGCCGGGGGT GCCGGGCAAG AGCTATGTAC GGGAAGGCGG      8460
GTTCCTGCGT TCCGCGGCCG AGTTCGACGC GGAGTTCTTC GGGATATCGC CGCGCGAGGC      8520
CACGGCCATG GACCCGCAGC AGCGGTTGCT GCTGGAGACG TCGTGGGAGG CGCTGGAGCG      8580
GGCCGGCATC GTTCCGGACT CGCTGCGCGG CACCCGGACC GGTGTCTTCA GCGGCATCTC      8640
CCAGCAGGAC TACGCGACCC AGCTGGGGGA CGCCGCCGAC ACCTACGGCG GGCATGTGCT      8700
CACGGGGACC CTCGGCAGTG TGATCTCCGG TCGGGTTGCC TATGCGTTGG GGTTGGAGGG      8760
GCCGGCGCTG ACGGTGGACA CGGCGTGTTC GTCGTCGTTG GTGGCGTTGC ATCTGGCGGT      8820
GCAGTCGTTG CGGCGGGGTG AGTGTGATCT GGCGTTGGCC GGTGGGGTGA CGGTGATGGC      8880
GACGCCGACG GTGTTCGTGG AGTTCTCGCG GCAGCGGGGG CTGGCGGCGG ACGGGCGGTG      8940
CAAGGCGTTC GCGGAGGGTG CGGACGGGAC GGCGTGGGCG GAGGGTGTGG GTGTGCTGCT      9000
GGTGGAGCGG CTTTCCGACG CGCGCCGCAA CGGTCATCGG GTGCTGGCGG TGGTGCGGGG      9060
CAGTGCGGTC AATCAGGACG GTGCGAGCAA TGGGCTGACG GCGCCGAGTG GTCCGGCGCA      9120
GCAGCGGGTG ATCCGTGAGG CGCTGGCTGA TGCGGGGCTG GTGCCCGCCG ACGTGGATGT      9180
GGTGGAGGCG CACGGTACGG GGACGGCGCT GGGTGATCCG ATCGAGGCGG GTGCGCTGCT      9240
GGCCACGTAC GGGCGGGAGC GGGTCGGCGA TCCGTTGTGG CTCGGGTCGT TGAAGTCGAA      9300
CATCGGGCAT GCGCAGGCGG CTGCGGGTGT GGGTGGTGTG ATCAAGGTGG TGCAGGGGAT      9360
GCGGCATGGG TCGTTGCCGC GGACGCTGCA TGTGGATGCG CCGTCGTCGA AGGTGGAGTG      9420
GGCTTCGGGT GCGGTGGAGC TGCTGACCGA GACCCGGTCG TGGCCGCGGC GGGTGGAGCG      9480
GGTGCGGCGG GCCGCGGTGT CGGCGTTCGG GGTGAGCGGG ACCAACGCCC ATGTGGTCCT      9540
GGAGGAAGCG CCGGCGGAGG CCGGGAGCGA GCACGGGGAC GGCCCTGAAC CTGAGCGGCC      9600
CGACGCGGTG ACGGGTCCGT TGTCGTGGGT GCTTTCTGCG CGGTCGGAGG GGGCGTTGCG      9660
GGCGCAGGCG GTGCGGTTGC GTGAGTGTGT GGAGCGGGTG GGTGCGGATC CGCGGGATGT      9720
GGCGGGGTCG TTGGTGGTGT CGCGTGCGTC GTTCGGTGAG CGTGCGGTGG TGGTGGGCCG      9780
```

-continued

| | | | | | | |
|---|---|---|---|---|---|---|
| GGGGCGTGAG | GAGTTGCTGG | CGGGTCTGGA | TGTGGTGGCT | GCCGGGGCTC | CTGTGGGTGT | 9840 |
| GTCTTCGGGG | GCCGGTGCTG | TGGTGCGGGG | GAGTGCGGTG | CGGGGTCGTG | GGGTGGGGGT | 9900 |
| GTTGTTCACG | GGTCAGGGTG | CGCAGTGGGT | TGGTATGGGG | CGTGGGTTGT | ATGCGGGGGG | 9960 |
| TGGGGTGTTT | GCGGAGGTGC | TGGATGAGGT | GTTGTCGGTG | GTGGGGGAGG | TGGATGGTCG | 10020 |
| GTCGTTGCGG | GATGTGATGT | TCGCGGATGC | TGACTCGGTT | TTGGGTGGGT | TGTTGGGTCG | 10080 |
| GACGGAGTTT | GCTCAGCCTG | CGTTGTTTGC | GTTGGAGGTG | GCGTTGTTCC | GGGCGTTGGA | 10140 |
| GGCTCGGGGT | GTGGAGGTGT | CGGTGGTGTT | GGGTCATTCG | GTGGGGGAGG | TGGCTGCTGC | 10200 |
| GTATGTGGCG | GGGGTGTTGT | CGTTGGGTGA | TGCGGTGCGG | TTGGTGGTGG | CGCGGGGTGG | 10260 |
| GTTGATGGGT | GGGTTGCCGG | TGGGTGGGGG | GATGTGGTCG | GTGGGGGCGT | CGGAGTCGGT | 10320 |
| GGTGCGGGGG | GTTGTTGAGG | GGTTGGGGGA | GTGGGTGTCG | GTTGCGGCGG | TGAATGGGCC | 10380 |
| GCGGTCGGTG | GTGTTGTCGG | GTGATGTGGG | TGTGCTGGAG | TCGGTGGTTG | TCACGCTGAT | 10440 |
| GGGGGATGGG | GTGGAGTGCC | GGCGGTTGGA | TGTGTCGCAT | GGGTTTCATT | CGGTGTTGAT | 10500 |
| GGAGCCGGTG | TTGGGGGAGT | TCCGGGGGGT | TGTGGAGTCG | TTGGAGTTCG | GTCGGGTGCG | 10560 |
| GCCGGGTGTG | GTGGTGGTGT | CGGGTGTGTC | GGGTGGGGTG | GTGGGTTCGG | GGGAGTTGGG | 10620 |
| GGATCCGGGG | TATTGGGTGC | GTCATGCGCG | GGAGGCGGTG | CGTTTCGCGG | ATGGGGTGGG | 10680 |
| GGTGGTGCGT | GGTCTGGGTG | TGGGGACGTT | GGTGGAGGTG | GGTCCGCATG | GGGTGCTGAC | 10740 |
| GGGGATGGCG | GGTCAGTGCC | TGGAGGCCGG | TGATGATGTG | GTGGTGGTGC | CGGCGATGCG | 10800 |
| GCGGGGCCGT | CCGGAGCGGG | AGGTGTTCGA | GGCGGCGCTG | GCGACGGTGT | TCACCCGGGA | 10860 |
| CGCCGGCCTC | GACGCCACGA | CACTCCACAC | CGGGAGCACC | GGCCGACGCA | TCGACCTCCC | 10920 |
| CACCTACCCC | TTCCAACACA | ACCGCTACTG | GGCAACCGGC | TCAGTGACCG | GTGCGACCGG | 10980 |
| CACCTCGGCA | GCCGCGCGCT | TCGGCCTGGA | GTGGAAGGAC | CACCCCTTCC | TCAGCGGCGC | 11040 |
| CACGCCGATA | GCCGGCTCCG | GCGCGCTGCT | CCTCACCGGC | AGGGTGGGGC | TCGCTGCCCA | 11100 |
| CCCGTGGCTG | GCCGACCACG | CCATCTCCGG | CACGGTGCTG | CTCCCCGGAA | CGGCGATCGC | 11160 |
| CGACCTGCTG | CTGCGGGCGG | TCGAGGAGGT | CGGCGCCGGA | GGGGTCGAGG | AACTGACGCT | 11220 |
| CCATGAGCCC | CTGCTCCTCC | CCGAGCGAGG | CGGCCTGCAC | GTCCAGGTGC | TGGTCGAGGC | 11280 |
| GGCCGACGAG | CAGGGACGGC | GTGCCGTGGC | AGTCGCCGCA | CGCCCGGAGG | GCCCTGGGCG | 11340 |
| GGACGGTGAG | GAACAGGAGT | GGACCCGGCA | CGCGGAAGGC | GTGCTCACCT | CCACCGAGAC | 11400 |
| GGCCGTTCCG | GACATGGGCT | GGGCCGCCGG | GGCCTGGCCG | CCGCCCGGTG | CCGAGCCGAT | 11460 |
| CGACGTCGAG | GAGCTGTACG | ACGCGTTCGC | CGCGGACGGC | TACGGCTACG | GCCCGGCCTT | 11520 |
| CACCGCACTG | TCCGGCGTGT | GGCGTCTCGG | CGACGAACTC | TTCGCCGAGG | TGCGGCGGCC | 11580 |
| CGCGGGGGGC | GCGGGCACGA | CCGGTGACGG | TTTCGGCGTC | CACCCCGCAC | TCTTCGATGC | 11640 |
| GGCCCTCCAC | CCGTGGCGCG | CCGGCGGGCT | GCTGCCCGAC | ACGGGCGGCA | CCACCTGGGC | 11700 |
| GCCGTTCTCC | TGGCAGGGCA | TCGCGCTCCA | CACCACCGGA | GCCGAGACGC | TCCGCGTCAG | 11760 |
| ACTGGCCCCT | GCGGCCGGCG | GCACCGAGTC | GGCCTTCTCC | GTACAGGCCG | CCGACCCGGC | 11820 |
| GGGCACCCCG | GTCCTCACCC | TCGACGCACT | GCTGCTCCGC | CCGGTGACCC | TGGGGAGGGC | 11880 |
| CGACGCGCCG | CAACCGCTGT | ACCGCGTCGA | CTGGCAGCCG | GTCGGCCAGG | GACCGAGGC | 11940 |
| CTCCGGCGCC | CAGGGCTGGA | CGGTGCTCGG | GCAGGCCGCG | GCCGAGACGG | TCGCGCAGCC | 12000 |
| CGCCGCCCAT | GCGGACCTCA | CCGCCCTGCG | TACGGCTGTG | GCCGCGGCGG | GAACACCCGT | 12060 |
| GCCCCGGCTG | GTGGTCGTGT | CGCCGGTGGA | CACCCGGCTG | GACGAGGGGC | CGGTGCTGGC | 12120 |
| GGACGCCGAG | GCTCGGGCCC | GTGCGGGTGA | CGGCTGGGAC | GACGATCCCC | TACGTGTCGC | 12180 |

```
CCTCGGGCGC GGCCTGACCC TGGTCCGGGA GTGGGTCGAG GACGAACGGT TGGCGGACTC    12240
CCGGCTCGTC GTCCTCACCC GTGGCGCGGT GGCGGCCGGT CCCGGCGATG TGCCGGACCT    12300
GACAGGTGCG GCCCTGTGGG GGCTGCTCCG CTCCGCGCAG TCGGAGTATC CGGACCGCTT    12360
CACCCTCATC GACGTGGACG ATTCCCCCGA GTCCGTGCG GCTCTGCCCC GGGCTCTGGG     12420
ATCGGCCGAG CGACAACTCG CCCTGCGGAC GGGCGACGTG CTGGCGCCGG CCCTGGTCCC    12480
GATGGCCACC CGGCCGGCGG AGACCACTCC AGCGACGGCG GTCGCCTCGG CGACAACACA    12540
GACACAGGTC ACCGCGCCCG CTCCCGACGA CCCGGCTGCG GATGCCGTGT CGACCCGGC     12600
GGGCACCGTA CTGATCACCG GCGGCACCGG CGCCCTGGGA CGGCGTGTCG CCTCGCACCT    12660
CGCGCGCCGG TACGGCGTAC GCCACATGCT TCTGGTCAGC AGGCGTGGAC CGGACGCCCC    12720
CGAGGCCGGT CCCCTGGAAC GGGAACTCGC CGGTCTCGGA GTCACCGCCA CCTTCCTGGC    12780
ATGCGACCTC ACCGACATCG AGGCCGTACG GAAGGCCGTC GCCGCGGTGC CGTCGGACCA    12840
CCCGCTGACC GGTGTGGTGC ACACCGCCGG CGTGCTGGAC GACGGCGCCC TGACCGGCCT    12900
GACCCGGCAA CGCCTCGACA CCGTGCTGCG GCCCAAGGCC GACGCCGTGC GGAACCTCCA    12960
CGAGGCGACC CTCGACCGGC CGCTGCGCGC GTTCGTCCTG TTCTCCGCCG CCGCCGGACT    13020
CCTGGGCCGC CCCGGGCAGG CCTCCTACGC CGCCGCCAAC GCGGTCCTCG ACGCGCTCGC    13080
GGGAGCCCGC CGCGCGGCCG GACTGCCCGC AGTGTCCCTG GCGTGGGGCC TGTGGGACGA    13140
GCAGACGGGC ATGGCAGGAG GCCTCGACGA GATGGCCCTG CGCGTGCTGC GCCGGGACGG    13200
CATCGCCGCG ATGCCTCCGG AGCAGGGGCT CGAACTGCTC GACCTGGCCC TGACCGGACA    13260
CCGGGACGGA CCCGCCGTCC TCGTCCCCCT CCTCCTCGAC GGCGCGGCCC TGCGCCGCAC    13320
GGCGAAGGAG CGCGGCGCGG CCACGATGTC CCCCTTGCTG CGCGCCCTGC TGCCCGCCGC    13380
CCTGCGCCGC AGCGGTGGAG CCGGCGCCCC CGCGGCGGCC GACCGGCACG GCAAGGAGGC    13440
GGACCCCGGT GCGGGACGCC TCGCAGGGAT GGTGGCACTC GAAGCGGCGG AGCGTTCCGC    13500
GGCCGTCCTT GAGCTGGTCA CCGAACAGGT CGCCGAGGTC CTCGGCTACG CGTCGGCCGC    13560
GGAGATCGAG CCCGAACGAC CCTTCCGGGA GATCGGCGTC GACTCCCTGG CGGCGGTGGA    13620
GCTGCGCAAC CGGCTCAGCC GTCTGGTCGG CCTGCGGTTG CCGACCACGC TGTCCTTCGA    13680
CCACCCCACG CCGAAGGACA TGGCGCAGCA CATCGACGGG CAGCTCCCCC GCCCGGCCGG    13740
AGCCTCGCCC GCGGACGCAG CGCTGGAAGG GATCGGCGAC CTCGCGCGGG CGGTCGCCCT    13800
GCTGGGCACG GGCGACGCCC GCCGGGCCGA GGTACGAGAG CAGCTCGTCG GACTGCTGGC    13860
CGCGCTCGAC CCACCTGGGC GGACGGGCAC CGCCGCACCC GGCGTCCCCT CCGGTGCCGA    13920
TGGCGCGGAA CCGACCGTGA CGGACCGGCT CGACGAGGCG ACCGACGACG AGATCTTCGC    13980
CTTCCTGGAC GAGCAGCTGT GACCACACCG TGGACCGACC GCATGCCGAG GAGTTGGTGG    14040
CAGCAATGAC CGCCGAGAAC GACAAGATCC GCAGCTACCT GAAGCGTGCC ACCGCCGAAC    14100
TGCACCGGAC CAAGTCCCGC CTGGCCGAGG TCGAGTCGGC GAGCCGCGAG CCGATCGCGA    14160
TCGTGGGCAT GGCGTGCCGT TACCCGGGCG GTGTGGCGTC GCCGGACGAC CTGTGGGACC    14220
TGGTGGCAGC CGGTACGGAC GCGGTCTCCG CGTTCCCCGT CGACCGTGGC TGGGACGTCG    14280
AGGGGCTGTA CGACCCCGAT CCGGAGGCGG TGGGGCGTAG TTACGTGCGG GAGGGCGGGT    14340
TCCTGCACTC GGCGGCCGAG TTCGACGCGG AGTTCTTCGG GATCTCGCCC CGTGAGGCGG    14400
CGGCGATGGA TCCGCAGCAG CGGTTGCTGC TGGAGACGTC GTGGGAGGCG CTGGAGCGGG    14460
CGGGGATCGT CCCCGCGTCG CTGCGCGGCA CCCGTACCGG CGTCTTCACC GGCGTCATGT    14520
ACGACGACTA CGGGTCGCGG TTCGACTCGG CTCCGCCGGA GTACGAGGGC TACCTCGTGA    14580
```

| | | | | | | |
|---|---|---|---|---|---|---|
| ACGGCAGCGC | CGGCAGCATC | GCGTCCGGTC | GGGTTGCCTA | TGCGTTGGGG | TTGGAGGGGC | 14640 |
| CGGCGCTGAC | GGTGGACACG | GCGTGTTCGT | CGTCGTTGGT | GGCGTTGCAT | CTGGCGGTGC | 14700 |
| AGTCGTTGCG | GCGGGGTGAG | TGTGATCTGG | CGTTGGCCGG | TGGGGTGACG | GTGATGGCGA | 14760 |
| CGCCGACGGT | GCTCGTGGAG | TTCTCGCGGC | AGCGGGGGCT | GGCGGCGGAC | GGGCGGTGCA | 14820 |
| AGGCGTTCGC | GGAGGGTGCG | GACGGGACGG | CGTGGGCCGA | GGGTGTGGGC | GTGCTGCTGG | 14880 |
| TGGAGCGGCT | CTCCGACGCC | CGCCGCAATG | GCCATCGGGT | GCTGGCGGTG | GTGCGGGGCA | 14940 |
| GTGCGGTCAA | TCAGGACGGT | GCGAGCAACG | GGCTGACGGC | GCCGAGTGGT | CCTGCGCAGC | 15000 |
| AGCGGGTGAT | CCGTGAGGCG | CTGGCCGACG | CGGGGCTGAC | GCCCGCCGAC | GTCGACGCGG | 15060 |
| TCGAGGCGCA | CGGCACCGGC | ACACCCCTGG | GCGACCCCAT | CGAGGCGGGT | GCGTTGCTGG | 15120 |
| CCACCTATGG | CAGTGAGCGC | CAGGGCCAAG | GTCCGTTGTG | GTTGGGGTCG | TTGAAGTCGA | 15180 |
| ACATCGGGCA | TGCGCAGGCG | GCTGCGGGTG | TGGGTGGCGT | GATCAAGGTG | GTGCAGGCGA | 15240 |
| TGCGGCATGG | GTCGTTGCCG | CGGACGCTGC | ATGTGGATGC | GCCGTCGTCG | AAGGTGGAGT | 15300 |
| GGGCTTCGGG | TGCGGTGGAG | CTGCTGACCG | AGACCCGGTC | GTGGCCGCGG | CGGGTGGAGC | 15360 |
| GGGTGCGGCG | GGCCGCGGTG | TCGGCGTTCG | GGGTGAGCGG | GACCAACGCC | CATGTGGTCC | 15420 |
| TGGAGGAAGC | GCCGGCGGAG | GCCGGGAGCG | AGCACGGGGA | CGGCCCTGAA | CCCGAGCGGC | 15480 |
| CCGACGCGGT | GACGGGTCCG | TTGTCGTGGG | TGCTTTCTGC | GCGGTCGGAG | GGGGCGTTGC | 15540 |
| GGGCGCAGGC | GGTGCGGTTG | CGTGAGTGTG | TGGAGCGGGT | GGGTGCGGAT | CCGCGGGATG | 15600 |
| TGGCGGGGTC | GTTGGTGGTG | TCGCGTGCGT | CGTTCGGTGA | GCGTGCGGTG | GTGGTGGGCC | 15660 |
| GGGGGCGTGA | GGAGTTGCTG | GCGGGTCTGG | ATGTGGTGGC | TGCCGGGGCT | CCTGTGGGTG | 15720 |
| TGTCCGGGGG | CGTGTCTTCG | GGGGCCGGTG | CTGTGGTGCG | GGGGAGTGCG | GTGCGGGGTC | 15780 |
| GTGGGGTGGG | GGTGTTGTTC | ACGGGTCAGG | GTGCGCAGTG | GGTTGGTATG | GGGCGTGGGT | 15840 |
| TGTATGCGGG | GGGTGGGGTG | TTTGCGGAGG | TGCTGGATGA | GGTGTTGTCG | GTGGTGGGGG | 15900 |
| AGGTGGGGGG | TTGGTCGTTG | CGGGATGTGA | TGTTCGGCGA | CGTCGACGTG | GACGCGGGTG | 15960 |
| CCGGGGCTGA | TGCGGGTGTC | GGTTCGGGTG | TTGGTGTGGG | TGGGTTGTTG | GGTCGGACGG | 16020 |
| AGTTTGCTCA | GCCTGCGTTG | TTTGCGTTGG | AGGTGGCGTT | GTTCCGGGCG | TTGGAGGCTC | 16080 |
| GGGGTGTGGA | GGTGTCGGTG | GTGTTGGGTC | ATTCGGTGGG | GGAGGTGGCT | GCTGCGTATG | 16140 |
| TGGCGGGGGT | GTTGTCGTTG | GGTGATGCGG | TGCGGTTGGT | GGTGGCGCGG | GGTGGGTTGA | 16200 |
| TGGGTGGGTT | GCCGGTGGGT | GGGGGGATGT | GGTCGGTGGG | GGCGTCGGAG | TCGGTGGTGC | 16260 |
| GGGGGGTTGT | TGAGGGGTTG | GGGGAGTGGG | TGTCGGTTGC | GGCGGTGAAT | GGGCCGCGGT | 16320 |
| CGGTGGTGTT | GTCGGGTGAT | GTGGGTGTGC | TGGAGTCGGT | GGTTGCCTCG | CTGATGGGGG | 16380 |
| ATGGGGTGGA | GTGCCGGCGG | TTGGATGTGT | CGCATGGGTT | TCATTCGGTG | TTGATGGAGC | 16440 |
| CGGTGTTGGG | GGAGTTCCGG | GGGGTTGTGG | AGTCGTTGGA | GTTCGGTCGG | GTGCGGCCGG | 16500 |
| GTGTGGTGGT | GGTGTCGAGT | GTGTCGGGTG | GGTGGTGGG | TTCGGGGGAG | TTGGGGGATC | 16560 |
| CGGGGTATTG | GGTGCGTCAT | GCGCGGGAGG | CGGTGCGTTT | CGCGGATGGG | GTGGGGGTGG | 16620 |
| TGCGTGGTCT | GGGTGTGGGG | ACGTTGGTGG | AGGTGGGTCC | GCATGGGGTG | CTGACGGGGA | 16680 |
| TGGCGGGTGA | GTGCCTGGGG | GCCGGTGATG | ATGTGGTGGT | GGTGCCGGCG | ATGCGGCGGG | 16740 |
| GCCGTGCGGA | GCGGGAGGTG | TTCGAGGCGG | CGCTGGCGAC | GGTGTTCACC | CGGGACGCCG | 16800 |
| GCCTGGACGC | CACGACACTC | CACACCGGGA | GCACCGGCCG | ACGCATCGAC | CTCCCCACCT | 16860 |
| ACCCCTTCCA | ACACGACCGC | TACTGGCTGG | CCGCCCCGTC | CCGGCCCAGG | ACGGACGGGC | 16920 |
| TGTCGGCGGC | GGGTCTGCGC | GAGGTGGAGC | ACCCCCTGCT | CACCGCCGCC | GTGGAACTGC | 16980 |

```
CCGGCACCGA CACCGAGGTG TGGACCGGCC GCATATCCGC TGCCGACCTG CCCTGGCTCG    17040
CCGACCACCT GGTGTGGGAC CGAGGCGTGG TGCCGGGGAC CGCGCTGCTG GAGACGGTGC    17100
TCCAGGTGGG AAGCCGGATC GGTCTGCCGC GCGTCGCCGA ACTGGTCCTG GAGACGCCGC    17160
TGACCTGGAC GTCGGACCGC CCGCTCCAGG TCCGGATCGT CGTGACCGCT GCCGCCACCG    17220
CCCCCGGGGG CGCGCGTGAG CTGACCCTCC ACTCGCGGCC CGAGCCCGTG GCCGCCTCCT    17280
CGTCCTCCCC GAGTCCCGCC TCTCCCCGGC ACCTCACGGC GCAGGAGAGC GACGACGACT    17340
GGACCCGGCA TGCCTCAGGG CTGCTCGCCC CGGCTGCCGG CCTCGCCGAC GACTTCGCCG    17400
AGCTCACCGG CGCCTGGCCC CCCGTCGGCG CCGAGCCCCT CGACCTCGCC GGTCAGTACC    17460
CGCTCTTCGC AGCCGCCGGA GTGCGCTACG AAGGCGCCTT CCGAGGGCTG CGCGCGGCAT    17520
GGCGTCGAGG CGACGAGGTC TTCGCCGACG TACGGCTGCC CGACGCGCAC GCGGTCGACG    17580
CTGATCGTTA CGGGGTGCAC CCCGCCCTGC TCGACGCGGT GCTCCACCCG ATCGCGTCGC    17640
TGGACCCGCT GGGCGACGGC GGGCACGGTC TGCTGCCGTT CTCCTGGACC GACGTACAGG    17700
GACACGGCGC CGGCGGACAC GCCCTCCGGG TACGGGTGGC GGCCGTCGAC GGCGGCGCGG    17760
TGTCGGTCAC CGCGGCCGAC CACGCGGGCA ACCGGTGTT ATCCGCCCGG TCCCTGGCAC    17820
TGCGTCGTAT CACCGCGGAC CGGCTTCCCG CCGCGCCCGT CGCCCCTCTC TACCGCGTGG    17880
ACTGGCTGCC GTTCCCGGGT CCGGTGCCCG TATCCGCGGG CGGCCGCTGG GCGGTCGTCG    17940
GACCCGAGGC CGAAGCCACG GCTGCCGGAC TGCGTGCGGT GGGCCTCGAC GTGCGTACCC    18000
ATGCGCTCCC CCTCGGAGAG CCCCTGCCTC CGCAGGCCGG TACCGACGCG GAGGTGATCA    18060
TCCTCGACCT GACCACCACC GCAGCCGGCC GTACGGCGTC GGACGGGGGG CGGCTCAGTC    18120
TCCTCGACGA GGTGCGTGCG ACGGTGCGCC GGACCCTCGA AGCCGTACAG GCCCGCCTCG    18180
CCGACACCGA AACGGCCCCC GACGTCGACG TCCGTACGGC CGCGCGCCCC CGCACAGCCG    18240
CCCGTACAAG CCCCCGCGTG GACACCCGCA CGGGAGCCCG CACCGCTGAC GGCCCCCGGC    18300
TCGTCGTCCT GACCCGGGGC GCGGCCGGAC CCGAGGGAGG CGCGGCCGAT CCCGCGGGTG    18360
CCGCTGTCTG GGGGCTCGTC CGGGTCGCCC AGGCCGAACA GCCCGGCCGC TTCACCCTGG    18420
TGGACGTCGA CGGCACCCAG GCGTCGCTGC GGGCCCTGCC CGGTCTGCTG GCCACGGATG    18480
CCGGCCAGTC GGCCGTGCGC GACGGACGTG TCACCGTCCC GCGCCTCGTC CCGGTGGCCG    18540
ACCCCGTCCC CCACGGCGGG GGCACGGCGG CCGACGGGAC GGGTGCCGGC GAGCCGTCCG    18600
CGACCCTGGA CCCCGAAGGC ACCGTGCTGA TCACCGGCGG CACCGGAGCA CTGGCCGCGG    18660
AAACCGCCCG GCACCTGGTC GACCGGCACA AGGTGCGCCA TCTCCTGCTG GTGGGCAGGC    18720
GCGGTCCCGA CGCACCCGGC GTCGATCGAC TGGTCGCCGA GTTGACCGAG TCGGGTGCCG    18780
AGGTCGCCGT ACGGGCCTGT GACGTCACGG ACCGCGACGC CCTGCGCCGC CTGCTCGACG    18840
CACTCCCCGA CGAACACCCG CTGACCTGCG TGGTGCACAC CGCCGGGGTG CTCGACGACG    18900
GCGTGCTCTC CGCCCAGACG GCCGAGCGGA TCGACACGGT GCTCCGGCCC AAGGCCGACG    18960
CCGCCGTCCA CCTGGACGAG CTGACCCGGG AGATCGGACG GGTGCCCCTG GTGCTGTACT    19020
CCTCGGTCTC GGCCACCCTG GGCAGCGCGG GGCAGGCCGG GTACGCGGCG GCCAACGCCT    19080
TCATGGACGC GCTGGCCGCC CGGCGGTGCG CCGCCGGGCA CCCCGCGCTG TCGCTCGGCT    19140
GGGGCTGGTG GTCCGGGGTG GGTCTCGCCA CCGGACTGGA CGGAGCGGAC GCGGCGCGGG    19200
TCAGGCGCTC GGGTCTCGCC CCGCTCGACG CCGGCGCCGC ACTGGACCTG CTCGACCGGG    19260
CGCTGACCCG GCCCGAGCCG GCCCTGCTGC CCGTGCGGCT CGACCTGCGC GCCGCGGCCG    19320
GTGCCACCGC TCTCCCGGAG GTCCTGCGTG ACCTGGCCGG CGTACCGGCG GACGCCCGCA    19380
```

```
GCACGCCCGG GGCCGCGGCG GGCACCGGGG ACGAGGACGG TGCCGTGCGC CCTGCCCCCG    19440
CCCCGGCCGA CGCCGCCGGG ACGCTGGCCG CGCGGCTCGC GGGACGTTCC GCACCCGAGC    19500
GTACGGCTCT CCTGCTCGAC CTGGTGCGGA CCGAGGTCGC GGCGGTGCTC GGACACGGCG    19560
ACCCCGCCGC GATCGGCGCC GCCCGCACCT TCAAGGACGC CGGATTCGAC TCCCTCACCG    19620
CTGTCGACCT CCGCAACCGG CTGAACACAC GCACCGGACT GCGGCTGCCC GCGACCCTCG    19680
TCTTCGACCA CCCCACACCG CTCGCCCTCG CCGAACTCCT GCTCGACGGG CTGGAGGCGG    19740
CCGGTCCAGC GGAACCGGCC GCTGAGGTCC CGGACGAAGC GGCCGGTGCC GAGACCCTGT    19800
CCGGCGTGAT CGACCGGCTG GAACGCAGCC TCGCCGCGAC CGACGACGGC GACGCCCGGG    19860
TCCGCGCGGC ACGGCGGCTG CGCGGCCTGC TGGACGCGCT CCCCGCCGGT CCCGGTGCCG    19920
CGTCCGGTCC GGATGCCGGA GAGCACGCCC CCGGTCGCGG CGACGTGGTG ATCGACCGGC    19980
TCAGGTCGGC CTCCGACGAC GACTTGTTCG ACCTGCTCGA CAGCGACTTC CAGTGAGCCG    20040
GACCGCGCCG CGCGCCGACC GCTGAACCGC TCTTCACCCA GACCCACGAG ACCACGCCTG    20100
AGGAGAACCG TGTCTGCGAC CAACGAGGAG AAGTTGCGGG AGTACCTGCG CGCGCGATG    20160
GCCGACCTGC ACAGCGCACG AGAGCGGTTG CGCGAGGTCG AGTCGGCGAG CCGTGAGCCG    20220
ATCGCGATCG TGGGCATGGC GTGCCGTTAC CCGGGCGGTG TGGCGTCGCC GGAGGAGCTG    20280
TGGGACCTGG TGGCCGCCGG TACGGACGCG ATCTCCCCGT TCCCCGTCGA CCGCGGCTGG    20340
GACGCCGAGG GTCTGTACGA CCCGGAGCCG GGGGTGCCGG GCAAGAGCTA CGTGCGCGAG    20400
GGCGGGTTCC TGCACTCGGC GGCCGAGTTC GACGCGGAGT TCTTCGGGAT CTCGCCGCGT    20460
GAGGCGGCGG CGATGGATCC GCAGCAGCGG TTGCTGCTGG AGACGTCGTG GGAGGCGCTG    20520
GAGCGGGCCG GGATCGTCCC CGCGTCGCTG CGCGGCACCC GTACCGGCGT CTTCACCGGC    20580
GTCATGTACC ACGACTACGG CAGCCACCAG GTCGGCACCG CCGCCGATCC CAGTGGACAG    20640
CTCGGCCTCG GCACCGCGGG GAGCGTCGCC TCGGGCCGGG TGGCGTACAC CCTCGGTCTA    20700
CAGGGGCCGG CCGTGACCAT GGACACGGCA TGCTCGTCCT CGCTGGTGGC GTTGCACCTG    20760
GCGGTGCAGT CGTTGCGGCG GGGCGAGTGC GATCTCGCGT TGGCCGGCGG GGCGACGGTC    20820
TTGGCGACGC CCACGGTGTT CGTGGAGTTC TCGCGGCAAC GGGGGCTGGC GGCGGACGGA    20880
CGGTGCAAGG CGTTCGCGGA GGGCGCCGAC GGCACGGCGT GGGCCGAGGG CGCCGGTGTG    20940
CTGCTGGTGG AGCGGCTCTC CGACGCCCGC CGCAACGGCC ATCGGGTGCT CGCGGTGGTG    21000
CGGGGCAGCG CGGTCAACCA GGACGGTGCC AGCAACGGCC TCACCGCACC CAGCGGGCCC    21060
GCCCAGCAGC GGGTGATCCG TGACGCGCTG GCCGACGCGG GGCTGACGCC CGCCGACGTG    21120
GACGCGGTCG AGGCGCACGG CACCGGCACA CCGCTCGGCG ACCCGATCGA GGCCGGCGCG    21180
CTGATGGCCA CCTACGGCAG TGAACGGGTG GGCGACCCGC TGTGGCTGGG TTCGCTGAAG    21240
TCGAACATCG GACACACCCA GGCCGCCGCC GGAGCCGCCG GCGTCATCAA GATGGTGCAG    21300
GCGTTACGGC AGTCCGAGCT GCCGCGCACC CTGCACGTCG ACGCGCCCTC GGCCAAGGTC    21360
GAATGGACG CGGGCGCCGT GCAACTGCTC ACCGGCGTCC GGCCATGGCC CCGGCGCGAG    21420
CACAGGCCCC GGCGGGCCGC GGTCTCCGCC TTCGGCGTCA GCGGCACCAA CGCCCACGTC    21480
ATCATCGAGG AACCGCCCGC GGCCGGTGAC ACCTCGCCCG CCGGCGACAC CCCTGAGCCG    21540
GGCGAGGCGA CCGCGTCCCC CTCCACCGCG GCCGGGCCGT CGTCCCCCTC CGCGGTGGCC    21600
GGGCCGCTGT CCCCCTCCTC CCCGGCCGTG GTCTGGCCCC TGTCCGCCGA GACCGCCCCC    21660
GCCCTGCGCG CCCAGGCCGC CGCCTGCGG GCGCACCTCG AACGCCTCCC CGGCACCTCG    21720
CCGACCGACA TCGGCCACGC CCTGGCCGCC GAACGCGCCG CCCTCACCCG ACGCGTCGTG    21780
```

```
CTGCTCGGCG  ACGACGGAGC  CCCGGTCGAC  GCACTCGCCG  CCCTCGCCGC  CGGCGAGACC    21840
ACCCCCGACG  CCGTCCACGG  CACCGCGGCG  GACATCCGCC  GGGTCGCCTT  CGTGTTCCCC    21900
GGCCAGGGTT  CCCAGTGGGC  CGGGATGGGC  GCCGAACTGC  TGGACACGGC  CCCGGCCTTC    21960
GCCGCCGAAC  TGGACCGCTG  CCAGGGCGCG  CTCTCCCCGT  ACGTGGACTG  GAACCTCGCG    22020
GACGTGCTGC  GCGGCGCGCC  CGCGGCGCCC  GGCCTCGACC  GGGTCGACGT  CGTCCAGCCG    22080
GCCACCTTCG  CCGTCATGGT  GGGACTCGCC  GCGCTGTGGC  GCTCCCTCGG  GGTCGAACCC    22140
GCCGCCGTCA  TCGGCCACTC  CCAGGGCGAG  ATCGCCGCGG  CCTGCGTGGC  GGGCGCGCTC    22200
TCCCTGGAGG  ACGCCGCCCG  GATCGTGGCC  CTGCGCTCCC  AGGTCATCGC  CCGCGAACTG    22260
GCCGGGCGGG  GCGGCATGGC  CTCGGTGGCC  CTGCCCGCGG  CGGAGGTCGA  GGCCCGCCTG    22320
GCCGGCGGCG  TCGAGATCGC  CGCCGTCAAC  GGCCCCGGCT  CGACCGTCGT  CTGCGGAGAG    22380
CCCGGCGCCC  TGGAGGCGTT  GCTCGTCACG  CTGGAGAGCG  AAGGCACCCG  GGTCCGCCGC    22440
ATCGACGTCG  ACTACGCGTC  CCACTCCCAC  TACGTCGAGA  GCATCCGGGC  GGAACTCGCC    22500
ACCGTCCTCG  GCCCCGTCCG  GCCGCGGAGG  GGCGACGTGC  CCTTCTACTC  CACCGTCGAG    22560
GCGGCGCTCC  TCGACACCGC  CACCCTGGAC  GCCGACTACT  GGTACCGCAA  CCTGCGCCTC    22620
CCGGTGCGCT  TCGAGCCGAC  CGTACGCGCC  ATGCTCGACG  ACGGCGTCGA  CGCGTTCGTG    22680
GAGTGCTCCG  CGCATCCCGT  CCTGACCGTC  GGCGTGCGCC  AGACCGTGGA  GAGCGCCGGC    22740
GGCGCGGTCC  CGGCCCTCGC  TTCGCTGCGC  CGCGACGAGG  GCGGGCTGCG  GCGCTTCCTC    22800
ACCTCCGCCG  CCGAGGCCCA  GGTCGTCGGC  GTCCCCGTGG  ACTGGGCGAC  GCTCCGCCCA    22860
GGCGCCGGCC  GGGTGGACCT  GCCGACCTAC  GCCTTCCAGC  GCGAACGCCA  CTGGGTCGGC    22920
CCCGCCCGGC  CCGACTCCGC  GGCGACGGCC  GCCACGACCG  GTGACGACGC  CCCGGAGCCC    22980
GGAGACCGGC  TCGGCTACCA  CGTCGCGTGG  AAGGGACTGC  GCTCCACCAC  CGGCGGCTGG    23040
CGCCCCGGCC  TGCGCCTGCT  GATCGTGCCC  ACCGGGGACC  AGTACACCGC  CCTCGCCGAC    23100
ACCCTGGAAC  AGGCGGTCGC  CTCCTTCGGC  GGAACGGTCC  GCCGCGTCGC  CTTCGACCCG    23160
GCACGCACCG  GACGCGCCGA  GCTGTTCGGC  CTGCTCGAGA  CGGAGATCAA  CGGCGACACC    23220
GCCGTCACCG  GCGTCGTCTC  GCTGCTCGGA  CTGTGCACCG  ACGGCAGGCC  GGACCACCCC    23280
GCCGTGCCCG  TCGCCGTCAC  CGCCACCCTC  GCCCTCGTCC  AGGCCCTGGC  CGACCTCGGC    23340
AGCACCGCAC  CGCTGTGGAC  CGTCACCTGC  GGCGCGGTCG  CCACCGCCCC  CGACGAACTG    23400
CCGTGCACCG  CCGGTGCCCA  GCTGTGGGGC  CTGGGCCGGG  TGGCCGCGCT  GGAGCTGCCC    23460
GAGGTGTGGG  GCGGCCTCAT  CGACCTTCCC  GCGCGGCCCG  ACGCCCGGGT  CCTGGACCGT    23520
CTCGCCGGCG  TCCTCGCCGA  ACCCGGCGGC  GAGGACCAGA  TCGCCGTACG  GATGGCGGGC    23580
GTCTTCGGCC  GCCGGGTCCT  GCGGAACCCG  GCCGACTCCC  GGCCCCGGC   CTGGCGCGCC    23640
CGGGGCACCG  TCCTCATCGC  CGGCGACCTC  ACGACGGTGC  CCGGCCGACT  GGTCCGGTCC    23700
CTCCTCGAGG  ACGGCGCGGA  CCGCGTGGTG  CTGGCCGGAC  CCGACGCCCC  CGCACAGGCC    23760
GCCGCCGCCG  GACTGACCGG  CGTCTCCCTC  GTCCCGTGC   GCTGCGACGT  CACCGACCGC    23820
GCCGCACTGG  CCGCGCTGCT  CGACGAGCAC  GCGCCCACCG  TCGCCGTGCA  CGCCCCGCCC    23880
CTGGTGCCCC  TGGCGCCGCT  GCGGGAGACG  GCACCGGCG   ACATCGCCGC  CGCCCTCGCC    23940
GCCAAGACCA  CGGCCGCCGG  CCACCTGGTC  GACCTGGCGC  CGGCCGCGGG  CCTCGACGCG    24000
CTGGTGCTGT  TCTCCTCGGT  CTCCGGAGTG  TGGGGCGGCG  CGGCCCAGGG  CGGCTACGCG    24060
GCCGCCAGCG  CGCACCTCGA  CGCGCTGGCC  GAACGCGCCC  GCGCCGCGGG  GGTGCCCGCG    24120
TTCTCCGTGG  CCTGGAGCCC  CTGGGCCGGA  GGCACGCCCG  CCGACGGTGC  CGAGGCGGAG    24180
```

```
TTCCTCAGCC  GGCGCGGGCT  GGCTCCCCTC  GACCCCGACC  AGGCGGTGCG  GACCCTGCGC    24240
CGCATGCTGG  AGCGCGGCAG  CGCCTGCGGT  GCGGTCGCCG  ACGTCGAGTG  GAGCCGGTTC    24300
GCCGCCTCCT  ACACCTGGGT  GCGTCCCGCC  GTACTCTTCG  ACGACATCCC  GGACGTGCAG    24360
CGGCTGCGCG  CGGCCGAACT  CGCCCCGAGC  ACCGGAGACT  CGACCACCTC  CGAACTCGTC    24420
CGCGAGCTGA  CCGCGCAGTC  CGGCCACAAG  CGGCACGCCA  CCCTGCTGCG  GCTGGTGCGC    24480
GCACACGCCG  CCGCCGTCCT  CGGACAGTCC  TCCGGCGACG  CGGTGAGCAG  CGCCCGCGCC    24540
TTCCGCGACC  TCGGCTTCGA  CTCGCTGACC  GCCCTCGAAC  TGCGCGACCG  GCTCAGCACC    24600
AGCACCGGGC  TCAAACTGCC  CACCTCCCTG  GTCTTCGACC  ACTCCAGCCC  GGCCGCGCTC    24660
GCCCGGCACC  TCGGTGAGGA  ACTCCTCGGC  CGGAACGACA  CCGCCGACCG  GCCGGCCCC    24720
GACACCCCGG  TACGGACGGA  CGAGCCCATC  GCCATCATCG  GCATGGCCTG  CCGGCTGCCC    24780
GGCGGGGTGC  AGTCCCCCGA  GGACCTGTGG  GACCTGCTGA  CCGGTGGGAC  CGACGCCATC    24840
ACCCCCTTCC  CGACCAACCG  GGGATGGGAC  AACGAGACCC  TCTACGACCC  CGACCCCGAC    24900
TCGCCCGGGC  ACCACACCTA  CGTGCGCGAG  GGCGGGTTCC  TGCACGACGC  GGCCGAGTTC    24960
GACCCCGGCT  TCTTCGGCAT  CAGCCCCCGC  GAGGCCCTGG  CCATGGACCC  GCAGCAGCGG    25020
CTGATCCTGG  AGACGTCCTG  GGAGTCCTTC  GAACGGGCCG  GCATCGACCC  GGTCGAACTG    25080
CGCGGCAGCC  GCACCGGGGT  CTTCGTCGGC  ACCAACGGAC  AGCACTACGT  GCCGCTCCTC    25140
CAGGACGGCG  ACGAGAACTT  CGACGGCTAC  ATCGCCACCG  GCAACTCCGC  CAGCGTGATG    25200
TCCGGCCGGC  TCTCCTACGT  CTTCGGACTG  GAGGGCCCCG  CCGTCACCGT  CGACACCGCC    25260
TGCTCGGCCT  CCCTGGCCGC  ACTGCACCTG  GCGGTGCAGT  CACTGCGCCG  CGGCGAATGC    25320
GACTACGCCC  TCGCCGGCGG  GGCCACGGTG  ATGTCCACCC  CCGAGATGCT  GGTGGAGTTC    25380
GCCCGTCAGC  GAGCGGTGTC  GCCGGACGGC  CGCAGCAAGG  CGTTCGCGGA  GGCGGCCGAC    25440
GGGGTCGGTC  TCGCCGAGGG  AGCCGGGATG  CTGCTCGTGG  AGCGGCTGTC  GGAGGCGCAG    25500
AAGAAGGGCC  ATCCGGTACT  GGCGGTGGTG  CGGGGCAGTG  CCGTCAACCA  GGACGGTGCC    25560
AGCAACGGCC  TCACCGCACC  CAGCGGGCCC  GCCCAGCAGC  GGGTGATACG  GGAGGCGCTG    25620
GCCGACGCGG  GGCTGACGCC  CGCCGACGTG  GACGCGGTCG  AGGCGCACGG  CACCGGCACG    25680
CCGCTCGGCG  ACCCCATCGA  GGCCGGCGCG  CTGCTCGCCA  CGTACGGCCG  GGACCGGCGC    25740
GACGGCCCGC  TGTGGCTGGG  TTCGCTGAAG  TCGAACATCG  GCACACCCA  GGCCGCCGCC    25800
GGCGTGGCCG  GGGTGATCAA  GATGGTGCTG  GCGCTGCGCC  ACGGCGAGCT  GCCGCGCACC    25860
CTGCACGCGT  CGACGGCGTC  GTCCAGGATC  GATTGGGACG  CGGGCGCCGT  GGAGTTGCTG    25920
GACGAGGCCA  GGCCCTGGCT  CCAGCGGGCC  GAGGGGCCGC  GCCGGGCGGG  CATCTCCTCG    25980
TTCGGCATCA  GCGGCACCAA  CGCGCACCTC  GTCATCGAGG  AGCCGCCGGA  GCCCACCGCG    26040
CCCGAACTGC  TCGCGCCCGA  ACCGGCCGCC  GACGGCGACG  TCTGGTCCGA  GGAGTGGTGG    26100
CACGAGGTGA  CCGTGCCCCT  GATGATGTCC  GCGCACAACG  AAGCCGCCCT  GCGCGACCAG    26160
GCGCGGCGCC  TGCGCGCCGA  CCTGCTCGCC  CACCCCGAGC  TGCACCCGGC  CGACGTCGGC    26220
TACACCCTCA  TCACCACCCG  CACCCGGTTC  GAGCAGCGGG  CCGCCGTCGT  CGGCGAGAAC    26280
TTCACGGAGC  TGATCGCGGC  CCTCGACGAC  CTCGTCGAAG  GCCGACCGCA  CCCGCTCGTG    26340
CTGCGGGGCA  CCGCCGGCAC  CTCCGACCAG  GTCGTGTTCG  TCTTCCCCGG  CCAGGGCTCG    26400
CAGTGGCCCG  AGATGGCCGA  CGGGCTGCTG  GCCCGCTCCA  GCGGCTCCGG  CTCCTTCCTG    26460
GAGACCGCCC  GCGCCTGCGA  CCTCGCGCTC  CGGCCCCACC  TCGGCTGGTC  CGTCCTGGAC    26520
GTACTGCGCC  GGGAACCCGG  CGCGCCCTCG  CTCGACCGGG  TCGACGTGGT  GCAGCCCGTG    26580
```

| | | | | | | |
|---|---|---|---|---|---|---|
| CTGTTCACCA | TGATGGTCTC | GCTCGCCGAG | ACGTGGCGTT | CGCTGGGCGT | CGAACCGGCC | 26640 |
| GCGGTCGTCG | GTCACTCCCA | GGGCGAGATC | GCCGCCGCCT | ACGTCGCCGG | CGCCCTGACG | 26700 |
| CTGGACGACG | CGGCGCGCAT | CGTCGCCCTG | CGCAGCCAGG | CGTGGCTGCG | GCTGGCCGGC | 26760 |
| AAGGGCGGCA | TGGTCGCCGT | GACCCTGTCC | GAACGCGACC | TGCGTCCCCG | CCTGGAGCCC | 26820 |
| TGGAGCGACC | GGCTCGCCGT | CGCCGCCGTC | AACGGCCCCG | AGACCTGCGC | CGTCTCCGGG | 26880 |
| GACCCGGACG | CCCTGGCGGA | GCTGGTCGCC | GAACTCGGTG | CGGAGGGCGT | GCACGCCCGC | 26940 |
| CCCATCCCCG | GCGTCGACAC | CGCCGGGCAC | TCGCCGCAGG | TCGACACGCT | GGAGGCCCAC | 27000 |
| CTGCGGAAGG | TGCTCGCGCC | CGTCGCGCCC | CGCACCTCCG | ACATCCCGTT | CTACTCGACG | 27060 |
| GTCACCGGAG | GACTGATCGA | CACCGCCGAG | CTGGACGCCG | ACTACTGGTA | CCGCAACATG | 27120 |
| CGCGAGCCGG | TGGAGTTCGA | GCAGGCCACC | CGCGCCCTGA | TCGCCGACGG | CCACGACGTG | 27180 |
| TTCCTGGAGT | CGAGCCCGCA | CCCCATGCTG | GCCGTCTCCC | TCCAGGAGAC | GATCAGCGAC | 27240 |
| GCCGGTTCCC | CGGCGGCCGT | CCTCGGCACC | CTGCGGCGCG | GCCAGGGCGG | CCCCCGCTGG | 27300 |
| CTGGGCGTCG | CCCTCTGCCG | CGCCTACACC | CACGGCCTGG | AGATCGACGC | CGAGGCCATC | 27360 |
| TTCGGCCCCG | ACTCACGCCA | GGTGGAACTG | CCCACGTACC | CCTTCCAGCG | CGAGCGCTAC | 27420 |
| TGGTACAGCC | CCGGCCACCG | CGGTGACGAC | CCCGCCTCCC | TCGGTCTGGA | CGCCGTCGAC | 27480 |
| CACCCGCTGC | TGGGCAGCGG | CGTCGAACTG | CCGGAGTCCG | GTGACCGGAT | GTACACCGCA | 27540 |
| CGGCTGGGCG | CCGACACCAC | CCCGTGGCTG | GCCGACCACG | CGCTGCTGGG | GTCGCCGCTG | 27600 |
| CTGCCCGGCG | CCGCCTTCGC | CGACCTGGCG | CTCTGGGCCG | GCCGCCAGGC | CGGCACCGGC | 27660 |
| CGCGTCGAGG | AGCTCACCCT | GGCCGCGCCC | CTGGTGCTGC | CCGGCTCCGG | GGGTGTCCGG | 27720 |
| CTGCGGCTGA | ACGTCGGCGC | CCCGGGCACC | GACGACGCCC | GCCGCTTCGC | CGTGCACGCC | 27780 |
| CGCGCCGAGG | GCGCCACGGA | CTGGACCCTG | CACGCCGAGG | GGCTGCTCAC | CGCGCAGGAC | 27840 |
| ACGGCCGACG | CGCCGGACGC | CTCGGCGGCC | ACCCCGCCCC | CCGGCGCCGA | ACAACTGGAC | 27900 |
| ATCGGCGACT | TCTACCAGCG | CTTCTCCGAA | CTCGGTTACG | GCTACGGCCC | GTTCTTCCGG | 27960 |
| GGACTGGTGA | GCGCCCACCG | CTGCGGCCCC | GACATCCACG | CGGAGGTCGC | GCTGCCCGTC | 28020 |
| CAGGCGCAGG | GCGACGCGGC | CCGCTTCGGC | ATCCATCCCG | CGCTGCTGGA | CGCGGCGCTG | 28080 |
| CAGACCATGA | GCCTCGGGGG | CTTCTTCCCC | GAGGACGGCC | GCGTCCGCAT | GCCGTTCGCC | 28140 |
| CTGCGCGGCG | TTCGGCTGTA | CCGCGCCGGA | GCCGACCGGC | TGCACGTGCG | CGTCTCGCCC | 28200 |
| GTCTCCGAGG | ACGCGGTCCG | CATCAGGTGC | GCCGACGGCG | AGGGACGGCC | GGTCGCCGAG | 28260 |
| ATCGAGTCCT | TCATCATGCG | GCCGGTCGAC | CCGGGACAGC | TCCTGGGCGG | CCGCCCGGTC | 28320 |
| GGCGCCGACG | CGCTCTTCCG | CATCGCCTGG | CGGGAACTCG | CCGCCGGCCC | GGGCACCCGT | 28380 |
| ACCGGCGACG | GCACCCCTCC | CCCGGTGCGC | TGGGTGCTGG | CGGGACCCGA | CGCGCTGGGC | 28440 |
| CTGGCCGAGG | CGGCCGACGC | CCACCTGCCC | GCCGTTCCCG | GCCCGGACGG | CGCACTGCCG | 28500 |
| TCCCCGACGG | GACGCCCGGC | GCCGGACGCC | GTCGTGTTCG | CGGTCCGTGC | CGGGACCGGC | 28560 |
| GACGTCGCCG | CCGACGCGCA | CACCGTGGCC | TGCCGGGTGC | TGGACCTCGT | CCAGCGCCGG | 28620 |
| CTCGCGGCCC | CGGAGGGCCC | GGACGGCGCC | CGCCTGGTGG | TGGCCACCCG | GGCGCGGTC | 28680 |
| GCCGTACGCG | ACGACGCCGA | GGTGGACGAC | CCGGCCGCGG | CCGCCGCGTG | GGGCCTGCTG | 28740 |
| CGCTCCGCGC | AGGCCGAGGA | GCCCGGCCGG | TTCCTGCTCG | TGGACCTGGA | CGACGACCCG | 28800 |
| GCGTCCGCCC | GGGCGCTGAC | CGACGCCCTC | GCCTCCGGCG | AACCGCAGAC | CGCGGTCCGG | 28860 |
| GCCGGGACGG | TGTACGTGCC | CCGGCTGGAG | CGGGCCGCCG | ACCGCACGGA | CGGGCCGCTC | 28920 |
| ACCCCGCCCG | ACGACGGTGC | CTGGCGGCTG | GGCCGGGGCA | CCGACCTCAC | CCTCGACGGC | 28980 |

| | | | | | | |
|---|---|---|---|---|---|---|
| CTCGCCCTGG | TGCCCGCCCC | GGACGCCGAG | GCGCCGCTGG | AGCCCGGCCA | GGTGCGCGTC | 29040 |
| GCCGTACGCG | CCGCGGGCGT | CAACTTCCGC | GACGCCCTCA | TCGCCCTCGG | CATGTACCCG | 29100 |
| GGCGAGGCGG | AGATGGGAAC | GGAGGGCGCC | GGCACCGTCG | TCGAGGTCGG | CCCCGGCGTC | 29160 |
| ACCGGTGTCG | CCGTCGGCGA | CCGCGTGCTC | GGCCTGTGGG | ACGGCGGCCT | GGGCCCGCTG | 29220 |
| TGCGTGGCCG | ACCACCGGCT | GCTCGCCCCC | GTCCCGGACG | GCTGGTCCTA | CGCCCAGGCC | 29280 |
| GCCTCGGTCC | CCGCGGTGTT | CCTCAGCGCC | TACTACGGTC | TGGTCACCCT | GGCCGGCCTC | 29340 |
| AGGCCGGGGG | AGCGGGTGCT | CGTGCACGCC | GCCGCCGGGG | GCGTCGGCAT | GGCCGCGGTG | 29400 |
| CAGATCGCCC | GCCACCTCGG | CGCGGAGGTG | CTGGCCACCG | CGAGCCCCGG | CAAGTGGGAC | 29460 |
| GCCCTGCGCG | CCATGGGCAT | CACCGACGAC | CACCTCGCCT | CCTCCCGCAC | CCTCGACTTC | 29520 |
| GCGACCGCCT | TCACCGGAGC | GGACGGCACG | TCCCGCGCGG | ACGTCGTCCT | GAACTCGCTC | 29580 |
| ACCAAGGAGT | TCGTGGACGC | CTCCCTCGGG | CTGCTCCGTC | CGGGCGGCCG | GTTCCTGGAG | 29640 |
| CTGGGCAAGA | CCGACGTCCG | GGACCCCGAG | CGGATCGCCG | CCGAACACCC | CGGGGTGCGC | 29700 |
| TACCGGGCGT | TCGACCTCAA | CGAGGCCGGA | CCCGACGCAC | TCGGCCGGCT | GCTGCGGGAA | 29760 |
| CTGATGGACC | TGTTCGCCGC | CGGCGTGCTG | CACCCGCTGC | CCGTCGTCAC | CCACGACGTG | 29820 |
| CGCCGGGCCG | CGGACGCCCT | GCGCACCATC | AGCCAGGCCC | GGCACACCGG | AAAGCTCGTC | 29880 |
| CTGACCATGC | CGCCCGCCTG | GCACCCGTAC | GGCACGGTCC | TGGTCACCGG | TGGCACCGGC | 29940 |
| GCCCTCGGCA | GCCGCATCGC | CCGCCACCTG | GCGAGCCGGC | ACGGCGTCCG | CCGGCTGCTG | 30000 |
| ATCGCCGCCC | GCCGGGGCCC | GGACGGCGAG | GGCGCCGCGG | AGCTGGTCGC | CGACCTCGCC | 30060 |
| GCCCTGGGCG | CGTCGGCCAC | CGTGGTCGCC | TGCGACGTCT | CCGACGCGGA | CGCCGTCCGC | 30120 |
| GGACTGCTCG | CCGGCATACC | GGCCGATCAC | CCGCTGACGG | CGGTGGTGCA | CAGCACCGGC | 30180 |
| GTCCTCGACG | ACGGCGTGCT | GCCCGGGCTC | ACCCCCGAGC | GGATGCGGCG | CGTGCTGCGG | 30240 |
| CCCAAGGTGG | AGGCCGCCGT | CCACCTGGAC | GAACTCACCC | GCGACCTCGA | CCTGTCGGCG | 30300 |
| TTCGTCCTCT | TCTCCTCCAG | CGCCGGTCTG | CTGGGCAGCC | CGGCCCAGGG | CAACTACGCG | 30360 |
| GCGGCCAACG | CCACCCTCGA | CGCCCTCGCC | GCCGGCGCC | GGTCCCTCGG | CCTCCCGTCG | 30420 |
| GTGTCACTCG | CCTGGGGTCT | GTGGTCCGAC | ACCAGCCGGA | TGGCACACGC | ACTGGACCAG | 30480 |
| GAGAGCCTCC | AGCGGCGCTT | CGCCCGCAGC | GGCTTCCCGC | CCCTGTCCGC | CACGCTGGGC | 30540 |
| GCCGCGCTGT | TCGACGCCGC | CCTGCGGGTC | GACGAGGCCG | TGCAGGTCCC | CATGCGGTTC | 30600 |
| GACCCGGCCG | CGCTGCGCGC | CACCGGAAGC | GTCCCCGCCC | TGCTGTCGGA | CCTCGTCGGG | 30660 |
| TCCGCCCCGG | CGACCGGGTC | CGCGGCCCCG | GCGTCCGGCC | CCCTTCCGGC | TCCGGACGCC | 30720 |
| GGGACCGTCG | GCGAGCCGCT | CGCCGAGCGG | TTGGCCGGAC | TCTCCGCCGA | GGAACGCCAC | 30780 |
| GACCGGCTGC | TCGGCCTGGT | CGGCGAACAC | GTGGCCGCGG | TACTGGGCCA | CGGCTCCGCC | 30840 |
| GCCGAGGTCC | GGCCCGACCG | GCCGTTCCGC | GAGGTCGGGT | TCGACTCGCT | CACGGCCGTG | 30900 |
| GAACTGCGCA | ACCGGATGGC | GGCGGTCACC | GGGGTCAGGC | TCCCCGCCAC | CCTGGTCTTC | 30960 |
| GACCACCCCA | CCCCCGCCGC | GCTGTCCTCG | CACCTCGACG | GCTGCTGGC | CCCGGCACAG | 31020 |
| CCGGTCACCA | CCACACCGCT | GCTGTCCGAA | CTGGACCGCA | TCGAGGAGGC | CCTGGCCGCC | 31080 |
| CTCACCCCCG | AGCACCTCGC | GGAGCTCGCC | CCCGCCCCCG | ACGACCGGGC | CGAGGTCGCC | 31140 |
| CTGCGCCTGG | ACGCCCTGGC | CGACCGCTGG | CGCGCCCTGC | ACGACGGCGC | GCCCGGCGCC | 31200 |
| GACGACGACA | TCACCGACGT | GCTGAGCAGC | GCCGACGACG | ACGAGATCTT | CGCGTTCATC | 31260 |
| GACGAGCGGT | ACGGCACGTC | GTGACCGCCG | GCCCGGAGCC | CCGCCCGTCA | TCGAAAGGAA | 31320 |
| GCACCACCAT | GGCGAACGAA | GAGAAGCTGC | GCGCCTACCT | CAAGCGCGTG | ACGGGTGAGC | 31380 |

```
TGCACCGGGC  CACCGAGCAG  CTGCGTGCCC  TGGACCGGCG  GGCCCACGAG  CCGATCGCGA   31440
TCGTCGGGGC  GGCCTGCCGA  CTCCCCGGCG  GCGTCGAGAG  TCCGGACGAC  CTGTGGGAGC   31500
TGCTGCACGC  CGGTGCCGAC  GCGGTCGGCC  CGGCCCCCGC  CGACCGCGGC  TGGGACGTGG   31560
AGGGAAGGTA  CTCGCCCGAC  CCCGACACGC  CCGGCACCTC  GTACTGCCGC  GAGGGCGGCT   31620
TCGTGCAGGG  GGCCGACCGG  TTCGACCCCG  CCCTCTTCGG  CATCTCGCCC  AACGAGGCGC   31680
TCACCATGGA  CCCCCAGCAG  CGGCTGCTGC  TGGAGACCTC  CTGGGAGGCG  CTGGAGCGAG   31740
CCGGTCTGGA  CCCCCAGTCC  CTGGCGGGCA  GCCGGACCGG  CGTGTTCGCC  GGGGCGTGGG   31800
AGAGCGGCTA  CCAGAAGGGC  GTCGAAGGGC  TCGAAGCCGA  TCTGGAGGCC  CAACTCCTGG   31860
CCGGCATCGT  CAGCTTCACC  GCCGGCCGCG  TCGCCTACGC  CCTGGGCCTG  GAGGGCCCGG   31920
CGCTGACGAT  CGACACGGCC  TGCTCCTCGT  CGCTGGTGGC  ACTGCACCTG  GCGGTGCAGT   31980
CACTGCGCCG  GGGCGAGTGC  GACCTCGCAC  TGGCGGGCGG  CGCCACGGTC  ATCGCCGACT   32040
TCGCGCTCTT  CACCCAGTTC  TCCCGGCAGC  GCGGGCTCGC  CCCCGACGGG  CGGTGCAAGG   32100
CCTTCGGTGA  GACGGCCGAC  GGCTTCGGCC  CCGCCGAGGG  CGCGGGGATG  CTGCTGGTCG   32160
AGCGGCTGTC  GGACGCCCGC  CGCAACGGGC  ACCCGGTGCT  GGCGGTGGTG  CGGGGCAGTG   32220
CCGTCAACCA  GGACGGTGCG  AGCAATGGGC  TGACGGCGCC  GAGTGGTCCT  GCGCAGCAGC   32280
GGGTGATCCG  TGAGGCGCTG  GCCGACGCGG  GGCTGACGCC  CGCCGACGTG  GACGCGGTCG   32340
AGGCGCACGG  CACCGGCACG  CCGCTCGGCG  ACCCCATCGA  GGCCGGCGCG  CTCATGGCGA   32400
CGTACGGGCA  CGAACGGACG  GGCGACCCGC  TGTGGCTGGG  TTCGCTGAAG  TCGAACATCG   32460
GGCACACCCA  GGCCGCCGCC  GGCGTGGCCG  GGGTGATCAA  GATGGTGCTG  GCGCTGCGCC   32520
ACGGTGAGCT  GCCGCGCACC  CTGCACGCGT  CGACGGCGTC  CTCCAGGATC  GAATGGGACG   32580
CGGGCGCCGT  GGAGTTGCTG  GACGAGGCCA  GGCCCTGGCC  CCGGCGTGCC  GAGGGGCCGC   32640
GCCGGGCGGG  CATCTCCTCG  TTCGGCATCA  GCGGCACCAA  CGCGCACCTC  GTCATCGAGG   32700
AGGAGCCGCC  CGCCCGGCCG  GAGCCCGAGG  AGGCCGCGCA  GCCGCCCGCC  CCGGCCACCA   32760
CCGTCCTCCC  GCTGTCGGCC  GCCGGCGCGC  GATCCCTGCG  CGAGCAGGCC  CGCAGGCTCG   32820
CCGCGCACCT  GGCCGGCCAC  GAGGAGATCA  CCGCCGCCGA  CGCCGCCCGC  TCCGCCGCCA   32880
CCACCCGTGC  CGCGCTCTCG  CACCGGGCCT  CGGTCCTGGC  CGACGACCGG  CGGGCGCTGA   32940
TCGACAGGCT  GACCGCGCTG  GCGGAGGACA  GGAAGGACCC  CGGCGTCACC  GTCGGCGAGG   33000
CGGGCAGCGG  CCGGCCCCCC  GTCTTCGTCT  TCCCGGGACA  GGGCTCCCAG  TGGACGGGCA   33060
TGGGCGCCGA  ACTCCTGGAC  AGGGCACCGG  TCTTCCGCGC  CAAGGCCGAG  GAGTGCGCGC   33120
GGGCCCTCGC  GGCCCACCTC  GACTGGTCGG  TGCTCGACGT  CCTGCGCGAC  GCGCCCGGCG   33180
CCCCGCCGAT  CGACCGCGCG  GACGTCGTCC  AGCCGACCCT  GTTCACCATG  ATGGTCTCCC   33240
TCGCGGCGCT  GTGGGAGTCC  CACGGTGTAC  GGCCCGCCGC  CGTGGTCGGC  CACTCCCAAG   33300
GCGAGATCGC  CGCCGCCCAC  GCGGCCGGTG  CCCTGTCCCT  CGACGACGCG  CCCGCGTGA   33360
TCGCCGAGCG  CAGCAGGCTC  TGGAAGCGGC  TGGCCGGAAA  CGGCGGCATG  CTCTCCGTGA   33420
TGGCCCCGGC  CGACCGGGTC  CGCGAACTGA  TGGAGCCCTG  GCGGAGCGG   ATGTCCGTGG   33480
CCGCCGTCAA  CGGCCCCGCC  TCGGTCACCG  TGGCCGGTGA  CGCGCGGGCG  CTGGAGGAGT   33540
TCGCGGCCG   GCTCTCCGCC  GCCGGGGTGC  TGCGCTGGCC  CCTCGCCGGC  GTCGACTTCG   33600
CCGGACACTC  ACCCCAGGTG  GAGCAGTTCC  GCGCCGAGCT  CCTCGACACG  CTGGGCACCG   33660
TCCGCCCGAC  CGCCGCCCGG  CTGCCCTTCT  TCTCCACCGT  GACCGCCGCG  GCGCACGAGC   33720
CCGAAGGCCT  GGACGCCGCG  TACTGGTACC  GGAACATGCG  CGAACCCGTG  GAGTTCGCGT   33780
```

-continued

| | | | | | | |
|---|---|---|---|---|---|---|
| CCACCCTGCG | GACGCTGCTG | CGCGAGGGCC | ACCGCACCTT | CGTCGAGATG | GGCCCGCACC | 33840 |
| CCCTGCTGGG | CGCCGCGATC | GACGAGGTCG | CCGAGGCCGA | GGGCGTGCAC | GCCACCGCCC | 33900 |
| TCGCCACCCT | CCACCGCGGC | TCCGGCGGCC | TGGACCGGTT | CCGCTCCTCG | GTGGGCGCCG | 33960 |
| CGTTCGCCCA | CGGAGTACGG | GTCGACTGGG | ACGCCCTCTT | CGAGGGCTCC | GGCGCCCGCC | 34020 |
| GGGTCCCGCT | GCCCACCTAC | GCCTTCAGCC | GGGACCGGTA | CTGGCTGCCC | ACCGCCATCG | 34080 |
| GCCGGCGCGC | CGTCGAGGCG | GCCCCCGTCG | ACGCGTCCGC | CCCCGGGCGC | TACCGCGTCA | 34140 |
| CCTGGACACC | CGTGGCATCC | GACGACTCCG | GCCGGCCCTC | CGGGCGCTGG | CTGCTGGTGC | 34200 |
| AGACCCCCGG | CACCGCGCCG | GACGAGGCGG | ACACCGCGGC | GTCGGCCCTC | GGTGCGGCCG | 34260 |
| GGGTGGTCGT | GGAGCGCTGC | CTGCTGGATC | CCACCGAGGC | CGCGCGCGTC | ACGCTCACCG | 34320 |
| AGCGACTGGC | CGAACTGGAC | GCGCAGCCGG | AGGGCCTGGC | CGGCGTGCTG | GTGCTGCCCG | 34380 |
| GCCGTCCGCA | GAGCACCGCA | CCGGCCGACG | CCTCCCCGCT | CGACCCGGGG | ACGGCCGCCG | 34440 |
| TCCTGCTCGT | GGTCCAGGCC | GTGCCGGACG | CCGCTCCGAA | GGCCCGGATC | TGGGTGGTGA | 34500 |
| CGCGGGGTGC | GGTGGCGGTG | GGGTCGGGTG | AGGTGCCGTG | TGCGGTGGGT | GCGCGGGTGT | 34560 |
| GGGGTCTGGG | GCGGGTGGCT | GCGTTGGAGG | TGCCGGTGCA | GTGGGGTGGG | TTGGTGGATG | 34620 |
| TGGCGGTGGG | GGCGGGTGTG | CGTGAGTGGC | GTCGTGTGGT | GGGTGTGGTT | GCGGGGGGTG | 34680 |
| GTGAGGATCA | GGTGGCGGTG | CGTGGTGGGG | GTGTGTTCGG | TCGTCGTCTG | GTGGGTGTGG | 34740 |
| GGGTGCGGGG | TGGTTCGGGG | GTGTGGCGTG | CGCGGGGGTG | TGTGGTGGTG | ACGGGTGGGT | 34800 |
| TGGGTGGTGT | GGGGGGTCAT | GTGGCGCGGT | GGTTGGCGCG | TTCGGGTGCG | GAGCATGTGG | 34860 |
| TGTTGGCGGG | GCGTCGGGGT | GGTGGGGTTG | TGGGGCGGT | GGAGTTGGAG | CGGGAGTTGG | 34920 |
| TGGGGTTGGG | GGCGAAGGTG | ACGTTCGTTT | CGTGTGATGT | GGGGGATCGG | GCGTCGATGG | 34980 |
| TGGGGTTGTT | GGGTGTGGTG | GAGGGGTTGG | GGGTGCCGTT | GCGTGGTGTG | TTTCATGCGG | 35040 |
| CGGGGGTGGC | TCAGGTGTCG | GGGTTGGGTG | AGGTGTCGTT | GGCGGAGGCG | GGTGGTGTGT | 35100 |
| TGGGGGGTAA | GGCGGTGGGG | GCTGAGTTGT | TGGACGAGTT | GACGGCGGGT | GTGGAGCTGG | 35160 |
| ATGCGTTCGT | GTTGTTCTCG | TCGGGTGCTG | GGGTGTGGGG | GAGTGGGGGG | CAGTCGGTGT | 35220 |
| ATGCGGCGGC | CAATGCGCAT | CTGGATGCGT | TGGCGGAGCG | TCGTCGTGCG | CAGGGGCGTC | 35280 |
| CCGCGACCTC | CGTCGCCTGG | GGCCTGTGGG | GCGGCGAGGG | CATGGGAGCG | GACGAAGGCG | 35340 |
| TCACGGAGTT | CTACGCCGAG | CGCGGCCTCG | CCCCCATGCG | GCCCGAGTCG | GGCATCGAGG | 35400 |
| CACTGCACAC | GGCACTGAAC | GAGGGCGACA | CCTGCGTCAC | GGTCGCCGAC | ATCGACTGGG | 35460 |
| AACACTTCGT | CACCGGGTTC | ACCGCCTACC | GGCCCAGCCC | GCTGATCTCC | GACATCCCCC | 35520 |
| AGGTCCGCGC | GTTGCGCACG | CCCGAACCCA | CCGTGGACGC | CTCGGACGGA | CTGCGCCGGC | 35580 |
| GCGTCGACGC | CGCCCTCACC | CCGCGCGAGC | GCACCAAGGT | CCTGGTCGAC | CTGGTCCGCA | 35640 |
| CGGTGGCGGC | GGAGGTCCTC | GGTCACGACG | GGATCGGCGG | CATCGGCCAC | GACGTGGCCT | 35700 |
| TCCGGGACCT | CGGCTTCGAC | TCGCTGGCCG | CGGTGCGGAT | GCGCGGCCGG | CTGGCCGAGG | 35760 |
| CGACCGGACT | CGTACTGCCC | GCGACGGTCA | TCTTCGACCA | CCCCACCGTG | GACCGGCTCG | 35820 |
| GCGGCGCGCT | GCTGGAGCGG | CTGTCCGCGG | ACGAACCCGC | GCCGGCGGG | GCGCCGGAGC | 35880 |
| CCGCCGGGGG | GAGGCCCGCG | ACCCCACCGC | CCGCACCGGA | GCCGGCCGTC | CACGACGCCG | 35940 |
| ACATCGACGA | ACTCGACGCG | GACGCCCTGA | TCCGGCTGGC | CACGGGAACC | GCCGGACCGG | 36000 |
| CCGACGGCAC | GCCGGCCGAC | GGCGGGCCCG | ACGCGGCGGC | GACCGCCCCC | GACGGAGCAC | 36060 |
| CGGAGCAGTA | GCGCGCCCTC | ACCGGCGCGC | CGACCGGCGG | AGCGCCGTAC | CGCCGACGCC | 36120 |
| CCCCACAGCC | AGCGAGCAGA | CGAGGAAGCC | GAAGATGTCA | CCGTCCATGG | ACGAAGTGCT | 36180 |

| | | | | | | |
|---|---|---|---|---|---|---|
| GGGTGCGCTG | CGCACCTCCG | TCAAGGAGAC | CGAGCGGCTG | CGCCGGCACA | ACCGGGAGCT | 36240 |
| CCTGGCCGGC | GCGCACGAGC | CGGTCGCCAT | CGTGGGCATG | GCCTGCCGCT | ACCCCGGTGG | 36300 |
| CGTGAGCACC | CCGGACGACC | TGTGGGAGCT | CGCCGCGGAC | GGCGTCGACG | CGATCACCCC | 36360 |
| CTTCCCGGCC | GACCGGGGCT | GGGACGAGGA | CGCCGTCTAC | TCGCCCGACC | CCGACACCCC | 36420 |
| CGGCACCACC | TACTGCCGTG | AGGGCGGCTT | CCTCACCGGC | GCCGGGGACT | TCGACGCGGC | 36480 |
| CTTCTTCGGC | ATCTCGCCGA | ACGAGGCGCT | GGTGATGGAC | CCGCAGCAGC | GGCTGTTGCT | 36540 |
| GGAGACGTCG | TGGGAGACGT | TGGAGCGGGC | CGGCATCGTC | CCCGCGTCGC | TGCGCGGCAG | 36600 |
| CCGTACCGGT | GTCTTCGTCG | GAGCCGCGCA | CACGGGATAC | GTCACCGACA | CCGCGCGAGC | 36660 |
| GCCCGAGGGC | ACCGAGGGCT | ATCTGCTGAC | GGGCAACGCC | GATGCCGTCA | TGTCCGGCCG | 36720 |
| GATCGCCTAC | TCCCTGGGTC | TGGAGGGGCC | GGCGCTGACG | ATCGGGACGG | CCTGCTCGTC | 36780 |
| GTCGTTGGTG | GCGTTGCATC | TGGCGGTGCA | GTCGTTGCGG | CGGGGCGAGT | GCGACCTGGC | 36840 |
| GTTGGCCGGC | GGCGTCGCGG | TCATGCCCGA | CCCGACGGTG | TTCGTGGAGT | TCTCGCGGCA | 36900 |
| GCGGGGGCTG | GCGGTGGACG | GGCGGTGCAA | GGCGTTCGCG | GAGGGTGCGG | ACGGGACGGC | 36960 |
| GTGGGCGGAG | GGAGTGGGTG | TGCTGCTGGT | GGAGCGGCTT | TCCGACGCGC | GCCGCAATGG | 37020 |
| CCATCGGGTG | CTGGCGGTGG | TGCGGGGCAG | TGCGGTCAAT | CAGGACGGGG | CGAGCAATGG | 37080 |
| GCTGACGGCG | CCGAGTGGTC | CTGCGCAGCA | GCGGGTGATC | CGTGAGGCGC | TGGCTGATGC | 37140 |
| GGGGCTGACG | CCCGCCGACG | TGGATGTGGT | GGAGGCGCAC | GGTACGGGGA | CGGCGTTGGG | 37200 |
| TGATCCGATC | GAGGCGGGTG | CGTTGCTGGC | CACGTACGGG | CGGGAGCGGG | TCGGTGATCC | 37260 |
| TTTGTGGTTG | GGGTCGTTGA | AGTCGAACAT | CGGGCATGCG | CAGGCGGCTG | CGGGTGTGGG | 37320 |
| TGGTGTGATC | AAGGTGGTGC | AGGCGATGCG | GCATGGGTCG | TTGCCGCGGA | CGCTGCATGT | 37380 |
| GGATGCGCCG | TCGTCGAAGG | TGGAGTGGGC | TTCGGGTGCG | GTGGAGCTGC | TGACCGAGGG | 37440 |
| CCGGTCGTGG | CCGCGGCGGG | TGGAGCGGGT | GCGGCGGGCC | GCGGTGTCGG | CGTTCGGGGT | 37500 |
| GAGCGGGACC | AACGCCCATG | TGGTCCTGGA | GGAAGCACCG | GTCGAGGCCG | GGAGCGAGCA | 37560 |
| CGGGGACGGC | CCCGGACCCG | ACCGGCCCGA | CGCCGTGACG | GGTCCGCTCC | CCTGGGTGCT | 37620 |
| CTCGGCACGC | TCGCGGGAGG | CGCTGCGCGG | CCAGGCCGGA | CGACTCGCCG | CTCTCGCCCG | 37680 |
| CCAGGGGCGC | ACGGAGGGCA | CCGGCGGCGG | CAGCGGACTC | GTCGTCCCCG | CGGCCGACAT | 37740 |
| CGGATACTCC | CTGGCCACCA | CCAGGGAGAC | CCTGGAGCAC | CGGGCGGTGG | CGCTGGTGCA | 37800 |
| GGAGAACCGG | ACGGCCGGGG | AGGACCTCGC | CGCGCTGGCC | GCCGGCCGCA | CACCGGAGAG | 37860 |
| CGTGGTCACG | GGTGTCGCGC | GACGTGGCCG | CGGGATCGCC | TTCCTCTGCT | CGGGGCAGGG | 37920 |
| CGCCCAGCGG | CTCGGCGCCG | GTCGGGAGCT | CCGCGGCAGG | TTCCCCGTCT | TCGCCGACGC | 37980 |
| CCTCGACGAG | ATCGCGGCGG | AGTTCGACGC | CCACCTCGAA | CGCCCTCTCC | TGTCGGTGAT | 38040 |
| GTTCGCCGAG | CCCGCCACGC | CGGACGCCGC | ACTCCTCGAC | CGCACCGACT | ACACCCAGCC | 38100 |
| GGCCCTCTTC | GCGGTGGAGA | CCGCGCTCTT | CCGGCTCCTG | GAGAGCTGGG | GCCTGGTCCC | 38160 |
| GGACGTCCTC | GTGGGCCACT | CGATCGGCGG | TCTGGTGGCG | GCTCACGTGG | CGGGCGTCTT | 38220 |
| CTCTGCGGCC | GACGCGGCCC | GGCTGGTCTC | CGCACGCGGC | CGGCTCATGC | GGGCCCTGCC | 38280 |
| CGAGGGCGGC | GCGATGGCGG | CCGTGCAGGC | CACCGAGCGG | GAGGCCGCCG | CGCTGGAGCC | 38340 |
| CGTCGCCGCC | GGCGGCGCGG | TGGTCGCCGC | GGTCAACGGC | CCGCAGGCCC | TCGTGCTCTC | 38400 |
| CGGGGACGAG | GCGGCCGTAC | TGGCGGCGGC | CGGTGAACTG | GCCGCCCGCG | ACGCCGCAC | 38460 |
| CAAGCGCCTG | AGGGTGAGCC | ACGCCTTCCA | CTCACCCCGT | ATGGACGCCA | TGCTCGCCGA | 38520 |
| CTTCCGCGCG | GTGGCGGACA | CGGTCGACTA | CCACGCCCCC | CGGCTGCCGG | TCGTCTCCGA | 38580 |

| | | | | | | |
|---|---|---|---|---|---|---|
| AGTGACCGGC | GACCTCGCCG | ACGCCGCCCA | GCTGACCGAC | CCCGGCTACT | GGACCCGCCA | 38640 |
| GGTGCGGCAG | CCGGTGCGCT | TCGCCGACGC | CGTGCGCACC | GCGAGCGCCC | GGGACGCCGC | 38700 |
| GACCTTCATC | GAGCTCGGGC | CCGACGCCGT | CCTGTGCGGC | ATGGCGGAGG | AGTCCCTGGC | 38760 |
| CGCGGAGGCC | GACGTCGTGT | TCGCCCCGGC | ACTGCGCCGC | GGGCGCCCGG | AGGGCGACAC | 38820 |
| CGTGCTCCGG | GCCGCCGCGA | GCGCGTACGT | CCGCGGCGCG | GGCCTCGACT | GGGCCGCGCT | 38880 |
| CTACGGCGGC | ACGGGAGCCC | GCCGCACCGA | CCTGCCCACC | TACGCCTTCC | AGCACAGCCG | 38940 |
| CTACTGGCTC | GCCCCCGCCT | CGGCCGCGGT | CGCCCCCGCG | ACGGCCGCCC | CCTCCGTCCG | 39000 |
| ATCCGTGCCG | GAAGCCGAGC | AGGACGGGGC | GCTGTGGGCC | GCCGTGCACG | CCGGTGACGT | 39060 |
| CGCCTCGGCC | GCGGCGCGAC | TGGGCGCCGA | CGACGCCGGT | ATCGAACACG | AACTGCGCGC | 39120 |
| GGTCCTGCCG | CACCTGGCCG | CCTGGCACGA | CCGCGACCGC | GCGACCGCGC | GGACCGCGGG | 39180 |
| CCTGCACTAC | CGCGTCACCT | GGCAGGCGAT | CGAGGCAGAC | GCTGTCAGGT | TCAGCCCCTC | 39240 |
| GGATCGCTGG | CTGATGGTCG | AGCATGGGCA | GCACACGGAA | TGCGCGGACG | CCGCGGAACG | 39300 |
| GGCGCTGCGC | GCGGCCGGCG | CGGAGGTCAC | CCGCCTGGTG | TGGCCGCTGG | AGCAGCACAC | 39360 |
| CGGATCACCG | CGGACGGAGA | CCCCGGACCG | CGGCACCCTG | GCGGCCCGGC | TGGCCGAGCT | 39420 |
| CGCACGGAGC | CCGGAGGGCC | TGGCCGGCGT | GCTGCTGCTC | CCCGACTCGG | GCGGTGCCGC | 39480 |
| GGTCGCCGGG | CACCCCGGGC | TGGACCAGGG | AACGGCGGCG | GTGCTGCTGA | CGATCCAGGC | 39540 |
| ACTGACCGAC | GCCGCGGTGC | GGGCACCGCT | GTGGGTGGTG | ACGCGGGGTG | CGGTGGCGGT | 39600 |
| GGGGTCGGGT | GAGGTGCCGT | GTGCGGTGGG | TGCGCGGGTG | TGGGGTCTGG | GGCGGGTGGC | 39660 |
| TGCGTTGGAG | GTGCCGGTGC | AGTGGGGTGG | GTTGGTGGAT | GTGGCGGTGG | GGGCGGGTGT | 39720 |
| GCGTGAGTGG | CGTCGTGTGG | TGGGTGTGGT | TGCGGGGGGT | GGTGAGGATC | AGGTGGCGGT | 39780 |
| GCGTGGTGGG | GGTGTGTTCG | GTCGTCGTCT | GGTGGGTGTG | GGGGTGCGGG | GTGGTTCGGG | 39840 |
| GGTGTGGCGT | GCGCGGGGGT | GTGTGGTGGT | GACGGGTGGG | TTGGGTGGTG | TGGGGGGTCA | 39900 |
| TGTGGCGCGG | TGGTTGGCGC | GTTCGGGTGC | GGAGCATGTG | GTGTTGGCGG | GGCGTCGGGG | 39960 |
| TGGTGGGGTT | GTGGGGGCGG | TGGAGTTGGA | GCGGGAGTTG | GTGGGGTTGG | GGGCGAAGGT | 40020 |
| GACGTTCGTT | TCGTGTGATG | TGGGGGATCG | GGCGTCGGTG | GTGGGGTTGT | GGGTGTGGT | 40080 |
| GGAGGGGTTG | GGGGTGCCGT | TGCGTGGTGT | GTTTCATGCG | GCGGGGGTGG | CTCAGGTGTC | 40140 |
| GGGGTTGGGT | GAGGTGTCGT | TGGCGGAGGC | GGGTGGTGTG | TTGGGGGGTA | AGGCGGTGGG | 40200 |
| GGCTGAGTTG | TTGGACGAGT | TGACGGCGGG | TGTGGAGCTG | GATGCGTTCG | TGTTGTTCTC | 40260 |
| GTCGGGTGCT | GGGGTGTGGG | GGAGTGGGGG | GCAGTCGGTG | TATGCGGCGG | CCAATGCGCA | 40320 |
| TCTGGATGCG | TTGGCGGAGC | GTCGTCGTGC | GCAGGGGCGT | CCCGCGACCT | CCGTCGCCTG | 40380 |
| GGGCCCGTGG | GACGGCGACG | GCATGGGCGA | GATGGCGCCC | GAGGGCTACT | TCGCCCGCCA | 40440 |
| CGGCGTGGCC | CCGCTCCACC | CCGAGACGGC | GCTCACCGCC | CTGCACCAGG | CCATCGACGG | 40500 |
| CGGCGAAGCC | ACGGTCACCG | TGGCGGACAT | CGACTGGGAA | CGGTTCGCCC | CCGGCTTCAC | 40560 |
| CGCCTTCCGT | CCCAGCCCCC | TGATCGCCGG | CATCCCCGCG | GCCCGTACGG | CGCCCGCCGC | 40620 |
| CGGCCGGCCC | GCCGAGGACA | CCCCCACCGC | CCCCGGCCTC | CTGCGGGCGC | GGCCCGAGGA | 40680 |
| CCGGCCGCGG | CTCGCCCTGG | ACCTGGTGCT | CCGCCACGTC | GCGGCGGTCC | TCGGCCACTC | 40740 |
| CGAGGACGCC | CGGGTCGACG | CCCGGGCCCC | CTTCCGGGAC | CTCGGCTTCG | ACTCGCTCGC | 40800 |
| CGCGGTGCGG | CTGCGCCGCC | GGCTGGCCGA | GGACACCGGG | CTCGACCTGC | CCGGCACCCT | 40860 |
| CGTCTTCGAC | CACGAGGACC | CCACCGCGCT | GGCCCACCAC | CTGGCCGGCC | TCGCCGACGC | 40920 |
| GGGGACCCCC | GGCCCCCAGG | AGGGCACGGC | TCGGGCCGAG | AGCGGGCTGT | TCGCCTCCTT | 40980 |

```
CCGCGCCGCC  GTCGAACAGC  GCAGGTCGAG  CGAGGTCGTG  GAGCTGATGG  CCGACCTGGC    41040
GGCGTTCCGG  CCCGCCTACT  CCCGGCAGCA  CCCCGGCTCC  GGCCGCCCCG  CGCCCGTACC    41100
CCTCGCGACC  GGACCGGCGA  CGCGTCCAC   GCTGTACTGC  TGCGCCGGCA  CCGCGGTCGG    41160
CTCCGGGCCC  GCCGAGTACG  TCCCGTTCGC  CGAAGGACTG  CGCGGCGTCC  GGGAGACGGT    41220
CGCCCTTCCC  CTGTCCGGCT  TCGGCGACCC  CGCGGAACCG  ATGCCCGCAT  CGCTCGACGC    41280
GCTGATCGAG  GTCCAGGCCG  ACGTCCTCCT  GGAGCACACC  GCGGGCAAGC  CCTTCGCCCT    41340
CGCCGGCCAC  TCCGCCGGCG  CGAACATCGC  CCACGCCCTG  GCCGCCCGGC  TGGAGGAACG    41400
CGGCTCGGGC  CCCGCAGCCG  TCGTACTGAT  GGACGTCTAC  CGTCCCGAGG  ACCCCGGTGC    41460
GATGGGCGAG  TGGCGCGACG  ACCTGCTCAG  CTGGGCGCTC  GAACGCAGCA  CGGTGCCCCT    41520
GGAGGACCAC  CGGCTCACCG  CCATGGCCGG  CTATCAGCGG  CTGGTGCTCG  GAACCCGGCT    41580
CACCGCCCTC  GAAGCCCCCG  TCCTGCTGGC  CCGGGCGTCC  GAACCCCTGT  GCGCGTGGCC    41640
GCCCGCGGGC  GGGGCGCGGG  GCGACTGGCG  GTCCCAGGTC  CCGTTCGCAC  GGACCGTCGC    41700
CGACGTGCCC  GGCAACCACT  TCACCATGCT  CACCGAACAC  GCCCGGCACA  CCGCGTCCCT    41760
GGTGCACGAA  TGGCTGGACA  GCCTCCCGCA  CCAGCCCGGT  CCCGCCCCGC  TCACCGGAGG    41820
GAAACACTGA  TGTACGCCGA  CGACATCGCG  GCCGTCTACG  ACCTGGTCCA  CGAGGGGAAG    41880
GGGAAGGACT  ACCGGCAGGA  GGCCGAGGAG  ATCGCCGCAC  TCGTGCGCGT  CCACCGGCCG    41940
GGCGCCCGGA  CCCTGCTCGA  CGTGGCCTGC  GGCACCGGCC  AGCACCTGCA  CCACCTGGAC    42000
GGCCTCTTCG  ACCACGTCGA  GGGCCTGGAA  CTCTCCGCCG  ACATGCTGGC  CCTCGCGACC    42060
GGCCGGAACC  CCGGTGTCAC  CTTCCACCAA  GGGGACATGC  GCTCGTTCTC  CCTGGGACGC    42120
CGGTTCGACG  CGGTGACCTG  CATGTTCAGC  TCCATAGGCC  ACCTGCGGAC  CACCGACGAA    42180
CTCGACAGCA  CGCTGCGGGC  CTTCACCGAC  CACCTCGAAC  CGTCCGGCGT  CATCGTCGTC    42240
GAACCCTGGT  GGTTCCCCGA  GTCCTTCACC  CCCGGTTACG  TCGGCGCCAG  CATCACGGAG    42300
GCGGGCGAGC  GCACCGTCTG  CCGGGTCTCG  CACTCCGTAC  GGGAGGGGAA  CGCCACCCGC    42360
ATCGAGGTGC  ACTACCTCCT  CGCCGGACCC  GGCGGCGTCC  GTCACCTGAC  CGAGGACCAC    42420
ACCATCACCC  TGTTCCCGCG  CGCCGACTAC  GAGGCGGCCT  TCGAGCGCGC  CGGCTGCGAC    42480
GTGGTCTACC  AGGAAGGCGG  CCCGTCCGGT  CGCGGGCTGT  TCATCGGCAC  CCGCCGCTGA    42540
CCCGGTGCCG  ACGCGGACCG  CCGCGGCCCG  GAGGCGGGTT  GCCCCGACCC  ACCCGGCACA    42600
CCCGGGTCCC  CCGATCGTGC  GAGCGCCCCC  ATCGACCCGA  GAAGAAAGGC  AGGGCAGCCA    42660
TGCCCACCCT  TGCCACGGAA  ACGGCCCCCG  CGAGCACGAG  CACGAGCGCG  GCACGAGCA    42720
CGGGCGTCCG  TGCGCTCGGC  CGTCGGCTCC  AGCTGACCCG  GCCGCACAC   TGGTGCGCCG    42780
GCAACCAGGG  CGACCCGTAC  GCGCTGATCC  TGCGCGCCGT  CGCCGACCCC  GAGCCGTTCG    42840
AACGGGAGAT  CCGGGCCCGC  GGACCGTGGT  TCCGCAGCGA  ACAGCTGGAC  GCCTGGGTGA    42900
CCGCGGACCC  CGAGGTGGCG  GCGGCCGTCC  TGGCCGACCC  GCGCTTCGGC  ACGCTGGACC    42960
GGGCCGGACG  CCGCCCGGAC  GAGGAACTGC  TGCCCCTCGC  CGAGGCGTTC  CCCCACCACG    43020
AACGCGCGGA  GCTCGTACGC  CTGCGGGCGC  TGGCCGCCCC  GGTGCTCAGC  CGGTACGCCC    43080
CGGCCCAGGC  GCCCTGCGCG  CGCGCACCA   CCGCCCGCAG  AGTGCTCGGC  CGCCTGCTGC    43140
CCACCGGTGA  CGCCGGGTTC  GACCTTGTCG  GCGAGGTCGC  CCGGCCCTAC  GCCGTCGAGC    43200
TGATGCTCAG  GCTCCTCGGA  GTGCCGGGCC  GCGACCGCGC  CACCGCCGCG  CGGGCACTCG    43260
CCGCCTGCGG  CCCCCAGCTC  GACGCCCGGA  TGGCCCCGCA  ACTGCTGACC  GTGGCCCGGG    43320
AGTCCGCCGA  CGCCGTCCGC  ACACTGGCCG  ACCTGGTCCC  CGAGCTCGTC  GCGGAGAAGT    43380
```

```
CCCGGGGCCT CGGGAACGCC GAGCCCCGGC CCGACGACGT GCTCGCCCTC CTCCTGCACG     43440
ACGGCGTCGC CCCCGGCGAC GTCGAGCGCA TCGCGCTGCT CCTCGCGGTC GGCGCACCCG     43500
AACCCGTCGT CACCGCCGTC GCGCACACGG TCCACCGGCT GCTCGGCCGG CCGGGGGAGT     43560
GGGAGAGGGC CCGCCGGACG CCGGCCGCGG CGAACGCCGT CGACCAGGTG CTGCGCGAGC     43620
GCCCCCCGGC CCGGCTGGAG AACCGGGTCG CGCACACCGG CCTCGAACTC GGCGGCCGCC     43680
GGATCACCGC CGACGAGCAC GTCGTGGTGC TGGCCGCCGC CGGACGGGAG ATCCCCGGGC     43740
CGGAGCCGCT CGGGGGCGCC GACGGACCGC ACCTGGCGCT CGCCCTCCCG CTGATCCGCC     43800
TGGCCGCCAC CACCGCGGTC CAGGTCACGG CCGGCCGCCT GCCCGGCCTG CGGGCCGAGG     43860
GACCGCCCCT GACCCGGCCG CGGTCACCGG TCCTGGGCGC CTGCGCCCGC CTCCGGGTCC     43920
ACCCGGGATG ACCCCGCCGT CCGTACGCCC CCTCCCAGAC CGGAGCCGCT GTGCGCGTCC     43980
TGCTGACATC CCTCGCCCAC AACACCCACT ACTACAGTCT GGTGCCCCTC GCCTGGGCGC     44040
TGCGCGCCGC CGGGCACGAG GTACGGGTGG CGAGCCCGCC CTCCCTCACC GACGTCATCA     44100
CCTCCACCGG TCTGACCGCC GTACCGGTGG GCGACGACCG ACCGGCCGCG GAGCTGCTCG     44160
CCGAGATGGG CAGAGACCTC GTCCCCTACC AGAGGGGCTT CGAGTTCGGT GAGGTGGAGA     44220
GCGAGGAGGA GACCACCTGG GAGTACCTGC TCGGCCAGCA GAGCATGATG GCCGCCCTGT     44280
GCTTCGCCCC GTTCAACGGC GCCGCCACGA TGGACGAGAT CGTCGACTTC GCCCGTGGCT     44340
GGCGGCCCGA CCTGGTCGTG TGGGAACCCT GGACCTA                              44377
```

(2) INFORMATION FOR SEQ ID NO:8:

(i) SEQUENCE CHARACTERISTICS:
        (A) LENGTH: 4550 amino acids
        (B) TYPE: amino acid
        (D) TOPOLOGY: unknown (ii) MOLECULE TYPE: peptide (xi) SEQUENCE DESCRIPTION: SEQ ID NO:8:

```
Met Ser Gly Glu Leu Ala Ile Ser Arg Ser Asp Asp Arg Ser Asp Ala
1               5                   10                  15

Val Ala Val Val Gly Met Ala Cys Arg Phe Pro Gly Ala Pro Gly Ile
                20                  25                  30

Ala Glu Phe Trp Lys Leu Leu Thr Asp Gly Arg Asp Ala Ile Gly Arg
            35                  40                  45

Asp Ala Asp Gly Arg Arg Arg Gly Met Ile Glu Ala Pro Gly Asp Phe
        50                  55                  60

Asp Ala Ala Phe Phe Gly Met Ser Pro Arg Glu Ala Ala Glu Thr Asp
65                  70                  75                  80

Pro Gln Gln Arg Leu Met Leu Glu Leu Gly Trp Glu Ala Leu Glu Asp
                85                  90                  95

Ala Gly Ile Val Pro Gly Ser Leu Arg Gly Glu Ala Val Gly Val Phe
            100                 105                 110

Val Gly Ala Met His Asp Asp Tyr Ala Thr Leu Leu His Arg Ala Gly
        115                 120                 125

Ala Pro Val Gly Pro His Thr Ala Thr Gly Leu Gln Arg Ala Met Leu
    130                 135                 140

Ala Asn Arg Leu Ser Tyr Val Leu Gly Thr Arg Gly Pro Ser Leu Ala
145                 150                 155                 160

Val Asp Thr Ala Gln Ser Ser Ser Leu Val Ala Val Ala Leu Ala Val
                165                 170                 175
```

-continued

| Glu | Ser | Leu | Arg | Ala | Gly | Thr | Ser | Arg | Val | Ala | Val | Ala | Gly | Gly | Val |
|  |  |  | 180 |  |  |  | 185 |  |  |  |  |  | 190 |  |  |
| Asn | Leu | Val | Leu | Ala | Asp | Glu | Gly | Thr | Ala | Ala | Met | Glu | Arg | Leu | Gly |
|  |  |  | 195 |  |  |  | 200 |  |  |  |  |  | 205 |  |  |
| Ala | Leu | Ser | Pro | Asp | Gly | Arg | Cys | His | Thr | Phe | Asp | Ala | Arg | Ala | Asn |
|  |  |  | 210 |  |  |  | 215 |  |  |  |  |  | 220 |  |  |
| Gly | Tyr | Val | Arg | Gly | Glu | Gly | Gly | Ala | Ala | Val | Val | Leu | Lys | Pro | Leu |
| 225 |  |  |  |  |  | 230 |  |  |  |  | 235 |  |  |  | 240 |
| Ala | Asp | Ala | Leu | Ala | Asp | Gly | Asp | Pro | Val | Tyr | Cys | Val | Val | Arg | Gly |
|  |  |  |  | 245 |  |  |  |  | 250 |  |  |  |  | 255 |  |
| Val | Ala | Val | Gly | Asn | Asp | Gly | Gly | Pro | Gly | Leu | Thr | Ala | Pro | Asp |
|  |  |  |  | 260 |  |  |  | 265 |  |  |  |  | 270 |  |  |
| Arg | Glu | Gly | Gln | Glu | Ala | Val | Leu | Arg | Ala | Ala | Cys | Ala | Gln | Ala | Arg |
|  |  |  | 275 |  |  |  |  | 280 |  |  |  |  | 285 |  |  |
| Val | Asp | Pro | Ala | Glu | Val | Arg | Phe | Val | Glu | Leu | His | Gly | Thr | Gly | Thr |
|  |  |  | 290 |  |  |  | 295 |  |  |  |  | 300 |  |  |  |
| Pro | Val | Gly | Asp | Pro | Val | Glu | Ala | His | Ala | Leu | Gly | Ala | Val | His | Gly |
| 305 |  |  |  |  |  | 310 |  |  |  |  | 315 |  |  |  | 320 |
| Ser | Gly | Arg | Pro | Ala | Asp | Asp | Pro | Leu | Leu | Val | Gly | Ser | Val | Lys | Thr |
|  |  |  |  | 325 |  |  |  |  | 330 |  |  |  |  | 335 |  |
| Asn | Ile | Gly | His | Leu | Glu | Gly | Ala | Ala | Gly | Ile | Ala | Gly | Leu | Val | Lys |
|  |  |  | 340 |  |  |  |  | 345 |  |  |  |  | 350 |  |  |
| Ala | Ala | Leu | Cys | Leu | Arg | Glu | Arg | Thr | Leu | Pro | Gly | Ser | Leu | Asn | Phe |
|  |  |  | 355 |  |  |  |  | 360 |  |  |  |  | 365 |  |  |
| Ala | Thr | Pro | Ser | Pro | Ala | Ile | Pro | Leu | Asp | Gln | Leu | Arg | Leu | Lys | Val |
|  |  |  | 370 |  |  |  |  | 375 |  |  |  |  | 380 |  |  |
| Gln | Thr | Ala | Ala | Ala | Glu | Leu | Pro | Leu | Ala | Pro | Gly | Gly | Ala | Pro | Leu |
| 385 |  |  |  |  |  | 390 |  |  |  |  | 395 |  |  |  | 400 |
| Leu | Ala | Gly | Val | Ser | Ser | Phe | Gly | Ile | Gly | Gly | Thr | Asn | Cys | His | Val |
|  |  |  |  | 405 |  |  |  |  | 410 |  |  |  |  | 415 |  |
| Val | Leu | Glu | His | Leu | Pro | Ser | Arg | Pro | Thr | Pro | Ala | Val | Ser | Val | Ala |
|  |  |  | 420 |  |  |  |  | 425 |  |  |  |  | 430 |  |  |
| Ala | Ser | Leu | Pro | Asp | Val | Pro | Pro | Leu | Leu | Leu | Ser | Ala | Arg | Ser | Glu |
|  |  |  | 435 |  |  |  |  | 440 |  |  |  |  | 445 |  |  |
| Gly | Ala | Leu | Arg | Ala | Gln | Ala | Val | Arg | Leu | Gly | Glu | Tyr | Val | Glu | Arg |
|  | 450 |  |  |  |  | 455 |  |  |  |  | 460 |  |  |  |  |
| Val | Gly | Ala | Asp | Pro | Arg | Asp | Val | Ala | Tyr | Ser | Leu | Ala | Ser | Thr | Arg |
| 465 |  |  |  |  |  | 470 |  |  |  |  | 475 |  |  |  | 480 |
| Thr | Leu | Phe | Glu | His | Arg | Ala | Val | Val | Pro | Cys | Gly | Gly | Arg | Gly | Glu |
|  |  |  |  | 485 |  |  |  |  | 490 |  |  |  |  | 495 |  |
| Leu | Val | Ala | Ala | Leu | Gly | Gly | Phe | Ala | Ala | Gly | Arg | Val | Ser | Gly | Gly |
|  |  |  |  | 500 |  |  |  |  | 505 |  |  |  |  | 510 |  |
| Val | Arg | Ser | Gly | Arg | Ala | Val | Pro | Gly | Gly | Val | Gly | Val | Leu | Phe | Thr |
|  |  |  | 515 |  |  |  |  | 520 |  |  |  |  | 525 |  |  |
| Gly | Gln | Gly | Ala | Gln | Trp | Val | Gly | Met | Gly | Arg | Gly | Leu | Tyr | Ala | Gly |
|  |  |  | 530 |  |  |  |  | 535 |  |  |  |  | 540 |  |  |
| Gly | Gly | Val | Phe | Ala | Glu | Val | Leu | Asp | Glu | Val | Leu | Ser | Met | Val | Gly |
| 545 |  |  |  |  |  | 550 |  |  |  |  | 555 |  |  |  | 560 |
| Glu | Val | Asp | Gly | Arg | Ser | Leu | Arg | Asp | Val | Met | Phe | Gly | Asp | Val | Asp |
|  |  |  |  | 565 |  |  |  |  | 570 |  |  |  |  | 575 |  |
| Val | Asp | Ala | Gly | Ala | Gly | Ala | Asp | Ala | Gly | Ala | Gly | Ala | Gly | Ala | Gly |
|  |  |  |  | 580 |  |  |  |  | 585 |  |  |  |  | 590 |  |
| Val | Gly | Ser | Gly | Ser | Gly | Ser | Val | Gly | Gly | Leu | Leu | Gly | Arg | Thr | Glu |
|  |  |  | 595 |  |  |  |  | 600 |  |  |  |  | 605 |  |  |

-continued

| | | | | | | | | | | | | | | |
|---|---|---|---|---|---|---|---|---|---|---|---|---|---|---|
| Phe | Ala | Gln | Pro | Ala | Leu | Phe | Ala | Leu | Glu | Val | Ala | Leu | Phe | Arg | Ala |
| | 610 | | | | | 615 | | | | 620 | | | | | |
| Leu | Glu | Ala | Arg | Gly | Val | Glu | Val | Ser | Val | Val | Leu | Gly | His | Ser | Val |
| 625 | | | | | 630 | | | | 635 | | | | | 640 | |
| Gly | Glu | Val | Ala | Ala | Ala | Tyr | Val | Ala | Gly | Val | Leu | Ser | Leu | Gly | Asp |
| | | | | 645 | | | | 650 | | | | | 655 | | |
| Ala | Val | Arg | Leu | Val | Val | Ala | Arg | Gly | Gly | Leu | Met | Gly | Gly | Leu | Pro |
| | | | 660 | | | | | 665 | | | | | 670 | | |
| Val | Gly | Gly | Gly | Met | Trp | Ser | Val | Gly | Ala | Ser | Glu | Ser | Val | Val | Arg |
| | | 675 | | | | | 680 | | | | | 685 | | | |
| Gly | Val | Val | Glu | Gly | Leu | Gly | Glu | Trp | Val | Ser | Val | Ala | Ala | Val | Asn |
| | 690 | | | | | 695 | | | | 700 | | | | | |
| Gly | Pro | Arg | Ser | Val | Val | Leu | Ser | Gly | Asp | Val | Gly | Val | Leu | Glu | Ser |
| 705 | | | | | 710 | | | | 715 | | | | | 720 | |
| Val | Val | Ala | Ser | Leu | Met | Gly | Asp | Gly | Val | Glu | Cys | Arg | Arg | Leu | Asp |
| | | | | 725 | | | | 730 | | | | | 735 | | |
| Val | Ser | His | Gly | Phe | His | Ser | Val | Leu | Met | Glu | Pro | Val | Leu | Gly | Glu |
| | | | 740 | | | | 745 | | | | | 750 | | | |
| Phe | Arg | Gly | Val | Val | Glu | Ser | Leu | Glu | Phe | Gly | Arg | Val | Arg | Pro | Gly |
| | | 755 | | | | | 760 | | | | | 765 | | | |
| Val | Val | Val | Val | Ser | Gly | Val | Ser | Gly | Gly | Val | Val | Gly | Ser | Gly | Glu |
| | 770 | | | | | 775 | | | | 780 | | | | | |
| Leu | Gly | Asp | Pro | Gly | Tyr | Trp | Val | Arg | His | Ala | Arg | Glu | Ala | Val | Arg |
| 785 | | | | | 790 | | | | 795 | | | | | 800 | |
| Phe | Ala | Asp | Gly | Val | Gly | Val | Val | Arg | Gly | Leu | Gly | Val | Gly | Thr | Leu |
| | | | | 805 | | | | 810 | | | | | 815 | | |
| Val | Glu | Val | Gly | Pro | His | Gly | Val | Leu | Thr | Gly | Met | Ala | Gly | Glu | Cys |
| | | | 820 | | | | 825 | | | | | 830 | | | |
| Leu | Gly | Ala | Gly | Asp | Asp | Val | Val | Val | Pro | Ala | Met | Arg | Arg | Gly | |
| | | 835 | | | | | 840 | | | | | 845 | | | |
| Arg | Ala | Glu | Arg | Glu | Val | Phe | Glu | Ala | Ala | Leu | Ala | Thr | Val | Phe | Thr |
| | 850 | | | | | 855 | | | | 860 | | | | | |
| Arg | Asp | Ala | Gly | Leu | Asp | Ala | Thr | Ala | Leu | His | Thr | Gly | Ser | Thr | Gly |
| 865 | | | | | 870 | | | | 875 | | | | | 880 | |
| Arg | Arg | Ile | Asp | Leu | Pro | Thr | Tyr | Pro | Phe | Gln | Arg | Arg | Thr | His | Trp |
| | | | | 885 | | | | | 890 | | | | | 895 | |
| Ser | Pro | Ala | Leu | Ser | Arg | Pro | Val | Thr | Ala | Asp | Ala | Gly | Ala | Gly | Val |
| | | | | 900 | | | | 905 | | | | | 910 | | |
| Thr | Ala | Thr | Asp | Ala | Val | Gly | His | Ser | Val | Ser | Pro | Asp | Pro | Glu | Ser |
| | | 915 | | | | | 920 | | | | | 925 | | | |
| Thr | Glu | Gly | Thr | Ser | His | Arg | Asp | Thr | Asp | Asp | Glu | Ala | Asp | Ser | Ala |
| | 930 | | | | | 935 | | | | 940 | | | | | |
| Ser | Pro | Glu | Pro | Met | Ser | Pro | Glu | Asp | Ala | Val | Arg | Leu | Val | Arg | Glu |
| 945 | | | | | 950 | | | | 955 | | | | | 960 | |
| Ser | Thr | Ala | Ala | Val | Leu | Gly | His | Asp | Asp | Pro | Gly | Glu | Val | Ala | Leu |
| | | | | 965 | | | | 970 | | | | | 975 | | |
| Asp | Arg | Thr | Phe | Thr | Ser | Gln | Gly | Met | Asp | Ser | Val | Thr | Ala | Val | Glu |
| | | | 980 | | | | | 985 | | | | | 990 | | |
| Leu | Cys | Asp | Leu | Leu | Lys | Gly | Ala | Ser | Gly | Leu | Pro | Leu | Ala | Ala | Thr |
| | | 995 | | | | | 1000 | | | | | 1005 | | | |
| Leu | Val | Tyr | Asp | Leu | Pro | Thr | Pro | Arg | Ala | Val | Ala | Glu | His | Ile | Val |
| | 1010 | | | | | 1015 | | | | 1020 | | | | | |
| Glu | Ala | Ala | Gly | Gly | Pro | Lys | Asp | Ser | Val | Ala | Gly | Gly | Pro | Gly | Val |

```
1025                    1030                    1035                    1040

Leu  Ser  Ser  Ala  Ala  Val  Gly  Val  Ser  Asp  Ala  Arg  Gly  Gly  Ser  Arg
                    1045                    1050                    1055

Asp  Asp  Asp  Asp  Pro  Ile  Ala  Ile  Val  Gly  Val  Gly  Cys  Arg  Leu  Pro
               1060                    1065                    1070

Gly  Gly  Val  Asp  Ser  Arg  Ala  Ala  Leu  Trp  Glu  Leu  Leu  Glu  Ser  Gly
               1075                    1080                    1085

Ala  Asp  Ala  Ile  Ser  Ser  Phe  Pro  Thr  Asp  Arg  Gly  Trp  Asp  Leu  Asp
               1090                    1095                    1100

Gly  Leu  Tyr  Asp  Pro  Glu  Pro  Gly  Thr  Pro  Gly  Lys  Thr  Tyr  Val  Arg
1105                    1110                    1115                    1120

Glu  Gly  Gly  Phe  Leu  His  Ser  Ala  Ala  Glu  Phe  Asp  Ala  Glu  Phe  Phe
                    1125                    1130                    1135

Gly  Ile  Ser  Pro  Arg  Glu  Ala  Thr  Ala  Met  Asp  Pro  Gln  Gln  Arg  Leu
                    1140                    1145                    1150

Leu  Leu  Glu  Ala  Ser  Trp  Glu  Ala  Leu  Glu  Asp  Ala  Gly  Val  Leu  Pro
                    1155                    1160                    1165

Glu  Ser  Leu  Arg  Gly  Gly  Asp  Ala  Gly  Val  Phe  Val  Gly  Ala  Thr  Ala
               1170                    1175                    1180

Pro  Glu  Tyr  Gly  Pro  Arg  Leu  His  Glu  Gly  Ala  Asp  Gly  Tyr  Glu  Gly
1185                    1190                    1195                    1200

Tyr  Leu  Leu  Thr  Gly  Thr  Thr  Ala  Ser  Val  Ala  Ser  Gly  Arg  Ile  Ala
                    1205                    1210                    1215

Tyr  Thr  Leu  Gly  Thr  Gly  Gly  Pro  Ala  Leu  Thr  Val  Asp  Thr  Ala  Cys
               1220                    1225                    1230

Ser  Ser  Ser  Leu  Val  Ala  Leu  His  Leu  Ala  Val  Gln  Ala  Leu  Arg  Arg
               1235                    1240                    1245

Gly  Glu  Cys  Gly  Leu  Ala  Leu  Ala  Gly  Gly  Ala  Thr  Val  Met  Ser  Gly
               1250                    1255                    1260

Pro  Gly  Met  Phe  Val  Glu  Phe  Ser  Arg  Gln  Arg  Gly  Leu  Ala  Pro  Asp
1265                    1270                    1275                    1280

Gly  Arg  Cys  Met  Pro  Phe  Ser  Ala  Asp  Ala  Asp  Gly  Thr  Ala  Trp  Ser
                    1285                    1290                    1295

Glu  Gly  Val  Ala  Val  Leu  Ala  Leu  Glu  Arg  Leu  Ser  Asp  Ala  Arg  Arg
               1300                    1305                    1310

Ala  Gly  His  Arg  Val  Leu  Gly  Val  Val  Arg  Gly  Ser  Ala  Val  Asn  Gln
               1315                    1320                    1325

Asp  Gly  Ala  Ser  Asn  Gly  Leu  Thr  Ala  Pro  Asn  Arg  Ser  Ala  Gln  Glu
               1330                    1335                    1340

Gly  Val  Ile  Arg  Ala  Ala  Leu  Ala  Asp  Ala  Gly  Leu  Ala  Pro  Gly  Asp
1345                    1350                    1355                    1360

Val  Asp  Ala  Val  Glu  Ala  His  Gly  Thr  Gly  Thr  Ala  Leu  Gly  Asp  Pro
                    1365                    1370                    1375

Ile  Glu  Ala  Ser  Ala  Leu  Leu  Ala  Thr  Tyr  Gly  Arg  Glu  Arg  Val  Gly
               1380                    1385                    1390

Asp  Pro  Leu  Trp  Leu  Gly  Ser  Leu  Lys  Ser  Asn  Val  Gly  His  Thr  Gln
               1395                    1400                    1405

Ala  Ala  Ala  Gly  Ala  Ala  Gly  Val  Val  Lys  Met  Leu  Leu  Ala  Leu  Glu
               1410                    1415                    1420

His  Gly  Thr  Leu  Pro  Arg  Thr  Leu  His  Ala  Asp  Arg  Pro  Ser  Thr  His
1425                    1430                    1435                    1440

Val  Asp  Trp  Ser  Ser  Gly  Thr  Val  Ala  Leu  Leu  Ala  Glu  Ala  Arg  Arg
                    1445                    1450                    1455
```

```
Trp Pro Arg Arg Ser Asp Arg Pro Arg Arg Ala Ala Val Ser Ser Phe
        1460                1465                1470

Gly Ile Ser Gly Thr Asn Ala His Leu Ile Ile Glu Glu Ala Pro Glu
        1475                1480                1485

Trp Val Glu Asp Ile Asp Gly Val Ala Ala Pro Asp Arg Gly Thr Ala
    1490                1495                1500

Asp Ala Ala Ala Pro Ser Pro Leu Leu Leu Ser Ala Arg Ser Glu Gly
1505                1510                1515                1520

Ala Leu Arg Ala Gln Ala Val Arg Leu Gly Glu Tyr Val Glu Arg Val
            1525                1530                1535

Gly Ala Asp Pro Arg Asp Val Ala Tyr Ser Leu Ala Ser Thr Arg Thr
                1540                1545                1550

Leu Phe Glu His Arg Ala Val Val Pro Cys Gly Gly Arg Gly Glu Leu
        1555                1560                1565

Val Ala Ala Leu Gly Gly Phe Ala Ala Gly Arg Val Ser Gly Gly Val
    1570                1575                1580

Arg Ser Gly Arg Ala Val Pro Gly Gly Val Gly Val Leu Phe Thr Gly
1585                1590                1595                1600

Gln Gly Ala Gln Trp Val Gly Met Gly Arg Gly Leu Tyr Ala Gly Gly
            1605                1610                1615

Gly Val Phe Ala Glu Val Leu Asp Glu Val Leu Ser Met Val Gly Glu
                1620                1625                1630

Val Asp Gly Arg Ser Leu Arg Asp Val Met Phe Gly Asp Val Asp Val
        1635                1640                1645

Asp Ala Gly Ala Gly Ala Asp Ala Gly Ala Gly Ala Gly Ala Gly Val
    1650                1655                1660

Gly Ser Gly Ser Gly Ser Val Gly Gly Leu Leu Gly Arg Thr Glu Phe
1665                1670                1675                1680

Ala Gln Pro Ala Leu Phe Ala Leu Glu Val Ala Leu Phe Arg Ala Leu
            1685                1690                1695

Glu Ala Arg Gly Val Glu Val Ser Val Val Leu Gly His Ser Val Gly
                1700                1705                1710

Glu Val Ala Ala Ala Tyr Val Ala Gly Val Leu Ser Leu Gly Asp Ala
        1715                1720                1725

Val Arg Leu Val Val Ala Arg Gly Gly Leu Met Gly Gly Leu Pro Val
    1730                1735                1740

Gly Gly Gly Met Trp Ser Val Gly Ala Ser Glu Ser Val Val Arg Gly
1745                1750                1755                1760

Val Val Glu Gly Leu Gly Glu Trp Val Ser Val Ala Ala Val Asn Gly
            1765                1770                1775

Pro Arg Ser Val Val Leu Ser Gly Asp Val Gly Val Leu Glu Ser Val
                1780                1785                1790

Val Ala Ser Leu Met Gly Asp Gly Val Glu Cys Arg Arg Leu Asp Val
        1795                1800                1805

Ser His Gly Phe His Ser Val Leu Met Glu Pro Val Leu Gly Glu Phe
    1810                1815                1820

Arg Gly Val Val Glu Ser Leu Glu Phe Gly Arg Val Arg Pro Gly Val
1825                1830                1835                1840

Val Val Val Ser Gly Val Ser Gly Gly Val Val Gly Ser Gly Glu Leu
            1845                1850                1855

Gly Asp Pro Gly Tyr Trp Val Arg His Ala Arg Glu Ala Val Arg Phe
                1860                1865                1870

Ala Asp Gly Val Gly Val Val Arg Gly Leu Gly Val Gly Thr Leu Val
        1875                1880                1885
```

```
Glu Val Gly Pro His Gly Val Leu Thr Gly Met Ala Gly Glu Cys Leu
        1890                1895                1900
Gly Ala Gly Asp Asp Val Val Val Pro Ala Met Arg Arg Gly Arg
1905                1910                1915                1920
Ala Glu Arg Glu Val Phe Glu Ala Ala Leu Ala Thr Val Phe Thr Arg
                1925                1930                1935
Asp Ala Gly Leu Asp Ala Thr Ala Leu His Thr Gly Ser Thr Gly Arg
        1940                1945                1950
Arg Ile Asp Leu Pro Thr Tyr Pro Phe Gln Arg Asp Arg Tyr Trp Leu
        1955                1960                1965
Asp Pro Val Arg Thr Ala Val Thr Gly Val Glu Pro Ala Gly Ser Pro
        1970                1975                1980
Ala Asp Ala Arg Ala Thr Glu Arg Gly Arg Ser Thr Thr Ala Gly Ile
1985                1990                1995                2000
Arg Tyr Arg Val Ala Trp Gln Pro Ala Val Val Asp Arg Gly Asn Pro
                2005                2010                2015
Gly Pro Ala Gly His Val Leu Leu Leu Ala Pro Asp Glu Asp Thr Ala
        2020                2025                2030
Asp Ser Gly Leu Ala Pro Ala Ile Ala Arg Glu Leu Ala Val Arg Gly
        2035                2040                2045
Ala Glu Val His Thr Val Ala Val Pro Val Gly Thr Gly Arg Glu Ala
        2050                2055                2060
Ala Gly Asp Leu Leu Arg Ala Ala Gly Asp Gly Ala Ala Arg Ser Thr
2065                2070                2075                2080
Arg Val Leu Trp Leu Ala Pro Ala Glu Pro Asp Ala Ala Asp Ala Val
                2085                2090                2095
Ala Leu Val Gln Ala Leu Gly Glu Ala Val Pro Glu Ala Pro Leu Trp
        2100                2105                2110
Ile Thr Thr Arg Glu Ala Ala Ala Val Arg Pro Asp Glu Thr Pro Ser
        2115                2120                2125
Val Gly Gly Ala Gln Leu Trp Gly Leu Gly Gln Val Ala Ala Leu Glu
        2130                2135                2140
Leu Gly Arg Arg Trp Gly Gly Leu Ala Asp Leu Pro Gly Ser Ala Ser
2145                2150                2155                2160
Pro Ala Val Leu Arg Thr Phe Val Gly Ala Leu Leu Ala Gly Gly Glu
                2165                2170                2175
Asn Gln Phe Ala Val Arg Pro Ser Gly Val His Val Arg Arg Val Val
                2180                2185                2190
Pro Ala Pro Val Pro Val Pro Ala Ser Ala Arg Thr Val Thr Thr Ala
        2195                2200                2205
Pro Ala Thr Ala Val Gly Glu Asp Ala Arg Asn Asp Thr Ser Asp Val
        2210                2215                2220
Val Val Pro Asp Asp Arg Trp Ser Ser Gly Thr Val Leu Ile Thr Gly
2225                2230                2235                2240
Gly Thr Gly Ala Leu Gly Ala Gln Val Ala Arg Arg Leu Ala Arg Ser
                2245                2250                2255
Gly Ala Ala Arg Leu Leu Leu Val Gly Arg Arg Gly Ala Ala Gly Pro
                2260                2265                2270
Gly Val Gly Glu Leu Val Glu Glu Leu Thr Ala Leu Gly Ser Glu Val
        2275                2280                2285
Ala Val Glu Ala Cys Asp Val Ala Asp Arg Asp Ala Leu Ala Ala Leu
        2290                2295                2300
Leu Ala Gly Leu Pro Glu Glu Arg Pro Leu Val Ala Val Leu His Ala
```

|      |      |      |      |      | 2305 |      |      |      |      | 2310 |      |      |      |      | 2315 |      |      |      |      | 2320 |
|------|------|------|------|------|------|------|------|------|------|------|------|------|------|------|------|------|------|------|------|------|

Ala Gly Val Leu Asp Asp Gly Val Leu Asp Ser Leu Thr Ser Asp Arg
                            2325                2330                2335
Val Asp Ala Val Leu Arg Asp Lys Val Thr Ala Ala Arg His Leu Asp
                2340                2345                2350
Glu Leu Thr Ala Asp Leu Pro Leu Asp Ala Phe Val Leu Phe Ser Ser
                2355                2360                2365
Ile Val Gly Val Trp Gly Asn Gly Gly Gln Ala Val Tyr Ala Ala Ala
                2370                2375                2380
Asn Ala Ala Leu Asp Ala Leu Ala Gln Arg Arg Ala Arg Gly Ala
2385                2390                2395                2400
Arg Ala Ala Ser Ile Ala Trp Gly Pro Trp Ala Gly Ala Gly Met Ala
                2405                2410                2415
Ser Gly Thr Ala Ala Lys Ser Phe Glu Arg Asp Gly Val Thr Ala Leu
                2420                2425                2430
Asp Pro Glu Arg Ala Leu Asp Val Leu Asp Asp Val Val Gly Ala Gly
                2435                2440                2445
Gly Thr Ser Ala Ala Gly Thr His Ala Ala Gly Glu Ser Ser Leu Leu
                2450                2455                2460
Val Ala Asp Val Asp Trp Glu Thr Phe Val Gly Arg Ser Val Thr Arg
2465                2470                2475                2480
Arg Thr Trp Ser Leu Phe Asp Gly Val Ser Ala Ala Arg Ser Ala Arg
                2485                2490                2495
Ala Gly His Ala Ala Asp Asp Arg Ala Ala Leu Thr Pro Gly Thr Arg
                2500                2505                2510
Pro Gly Asp Gly Ala Pro Gly Gly Ser Gly Gln Asp Gly Gly Glu Gly
                2515                2520                2525
Arg Pro Trp Leu Ser Val Gly Pro Ser Pro Ala Glu Arg Arg Arg Ala
                2530                2535                2540
Leu Leu Thr Leu Val Arg Ser Glu Ala Ala Gly Ile Leu Arg His Ala
2545                2550                2555                2560
Ser Ala Asp Ala Val Asp Pro Glu Leu Ala Phe Arg Ser Ala Gly Phe
                2565                2570                2575
Asp Ser Leu Thr Val Leu Glu Leu Arg Asn Arg Leu Thr Ala Ala Thr
                2580                2585                2590
Gly Leu Asn Leu Pro Asn Thr Leu Leu Phe Asp His Pro Thr Pro Leu
                2595                2600                2605
Ser Leu Ala Ser His Leu His Asp Glu Leu Phe Gly Pro Asp Ser Glu
                2610                2615                2620
Ala Glu Pro Ala Ala Ala Ala Pro Thr Pro Val Met Ala Asp Glu Arg
2625                2630                2635                2640
Glu Pro Ile Ala Ile Val Gly Met Ala Cys Arg Tyr Pro Gly Gly Val
                2645                2650                2655
Ala Ser Pro Asp Asp Leu Trp Asp Leu Val Ala Gly Asp Gly His Thr
                2660                2665                2670
Leu Ser Pro Phe Pro Ala Asp Arg Gly Trp Asp Val Glu Gly Leu Tyr
                2675                2680                2685
Asp Pro Glu Pro Gly Val Pro Gly Lys Ser Tyr Val Arg Glu Gly Gly
                2690                2695                2700
Phe Leu Arg Ser Ala Ala Glu Phe Asp Ala Glu Phe Phe Gly Ile Ser
                2705                2710                2715                2720
Pro Arg Glu Ala Thr Ala Met Asp Pro Gln Gln Arg Leu Leu Leu Glu
                2725                2730                2735

```
Thr Ser Trp Glu Ala Leu Glu Arg Ala Gly Ile Val Pro Asp Ser Leu
            2740                    2745                2750
Arg Gly Thr Arg Thr Gly Val Phe Ser Gly Ile Ser Gln Gln Asp Tyr
        2755                2760                2765
Ala Thr Gln Leu Gly Asp Ala Asp Thr Tyr Gly His Val Leu
        2770            2775                2780
Thr Gly Thr Leu Gly Ser Val Ile Ser Gly Arg Val Ala Tyr Ala Leu
2785                2790                2795                2800
Gly Leu Glu Gly Pro Ala Leu Thr Val Asp Thr Ala Cys Ser Ser Ser
                2805                2810                2815
Leu Val Ala Leu His Leu Ala Val Gln Ser Leu Arg Arg Gly Glu Cys
            2820                2825                2830
Asp Leu Ala Leu Ala Gly Gly Val Thr Val Met Ala Thr Pro Thr Val
            2835                2840                2845
Phe Val Glu Phe Ser Arg Gln Arg Gly Leu Ala Ala Asp Gly Arg Cys
            2850                2855                2860
Lys Ala Phe Ala Glu Gly Ala Asp Gly Thr Ala Trp Ala Glu Gly Val
2865                2870                2875                2880
Gly Val Leu Leu Val Glu Arg Leu Ser Asp Ala Arg Arg Asn Gly His
                2885                2890                2895
Arg Val Leu Ala Val Val Arg Gly Ser Ala Val Asn Gln Asp Gly Ala
            2900                2905                2910
Ser Asn Gly Leu Thr Ala Pro Ser Gly Pro Ala Gln Gln Arg Val Ile
            2915                2920                2925
Arg Glu Ala Leu Ala Asp Ala Gly Leu Val Pro Ala Asp Val Asp Val
            2930                2935                2940
Val Glu Ala His Gly Thr Gly Thr Ala Leu Gly Asp Pro Ile Glu Ala
2945                2950                2955                2960
Gly Ala Leu Leu Ala Thr Tyr Gly Arg Glu Arg Val Gly Asp Pro Leu
                2965                2970                2975
Trp Leu Gly Ser Leu Lys Ser Asn Ile Gly His Ala Gln Ala Ala Ala
            2980                2985                2990
Gly Val Gly Gly Val Ile Lys Val Val Gln Gly Met Arg His Gly Ser
            2995                3000                3005
Leu Pro Arg Thr Leu His Val Asp Ala Pro Ser Ser Lys Val Glu Trp
3010                3015                3020
Ala Ser Gly Ala Val Glu Leu Leu Thr Glu Thr Arg Ser Trp Pro Arg
3025                3030                3035                3040
Arg Val Glu Arg Val Arg Arg Ala Ala Val Ser Ala Phe Gly Val Ser
                3045                3050                3055
Gly Thr Asn Ala His Val Val Leu Glu Glu Ala Pro Ala Glu Ala Gly
            3060                3065                3070
Ser Glu His Gly Asp Gly Pro Glu Pro Glu Arg Pro Asp Ala Val Thr
        3075                3080                3085
Gly Pro Leu Ser Trp Val Leu Ser Ala Arg Ser Glu Gly Ala Leu Arg
        3090                3095                3100
Ala Gln Ala Val Arg Leu Arg Glu Cys Val Glu Arg Val Gly Ala Asp
3105                3110                3115                3120
Pro Arg Asp Val Ala Gly Ser Leu Val Val Ser Arg Ala Ser Phe Gly
                3125                3130                3135
Glu Arg Ala Val Val Val Gly Arg Gly Arg Glu Glu Leu Leu Ala Gly
                3140                3145                3150
Leu Asp Val Val Ala Ala Gly Ala Pro Val Gly Val Ser Ser Gly Ala
            3155                3160                3165
```

```
Gly  Ala  Val  Val  Arg  Gly  Ser  Ala  Val  Arg  Gly  Arg  Gly  Val  Gly  Val
               3170               3175                    3180

Leu  Phe  Thr  Gly  Gln  Gly  Ala  Gln  Trp  Val  Gly  Met  Gly  Arg  Gly  Leu
3185                    3190                    3195                         3200

Tyr  Ala  Gly  Gly  Gly  Val  Phe  Ala  Glu  Val  Leu  Asp  Glu  Val  Leu  Ser
                    3205                    3210                    3215

Val  Val  Gly  Glu  Val  Asp  Gly  Arg  Ser  Leu  Arg  Asp  Val  Met  Phe  Ala
               3220                    3225                    3230

Asp  Ala  Asp  Ser  Val  Leu  Gly  Gly  Leu  Leu  Gly  Arg  Thr  Glu  Phe  Ala
               3235                    3240                    3245

Gln  Pro  Ala  Leu  Phe  Ala  Leu  Glu  Val  Ala  Leu  Phe  Arg  Ala  Leu  Glu
               3250                    3255                    3260

Ala  Arg  Gly  Val  Glu  Val  Ser  Val  Val  Leu  Gly  His  Ser  Val  Gly  Glu
3265                    3270                    3275                         3280

Val  Ala  Ala  Ala  Tyr  Val  Ala  Gly  Val  Leu  Ser  Leu  Gly  Asp  Ala  Val
                    3285                    3290                    3295

Arg  Leu  Val  Val  Ala  Arg  Gly  Gly  Leu  Met  Gly  Gly  Leu  Pro  Val  Gly
               3300                    3305                    3310

Gly  Gly  Met  Trp  Ser  Val  Gly  Ala  Ser  Glu  Ser  Val  Val  Arg  Gly  Val
               3315                    3320                    3325

Val  Glu  Gly  Leu  Gly  Glu  Trp  Val  Ser  Val  Ala  Ala  Val  Asn  Gly  Pro
               3330                    3335                    3340

Arg  Ser  Val  Val  Leu  Ser  Gly  Asp  Val  Gly  Val  Leu  Glu  Ser  Val  Val
3345                    3350                    3355                         3360

Val  Thr  Leu  Met  Gly  Asp  Gly  Val  Glu  Cys  Arg  Arg  Leu  Asp  Val  Ser
                    3365                    3370                    3375

His  Gly  Phe  His  Ser  Val  Leu  Met  Glu  Pro  Val  Leu  Gly  Glu  Phe  Arg
                    3380                    3385                    3390

Gly  Val  Val  Glu  Ser  Leu  Glu  Phe  Gly  Arg  Val  Arg  Pro  Gly  Val  Val
               3395                    3400                    3405

Val  Val  Ser  Gly  Val  Ser  Gly  Gly  Val  Val  Gly  Ser  Gly  Glu  Leu  Gly
               3410                    3415                    3420

Asp  Pro  Gly  Tyr  Trp  Val  Arg  His  Ala  Arg  Glu  Ala  Val  Arg  Phe  Ala
3425                    3430                    3435                         3440

Asp  Gly  Val  Gly  Val  Val  Arg  Gly  Leu  Gly  Val  Gly  Thr  Leu  Val  Glu
                    3445                    3450                         3455

Val  Gly  Pro  His  Gly  Val  Leu  Thr  Gly  Met  Ala  Gly  Gln  Cys  Leu  Glu
               3460                    3465                    3470

Ala  Gly  Asp  Asp  Val  Val  Val  Pro  Ala  Met  Arg  Arg  Gly  Arg  Pro
               3475                    3480                    3485

Glu  Arg  Glu  Val  Phe  Glu  Ala  Ala  Leu  Ala  Thr  Val  Phe  Thr  Arg  Asp
     3490                    3495                    3500

Ala  Gly  Leu  Asp  Ala  Thr  Thr  Leu  His  Thr  Gly  Ser  Thr  Gly  Arg  Arg
3505                    3510                    3515                         3520

Ile  Asp  Leu  Pro  Thr  Tyr  Pro  Phe  Gln  His  Asn  Arg  Tyr  Trp  Ala  Thr
                    3525                    3530                    3535

Gly  Ser  Val  Thr  Gly  Ala  Thr  Gly  Thr  Ser  Ala  Ala  Ala  Arg  Phe  Gly
               3540                    3545                    3550

Leu  Glu  Trp  Lys  Asp  His  Pro  Phe  Leu  Ser  Gly  Ala  Thr  Pro  Ile  Ala
               3555                    3560                    3565

Gly  Ser  Gly  Ala  Leu  Leu  Leu  Thr  Gly  Arg  Val  Gly  Leu  Ala  Ala  His
               3570                    3575                    3580

Pro  Trp  Leu  Ala  Asp  His  Ala  Ile  Ser  Gly  Thr  Val  Leu  Leu  Pro  Gly
```

-continued

```
                3585                      3590                      3595                      3600
        Thr  Ala  Ile  Ala  Asp  Leu  Leu  Leu  Arg  Ala  Val  Glu  Glu  Val  Gly  Ala
                          3605                      3610                      3615
        Gly  Gly  Val  Glu  Glu  Leu  Thr  Leu  His  Glu  Pro  Leu  Leu  Leu  Pro  Glu
                          3620                      3625                      3630
        Arg  Gly  Gly  Leu  His  Val  Gln  Val  Leu  Val  Glu  Ala  Ala  Asp  Glu  Gln
                          3635                      3640                      3645
        Gly  Arg  Arg  Ala  Val  Ala  Val  Ala  Ala  Arg  Pro  Glu  Gly  Pro  Gly  Arg
                          3650                      3655                      3660
        Asp  Gly  Glu  Glu  Gln  Glu  Trp  Thr  Arg  His  Ala  Glu  Gly  Val  Leu  Thr
        3665                      3670                      3675                      3680
        Ser  Thr  Glu  Thr  Ala  Val  Pro  Asp  Met  Gly  Trp  Ala  Ala  Gly  Ala  Trp
                          3685                      3690                      3695
        Pro  Pro  Pro  Gly  Ala  Glu  Pro  Ile  Asp  Val  Glu  Glu  Leu  Tyr  Asp  Ala
                          3700                      3705                      3710
        Phe  Ala  Ala  Asp  Gly  Tyr  Gly  Tyr  Gly  Pro  Ala  Phe  Thr  Ala  Leu  Ser
                          3715                      3720                      3725
        Gly  Val  Trp  Arg  Leu  Gly  Asp  Glu  Leu  Phe  Ala  Glu  Val  Arg  Arg  Pro
                          3730                      3735                      3740
        Ala  Gly  Gly  Ala  Gly  Thr  Thr  Gly  Asp  Gly  Phe  Gly  Val  His  Pro  Ala
        3745                      3750                      3755                      3760
        Leu  Phe  Asp  Ala  Ala  Leu  His  Pro  Trp  Arg  Ala  Gly  Gly  Leu  Leu  Pro
                          3765                      3770                      3775
        Asp  Thr  Gly  Gly  Thr  Thr  Trp  Ala  Pro  Phe  Ser  Trp  Gln  Gly  Ile  Ala
                          3780                      3785                      3790
        Leu  His  Thr  Thr  Gly  Ala  Glu  Thr  Leu  Arg  Val  Arg  Leu  Ala  Pro  Ala
                          3795                      3800                      3805
        Ala  Gly  Gly  Thr  Glu  Ser  Ala  Phe  Ser  Val  Gln  Ala  Ala  Asp  Pro  Ala
                          3810                      3815                      3820
        Gly  Thr  Pro  Val  Leu  Thr  Leu  Asp  Ala  Leu  Leu  Leu  Arg  Pro  Val  Thr
        3825                      3830                      3835                      3840
        Leu  Gly  Arg  Ala  Asp  Ala  Pro  Gln  Pro  Leu  Tyr  Arg  Val  Asp  Trp  Gln
                          3845                      3850                      3855
        Pro  Val  Gly  Gln  Gly  Thr  Glu  Ala  Ser  Gly  Ala  Gln  Gly  Trp  Thr  Val
                          3860                      3865                      3870
        Leu  Gly  Gln  Ala  Ala  Ala  Glu  Thr  Val  Ala  Gln  Pro  Ala  Ala  His  Ala
                          3875                      3880                      3885
        Asp  Leu  Thr  Ala  Leu  Arg  Thr  Ala  Val  Ala  Ala  Ala  Gly  Thr  Pro  Val
                          3890                      3895                      3900
        Pro  Arg  Leu  Val  Val  Val  Ser  Pro  Val  Asp  Thr  Arg  Leu  Asp  Glu  Gly
        3905                      3910                      3915                      3920
        Pro  Val  Leu  Ala  Asp  Ala  Glu  Ala  Arg  Ala  Arg  Ala  Gly  Asp  Gly  Trp
                          3925                      3930                      3935
        Asp  Asp  Asp  Pro  Leu  Arg  Val  Ala  Leu  Gly  Arg  Gly  Leu  Thr  Leu  Val
                          3940                      3945                      3950
        Arg  Glu  Trp  Val  Glu  Asp  Glu  Arg  Leu  Ala  Asp  Ser  Arg  Leu  Val  Val
                          3955                      3960                      3965
        Leu  Thr  Arg  Gly  Ala  Val  Ala  Ala  Gly  Pro  Gly  Asp  Val  Pro  Asp  Leu
                          3970                      3975                      3980
        Thr  Gly  Ala  Ala  Leu  Trp  Gly  Leu  Leu  Arg  Ser  Ala  Gln  Ser  Glu  Tyr
        3985                      3990                      3995                      4000
        Pro  Asp  Arg  Phe  Thr  Leu  Ile  Asp  Val  Asp  Asp  Ser  Pro  Glu  Ser  Arg
                          4005                      4010                      4015
```

```
Ala  Ala  Leu  Pro  Arg  Ala  Leu  Gly  Ser  Ala  Glu  Arg  Gln  Leu  Ala  Leu
               4020                     4025                    4030

Arg  Thr  Gly  Asp  Val  Leu  Ala  Pro  Ala  Leu  Val  Pro  Met  Ala  Thr  Arg
          4035                     4040                    4045

Pro  Ala  Glu  Thr  Thr  Pro  Ala  Thr  Ala  Val  Ala  Ser  Ala  Thr  Thr  Gln
     4050                     4055                    4060

Thr  Gln  Val  Thr  Ala  Pro  Ala  Pro  Asp  Asp  Pro  Ala  Ala  Asp  Ala  Val
4065                     4070                    4075                     4080

Phe  Asp  Pro  Ala  Gly  Thr  Val  Leu  Ile  Thr  Gly  Gly  Thr  Gly  Ala  Leu
                    4085                    4090                    4095

Gly  Arg  Arg  Val  Ala  Ser  His  Leu  Ala  Arg  Arg  Tyr  Gly  Val  Arg  His
               4100                     4105                    4110

Met  Leu  Leu  Val  Ser  Arg  Arg  Gly  Pro  Asp  Ala  Pro  Glu  Ala  Gly  Pro
          4115                     4120                    4125

Leu  Glu  Arg  Glu  Leu  Ala  Gly  Leu  Gly  Val  Thr  Ala  Thr  Phe  Leu  Ala
     4130                     4135                    4140

Cys  Asp  Leu  Thr  Asp  Ile  Glu  Ala  Val  Arg  Lys  Ala  Val  Ala  Ala  Val
4145                     4150                    4155                     4160

Pro  Ser  Asp  His  Pro  Leu  Thr  Gly  Val  Val  His  Thr  Ala  Gly  Val  Leu
                    4165                    4170                    4175

Asp  Asp  Gly  Ala  Leu  Thr  Gly  Leu  Thr  Arg  Gln  Arg  Leu  Asp  Thr  Val
               4180                     4185                    4190

Leu  Arg  Pro  Lys  Ala  Asp  Ala  Val  Arg  Asn  Leu  His  Glu  Ala  Thr  Leu
          4195                     4200                    4205

Asp  Arg  Pro  Leu  Arg  Ala  Phe  Val  Leu  Phe  Ser  Ala  Ala  Ala  Gly  Leu
     4210                     4215                    4220

Leu  Gly  Arg  Pro  Gly  Gln  Ala  Ser  Tyr  Ala  Ala  Ala  Asn  Ala  Val  Leu
4225                     4230                    4235                     4240

Asp  Ala  Leu  Ala  Gly  Ala  Arg  Arg  Ala  Ala  Gly  Leu  Pro  Ala  Val  Ser
                    4245                    4250                    4255

Leu  Ala  Trp  Gly  Leu  Trp  Asp  Glu  Gln  Thr  Gly  Met  Ala  Gly  Gly  Leu
               4260                     4265                    4270

Asp  Glu  Met  Ala  Leu  Arg  Val  Leu  Arg  Arg  Asp  Gly  Ile  Ala  Ala  Met
          4275                     4280                    4285

Pro  Pro  Glu  Gln  Gly  Leu  Glu  Leu  Leu  Asp  Leu  Ala  Leu  Thr  Gly  His
     4290                     4295                    4300

Arg  Asp  Gly  Pro  Ala  Val  Leu  Val  Pro  Leu  Leu  Leu  Asp  Gly  Ala  Ala
4305                     4310                    4315                     4320

Leu  Arg  Arg  Thr  Ala  Lys  Glu  Arg  Gly  Ala  Ala  Thr  Met  Ser  Pro  Leu
                    4325                    4330                    4335

Leu  Arg  Ala  Leu  Leu  Pro  Ala  Ala  Leu  Arg  Arg  Ser  Gly  Gly  Ala  Gly
               4340                     4345                    4350

Ala  Pro  Ala  Ala  Ala  Asp  Arg  His  Gly  Lys  Glu  Ala  Asp  Pro  Gly  Ala
          4355                     4360                    4365

Gly  Arg  Leu  Ala  Gly  Met  Val  Ala  Leu  Glu  Ala  Ala  Glu  Arg  Ser  Ala
     4370                     4375                    4380

Ala  Val  Leu  Glu  Leu  Val  Thr  Glu  Gln  Val  Ala  Glu  Val  Leu  Gly  Tyr
4385                     4390                    4395                     4400

Ala  Ser  Ala  Ala  Glu  Ile  Glu  Pro  Glu  Arg  Pro  Phe  Arg  Glu  Ile  Gly
                    4405                    4410                    4415

Val  Asp  Ser  Leu  Ala  Ala  Val  Glu  Leu  Arg  Asn  Arg  Leu  Ser  Arg  Leu
               4420                     4425                    4430

Val  Gly  Leu  Arg  Leu  Pro  Thr  Thr  Leu  Ser  Phe  Asp  His  Pro  Thr  Pro
          4435                     4440                    4445
```

| | | | | | | | | | | | | | | |
|---|---|---|---|---|---|---|---|---|---|---|---|---|---|---|
| Lys | Asp | Met | Ala | Gln | His | Ile | Asp | Gly | Gln | Leu | Pro | Arg | Pro | Ala | Gly |
| | | | 4450 | | | | 4455 | | | | 4460 | | | | |
| Ala | Ser | Pro | Ala | Asp | Ala | Ala | Leu | Glu | Gly | Ile | Gly | Asp | Leu | Ala | Arg |
| 4465 | | | | | 4470 | | | | | 4475 | | | | | 4480 |
| Ala | Val | Ala | Leu | Leu | Gly | Thr | Gly | Asp | Ala | Arg | Arg | Ala | Glu | Val | Arg |
| | | | | 4485 | | | | | 4490 | | | | | 4495 | |
| Glu | Gln | Leu | Val | Gly | Leu | Leu | Ala | Ala | Leu | Asp | Pro | Pro | Gly | Arg | Thr |
| | | | | 4500 | | | | | 4505 | | | | | 4510 | |
| Gly | Thr | Ala | Ala | Pro | Gly | Val | Pro | Ser | Gly | Ala | Asp | Gly | Ala | Glu | Pro |
| | | | 4515 | | | | 4520 | | | | | 4525 | | | |
| Thr | Val | Thr | Asp | Arg | Leu | Asp | Glu | Ala | Thr | Asp | Asp | Glu | Ile | Phe | Ala |
| | | | 4530 | | | | 4535 | | | | 4540 | | | | |
| Phe | Leu | Asp | Glu | Gln | Leu | | | | | | | | | | |
| 4545 | | | | | 4550 | | | | | | | | | | |

( 2 ) INFORMATION FOR SEQ ID NO:9:

( i ) SEQUENCE CHARACTERISTICS:
        ( A ) LENGTH: 1996 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:9:

| | | | | | | | | | | | | | | | |
|---|---|---|---|---|---|---|---|---|---|---|---|---|---|---|---|
| Met | Thr | Ala | Glu | Asn | Asp | Lys | Ile | Arg | Ser | Tyr | Leu | Lys | Arg | Ala | Thr |
| 1 | | | | 5 | | | | | 10 | | | | | 15 | |
| Ala | Glu | Leu | His | Arg | Thr | Lys | Ser | Arg | Leu | Ala | Glu | Val | Glu | Ser | Ala |
| | | | | 20 | | | | | 25 | | | | | 30 | |
| Ser | Arg | Glu | Pro | Ile | Ala | Ile | Val | Gly | Met | Ala | Cys | Arg | Tyr | Pro | Gly |
| | | | 35 | | | | | 40 | | | | | 45 | | |
| Gly | Val | Ala | Ser | Pro | Asp | Asp | Leu | Trp | Asp | Leu | Val | Ala | Ala | Gly | Thr |
| | | | 50 | | | | | 55 | | | | | 60 | | |
| Asp | Ala | Val | Ser | Ala | Phe | Pro | Val | Asp | Arg | Gly | Trp | Asp | Val | Glu | Gly |
| 65 | | | | | 70 | | | | | 75 | | | | | 80 |
| Leu | Tyr | Asp | Pro | Asp | Pro | Glu | Ala | Val | Gly | Arg | Ser | Tyr | Val | Arg | Glu |
| | | | | 85 | | | | | 90 | | | | | 95 | |
| Gly | Gly | Phe | Leu | His | Ser | Ala | Ala | Glu | Phe | Asp | Ala | Glu | Phe | Phe | Gly |
| | | | | 100 | | | | | 105 | | | | | 110 | |
| Ile | Ser | Pro | Arg | Glu | Ala | Ala | Ala | Met | Asp | Pro | Gln | Gln | Arg | Leu | Leu |
| | | | 115 | | | | | 120 | | | | | 125 | | |
| Leu | Glu | Thr | Ser | Trp | Glu | Ala | Leu | Glu | Arg | Ala | Gly | Ile | Val | Pro | Ala |
| | | 130 | | | | | 135 | | | | | 140 | | | |
| Ser | Leu | Arg | Gly | Thr | Arg | Thr | Gly | Val | Phe | Thr | Gly | Val | Met | Tyr | Asp |
| 145 | | | | | 150 | | | | | 155 | | | | | 160 |
| Asp | Tyr | Gly | Ser | Arg | Phe | Asp | Ser | Ala | Pro | Pro | Glu | Tyr | Glu | Gly | Tyr |
| | | | | 165 | | | | | 170 | | | | | 175 | |
| Leu | Val | Asn | Gly | Ser | Ala | Gly | Ser | Ile | Ala | Ser | Gly | Arg | Val | Ala | Tyr |
| | | | | 180 | | | | | 185 | | | | | 190 | |
| Ala | Leu | Gly | Leu | Glu | Gly | Pro | Ala | Leu | Thr | Val | Asp | Thr | Ala | Cys | Ser |
| | | | 195 | | | | | 200 | | | | | 205 | | |
| Ser | Ser | Leu | Val | Ala | Leu | His | Leu | Ala | Val | Gln | Ser | Leu | Arg | Arg | Gly |
| | | 210 | | | | | 215 | | | | | 220 | | | |
| Glu | Cys | Asp | Leu | Ala | Leu | Ala | Gly | Gly | Val | Thr | Val | Met | Ala | Thr | Pro |
| 225 | | | | | 230 | | | | | 235 | | | | | 240 |
| Thr | Val | Leu | Val | Glu | Phe | Ser | Arg | Gln | Arg | Gly | Leu | Ala | Ala | Asp | Gly |

|   |   |   |   |   | 245 |   |   |   | 250 |   |   |   |   | 255 |   |
|---|---|---|---|---|-----|---|---|---|-----|---|---|---|---|-----|---|

Arg Cys Lys Ala Phe Ala Glu Gly Ala Asp Gly Thr Ala Trp Ala Glu
            260                 265             270

Gly Val Gly Val Leu Leu Val Glu Arg Leu Ser Asp Ala Arg Arg Asn
            275                 280             285

Gly His Arg Val Leu Ala Val Val Arg Gly Ser Ala Val Asn Gln Asp
            290                 295             300

Gly Ala Ser Asn Gly Leu Thr Ala Pro Ser Gly Pro Ala Gln Gln Arg
305                     310             315                 320

Val Ile Arg Glu Ala Leu Ala Asp Ala Gly Leu Thr Pro Ala Asp Val
                325                 330             335

Asp Ala Val Glu Ala His Gly Thr Gly Thr Pro Leu Gly Asp Pro Ile
            340                 345             350

Glu Ala Gly Ala Leu Leu Ala Thr Tyr Gly Ser Glu Arg Gln Gly Gln
                355                 360             365

Gly Pro Leu Trp Leu Gly Ser Leu Lys Ser Asn Ile Gly His Ala Gln
            370                 375             380

Ala Ala Ala Gly Val Gly Gly Val Ile Lys Val Val Gln Ala Met Arg
385                     390                 395                 400

His Gly Ser Leu Pro Arg Thr Leu His Val Asp Ala Pro Ser Ser Lys
                405                 410             415

Val Glu Trp Ala Ser Gly Ala Val Glu Leu Leu Thr Glu Thr Arg Ser
            420                 425             430

Trp Pro Arg Arg Val Glu Arg Val Arg Arg Ala Ala Val Ser Ala Phe
            435                 440             445

Gly Val Ser Gly Thr Asn Ala His Val Val Leu Glu Glu Ala Pro Ala
450                     455                 460

Glu Ala Gly Ser Glu His Gly Asp Gly Pro Glu Pro Glu Arg Pro Asp
465                     470             475                     480

Ala Val Thr Gly Pro Leu Ser Trp Val Leu Ser Ala Arg Ser Glu Gly
                485                 490             495

Ala Leu Arg Ala Gln Ala Val Arg Leu Arg Glu Cys Val Glu Arg Val
                500                 505             510

Gly Ala Asp Pro Arg Asp Val Ala Gly Ser Leu Val Val Ser Arg Ala
            515                 520             525

Ser Phe Gly Glu Arg Ala Val Val Val Gly Arg Gly Arg Glu Glu Leu
    530                     535             540

Leu Ala Gly Leu Asp Val Ala Ala Gly Ala Pro Val Gly Val Ser
545                     550                 555                 560

Gly Gly Val Ser Ser Gly Ala Gly Ala Val Val Arg Gly Ser Ala Val
                565                 570             575

Arg Gly Arg Gly Val Gly Val Leu Phe Thr Gly Gln Gly Ala Gln Trp
            580                 585             590

Val Gly Met Gly Arg Gly Leu Tyr Ala Gly Gly Gly Val Phe Ala Glu
        595                 600                 605

Val Leu Asp Glu Val Leu Ser Val Val Gly Glu Val Gly Gly Trp Ser
    610                     615                 620

Leu Arg Asp Val Met Phe Gly Asp Val Asp Val Asp Ala Gly Ala Gly
625                     630                 635                 640

Ala Asp Ala Gly Val Gly Ser Gly Val Gly Val Gly Gly Leu Leu Gly
                645                 650                 655

Arg Thr Glu Phe Ala Gln Pro Ala Leu Phe Ala Leu Glu Val Ala Leu
            660                 665             670

-continued

```
Phe  Arg  Ala  Leu  Glu  Ala  Arg  Gly  Val  Glu  Val  Ser  Val  Val  Leu  Gly
          675                 680                 685

His  Ser  Val  Gly  Glu  Val  Ala  Ala  Ala  Tyr  Val  Ala  Gly  Val  Leu  Ser
     690                 695                 700

Leu  Gly  Asp  Ala  Val  Arg  Leu  Val  Val  Ala  Arg  Gly  Gly  Leu  Met  Gly
705                      710                 715                      720

Gly  Leu  Pro  Val  Gly  Gly  Met  Trp  Ser  Val  Gly  Ala  Ser  Glu  Ser
               725                 730                      735

Val  Val  Arg  Gly  Val  Val  Glu  Gly  Leu  Gly  Glu  Trp  Val  Ser  Val  Ala
          740                 745                      750

Ala  Val  Asn  Gly  Pro  Arg  Ser  Val  Val  Leu  Ser  Gly  Asp  Val  Gly  Val
          755                 760                 765

Leu  Glu  Ser  Val  Val  Ala  Ser  Leu  Met  Gly  Asp  Gly  Val  Glu  Cys  Arg
770                      775                 780

Arg  Leu  Asp  Val  Ser  His  Gly  Phe  His  Ser  Val  Leu  Met  Glu  Pro  Val
785                      790                 795                      800

Leu  Gly  Glu  Phe  Arg  Gly  Val  Val  Glu  Ser  Leu  Glu  Phe  Gly  Arg  Val
               805                 810                 815

Arg  Pro  Gly  Val  Val  Val  Ser  Ser  Val  Ser  Gly  Gly  Val  Gly
               820                 825                 830

Ser  Gly  Glu  Leu  Gly  Asp  Pro  Gly  Tyr  Trp  Val  Arg  His  Ala  Arg  Glu
          835                 840                      845

Ala  Val  Arg  Phe  Ala  Asp  Gly  Val  Gly  Val  Val  Arg  Gly  Leu  Gly  Val
850                      855                 860

Gly  Thr  Leu  Val  Glu  Val  Gly  Pro  His  Gly  Val  Leu  Thr  Gly  Met  Ala
865                      870                 875                      880

Gly  Glu  Cys  Leu  Gly  Ala  Gly  Asp  Asp  Val  Val  Val  Pro  Ala  Met
                    885                 890                 895

Arg  Arg  Gly  Arg  Ala  Glu  Arg  Glu  Val  Phe  Glu  Ala  Ala  Leu  Ala  Thr
               900                 905                 910

Val  Phe  Thr  Arg  Asp  Ala  Gly  Leu  Asp  Ala  Thr  Thr  Leu  His  Thr  Gly
               915                 920                 925

Ser  Thr  Gly  Arg  Arg  Ile  Asp  Leu  Pro  Thr  Tyr  Pro  Phe  Gln  His  Asp
     930                 935                 940

Arg  Tyr  Trp  Leu  Ala  Ala  Pro  Ser  Arg  Pro  Arg  Thr  Asp  Gly  Leu  Ser
945                      950                 955                      960

Ala  Ala  Gly  Leu  Arg  Glu  Val  Glu  His  Pro  Leu  Leu  Thr  Ala  Ala  Val
               965                 970                 975

Glu  Leu  Pro  Gly  Thr  Asp  Thr  Glu  Val  Trp  Thr  Gly  Arg  Ile  Ser  Ala
               980                 985                 990

Ala  Asp  Leu  Pro  Trp  Leu  Ala  Asp  His  Leu  Val  Trp  Asp  Arg  Gly  Val
          995                 1000                1005

Val  Pro  Gly  Thr  Ala  Leu  Leu  Glu  Thr  Val  Leu  Gln  Val  Gly  Ser  Arg
     1010                1015                1020

Ile  Gly  Leu  Pro  Arg  Val  Ala  Glu  Leu  Val  Leu  Glu  Thr  Pro  Leu  Thr
1025                     1030                1035                     1040

Trp  Thr  Ser  Asp  Arg  Pro  Leu  Gln  Val  Arg  Ile  Val  Val  Thr  Ala
                    1045                1050                1055

Ala  Thr  Ala  Pro  Gly  Gly  Ala  Arg  Glu  Leu  Thr  Leu  His  Ser  Arg  Pro
               1060                1065                1070

Glu  Pro  Val  Ala  Ala  Ser  Ser  Ser  Ser  Pro  Ser  Pro  Ala  Ser  Pro  Arg
          1075                1080                1085

His  Leu  Thr  Ala  Gln  Glu  Ser  Asp  Asp  Asp  Trp  Thr  Arg  His  Ala  Ser
          1090                1095                1100
```

```
Gly Leu Leu Ala Pro Ala Ala Gly Leu Ala Asp Asp Phe Ala Glu Leu
1105                1110                1115                1120

Thr Gly Ala Trp Pro Pro Val Gly Ala Glu Pro Leu Asp Leu Ala Gly
                1125                1130                1135

Gln Tyr Pro Leu Phe Ala Ala Ala Gly Val Arg Tyr Glu Gly Ala Phe
                1140                1145                1150

Arg Gly Leu Arg Ala Ala Trp Arg Arg Gly Asp Glu Val Phe Ala Asp
            1155                1160                1165

Val Arg Leu Pro Asp Ala His Ala Val Asp Ala Asp Arg Tyr Gly Val
            1170                1175                1180

His Pro Ala Leu Leu Asp Ala Val Leu His Pro Ile Ala Ser Leu Asp
1185                1190                1195                1200

Pro Leu Gly Asp Gly Gly His Gly Leu Leu Pro Phe Ser Trp Thr Asp
                1205                1210                1215

Val Gln Gly His Gly Ala Gly Gly His Ala Leu Arg Val Arg Val Ala
                1220                1225                1230

Ala Val Asp Gly Gly Ala Val Ser Val Thr Ala Ala Asp His Ala Gly
            1235                1240                1245

Asn Pro Val Leu Ser Ala Arg Ser Leu Ala Leu Arg Arg Ile Thr Ala
            1250                1255                1260

Asp Arg Leu Pro Ala Ala Pro Val Ala Pro Leu Tyr Arg Val Asp Trp
1265                1270                1275                1280

Leu Pro Phe Pro Gly Pro Val Pro Val Ser Ala Gly Gly Arg Trp Ala
                1285                1290                1295

Val Val Gly Pro Glu Ala Glu Ala Thr Ala Ala Gly Leu Arg Ala Val
                1300                1305                1310

Gly Leu Asp Val Arg Thr His Ala Leu Pro Leu Gly Glu Pro Leu Pro
            1315                1320                1325

Pro Gln Ala Gly Thr Asp Ala Glu Val Ile Ile Leu Asp Leu Thr Thr
            1330                1335                1340

Thr Ala Ala Gly Arg Thr Ala Ser Asp Gly Gly Arg Leu Ser Leu Leu
1345                1350                1355                1360

Asp Glu Val Arg Ala Thr Val Arg Arg Thr Leu Glu Ala Val Gln Ala
                1365                1370                1375

Arg Leu Ala Asp Thr Glu Thr Ala Pro Asp Val Asp Val Arg Thr Ala
            1380                1385                1390

Ala Arg Pro Arg Thr Ala Ala Arg Thr Ser Pro Arg Val Asp Thr Arg
            1395                1400                1405

Thr Gly Ala Arg Thr Ala Asp Gly Pro Arg Leu Val Val Leu Thr Arg
            1410                1415                1420

Gly Ala Ala Gly Pro Glu Gly Gly Ala Ala Asp Pro Ala Gly Ala Ala
1425                1430                1435                1440

Val Trp Gly Leu Val Arg Val Ala Gln Ala Glu Gln Pro Gly Arg Phe
                1445                1450                1455

Thr Leu Val Asp Val Asp Gly Thr Gln Ala Ser Leu Arg Ala Leu Pro
                1460                1465                1470

Gly Leu Leu Ala Thr Asp Ala Gly Gln Ser Ala Val Arg Asp Gly Arg
            1475                1480                1485

Val Thr Val Pro Arg Leu Val Pro Val Ala Asp Pro Val Pro His Gly
            1490                1495                1500

Gly Gly Thr Ala Ala Asp Gly Thr Gly Ala Gly Glu Pro Ser Ala Thr
1505                1510                1515                1520

Leu Asp Pro Glu Gly Thr Val Leu Ile Thr Gly Gly Thr Gly Ala Leu
```

-continued

```
                      1525                    1530                    1535
Ala  Ala  Glu  Thr  Ala  Arg  His  Leu  Val  Asp  Arg  His  Lys  Val  Arg  His
                1540                    1545                    1550
Leu  Leu  Leu  Val  Gly  Arg  Arg  Gly  Pro  Asp  Ala  Pro  Gly  Val  Asp  Arg
                1555                    1560                    1565
Leu  Val  Ala  Glu  Leu  Thr  Glu  Ser  Gly  Ala  Glu  Val  Ala  Val  Arg  Ala
                1570                    1575                    1580
Cys  Asp  Val  Thr  Asp  Arg  Asp  Ala  Leu  Arg  Arg  Leu  Leu  Asp  Ala  Leu
1585                    1590                    1595                    1600
Pro  Asp  Glu  His  Pro  Leu  Thr  Cys  Val  Val  His  Thr  Ala  Gly  Val  Leu
                1605                    1610                    1615
Asp  Asp  Gly  Val  Leu  Ser  Ala  Gln  Thr  Ala  Glu  Arg  Ile  Asp  Thr  Val
                1620                    1625                    1630
Leu  Arg  Pro  Lys  Ala  Asp  Ala  Ala  Val  His  Leu  Asp  Glu  Leu  Thr  Arg
                1635                    1640                    1645
Glu  Ile  Gly  Arg  Val  Pro  Leu  Val  Leu  Tyr  Ser  Ser  Val  Ser  Ala  Thr
                1650                    1655                    1660
Leu  Gly  Ser  Ala  Gly  Gln  Ala  Gly  Tyr  Ala  Ala  Ala  Asn  Ala  Phe  Met
1665                    1670                    1675                    1680
Asp  Ala  Leu  Ala  Ala  Arg  Arg  Cys  Ala  Ala  Gly  His  Pro  Ala  Leu  Ser
                1685                    1690                    1695
Leu  Gly  Trp  Gly  Trp  Trp  Ser  Gly  Val  Gly  Leu  Ala  Thr  Gly  Leu  Asp
                1700                    1705                    1710
Gly  Ala  Asp  Ala  Ala  Arg  Val  Arg  Arg  Ser  Gly  Leu  Ala  Pro  Leu  Asp
                1715                    1720                    1725
Ala  Gly  Ala  Ala  Leu  Asp  Leu  Leu  Asp  Arg  Ala  Leu  Thr  Arg  Pro  Glu
                1730                    1735                    1740
Pro  Ala  Leu  Leu  Pro  Val  Arg  Leu  Asp  Leu  Arg  Ala  Ala  Ala  Gly  Ala
1745                    1750                    1755                    1760
Thr  Ala  Leu  Pro  Glu  Val  Leu  Arg  Asp  Leu  Ala  Gly  Val  Pro  Ala  Asp
                1765                    1770                    1775
Ala  Arg  Ser  Thr  Pro  Gly  Ala  Ala  Ala  Gly  Thr  Gly  Asp  Glu  Asp  Gly
                1780                    1785                    1790
Ala  Val  Arg  Pro  Ala  Pro  Ala  Pro  Ala  Asp  Ala  Ala  Gly  Thr  Leu  Ala
                1795                    1800                    1805
Ala  Arg  Leu  Ala  Gly  Arg  Ser  Ala  Pro  Glu  Arg  Thr  Ala  Leu  Leu  Leu
                1810                    1815                    1820
Asp  Leu  Val  Arg  Thr  Glu  Val  Ala  Ala  Val  Leu  Gly  His  Gly  Asp  Pro
1825                    1830                    1835                    1840
Ala  Ala  Ile  Gly  Ala  Ala  Arg  Thr  Phe  Lys  Asp  Ala  Gly  Phe  Asp  Ser
                1845                    1850                    1855
Leu  Thr  Ala  Val  Asp  Leu  Arg  Asn  Arg  Leu  Asn  Thr  Arg  Thr  Gly  Leu
                1860                    1865                    1870
Arg  Leu  Pro  Ala  Thr  Leu  Val  Phe  Asp  His  Pro  Thr  Pro  Leu  Ala  Leu
                1875                    1880                    1885
Ala  Glu  Leu  Leu  Leu  Asp  Gly  Leu  Glu  Ala  Ala  Gly  Pro  Ala  Glu  Pro
                1890                    1895                    1900
Ala  Ala  Glu  Val  Pro  Asp  Glu  Ala  Ala  Gly  Ala  Glu  Thr  Leu  Ser  Gly
1905                    1910                    1915                    1920
Val  Ile  Asp  Arg  Leu  Glu  Arg  Ser  Leu  Ala  Ala  Thr  Asp  Asp  Gly  Asp
                1925                    1930                    1935
Ala  Arg  Val  Arg  Ala  Ala  Arg  Arg  Leu  Arg  Gly  Leu  Leu  Asp  Ala  Leu
                1940                    1945                    1950
```

| Pro | Ala | Gly | Pro | Gly | Ala | Ala | Ser | Gly | Pro | Asp | Ala | Gly | Glu | His | Ala |
|-----|-----|-----|-----|-----|-----|-----|-----|-----|-----|-----|-----|-----|-----|-----|-----|
|     |     |     | 1955 |     |     |     | 1960 |     |     |     |     | 1965 |     |     |     |

| Pro | Gly | Arg | Gly | Asp | Val | Val | Ile | Asp | Arg | Leu | Arg | Ser | Ala | Ser | Asp |
|-----|-----|-----|-----|-----|-----|-----|-----|-----|-----|-----|-----|-----|-----|-----|-----|
|     |     |     | 1970 |     |     | 1975 |     |     |     |     | 1980 |     |     |     |     |

| Asp | Asp | Leu | Phe | Asp | Leu | Leu | Asp | Ser | Asp | Phe | Gln |
|-----|-----|-----|-----|-----|-----|-----|-----|-----|-----|-----|-----|
| 1985 |     |     |     |     | 1990 |     |     |     |     | 1995 |     |

( 2 ) INFORMATION FOR SEQ ID NO:10:

( i ) SEQUENCE CHARACTERISTICS:
        ( A ) LENGTH: 3724 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:10:

| Met | Ser | Ala | Thr | Asn | Glu | Glu | Lys | Leu | Arg | Glu | Tyr | Leu | Arg | Arg | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Met | Ala | Asp | Leu | His | Ser | Ala | Arg | Glu | Arg | Leu | Arg | Glu | Val | Glu | Ser |
|-----|-----|-----|-----|-----|-----|-----|-----|-----|-----|-----|-----|-----|-----|-----|-----|
|     |     |     |     | 20  |     |     |     |     | 25  |     |     |     |     | 30  |     |

| Ala | Ser | Arg | Glu | Pro | Ile | Ala | Ile | Val | Gly | Met | Ala | Cys | Arg | Tyr | Pro |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gly | Gly | Val | Ala | Ser | Pro | Glu | Glu | Leu | Trp | Asp | Leu | Val | Ala | Ala | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Thr | Asp | Ala | Ile | Ser | Pro | Phe | Pro | Val | Asp | Arg | Gly | Trp | Asp | Ala | Glu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gly | Leu | Tyr | Asp | Pro | Glu | Pro | Gly | Val | Pro | Gly | Lys | Ser | Tyr | Val | Arg |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Glu | Gly | Gly | Phe | Leu | His | Ser | Ala | Ala | Glu | Phe | Asp | Ala | Glu | Phe | Phe |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| Gly | Ile | Ser | Pro | Arg | Glu | Ala | Ala | Ala | Met | Asp | Pro | Gln | Gln | Arg | Leu |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Leu | Leu | Glu | Thr | Ser | Trp | Glu | Ala | Leu | Glu | Arg | Ala | Gly | Ile | Val | Pro |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ala | Ser | Leu | Arg | Gly | Thr | Arg | Thr | Gly | Val | Phe | Thr | Gly | Val | Met | Tyr |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| His | Asp | Tyr | Gly | Ser | His | Gln | Val | Gly | Thr | Ala | Ala | Asp | Pro | Ser | Gly |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gln | Leu | Gly | Leu | Gly | Thr | Ala | Gly | Ser | Val | Ala | Ser | Gly | Arg | Val | Ala |
|-----|-----|-----|-----|-----|-----|-----|-----|-----|-----|-----|-----|-----|-----|-----|-----|
|     |     |     |     | 180 |     |     |     |     | 185 |     |     |     |     | 190 |     |

| Tyr | Thr | Leu | Gly | Leu | Gln | Gly | Pro | Ala | Val | Thr | Met | Asp | Thr | Ala | Cys |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Ser | Ser | Ser | Leu | Val | Ala | Leu | His | Leu | Ala | Val | Gln | Ser | Leu | Arg | Arg |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Gly | Glu | Cys | Asp | Leu | Ala | Leu | Ala | Gly | Gly | Ala | Thr | Val | Leu | Ala | Thr |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Pro | Thr | Val | Phe | Val | Glu | Phe | Ser | Arg | Gln | Arg | Gly | Leu | Ala | Ala | Asp |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Gly | Arg | Cys | Lys | Ala | Phe | Ala | Glu | Gly | Ala | Asp | Gly | Thr | Ala | Trp | Ala |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Glu | Gly | Ala | Gly | Val | Leu | Leu | Val | Glu | Arg | Leu | Ser | Asp | Ala | Arg | Arg |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Asn | Gly | His | Arg | Val | Leu | Ala | Val | Val | Arg | Gly | Ser | Ala | Val | Asn | Gln |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Asp | Gly | Ala | Ser | Asn | Gly | Leu | Thr | Ala | Pro | Ser | Gly | Pro | Ala | Gln | Gln |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

```
Arg  Val  Ile  Arg  Asp  Ala  Leu  Ala  Asp  Ala  Gly  Leu  Thr  Pro  Ala  Asp
               325                      330                      335

Val  Asp  Ala  Val  Glu  Ala  His  Gly  Thr  Gly  Thr  Pro  Leu  Gly  Asp  Pro
               340                      345                      350

Ile  Glu  Ala  Gly  Ala  Leu  Met  Ala  Thr  Tyr  Gly  Ser  Glu  Arg  Val  Gly
               355                      360                      365

Asp  Pro  Leu  Trp  Leu  Gly  Ser  Leu  Lys  Ser  Asn  Ile  Gly  His  Thr  Gln
          370                      375                      380

Ala  Ala  Ala  Gly  Ala  Ala  Gly  Val  Ile  Lys  Met  Val  Gln  Ala  Leu  Arg
385                      390                      395                      400

Gln  Ser  Glu  Leu  Pro  Arg  Thr  Leu  His  Val  Asp  Ala  Pro  Ser  Ala  Lys
               405                      410                      415

Val  Glu  Trp  Asp  Ala  Gly  Ala  Val  Gln  Leu  Leu  Thr  Gly  Val  Arg  Pro
               420                      425                      430

Trp  Pro  Arg  Arg  Glu  His  Arg  Pro  Arg  Arg  Ala  Ala  Val  Ser  Ala  Phe
          435                      440                      445

Gly  Val  Ser  Gly  Thr  Asn  Ala  His  Val  Ile  Ile  Glu  Glu  Pro  Pro  Ala
     450                      455                      460

Ala  Gly  Asp  Thr  Ser  Pro  Ala  Gly  Asp  Thr  Pro  Glu  Pro  Gly  Glu  Ala
465                      470                      475                      480

Thr  Ala  Ser  Pro  Ser  Thr  Ala  Ala  Gly  Pro  Ser  Ser  Pro  Ser  Ala  Val
               485                      490                      495

Ala  Gly  Pro  Leu  Ser  Pro  Ser  Ser  Pro  Ala  Val  Val  Trp  Pro  Leu  Ser
               500                      505                      510

Ala  Glu  Thr  Ala  Pro  Ala  Leu  Arg  Ala  Gln  Ala  Ala  Arg  Leu  Arg  Ala
          515                      520                      525

His  Leu  Glu  Arg  Leu  Pro  Gly  Thr  Ser  Pro  Thr  Asp  Ile  Gly  His  Ala
     530                      535                      540

Leu  Ala  Ala  Glu  Arg  Ala  Ala  Leu  Thr  Arg  Arg  Val  Val  Leu  Leu  Gly
545                      550                      555                      560

Asp  Asp  Gly  Ala  Pro  Val  Asp  Ala  Leu  Ala  Ala  Leu  Ala  Ala  Gly  Glu
               565                      570                      575

Thr  Thr  Pro  Asp  Ala  Val  His  Gly  Thr  Ala  Ala  Asp  Ile  Arg  Arg  Val
               580                      585                      590

Ala  Phe  Val  Phe  Pro  Gly  Gln  Gly  Ser  Gln  Trp  Ala  Gly  Met  Gly  Ala
          595                      600                      605

Glu  Leu  Leu  Asp  Thr  Ala  Pro  Ala  Phe  Ala  Ala  Glu  Leu  Asp  Arg  Cys
     610                      615                      620

Gln  Gly  Ala  Leu  Ser  Pro  Tyr  Val  Asp  Trp  Asn  Leu  Ala  Asp  Val  Leu
625                      630                      635                      640

Arg  Gly  Ala  Pro  Ala  Ala  Pro  Gly  Leu  Asp  Arg  Val  Asp  Val  Val  Gln
               645                      650                      655

Pro  Ala  Thr  Phe  Ala  Val  Met  Val  Gly  Leu  Ala  Ala  Leu  Trp  Arg  Ser
               660                      665                      670

Leu  Gly  Val  Glu  Pro  Ala  Ala  Val  Ile  Gly  His  Ser  Gln  Gly  Glu  Ile
          675                      680                      685

Ala  Ala  Ala  Cys  Val  Ala  Gly  Ala  Leu  Ser  Leu  Glu  Asp  Ala  Ala  Arg
          690                      695                      700

Ile  Val  Ala  Leu  Arg  Ser  Gln  Val  Ile  Ala  Arg  Glu  Leu  Ala  Gly  Arg
705                      710                      715                      720

Gly  Gly  Met  Ala  Ser  Val  Ala  Leu  Pro  Ala  Ala  Glu  Val  Glu  Ala  Arg
               725                      730                      735

Leu  Ala  Gly  Gly  Val  Glu  Ile  Ala  Ala  Val  Asn  Gly  Pro  Gly  Ser  Thr
```

|  |  |  |  |  | 740 |  |  |  |  | 745 |  |  |  |  | 750 |  |
|---|---|---|---|---|---|---|---|---|---|---|---|---|---|---|---|---|

Val Val Cys Gly Glu Pro Gly Ala Leu Glu Ala Leu Leu Val Thr Leu
            755                 760                 765

Glu Ser Glu Gly Thr Arg Val Arg Arg Ile Asp Val Asp Tyr Ala Ser
    770                 775                 780

His Ser His Tyr Val Glu Ser Ile Arg Ala Glu Leu Ala Thr Val Leu
785             790                 795                         800

Gly Pro Val Arg Pro Arg Arg Gly Asp Val Pro Phe Tyr Ser Thr Val
                805                 810                 815

Glu Ala Ala Leu Leu Asp Thr Ala Thr Leu Asp Ala Asp Tyr Trp Tyr
            820                 825                 830

Arg Asn Leu Arg Leu Pro Val Arg Phe Glu Pro Thr Val Arg Ala Met
            835                 840                 845

Leu Asp Asp Gly Val Asp Ala Phe Val Glu Cys Ser Ala His Pro Val
    850                 855                 860

Leu Thr Val Gly Val Arg Gln Thr Val Glu Ser Ala Gly Gly Ala Val
865             870                 875                         880

Pro Ala Leu Ala Ser Leu Arg Arg Asp Glu Gly Gly Leu Arg Arg Phe
                885                 890                 895

Leu Thr Ser Ala Ala Glu Ala Gln Val Val Gly Val Pro Val Asp Trp
            900                 905                 910

Ala Thr Leu Arg Pro Gly Ala Gly Arg Val Asp Leu Pro Thr Tyr Ala
            915                 920                 925

Phe Gln Arg Glu Arg His Trp Val Gly Pro Ala Arg Pro Asp Ser Ala
    930                 935                 940

Ala Thr Ala Ala Thr Thr Gly Asp Asp Ala Pro Glu Pro Gly Asp Arg
945             950                 955                         960

Leu Gly Tyr His Val Ala Trp Lys Gly Leu Arg Ser Thr Thr Gly Gly
                965                 970                 975

Trp Arg Pro Gly Leu Arg Leu Leu Ile Val Pro Thr Gly Asp Gln Tyr
            980                 985                 990

Thr Ala Leu Ala Asp Thr Leu Glu Gln Ala Val Ala Ser Phe Gly Gly
            995                 1000                1005

Thr Val Arg Arg Val Ala Phe Asp Pro Ala Arg Thr Gly Arg Ala Glu
            1010                1015                1020

Leu Phe Gly Leu Leu Glu Thr Glu Ile Asn Gly Asp Thr Ala Val Thr
1025            1030                1035                        1040

Gly Val Val Ser Leu Leu Gly Leu Cys Thr Asp Gly Arg Pro Asp His
                1045                1050                1055

Pro Ala Val Pro Val Ala Val Thr Ala Thr Leu Ala Leu Val Gln Ala
            1060                1065                1070

Leu Ala Asp Leu Gly Ser Thr Ala Pro Leu Trp Thr Val Thr Cys Gly
            1075                1080                1085

Ala Val Ala Thr Ala Pro Asp Glu Leu Pro Cys Thr Ala Gly Ala Gln
            1090                1095                1100

Leu Trp Gly Leu Gly Arg Val Ala Ala Leu Glu Leu Pro Glu Val Trp
1105                1110                1115                    1120

Gly Gly Leu Ile Asp Leu Pro Ala Arg Pro Asp Ala Arg Val Leu Asp
                1125                1130                1135

Arg Leu Ala Gly Val Leu Ala Glu Pro Gly Gly Glu Asp Gln Ile Ala
            1140                1145                1150

Val Arg Met Ala Gly Val Phe Gly Arg Arg Val Leu Arg Asn Pro Ala
    1155                1160                1165

```
Asp  Ser  Arg  Pro  Pro  Ala  Trp  Arg  Ala  Arg  Gly  Thr  Val  Leu  Ile  Ala
     1170               1175                    1180

Gly  Asp  Leu  Thr  Thr  Val  Pro  Gly  Arg  Leu  Val  Arg  Ser  Leu  Leu  Glu
1185                     1190                    1195                         1200

Asp  Gly  Ala  Asp  Arg  Val  Val  Leu  Ala  Gly  Pro  Asp  Ala  Pro  Ala  Gln
               1205                    1210                         1215

Ala  Ala  Ala  Ala  Gly  Leu  Thr  Gly  Val  Ser  Leu  Val  Pro  Val  Arg  Cys
               1220                    1225                         1230

Asp  Val  Thr  Asp  Arg  Ala  Ala  Leu  Ala  Ala  Leu  Leu  Asp  Glu  His  Ala
               1235                    1240                         1245

Pro  Thr  Val  Ala  Val  His  Ala  Pro  Pro  Leu  Val  Pro  Leu  Ala  Pro  Leu
               1250                    1255                         1260

Arg  Glu  Thr  Ala  Pro  Gly  Asp  Ile  Ala  Ala  Ala  Leu  Ala  Ala  Lys  Thr
1265                     1270                    1275                         1280

Thr  Ala  Ala  Gly  His  Leu  Val  Asp  Leu  Ala  Pro  Ala  Ala  Gly  Leu  Asp
               1285                    1290                         1295

Ala  Leu  Val  Leu  Phe  Ser  Ser  Val  Ser  Gly  Val  Trp  Gly  Gly  Ala  Ala
               1300                    1305                         1310

Gln  Gly  Gly  Tyr  Ala  Ala  Ala  Ser  Ala  His  Leu  Asp  Ala  Leu  Ala  Glu
               1315                    1320                         1325

Arg  Ala  Arg  Ala  Ala  Gly  Val  Pro  Ala  Phe  Ser  Val  Ala  Trp  Ser  Pro
1330                     1335                    1340

Trp  Ala  Gly  Gly  Thr  Pro  Ala  Asp  Gly  Ala  Glu  Ala  Glu  Phe  Leu  Ser
1345                     1350                    1355                         1360

Arg  Arg  Gly  Leu  Ala  Pro  Leu  Asp  Pro  Asp  Gln  Ala  Val  Arg  Thr  Leu
               1365                    1370                         1375

Arg  Arg  Met  Leu  Glu  Arg  Gly  Ser  Ala  Cys  Gly  Ala  Val  Ala  Asp  Val
               1380                    1385                         1390

Glu  Trp  Ser  Arg  Phe  Ala  Ala  Ser  Tyr  Thr  Trp  Val  Arg  Pro  Ala  Val
               1395                    1400                         1405

Leu  Phe  Asp  Asp  Ile  Pro  Asp  Val  Gln  Arg  Leu  Arg  Ala  Ala  Glu  Leu
               1410                    1415                         1420

Ala  Pro  Ser  Thr  Gly  Asp  Ser  Thr  Thr  Ser  Glu  Leu  Val  Arg  Glu  Leu
1425                     1430                    1435                         1440

Thr  Ala  Gln  Ser  Gly  His  Lys  Arg  His  Ala  Thr  Leu  Leu  Arg  Leu  Val
               1445                    1450                         1455

Arg  Ala  His  Ala  Ala  Ala  Val  Leu  Gly  Gln  Ser  Ser  Gly  Asp  Ala  Val
               1460                    1465                         1470

Ser  Ser  Ala  Arg  Ala  Phe  Arg  Asp  Leu  Gly  Phe  Asp  Ser  Leu  Thr  Ala
               1475                    1480                         1485

Leu  Glu  Leu  Arg  Asp  Arg  Leu  Ser  Thr  Ser  Thr  Gly  Leu  Lys  Leu  Pro
               1490                    1495                         1500

Thr  Ser  Leu  Val  Phe  Asp  His  Ser  Ser  Pro  Ala  Ala  Leu  Ala  Arg  His
1505                     1510                    1515                         1520

Leu  Gly  Glu  Glu  Leu  Leu  Gly  Arg  Asn  Asp  Thr  Ala  Asp  Arg  Ala  Gly
               1525                    1530                         1535

Pro  Asp  Thr  Pro  Val  Arg  Thr  Asp  Glu  Pro  Ile  Ala  Ile  Ile  Gly  Met
               1540                    1545                         1550

Ala  Cys  Arg  Leu  Pro  Gly  Gly  Val  Gln  Ser  Pro  Glu  Asp  Leu  Trp  Asp
               1555                    1560                         1565

Leu  Leu  Thr  Gly  Gly  Thr  Asp  Ala  Ile  Thr  Pro  Phe  Pro  Thr  Asn  Arg
               1570                    1575                         1580

Gly  Trp  Asp  Asn  Glu  Thr  Leu  Tyr  Asp  Pro  Asp  Pro  Asp  Ser  Pro  Gly
1585                     1590                    1595                         1600
```

His His Thr Tyr Val Arg Glu Gly Gly Phe Leu His Asp Ala Ala Glu
            1605                1610                1615

Phe Asp Pro Gly Phe Phe Gly Ile Ser Pro Arg Glu Ala Leu Ala Met
            1620                1625                1630

Asp Pro Gln Gln Arg Leu Ile Leu Glu Thr Ser Trp Glu Ser Phe Glu
            1635                1640                1645

Arg Ala Gly Ile Asp Pro Val Glu Leu Arg Gly Ser Arg Thr Gly Val
            1650                1655                1660

Phe Val Gly Thr Asn Gly Gln His Tyr Val Pro Leu Leu Gln Asp Gly
1665                1670                1675                1680

Asp Glu Asn Phe Asp Gly Tyr Ile Ala Thr Gly Asn Ser Ala Ser Val
                1685                1690                1695

Met Ser Gly Arg Leu Ser Tyr Val Phe Gly Leu Glu Gly Pro Ala Val
            1700                1705                1710

Thr Val Asp Thr Ala Cys Ser Ala Ser Leu Ala Ala Leu His Leu Ala
            1715                1720                1725

Val Gln Ser Leu Arg Arg Gly Glu Cys Asp Tyr Ala Leu Ala Gly Gly
            1730                1735                1740

Ala Thr Val Met Ser Thr Pro Glu Met Leu Val Glu Phe Ala Arg Gln
1745                1750                1755                1760

Arg Ala Val Ser Pro Asp Gly Arg Ser Lys Ala Phe Ala Glu Ala Ala
                1765                1770                1775

Asp Gly Val Gly Leu Ala Glu Gly Ala Gly Met Leu Leu Val Glu Arg
            1780                1785                1790

Leu Ser Glu Ala Gln Lys Lys Gly His Pro Val Leu Ala Val Val Arg
            1795                1800                1805

Gly Ser Ala Val Asn Gln Asp Gly Ala Ser Asn Gly Leu Thr Ala Pro
            1810                1815                1820

Ser Gly Pro Ala Gln Gln Arg Val Ile Arg Glu Ala Leu Ala Asp Ala
1825                1830                1835                1840

Gly Leu Thr Pro Ala Asp Val Asp Ala Val Glu Ala His Gly Thr Gly
                1845                1850                1855

Thr Pro Leu Gly Asp Pro Ile Glu Ala Gly Ala Leu Leu Ala Thr Tyr
            1860                1865                1870

Gly Arg Asp Arg Arg Asp Gly Pro Leu Trp Leu Gly Ser Leu Lys Ser
            1875                1880                1885

Asn Ile Gly His Thr Gln Ala Ala Ala Gly Val Ala Gly Val Ile Lys
            1890                1895                1900

Met Val Leu Ala Leu Arg His Gly Glu Leu Pro Arg Thr Leu His Ala
1905                1910                1915                1920

Ser Thr Ala Ser Ser Arg Ile Asp Trp Asp Ala Gly Ala Val Glu Leu
                1925                1930                1935

Leu Asp Glu Ala Arg Pro Trp Leu Gln Arg Ala Glu Gly Pro Arg Arg
            1940                1945                1950

Ala Gly Ile Ser Ser Phe Gly Ile Ser Gly Thr Asn Ala His Leu Val
            1955                1960                1965

Ile Glu Glu Pro Pro Glu Pro Thr Ala Pro Glu Leu Leu Ala Pro Glu
            1970                1975                1980

Pro Ala Ala Asp Gly Asp Val Trp Ser Glu Glu Trp Trp His Glu Val
1985                1990                1995                2000

Thr Val Pro Leu Met Met Ser Ala His Asn Glu Ala Ala Leu Arg Asp
                2005                2010                2015

Gln Ala Arg Arg Leu Arg Ala Asp Leu Leu Ala His Pro Glu Leu His

-continued

```
                2020                    2025                    2030
Pro  Ala  Asp  Val  Gly  Tyr  Thr  Leu  Ile  Thr  Thr  Arg  Thr  Arg  Phe  Glu
               2035                    2040                    2045
Gln  Arg  Ala  Ala  Val  Val  Gly  Glu  Asn  Phe  Thr  Glu  Leu  Ile  Ala  Ala
               2050                    2055                    2060
Leu  Asp  Asp  Leu  Val  Glu  Gly  Arg  Pro  His  Pro  Leu  Val  Leu  Arg  Gly
2065                    2070                    2075                    2080
Thr  Ala  Gly  Thr  Ser  Asp  Gln  Val  Val  Phe  Val  Phe  Pro  Gly  Gln  Gly
               2085                    2090                    2095
Ser  Gln  Trp  Pro  Glu  Met  Ala  Asp  Gly  Leu  Leu  Ala  Arg  Ser  Ser  Gly
               2100                    2105                    2110
Ser  Gly  Ser  Phe  Leu  Glu  Thr  Ala  Arg  Ala  Cys  Asp  Leu  Ala  Leu  Arg
               2115                    2120                    2125
Pro  His  Leu  Gly  Trp  Ser  Val  Leu  Asp  Val  Leu  Arg  Arg  Glu  Pro  Gly
               2130                    2135                    2140
Ala  Pro  Ser  Leu  Asp  Arg  Val  Asp  Val  Val  Gln  Pro  Val  Leu  Phe  Thr
2145                    2150                    2155                    2160
Met  Met  Val  Ser  Leu  Ala  Glu  Thr  Trp  Arg  Ser  Leu  Gly  Val  Glu  Pro
               2165                    2170                    2175
Ala  Ala  Val  Val  Gly  His  Ser  Gln  Gly  Glu  Ile  Ala  Ala  Ala  Tyr  Val
               2180                    2185                    2190
Ala  Gly  Ala  Leu  Thr  Leu  Asp  Asp  Ala  Ala  Arg  Ile  Val  Ala  Leu  Arg
               2195                    2200                    2205
Ser  Gln  Ala  Trp  Leu  Arg  Leu  Ala  Gly  Lys  Gly  Gly  Met  Val  Ala  Val
               2210                    2215                    2220
Thr  Leu  Ser  Glu  Arg  Asp  Leu  Arg  Pro  Arg  Leu  Glu  Pro  Trp  Ser  Asp
2225                    2230                    2235                    2240
Arg  Leu  Ala  Val  Ala  Ala  Val  Asn  Gly  Pro  Glu  Thr  Cys  Ala  Val  Ser
               2245                    2250                    2255
Gly  Asp  Pro  Asp  Ala  Leu  Ala  Glu  Leu  Val  Ala  Glu  Leu  Gly  Ala  Glu
               2260                    2265                    2270
Gly  Val  His  Ala  Arg  Pro  Ile  Pro  Gly  Val  Asp  Thr  Ala  Gly  His  Ser
               2275                    2280                    2285
Pro  Gln  Val  Asp  Thr  Leu  Glu  Ala  His  Leu  Arg  Lys  Val  Leu  Ala  Pro
               2290                    2295                    2300
Val  Ala  Pro  Arg  Thr  Ser  Asp  Ile  Pro  Phe  Tyr  Ser  Thr  Val  Thr  Gly
2305                    2310                    2315                    2320
Gly  Leu  Ile  Asp  Thr  Ala  Glu  Leu  Asp  Ala  Asp  Tyr  Trp  Tyr  Arg  Asn
               2325                    2330                    2335
Met  Arg  Glu  Pro  Val  Glu  Phe  Glu  Gln  Ala  Thr  Arg  Ala  Leu  Ile  Ala
               2340                    2345                    2350
Asp  Gly  His  Asp  Val  Phe  Leu  Glu  Ser  Ser  Pro  His  Pro  Met  Leu  Ala
               2355                    2360                    2365
Val  Ser  Leu  Gln  Glu  Thr  Ile  Ser  Asp  Ala  Gly  Ser  Pro  Ala  Ala  Val
               2370                    2375                    2380
Leu  Gly  Thr  Leu  Arg  Arg  Gly  Gln  Gly  Gly  Pro  Arg  Trp  Leu  Gly  Val
2385                    2390                    2395                    2400
Ala  Leu  Cys  Arg  Ala  Tyr  Thr  His  Gly  Leu  Glu  Ile  Asp  Ala  Glu  Ala
               2405                    2410                    2415
Ile  Phe  Gly  Pro  Asp  Ser  Arg  Gln  Val  Glu  Leu  Pro  Thr  Tyr  Pro  Phe
               2420                    2425                    2430
Gln  Arg  Glu  Arg  Tyr  Trp  Tyr  Ser  Pro  Gly  His  Arg  Gly  Asp  Asp  Pro
               2435                    2440                    2445
```

```
Ala  Ser  Leu  Gly  Leu  Asp  Ala  Val  Asp  His  Pro  Leu  Leu  Gly  Ser  Gly
     2450                2455                2460

Val  Glu  Leu  Pro  Glu  Ser  Gly  Asp  Arg  Met  Tyr  Thr  Ala  Arg  Leu  Gly
2465                2470                2475                          2480

Ala  Asp  Thr  Thr  Pro  Trp  Leu  Ala  Asp  His  Ala  Leu  Leu  Gly  Ser  Pro
               2485                2490                          2495

Leu  Leu  Pro  Gly  Ala  Ala  Phe  Ala  Asp  Leu  Ala  Leu  Trp  Ala  Gly  Arg
          2500                     2505                     2510

Gln  Ala  Gly  Thr  Gly  Arg  Val  Glu  Glu  Leu  Thr  Leu  Ala  Ala  Pro  Leu
          2515                2520                     2525

Val  Leu  Pro  Gly  Ser  Gly  Gly  Val  Arg  Leu  Arg  Leu  Asn  Val  Gly  Ala
          2530                2535                     2540

Pro  Gly  Thr  Asp  Asp  Ala  Arg  Arg  Phe  Ala  Val  His  Ala  Arg  Ala  Glu
2545                2550                     2555                          2560

Gly  Ala  Thr  Asp  Trp  Thr  Leu  His  Ala  Glu  Gly  Leu  Leu  Thr  Ala  Gln
               2565                2570                          2575

Asp  Thr  Ala  Asp  Ala  Pro  Asp  Ala  Ser  Ala  Ala  Thr  Pro  Pro  Pro  Gly
               2580                2585                          2590

Ala  Glu  Gln  Leu  Asp  Ile  Gly  Asp  Phe  Tyr  Gln  Arg  Phe  Ser  Glu  Leu
          2595                2600                     2605

Gly  Tyr  Gly  Tyr  Gly  Pro  Phe  Phe  Arg  Gly  Leu  Val  Ser  Ala  His  Arg
2610                     2615                     2620

Cys  Gly  Pro  Asp  Ile  His  Ala  Glu  Val  Ala  Leu  Pro  Val  Gln  Ala  Gln
2625                2630                     2635                          2640

Gly  Asp  Ala  Ala  Arg  Phe  Gly  Ile  His  Pro  Ala  Leu  Leu  Asp  Ala  Ala
               2645                2650                          2655

Leu  Gln  Thr  Met  Ser  Leu  Gly  Gly  Phe  Phe  Pro  Glu  Asp  Gly  Arg  Val
               2660                2665                     2670

Arg  Met  Pro  Phe  Ala  Leu  Arg  Gly  Val  Arg  Leu  Tyr  Arg  Ala  Gly  Ala
               2675                2680                     2685

Asp  Arg  Leu  His  Val  Arg  Val  Ser  Pro  Val  Ser  Glu  Asp  Ala  Val  Arg
          2690                2695                     2700

Ile  Arg  Cys  Ala  Asp  Gly  Glu  Gly  Arg  Pro  Val  Ala  Glu  Ile  Glu  Ser
2705                2710                     2715                          2720

Phe  Ile  Met  Arg  Pro  Val  Asp  Pro  Gly  Gln  Leu  Leu  Gly  Gly  Arg  Pro
               2725                2730                          2735

Val  Gly  Ala  Asp  Ala  Leu  Phe  Arg  Ile  Ala  Trp  Arg  Glu  Leu  Ala  Ala
               2740                2745                     2750

Gly  Pro  Gly  Thr  Arg  Thr  Gly  Asp  Gly  Thr  Pro  Pro  Val  Arg  Trp
          2755                2760                     2765

Val  Leu  Ala  Gly  Pro  Asp  Ala  Leu  Gly  Leu  Ala  Glu  Ala  Ala  Asp  Ala
     2770                2775                     2780

His  Leu  Pro  Ala  Val  Pro  Gly  Pro  Asp  Gly  Ala  Leu  Pro  Ser  Pro  Thr
2785                2790                     2795                          2800

Gly  Arg  Pro  Ala  Pro  Asp  Ala  Val  Val  Phe  Ala  Val  Arg  Ala  Gly  Thr
               2805                2810                          2815

Gly  Asp  Val  Ala  Ala  Asp  Ala  His  Thr  Val  Ala  Cys  Arg  Val  Leu  Asp
               2820                2825                          2830

Leu  Val  Gln  Arg  Arg  Leu  Ala  Ala  Pro  Glu  Gly  Pro  Asp  Gly  Ala  Arg
          2835                2840                     2845

Leu  Val  Val  Ala  Thr  Arg  Gly  Ala  Val  Ala  Val  Arg  Asp  Asp  Ala  Glu
          2850                2855                     2860

Val  Asp  Asp  Pro  Ala  Ala  Ala  Ala  Ala  Trp  Gly  Leu  Leu  Arg  Ser  Ala
2865                2870                     2875                          2880
```

-continued

```
Gln Ala Glu Glu Pro Gly Arg Phe Leu Leu Val Asp Leu Asp Asp
              2885                2890                2895
Pro Ala Ser Ala Arg Ala Leu Thr Asp Ala Leu Ala Ser Gly Glu Pro
              2900                2905                2910
Gln Thr Ala Val Arg Ala Gly Thr Val Tyr Val Pro Arg Leu Glu Arg
              2915                2920                2925
Ala Ala Asp Arg Thr Asp Gly Pro Leu Thr Pro Pro Asp Asp Gly Ala
              2930                2935                2940
Trp Arg Leu Gly Arg Gly Thr Asp Leu Thr Leu Asp Gly Leu Ala Leu
2945                2950                2955                2960
Val Pro Ala Pro Asp Ala Glu Ala Pro Leu Glu Pro Gly Gln Val Arg
              2965                2970                2975
Val Ala Val Arg Ala Ala Gly Val Asn Phe Arg Asp Ala Leu Ile Ala
              2980                2985                2990
Leu Gly Met Tyr Pro Gly Glu Ala Glu Met Gly Thr Glu Gly Ala Gly
              2995                3000                3005
Thr Val Val Glu Val Gly Pro Gly Val Thr Gly Val Ala Val Gly Asp
              3010                3015                3020
Arg Val Leu Gly Leu Trp Asp Gly Gly Leu Gly Pro Leu Cys Val Ala
3025                3030                3035                3040
Asp His Arg Leu Leu Ala Pro Val Pro Asp Gly Trp Ser Tyr Ala Gln
              3045                3050                3055
Ala Ala Ser Val Pro Ala Val Phe Leu Ser Ala Tyr Tyr Gly Leu Val
              3060                3065                3070
Thr Leu Ala Gly Leu Arg Pro Gly Glu Arg Val Leu Val His Ala Ala
              3075                3080                3085
Ala Gly Gly Val Gly Met Ala Ala Val Gln Ile Ala Arg His Leu Gly
              3090                3095                3100
Ala Glu Val Leu Ala Thr Ala Ser Pro Gly Lys Trp Asp Ala Leu Arg
3105                3110                3115                3120
Ala Met Gly Ile Thr Asp Asp His Leu Ala Ser Ser Arg Thr Leu Asp
              3125                3130                3135
Phe Ala Thr Ala Phe Thr Gly Ala Asp Gly Thr Ser Arg Ala Asp Val
              3140                3145                3150
Val Leu Asn Ser Leu Thr Lys Glu Phe Val Asp Ala Ser Leu Gly Leu
              3155                3160                3165
Leu Arg Pro Gly Gly Arg Phe Leu Glu Leu Gly Lys Thr Asp Val Arg
              3170                3175                3180
Asp Pro Glu Arg Ile Ala Ala Glu His Pro Gly Val Arg Tyr Arg Ala
3185                3190                3195                3200
Phe Asp Leu Asn Glu Ala Gly Pro Asp Ala Leu Gly Arg Leu Leu Arg
              3205                3210                3215
Glu Leu Met Asp Leu Phe Ala Ala Gly Val Leu His Pro Leu Pro Val
              3220                3225                3230
Val Thr His Asp Val Arg Arg Ala Ala Asp Ala Leu Arg Thr Ile Ser
              3235                3240                3245
Gln Ala Arg His Thr Gly Lys Leu Val Leu Thr Met Pro Pro Ala Trp
              3250                3255                3260
His Pro Tyr Gly Thr Val Leu Val Thr Gly Gly Thr Gly Ala Leu Gly
3265                3270                3275                3280
Ser Arg Ile Ala Arg His Leu Ala Ser Arg His Gly Val Arg Arg Leu
              3285                3290                3295
Leu Ile Ala Ala Arg Arg Gly Pro Asp Gly Glu Gly Ala Ala Glu Leu
```

-continued

```
                      3300                       3305                        3310
Val Ala Asp Leu Ala Ala Leu Gly Ala Ser Ala Thr Val Ala Cys
            3315                   3320                   3325
Asp Val Ser Asp Ala Asp Ala Val Arg Gly Leu Leu Ala Gly Ile Pro
        3330                   3335                   3340
Ala Asp His Pro Leu Thr Ala Val Val His Ser Thr Gly Val Leu Asp
3345                   3350                   3355                       3360
Asp Gly Val Leu Pro Gly Leu Thr Pro Glu Arg Met Arg Arg Val Leu
                3365                   3370                   3375
Arg Pro Lys Val Glu Ala Ala Val His Leu Asp Glu Leu Thr Arg Asp
            3380                   3385                   3390
Leu Asp Leu Ser Ala Phe Val Leu Phe Ser Ser Ala Gly Leu Leu
            3395                   3400                   3405
Gly Ser Pro Ala Gln Gly Asn Tyr Ala Ala Ala Asn Ala Thr Leu Asp
            3410                   3415                   3420
Ala Leu Ala Ala Arg Arg Arg Ser Leu Gly Leu Pro Ser Val Ser Leu
3425                   3430                   3435                       3440
Ala Trp Gly Leu Trp Ser Asp Thr Ser Arg Met Ala His Ala Leu Asp
                3445                   3450                   3455
Gln Glu Ser Leu Gln Arg Arg Phe Ala Arg Ser Gly Phe Pro Pro Leu
                3460                   3465                   3470
Ser Ala Thr Leu Gly Ala Ala Leu Phe Asp Ala Ala Leu Arg Val Asp
            3475                   3480                   3485
Glu Ala Val Gln Val Pro Met Arg Phe Asp Pro Ala Ala Leu Arg Ala
            3490                   3495                   3500
Thr Gly Ser Val Pro Ala Leu Leu Ser Asp Leu Val Gly Ser Ala Pro
3505                   3510                   3515                       3520
Ala Thr Gly Ser Ala Ala Pro Ala Ser Gly Pro Leu Pro Ala Pro Asp
                3525                   3530                   3535
Ala Gly Thr Val Gly Glu Pro Leu Ala Glu Arg Leu Ala Gly Leu Ser
                3540                   3545                   3550
Ala Glu Glu Arg His Asp Arg Leu Leu Gly Leu Val Gly Glu His Val
                3555                   3560                   3565
Ala Ala Val Leu Gly His Gly Ser Ala Ala Glu Val Arg Pro Asp Arg
            3570                   3575                   3580
Pro Phe Arg Glu Val Gly Phe Asp Ser Leu Thr Ala Val Glu Leu Arg
3585                   3590                   3595                       3600
Asn Arg Met Ala Ala Val Thr Gly Val Arg Leu Pro Ala Thr Leu Val
                3605                   3610                   3615
Phe Asp His Pro Thr Pro Ala Ala Leu Ser Ser His Leu Asp Gly Leu
                3620                   3625                   3630
Leu Ala Pro Ala Gln Pro Val Thr Thr Thr Pro Leu Leu Ser Glu Leu
            3635                   3640                   3645
Asp Arg Ile Glu Glu Ala Leu Ala Ala Leu Thr Pro Glu His Leu Ala
        3650                   3655                   3660
Glu Leu Ala Pro Ala Pro Asp Asp Arg Ala Glu Val Ala Leu Arg Leu
3665                   3670                   3675                       3680
Asp Ala Leu Ala Asp Arg Trp Arg Ala Leu His Asp Gly Ala Pro Gly
                3685                   3690                   3695
Ala Asp Asp Asp Ile Thr Asp Val Leu Ser Ser Ala Asp Asp Glu
                3700                   3705                   3710
Ile Phe Ala Phe Ile Asp Glu Arg Tyr Gly Thr Ser
        3715                   3720
```

( 2 ) INFORMATION FOR SEQ ID NO:11:

( i ) SEQUENCE CHARACTERISTICS:
        ( A ) LENGTH: 1580 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:11:

```
Met Ala Asn Glu Glu Lys Leu Arg Ala Tyr Leu Lys Arg Val Thr Gly
 1               5                  10                  15
Glu Leu His Arg Ala Thr Glu Gln Leu Arg Ala Leu Asp Arg Arg Ala
                20                  25                  30
His Glu Pro Ile Ala Ile Val Gly Ala Ala Cys Arg Leu Pro Gly Gly
                35                  40                  45
Val Glu Ser Pro Asp Asp Leu Trp Glu Leu Leu His Ala Gly Ala Asp
 50                  55                  60
Ala Val Gly Pro Ala Pro Ala Asp Arg Gly Trp Asp Val Glu Gly Arg
 65                  70                  75                  80
Tyr Ser Pro Asp Pro Asp Thr Pro Gly Thr Ser Tyr Cys Arg Glu Gly
                85                  90                  95
Gly Phe Val Gln Gly Ala Asp Arg Phe Asp Pro Ala Leu Phe Gly Ile
                100                 105                 110
Ser Pro Asn Glu Ala Leu Thr Met Asp Pro Gln Gln Arg Leu Leu Leu
                115                 120                 125
Glu Thr Ser Trp Glu Ala Leu Glu Arg Ala Gly Leu Asp Pro Gln Ser
    130                 135                 140
Leu Ala Gly Ser Arg Thr Gly Val Phe Ala Gly Ala Trp Glu Ser Gly
145                 150                 155                 160
Tyr Gln Lys Gly Val Glu Gly Leu Glu Ala Asp Leu Glu Ala Gln Leu
                165                 170                 175
Leu Ala Gly Ile Val Ser Phe Thr Ala Gly Arg Val Ala Tyr Ala Leu
                180                 185                 190
Gly Leu Glu Gly Pro Ala Leu Thr Ile Asp Thr Ala Cys Ser Ser Ser
    195                 200                 205
Leu Val Ala Leu His Leu Ala Val Gln Ser Leu Arg Arg Gly Glu Cys
    210                 215                 220
Asp Leu Ala Leu Ala Gly Gly Ala Thr Val Ile Ala Asp Phe Ala Leu
225                 230                 235                 240
Phe Thr Gln Phe Ser Arg Gln Arg Gly Leu Ala Pro Asp Gly Arg Cys
                245                 250                 255
Lys Ala Phe Gly Glu Thr Ala Asp Gly Phe Gly Pro Ala Glu Gly Ala
                260                 265                 270
Gly Met Leu Leu Val Glu Arg Leu Ser Asp Ala Arg Arg Asn Gly His
    275                 280                 285
Pro Val Leu Ala Val Val Arg Gly Ser Ala Val Asn Gln Asp Gly Ala
    290                 295                 300
Ser Asn Gly Leu Thr Ala Pro Ser Gly Pro Ala Gln Gln Arg Val Ile
305                 310                 315                 320
Arg Glu Ala Leu Ala Asp Ala Gly Leu Thr Pro Ala Asp Val Asp Ala
                325                 330                 335
Val Glu Ala His Gly Thr Gly Thr Pro Leu Gly Asp Pro Ile Glu Ala
                340                 345                 350
Gly Ala Leu Met Ala Thr Tyr Gly His Glu Arg Thr Gly Asp Pro Leu
    355                 360                 365
```

| | | | | | | | | | | | | |
|---|---|---|---|---|---|---|---|---|---|---|---|---|
| Trp | Leu 370 | Gly | Ser | Leu | Lys 375 | Ser | Asn | Ile | Gly | His 380 | Thr | Gln | Ala | Ala | Ala |
| Gly 385 | Val | Ala | Gly | Val 390 | Ile | Lys | Met | Val | Leu 395 | Ala | Leu | Arg | His | Gly | Glu 400 |
| Leu | Pro | Arg | Thr | Leu 405 | His | Ala | Ser | Thr | Ala 410 | Ser | Ser | Arg | Ile | Glu 415 | Trp |
| Asp | Ala | Gly | Ala 420 | Val | Glu | Leu | Leu | Asp 425 | Glu | Ala | Arg | Pro | Trp 430 | Pro | Arg |
| Arg | Ala | Glu 435 | Gly | Pro | Arg | Arg | Ala 440 | Gly | Ile | Ser | Ser | Phe 445 | Gly | Ile | Ser |
| Gly | Thr 450 | Asn | Ala | His | Leu | Val 455 | Ile | Glu | Glu | Glu | Pro 460 | Pro | Ala | Arg | Pro |
| Glu 465 | Pro | Glu | Glu | Ala | Ala 470 | Gln | Pro | Pro | Ala | Pro 475 | Ala | Thr | Thr | Val | Leu 480 |
| Pro | Leu | Ser | Ala | Ala 485 | Gly | Ala | Arg | Ser | Leu 490 | Arg | Glu | Gln | Ala | Arg 495 | Arg |
| Leu | Ala | Ala | His 500 | Leu | Ala | Gly | His | Glu 505 | Glu | Ile | Thr | Ala | Ala 510 | Asp | Ala |
| Ala | Arg | Ser 515 | Ala | Ala | Thr | Thr | Arg 520 | Ala | Ala | Leu | Ser | His 525 | Arg | Ala | Ser |
| Val | Leu 530 | Ala | Asp | Asp | Arg | Arg 535 | Ala | Leu | Ile | Asp | Arg 540 | Leu | Thr | Ala | Leu |
| Ala 545 | Glu | Asp | Arg | Lys | Asp 550 | Pro | Gly | Val | Thr | Val 555 | Gly | Glu | Ala | Gly | Ser 560 |
| Gly | Arg | Pro | Pro | Val 565 | Phe | Val | Phe | Pro | Gly 570 | Gln | Gly | Ser | Gln | Trp 575 | Thr |
| Gly | Met | Gly | Ala 580 | Glu | Leu | Leu | Asp | Arg 585 | Ala | Pro | Val | Phe | Arg 590 | Ala | Lys |
| Ala | Glu | Glu 595 | Cys | Ala | Arg | Ala | Leu 600 | Ala | Ala | His | Leu | Asp 605 | Trp | Ser | Val |
| Leu | Asp 610 | Val | Leu | Arg | Asp | Ala 615 | Pro | Gly | Ala | Pro | Pro 620 | Ile | Asp | Arg | Ala |
| Asp 625 | Val | Val | Gln | Pro | Thr 630 | Leu | Phe | Thr | Met | Met 635 | Val | Ser | Leu | Ala | Ala 640 |
| Leu | Trp | Glu | Ser | His 645 | Gly | Val | Arg | Pro | Ala 650 | Val | Val | Gly | His | Ser 655 |
| Gln | Gly | Glu | Ile 660 | Ala | Ala | Ala | His | Ala 665 | Ala | Gly | Ala | Leu | Ser 670 | Leu | Asp |
| Asp | Ala | Ala | Arg 675 | Val | Ile | Ala | Glu | Arg 680 | Ser | Arg | Leu | Trp 685 | Lys | Arg | Leu |
| Ala | Gly 690 | Asn | Gly | Gly | Met | Leu 695 | Ser | Val | Met | Ala | Pro 700 | Ala | Asp | Arg | Val |
| Arg 705 | Glu | Leu | Met | Glu | Pro 710 | Trp | Ala | Glu | Arg | Met 715 | Ser | Val | Ala | Ala | Val 720 |
| Asn | Gly | Pro | Ala | Ser 725 | Val | Thr | Val | Ala | Gly 730 | Asp | Ala | Arg | Ala | Leu 735 | Glu |
| Glu | Phe | Gly | Gly 740 | Arg | Leu | Ser | Ala | Ala 745 | Gly | Val | Leu | Arg | Trp 750 | Pro | Leu |
| Ala | Gly | Val 755 | Asp | Phe | Ala | Gly | His 760 | Ser | Pro | Gln | Val | Glu 765 | Gln | Phe | Arg |
| Ala | Glu 770 | Leu | Leu | Asp | Thr | Leu 775 | Gly | Thr | Val | Arg | Pro 780 | Thr | Ala | Ala | Arg |
| Leu | Pro | Phe | Phe | Ser | Thr | Val | Thr | Ala | Ala | Ala | His | Glu | Pro | Glu | Gly |

-continued

```
            785                     790                     795                     800
Leu  Asp  Ala  Ala  Tyr  Trp  Tyr  Arg  Asn  Met  Arg  Glu  Pro  Val  Glu  Phe
                    805                     810                     815

Ala  Ser  Thr  Leu  Arg  Thr  Leu  Leu  Arg  Glu  Gly  His  Arg  Thr  Phe  Val
                    820                     825                     830

Glu  Met  Gly  Pro  His  Pro  Leu  Leu  Gly  Ala  Ala  Ile  Asp  Glu  Val  Ala
                    835                     840                     845

Glu  Ala  Glu  Gly  Val  His  Ala  Thr  Ala  Leu  Ala  Thr  Leu  His  Arg  Gly
          850                     855                     860

Ser  Gly  Gly  Leu  Asp  Arg  Phe  Arg  Ser  Ser  Val  Gly  Ala  Ala  Phe  Ala
865                     870                     875                     880

His  Gly  Val  Arg  Val  Asp  Trp  Asp  Ala  Leu  Phe  Glu  Gly  Ser  Gly  Ala
                    885                     890                     895

Arg  Arg  Val  Pro  Leu  Pro  Thr  Tyr  Ala  Phe  Ser  Arg  Asp  Arg  Tyr  Trp
                    900                     905                     910

Leu  Pro  Thr  Ala  Ile  Gly  Arg  Arg  Ala  Val  Glu  Ala  Ala  Pro  Val  Asp
                    915                     920                     925

Ala  Ser  Ala  Pro  Gly  Arg  Tyr  Arg  Val  Thr  Trp  Thr  Pro  Val  Ala  Ser
          930                     935                     940

Asp  Asp  Ser  Gly  Arg  Pro  Ser  Gly  Arg  Trp  Leu  Leu  Val  Gln  Thr  Pro
945                     950                     955                     960

Gly  Thr  Ala  Pro  Asp  Glu  Ala  Asp  Thr  Ala  Ala  Ser  Ala  Leu  Gly  Ala
                    965                     970                     975

Ala  Gly  Val  Val  Val  Glu  Arg  Cys  Leu  Leu  Asp  Pro  Thr  Glu  Ala  Ala
                    980                     985                     990

Arg  Val  Thr  Leu  Thr  Glu  Arg  Leu  Ala  Glu  Leu  Asp  Ala  Gln  Pro  Glu
                    995                     1000                    1005

Gly  Leu  Ala  Gly  Val  Leu  Val  Leu  Pro  Gly  Arg  Pro  Gln  Ser  Thr  Ala
          1010                    1015                    1020

Pro  Ala  Asp  Ala  Ser  Pro  Leu  Asp  Pro  Gly  Thr  Ala  Ala  Val  Leu  Leu
1025                    1030                    1035                    1040

Val  Val  Gln  Ala  Val  Pro  Asp  Ala  Ala  Pro  Lys  Ala  Arg  Ile  Trp  Val
                    1045                    1050                    1055

Val  Thr  Arg  Gly  Ala  Val  Ala  Val  Gly  Ser  Gly  Glu  Val  Pro  Cys  Ala
                    1060                    1065                    1070

Val  Gly  Ala  Arg  Val  Trp  Gly  Leu  Gly  Arg  Val  Ala  Ala  Leu  Glu  Val
                    1075                    1080                    1085

Pro  Val  Gln  Trp  Gly  Gly  Leu  Val  Asp  Val  Ala  Val  Gly  Ala  Gly  Val
                    1090                    1095                    1100

Arg  Glu  Trp  Arg  Arg  Val  Val  Gly  Val  Val  Ala  Gly  Gly  Gly  Glu  Asp
1105                    1110                    1115                    1120

Gln  Val  Ala  Val  Arg  Gly  Gly  Gly  Val  Phe  Gly  Arg  Arg  Leu  Val  Gly
                    1125                    1130                    1135

Val  Gly  Val  Arg  Gly  Gly  Ser  Gly  Val  Trp  Arg  Ala  Arg  Gly  Cys  Val
                    1140                    1145                    1150

Val  Val  Thr  Gly  Gly  Leu  Gly  Gly  Val  Gly  Gly  His  Val  Ala  Arg  Trp
                    1155                    1160                    1165

Leu  Ala  Arg  Ser  Gly  Ala  Glu  His  Val  Val  Leu  Ala  Gly  Arg  Arg  Gly
                    1170                    1175                    1180

Gly  Gly  Val  Val  Gly  Ala  Val  Glu  Leu  Glu  Arg  Glu  Leu  Val  Gly  Leu
1185                    1190                    1195                    1200

Gly  Ala  Lys  Val  Thr  Phe  Val  Ser  Cys  Asp  Val  Gly  Asp  Arg  Ala  Ser
                    1205                    1210                    1215
```

Met Val Gly Leu Leu Gly Val Val Glu Gly Leu Gly Val Pro Leu Arg
            1220                1225                1230

Gly Val Phe His Ala Ala Gly Val Ala Gln Val Ser Gly Leu Gly Glu
            1235                1240                1245

Val Ser Leu Ala Glu Ala Gly Gly Val Leu Gly Gly Lys Ala Val Gly
        1250                1255                1260

Ala Glu Leu Leu Asp Glu Leu Thr Ala Gly Val Glu Leu Asp Ala Phe
1265                1270                1275                1280

Val Leu Phe Ser Ser Gly Ala Gly Val Trp Gly Ser Gly Gly Gln Ser
            1285                1290                1295

Val Tyr Ala Ala Ala Asn Ala His Leu Asp Ala Leu Ala Glu Arg Arg
            1300                1305                1310

Arg Ala Gln Gly Arg Pro Ala Thr Ser Val Ala Trp Gly Leu Trp Gly
            1315                1320                1325

Gly Glu Gly Met Gly Ala Asp Glu Gly Val Thr Glu Phe Tyr Ala Glu
            1330                1335                1340

Arg Gly Leu Ala Pro Met Arg Pro Glu Ser Gly Ile Glu Ala Leu His
1345                1350                1355                1360

Thr Ala Leu Asn Glu Gly Asp Thr Cys Val Thr Val Ala Asp Ile Asp
            1365                1370                1375

Trp Glu His Phe Val Thr Gly Phe Thr Ala Tyr Arg Pro Ser Pro Leu
            1380                1385                1390

Ile Ser Asp Ile Pro Gln Val Arg Ala Leu Arg Thr Pro Glu Pro Thr
            1395                1400                1405

Val Asp Ala Ser Asp Gly Leu Arg Arg Arg Val Asp Ala Ala Leu Thr
            1410                1415                1420

Pro Arg Glu Arg Thr Lys Val Leu Val Asp Leu Val Arg Thr Val Ala
1425                1430                1435                1440

Ala Glu Val Leu Gly His Asp Gly Ile Gly Gly Ile Gly His Asp Val
            1445                1450                1455

Ala Phe Arg Asp Leu Gly Phe Asp Ser Leu Ala Ala Val Arg Met Arg
            1460                1465                1470

Gly Arg Leu Ala Glu Ala Thr Gly Leu Val Leu Pro Ala Thr Val Ile
            1475                1480                1485

Phe Asp His Pro Thr Val Asp Arg Leu Gly Gly Ala Leu Leu Glu Arg
            1490                1495                1500

Leu Ser Ala Asp Glu Pro Ala Pro Gly Gly Ala Pro Glu Pro Ala Gly
1505                1510                1515                1520

Gly Arg Pro Ala Thr Pro Pro Pro Ala Pro Glu Pro Ala Val His Asp
            1525                1530                1535

Ala Asp Ile Asp Glu Leu Asp Ala Asp Ala Leu Ile Arg Leu Ala Thr
            1540                1545                1550

Gly Thr Ala Gly Pro Ala Asp Gly Thr Pro Ala Asp Gly Gly Pro Asp
            1555                1560                1565

Ala Ala Ala Thr Ala Pro Asp Gly Ala Pro Glu Gln
            1570                1575                1580

( 2 ) INFORMATION FOR SEQ ID NO:12:

( i ) SEQUENCE CHARACTERISTICS:
        ( A ) LENGTH: 1891 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:12:

| | | | | | | | | | | | | | | |
|---|---|---|---|---|---|---|---|---|---|---|---|---|---|---|
| Met | Ser | Pro | Ser | Met | Asp | Glu | Val | Leu | Gly | Ala | Leu | Arg | Thr | Ser | Val |
| 1 | | | | 5 | | | | | 10 | | | | | 15 | |
| Lys | Glu | Thr | Glu | Arg | Leu | Arg | Arg | His | Asn | Arg | Glu | Leu | Leu | Ala | Gly |
| | | | 20 | | | | | 25 | | | | | 30 | | |
| Ala | His | Glu | Pro | Val | Ala | Ile | Val | Gly | Met | Ala | Cys | Arg | Tyr | Pro | Gly |
| | | 35 | | | | | 40 | | | | | 45 | | | |
| Gly | Val | Ser | Thr | Pro | Asp | Asp | Leu | Trp | Glu | Leu | Ala | Ala | Asp | Gly | Val |
| | 50 | | | | | 55 | | | | | 60 | | | | |
| Asp | Ala | Ile | Thr | Pro | Phe | Pro | Ala | Asp | Arg | Gly | Trp | Asp | Glu | Asp | Ala |
| 65 | | | | 70 | | | | | 75 | | | | | 80 | |
| Val | Tyr | Ser | Pro | Asp | Pro | Asp | Thr | Pro | Gly | Thr | Thr | Tyr | Cys | Arg | Glu |
| | | | | 85 | | | | | 90 | | | | | 95 | |
| Gly | Gly | Phe | Leu | Thr | Gly | Ala | Gly | Asp | Phe | Asp | Ala | Ala | Phe | Phe | Gly |
| | | | 100 | | | | | 105 | | | | | 110 | | |
| Ile | Ser | Pro | Asn | Glu | Ala | Leu | Val | Met | Asp | Pro | Gln | Gln | Arg | Leu | Leu |
| | | | 115 | | | | | 120 | | | | | 125 | | |
| Leu | Glu | Thr | Ser | Trp | Glu | Thr | Leu | Glu | Arg | Ala | Gly | Ile | Val | Pro | Ala |
| | | 130 | | | | | 135 | | | | | 140 | | | |
| Ser | Leu | Arg | Gly | Ser | Arg | Thr | Gly | Val | Phe | Val | Gly | Ala | Ala | His | Thr |
| 145 | | | | | 150 | | | | | 155 | | | | | 160 |
| Gly | Tyr | Val | Thr | Asp | Thr | Ala | Arg | Ala | Pro | Glu | Gly | Thr | Glu | Gly | Tyr |
| | | | | 165 | | | | | 170 | | | | | 175 | |
| Leu | Leu | Thr | Gly | Asn | Ala | Asp | Ala | Val | Met | Ser | Gly | Arg | Ile | Ala | Tyr |
| | | | | 180 | | | | | 185 | | | | | 190 | |
| Ser | Leu | Gly | Leu | Glu | Gly | Pro | Ala | Leu | Thr | Ile | Gly | Thr | Ala | Cys | Ser |
| | | | 195 | | | | | 200 | | | | | 205 | | |
| Ser | Ser | Leu | Val | Ala | Leu | His | Leu | Ala | Val | Gln | Ser | Leu | Arg | Arg | Gly |
| | 210 | | | | | 215 | | | | | 220 | | | | |
| Glu | Cys | Asp | Leu | Ala | Leu | Ala | Gly | Gly | Val | Ala | Val | Met | Pro | Asp | Pro |
| 225 | | | | | 230 | | | | | 235 | | | | | 240 |
| Thr | Val | Phe | Val | Glu | Phe | Ser | Arg | Gln | Arg | Gly | Leu | Ala | Val | Asp | Gly |
| | | | | 245 | | | | | 250 | | | | | 255 | |
| Arg | Cys | Lys | Ala | Phe | Ala | Glu | Gly | Ala | Asp | Gly | Thr | Ala | Trp | Ala | Glu |
| | | | 260 | | | | | 265 | | | | | 270 | | |
| Gly | Val | Gly | Val | Leu | Leu | Val | Glu | Arg | Leu | Ser | Asp | Ala | Arg | Arg | Asn |
| | | | 275 | | | | | 280 | | | | | 285 | | |
| Gly | His | Arg | Val | Leu | Ala | Val | Val | Arg | Gly | Ser | Ala | Val | Asn | Gln | Asp |
| | | 290 | | | | | 295 | | | | | 300 | | | |
| Gly | Ala | Ser | Asn | Gly | Leu | Thr | Ala | Pro | Ser | Gly | Pro | Ala | Gln | Gln | Arg |
| 305 | | | | | 310 | | | | | 315 | | | | | 320 |
| Val | Ile | Arg | Glu | Ala | Leu | Ala | Asp | Ala | Gly | Leu | Thr | Pro | Ala | Asp | Val |
| | | | | 325 | | | | | 330 | | | | | 335 | |
| Asp | Val | Val | Glu | Ala | His | Gly | Thr | Gly | Thr | Ala | Leu | Gly | Asp | Pro | Ile |
| | | | 340 | | | | | 345 | | | | | 350 | | |
| Glu | Ala | Gly | Ala | Leu | Leu | Ala | Thr | Tyr | Gly | Arg | Glu | Arg | Val | Gly | Asp |
| | | | 355 | | | | | 360 | | | | | 365 | | |
| Pro | Leu | Trp | Leu | Gly | Ser | Leu | Lys | Ser | Asn | Ile | Gly | His | Ala | Gln | Ala |
| | | | 370 | | | | | 375 | | | | | 380 | | |
| Ala | Ala | Gly | Val | Gly | Gly | Val | Ile | Lys | Val | Val | Gln | Ala | Met | Arg | His |
| 385 | | | | | 390 | | | | | 395 | | | | | 400 |
| Gly | Ser | Leu | Pro | Arg | Thr | Leu | His | Val | Asp | Ala | Pro | Ser | Ser | Lys | Val |
| | | | | 405 | | | | | 410 | | | | | 415 | |
| Glu | Trp | Ala | Ser | Gly | Ala | Val | Glu | Leu | Leu | Thr | Glu | Gly | Arg | Ser | Trp |

-continued

```
                            420                        425                        430
Pro  Arg  Arg  Val  Glu  Arg  Val  Arg  Ala  Ala  Val  Ser  Ala  Phe  Gly
          435                      440                      445
Val  Ser  Gly  Thr  Asn  Ala  His  Val  Val  Leu  Glu  Glu  Ala  Pro  Val  Glu
450                                455                      460
Ala  Gly  Ser  Glu  His  Gly  Asp  Gly  Pro  Gly  Pro  Asp  Arg  Pro  Asp  Ala
465                      470                      475                      480
Val  Thr  Gly  Pro  Leu  Pro  Trp  Val  Leu  Ser  Ala  Arg  Ser  Arg  Glu  Ala
                    485                      490                      495
Leu  Arg  Gly  Gln  Ala  Gly  Arg  Leu  Ala  Ala  Leu  Ala  Arg  Gln  Gly  Arg
               500                      505                      510
Thr  Glu  Gly  Thr  Gly  Gly  Gly  Ser  Gly  Leu  Val  Val  Pro  Ala  Ala  Asp
          515                      520                      525
Ile  Gly  Tyr  Ser  Leu  Ala  Thr  Thr  Arg  Glu  Thr  Leu  Glu  His  Arg  Ala
     530                      535                      540
Val  Ala  Leu  Val  Gln  Glu  Asn  Arg  Thr  Ala  Gly  Glu  Asp  Leu  Ala  Ala
545                      550                      555                      560
Leu  Ala  Ala  Gly  Arg  Thr  Pro  Glu  Ser  Val  Val  Thr  Gly  Val  Ala  Arg
               565                      570                      575
Arg  Gly  Arg  Gly  Ile  Ala  Phe  Leu  Cys  Ser  Gly  Gln  Gly  Ala  Gln  Arg
               580                      585                      590
Leu  Gly  Ala  Gly  Arg  Glu  Leu  Arg  Gly  Arg  Phe  Pro  Val  Phe  Ala  Asp
          595                      600                      605
Ala  Leu  Asp  Glu  Ile  Ala  Ala  Glu  Phe  Asp  Ala  His  Leu  Glu  Arg  Pro
     610                      615                      620
Leu  Leu  Ser  Val  Met  Phe  Ala  Glu  Pro  Ala  Thr  Pro  Asp  Ala  Ala  Leu
625                      630                      635                      640
Leu  Asp  Arg  Thr  Asp  Tyr  Thr  Gln  Pro  Ala  Leu  Phe  Ala  Val  Glu  Thr
               645                      650                      655
Ala  Leu  Phe  Arg  Leu  Leu  Glu  Ser  Trp  Gly  Leu  Val  Pro  Asp  Val  Leu
               660                      665                      670
Val  Gly  His  Ser  Ile  Gly  Gly  Leu  Val  Ala  Ala  His  Val  Ala  Gly  Val
          675                      680                      685
Phe  Ser  Ala  Ala  Asp  Ala  Ala  Arg  Leu  Val  Ser  Ala  Arg  Gly  Arg  Leu
     690                      695                      700
Met  Arg  Ala  Leu  Pro  Glu  Gly  Gly  Ala  Met  Ala  Ala  Val  Gln  Ala  Thr
705                      710                      715                      720
Glu  Arg  Glu  Ala  Ala  Ala  Leu  Glu  Pro  Val  Ala  Ala  Gly  Gly  Ala  Val
               725                      730                      735
Val  Ala  Ala  Val  Asn  Gly  Pro  Gln  Ala  Leu  Val  Leu  Ser  Gly  Asp  Glu
               740                      745                      750
Ala  Ala  Val  Leu  Ala  Ala  Ala  Gly  Glu  Leu  Ala  Ala  Arg  Gly  Arg  Arg
          755                      760                      765
Thr  Lys  Arg  Leu  Arg  Val  Ser  His  Ala  Phe  His  Ser  Pro  Arg  Met  Asp
     770                      775                      780
Ala  Met  Leu  Ala  Asp  Phe  Arg  Ala  Val  Ala  Asp  Thr  Val  Asp  Tyr  His
785                      790                      795                      800
Ala  Pro  Arg  Leu  Pro  Val  Val  Ser  Glu  Val  Thr  Gly  Asp  Leu  Ala  Asp
                    805                      810                      815
Ala  Ala  Gln  Leu  Thr  Asp  Pro  Gly  Tyr  Trp  Thr  Arg  Gln  Val  Arg  Gln
               820                      825                      830
Pro  Val  Arg  Phe  Ala  Asp  Ala  Val  Arg  Thr  Ala  Ser  Ala  Arg  Asp  Ala
          835                      840                      845
```

```
Ala  Thr  Phe  Ile  Glu  Leu  Gly  Pro  Asp  Ala  Val  Leu  Cys  Gly  Met  Ala
     850                 855                 860

Glu  Glu  Ser  Leu  Ala  Ala  Glu  Ala  Asp  Val  Val  Phe  Ala  Pro  Ala  Leu
865                      870                 875                           880

Arg  Arg  Gly  Arg  Pro  Glu  Gly  Asp  Thr  Val  Leu  Arg  Ala  Ala  Ala  Ser
               885                      890                      895

Ala  Tyr  Val  Arg  Gly  Ala  Gly  Leu  Asp  Trp  Ala  Ala  Leu  Tyr  Gly  Gly
               900                 905                      910

Thr  Gly  Ala  Arg  Arg  Thr  Asp  Leu  Pro  Thr  Tyr  Ala  Phe  Gln  His  Ser
     915                      920                      925

Arg  Tyr  Trp  Leu  Ala  Pro  Ala  Ser  Ala  Ala  Val  Ala  Pro  Ala  Thr  Ala
     930                 935                      940

Ala  Pro  Ser  Val  Arg  Ser  Val  Pro  Glu  Ala  Glu  Gln  Asp  Gly  Ala  Leu
945                      950                      955                           960

Trp  Ala  Ala  Val  His  Ala  Gly  Asp  Val  Ala  Ser  Ala  Ala  Ala  Arg  Leu
                    965                      970                      975

Gly  Ala  Asp  Asp  Ala  Gly  Ile  Glu  His  Glu  Leu  Arg  Ala  Val  Leu  Pro
               980                      985                      990

His  Leu  Ala  Ala  Trp  His  Asp  Asp  Arg  Ala  Thr  Ala  Arg  Thr  Ala
                    995                 1000                1005

Gly  Leu  His  Tyr  Arg  Val  Thr  Trp  Gln  Ala  Ile  Glu  Ala  Asp  Ala  Val
     1010                     1015                1020

Arg  Phe  Ser  Pro  Ser  Asp  Arg  Trp  Leu  Met  Val  Glu  His  Gly  Gln  His
1025                     1030                1035                          1040

Thr  Glu  Cys  Ala  Asp  Ala  Ala  Glu  Arg  Ala  Leu  Arg  Ala  Ala  Gly  Ala
               1045                     1050                     1055

Glu  Val  Thr  Arg  Leu  Val  Trp  Pro  Leu  Glu  Gln  His  Thr  Gly  Ser  Pro
          1060                     1065                     1070

Arg  Thr  Glu  Thr  Pro  Asp  Arg  Gly  Thr  Leu  Ala  Ala  Arg  Leu  Ala  Glu
          1075                     1080                     1085

Leu  Ala  Arg  Ser  Pro  Glu  Gly  Leu  Ala  Gly  Val  Leu  Leu  Leu  Pro  Asp
     1090                     1095                     1100

Ser  Gly  Gly  Ala  Ala  Val  Ala  Gly  His  Pro  Gly  Leu  Asp  Gln  Gly  Thr
1105                     1110                     1115                     1120

Ala  Ala  Val  Leu  Leu  Thr  Ile  Gln  Ala  Leu  Thr  Asp  Ala  Ala  Val  Arg
                    1125                     1130                     1135

Ala  Pro  Leu  Trp  Val  Val  Thr  Arg  Gly  Ala  Val  Ala  Val  Gly  Ser  Gly
               1140                     1145                     1150

Glu  Val  Pro  Cys  Ala  Val  Gly  Ala  Arg  Val  Trp  Gly  Leu  Gly  Arg  Val
               1155                     1160                     1165

Ala  Ala  Leu  Glu  Val  Pro  Val  Gln  Trp  Gly  Gly  Leu  Val  Asp  Val  Ala
     1170                     1175                     1180

Val  Gly  Ala  Gly  Val  Arg  Glu  Trp  Arg  Arg  Val  Val  Gly  Val  Val  Ala
1185                     1190                     1195                     1200

Gly  Gly  Gly  Glu  Asp  Gln  Val  Ala  Val  Arg  Gly  Gly  Gly  Val  Phe  Gly
               1205                     1210                     1215

Arg  Arg  Leu  Val  Gly  Val  Gly  Val  Arg  Gly  Gly  Ser  Gly  Val  Trp  Arg
               1220                     1225                     1230

Ala  Arg  Gly  Cys  Val  Val  Val  Thr  Gly  Gly  Leu  Gly  Gly  Val  Gly  Gly
               1235                     1240                     1245

His  Val  Ala  Arg  Trp  Leu  Ala  Arg  Ser  Gly  Ala  Glu  His  Val  Val  Leu
     1250                     1255                     1260

Ala  Gly  Arg  Arg  Gly  Gly  Gly  Val  Val  Gly  Ala  Val  Glu  Leu  Glu  Arg
1265                     1270                     1275                     1280
```

```
Glu Leu Val Gly Leu Gly Ala Lys Val Thr Phe Val Ser Cys Asp Val
                1285                1290                1295

Gly Asp Arg Ala Ser Val Val Gly Leu Leu Gly Val Val Glu Gly Leu
                1300                1305                1310

Gly Val Pro Leu Arg Gly Val Phe His Ala Ala Gly Val Ala Gln Val
                1315                1320                1325

Ser Gly Leu Gly Glu Val Ser Leu Ala Glu Ala Gly Gly Val Leu Gly
                1330                1335                1340

Gly Lys Ala Val Gly Ala Glu Leu Leu Asp Glu Leu Thr Ala Gly Val
1345                1350                1355                1360

Glu Leu Asp Ala Phe Val Leu Phe Ser Ser Gly Ala Gly Val Trp Gly
                1365                1370                1375

Ser Gly Gly Gln Ser Val Tyr Ala Ala Ala Asn Ala His Leu Asp Ala
                1380                1385                1390

Leu Ala Glu Arg Arg Arg Ala Gln Gly Arg Pro Ala Thr Ser Val Ala
                1395                1400                1405

Trp Gly Pro Trp Asp Gly Asp Gly Met Gly Glu Met Ala Pro Glu Gly
                1410                1415                1420

Tyr Phe Ala Arg His Gly Val Ala Pro Leu His Pro Glu Thr Ala Leu
1425                1430                1435                1440

Thr Ala Leu His Gln Ala Ile Asp Gly Gly Glu Ala Thr Val Thr Val
                1445                1450                1455

Ala Asp Ile Asp Trp Glu Arg Phe Ala Pro Gly Phe Thr Ala Phe Arg
                1460                1465                1470

Pro Ser Pro Leu Ile Ala Gly Ile Pro Ala Ala Arg Thr Ala Pro Ala
                1475                1480                1485

Ala Gly Arg Pro Ala Glu Asp Thr Pro Thr Ala Pro Gly Leu Leu Arg
                1490                1495                1500

Ala Arg Pro Glu Asp Arg Pro Arg Leu Ala Leu Asp Leu Val Leu Arg
1505                1510                1515                1520

His Val Ala Ala Val Leu Gly His Ser Glu Asp Ala Arg Val Asp Ala
                1525                1530                1535

Arg Ala Pro Phe Arg Asp Leu Gly Phe Asp Ser Leu Ala Ala Val Arg
                1540                1545                1550

Leu Arg Arg Arg Leu Ala Glu Asp Thr Gly Leu Asp Leu Pro Gly Thr
                1555                1560                1565

Leu Val Phe Asp His Glu Asp Pro Thr Ala Leu Ala His His Leu Ala
                1570                1575                1580

Gly Leu Ala Asp Ala Gly Thr Pro Gly Pro Gln Glu Gly Thr Ala Arg
1585                1590                1595                1600

Ala Glu Ser Gly Leu Phe Ala Ser Phe Arg Ala Ala Val Glu Gln Arg
                1605                1610                1615

Arg Ser Ser Glu Val Val Glu Leu Met Ala Asp Leu Ala Ala Phe Arg
                1620                1625                1630

Pro Ala Tyr Ser Arg Gln His Pro Gly Ser Gly Arg Pro Ala Pro Val
                1635                1640                1645

Pro Leu Ala Thr Gly Pro Ala Thr Arg Pro Thr Leu Tyr Cys Cys Ala
                1650                1655                1660

Gly Thr Ala Val Gly Ser Gly Pro Ala Glu Tyr Val Pro Phe Ala Glu
1665                1670                1675                1680

Gly Leu Arg Gly Val Arg Glu Thr Val Ala Leu Pro Leu Ser Gly Phe
                1685                1690                1695

Gly Asp Pro Ala Glu Pro Met Pro Ala Ser Leu Asp Ala Leu Ile Glu
```

|  | | | 1700 | | | | | | | 1705 | | | | | | | 1710 | | |
|---|---|---|---|---|---|---|---|---|---|---|---|---|---|---|---|---|---|---|---|
| Val | Gln | Ala | Asp | Val | Leu | Leu | Glu | His | Thr | Ala | Gly | Lys | Pro | Phe | Ala |
|  |  |  | 1715 |  |  |  | 1720 |  |  |  |  | 1725 |  |  |  |
| Leu | Ala | Gly | His | Ser | Ala | Gly | Ala | Asn | Ile | Ala | His | Ala | Leu | Ala | Ala |
|  |  |  | 1730 |  |  | 1735 |  |  |  |  | 1740 |  |  |  |  |
| Arg | Leu | Glu | Glu | Arg | Gly | Ser | Gly | Pro | Ala | Ala | Val | Val | Leu | Met | Asp |
| 1745 |  |  |  |  | 1750 |  |  |  |  | 1755 |  |  |  |  | 1760 |
| Val | Tyr | Arg | Pro | Glu | Asp | Pro | Gly | Ala | Met | Gly | Glu | Trp | Arg | Asp | Asp |
|  |  |  |  | 1765 |  |  |  |  | 1770 |  |  |  |  | 1775 |  |
| Leu | Leu | Ser | Trp | Ala | Leu | Glu | Arg | Ser | Thr | Val | Pro | Leu | Glu | Asp | His |
|  |  |  |  | 1780 |  |  |  |  | 1785 |  |  |  |  | 1790 |  |
| Arg | Leu | Thr | Ala | Met | Ala | Gly | Tyr | Gln | Arg | Leu | Val | Leu | Gly | Thr | Arg |
|  |  |  | 1795 |  |  |  |  | 1800 |  |  |  |  | 1805 |  |  |
| Leu | Thr | Ala | Leu | Glu | Ala | Pro | Val | Leu | Leu | Ala | Arg | Ala | Ser | Glu | Pro |
|  |  |  | 1810 |  |  |  |  | 1815 |  |  |  |  | 1820 |  |  |
| Leu | Cys | Ala | Trp | Pro | Pro | Ala | Gly | Gly | Ala | Arg | Gly | Asp | Trp | Arg | Ser |
| 1825 |  |  |  |  | 1830 |  |  |  |  | 1835 |  |  |  |  | 1840 |
| Gln | Val | Pro | Phe | Ala | Arg | Thr | Val | Ala | Asp | Val | Pro | Gly | Asn | His | Phe |
|  |  |  |  | 1845 |  |  |  |  | 1850 |  |  |  |  | 1855 |  |
| Thr | Met | Leu | Thr | Glu | His | Ala | Arg | His | Thr | Ala | Ser | Leu | Val | His | Glu |
|  |  |  | 1860 |  |  |  |  | 1865 |  |  |  |  | 1870 |  |  |
| Trp | Leu | Asp | Ser | Leu | Pro | His | Gln | Pro | Gly | Pro | Ala | Pro | Leu | Thr | Gly |
|  |  |  | 1875 |  |  |  |  | 1880 |  |  |  |  | 1885 |  |  |
| Gly | Lys | His |  |  |  |  |  |  |  |  |  |  |  |  |  |
|  |  | 1890 |  |  |  |  |  |  |  |  |  |  |  |  |  |

( 2 ) INFORMATION FOR SEQ ID NO:13:

( i ) SEQUENCE CHARACTERISTICS:
    ( A ) LENGTH: 13987 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 350..13987

( x i ) SEQUENCE DESCRIPTION: SEQ ID NO:13:

| | | | | | |
|---|---|---|---|---|---|
| GACCGCTCGG | GGAGACCTGA | CATATTCGTC | GCGAAGTGGT | TGTCCGCGCC | GCGAGGTACT | 60 |
| GAAATCTTCT | CCGCTCGCCC | AGGACTCCGC | GTGCAGGTCA | CCGGAGTGCG | CGACCGGCCG | 120 |
| GGACGTCGGA | GCGCCGACCC | TGCGGACCTG | GTGCGATGCC | GTGTGGTCCC | GCATGATCCC | 180 |
| GCGCCGTCTC | CGGTGACGAG | AATCGGTGGA | CAATCTCCGA | ACTTGACACA | ATTGATTGTC | 240 |
| GTTCACCGGC | CGTTCCTGTC | GCCCGGCAGT | TCGCCCGCTG | TACGCTCGGG | AAGATCAAGA | 300 |
| AAAGGCAGAA | AAGCCACGGC | GTGGTACGGC | GAACATATGA | GGGATGCAG | GTG TCT | 355 |

|  |  |  |  |  |  |  |  |  |  |  |  |  |  |  |  |
|---|---|---|---|---|---|---|---|---|---|---|---|---|---|---|---|
|  |  |  |  |  |  |  |  |  |  |  |  | Met | Ser |  |  |
|  |  |  |  |  |  |  |  |  |  |  |  | 1 |  |  |  |
| GGA | GAA | CTC | GCG | ATT | TCC | CGC | AGT | GAC | GAC | CGG | TCC | GAC | GCC | GTT | GCC | 403 |
| Gly | Glu | Leu | Ala | Ile | Ser | Arg | Ser | Asp | Asp | Arg | Ser | Asp | Ala | Val | Ala |
|  |  |  | 5 |  |  |  | 10 |  |  |  |  | 15 |  |  |  |
| GTG | GTC | GGA | ATG | GCG | TGC | CGG | TTT | CCC | GGC | GCC | CCG | GGA | ATT | GCC | GAA | 451 |
| Val | Val | Gly | Met | Ala | Cys | Arg | Phe | Pro | Gly | Ala | Pro | Gly | Ile | Ala | Glu |
|  | 20 |  |  |  |  | 25 |  |  |  |  | 30 |  |  |  |  |
| TTC | TGG | GAA | CTG | CTG | CGC | AGC | GGA | CGC | GGT | ATG | CCC | ACC | CGT | CAG | GAC | 499 |
| Phe | Trp | Glu | Leu | Leu | Arg | Ser | Gly | Arg | Gly | Met | Pro | Thr | Arg | Gln | Asp |
| 35 |  |  |  |  | 40 |  |  |  |  | 45 |  |  |  |  | 50 |

| | | | | | | | | | | | | | | | | |
|---|---|---|---|---|---|---|---|---|---|---|---|---|---|---|---|---|
| GAC | GGC | ACC | TGG | CGG | GCC | GCC | CTG | GAG | GAC | CAC | GCC | GGC | TTC | GAC | GCC | 547 |
| Asp | Gly | Thr | Trp | Arg | Ala | Ala | Leu | Glu | Asp | His | Ala | Gly | Phe | Asp | Ala | |
| | | | | 55 | | | | | 60 | | | | | 65 | | |
| GGG | TTC | TTC | GGC | ATG | AAC | GCC | CGG | CAG | GCC | GCC | GCC | ACC | GAC | CCG | CAG | 595 |
| Gly | Phe | Phe | Gly | Met | Asn | Ala | Arg | Gln | Ala | Ala | Ala | Thr | Asp | Pro | Gln | |
| | | | | 70 | | | | | 75 | | | | | 80 | | |
| CAC | CGA | CTG | ATG | CTG | GAA | CTC | GGA | TGG | GAG | GCA | CTG | GAG | GAC | GCG | GGC | 643 |
| His | Arg | Leu | Met | Leu | Glu | Leu | Gly | Trp | Glu | Ala | Leu | Glu | Asp | Ala | Gly | |
| | | | | 85 | | | | | 90 | | | | | 95 | | |
| ATC | GTC | CCC | GGC | GAT | CTC | ACC | GGC | ACC | GAC | ACC | GGA | GTC | TTC | GCC | GGC | 691 |
| Ile | Val | Pro | Gly | Asp | Leu | Thr | Gly | Thr | Asp | Thr | Gly | Val | Phe | Ala | Gly | |
| | | | | 100 | | | | | 105 | | | | | 110 | | |
| GTG | GCG | TCC | GAC | GAC | TAT | GCC | GTT | CTC | ACC | CGC | CGT | TCC | GCC | GTC | TCC | 739 |
| Val | Ala | Ser | Asp | Asp | Tyr | Ala | Val | Leu | Thr | Arg | Arg | Ser | Ala | Val | Ser | |
| 115 | | | | | 120 | | | | | 125 | | | | | 130 | |
| GCC | GGG | GGA | TAC | ACC | GCC | ACG | GGG | CTG | CAC | CGC | GCC | CTG | GCC | GCC | AAC | 787 |
| Ala | Gly | Gly | Tyr | Thr | Ala | Thr | Gly | Leu | His | Arg | Ala | Leu | Ala | Ala | Asn | |
| | | | | 135 | | | | | 140 | | | | | 145 | | |
| CGC | CTC | TCC | CAC | TTC | CTG | GGC | CTG | CGC | GGC | CCC | AGC | CTG | GTC | GTC | GAC | 835 |
| Arg | Leu | Ser | His | Phe | Leu | Gly | Leu | Arg | Gly | Pro | Ser | Leu | Val | Val | Asp | |
| | | | | 150 | | | | | 155 | | | | | 160 | | |
| TCG | GCC | CAG | TCC | GCC | TCA | CTG | GTG | GCC | GTC | CAG | CTC | GCC | TGC | GAG | AGT | 883 |
| Ser | Ala | Gln | Ser | Ala | Ser | Leu | Val | Ala | Val | Gln | Leu | Ala | Cys | Glu | Ser | |
| | | | | 165 | | | | | 170 | | | | | 175 | | |
| CTG | CGC | CGG | GGT | GAG | ACG | TCG | CTC | GCC | GTC | GCG | GGC | GGT | GTC | AAC | CTC | 931 |
| Leu | Arg | Arg | Gly | Glu | Thr | Ser | Leu | Ala | Val | Ala | Gly | Gly | Val | Asn | Leu | |
| | | | | 180 | | | | | 185 | | | | | 190 | | |
| ATC | CTC | ACC | GAG | GAG | AGC | ACC | ACC | GTC | ATG | GAG | CGT | ATG | GGA | GCG | CTC | 979 |
| Ile | Leu | Thr | Glu | Glu | Ser | Thr | Thr | Val | Met | Glu | Arg | Met | Gly | Ala | Leu | |
| 195 | | | | | 200 | | | | | 205 | | | | | 210 | |
| TCA | CCC | GAC | GGC | CGC | TGC | CAC | ACC | TTC | GAC | GCC | CGC | GCC | AAC | GGC | TAC | 1027 |
| Ser | Pro | Asp | Gly | Arg | Cys | His | Thr | Phe | Asp | Ala | Arg | Ala | Asn | Gly | Tyr | |
| | | | | 215 | | | | | 220 | | | | | 225 | | |
| GTA | CGC | GGC | GAG | GGC | GGC | GGA | GCC | GTC | GTG | CTC | AAG | CCA | CTG | GAC | GCC | 1075 |
| Val | Arg | Gly | Glu | Gly | Gly | Gly | Ala | Val | Val | Leu | Lys | Pro | Leu | Asp | Ala | |
| | | | | 230 | | | | | 235 | | | | | 240 | | |
| GCA | CTC | GCC | GAC | GGC | GAC | CGC | GTG | TAC | TGC | GTC | ATC | AAG | GGA | GGT | GCC | 1123 |
| Ala | Leu | Ala | Asp | Gly | Asp | Arg | Val | Tyr | Cys | Val | Ile | Lys | Gly | Gly | Ala | |
| | | | | 245 | | | | | 250 | | | | | 255 | | |
| GTC | AAC | AAC | GAC | GGC | GGC | GGC | GCG | AGC | CTC | ACC | ACT | CCC | GAC | CGG | GAG | 1171 |
| Val | Asn | Asn | Asp | Gly | Gly | Gly | Ala | Ser | Leu | Thr | Thr | Pro | Asp | Arg | Glu | |
| | | | | 260 | | | | | 265 | | | | | 270 | | |
| GCG | CAG | GAA | GCT | GTG | CTG | CGC | CAG | GCC | TAC | CGG | CGG | GCG | GGC | GTC | AGC | 1219 |
| Ala | Gln | Glu | Ala | Val | Leu | Arg | Gln | Ala | Tyr | Arg | Arg | Ala | Gly | Val | Ser | |
| 275 | | | | | 280 | | | | | 285 | | | | | 290 | |
| ACC | GGC | GCC | GTC | CGC | TAC | GTC | GAG | CTG | CAC | GGG | ACC | GGC | ACC | CGG | GCC | 1267 |
| Thr | Gly | Ala | Val | Arg | Tyr | Val | Glu | Leu | His | Gly | Thr | Gly | Thr | Arg | Ala | |
| | | | | 295 | | | | | 300 | | | | | 305 | | |
| GGC | GAC | CCC | GTC | GAG | GCG | GCC | GCA | CTG | GGC | GCC | GTG | CTC | GGG | GCG | GGG | 1315 |
| Gly | Asp | Pro | Val | Glu | Ala | Ala | Ala | Leu | Gly | Ala | Val | Leu | Gly | Ala | Gly | |
| | | | | 310 | | | | | 315 | | | | | 320 | | |
| GCG | GAC | AGC | GGC | CGC | AGC | ACG | CCG | CTC | GCC | GTC | GGC | TCG | GTG | AAG | ACC | 1363 |
| Ala | Asp | Ser | Gly | Arg | Ser | Thr | Pro | Leu | Ala | Val | Gly | Ser | Val | Lys | Thr | |
| | | | | 325 | | | | | 330 | | | | | 335 | | |
| AAC | GTC | GGC | CAT | CTG | GAG | GGC | GCG | GCG | GGC | ATC | GTC | GGA | CTG | ATC | AAG | 1411 |
| Asn | Val | Gly | His | Leu | Glu | Gly | Ala | Ala | Gly | Ile | Val | Gly | Leu | Ile | Lys | |
| | | | | 340 | | | | | 345 | | | | | 350 | | |
| GCC | ACG | CTG | TGC | GTA | CGG | AAG | GGC | GAA | CTC | GTC | CCC | AGC | CTC | AAC | TTC | 1459 |
| Ala | Thr | Leu | Cys | Val | Arg | Lys | Gly | Glu | Leu | Val | Pro | Ser | Leu | Asn | Phe | |
| 355 | | | | | 360 | | | | | 365 | | | | | 370 | |

| | | | | | | | | | | | | | | | | |
|---|---|---|---|---|---|---|---|---|---|---|---|---|---|---|---|---|
| AGC | ACG | CCG | AAC | CCT | GAC | ATC | CCC | CTC | GAC | GAC | CTG | CGG | CTG | CGC | GTC | 1507 |
| Ser | Thr | Pro | Asn | Pro | Asp | Ile | Pro | Leu | Asp | Asp | Leu | Arg | Leu | Arg | Val | |
| | | | | 375 | | | | | 380 | | | | | 385 | | |
| CAG | ACC | GAA | CGG | CAG | GAG | TGG | AAC | GAG | GAG | GAC | GAC | CGG | CCG | CGC | GTG | 1555 |
| Gln | Thr | Glu | Arg | Gln | Glu | Trp | Asn | Glu | Glu | Asp | Asp | Arg | Pro | Arg | Val | |
| | | | 390 | | | | | 395 | | | | | 400 | | | |
| GCC | GGC | GTC | TCC | TCC | TTC | GGT | ATG | GGC | GGA | ACC | AAT | GTC | CAC | CTC | GTG | 1603 |
| Ala | Gly | Val | Ser | Ser | Phe | Gly | Met | Gly | Gly | Thr | Asn | Val | His | Leu | Val | |
| | | 405 | | | | | 410 | | | | | 415 | | | | |
| ATC | GCG | GAG | GCT | CCG | GCC | GCG | GCG | GGG | TCC | TCC | GGG | GCG | GGG | GGT | TCG | 1651 |
| Ile | Ala | Glu | Ala | Pro | Ala | Ala | Ala | Gly | Ser | Ser | Gly | Ala | Gly | Gly | Ser | |
| | 420 | | | | 425 | | | | | 430 | | | | | | |
| GGC | GCT | GGT | TCC | GGT | GCC | GGT | ATC | AGC | GCT | GTT | TCT | GGT | GTG | GTG | CCG | 1699 |
| Gly | Ala | Gly | Ser | Gly | Ala | Gly | Ile | Ser | Ala | Val | Ser | Gly | Val | Val | Pro | |
| 435 | | | | 440 | | | | | 445 | | | | | 450 | | |
| GTG | GTG | GTT | TCG | GGG | CGT | TCG | CGG | GTG | GTG | GTG | CGG | GAG | GCT | GCG | GGC | 1747 |
| Val | Val | Val | Ser | Gly | Arg | Ser | Arg | Val | Val | Val | Arg | Glu | Ala | Ala | Gly | |
| | | | | 455 | | | | | 460 | | | | | 465 | | |
| CGG | TTG | GCG | GAG | GTG | GTG | GAG | GCC | GGT | GGT | GTG | GGG | CTG | GCG | GAT | GTG | 1795 |
| Arg | Leu | Ala | Glu | Val | Val | Glu | Ala | Gly | Gly | Val | Gly | Leu | Ala | Asp | Val | |
| | | | 470 | | | | | 475 | | | | | 480 | | | |
| GCG | GTG | ACG | ATG | GCG | GAC | CGG | TCG | CGG | TTT | GGG | TAT | CGG | GCG | GTT | GTG | 1843 |
| Ala | Val | Thr | Met | Ala | Asp | Arg | Ser | Arg | Phe | Gly | Tyr | Arg | Ala | Val | Val | |
| | | 485 | | | | | 490 | | | | | 495 | | | | |
| CTG | GCT | CGG | GGT | GAG | GCT | GAG | CTT | GCC | GGG | CGT | TTG | CGG | GCG | TTG | GCG | 1891 |
| Leu | Ala | Arg | Gly | Glu | Ala | Glu | Leu | Ala | Gly | Arg | Leu | Arg | Ala | Leu | Ala | |
| | 500 | | | | 505 | | | | | 510 | | | | | | |
| GGG | GGT | GAT | CCG | GAC | GCG | GGT | GTG | GTC | ACC | GGT | GCG | GTT | CTC | GAC | GGT | 1939 |
| Gly | Gly | Asp | Pro | Asp | Ala | Gly | Val | Val | Thr | Gly | Ala | Val | Leu | Asp | Gly | |
| 515 | | | | | 520 | | | | | 525 | | | | | 530 | |
| GGT | GTG | GTT | GTC | GGT | GCT | GCC | CCC | GGC | GGT | GCC | GGT | GCT | GCC | GGT | GGT | 1987 |
| Gly | Val | Val | Val | Gly | Ala | Ala | Pro | Gly | Gly | Ala | Gly | Ala | Ala | Gly | Gly | |
| | | | | 535 | | | | | 540 | | | | | 545 | | |
| GCC | GGT | GCT | GCC | GGT | GGT | GCC | GGT | GGT | GGG | GGC | GTG | GTG | TTG | GTT | TTC | 2035 |
| Ala | Gly | Ala | Ala | Gly | Gly | Ala | Gly | Gly | Gly | Gly | Val | Val | Leu | Val | Phe | |
| | | | 550 | | | | | 555 | | | | | 560 | | | |
| CCT | GGT | CAG | GGG | ACG | CAG | TGG | GTG | GGG | ATG | GGT | GCG | GGG | CTG | CTG | GGG | 2083 |
| Pro | Gly | Gln | Gly | Thr | Gln | Trp | Val | Gly | Met | Gly | Ala | Gly | Leu | Leu | Gly | |
| | | 565 | | | | | 570 | | | | | 575 | | | | |
| TCT | TCG | GAG | GTG | TTT | GCG | GCG | TCG | ATG | CGG | GAG | TGT | GCG | CGG | GCG | CTG | 2131 |
| Ser | Ser | Glu | Val | Phe | Ala | Ala | Ser | Met | Arg | Glu | Cys | Ala | Arg | Ala | Leu | |
| | 580 | | | | 585 | | | | | 590 | | | | | | |
| AGT | GTT | CAT | GTG | GGG | TGG | GAT | TTG | CTG | GAG | GTG | GTG | TCG | GGC | GGG | GCC | 2179 |
| Ser | Val | His | Val | Gly | Trp | Asp | Leu | Leu | Glu | Val | Val | Ser | Gly | Gly | Ala | |
| 595 | | | | 600 | | | | | 605 | | | | | 610 | | |
| GGG | TTG | GAG | CGG | GTG | GAT | GTG | GTG | CAG | CCG | GTG | ACG | TGG | GCG | GTG | ATG | 2227 |
| Gly | Leu | Glu | Arg | Val | Asp | Val | Val | Gln | Pro | Val | Thr | Trp | Ala | Val | Met | |
| | | | | 615 | | | | | 620 | | | | | 625 | | |
| GTG | TCG | CTG | GCC | CGG | TAC | TGG | CAG | GCG | ATG | GGT | GTG | GAC | GTG | GCT | GCG | 2275 |
| Val | Ser | Leu | Ala | Arg | Tyr | Trp | Gln | Ala | Met | Gly | Val | Asp | Val | Ala | Ala | |
| | | | 630 | | | | | 635 | | | | | 640 | | | |
| GTG | GTG | GGT | CAT | TCC | CAG | GGG | GAG | ATC | GCC | GCT | GCC | ACG | GTG | GCG | GGG | 2323 |
| Val | Val | Gly | His | Ser | Gln | Gly | Glu | Ile | Ala | Ala | Ala | Thr | Val | Ala | Gly | |
| | | 645 | | | | | 650 | | | | | 655 | | | | |
| GCG | TTG | TCG | CTG | GAG | GAT | GCG | GCG | GCT | GTG | GTC | GCT | CTG | CGG | GCG | GGG | 2371 |
| Ala | Leu | Ser | Leu | Glu | Asp | Ala | Ala | Ala | Val | Val | Ala | Leu | Arg | Ala | Gly | |
| | 660 | | | | 665 | | | | | 670 | | | | | | |
| TTG | ATT | GGC | CGG | TAT | CTG | GCG | GGT | CGT | GGT | GCG | ATG | GCG | GCT | GTT | CCG | 2419 |
| Leu | Ile | Gly | Arg | Tyr | Leu | Ala | Gly | Arg | Gly | Ala | Met | Ala | Ala | Val | Pro | |
| 675 | | | | 680 | | | | | 685 | | | | | 690 | | |

| | | | | | | | | | | | | | | | |
|---|---|---|---|---|---|---|---|---|---|---|---|---|---|---|---|
| CTG | CCT | GCC | GGC | GAG | GTC | GAG | GCC | GGG | CTG | GCG | AAG | TGG | CCG | GGT | GTG | 2467 |
| Leu | Pro | Ala | Gly | Glu | Val | Glu | Ala | Gly | Leu | Ala | Lys | Trp | Pro | Gly | Val | |
| | | | 695 | | | | 700 | | | | | | 705 | | | |
| GAG | GTC | GCG | GCG | GTC | AAC | GGT | CCG | GCG | TCT | ACG | GTG | GTT | TCC | GGG | GAT | 2515 |
| Glu | Val | Ala | Ala | Val | Asn | Gly | Pro | Ala | Ser | Thr | Val | Val | Ser | Gly | Asp | |
| | | | 710 | | | | 715 | | | | | 720 | | | | |
| CGG | CGG | GCG | GTG | GCC | GGT | TAT | GTG | GCC | GTC | TGT | CAG | GCG | GAG | GGT | GTG | 2563 |
| Arg | Arg | Ala | Val | Ala | Gly | Tyr | Val | Ala | Val | Cys | Gln | Ala | Glu | Gly | Val | |
| | | 725 | | | | 730 | | | | | 735 | | | | | |
| CAG | GCC | CGG | TTG | ATA | CCG | GTG | GAC | TAC | GCC | TCT | CAC | TCC | CGC | CAT | GTG | 2611 |
| Gln | Ala | Arg | Leu | Ile | Pro | Val | Asp | Tyr | Ala | Ser | His | Ser | Arg | His | Val | |
| | 740 | | | | 745 | | | | 750 | | | | | | | |
| GAG | GAC | CTG | AAG | GGC | GAG | TTG | GAG | CGG | GTG | CTG | TCC | GGT | ATC | CGC | CCC | 2659 |
| Glu | Asp | Leu | Lys | Gly | Glu | Leu | Glu | Arg | Val | Leu | Ser | Gly | Ile | Arg | Pro | |
| 755 | | | | 760 | | | | 765 | | | | | 770 | | | |
| CGC | AGT | CCG | CGG | GTG | CCG | GTG | TGT | TCC | ACC | GTC | GCC | GGA | GAG | CAG | CCG | 2707 |
| Arg | Ser | Pro | Arg | Val | Pro | Val | Cys | Ser | Thr | Val | Ala | Gly | Glu | Gln | Pro | |
| | | | | 775 | | | | 780 | | | | | 785 | | | |
| GGC | GAG | CCG | GTT | TTC | GAT | GCG | GGG | TAT | TGG | TTC | CGT | AAT | CTG | CGG | AAC | 2755 |
| Gly | Glu | Pro | Val | Phe | Asp | Ala | Gly | Tyr | Trp | Phe | Arg | Asn | Leu | Arg | Asn | |
| | | | 790 | | | | 795 | | | | | | 800 | | | |
| CGG | GTT | GAG | TTC | TCC | GCG | GTG | GTC | GGT | GGT | TTG | TTG | GAG | GAG | GGC | CAC | 2803 |
| Arg | Val | Glu | Phe | Ser | Ala | Val | Val | Gly | Gly | Leu | Leu | Glu | Glu | Gly | His | |
| | | 805 | | | | 810 | | | | | 815 | | | | | |
| CGT | CGG | TTC | ATC | GAG | GTC | AGT | GCC | CAC | CCG | GTA | CTC | GTC | CAT | GCG | ATC | 2851 |
| Arg | Arg | Phe | Ile | Glu | Val | Ser | Ala | His | Pro | Val | Leu | Val | His | Ala | Ile | |
| | 820 | | | | 825 | | | | | 830 | | | | | | |
| GAG | CAG | ACG | GCC | GAG | GCC | GCG | GAC | CGG | AGT | GTC | CAT | GCC | ACC | GGG | ACC | 2899 |
| Glu | Gln | Thr | Ala | Glu | Ala | Ala | Asp | Arg | Ser | Val | His | Ala | Thr | Gly | Thr | |
| 835 | | | | 840 | | | | 845 | | | | | 850 | | | |
| CTG | CGC | CGC | CAG | GAC | GAC | AGC | CCG | CAC | CGC | CTG | CTG | ACC | TCC | ACC | GCC | 2947 |
| Leu | Arg | Arg | Gln | Asp | Asp | Ser | Pro | His | Arg | Leu | Leu | Thr | Ser | Thr | Ala | |
| | | | 855 | | | | 860 | | | | | 865 | | | | |
| GAG | GCC | TGG | GCC | CAC | GGC | GCC | ACC | CTC | ACC | TGG | GAC | CCC | GCC | CTG | CCC | 2995 |
| Glu | Ala | Trp | Ala | His | Gly | Ala | Thr | Leu | Thr | Trp | Asp | Pro | Ala | Leu | Pro | |
| | | | 870 | | | | 875 | | | | | 880 | | | | |
| CCA | GGC | CAC | CTC | ACC | ACC | CTC | CCC | ACC | TAC | CCC | TTC | AAC | CAC | CAC | CAC | 3043 |
| Pro | Gly | His | Leu | Thr | Thr | Leu | Pro | Thr | Tyr | Pro | Phe | Asn | His | His | His | |
| | | 885 | | | | 890 | | | | | 895 | | | | | |
| TAC | TGG | CTC | GAC | ACC | ATT | GAC | GGG | GGC | GGA | GGG | GAC | GAC | GCG | ACC | CAG | 3091 |
| Tyr | Trp | Leu | Asp | Thr | Ile | Asp | Gly | Gly | Gly | Gly | Asp | Asp | Ala | Thr | Gln | |
| | 900 | | | | 905 | | | | | 910 | | | | | | |
| GAG | AAG | GAG | AGC | GGC | CCT | CTG | ACG | CGG | GAA | CTG | CGT | GGG | CTG | CCG | TCC | 3139 |
| Glu | Lys | Glu | Ser | Gly | Pro | Leu | Thr | Arg | Glu | Leu | Arg | Gly | Leu | Pro | Ser | |
| 915 | | | | 920 | | | | 925 | | | | | 930 | | | |
| TCT | CAG | AAG | CAA | CTG | GGT | TTC | CTG | CTC | GAT | CTG | GTG | TGC | CGG | CAC | ACG | 3187 |
| Ser | Gln | Lys | Gln | Leu | Gly | Phe | Leu | Leu | Asp | Leu | Val | Cys | Arg | His | Thr | |
| | | | | 935 | | | | | 940 | | | | | 945 | | |
| GCC | GTC | GTA | CTC | GGC | CTG | GAC | ACG | GCC | GCC | GAG | GTG | GAC | CCG | GAC | CTG | 3235 |
| Ala | Val | Val | Leu | Gly | Leu | Asp | Thr | Ala | Ala | Glu | Val | Asp | Pro | Asp | Leu | |
| | | | | 950 | | | | | 955 | | | | | 960 | | |
| TCC | TTC | AAG | AAG | CAG | GGC | ATC | CAG | TCC | ATG | ACC | GGC | GTC | GAG | CTG | CGC | 3283 |
| Ser | Phe | Lys | Lys | Gln | Gly | Ile | Gln | Ser | Met | Thr | Gly | Val | Glu | Leu | Arg | |
| | | 965 | | | | 970 | | | | | 975 | | | | | |
| AAC | AGG | CTG | CTG | ACC | GAG | ACC | GGC | CTG | GCA | TTG | CCC | ACC | ACC | CTC | GTC | 3331 |
| Asn | Arg | Leu | Leu | Thr | Glu | Thr | Gly | Leu | Ala | Leu | Pro | Thr | Thr | Leu | Val | |
| | 980 | | | | 985 | | | | | 990 | | | | | | |
| TAC | GAC | CGG | CCC | ACC | CCT | CGC | GCC | CTG | GCG | CAG | TTC | CTC | CAC | ACC | GAG | 3379 |
| Tyr | Asp | Arg | Pro | Thr | Pro | Arg | Ala | Leu | Ala | Gln | Phe | Leu | His | Thr | Glu | |
| 995 | | | | 1000 | | | | | 1005 | | | | | 1010 | | |

| | | | | | | | | | | | | | | | | |
|---|---|---|---|---|---|---|---|---|---|---|---|---|---|---|---|---|
| TTG | CTC | GAC | GGC | TCC | CCC | TCG | GGC | TCC | GTC | CTC | GCA | CCG | GCG | CAG | AAG | 3427 |
| Leu | Leu | Asp | Gly | Ser | Pro | Ser | Gly | Ser | Val | Leu | Ala | Pro | Ala | Gln | Lys | |
| | | | | 1015 | | | | 1020 | | | | | | 1025 | | |
| AGC | TTC | GAG | GCC | GGC | GGG | CCC | GGA | GTG | CTC | TCG | TCG | GCC | GCG | GTA | GGG | 3475 |
| Ser | Phe | Glu | Ala | Gly | Gly | Pro | Gly | Val | Leu | Ser | Ser | Ala | Ala | Val | Gly | |
| | | | 1030 | | | | | 1035 | | | | | 1040 | | | |
| GTG | TCG | GAC | GCC | CGG | GGC | GGC | AGC | CGG | GAC | GAC | GAC | GAC | CCG | ATC | GCC | 3523 |
| Val | Ser | Asp | Ala | Arg | Gly | Gly | Ser | Arg | Asp | Asp | Asp | Asp | Pro | Ile | Ala | |
| | | | 1045 | | | | | 1050 | | | | | 1055 | | | |
| ATC | GTG | GGT | GTC | GGC | TGC | CGG | CTC | CCC | GGC | GGC | GTC | GAC | TCG | CGC | GCC | 3571 |
| Ile | Val | Gly | Val | Gly | Cys | Arg | Leu | Pro | Gly | Gly | Val | Asp | Ser | Arg | Ala | |
| | | | 1060 | | | | 1065 | | | | | 1070 | | | | |
| GCT | CTC | TGG | GAG | CTG | CTG | GAG | TCC | GGC | GCC | GAC | GCC | ATC | TCG | TCC | TTC | 3619 |
| Ala | Leu | Trp | Glu | Leu | Leu | Glu | Ser | Gly | Ala | Asp | Ala | Ile | Ser | Ser | Phe | |
| 1075 | | | | | 1080 | | | | | 1085 | | | | | 1090 | |
| CCC | ACC | GAC | CGC | GGC | TGG | GAC | CTC | GAC | GGG | CTG | TAC | GAC | CCC | GAG | CCC | 3667 |
| Pro | Thr | Asp | Arg | Gly | Trp | Asp | Leu | Asp | Gly | Leu | Tyr | Asp | Pro | Glu | Pro | |
| | | | | 1095 | | | | 1100 | | | | | | 1105 | | |
| GGG | ACG | CCC | GGC | AAG | ACC | TAT | GTG | CGG | GAG | GGC | GGG | TTC | CTG | CAC | TCG | 3715 |
| Gly | Thr | Pro | Gly | Lys | Thr | Tyr | Val | Arg | Glu | Gly | Gly | Phe | Leu | His | Ser | |
| | | | 1110 | | | | | 1115 | | | | | 1120 | | | |
| GCG | GCC | GAG | TTC | GAC | GCG | GAG | TTC | TTC | GGG | ATA | TCG | CCG | CGC | GAG | GCC | 3763 |
| Ala | Ala | Glu | Phe | Asp | Ala | Glu | Phe | Phe | Gly | Ile | Ser | Pro | Arg | Glu | Ala | |
| | | | 1125 | | | | | 1130 | | | | | 1135 | | | |
| ACG | GCC | ATG | GAC | CCG | CAG | CAG | CGC | TTG | CTG | CTG | GAA | GCG | TCG | TGG | GAG | 3811 |
| Thr | Ala | Met | Asp | Pro | Gln | Gln | Arg | Leu | Leu | Leu | Glu | Ala | Ser | Trp | Glu | |
| | 1140 | | | | | 1145 | | | | | 1150 | | | | | |
| GCC | CTC | GAG | GAC | GCC | GGA | GTG | CTC | CCC | GAG | TCA | CTG | CGC | GGC | GGC | GAC | 3859 |
| Ala | Leu | Glu | Asp | Ala | Gly | Val | Leu | Pro | Glu | Ser | Leu | Arg | Gly | Gly | Asp | |
| 1155 | | | | | 1160 | | | | | 1165 | | | | | 1170 | |
| GCC | GGA | GTG | TTC | GTC | GGC | GCC | ACC | GCA | CCG | GAG | TAC | GGG | CCG | AGG | CTT | 3907 |
| Ala | Gly | Val | Phe | Val | Gly | Ala | Thr | Ala | Pro | Glu | Tyr | Gly | Pro | Arg | Leu | |
| | | | | 1175 | | | | | 1180 | | | | | 1185 | | |
| CAC | GAG | GGA | GCG | GAC | GGA | TAC | GAG | GGG | TAC | CTG | CTC | ACC | GGC | ACC | ACC | 3955 |
| His | Glu | Gly | Ala | Asp | Gly | Tyr | Glu | Gly | Tyr | Leu | Leu | Thr | Gly | Thr | Thr | |
| | | | | 1190 | | | | | 1195 | | | | | 1200 | | |
| GCG | AGC | GTG | GCC | TCC | GGC | CGG | ATC | GCC | TAC | ACC | CTC | GGC | ACC | GGC | GGA | 4003 |
| Ala | Ser | Val | Ala | Ser | Gly | Arg | Ile | Ala | Tyr | Thr | Leu | Gly | Thr | Gly | Gly | |
| | | | | 1205 | | | | | 1210 | | | | | 1215 | | |
| CCG | GCG | CTC | ACC | GTC | GAC | ACC | GCG | TGC | TCC | TCG | TCC | CTG | GTG | GCG | CTG | 4051 |
| Pro | Ala | Leu | Thr | Val | Asp | Thr | Ala | Cys | Ser | Ser | Ser | Leu | Val | Ala | Leu | |
| | 1220 | | | | | 1225 | | | | | 1230 | | | | | |
| CAC | CTG | GCC | GTG | CAG | GCG | CTG | CGC | CGG | GGC | GAG | TGC | GGG | CTG | GCT | CTG | 4099 |
| His | Leu | Ala | Val | Gln | Ala | Leu | Arg | Arg | Gly | Glu | Cys | Gly | Leu | Ala | Leu | |
| 1235 | | | | | 1240 | | | | | 1245 | | | | | 1250 | |
| GCG | GGC | GGC | GCC | ACG | GTG | ATG | TCG | GGG | CCC | GGC | ATG | TTC | GTG | GAG | TTC | 4147 |
| Ala | Gly | Gly | Ala | Thr | Val | Met | Ser | Gly | Pro | Gly | Met | Phe | Val | Glu | Phe | |
| | | | | 1255 | | | | | 1260 | | | | | 1265 | | |
| TCG | CGG | CAG | CGC | GGG | CTC | GCC | CCC | GAC | GGC | CGC | TGC | ATG | CCG | TTC | TCC | 4195 |
| Ser | Arg | Gln | Arg | Gly | Leu | Ala | Pro | Asp | Gly | Arg | Cys | Met | Pro | Phe | Ser | |
| | | | 1270 | | | | | 1275 | | | | | 1280 | | | |
| GCC | GAT | GCC | GAC | GGT | ACG | GCC | TGG | TCC | GAG | GGT | GTC | GCC | GTA | CTG | GCA | 4243 |
| Ala | Asp | Ala | Asp | Gly | Thr | Ala | Trp | Ser | Glu | Gly | Val | Ala | Val | Leu | Ala | |
| | | | | 1285 | | | | | 1290 | | | | | 1295 | | |
| CTG | GAG | CGG | CTC | TCC | GAC | GCC | CGG | CGT | GCG | GGA | CAC | CGG | GTG | CTG | GGC | 4291 |
| Leu | Glu | Arg | Leu | Ser | Asp | Ala | Arg | Arg | Ala | Gly | His | Arg | Val | Leu | Gly | |
| | 1300 | | | | | 1305 | | | | | 1310 | | | | | |
| GTG | GTG | CGG | GGC | AGT | GCG | GTC | AAC | CAG | GAC | GGT | GCC | AGC | AAC | GGC | CTG | 4339 |
| Val | Val | Arg | Gly | Ser | Ala | Val | Asn | Gln | Asp | Gly | Ala | Ser | Asn | Gly | Leu | |
| 1315 | | | | | 1320 | | | | | 1325 | | | | | 1330 | |

| | | | | | | | | | | | | | | | | |
|---|---|---|---|---|---|---|---|---|---|---|---|---|---|---|---|---|
| ACC | GCT | CCC | AAC | CGC | TCC | GCG | CAG | GAG | GGC | GTC | ATC | CGA | GCT | GCC | CTG | 4387 |
| Thr | Ala | Pro | Asn 1335 | Arg | Ser | Ala | Gln | Glu 1340 | Gly | Val | Ile | Arg | Ala | Ala 1345 | Leu | |
| GCC | GAC | GCC | GGC | CTC | GCG | CCG | GGT | GAC | GTG | GAC | GCG | GTG | GAG | GCG | CAC | 4435 |
| Ala | Asp | Ala | Gly 1350 | Leu | Ala | Pro | Gly | Asp 1355 | Val | Asp | Ala | Val | Glu 1360 | Ala | His | |
| GGT | ACG | GGG | ACG | GCG | CTG | GGC | GAT | CCG | ATC | GAG | GCG | AGC | GCG | CTG | CTG | 4483 |
| Gly | Thr | Gly | Thr 1365 | Ala | Leu | Gly | Asp | Pro 1370 | Ile | Glu | Ala | Ser | Ala 1375 | Leu | Leu | |
| GCC | ACG | TAC | GGG | CGT | GAG | CGG | GTG | GGC | GAC | CCC | TTG | TGG | CTC | GGG | TCG | 4531 |
| Ala | Thr | Tyr | Gly 1380 | Arg | Glu | Arg | Val | Gly 1385 | Asp | Pro | Leu | Trp | Leu 1390 | Gly | Ser | |
| CTG | AAG | TCC | AAC | GTC | GGT | CAC | ACC | CAG | GCC | GCC | GCG | GGG | GCC | GCG | GGT | 4579 |
| Leu | Lys | Ser | Asn | Val | Gly | His | Thr | Gln | Ala | Ala | Ala | Gly | Ala | Ala | Gly | |
| 1395 | | | | | 1400 | | | | | 1405 | | | | | 1410 | |
| GTG | GTC | AAG | ATG | CTG | CTT | GCC | CTG | GAG | CAC | GGC | ACG | CTG | CCG | CGG | ACA | 4627 |
| Val | Val | Lys | Met 1415 | Leu | Leu | Ala | Leu | Glu 1420 | His | Gly | Thr | Leu | Pro 1425 | Arg | Thr | |
| CTT | CAC | GCG | GAC | CGG | CCC | AGC | ACG | CAC | GTC | GAC | TGG | TCG | TCG | GGC | ACC | 4675 |
| Leu | His | Ala | Asp 1430 | Arg | Pro | Ser | Thr | His 1435 | Val | Asp | Trp | Ser | Ser 1440 | Gly | Thr | |
| GTC | GCC | CTG | CTG | GCA | GAG | GCG | CGC | CGG | TGG | CCC | CGG | CGG | TCG | GAC | CGC | 4723 |
| Val | Ala | Leu | Leu 1445 | Ala | Glu | Ala | Arg | Arg 1450 | Trp | Pro | Arg | Arg | Ser 1455 | Asp | Arg | |
| CCG | CGC | CGG | GCG | GCT | GTG | TCG | TCG | TTC | GGG | ATC | AGT | GGG | ACG | AAC | GCG | 4771 |
| Pro | Arg | Arg | Ala 1460 | Ala | Val | Ser | Ser | Phe 1465 | Gly | Ile | Ser | Gly | Thr 1470 | Asn | Ala | |
| CAT | CTG | ATC | ATC | GAG | GAG | GCG | CCG | GAG | TGG | GTC | GAG | GAC | ATC | GAC | GGC | 4819 |
| His | Leu | Ile | Ile | Glu | Glu | Ala | Pro | Glu | Trp | Val | Glu | Asp | Ile | Asp | Gly | |
| 1475 | | | | | 1480 | | | | | 1485 | | | | | 1490 | |
| GTC | GCT | GCT | CCT | GAC | CGC | GGT | ACC | GCG | GAC | GCG | GCT | GCT | CCG | TCG | CCG | 4867 |
| Val | Ala | Ala | Pro 1495 | Asp | Arg | Gly | Thr | Ala 1500 | Asp | Ala | Ala | Ala | Pro 1505 | Ser | Pro | |
| CTG | TTG | TTG | TCC | GCG | CGG | TCG | GAG | GGG | GCG | TTG | CGG | GCG | CAG | GCG | GTG | 4915 |
| Leu | Leu | Leu | Ser | Ala 1510 | Arg | Ser | Glu | Gly | Ala 1515 | Leu | Arg | Ala | Gln | Ala 1520 | Val | |
| CGG | TTG | GGT | GAG | TAC | GTG | GAG | CGG | GTG | GGT | GCG | GAT | CCG | CGG | GAT | GTG | 4963 |
| Arg | Leu | Gly | Glu 1525 | Tyr | Val | Glu | Arg | Val 1530 | Gly | Ala | Asp | Pro | Arg 1535 | Asp | Val | |
| GCT | TAT | TCG | CTG | GCT | TCG | ACG | CGG | ACT | CTT | TTC | GAG | CAC | CGT | GCG | GTG | 5011 |
| Ala | Tyr | Ser | Leu 1540 | Ala | Ser | Thr | Arg | Thr 1545 | Leu | Phe | Glu | His | Arg 1550 | Ala | Val | |
| GTG | CCG | TGT | GGT | GGG | CGT | GGG | GAG | CTC | GTC | GCT | GCT | CTT | GGT | GGG | TTT | 5059 |
| Val | Pro | Cys | Gly | Gly | Arg | Gly | Glu | Leu | Val | Ala | Ala | Leu | Gly | Gly | Phe | |
| 1555 | | | | | 1560 | | | | | 1565 | | | | | 1570 | |
| GCT | GCC | GGG | AGG | GTG | TCT | GGG | GGT | GTG | CGG | TCC | GGG | CGG | GCT | GTG | CCG | 5107 |
| Ala | Ala | Gly | Arg | Val 1575 | Ser | Gly | Gly | Val | Arg 1580 | Ser | Gly | Arg | Ala | Val 1585 | Pro | |
| GGT | GGG | GTG | GGG | GTG | TTG | TTC | ACG | GGT | CAG | GGT | GCG | CAG | TGG | GTT | GGT | 5155 |
| Gly | Gly | Val | Gly | Val 1590 | Leu | Phe | Thr | Gly | Gln 1595 | Gly | Ala | Gln | Trp | Val 1600 | Gly | |
| ATG | GGG | CGT | GGG | TTG | TAT | GCG | GGG | GGT | GGG | GTG | TTT | GCG | GAG | GTG | CTG | 5203 |
| Met | Gly | Arg | Gly 1605 | Leu | Tyr | Ala | Gly | Gly 1610 | Gly | Val | Phe | Ala | Glu 1615 | Val | Leu | |
| GAT | GAG | GTG | TTG | TCG | ATG | GTG | GGG | GAG | GTG | GAT | GGT | CGG | TCG | TTG | CGG | 5251 |
| Asp | Glu | Val | Leu 1620 | Ser | Met | Val | Gly | Glu 1625 | Val | Asp | Gly | Arg | Ser 1630 | Leu | Arg | |
| GAT | GTG | ATG | TTC | GGC | GAC | GTC | GAC | GTG | GAC | GCG | GGT | GCC | GGG | GCT | GAT | 5299 |
| Asp | Val | Met | Phe | Gly | Asp | Val | Asp | Val | Asp | Ala | Gly | Ala | Gly | Ala | Asp | |
| 1635 | | | | | 1640 | | | | | 1645 | | | | | 1650 | |

| | |
|---|---|
| GCG GGT GCC GGT GCG GGT GCT GGG GTC GGT TCT GGT TCC GGT TCT GTG<br>Ala Gly Ala Gly Ala Gly Ala Gly Val Gly Ser Gly Ser Gly Ser Val<br>            1655                               1660                          1665 | 5347 |
| GGT GGG TTG TTG GGT CGG ACG GAG TTT GCT CAG CCT GCG CTG TTT GCG<br>Gly Gly Leu Leu Gly Arg Thr Glu Phe Ala Gln Pro Ala Leu Phe Ala<br>            1670                              1675                          1680 | 5395 |
| TTG GAG GTG GCG TTG TTC CGG GCG TTG GAG GCT CGG GGT GTG GAG GTG<br>Leu Glu Val Ala Leu Phe Arg Ala Leu Glu Ala Arg Gly Val Glu Val<br>            1685                              1690                          1695 | 5443 |
| TCG GTG GTG TTG GGT CAT TCG GTG GGG GAG GTG GCT GCT GCG TAT GTG<br>Ser Val Val Leu Gly His Ser Val Gly Glu Val Ala Ala Ala Tyr Val<br>            1700                              1705                          1710 | 5491 |
| GCG GGG GTG TTG TCG TTG GGT GAT GCG GTG CGG TTG GTG GTG GCG CGG<br>Ala Gly Val Leu Ser Leu Gly Asp Ala Val Arg Leu Val Val Ala Arg<br>1715                          1720                              1725                          1730 | 5539 |
| GGT GGG TTG ATG GGT GGG TTG CCG GTG GGT GGG GGG ATG TGG TCG GTG<br>Gly Gly Leu Met Gly Gly Leu Pro Val Gly Gly Gly Met Trp Ser Val<br>                        1735                              1740                          1745 | 5587 |
| GGG GCG TCG GAG TCG GTG GTG CGG GGG GTT GTT GAG GGG TTG GGG GAG<br>Gly Ala Ser Glu Ser Val Val Arg Gly Val Val Glu Gly Leu Gly Glu<br>                      1750                              1755                          1760 | 5635 |
| TGG GTG TCG GTT GCG GCG GTG AAT GGG CCG CGG TCG GTG GTG TTG TCG<br>Trp Val Ser Val Ala Ala Val Asn Gly Pro Arg Ser Val Val Leu Ser<br>            1765                              1770                          1775 | 5683 |
| GGT GAT GTG GGT GTG CTG GAG TCG GTG GTT GCC TCG CTG ATG GGG GAT<br>Gly Asp Val Gly Val Leu Glu Ser Val Val Ala Ser Leu Met Gly Asp<br>            1780                              1785                          1790 | 5731 |
| GGG GTG GAG TGC CGG CGG TTG GAT GTG TCG CAT GGG TTT CAT TCG GTG<br>Gly Val Glu Cys Arg Arg Leu Asp Val Ser His Gly Phe His Ser Val<br>1795                          1800                              1805                          1810 | 5779 |
| TTG ATG GAG CCG GTG TTG GGG GAG TTC CGG GGG GTT GTG GAG TCG TTG<br>Leu Met Glu Pro Val Leu Gly Glu Phe Arg Gly Val Val Glu Ser Leu<br>                      1815                              1820                          1825 | 5827 |
| GAG TTC GGT CGG GTG CGG CCG GGT GTG GTG GTG GTG TCG GGT GTG TCG<br>Glu Phe Gly Arg Val Arg Pro Gly Val Val Val Val Ser Gly Val Ser<br>                        1830                              1835                          1840 | 5875 |
| GGT GGG GTG GTG GGT TCG GGG GAG TTG GGG GAT CCG GGG TAT TGG GTG<br>Gly Gly Val Val Gly Ser Gly Glu Leu Gly Asp Pro Gly Tyr Trp Val<br>            1845                              1850                          1855 | 5923 |
| CGT CAT GCG CGG GAG GCG GTG CGT TTC GCG GAT GGG GTG GGG GTG GTG<br>Arg His Ala Arg Glu Ala Val Arg Phe Ala Asp Gly Val Gly Val Val<br>            1860                              1865                          1870 | 5971 |
| CGT GGT CTG GGT GTG GGG ACG TTG GTG GAG GTG GGT CCG CAT GGG GTG<br>Arg Gly Leu Gly Val Gly Thr Leu Val Glu Val Gly Pro His Gly Val<br>1875                          1880                              1885                          1890 | 6019 |
| CTG ACG GGG ATG GCG GGT GAG TGC CTG GGG GCC GGT GAT GAT GTG GTG<br>Leu Thr Gly Met Ala Gly Glu Cys Leu Gly Ala Gly Asp Asp Val Val<br>                      1895                              1900                          1905 | 6067 |
| GTG GTG CCG GCG ATG CGG CGG GGC CGT GCG GAG CGG GAG GTG TTC GAG<br>Val Val Pro Ala Met Arg Arg Gly Arg Ala Glu Arg Glu Val Phe Glu<br>                      1910                              1915                          1920 | 6115 |
| GCG GCG CTG GCG ACG GTG TTC ACC CGG GAC GCC GGC CTG GAC GCC ACG<br>Ala Ala Leu Ala Thr Val Phe Thr Arg Asp Ala Gly Leu Asp Ala Thr<br>                      1925                              1930                          1935 | 6163 |
| GCA CTC CAC ACC GGG AGC ACC GGC CGG CGC ATC GAC CTC CCC ACC TAC<br>Ala Leu His Thr Gly Ser Thr Gly Arg Arg Ile Asp Leu Pro Thr Tyr<br>            1940                              1945                          1950 | 6211 |
| CCC TTC CAA CGC GAC CGC TAC TGG CTG GAC CCC GTT CGC ACC GCC GTG<br>Pro Phe Gln Arg Asp Arg Tyr Trp Leu Asp Pro Val Arg Thr Ala Val<br>1955                          1960                              1965                          1970 | 6259 |

| | | | | | | | | | | | | | | | | |
|---|---|---|---|---|---|---|---|---|---|---|---|---|---|---|---|---|
| ACC | GGC | GTC | GAG | CCC | GCC | GGC | TCG | CCG | GCG | GAC | GCT | CGG | GCC | ACT | GAG | 6307 |
| Thr | Gly | Val | Glu | Pro | Ala | Gly | Ser | Pro | Ala | Asp | Ala | Arg | Ala | Thr | Glu | |
| | | | 1975 | | | | 1980 | | | | | 1985 | | | | |
| CGG | GGA | CGG | TCG | ACG | ACG | GCC | GGG | ATC | CGC | TAC | CGC | GTC | GCT | TGG | CAG | 6355 |
| Arg | Gly | Arg | Ser | Thr | Thr | Ala | Gly | Ile | Arg | Tyr | Arg | Val | Ala | Trp | Gln | |
| | | 1990 | | | | | 1995 | | | | | | 2000 | | | |
| CCG | GCC | GTC | GTC | GAC | CGC | GGC | AAC | CCC | GGG | CCT | GCC | GGT | CAT | GTG | CTG | 6403 |
| Pro | Ala | Val | Val | Asp | Arg | Gly | Asn | Pro | Gly | Pro | Ala | Gly | His | Val | Leu | |
| | | 2005 | | | | | 2010 | | | | | 2015 | | | | |
| CTT | CTG | GCC | CCG | GAC | GAG | GAC | ACG | GCC | GAC | TCC | GGA | CTC | GCC | CCC | GCG | 6451 |
| Leu | Leu | Ala | Pro | Asp | Glu | Asp | Thr | Ala | Asp | Ser | Gly | Leu | Ala | Pro | Ala | |
| | | 2020 | | | | | 2025 | | | | | 2030 | | | | |
| ATC | GCA | CGT | GAA | CTC | GCC | GTG | CGC | GGG | GCC | GAG | GTC | CAC | ACC | GTC | GCC | 6499 |
| Ile | Ala | Arg | Glu | Leu | Ala | Val | Arg | Gly | Ala | Glu | Val | His | Thr | Val | Ala | |
| 2035 | | | | | 2040 | | | | | 2045 | | | | | 2050 | |
| GTG | CCG | GTC | GGT | ACA | GGC | CGG | GAG | GCA | GCC | GGG | GAC | CTG | TTG | CGG | GCC | 6547 |
| Val | Pro | Val | Gly | Thr | Gly | Arg | Glu | Ala | Ala | Gly | Asp | Leu | Leu | Arg | Ala | |
| | | | | 2055 | | | | | 2060 | | | | | 2065 | | |
| GCC | GGT | GAC | GGT | GCC | GCC | CGC | AGC | ACC | CGA | GTT | CTG | TGG | CTC | GCC | CCG | 6595 |
| Ala | Gly | Asp | Gly | Ala | Ala | Arg | Ser | Thr | Arg | Val | Leu | Trp | Leu | Ala | Pro | |
| | | | 2070 | | | | | 2075 | | | | | 2080 | | | |
| GCC | GAG | CCG | GAC | GCG | GCC | GAC | GCC | GTC | GCC | CTC | GTC | CAG | GCG | CTG | GGC | 6643 |
| Ala | Glu | Pro | Asp | Ala | Ala | Asp | Ala | Val | Ala | Leu | Val | Gln | Ala | Leu | Gly | |
| | | 2085 | | | | | 2090 | | | | | 2095 | | | | |
| GAG | GCG | GTA | CCC | GAA | GCC | CCG | CTC | TGG | ATC | ACC | ACC | CGT | GAG | GCG | GCG | 6691 |
| Glu | Ala | Val | Pro | Glu | Ala | Pro | Leu | Trp | Ile | Thr | Thr | Arg | Glu | Ala | Ala | |
| 2100 | | | | | 2105 | | | | | 2110 | | | | | | |
| GCC | GTG | CGG | CCG | GAC | GAG | ACC | CCT | TCC | GTC | GGG | GGC | GCT | CAG | CTG | TGG | 6739 |
| Ala | Val | Arg | Pro | Asp | Glu | Thr | Pro | Ser | Val | Gly | Gly | Ala | Gln | Leu | Trp | |
| 2115 | | | | | 2120 | | | | | 2125 | | | | | 2130 | |
| GGA | CTC | GGA | CAG | GTC | GCC | GCG | CTC | GAA | CTG | GGG | CGG | CGC | TGG | GGC | GGC | 6787 |
| Gly | Leu | Gly | Gln | Val | Ala | Ala | Leu | Glu | Leu | Gly | Arg | Arg | Trp | Gly | Gly | |
| | | | | 2135 | | | | | 2140 | | | | | 2145 | | |
| TTG | GCG | GAC | CTG | CCC | GGG | AGT | GCG | TCG | CCC | GCG | GTG | CTC | CGT | ACG | TTC | 6835 |
| Leu | Ala | Asp | Leu | Pro | Gly | Ser | Ala | Ser | Pro | Ala | Val | Leu | Arg | Thr | Phe | |
| | | | | 2150 | | | | | 2155 | | | | | 2160 | | |
| GTC | GGG | GCG | CTG | CTC | GCC | GGG | GGA | GAG | AAC | CAG | TTC | GCG | GTA | CGG | CCC | 6883 |
| Val | Gly | Ala | Leu | Leu | Ala | Gly | Gly | Glu | Asn | Gln | Phe | Ala | Val | Arg | Pro | |
| | | 2165 | | | | | 2170 | | | | | 2175 | | | | |
| TCC | GGC | GTC | CAT | GTC | CGC | CGT | GTG | GTT | CCC | GCG | CCC | GTC | CCC | GTC | CCG | 6931 |
| Ser | Gly | Val | His | Val | Arg | Arg | Val | Val | Pro | Ala | Pro | Val | Pro | Val | Pro | |
| | | 2180 | | | | | 2185 | | | | | 2190 | | | | |
| GCC | TCC | GCT | CGC | ACC | GTC | ACC | ACG | GCC | CCC | GCC | ACC | GCC | GTC | GGC | GAG | 6979 |
| Ala | Ser | Ala | Arg | Thr | Val | Thr | Thr | Ala | Pro | Ala | Thr | Ala | Val | Gly | Glu | |
| 2195 | | | | | 2200 | | | | | 2205 | | | | | 2210 | |
| GAC | GCA | CGG | AAC | GAC | ACC | TCG | GAC | GTG | GTC | GTG | CCG | GAC | GAC | CGG | TGG | 7027 |
| Asp | Ala | Arg | Asn | Asp | Thr | Ser | Asp | Val | Val | Val | Pro | Asp | Asp | Arg | Trp | |
| | | | | 2215 | | | | | 2220 | | | | | 2225 | | |
| TCC | TCC | GGC | ACC | GTA | CTG | ATC | ACC | GGG | GGC | ACC | GGT | GCC | CTG | GGT | GCG | 7075 |
| Ser | Ser | Gly | Thr | Val | Leu | Ile | Thr | Gly | Gly | Thr | Gly | Ala | Leu | Gly | Ala | |
| | | | | 2230 | | | | | 2235 | | | | | 2240 | | |
| CAG | GTC | GCC | CGC | AGG | CTC | GCC | CGG | TCG | GGC | GCC | GCG | CGT | CTG | CTC | CTG | 7123 |
| Gln | Val | Ala | Arg | Arg | Leu | Ala | Arg | Ser | Gly | Ala | Ala | Arg | Leu | Leu | Leu | |
| | | | 2245 | | | | | 2250 | | | | | 2255 | | | |
| GTG | GGC | CGG | CGC | GGC | GCG | GCC | GGC | CCC | GGA | GTG | GGC | GAA | CTC | GTC | GAG | 7171 |
| Val | Gly | Arg | Arg | Gly | Ala | Ala | Gly | Pro | Gly | Val | Gly | Glu | Leu | Val | Glu | |
| | | 2260 | | | | | 2265 | | | | | 2270 | | | | |
| GAG | CTG | ACG | GCG | CTC | GGT | TCC | GAA | GTG | GCC | GTC | GAG | GCC | TGC | GAC | GTC | 7219 |
| Glu | Leu | Thr | Ala | Leu | Gly | Ser | Glu | Val | Ala | Val | Glu | Ala | Cys | Asp | Val | |
| 2275 | | | | | 2280 | | | | | 2285 | | | | | 2290 | |

| | |
|---|---|
| GCC GAC CGG GAC GCA CTG GCC GCG CTC CTC GCG GGC CTC CCC GAG GAG<br>Ala Asp Arg Asp Ala Leu Ala Ala Leu Leu Ala Gly Leu Pro Glu Glu<br>                2295                          2300                   2305 | 7267 |
| CGG CCC CTC GTC GCC GTA CTG CAC GCG GCA GGT GTG CTC GAC GAC GGT<br>Arg Pro Leu Val Ala Val Leu His Ala Ala Gly Val Leu Asp Asp Gly<br>                2310                          2315                   2320 | 7315 |
| GTG CTC GAC TCG CTC ACC TCC GAC CGG GTG GAC GCC GTA CTG CGG GAC<br>Val Leu Asp Ser Leu Thr Ser Asp Arg Val Asp Ala Val Leu Arg Asp<br>                2325                          2330                   2335 | 7363 |
| AAG GTC ACC GCC GCC CGT CAC CTG GAC GAG CTG ACC GCG GAC CTT CCG<br>Lys Val Thr Ala Ala Arg His Leu Asp Glu Leu Thr Ala Asp Leu Pro<br>                2340                          2345                   2350 | 7411 |
| CTC GAC GCC TTC GTG CTC TTC TCC TCC ATC GTC GGC GTG TGG GGC AAC<br>Leu Asp Ala Phe Val Leu Phe Ser Ser Ile Val Gly Val Trp Gly Asn<br>2355                          2360                          2365                   2370 | 7459 |
| GGA GGG CAG GCC GTC TAC GCG GCC GCC AAC GCC GCG CTC GAC GCC CTG<br>Gly Gly Gln Ala Val Tyr Ala Ala Ala Asn Ala Ala Leu Asp Ala Leu<br>                        2375                          2380                   2385 | 7507 |
| GCG CAG CGG CGC CGG GCC AGG GGA GCC CGT GCC GCC TCG ATC GCC TGG<br>Ala Gln Arg Arg Arg Ala Arg Gly Ala Arg Ala Ala Ser Ile Ala Trp<br>                        2390                          2395                   2400 | 7555 |
| GGG CCG TGG GCC GGT GCC GGA ATG GCC TCC GGA ACG GCG GCG AAG TCC<br>Gly Pro Trp Ala Gly Ala Gly Met Ala Ser Gly Thr Ala Ala Lys Ser<br>                2405                          2410                   2415 | 7603 |
| TTC GAA CGG GAC GGC GTC ACG GCC CTG GAC CCC GAG CGC GCG CTC GAC<br>Phe Glu Arg Asp Gly Val Thr Ala Leu Asp Pro Glu Arg Ala Leu Asp<br>                2420                          2425                   2430 | 7651 |
| GTC CTC GAC GAC GTG GTG GGC GCC GGC GGG ACC TCT GCC GCA GGG ACG<br>Val Leu Asp Asp Val Val Gly Ala Gly Gly Thr Ser Ala Ala Gly Thr<br>2435                          2440                          2445                   2450 | 7699 |
| CAC GCG GCC GGC GAG AGC TCC CTG CTC GTC GCC GAC GTG GAC TGG GAG<br>His Ala Ala Gly Glu Ser Ser Leu Leu Val Ala Asp Val Asp Trp Glu<br>                        2455                          2460                   2465 | 7747 |
| ACC TTC GTC GGG CGT TCG GTC ACC CGC CGT ACC TGG TCG CTC TTC GAC<br>Thr Phe Val Gly Arg Ser Val Thr Arg Arg Thr Trp Ser Leu Phe Asp<br>                        2470                          2475                   2480 | 7795 |
| GGC GTC TCC GCC GCC CGT TCG GCG CGT GCC GGC CAT GCC GCG GAC GAC<br>Gly Val Ser Ala Ala Arg Ser Ala Arg Ala Gly His Ala Ala Asp Asp<br>                2485                          2490                   2495 | 7843 |
| CGT GCC GCT CTC ACC CCA GGG ACG CGG CCG GGC GAC GGC GCA CCG GGC<br>Arg Ala Ala Leu Thr Pro Gly Thr Arg Pro Gly Asp Gly Ala Pro Gly<br>                2500                          2505                   2510 | 7891 |
| GGG AGC GGA CAG GAC GGG GGC GAG GGC CGG CCG TGG CTC TCC GTC GGC<br>Gly Ser Gly Gln Asp Gly Gly Glu Gly Arg Pro Trp Leu Ser Val Gly<br>2515                          2520                          2525                   2530 | 7939 |
| CCC TCG CCG GCG GAA CGC CGT CGT GCT CTG CTC ACG CTT GTG CGC TCG<br>Pro Ser Pro Ala Glu Arg Arg Arg Ala Leu Leu Thr Leu Val Arg Ser<br>                        2535                          2540                   2545 | 7987 |
| GAG GCC GCC GGG ATC CTG CGC CAC GCC TCG GCC GAC GCG GTC GAC CCG<br>Glu Ala Ala Gly Ile Leu Arg His Ala Ser Ala Asp Ala Val Asp Pro<br>                2550                          2555                   2560 | 8035 |
| GAG CTG GCC TTC CGG TCC GCC GGG TTC GAC TCC CTC ACC GTT CTC GAA<br>Glu Leu Ala Phe Arg Ser Ala Gly Phe Asp Ser Leu Thr Val Leu Glu<br>                        2565                          2570                   2575 | 8083 |
| CTG CGT AAC CGC CTG ACC GCT GCC ACC GGC CTG AAC CTG CCG AAC ACG<br>Leu Arg Asn Arg Leu Thr Ala Ala Thr Gly Leu Asn Leu Pro Asn Thr<br>                2580                          2585                   2590 | 8131 |
| CTG CTC TTC GAC CAC CCG ACC CCC CTC TCG CTC GCC TCC CAC CTG CAC<br>Leu Leu Phe Asp His Pro Thr Pro Leu Ser Leu Ala Ser His Leu His<br>2595                          2600                          2605                   2610 | 8179 |

```
GAC GAA CTG TTC GGT CCC GAC AGC GAG GCG GAG CCG GCA GCG GCC GCC      8227
Asp Glu Leu Phe Gly Pro Asp Ser Glu Ala Glu Pro Ala Ala Ala Ala
            2615                2620                2625

CCC ACG CCG GTC ATG GCC GAC GAG CGT GAG CCG ATC GCG ATC GTG GGC      8275
Pro Thr Pro Val Met Ala Asp Glu Arg Glu Pro Ile Ala Ile Val Gly
        2630                2635                2640

ATG GCG TGC CGT TAC CCG GGC GGT GTG GCG TCG CCG GAC GAC CTG TGG      8323
Met Ala Cys Arg Tyr Pro Gly Gly Val Ala Ser Pro Asp Asp Leu Trp
        2645                2650                2655

GAC CTG GTG GCC GGT GAC GGG CAC ACG CTC TCC CCG TTC CCG GCC GAC      8371
Asp Leu Val Ala Gly Asp Gly His Thr Leu Ser Pro Phe Pro Ala Asp
        2660                2665                2670

CGT GGC TGG GAC GTC GAG GGG CTG TAC GAC CCG GAG CCG GGG GTG CCG      8419
Arg Gly Trp Asp Val Glu Gly Leu Tyr Asp Pro Glu Pro Gly Val Pro
2675                2680                2685                2690

GGC AAG AGC TAT GTA CGG GAA GGC GGG TTC CTG CGT TCC GCG GCC GAG      8467
Gly Lys Ser Tyr Val Arg Glu Gly Gly Phe Leu Arg Ser Ala Ala Glu
            2695                2700                2705

TTC GAC GCG GAG TTC TTC GGG ATA TCG CCG CGC GAG GCC ACG GCC ATG      8515
Phe Asp Ala Glu Phe Phe Gly Ile Ser Pro Arg Glu Ala Thr Ala Met
            2710                2715                2720

GAC CCG CAG CAG CGG TTG CTG CTG GAG ACG TCG TGG GAG GCG CTG GAG      8563
Asp Pro Gln Gln Arg Leu Leu Leu Glu Thr Ser Trp Glu Ala Leu Glu
            2725                2730                2735

CGG GCC GGC ATC GTT CCG GAC TCG CTG CGC GGC ACC CGG ACC GGT GTC      8611
Arg Ala Gly Ile Val Pro Asp Ser Leu Arg Gly Thr Arg Thr Gly Val
            2740                2745                2750

TTC AGC GGC ATC TCC CAG CAG GAC TAC GCG ACC CAG CTG GGG GAC GCC      8659
Phe Ser Gly Ile Ser Gln Gln Asp Tyr Ala Thr Gln Leu Gly Asp Ala
2755                2760                2765                2770

GCC GAC ACC TAC GGC GGG CAT GTG CTC ACG GGG ACC CTC GGC AGT GTG      8707
Ala Asp Thr Tyr Gly Gly His Val Leu Thr Gly Thr Leu Gly Ser Val
            2775                2780                2785

ATC TCC GGT CGG GTT GCC TAT GCG TTG GGG TTG GAG GGG CCG GCG CTG      8755
Ile Ser Gly Arg Val Ala Tyr Ala Leu Gly Leu Glu Gly Pro Ala Leu
            2790                2795                2800

ACG GTG GAC ACG GCG TGT TCG TCG TCG TTG GTG GCG TTG CAT CTG GCG      8803
Thr Val Asp Thr Ala Cys Ser Ser Ser Leu Val Ala Leu His Leu Ala
            2805                2810                2815

GTG CAG TCG TTG CGG CGG GGT GAG TGT GAT CTG GCG TTG GCC GGT GGG      8851
Val Gln Ser Leu Arg Arg Gly Glu Cys Asp Leu Ala Leu Ala Gly Gly
            2820                2825                2830

GTG ACG GTG ATG GCG ACG CCG ACG GTG TTC GTG GAG TTC TCG CGG CAG      8899
Val Thr Val Met Ala Thr Pro Thr Val Phe Val Glu Phe Ser Arg Gln
2835                2840                2845                2850

CGG GGG CTG GCG GCG GAC GGG CGG TGC AAG GCG TTC GCG GAG GGT GCG      8947
Arg Gly Leu Ala Ala Asp Gly Arg Cys Lys Ala Phe Ala Glu Gly Ala
            2855                2860                2865

GAC GGG ACG GCG TGG GCG GAG GGT GTG GGT GTG CTG CTG GTG GAG CGG      8995
Asp Gly Thr Ala Trp Ala Glu Gly Val Gly Val Leu Leu Val Glu Arg
            2870                2875                2880

CTT TCC GAC GCG CGC CGC AAC GGT CAT CGG GTG CTG GCG GTG GTG CGG      9043
Leu Ser Asp Ala Arg Arg Asn Gly His Arg Val Leu Ala Val Val Arg
            2885                2890                2895

GGC AGT GCG GTC AAT CAG GAC GGT GCG AGC AAT GGG CTG ACG GCG CCG      9091
Gly Ser Ala Val Asn Gln Asp Gly Ala Ser Asn Gly Leu Thr Ala Pro
            2900                2905                2910

AGT GGT CCG GCG CAG CAG CGG GTG ATC CGT GAG GCG CTG GCT GAT GCG      9139
Ser Gly Pro Ala Gln Gln Arg Val Ile Arg Glu Ala Leu Ala Asp Ala
2915                2920                2925                2930
```

| | |
|---|---|
| GGG CTG GTG CCC GCC GAC GTG GAT GTG GTG GAG GCG CAC GGT ACG GGG<br>Gly Leu Val Pro Ala Asp Val Asp Val Val Glu Ala His Gly Thr Gly<br>2935                          2940                     2945 | 9187 |
| ACG GCG CTG GGT GAT CCG ATC GAG GCG GGT GCG CTG CTG GCC ACG TAC<br>Thr Ala Leu Gly Asp Pro Ile Glu Ala Gly Ala Leu Leu Ala Thr Tyr<br>2950                          2955                     2960 | 9235 |
| GGG CGG GAG CGG GTC GGC GAT CCG TTG TGG CTC GGG TCG TTG AAG TCG<br>Gly Arg Glu Arg Val Gly Asp Pro Leu Trp Leu Gly Ser Leu Lys Ser<br>2965                          2970                     2975 | 9283 |
| AAC ATC GGG CAT GCG CAG GCG GCT GCG GGT GTG GGT GGT GTG ATC AAG<br>Asn Ile Gly His Ala Gln Ala Ala Ala Gly Val Gly Gly Val Ile Lys<br>2980                          2985                     2990 | 9331 |
| GTG GTG CAG GGG ATG CGG CAT GGG TCG TTG CCG CGG ACG CTG CAT GTG<br>Val Val Gln Gly Met Arg His Gly Ser Leu Pro Arg Thr Leu His Val<br>2995                          3000                     3005                     3010 | 9379 |
| GAT GCG CCG TCG TCG AAG GTG GAG TGG GCT TCG GGT GCG GTG GAG CTG<br>Asp Ala Pro Ser Ser Lys Val Glu Trp Ala Ser Gly Ala Val Glu Leu<br>                          3015                     3020                     3025 | 9427 |
| CTG ACC GAG ACC CGG TCG TGG CCG CGG CGG GTG GAG CGG GTG CGG CGG<br>Leu Thr Glu Thr Arg Ser Trp Pro Arg Arg Val Glu Arg Val Arg Arg<br>                          3030                     3035                     3040 | 9475 |
| GCC GCG GTG TCG GCG TTC GGG GTG AGC GGG ACC AAC GCC CAT GTG GTC<br>Ala Ala Val Ser Ala Phe Gly Val Ser Gly Thr Asn Ala His Val Val<br>                          3045                     3050                     3055 | 9523 |
| CTG GAG GAA GCG CCG GCG GAG GCC GGG AGC GAG CAC GGG GAC GGC CCT<br>Leu Glu Glu Ala Pro Ala Glu Ala Gly Ser Glu His Gly Asp Gly Pro<br>3060                          3065                     3070 | 9571 |
| GAA CCT GAG CGG CCC GAC GCG GTG ACG GGT CCG TTG TCG TGG GTG CTT<br>Glu Pro Glu Arg Pro Asp Ala Val Thr Gly Pro Leu Ser Trp Val Leu<br>3075                          3080                     3085                     3090 | 9619 |
| TCT GCG CGG TCG GAG GGG GCG TTG CGG GCG CAG GCG GTG CGG TTG CGT<br>Ser Ala Arg Ser Glu Gly Ala Leu Arg Ala Gln Ala Val Arg Leu Arg<br>                          3095                     3100                     3105 | 9667 |
| GAG TGT GTG GAG CGG GTG GGT GCG GAT CCG CGG GAT GTG GCG GGG TCG<br>Glu Cys Val Glu Arg Val Gly Ala Asp Pro Arg Asp Val Ala Gly Ser<br>                          3110                     3115                     3120 | 9715 |
| TTG GTG GTG TCG CGT GCG TCG TTC GGT GAG CGT GCG GTG GTG GTG GGC<br>Leu Val Val Ser Arg Ala Ser Phe Gly Glu Arg Ala Val Val Val Gly<br>                          3125                     3130                     3135 | 9763 |
| CGG GGG CGT GAG GAG TTG CTG GCG GGT CTG GAT GTG GTG GCT GCC GGG<br>Arg Gly Arg Glu Glu Leu Leu Ala Gly Leu Asp Val Val Ala Ala Gly<br>3140                          3145                     3150 | 9811 |
| GCT CCT GTG GGT GTG TCT TCG GGG GCC GGT GCT GTG GTG CGG GGG AGT<br>Ala Pro Val Gly Val Ser Ser Gly Ala Gly Ala Val Val Arg Gly Ser<br>3155                          3160                     3165                     3170 | 9859 |
| GCG GTG CGG GGT CGT GGG GTG GGG GTG TTG TTC ACG GGT CAG GGT GCG<br>Ala Val Arg Gly Arg Gly Val Gly Val Leu Phe Thr Gly Gln Gly Ala<br>                          3175                     3180                     3185 | 9907 |
| CAG TGG GTT GGT ATG GGG CGT GGG TTG TAT GCG GGG GGT GGG GTG TTT<br>Gln Trp Val Gly Met Gly Arg Gly Leu Tyr Ala Gly Gly Gly Val Phe<br>                          3190                     3195                     3200 | 9955 |
| GCG GAG GTG CTG GAT GAG GTG TTG TCG GTG GTG GGG GAG GTG GAT GGT<br>Ala Glu Val Leu Asp Glu Val Leu Ser Val Val Gly Glu Val Asp Gly<br>                          3205                     3210                     3215 | 10003 |
| CGG TCG TTG CGG GAT GTG ATG TTC GCG GAT GCT GAC TCG GTT TTG GGT<br>Arg Ser Leu Arg Asp Val Met Phe Ala Asp Ala Asp Ser Val Leu Gly<br>                          3220                     3225                     3230 | 10051 |
| GGG TTG TTG GGT CGG ACG GAG TTT GCT CAG CCT GCG TTG TTT GCG TTG<br>Gly Leu Leu Gly Arg Thr Glu Phe Ala Gln Pro Ala Leu Phe Ala Leu<br>3235                          3240                     3245                     3250 | 10099 |

| | | | | | | | | | | | | | | | | |
|---|---|---|---|---|---|---|---|---|---|---|---|---|---|---|---|---|
| GAG | GTG | GCG | TTG | TTC | CGG | GCG | TTG | GAG | GCT | CGG | GGT | GTG | GAG | GTG | TCG | 10147 |
| Glu | Val | Ala | Leu | Phe | Arg | Ala | Leu | Glu | Ala | Arg | Gly | Val | Glu | Val | Ser | |
| | | | 3255 | | | | | 3260 | | | | | 3265 | | | |
| GTG | GTG | TTG | GGT | CAT | TCG | GTG | GGG | GAG | GTG | GCT | GCT | GCG | TAT | GTG | GCG | 10195 |
| Val | Val | Leu | Gly | His | Ser | Val | Gly | Glu | Val | Ala | Ala | Ala | Tyr | Val | Ala | |
| | | 3270 | | | | | 3275 | | | | | 3280 | | | | |
| GGG | GTG | TTG | TCG | TTG | GGT | GAT | GCG | GTG | CGG | TTG | GTG | GTG | GCG | CGG | GGT | 10243 |
| Gly | Val | Leu | Ser | Leu | Gly | Asp | Ala | Val | Arg | Leu | Val | Val | Ala | Arg | Gly | |
| | 3285 | | | | | 3290 | | | | | 3295 | | | | | |
| GGG | TTG | ATG | GGT | GGG | TTG | CCG | GTG | GGT | GGG | GGG | ATG | TGG | TCG | GTG | GGG | 10291 |
| Gly | Leu | Met | Gly | Gly | Leu | Pro | Val | Gly | Gly | Gly | Met | Trp | Ser | Val | Gly | |
| | 3300 | | | | | 3305 | | | | | 3310 | | | | | |
| GCG | TCG | GAG | TCG | GTG | GTG | CGG | GGG | GTT | GTT | GAG | GGG | TTG | GGG | GAG | TGG | 10339 |
| Ala | Ser | Glu | Ser | Val | Val | Arg | Gly | Val | Val | Glu | Gly | Leu | Gly | Glu | Trp | |
| 3315 | | | | | 3320 | | | | | 3325 | | | | | 3330 | |
| GTG | TCG | GTT | GCG | GCG | GTG | AAT | GGG | CCG | CGG | TCG | GTG | GTG | TTG | TCG | GGT | 10387 |
| Val | Ser | Val | Ala | Ala | Val | Asn | Gly | Pro | Arg | Ser | Val | Val | Leu | Ser | Gly | |
| | | | | 3335 | | | | | 3340 | | | | | 3345 | | |
| GAT | GTG | GGT | GTG | CTG | GAG | TCG | GTG | GTT | GTC | ACG | CTG | ATG | GGG | GAT | GGG | 10435 |
| Asp | Val | Gly | Val | Leu | Glu | Ser | Val | Val | Val | Thr | Leu | Met | Gly | Asp | Gly | |
| | | | 3350 | | | | | 3355 | | | | | 3360 | | | |
| GTG | GAG | TGC | CGG | CGG | TTG | GAT | GTG | TCG | CAT | GGG | TTT | CAT | TCG | GTG | TTG | 10483 |
| Val | Glu | Cys | Arg | Arg | Leu | Asp | Val | Ser | His | Gly | Phe | His | Ser | Val | Leu | |
| | | 3365 | | | | | 3370 | | | | | 3375 | | | | |
| ATG | GAG | CCG | GTG | TTG | GGG | GAG | TTC | CGG | GGG | GTT | GTG | GAG | TCG | TTG | GAG | 10531 |
| Met | Glu | Pro | Val | Leu | Gly | Glu | Phe | Arg | Gly | Val | Val | Glu | Ser | Leu | Glu | |
| | 3380 | | | | | 3385 | | | | | 3390 | | | | | |
| TTC | GGT | CGG | GTG | CGG | CCG | GGT | GTG | GTG | GTG | GTG | TCG | GGT | GTG | TCG | GGT | 10579 |
| Phe | Gly | Arg | Val | Arg | Pro | Gly | Val | Val | Val | Val | Ser | Gly | Val | Ser | Gly | |
| 3395 | | | | | 3400 | | | | | 3405 | | | | | 3410 | |
| GGG | GTG | GTG | GGT | TCG | GGG | GAG | TTG | GGG | GAT | CCG | GGG | TAT | TGG | GTG | CGT | 10627 |
| Gly | Val | Val | Gly | Ser | Gly | Glu | Leu | Gly | Asp | Pro | Gly | Tyr | Trp | Val | Arg | |
| | | | | 3415 | | | | | 3420 | | | | | 3425 | | |
| CAT | GCG | CGG | GAG | GCG | GTG | CGT | TTC | GCG | GAT | GGG | GTG | GGG | GTG | GTG | CGT | 10675 |
| His | Ala | Arg | Glu | Ala | Val | Arg | Phe | Ala | Asp | Gly | Val | Gly | Val | Val | Arg | |
| | | | 3430 | | | | | 3435 | | | | | 3440 | | | |
| GGT | CTG | GGT | GTG | GGG | ACG | TTG | GTG | GAG | GTG | GGT | CCG | CAT | GGG | GTG | CTG | 10723 |
| Gly | Leu | Gly | Val | Gly | Thr | Leu | Val | Glu | Val | Gly | Pro | His | Gly | Val | Leu | |
| | | 3445 | | | | | 3450 | | | | | 3455 | | | | |
| ACG | GGG | ATG | GCG | GGT | CAG | TGC | CTG | GAG | GCC | GGT | GAT | GAT | GTG | GTG | GTG | 10771 |
| Thr | Gly | Met | Ala | Gly | Gln | Cys | Leu | Glu | Ala | Gly | Asp | Asp | Val | Val | Val | |
| | 3460 | | | | | 3465 | | | | | 3470 | | | | | |
| GTG | CCG | GCG | ATG | CGG | CGG | GGC | CGT | CCG | GAG | CGG | GAG | GTG | TTC | GAG | GCG | 10819 |
| Val | Pro | Ala | Met | Arg | Arg | Gly | Arg | Pro | Glu | Arg | Glu | Val | Phe | Glu | Ala | |
| 3475 | | | | | 3480 | | | | | 3485 | | | | | 3490 | |
| GCG | CTG | GCG | ACG | GTG | TTC | ACC | CGG | GAC | GCC | GGC | CTC | GAC | GCC | ACG | ACA | 10867 |
| Ala | Leu | Ala | Thr | Val | Phe | Thr | Arg | Asp | Ala | Gly | Leu | Asp | Ala | Thr | Thr | |
| | | | | 3495 | | | | | 3500 | | | | | 3505 | | |
| CTC | CAC | ACC | GGG | AGC | ACC | GGC | CGA | CGC | ATC | GAC | CTC | CCC | ACC | TAC | CCC | 10915 |
| Leu | His | Thr | Gly | Ser | Thr | Gly | Arg | Arg | Ile | Asp | Leu | Pro | Thr | Tyr | Pro | |
| | | | 3510 | | | | | 3515 | | | | | 3520 | | | |
| TTC | CAA | CAC | AAC | CGC | TAC | TGG | GCA | ACC | GGC | TCA | GTG | ACC | GGT | GCG | ACC | 10963 |
| Phe | Gln | His | Asn | Arg | Tyr | Trp | Ala | Thr | Gly | Ser | Val | Thr | Gly | Ala | Thr | |
| | | | 3525 | | | | | 3530 | | | | | 3535 | | | |
| GGC | ACC | TCG | GCA | GCC | GCG | CGC | TTC | GGC | CTG | GAG | TGG | AAG | GAC | CAC | CCC | 11011 |
| Gly | Thr | Ser | Ala | Ala | Ala | Arg | Phe | Gly | Leu | Glu | Trp | Lys | Asp | His | Pro | |
| | | 3540 | | | | | 3545 | | | | | 3550 | | | | |
| TTC | CTC | AGC | GGC | GCC | ACG | CCG | ATA | GCC | GGC | TCC | GGC | GCG | CTG | CTC | CTC | 11059 |
| Phe | Leu | Ser | Gly | Ala | Thr | Pro | Ile | Ala | Gly | Ser | Gly | Ala | Leu | Leu | Leu | |
| 3555 | | | | | 3560 | | | | | 3565 | | | | | 3570 | |

```
ACC GGC AGG GTG GGG CTC GCT GCC CAC CCG TGG CTG GCC GAC CAC GCC        11107
Thr Gly Arg Val Gly Leu Ala Ala His Pro Trp Leu Ala Asp His Ala
            3575                3580                3585

ATC TCC GGC ACG GTG CTG CTC CCC GGA ACG GCG ATC GCC GAC CTG CTG        11155
Ile Ser Gly Thr Val Leu Leu Pro Gly Thr Ala Ile Ala Asp Leu Leu
            3590                3595                3600

CTG CGG GCG GTC GAG GAG GTC GGC GCC GGA GGG GTC GAG GAA CTG ACG        11203
Leu Arg Ala Val Glu Glu Val Gly Ala Gly Gly Val Glu Glu Leu Thr
            3605                3610                3615

CTC CAT GAG CCC CTG CTC CTC CCC GAG CGA GGC GGC CTG CAC GTC CAG        11251
Leu His Glu Pro Leu Leu Leu Pro Glu Arg Gly Gly Leu His Val Gln
            3620                3625                3630

GTG CTG GTC GAG GCG GCC GAC GAG CAG GGA CGG CGT GCC GTG GCA GTC        11299
Val Leu Val Glu Ala Ala Asp Glu Gln Gly Arg Arg Ala Val Ala Val
3635                3640                3645                3650

GCC GCA CGC CCG GAG GGC CCT GGG CGG GAC GGT GAG GAA CAG GAG TGG        11347
Ala Ala Arg Pro Glu Gly Pro Gly Arg Asp Gly Glu Glu Gln Glu Trp
            3655                3660                3665

ACC CGG CAC GCG GAA GGC GTG CTC ACC TCC ACC GAG ACG GCC GTT CCG        11395
Thr Arg His Ala Glu Gly Val Leu Thr Ser Thr Glu Thr Ala Val Pro
            3670                3675                3680

GAC ATG GGC TGG GCC GCC GGG GCC TGG CCG CCG CCC GGT GCC GAG CCG        11443
Asp Met Gly Trp Ala Ala Gly Ala Trp Pro Pro Pro Gly Ala Glu Pro
            3685                3690                3695

ATC GAC GTC GAG GAG CTG TAC GAC GCG TTC GCC GCG GAC GGC TAC GGC        11491
Ile Asp Val Glu Glu Leu Tyr Asp Ala Phe Ala Ala Asp Gly Tyr Gly
            3700                3705                3710

TAC GGC CCG GCC TTC ACC GCA CTG TCC GGC GTG TGG CGT CTC GGC GAC        11539
Tyr Gly Pro Ala Phe Thr Ala Leu Ser Gly Val Trp Arg Leu Gly Asp
3715                3720                3725                3730

GAA CTC TTC GCC GAG GTG CGG CGG CCC GCG GGG GGC GCG GGC ACG ACC        11587
Glu Leu Phe Ala Glu Val Arg Arg Pro Ala Gly Gly Ala Gly Thr Thr
            3735                3740                3745

GGT GAC GGT TTC GGC GTC CAC CCC GCA CTC TTC GAT GCG GCC CTC CAC        11635
Gly Asp Gly Phe Gly Val His Pro Ala Leu Phe Asp Ala Ala Leu His
            3750                3755                3760

CCG TGG CGC GCC GGC GGG CTG CTG CCC GAC ACG GGC GGC ACC ACC TGG        11683
Pro Trp Arg Ala Gly Gly Leu Leu Pro Asp Thr Gly Gly Thr Thr Trp
            3765                3770                3775

GCG CCG TTC TCC TGG CAG GGC ATC GCG CTC CAC ACC ACC GGA GCC GAG        11731
Ala Pro Phe Ser Trp Gln Gly Ile Ala Leu His Thr Thr Gly Ala Glu
            3780                3785                3790

ACG CTC CGC GTC AGA CTG GCC CCT GCG GCC GGC GGC ACC GAG TCG GCC        11779
Thr Leu Arg Val Arg Leu Ala Pro Ala Ala Gly Gly Thr Glu Ser Ala
3795                3800                3805                3810

TTC TCC GTA CAG GCC GCC GAC CCG GCG GGC ACC CCG GTC CTC ACC CTC        11827
Phe Ser Val Gln Ala Ala Asp Pro Ala Gly Thr Pro Val Leu Thr Leu
            3815                3820                3825

GAC GCA CTG CTG CTC CGC CCG GTG ACC CTG GGG AGG GCC GAC GCG CCG        11875
Asp Ala Leu Leu Leu Arg Pro Val Thr Leu Gly Arg Ala Asp Ala Pro
            3830                3835                3840

CAA CCG CTG TAC CGC GTC GAC TGG CAG CCG GTC GGC CAG GGG ACC GAG        11923
Gln Pro Leu Tyr Arg Val Asp Trp Gln Pro Val Gly Gln Gly Thr Glu
            3845                3850                3855

GCC TCC GGC GCC CAG GGC TGG ACG GTG CTC GGG CAG GCC GCG GCC GAG        11971
Ala Ser Gly Ala Gln Gly Trp Thr Val Leu Gly Gln Ala Ala Ala Glu
            3860                3865                3870

ACG GTC GCG CAG CCC GCC GCC CAT GCG GAC CTC ACC GCC CTG CGT ACG        12019
Thr Val Ala Gln Pro Ala Ala His Ala Asp Leu Thr Ala Leu Arg Thr
3875                3880                3885                3890
```

```
GCT GTG GCC GCG GCG GGA ACA CCC GTG CCC CGG CTG GTG GTC GTG TCG      12067
Ala Val Ala Ala Ala Gly Thr Pro Val Pro Arg Leu Val Val Val Ser
        3895                3900                3905

CCG GTG GAC ACC CGG CTG GAC GAG GGG CCG GTG CTG GCG GAC GCC GAG      12115
Pro Val Asp Thr Arg Leu Asp Glu Gly Pro Val Leu Ala Asp Ala Glu
        3910                3915                3920

GCT CGG GCC CGT GCG GGT GAC GGC TGG GAC GAC GAT CCC CTA CGT GTC      12163
Ala Arg Ala Arg Ala Gly Asp Gly Trp Asp Asp Asp Pro Leu Arg Val
        3925                3930                3935

GCC CTC GGG CGC GGC CTG ACC CTG GTC CGG GAG TGG GTC GAG GAC GAA      12211
Ala Leu Gly Arg Gly Leu Thr Leu Val Arg Glu Trp Val Glu Asp Glu
        3940                3945                3950

CGG TTG GCG GAC TCC CGG CTC GTC GTC CTC ACC CGT GGC GCG GTG GCG      12259
Arg Leu Ala Asp Ser Arg Leu Val Val Leu Thr Arg Gly Ala Val Ala
3955                3960                3965                3970

GCC GGT CCC GGC GAT GTG CCG GAC CTG ACA GGT GCG GCC CTG TGG GGG      12307
Ala Gly Pro Gly Asp Val Pro Asp Leu Thr Gly Ala Ala Leu Trp Gly
                3975                3980                3985

CTG CTC CGC TCC GCG CAG TCG GAG TAT CCG GAC CGC TTC ACC CTC ATC      12355
Leu Leu Arg Ser Ala Gln Ser Glu Tyr Pro Asp Arg Phe Thr Leu Ile
        3990                3995                4000

GAC GTG GAC GAT TCC CCC GAG TCC CGT GCG GCT CTG CCC CGG GCT CTG      12403
Asp Val Asp Asp Ser Pro Glu Ser Arg Ala Ala Leu Pro Arg Ala Leu
        4005                4010                4015

GGA TCG GCC GAG CGA CAA CTC GCC CTG CGG ACG GGC GAC GTG CTG GCG      12451
Gly Ser Ala Glu Arg Gln Leu Ala Leu Arg Thr Gly Asp Val Leu Ala
        4020                4025                4030

CCG GCC CTG GTC CCG ATG GCC ACC CGG CCG GCG GAG ACC ACT CCA GCG      12499
Pro Ala Leu Val Pro Met Ala Thr Arg Pro Ala Glu Thr Thr Pro Ala
4035                4040                4045                4050

ACG GCG GTC GCC TCG GCG ACA ACA CAG ACA CAG GTC ACC GCG CCC GCT      12547
Thr Ala Val Ala Ser Ala Thr Thr Gln Thr Gln Val Thr Ala Pro Ala
                4055                4060                4065

CCC GAC GAC CCG GCT GCG GAT GCC GTG TTC GAC CCG GCG GGC ACC GTA      12595
Pro Asp Asp Pro Ala Ala Asp Ala Val Phe Asp Pro Ala Gly Thr Val
        4070                4075                4080

CTG ATC ACC GGC GGC ACC GGC GCC CTG GGA CGG CGT GTC GCC TCG CAC      12643
Leu Ile Thr Gly Gly Thr Gly Ala Leu Gly Arg Arg Val Ala Ser His
        4085                4090                4095

CTC GCG CGC CGG TAC GGC GTA CGC CAC ATG CTT CTG GTC AGC AGG CGT      12691
Leu Ala Arg Arg Tyr Gly Val Arg His Met Leu Leu Val Ser Arg Arg
        4100                4105                4110

GGA CCG GAC GCC CCC GAG GCC GGT CCC CTG GAA CGG GAA CTC GCC GGT      12739
Gly Pro Asp Ala Pro Glu Ala Gly Pro Leu Glu Arg Glu Leu Ala Gly
4115                4120                4125                4130

CTC GGA GTC ACC GCC ACC TTC CTG GCA TGC GAC CTC ACC GAC ATC GAG      12787
Leu Gly Val Thr Ala Thr Phe Leu Ala Cys Asp Leu Thr Asp Ile Glu
                4135                4140                4145

GCC GTA CGG AAG GCC GTC GCC GCG GTG CCG TCG GAC CAC CCG CTG ACC      12835
Ala Val Arg Lys Ala Val Ala Ala Val Pro Ser Asp His Pro Leu Thr
                4150                4155                4160

GGT GTG GTG CAC ACC GCC GGC GTG CTG GAC GAC GGC GCC CTG ACC GGC      12883
Gly Val Val His Thr Ala Gly Val Leu Asp Asp Gly Ala Leu Thr Gly
                4165                4170                4175

CTG ACC CGG CAA CGC CTC GAC ACC GTG CTG CGG CCC AAG GCC GAC GCC      12931
Leu Thr Arg Gln Arg Leu Asp Thr Val Leu Arg Pro Lys Ala Asp Ala
        4180                4185                4190

GTG CGG AAC CTC CAC GAG GCG ACC CTC GAC CGG CCG CTG CGC GCG TTC      12979
Val Arg Asn Leu His Glu Ala Thr Leu Asp Arg Pro Leu Arg Ala Phe
4195                4200                4205                4210
```

| | | | | | | | | | | | | | | | | |
|---|---|---|---|---|---|---|---|---|---|---|---|---|---|---|---|---|
| GTC | CTG | TTC | TCC | GCC | GCC | GCC | GGA | CTC | CTG | GGC | CGC | CCC | GGG | CAG | GCC | 13027 |
| Val | Leu | Phe | Ser | Ala | Ala | Ala | Gly | Leu | Leu | Gly | Arg | Pro | Gly | Gln | Ala | |
| | | | | 4215 | | | | | 4220 | | | | | 4225 | | |
| TCC | TAC | GCC | GCC | GCC | AAC | GCG | GTC | CTC | GAC | GCG | CTC | GCG | GGA | GCC | CGC | 13075 |
| Ser | Tyr | Ala | Ala | Ala | Asn | Ala | Val | Leu | Asp | Ala | Leu | Ala | Gly | Ala | Arg | |
| | | | | 4230 | | | | | 4235 | | | | | 4240 | | |
| CGC | GCG | GCC | GGA | CTG | CCC | GCA | GTG | TCC | CTG | GCG | TGG | GGC | CTG | TGG | GAC | 13123 |
| Arg | Ala | Ala | Gly | Leu | Pro | Ala | Val | Ser | Leu | Ala | Trp | Gly | Leu | Trp | Asp | |
| | | | | 4245 | | | | | 4250 | | | | | 4255 | | |
| GAG | CAG | ACG | GGC | ATG | GCA | GGA | GGC | CTC | GAC | GAG | ATG | GCC | CTG | CGC | GTG | 13171 |
| Glu | Gln | Thr | Gly | Met | Ala | Gly | Gly | Leu | Asp | Glu | Met | Ala | Leu | Arg | Val | |
| | | | | 4260 | | | | | 4265 | | | | | 4270 | | |
| CTG | CGC | CGG | GAC | GGC | ATC | GCC | GCG | ATG | CCT | CCG | GAG | CAG | GGG | CTC | GAA | 13219 |
| Leu | Arg | Arg | Asp | Gly | Ile | Ala | Ala | Met | Pro | Pro | Glu | Gln | Gly | Leu | Glu | |
| 4275 | | | | | 4280 | | | | | 4285 | | | | | 4290 | |
| CTG | CTC | GAC | CTG | GCC | CTG | ACC | GGA | CAC | CGG | GAC | GGA | CCC | GCC | GTC | CTC | 13267 |
| Leu | Leu | Asp | Leu | Ala | Leu | Thr | Gly | His | Arg | Asp | Gly | Pro | Ala | Val | Leu | |
| | | | | 4295 | | | | | 4300 | | | | | 4305 | | |
| GTC | CCC | CTC | CTC | CTC | GAC | GGC | GCG | GCC | CTG | CGC | CGC | ACG | GCG | AAG | GAG | 13315 |
| Val | Pro | Leu | Leu | Leu | Asp | Gly | Ala | Ala | Leu | Arg | Arg | Thr | Ala | Lys | Glu | |
| | | | | 4310 | | | | | 4315 | | | | | 4320 | | |
| CGC | GGC | GCG | GCC | ACG | ATG | TCC | CCC | TTG | CTG | CGC | GCC | CTG | CTG | CCC | GCC | 13363 |
| Arg | Gly | Ala | Ala | Thr | Met | Ser | Pro | Leu | Leu | Arg | Ala | Leu | Leu | Pro | Ala | |
| | | | | 4325 | | | | | 4330 | | | | | 4335 | | |
| GCC | CTG | CGC | CGC | AGC | GGT | GGA | GCC | GGC | GCC | CCC | GCG | GCG | GCC | GAC | CGG | 13411 |
| Ala | Leu | Arg | Arg | Ser | Gly | Gly | Ala | Gly | Ala | Pro | Ala | Ala | Ala | Asp | Arg | |
| | | | | 4340 | | | | | 4345 | | | | | 4350 | | |
| CAC | GGC | AAG | GAG | GCG | GAC | CCC | GGT | GCG | GGA | CGC | CTC | GCA | GGG | ATG | GTG | 13459 |
| His | Gly | Lys | Glu | Ala | Asp | Pro | Gly | Ala | Gly | Arg | Leu | Ala | Gly | Met | Val | |
| 4355 | | | | | 4360 | | | | | 4365 | | | | | 4370 | |
| GCA | CTC | GAA | GCG | GCG | GAG | CGT | TCC | GCG | GCC | GTC | CTT | GAG | CTG | GTC | ACC | 13507 |
| Ala | Leu | Glu | Ala | Ala | Glu | Arg | Ser | Ala | Ala | Val | Leu | Glu | Leu | Val | Thr | |
| | | | | 4375 | | | | | 4380 | | | | | 4385 | | |
| GAA | CAG | GTC | GCC | GAG | GTC | CTC | GGC | TAC | GCG | TCG | GCC | GCG | GAG | ATC | GAG | 13555 |
| Glu | Gln | Val | Ala | Glu | Val | Leu | Gly | Tyr | Ala | Ser | Ala | Ala | Glu | Ile | Glu | |
| | | | | 4390 | | | | | 4395 | | | | | 4400 | | |
| CCC | GAA | CGA | CCC | TTC | CGG | GAG | ATC | GGC | GTC | GAC | TCC | CTG | GCG | GCG | GTG | 13603 |
| Pro | Glu | Arg | Pro | Phe | Arg | Glu | Ile | Gly | Val | Asp | Ser | Leu | Ala | Ala | Val | |
| | | | | 4405 | | | | | 4410 | | | | | 4415 | | |
| GAG | CTG | CGC | AAC | CGG | CTC | AGC | CGT | CTG | GTC | GGC | CTG | CGG | TTG | CCG | ACC | 13651 |
| Glu | Leu | Arg | Asn | Arg | Leu | Ser | Arg | Leu | Val | Gly | Leu | Arg | Leu | Pro | Thr | |
| | | | | 4420 | | | | | 4425 | | | | | 4430 | | |
| ACG | CTG | TCC | TTC | GAC | CAC | CCC | ACG | CCG | AAG | GAC | ATG | GCG | CAG | CAC | ATC | 13699 |
| Thr | Leu | Ser | Phe | Asp | His | Pro | Thr | Pro | Lys | Asp | Met | Ala | Gln | His | Ile | |
| 4435 | | | | | 4440 | | | | | 4445 | | | | | 4450 | |
| GAC | GGG | CAG | CTC | CCC | CGC | CCG | GCC | GGA | GCC | TCG | CCC | GCG | GAC | GCA | GCG | 13747 |
| Asp | Gly | Gln | Leu | Pro | Arg | Pro | Ala | Gly | Ala | Ser | Pro | Ala | Asp | Ala | Ala | |
| | | | | 4455 | | | | | 4460 | | | | | 4465 | | |
| CTG | GAA | GGG | ATC | GGC | GAC | CTC | GCG | CGG | GCG | GTC | GCC | CTG | CTG | GGC | ACG | 13795 |
| Leu | Glu | Gly | Ile | Gly | Asp | Leu | Ala | Arg | Ala | Val | Ala | Leu | Leu | Gly | Thr | |
| | | | | 4470 | | | | | 4475 | | | | | 4480 | | |
| GGC | GAC | GCC | CGC | CGG | GCC | GAG | GTA | CGA | GAG | CAG | CTC | GTC | GGA | CTG | CTG | 13843 |
| Gly | Asp | Ala | Arg | Arg | Ala | Glu | Val | Arg | Glu | Gln | Leu | Val | Gly | Leu | Leu | |
| | | | | 4485 | | | | | 4490 | | | | | 4495 | | |
| GCC | GCG | CTC | GAC | CCA | CCT | GGG | CGG | ACG | GGC | ACC | GCC | GCA | CCC | GGC | GTC | 13891 |
| Ala | Ala | Leu | Asp | Pro | Pro | Gly | Arg | Thr | Gly | Thr | Ala | Ala | Pro | Gly | Val | |
| | | | | 4500 | | | | | 4505 | | | | | 4510 | | |
| CCC | TCC | GGT | GCC | GAT | GGC | GCG | GAA | CCG | ACC | GTG | ACG | GAC | CGG | CTC | GAC | 13939 |
| Pro | Ser | Gly | Ala | Asp | Gly | Ala | Glu | Pro | Thr | Val | Thr | Asp | Arg | Leu | Asp | |
| 4515 | | | | | 4520 | | | | | 4525 | | | | | 4530 | |

| GAG | GCG | ACC | GAC | GAC | GAG | ATC | TTC | GCC | TTC | CTG | GAC | GAG | CAG | CTG | TGA | 13987 |
|---|---|---|---|---|---|---|---|---|---|---|---|---|---|---|---|---|
| Glu | Ala | Thr | Asp | Asp | Glu | Ile | Phe | Ala | Phe | Leu | Asp | Glu | Gln | Leu | | |
| | | | | 4535 | | | | 4540 | | | | | | 4545 | | |

( 2 ) INFORMATION FOR SEQ ID NO:14:

( i ) SEQUENCE CHARACTERISTICS:
        ( A ) LENGTH: 4545 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:14:

| Met | Ser | Gly | Glu | Leu | Ala | Ile | Ser | Arg | Ser | Asp | Asp | Arg | Ser | Asp | Ala |
|---|---|---|---|---|---|---|---|---|---|---|---|---|---|---|---|
| 1 | | | | 5 | | | | | 10 | | | | | 15 | |
| Val | Ala | Val | Val | Gly | Met | Ala | Cys | Arg | Phe | Pro | Gly | Ala | Pro | Gly | Ile |
| | | | 20 | | | | 25 | | | | | 30 | | | |
| Ala | Glu | Phe | Trp | Glu | Leu | Leu | Arg | Ser | Gly | Arg | Gly | Met | Pro | Thr | Arg |
| | | 35 | | | | | 40 | | | | | 45 | | | |
| Gln | Asp | Asp | Gly | Thr | Trp | Arg | Ala | Ala | Leu | Glu | Asp | His | Ala | Gly | Phe |
| | 50 | | | | | 55 | | | | | 60 | | | | |
| Asp | Ala | Gly | Phe | Phe | Gly | Met | Asn | Ala | Arg | Gln | Ala | Ala | Ala | Thr | Asp |
| 65 | | | | | 70 | | | | | 75 | | | | | 80 |
| Pro | Gln | His | Arg | Leu | Met | Leu | Glu | Leu | Gly | Trp | Glu | Ala | Leu | Glu | Asp |
| | | | | 85 | | | | | 90 | | | | | 95 | |
| Ala | Gly | Ile | Val | Pro | Gly | Asp | Leu | Thr | Gly | Thr | Asp | Thr | Gly | Val | Phe |
| | | | 100 | | | | | 105 | | | | | 110 | | |
| Ala | Gly | Val | Ala | Ser | Asp | Asp | Tyr | Ala | Val | Leu | Thr | Arg | Arg | Ser | Ala |
| | | 115 | | | | | 120 | | | | | 125 | | | |
| Val | Ser | Ala | Gly | Gly | Tyr | Thr | Ala | Thr | Gly | Leu | His | Arg | Ala | Leu | Ala |
| | 130 | | | | | 135 | | | | | 140 | | | | |
| Ala | Asn | Arg | Leu | Ser | His | Phe | Leu | Gly | Leu | Arg | Gly | Pro | Ser | Leu | Val |
| 145 | | | | | 150 | | | | | 155 | | | | | 160 |
| Val | Asp | Ser | Ala | Gln | Ser | Ala | Ser | Leu | Val | Ala | Val | Gln | Leu | Ala | Cys |
| | | | | 165 | | | | | 170 | | | | | 175 | |
| Glu | Ser | Leu | Arg | Arg | Gly | Glu | Thr | Ser | Leu | Ala | Val | Ala | Gly | Gly | Val |
| | | | 180 | | | | | 185 | | | | | 190 | | |
| Asn | Leu | Ile | Leu | Thr | Glu | Glu | Ser | Thr | Thr | Val | Met | Glu | Arg | Met | Gly |
| | | 195 | | | | | 200 | | | | | 205 | | | |
| Ala | Leu | Ser | Pro | Asp | Gly | Arg | Cys | His | Thr | Phe | Asp | Ala | Arg | Ala | Asn |
| | 210 | | | | | 215 | | | | | 220 | | | | |
| Gly | Tyr | Val | Arg | Gly | Glu | Gly | Gly | Ala | Val | Val | Leu | Lys | Pro | Leu |
| 225 | | | | | 230 | | | | | 235 | | | | | 240 |
| Asp | Ala | Ala | Leu | Ala | Asp | Gly | Asp | Arg | Val | Tyr | Cys | Val | Ile | Lys | Gly |
| | | | | 245 | | | | | 250 | | | | | 255 | |
| Gly | Ala | Val | Asn | Asn | Asp | Gly | Gly | Ala | Ser | Leu | Thr | Thr | Pro | Asp |
| | | | 260 | | | | | 265 | | | | | 270 | | |
| Arg | Glu | Ala | Gln | Glu | Ala | Val | Leu | Arg | Gln | Ala | Tyr | Arg | Arg | Ala | Gly |
| | | 275 | | | | | 280 | | | | | 285 | | | |
| Val | Ser | Thr | Gly | Ala | Val | Arg | Tyr | Val | Glu | Leu | His | Gly | Thr | Gly | Thr |
| | 290 | | | | | 295 | | | | | 300 | | | | |
| Arg | Ala | Gly | Asp | Pro | Val | Glu | Ala | Ala | Leu | Gly | Ala | Val | Leu | Gly |
| 305 | | | | | 310 | | | | | 315 | | | | | 320 |
| Ala | Gly | Ala | Asp | Ser | Gly | Arg | Ser | Thr | Pro | Leu | Ala | Val | Gly | Ser | Val |
| | | | | 325 | | | | | 330 | | | | | 335 | |

| | | | | | | | | | | | | | |
|---|---|---|---|---|---|---|---|---|---|---|---|---|---|
|Lys|Thr|Asn|Val|Gly|His|Leu|Glu|Gly|Ala|Ala|Gly|Ile|Val|Gly|Leu|
| | | |340| | |345| | | | |350| | |
|Ile|Lys|Ala|Thr|Leu|Cys|Val|Arg|Lys|Gly|Glu|Leu|Val|Pro|Ser|Leu|
| |355| | | | |360| | | | |365| | | |
|Asn|Phe|Ser|Thr|Pro|Asn|Pro|Asp|Ile|Pro|Leu|Asp|Asp|Leu|Arg|Leu|
|370| | | | |375| | | | |380| | | | |
|Arg|Val|Gln|Thr|Glu|Arg|Gln|Glu|Trp|Asn|Glu|Glu|Asp|Arg|Pro|
|385| | | | |390| | | | |395| | | |400|
|Arg|Val|Ala|Gly|Val|Ser|Ser|Phe|Gly|Met|Gly|Gly|Thr|Asn|Val|His|
| | | | |405| | | |410| | | | |415| |
|Leu|Val|Ile|Ala|Glu|Ala|Pro|Ala|Ala|Gly|Ser|Ser|Gly|Ala|Gly|
| | | |420| | | |425| | | |430| | |
|Gly|Ser|Gly|Ala|Gly|Ser|Gly|Ala|Gly|Ile|Ser|Ala|Val|Ser|Gly|Val|
| | |435| | | | |440| | | |445| | | |
|Val|Pro|Val|Val|Val|Ser|Gly|Arg|Ser|Arg|Val|Val|Val|Arg|Glu|Ala|
| |450| | | |455| | | | |460| | | | |
|Ala|Gly|Arg|Leu|Ala|Glu|Val|Val|Glu|Ala|Gly|Gly|Val|Gly|Leu|Ala|
|465| | | | |470| | | |475| | | | |480|
|Asp|Val|Ala|Val|Thr|Met|Ala|Asp|Arg|Ser|Arg|Phe|Gly|Tyr|Arg|Ala|
| | | | |485| | | | |490| | | | |495| |
|Val|Val|Leu|Ala|Arg|Gly|Glu|Ala|Glu|Leu|Ala|Gly|Arg|Leu|Arg|Ala|
| | | |500| | | | |505| | | |510| | |
|Leu|Ala|Gly|Gly|Asp|Pro|Asp|Ala|Gly|Val|Val|Thr|Gly|Ala|Val|Leu|
| | |515| | | |520| | | | |525| | | |
|Asp|Gly|Gly|Val|Val|Val|Gly|Ala|Ala|Pro|Gly|Gly|Ala|Gly|Ala|Ala|
| |530| | | | |535| | | | |540| | | |
|Gly|Gly|Ala|Gly|Ala|Ala|Gly|Gly|Ala|Gly|Gly|Gly|Val|Val|Leu|
|545| | | | |550| | | | |555| | | |560|
|Val|Phe|Pro|Gly|Gln|Gly|Thr|Gln|Trp|Val|Gly|Met|Gly|Ala|Gly|Leu|
| | | | |565| | | |570| | | | |575| |
|Leu|Gly|Ser|Ser|Glu|Val|Phe|Ala|Ala|Ser|Met|Arg|Glu|Cys|Ala|Arg|
| | | |580| | | |585| | | | |590| | |
|Ala|Leu|Ser|Val|His|Val|Gly|Trp|Asp|Leu|Leu|Glu|Val|Val|Ser|Gly|
| | |595| | | | |600| | | | |605| | |
|Gly|Ala|Gly|Leu|Glu|Arg|Val|Asp|Val|Val|Gln|Pro|Val|Thr|Trp|Ala|
| |610| | | | |615| | | | |620| | | |
|Val|Met|Val|Ser|Leu|Ala|Arg|Tyr|Trp|Gln|Ala|Met|Gly|Val|Asp|Val|
|625| | | | |630| | | | |635| | | | |640|
|Ala|Ala|Val|Val|Gly|His|Ser|Gln|Gly|Glu|Ile|Ala|Ala|Ala|Thr|Val|
| | | | |645| | | | |650| | | | |655| |
|Ala|Gly|Ala|Leu|Ser|Leu|Glu|Asp|Ala|Ala|Ala|Val|Val|Ala|Leu|Arg|
| | | |660| | | | |665| | | | |670| | |
|Ala|Gly|Leu|Ile|Gly|Arg|Tyr|Leu|Ala|Gly|Arg|Gly|Ala|Met|Ala|Ala|
| | |675| | | | |680| | | | |685| | |
|Val|Pro|Leu|Pro|Ala|Gly|Glu|Val|Glu|Ala|Gly|Leu|Ala|Lys|Trp|Pro|
| |690| | | | |695| | | | |700| | | |
|Gly|Val|Glu|Val|Ala|Ala|Val|Asn|Gly|Pro|Ala|Ser|Thr|Val|Val|Ser|
|705| | | | |710| | | | |715| | | | |720|
|Gly|Asp|Arg|Arg|Ala|Val|Ala|Gly|Tyr|Val|Ala|Val|Cys|Gln|Ala|Glu|
| | | | |725| | | | |730| | | | |735| |
|Gly|Val|Gln|Ala|Arg|Leu|Ile|Pro|Val|Asp|Tyr|Ala|Ser|His|Ser|Arg|
| | | |740| | | | |745| | | | |750| | |
|His|Val|Glu|Asp|Leu|Lys|Gly|Glu|Leu|Glu|Arg|Val|Leu|Ser|Gly|Ile|
| | |755| | | | |760| | | | |765| | |

```
Arg  Pro  Arg  Ser  Pro  Arg  Val  Pro  Val  Cys  Ser  Thr  Val  Ala  Gly  Glu
     770            775                 780
Gln  Pro  Gly  Glu  Pro  Val  Phe  Asp  Ala  Gly  Tyr  Trp  Phe  Arg  Asn  Leu
785            790                 795                                 800
Arg  Asn  Arg  Val  Glu  Phe  Ser  Ala  Val  Val  Gly  Gly  Leu  Leu  Glu  Glu
               805                 810                           815
Gly  His  Arg  Arg  Phe  Ile  Glu  Val  Ser  Ala  His  Pro  Val  Leu  Val  His
               820                 825                           830
Ala  Ile  Glu  Gln  Thr  Ala  Glu  Ala  Ala  Asp  Arg  Ser  Val  His  Ala  Thr
               835                 840                 845
Gly  Thr  Leu  Arg  Arg  Gln  Asp  Asp  Ser  Pro  His  Arg  Leu  Leu  Thr  Ser
     850                 855                      860
Thr  Ala  Glu  Ala  Trp  Ala  His  Gly  Ala  Thr  Leu  Thr  Trp  Asp  Pro  Ala
865                      870                 875                           880
Leu  Pro  Pro  Gly  His  Leu  Thr  Thr  Leu  Pro  Thr  Tyr  Pro  Phe  Asn  His
               885                 890                           895
His  His  Tyr  Trp  Leu  Asp  Thr  Ile  Asp  Gly  Gly  Gly  Asp  Asp  Ala
               900                 905                           910
Thr  Gln  Glu  Lys  Glu  Ser  Gly  Pro  Leu  Thr  Arg  Glu  Leu  Arg  Gly  Leu
               915                 920                 925
Pro  Ser  Ser  Gln  Lys  Gln  Leu  Gly  Phe  Leu  Leu  Asp  Leu  Val  Cys  Arg
     930                 935                      940
His  Thr  Ala  Val  Val  Leu  Gly  Leu  Asp  Thr  Ala  Ala  Glu  Val  Asp  Pro
945                      950                 955                           960
Asp  Leu  Ser  Phe  Lys  Lys  Gln  Gly  Ile  Gln  Ser  Met  Thr  Gly  Val  Glu
               965                 970                           975
Leu  Arg  Asn  Arg  Leu  Leu  Thr  Glu  Thr  Gly  Leu  Ala  Leu  Pro  Thr  Thr
               980                 985                           990
Leu  Val  Tyr  Asp  Arg  Pro  Thr  Pro  Arg  Ala  Leu  Ala  Gln  Phe  Leu  His
               995                 1000                     1005
Thr  Glu  Leu  Leu  Asp  Gly  Ser  Pro  Ser  Gly  Ser  Val  Leu  Ala  Pro  Ala
     1010                1015                     1020
Gln  Lys  Ser  Phe  Glu  Ala  Gly  Gly  Pro  Gly  Val  Leu  Ser  Ser  Ala  Ala
1025                     1030                     1035                     1040
Val  Gly  Val  Ser  Asp  Ala  Arg  Gly  Gly  Ser  Arg  Asp  Asp  Asp  Asp  Pro
               1045                1050                          1055
Ile  Ala  Ile  Val  Gly  Val  Gly  Cys  Arg  Leu  Pro  Gly  Gly  Val  Asp  Ser
               1060                1065                          1070
Arg  Ala  Ala  Leu  Trp  Glu  Leu  Leu  Glu  Ser  Gly  Ala  Asp  Ala  Ile  Ser
               1075                1080                          1085
Ser  Phe  Pro  Thr  Asp  Arg  Gly  Trp  Asp  Leu  Asp  Gly  Leu  Tyr  Asp  Pro
               1090                1095                          1100
Glu  Pro  Gly  Thr  Pro  Gly  Lys  Thr  Tyr  Val  Arg  Glu  Gly  Gly  Phe  Leu
1105                     1110                     1115                     1120
His  Ser  Ala  Ala  Glu  Phe  Asp  Ala  Glu  Phe  Phe  Gly  Ile  Ser  Pro  Arg
               1125                1130                          1135
Glu  Ala  Thr  Ala  Met  Asp  Pro  Gln  Gln  Arg  Leu  Leu  Leu  Glu  Ala  Ser
               1140                1145                          1150
Trp  Glu  Ala  Leu  Glu  Asp  Ala  Gly  Val  Leu  Pro  Glu  Ser  Leu  Arg  Gly
               1155                1160                          1165
Gly  Asp  Ala  Gly  Val  Phe  Val  Gly  Ala  Thr  Ala  Pro  Glu  Tyr  Gly  Pro
     1170                1175                     1180
Arg  Leu  His  Glu  Gly  Ala  Asp  Gly  Tyr  Glu  Gly  Tyr  Leu  Leu  Thr  Gly
```

-continued

```
          1185                1190                1195                1200
Thr Thr Ala Ser Val Ala Ser Gly Arg Ile Ala Tyr Thr Leu Gly Thr
                1205                1210                1215
Gly Gly Pro Ala Leu Thr Val Asp Thr Ala Cys Ser Ser Ser Leu Val
                1220                1225                1230
Ala Leu His Leu Ala Val Gln Ala Leu Arg Arg Gly Glu Cys Gly Leu
                1235                1240                1245
Ala Leu Ala Gly Gly Ala Thr Val Met Ser Gly Pro Gly Met Phe Val
                1250                1255                1260
Glu Phe Ser Arg Gln Arg Gly Leu Ala Pro Asp Gly Arg Cys Met Pro
1265                1270                1275                1280
Phe Ser Ala Asp Ala Asp Gly Thr Ala Trp Ser Glu Gly Val Ala Val
                1285                1290                1295
Leu Ala Leu Glu Arg Leu Ser Asp Ala Arg Arg Ala Gly His Arg Val
                1300                1305                1310
Leu Gly Val Val Arg Gly Ser Ala Val Asn Gln Asp Gly Ala Ser Asn
                1315                1320                1325
Gly Leu Thr Ala Pro Asn Arg Ser Ala Gln Glu Gly Val Ile Arg Ala
                1330                1335                1340
Ala Leu Ala Asp Ala Gly Leu Ala Pro Gly Asp Val Asp Ala Val Glu
1345                1350                1355                1360
Ala His Gly Thr Gly Thr Ala Leu Gly Asp Pro Ile Glu Ala Ser Ala
                1365                1370                1375
Leu Leu Ala Thr Tyr Gly Arg Glu Arg Val Gly Asp Pro Leu Trp Leu
                1380                1385                1390
Gly Ser Leu Lys Ser Asn Val Gly His Thr Gln Ala Ala Ala Gly Ala
                1395                1400                1405
Ala Gly Val Val Lys Met Leu Leu Ala Leu Glu His Gly Thr Leu Pro
                1410                1415                1420
Arg Thr Leu His Ala Asp Arg Pro Ser Thr His Val Asp Trp Ser Ser
1425                1430                1435                1440
Gly Thr Val Ala Leu Leu Ala Glu Ala Arg Arg Trp Pro Arg Arg Ser
                1445                1450                1455
Asp Arg Pro Arg Arg Ala Ala Val Ser Ser Phe Gly Ile Ser Gly Thr
                1460                1465                1470
Asn Ala His Leu Ile Ile Glu Glu Ala Pro Glu Trp Val Glu Asp Ile
                1475                1480                1485
Asp Gly Val Ala Ala Pro Asp Arg Gly Thr Ala Asp Ala Ala Ala Pro
                1490                1495                1500
Ser Pro Leu Leu Leu Ser Ala Arg Ser Glu Gly Ala Leu Arg Ala Gln
1505                1510                1515                1520
Ala Val Arg Leu Gly Glu Tyr Val Glu Arg Val Gly Ala Asp Pro Arg
                1525                1530                1535
Asp Val Ala Tyr Ser Leu Ala Ser Thr Arg Thr Leu Phe Glu His Arg
                1540                1545                1550
Ala Val Val Pro Cys Gly Gly Arg Gly Glu Leu Val Ala Ala Leu Gly
                1555                1560                1565
Gly Phe Ala Ala Gly Arg Val Ser Gly Gly Val Arg Ser Gly Arg Ala
                1570                1575                1580
Val Pro Gly Gly Val Gly Val Leu Phe Thr Gly Gln Gly Ala Gln Trp
1585                1590                1595                1600
Val Gly Met Gly Arg Gly Leu Tyr Ala Gly Gly Gly Val Phe Ala Glu
                1605                1610                1615
```

-continued

```
Val Leu Asp Glu Val Leu Ser Met Val Gly Glu Val Asp Gly Arg Ser
            1620                1625                1630
Leu Arg Asp Val Met Phe Gly Asp Val Asp Val Asp Ala Gly Ala Gly
        1635                1640                1645
Ala Asp Ala Gly Ala Gly Ala Gly Ala Gly Val Gly Ser Gly Ser Gly
    1650                1655                1660
Ser Val Gly Gly Leu Leu Gly Arg Thr Glu Phe Ala Gln Pro Ala Leu
1665                1670                1675                1680
Phe Ala Leu Glu Val Ala Leu Phe Arg Ala Leu Glu Ala Arg Gly Val
            1685                1690                1695
Glu Val Ser Val Val Leu Gly His Ser Val Gly Glu Val Ala Ala Ala
                1700                1705                1710
Tyr Val Ala Gly Val Leu Ser Leu Gly Asp Ala Val Arg Leu Val Val
            1715                1720                1725
Ala Arg Gly Gly Leu Met Gly Gly Leu Pro Val Gly Gly Gly Met Trp
    1730                1735                1740
Ser Val Gly Ala Ser Glu Ser Val Val Arg Gly Val Val Glu Gly Leu
1745                1750                1755                1760
Gly Glu Trp Val Ser Val Ala Ala Val Asn Gly Pro Arg Ser Val Val
                1765                1770                1775
Leu Ser Gly Asp Val Gly Val Leu Glu Ser Val Val Ala Ser Leu Met
            1780                1785                1790
Gly Asp Gly Val Glu Cys Arg Arg Leu Asp Val Ser His Gly Phe His
        1795                1800                1805
Ser Val Leu Met Glu Pro Val Leu Gly Glu Phe Arg Gly Val Val Glu
    1810                1815                1820
Ser Leu Glu Phe Gly Arg Val Arg Pro Gly Val Val Val Val Ser Gly
1825                1830                1835                1840
Val Ser Gly Gly Val Val Gly Ser Gly Glu Leu Gly Asp Pro Gly Tyr
                1845                1850                1855
Trp Val Arg His Ala Arg Glu Ala Val Arg Phe Ala Asp Gly Val Gly
            1860                1865                1870
Val Val Arg Gly Leu Gly Val Gly Thr Leu Val Glu Val Gly Pro His
        1875                1880                1885
Gly Val Leu Thr Gly Met Ala Gly Glu Cys Leu Gly Ala Gly Asp Asp
    1890                1895                1900
Val Val Val Val Pro Ala Met Arg Arg Gly Arg Ala Glu Arg Glu Val
1905                1910                1915                1920
Phe Glu Ala Ala Leu Ala Thr Val Phe Thr Arg Asp Ala Gly Leu Asp
            1925                1930                1935
Ala Thr Ala Leu His Thr Gly Ser Thr Gly Arg Arg Ile Asp Leu Pro
        1940                1945                1950
Thr Tyr Pro Phe Gln Arg Asp Arg Tyr Trp Leu Asp Pro Val Arg Thr
    1955                1960                1965
Ala Val Thr Gly Val Glu Pro Ala Gly Ser Pro Ala Asp Ala Arg Ala
    1970                1975                1980
Thr Glu Arg Gly Arg Ser Thr Thr Ala Gly Ile Arg Tyr Arg Val Ala
1985                1990                1995                2000
Trp Gln Pro Ala Val Val Asp Arg Gly Asn Pro Gly Pro Ala Gly His
            2005                2010                2015
Val Leu Leu Leu Ala Pro Asp Glu Asp Thr Ala Asp Ser Gly Leu Ala
        2020                2025                2030
Pro Ala Ile Ala Arg Glu Leu Ala Val Arg Gly Ala Glu Val His Thr
    2035                2040                2045
```

```
Val Ala Val Pro Val Gly Thr Gly Arg Glu Ala Ala Gly Asp Leu Leu
        2050                2055                2060

Arg Ala Ala Gly Asp Gly Ala Ala Arg Ser Thr Arg Val Leu Trp Leu
2065            2070                2075                    2080

Ala Pro Ala Glu Pro Asp Ala Ala Asp Ala Val Ala Leu Val Gln Ala
            2085                2090                2095

Leu Gly Glu Ala Val Pro Glu Ala Pro Leu Trp Ile Thr Thr Arg Glu
            2100                2105                2110

Ala Ala Ala Val Arg Pro Asp Glu Thr Pro Ser Val Gly Gly Ala Gln
            2115                2120                2125

Leu Trp Gly Leu Gly Gln Val Ala Ala Leu Glu Leu Gly Arg Arg Trp
        2130                2135                2140

Gly Gly Leu Ala Asp Leu Pro Gly Ser Ala Ser Pro Ala Val Leu Arg
2145                2150                2155                    2160

Thr Phe Val Gly Ala Leu Leu Ala Gly Gly Glu Asn Gln Phe Ala Val
                2165                2170                2175

Arg Pro Ser Gly Val His Val Arg Arg Val Val Pro Ala Pro Val Pro
            2180                2185                2190

Val Pro Ala Ser Ala Arg Thr Val Thr Thr Ala Pro Ala Thr Ala Val
            2195                2200                2205

Gly Glu Asp Ala Arg Asn Asp Thr Ser Asp Val Val Pro Asp Asp
        2210                2215                2220

Arg Trp Ser Ser Gly Thr Val Leu Ile Thr Gly Gly Thr Gly Ala Leu
2225            2230                2235                    2240

Gly Ala Gln Val Ala Arg Arg Leu Ala Arg Ser Gly Ala Ala Arg Leu
                2245                2250                2255

Leu Leu Val Gly Arg Arg Gly Ala Ala Gly Pro Gly Val Gly Glu Leu
            2260                2265                2270

Val Glu Glu Leu Thr Ala Leu Gly Ser Glu Val Ala Val Glu Ala Cys
        2275                2280                2285

Asp Val Ala Asp Arg Asp Ala Leu Ala Ala Leu Leu Ala Gly Leu Pro
        2290                2295                2300

Glu Glu Arg Pro Leu Val Ala Val Leu His Ala Ala Gly Val Leu Asp
2305                2310                2315                    2320

Asp Gly Val Leu Asp Ser Leu Thr Ser Asp Arg Val Asp Ala Val Leu
                2325                2330                2335

Arg Asp Lys Val Thr Ala Ala Arg His Leu Asp Glu Leu Thr Ala Asp
                2340                2345                2350

Leu Pro Leu Asp Ala Phe Val Leu Phe Ser Ser Ile Val Gly Val Trp
            2355                2360                2365

Gly Asn Gly Gly Gln Ala Val Tyr Ala Ala Ala Asn Ala Ala Leu Asp
        2370                2375                2380

Ala Leu Ala Gln Arg Arg Arg Ala Arg Gly Ala Arg Ala Ala Ser Ile
2385                2390                2395                    2400

Ala Trp Gly Pro Trp Ala Gly Ala Gly Met Ala Ser Gly Thr Ala Ala
                2405                2410                2415

Lys Ser Phe Glu Arg Asp Gly Val Thr Ala Leu Asp Pro Glu Arg Ala
            2420                2425                2430

Leu Asp Val Leu Asp Asp Val Val Gly Ala Gly Gly Thr Ser Ala Ala
        2435                2440                2445

Gly Thr His Ala Ala Gly Glu Ser Ser Leu Leu Val Ala Asp Val Asp
        2450                2455                2460

Trp Glu Thr Phe Val Gly Arg Ser Val Thr Arg Arg Thr Trp Ser Leu
```

```
              2465                2470                2475                2480

Phe  Asp  Gly  Val  Ser  Ala  Ala  Arg  Ser  Ala  Arg  Ala  Gly  His  Ala  Ala
                         2485                2490                2495

Asp  Asp  Arg  Ala  Ala  Leu  Thr  Pro  Gly  Thr  Arg  Pro  Gly  Asp  Gly  Ala
                         2500                2505                2510

Pro  Gly  Gly  Ser  Gly  Gln  Asp  Gly  Gly  Glu  Gly  Arg  Pro  Trp  Leu  Ser
                         2515                2520                2525

Val  Gly  Pro  Ser  Pro  Ala  Glu  Arg  Arg  Arg  Ala  Leu  Leu  Thr  Leu  Val
                         2530                2535                2540

Arg  Ser  Glu  Ala  Ala  Gly  Ile  Leu  Arg  His  Ala  Ser  Ala  Asp  Ala  Val
2545                2550                2555                2560

Asp  Pro  Glu  Leu  Ala  Phe  Arg  Ser  Ala  Gly  Phe  Asp  Ser  Leu  Thr  Val
                         2565                2570                2575

Leu  Glu  Leu  Arg  Asn  Arg  Leu  Thr  Ala  Ala  Thr  Gly  Leu  Asn  Leu  Pro
                         2580                2585                2590

Asn  Thr  Leu  Leu  Phe  Asp  His  Pro  Thr  Pro  Leu  Ser  Leu  Ala  Ser  His
                         2595                2600                2605

Leu  His  Asp  Glu  Leu  Phe  Gly  Pro  Asp  Ser  Glu  Ala  Glu  Pro  Ala  Ala
                         2610                2615                2620

Ala  Ala  Pro  Thr  Pro  Val  Met  Ala  Asp  Glu  Arg  Glu  Pro  Ile  Ala  Ile
2625                2630                2635                2640

Val  Gly  Met  Ala  Cys  Arg  Tyr  Pro  Gly  Gly  Val  Ala  Ser  Pro  Asp  Asp
                         2645                2650                2655

Leu  Trp  Asp  Leu  Val  Ala  Gly  Asp  Gly  His  Thr  Leu  Ser  Phe  Pro
                         2660                2665                2670

Ala  Asp  Arg  Gly  Trp  Asp  Val  Glu  Gly  Leu  Tyr  Asp  Pro  Glu  Pro  Gly
                         2675                2680                2685

Val  Pro  Gly  Lys  Ser  Tyr  Val  Arg  Glu  Gly  Gly  Phe  Leu  Arg  Ser  Ala
                         2690                2695                2700

Ala  Glu  Phe  Asp  Ala  Glu  Phe  Phe  Gly  Ile  Ser  Pro  Arg  Glu  Ala  Thr
2705                2710                2715                2720

Ala  Met  Asp  Pro  Gln  Gln  Arg  Leu  Leu  Leu  Glu  Thr  Ser  Trp  Glu  Ala
                         2725                2730                2735

Leu  Glu  Arg  Ala  Gly  Ile  Val  Pro  Asp  Ser  Leu  Arg  Gly  Thr  Arg  Thr
                         2740                2745                2750

Gly  Val  Phe  Ser  Gly  Ile  Ser  Gln  Gln  Asp  Tyr  Ala  Thr  Gln  Leu  Gly
                         2755                2760                2765

Asp  Ala  Ala  Asp  Thr  Tyr  Gly  Gly  His  Val  Leu  Thr  Gly  Thr  Leu  Gly
                         2770                2775                2780

Ser  Val  Ile  Ser  Gly  Arg  Val  Ala  Tyr  Ala  Leu  Gly  Leu  Glu  Gly  Pro
2785                2790                2795                2800

Ala  Leu  Thr  Val  Asp  Thr  Ala  Cys  Ser  Ser  Ser  Leu  Val  Ala  Leu  His
                         2805                2810                2815

Leu  Ala  Val  Gln  Ser  Leu  Arg  Arg  Gly  Glu  Cys  Asp  Leu  Ala  Leu  Ala
                         2820                2825                2830

Gly  Gly  Val  Thr  Val  Met  Ala  Thr  Pro  Thr  Val  Phe  Val  Glu  Phe  Ser
                         2835                2840                2845

Arg  Gln  Arg  Gly  Leu  Ala  Ala  Asp  Gly  Arg  Cys  Lys  Ala  Phe  Ala  Glu
                         2850                2855                2860

Gly  Ala  Asp  Gly  Thr  Ala  Trp  Ala  Glu  Gly  Val  Gly  Val  Leu  Leu  Val
                         2865                2870                2875                2880

Glu  Arg  Leu  Ser  Asp  Ala  Arg  Arg  Asn  Gly  His  Arg  Val  Leu  Ala  Val
                         2885                2890                2895
```

```
Val  Arg  Gly  Ser  Ala  Val  Asn  Gln  Asp  Gly  Ala  Ser  Asn  Gly  Leu  Thr
                         2900                2905                2910

Ala  Pro  Ser  Gly  Pro  Ala  Gln  Gln  Arg  Val  Ile  Arg  Glu  Ala  Leu  Ala
                    2915                2920                2925

Asp  Ala  Gly  Leu  Val  Pro  Ala  Asp  Val  Asp  Val  Glu  Ala  His  Gly
               2930                2935                2940

Thr  Gly  Thr  Ala  Leu  Gly  Asp  Pro  Ile  Glu  Ala  Gly  Ala  Leu  Leu  Ala
2945                2950                2955                               2960

Thr  Tyr  Gly  Arg  Glu  Arg  Val  Gly  Asp  Pro  Leu  Trp  Leu  Gly  Ser  Leu
                         2965                2970                2975

Lys  Ser  Asn  Ile  Gly  His  Ala  Gln  Ala  Ala  Ala  Gly  Val  Gly  Gly  Val
                    2980                2985                2990

Ile  Lys  Val  Val  Gln  Gly  Met  Arg  His  Gly  Ser  Leu  Pro  Arg  Thr  Leu
                    2995                3000                3005

His  Val  Asp  Ala  Pro  Ser  Ser  Lys  Val  Glu  Trp  Ala  Ser  Gly  Ala  Val
               3010                3015                3020

Glu  Leu  Leu  Thr  Glu  Thr  Arg  Ser  Trp  Pro  Arg  Arg  Val  Glu  Arg  Val
3025                3030                3035                               3040

Arg  Arg  Ala  Ala  Val  Ser  Ala  Phe  Gly  Val  Ser  Gly  Thr  Asn  Ala  His
                    3045                3050                3055

Val  Val  Leu  Glu  Glu  Ala  Pro  Ala  Glu  Ala  Gly  Ser  Glu  His  Gly  Asp
               3060                3065                3070

Gly  Pro  Glu  Pro  Glu  Arg  Pro  Asp  Ala  Val  Thr  Gly  Pro  Leu  Ser  Trp
                    3075                3080                3085

Val  Leu  Ser  Ala  Arg  Ser  Glu  Gly  Ala  Leu  Arg  Ala  Gln  Ala  Val  Arg
               3090                3095                3100

Leu  Arg  Glu  Cys  Val  Glu  Arg  Val  Gly  Ala  Asp  Pro  Arg  Asp  Val  Ala
3105                3110                3115                               3120

Gly  Ser  Leu  Val  Val  Ser  Arg  Ala  Ser  Phe  Gly  Glu  Arg  Ala  Val  Val
                    3125                3130                3135

Val  Gly  Arg  Gly  Arg  Glu  Glu  Leu  Leu  Ala  Gly  Leu  Asp  Val  Val  Ala
                    3140                3145                3150

Ala  Gly  Ala  Pro  Val  Gly  Val  Ser  Ser  Gly  Ala  Gly  Ala  Val  Val  Arg
               3155                3160                3165

Gly  Ser  Ala  Val  Arg  Gly  Arg  Gly  Val  Gly  Val  Leu  Phe  Thr  Gly  Gln
3170                3175                3180

Gly  Ala  Gln  Trp  Val  Gly  Met  Gly  Arg  Gly  Leu  Tyr  Ala  Gly  Gly  Gly
3185                3190                3195                               3200

Val  Phe  Ala  Glu  Val  Leu  Asp  Glu  Val  Leu  Ser  Val  Val  Gly  Glu  Val
                    3205                3210                3215

Asp  Gly  Arg  Ser  Leu  Arg  Asp  Val  Met  Phe  Ala  Asp  Ala  Asp  Ser  Val
               3220                3225                3230

Leu  Gly  Gly  Leu  Leu  Gly  Arg  Thr  Glu  Phe  Ala  Gln  Pro  Ala  Leu  Phe
               3235                3240                3245

Ala  Leu  Glu  Val  Ala  Leu  Phe  Arg  Ala  Leu  Glu  Ala  Arg  Gly  Val  Glu
               3250                3255                3260

Val  Ser  Val  Val  Leu  Gly  His  Ser  Val  Gly  Glu  Val  Ala  Ala  Ala  Tyr
3265                3270                3275                               3280

Val  Ala  Gly  Val  Leu  Ser  Leu  Gly  Asp  Ala  Val  Arg  Leu  Val  Val  Ala
                    3285                3290                3295

Arg  Gly  Gly  Leu  Met  Gly  Gly  Leu  Pro  Val  Gly  Gly  Gly  Met  Trp  Ser
                    3300                3305                3310

Val  Gly  Ala  Ser  Glu  Ser  Val  Val  Arg  Gly  Val  Val  Glu  Gly  Leu  Gly
               3315                3320                3325
```

```
Glu Trp Val Ser Val Ala Ala Val Asn Gly Pro Arg Ser Val Val Leu
    3330                3335                3340

Ser Gly Asp Val Gly Val Leu Glu Ser Val Val Thr Leu Met Gly
3345                3350                3355                3360

Asp Gly Val Glu Cys Arg Arg Leu Asp Val Ser His Gly Phe His Ser
                3365                3370                3375

Val Leu Met Glu Pro Val Leu Gly Glu Phe Arg Gly Val Glu Ser
            3380                3385                3390

Leu Glu Phe Gly Arg Val Arg Pro Gly Val Val Val Ser Gly Val
        3395                3400                3405

Ser Gly Gly Val Val Gly Ser Gly Glu Leu Gly Asp Pro Gly Tyr Trp
    3410                3415                3420

Val Arg His Ala Arg Glu Ala Val Arg Phe Ala Asp Gly Val Gly Val
3425                3430                3435                3440

Val Arg Gly Leu Gly Val Gly Thr Leu Val Glu Val Gly Pro His Gly
            3445                3450                3455

Val Leu Thr Gly Met Ala Gly Gln Cys Leu Glu Ala Gly Asp Asp Val
                3460                3465                3470

Val Val Val Pro Ala Met Arg Arg Gly Arg Pro Glu Arg Glu Val Phe
            3475                3480                3485

Glu Ala Ala Leu Ala Thr Val Phe Thr Arg Asp Ala Gly Leu Asp Ala
        3490                3495                3500

Thr Thr Leu His Thr Gly Ser Thr Gly Arg Arg Ile Asp Leu Pro Thr
3505                3510                3515                3520

Tyr Pro Phe Gln His Asn Arg Tyr Trp Ala Thr Gly Ser Val Thr Gly
                3525                3530                3535

Ala Thr Gly Thr Ser Ala Ala Ala Arg Phe Gly Leu Glu Trp Lys Asp
            3540                3545                3550

His Pro Phe Leu Ser Gly Ala Thr Pro Ile Ala Gly Ser Gly Ala Leu
        3555                3560                3565

Leu Leu Thr Gly Arg Val Gly Leu Ala Ala His Pro Trp Leu Ala Asp
    3570                3575                3580

His Ala Ile Ser Gly Thr Val Leu Leu Pro Gly Thr Ala Ile Ala Asp
3585                3590                3595                3600

Leu Leu Leu Arg Ala Val Glu Glu Val Gly Ala Gly Val Gly Glu
            3605                3610                3615

Leu Thr Leu His Glu Pro Leu Leu Leu Pro Glu Arg Gly Gly Leu His
                3620                3625                3630

Val Gln Val Leu Val Glu Ala Ala Asp Glu Gln Gly Arg Arg Ala Val
        3635                3640                3645

Ala Val Ala Ala Arg Pro Glu Gly Pro Gly Arg Asp Gly Glu Glu Gln
    3650                3655                3660

Glu Trp Thr Arg His Ala Glu Gly Val Leu Thr Ser Thr Glu Thr Ala
3665                3670                3675                3680

Val Pro Asp Met Gly Trp Ala Ala Gly Ala Trp Pro Pro Gly Ala
                3685                3690                3695

Glu Pro Ile Asp Val Glu Glu Leu Tyr Asp Ala Phe Ala Ala Asp Gly
            3700                3705                3710

Tyr Gly Tyr Gly Pro Ala Phe Thr Ala Leu Ser Gly Val Trp Arg Leu
        3715                3720                3725

Gly Asp Glu Leu Phe Ala Glu Val Arg Arg Pro Ala Gly Gly Ala Gly
    3730                3735                3740

Thr Thr Gly Asp Gly Phe Gly Val His Pro Ala Leu Phe Asp Ala Ala
```

-continued

```
              3745                    3750                    3755                    3760
Leu His Pro Trp Arg Ala Gly Gly Leu Leu Pro Asp Thr Gly Gly Thr
                       3765                    3770                    3775
Thr Trp Ala Pro Phe Ser Trp Gln Gly Ile Ala Leu His Thr Thr Gly
                       3780                    3785                    3790
Ala Glu Thr Leu Arg Val Arg Leu Ala Pro Ala Ala Gly Gly Thr Glu
                       3795                    3800                    3805
Ser Ala Phe Ser Val Gln Ala Ala Asp Pro Ala Gly Thr Pro Val Leu
     3810                    3815                    3820
Thr Leu Asp Ala Leu Leu Leu Arg Pro Val Thr Leu Gly Arg Ala Asp
3825                    3830                    3835                    3840
Ala Pro Gln Pro Leu Tyr Arg Val Asp Trp Gln Pro Val Gly Gln Gly
                       3845                    3850                    3855
Thr Glu Ala Ser Gly Ala Gln Gly Trp Thr Val Leu Gly Gln Ala Ala
                       3860                    3865                    3870
Ala Glu Thr Val Ala Gln Pro Ala Ala His Ala Asp Leu Thr Ala Leu
                       3875                    3880                    3885
Arg Thr Ala Val Ala Ala Ala Gly Thr Pro Val Pro Arg Leu Val Val
                       3890                    3895                    3900
Val Ser Pro Val Asp Thr Arg Leu Asp Glu Gly Pro Val Leu Ala Asp
3905                    3910                    3915                    3920
Ala Glu Ala Arg Ala Arg Ala Gly Asp Gly Trp Asp Asp Pro Leu
                       3925                    3930                    3935
Arg Val Ala Leu Gly Arg Gly Leu Thr Leu Val Arg Glu Trp Val Glu
                       3940                    3945                    3950
Asp Glu Arg Leu Ala Asp Ser Arg Leu Val Val Leu Thr Arg Gly Ala
                       3955                    3960                    3965
Val Ala Ala Gly Pro Gly Asp Val Pro Asp Leu Thr Gly Ala Ala Leu
                       3970                    3975                    3980
Trp Gly Leu Leu Arg Ser Ala Gln Ser Glu Tyr Pro Asp Arg Phe Thr
3985                    3990                    3995                    4000
Leu Ile Asp Val Asp Asp Ser Pro Glu Ser Arg Ala Ala Leu Pro Arg
                       4005                    4010                    4015
Ala Leu Gly Ser Ala Glu Arg Gln Leu Ala Leu Arg Thr Gly Asp Val
                       4020                    4025                    4030
Leu Ala Pro Ala Leu Val Pro Met Ala Thr Arg Pro Ala Glu Thr Thr
                       4035                    4040                    4045
Pro Ala Thr Ala Val Ala Ser Ala Thr Thr Gln Thr Gln Val Thr Ala
                       4050                    4055                    4060
Pro Ala Pro Asp Asp Pro Ala Ala Asp Ala Val Phe Asp Pro Ala Gly
4065                    4070                    4075                    4080
Thr Val Leu Ile Thr Gly Gly Thr Gly Ala Leu Gly Arg Arg Val Ala
                       4085                    4090                    4095
Ser His Leu Ala Arg Arg Tyr Gly Val Arg His Met Leu Leu Val Ser
                       4100                    4105                    4110
Arg Arg Gly Pro Asp Ala Pro Glu Ala Gly Pro Leu Glu Arg Glu Leu
                       4115                    4120                    4125
Ala Gly Leu Gly Val Thr Ala Thr Phe Leu Ala Cys Asp Leu Thr Asp
                       4130                    4135                    4140
Ile Glu Ala Val Arg Lys Ala Val Ala Ala Val Pro Ser Asp His Pro
4145                    4150                    4155                    4160
Leu Thr Gly Val Val His Thr Ala Gly Val Leu Asp Asp Gly Ala Leu
                       4165                    4170                    4175
```

```
Thr  Gly  Leu  Thr  Arg  Gln  Arg  Leu  Asp  Thr  Val  Leu  Arg  Pro  Lys  Ala
               4180                    4185                    4190

Asp  Ala  Val  Arg  Asn  Leu  His  Glu  Ala  Thr  Leu  Asp  Arg  Pro  Leu  Arg
               4195                    4200                    4205

Ala  Phe  Val  Leu  Phe  Ser  Ala  Ala  Gly  Leu  Leu  Gly  Arg  Pro  Gly
     4210                    4215                    4220

Gln  Ala  Ser  Tyr  Ala  Ala  Ala  Asn  Ala  Val  Leu  Asp  Ala  Leu  Ala  Gly
4225                     4230                    4235                         4240

Ala  Arg  Arg  Ala  Ala  Gly  Leu  Pro  Ala  Val  Ser  Leu  Ala  Trp  Gly  Leu
               4245                    4250                         4255

Trp  Asp  Glu  Gln  Thr  Gly  Met  Ala  Gly  Gly  Leu  Asp  Glu  Met  Ala  Leu
               4260                    4265                         4270

Arg  Val  Leu  Arg  Arg  Asp  Gly  Ile  Ala  Ala  Met  Pro  Pro  Glu  Gln  Gly
               4275                    4280                    4285

Leu  Glu  Leu  Leu  Asp  Leu  Ala  Leu  Thr  Gly  His  Arg  Asp  Gly  Pro  Ala
     4290                    4295                    4300

Val  Leu  Val  Pro  Leu  Leu  Leu  Asp  Gly  Ala  Ala  Leu  Arg  Arg  Thr  Ala
4305                     4310                    4315                         4320

Lys  Glu  Arg  Gly  Ala  Ala  Thr  Met  Ser  Pro  Leu  Leu  Arg  Ala  Leu  Leu
               4325                    4330                         4335

Pro  Ala  Ala  Leu  Arg  Arg  Ser  Gly  Gly  Ala  Gly  Ala  Pro  Ala  Ala  Ala
               4340                    4345                    4350

Asp  Arg  His  Gly  Lys  Glu  Ala  Asp  Pro  Gly  Ala  Gly  Arg  Leu  Ala  Gly
               4355                    4360                    4365

Met  Val  Ala  Leu  Glu  Ala  Ala  Glu  Arg  Ser  Ala  Ala  Val  Leu  Glu  Leu
     4370                    4375                    4380

Val  Thr  Glu  Gln  Val  Ala  Glu  Val  Leu  Gly  Tyr  Ala  Ser  Ala  Ala  Glu
4385                     4390                    4395                         4400

Ile  Glu  Pro  Glu  Arg  Pro  Phe  Arg  Glu  Ile  Gly  Val  Asp  Ser  Leu  Ala
               4405                    4410                         4415

Ala  Val  Glu  Leu  Arg  Asn  Arg  Leu  Ser  Arg  Leu  Val  Gly  Leu  Arg  Leu
               4420                    4425                    4430

Pro  Thr  Thr  Leu  Ser  Phe  Asp  His  Pro  Thr  Pro  Lys  Asp  Met  Ala  Gln
          4435                    4440                    4445

His  Ile  Asp  Gly  Gln  Leu  Pro  Arg  Pro  Ala  Gly  Ala  Ser  Pro  Ala  Asp
4450                     4455                    4460

Ala  Ala  Leu  Glu  Gly  Ile  Gly  Asp  Leu  Ala  Arg  Ala  Val  Ala  Leu  Leu
4465                     4470                    4475                         4480

Gly  Thr  Gly  Asp  Ala  Arg  Arg  Ala  Glu  Val  Arg  Glu  Gln  Leu  Val  Gly
                    4485                    4490                         4495

Leu  Leu  Ala  Ala  Leu  Asp  Pro  Pro  Gly  Arg  Thr  Gly  Thr  Ala  Ala  Pro
                    4500                    4505                    4510

Gly  Val  Pro  Ser  Gly  Ala  Asp  Gly  Ala  Glu  Pro  Thr  Val  Thr  Asp  Arg
          4515                    4520                    4525

Leu  Asp  Glu  Ala  Thr  Asp  Asp  Glu  Ile  Phe  Ala  Phe  Leu  Asp  Glu  Gln
          4530                    4535                    4540

Leu
4545
```

(2) INFORMATION FOR SEQ ID NO:15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:15:

CGAGGCCGGC GGGCC    15

POLYKETIDE SYNTHASE GENES

This application claims the benefit of U.S. Provisional Application No. 60/012,078, filed Feb. 22, 1996 now abandoned.

BACKGROUND OF THE INVENTION

The present invention relates to DNA molecules responsible for encoding the multi-functional proteins that direct the biosynthesis of polyketide compounds, the products encoded by said DNA molecules, recombinant DNA expression vectors, and transformed microbial host cells.

Polyketides are a family of compounds that include a large number of structurally and functionally diverse natural products. For example, the polyketides provide the structural backbone for compounds that exhibit a variety of biological activities, such as, antibiotic, antitumor, and immunosuppressive agents.

Although the polyketides are quite diverse as indicated, they share a common mechanistic scheme of biosynthesis. The polyketides are synthesized by the successive condensation of small carboxylic acid residues followed by variable reduction steps at the resulting β-keto carbon (i.e., β-carbonyl) moiety in a process that is similar to the synthesis of fatty acids. The iterative synthetic process for many of these polyketides is controlled by a complex of large, multi-functional polypeptides that have distinct sites for the variety of activities that are required.

The general scheme for polyketide biosynthesis has been reviewed, for example, in Hopwood and Sherman, Annu. Rev. Genet., 1990, 24:37 and Katz and Donadio, Annu. Rev. Microbial., 1993, 47:875.

Naturally-occurring DNA sequences that encode the polyketide synthase enzymes have generally been found to be organized into repeated subunits, or modules, each of which encodes all the activities required in a single round of synthesis, which includes the condensation step itself and the post-condensation processing steps. Each activity is associated with a distinct site, which contributes to the specificity for the particular carboxylic acid building block that is incorporated at each condensation step, or which dictates the particular post-condensation processing functions that will be executed.

For example, PCT publication WO 93/13663 describes the organization of the gene encoding the polyketide synthase of Saccharopolyspora erythraea. The gene is organized in modules, with each module effecting one condensation step. The precise sequence of chain growth and the processing of the growing chain is determined by the genetic information in each module. This PCT application describes an approach for synthesizing novel polyketide structures by manipulating in several ways the DNA governing the biosynthesis of the cyclic lactone framework. In order to adapt this methodology to other polyketides, however, the DNA molecules directing the biosynthetic processing must first be isolated.

The present invention is directed to the DNA sequence for the gene cluster responsible for encoding tylactone synthase, the building machinery of tylactone, which is the basic building block of tylosin. As a result, the present invention enables modification of the DNA sequence so as to alter the type of carboxylic acids incorporated, the number of carboxylic acids incorporated, the post-condensation reactions performed, or any combination thereof, thereby resulting in novel tylosin-related polyketides.

SUMMARY OF THE INVENTION

The present invention provides a DNA molecule comprising an isolated DNA sequence that encodes a tylactone synthase domain. Thus, the present invention provides the DNA molecule of SEQ ID NO:1 and DNA molecules that contain submodules thereof. The present invention also provides the products encoded by said DNA molecules, recombinant DNA expression vectors, and transformed microbial host cells.

E—EcoRI
B—BamHI

Predicted functional domains are labeled as follows:

ACP—acyl carrier protein
AT—acyltransferase
DH—dehydratase
ER—enoylreductase
KR—ketoreductase
KR'—ketoreductase-like domain predicted to be inactive
KS—ketosynthase
KS'—ketosynthase-like domain in which a glutamine residue is present in the position occupied by an active site cysteine in a normal ketosynthase
TE—thioesterase.

Figure 2:
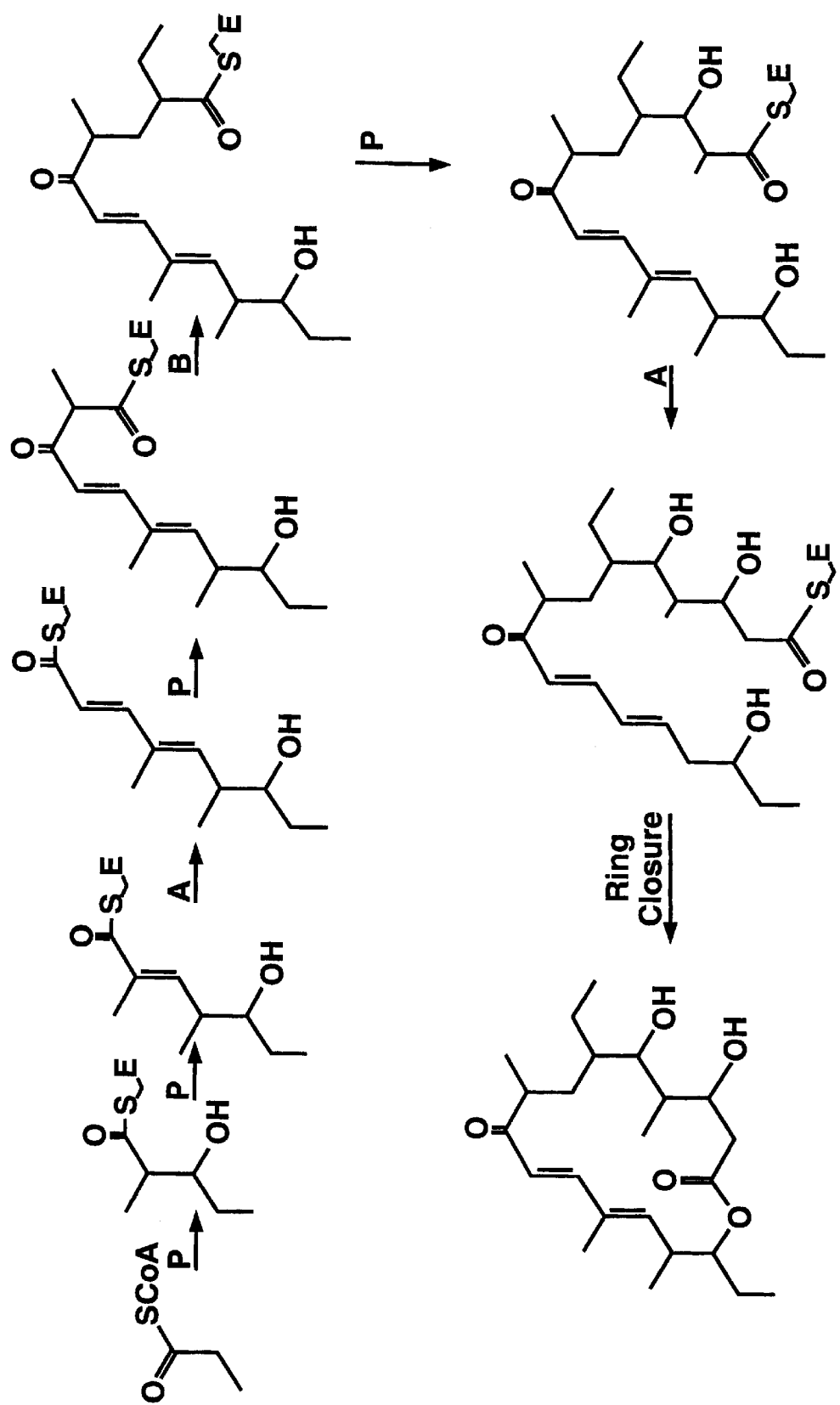

FIG. 2 depicts the biosynthetic pathway for tylactone synthesis.

Figure 3:
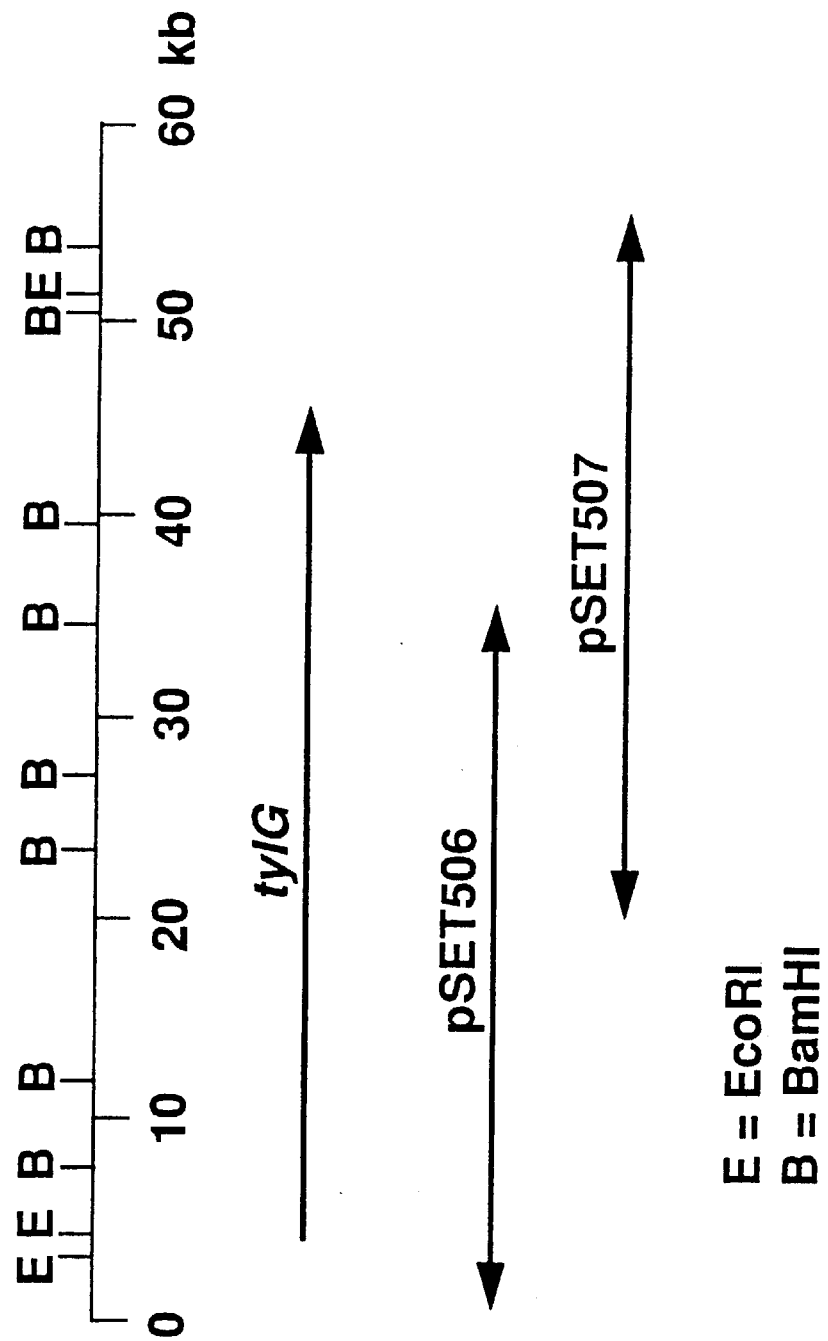

FIG. 3 is a map of the two clones that span the whole region of the tylG DNA.

Figure 4:
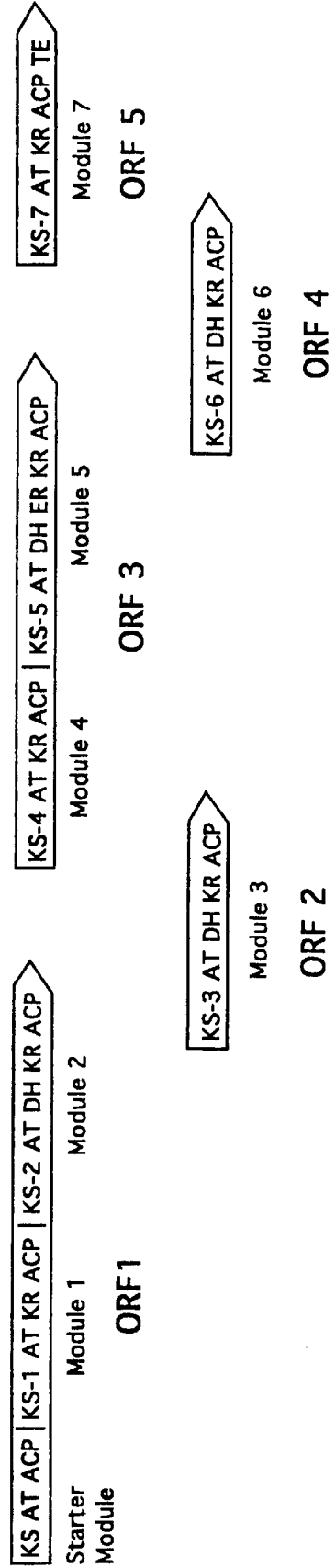

FIG. 4 is a map of the srmG region of the Streptomyces ambofaciens DNA. Distances in kb are relative to the beginning of srmG. Open reading frames are indicated by arrows. The srmG DNA (0–42 kb) is the platenolide polyketide synthase region. Restriction sites are denoted as above with additions as follows:

AP—ApaI
G—BglII
K—KpnI
P—PstI
X—XhoI

Predicted functional domains are labeled as above.

Figure 5:
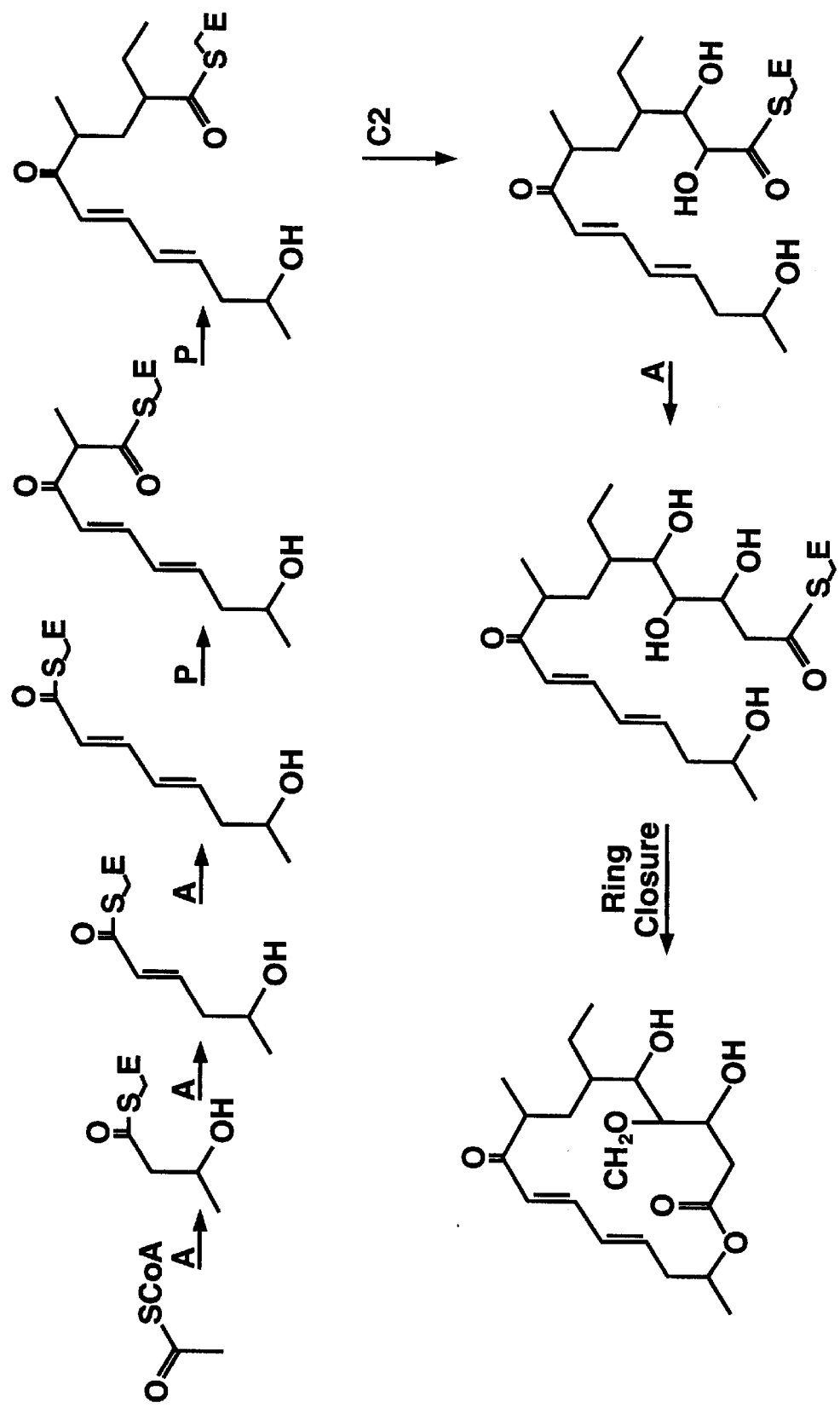

FIG. 5 demonstrates the biosynthetic pathway for platenolide synthesis.

Figure 6:
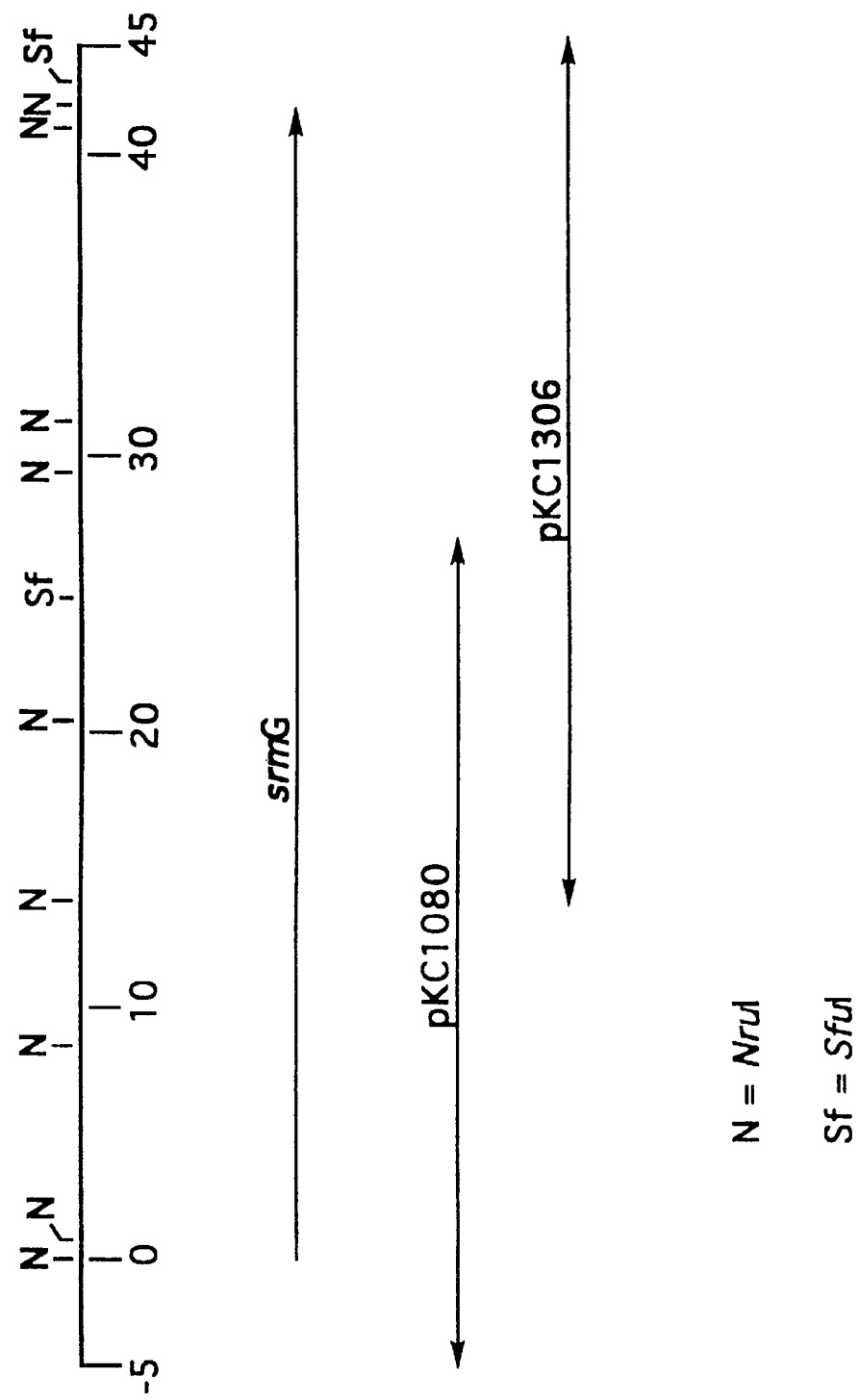

FIG. 6 is a map of the two clones that span the whole region of the srmG DNA.

DETAILED DESCRIPTION OF THE INVENTION

Polyketides are a large class of structurally and functionally diverse natural products. A common feature of compounds in this class is that their synthesis is accomplished under the direction of a complex of multi-functional peptides, termed a "polyketide synthase." Molecular genetic analysis of polyketide synthase genes has revealed two distinct classes of enzymes operating for different polyketides: 1) the aromatics, which are made through an essentially iterative process, and 2) the complex polyketides, which comprise several repeats of the same activities arranged in few very large polypeptides.

Among the complex polyketide synthase genes, a polyketide synthase includes enzymatic and regulatory activities responsible for exercising substrate specificity, catalyzing the condensation of small carboxylic acid building blocks (in the form of coenzyme A thioesters) to a growing polyketide carbon chain, and catalyzing the post-condensation processing reactions at the β-carbonyl functional group that results from the condensation reaction.

The condensation reaction requires several activities including acyl carrier protein (ACP), β-ketosynthase (KS), and acyltransferase (AT). Once a condensation has occurred, the resulting β-carbonyl functional group may be modified. Post-condensation activities that may be involved include β-ketoreductase (KR), dehydratase (DH), and enoylreductase (ER). Polyketide biosynthesis is terminated by a thioesterase (TE) activity. Whether all, some, or none of these activities act after a particular condensation step determines the structure of the final product.

The present invention provides, in particular, the DNA sequence encoding the polyketide synthase responsible for biosynthesis of tylactone, i.e., tylactone synthase. Tylactone itself is the polyketide backbone of the commercially significant antibiotic tylosin. The tylactone synthase DNA sequence, which defines the tylactone synthase gene cluster, directs biosynthesis of the tylactone polyketide by encoding the various distinct activities of tylactone synthase.

The gene cluster for tylactone synthase, like other complex polyketide biosynthetic genes whose organization has been elucidated, is characterized by the presence of several open reading frames (ORFs), each of which contains one or more repeated units termed "modules." A module is defined as the genetic element encoding all of the distinct activities required in a single round of synthesis, i.e., one condensation step and all the β-carbonyl processing steps associated therewith. Each module encodes an ACP, a KS, and an AT activity to accomplish the condensation portion of the synthesis, and selected post-condensation activities to effect β-carbonyl processing. The polypeptides encoded by such modules are termed "synthase units" (SUs).

Each module is further characterized by the inclusion of submodules that are responsible for encoding the distinct activities of tylactone synthase. For purposes of the present invention, the term "submodule" is defined as the portion of the polyketide synthase DNA sequence that encodes a distinct activity, or "domain". Thus, a domain is taken as commonly understood to mean that part of the polyketide synthase polypeptide necessary for a given distinct activity.

Figure 1:
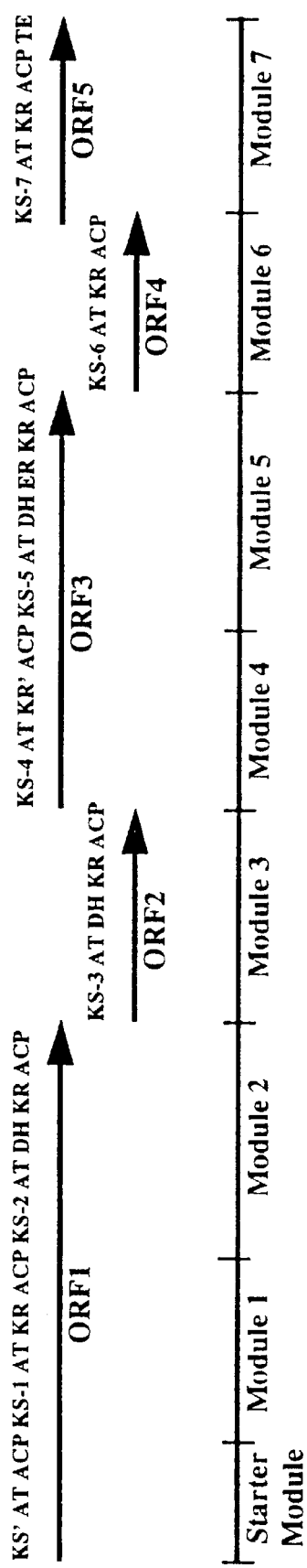
FIG. 1 is a map of the tylactone polyketide synthase region (tylG) of the Streptomyces fradiae DNA (~45 kb). Distances in kb are relative to the beginning of tylG. Open reading frames (ORFs) are indicated by arrows. Restriction sites are denoted as follows.

Organization of the tylactone synthase gene cluster derived from *Streptomyces fradiae*, is shown in FIG. 1. The tylactone synthetic pathway, with indications of the specific carboxylic acid substrates used for each condensation reaction and the various post-condensation activities, is shown in FIG. 2.

A preferred DNA molecule comprising the tylactone synthase gene cluster isolated from *Streptomyces fradiae* is represented by SEQ ID NO:1. Other preferred DNA molecules of the present invention include the various open reading frames of SEQ ID NO:1 that encode individual multi-functional polypeptides. These are represented by the following nucleotide residues of SEQ ID NO:1: ORF1 816 to 14234, ORF2 14351 to 19945, ORF3 20010 to 31199, ORF4 31232 to 36067, and ORF5 36249 to 41774. The predicted amino acid sequences of the various peptides encoded by these sequences are shown in SEQ ID NO:2, 3, 4, 5, and 6, respectively.

Yet other preferred DNA molecules of the present invention include the modules that encode the synthase units, which include all the activities necessary for a single round of synthesis. These are represented by the following nucleotide residues of SEQ ID NO:1: Starter Module 942 to 3929, Module 1 3993 to 8471, Module 2 8541 to 13970, Module 3 14411 to 19666, Module 4 20136 to 24611, Module 5 24675 to 30902, Module 6 31337 to 35743, and Module 7 36360 to 40826. The predicted amino acid sequences of the various synthase units encoded by these modules are represented, respectively, by the following amino acid residues: Starter SU 43 to 1038, SU1 1060 to 2552 and SU2 2576 to 4385 in SEQ ID NO:2; SU3 21 to 1772 in SEQ ID NO:3; SU4 43 to 1534 and SU5 1556 to 3631 in SEQ ID NO:4; SU6 36 to 1504 in SEQ ID NO:5; and SU7 38 to 1526 in SEQ ID NO:6.

Still other preferred DNA molecules include the various submodules that encode the various domains of tylactone synthase. These submodules are represented by the following nucleotide residues: $KS^Q(S)$ 942 to 2156, AT(s) 2571 to 3557, ACP(s) 3675 to 3929, KS1 3993 to 5264, AT1 5631 to 6617, KR1 7410 to 7949, and ACP1 8220 to 8471 of Module 1 in SEQ ID NO:1; KS2 8541 to 9812, AT2 10260 to 11246, DH2 11319 to 11876, KR2 12861 to 13415, and ACP2 13719 to 13970 of Module 2 in SEQ ID NO:1; KS3 14411 to 15697, AT3 16055 to 17122, DH3 17198 to 17794, KR3 18584 to 19138, and ACP3 19415 to 19666 of Module 3 in SEQ ID NO:1; KS4 20136 to 21404, AT4 21771 to 22757, KR'4 23541 to 24077, and ACP4 24360 to 24611 of Module 4 in SEQ ID NO:1; KS5 24675 to 25949, AT5 26292 to 27284, DH5 27360 to 27917, ER5 28767 to 29813, KR5 29829 to 30368, and ACP5 30651 to 30902 of Module 5 in SEQ ID NO:1; KS6 31337 to 32608, AT6 32975 to 33961, KR6 34694 to 35236, and ACP6 35492 to 35743 of Module 6 in SEQ ID NO:1; KS7 36360 to 37631, AT7 37989 to 38987, KR7 39759 to 40313, ACP7 40575 to 40826, and TE7 41235 to 41333 of Module 7 in SEQ ID NO:1.

The predicted amino acid sequences of the various domains encoded by these submodules are represented, respectively, by $KS^Q(s)$ 43 to 447, AT(s) 586 to 914, ACP(s) 954 to 1038, KS1 1060 to 1483, AT1 1606 to 1934, KR1 2199 to 2378, and ACP1 2469 to 2552 in SEQ ID NO:2; KS2 2576 to 2999, AT2 3149 to 3477, DH2 3502 to 3687, KR2 4016 to 4200, and ACP2 4302 to 4385 in SEQ ID NO:2; KS3 21 to 449, AT3 569 to 924, DH3 950 to 1148, KR3 1412 to 1596, and ACP3 1689 to 1772 in SEQ ID NO:3; KS4 43 to 465, AT4 588 to 916, KR'4 1178 to 1356, and ACP4 1451 to 1534 in SEQ ID NO:4; KS5 1556 to 1980, AT5 2095 to 2425, DH5 2451 to 2636, KR5 3274 to 3453, and ACP5 3548 to 3631 in SEQ ID NO:4; KS6 36 to 459, AT6 582 to 910, KR6 1155 to 1335, and ACP6 1421 to 1504 in SEQ ID NO:5; KS7 38 to 461, AT7 581 to 913, KR7 1171 to 1355, ACP7 1443 to 1526, and TE7 1663 to 1695 in SEQ ID NO:6.

Although not wishing to be bound to any particular technical explanation, sequence similarity exists among domain boundaries in various polyketide synthase genes. Thus, one skilled in the art is able to predict the domain boundaries of newly discovered polyketide synthase genes based on the sequence information of known polyketide synthase genes. In particular, the boundaries of submodules, domains, and open reading frames in the instant application are predicted based on sequence information disclosed in the instant application and the locations of the domain boundaries of the erythromycin polyketide synthase (Donadio et al., Gene 111:51 (1992)).

The DNA sequence of the tylactone synthase gene was determined from recombinant DNA clones prepared from the DNA of *Streptomyces fradiae*. The tylactone synthase gene is contained in recombinant DNA vectors pSET506 and pSET507 (FIG. 3), which are available from the National Center for Agricultural Utilization Research, 1815 North University Street, Peoria, Ill. 61604-3999, in *E. coli* K12 MM294 under accession numbers NRRL B-18688 (deposited Jul. 19, 1990) and NRRL B-18689 (deposited Jul. 19, 1990), respectively.

Tehcniques for isolating bacterial DNA are readily available and well known in the art. Any such technique can be employed in this invention. In particular, DNA from these cultures is isolated as follows. Lyophils of *E. coli* K12 MM294/pSET506 or *E. coli* K12 MM294/pSET507 are plated onto L-agar (10 g tryptone, 10 g NaCl, 5 g yeast extract, and 15 g agar per liter) plates containing 100 µg/ml ampicillin to obtain a single colony isolate of the strain. This colony is used to inoculate about 500 ml of L-broth (10 g tryptone, 10 g NaCl, 5 g yeast extract per liter) containing 100 µg/ml ampicillin, and the resulting culture is incubated at 37° C. with aeration until the cells reach stationary phase. Cosmid DNA is obtained from the cells in accordance with procedures known in the art (see e.g., Rao et al., 1987 in Methods in Enzymology, 153:166).

DNA of the current invention can be sequenced using any known techniques in the art such as the dideoxynucleotide chain-termination method (Sanger, et al., Proc. Natl. Acad. Sci. 74:5463 (1977)) with either radioisotopic or fluorescent labels. Double-stranded, supercoiled DNA was used directly for templates in sequence reactions with sequence-specific oligonucleotide primers. Alternatively, fragments were used to prepare libraries of either random, overlapping sequences in the bacteriophage M13 or nested, overlapping deletions in a plasmid vector. Individual recombinant DNA subclones were then sequenced with vector-specific oligonucleotide primers. Radioactive reaction products were electrophoresed on denaturing polyacrylamide gels and analyzed by autoradiography. Fluorescent-labeled reaction products were electrophoresed and analyzed on Applied Biosystems (ABI Division, Perkin Elmer, Foster City, Calif. 94404) model 370A and 373A or DuPont (Wilmington, Del.) Genesis DNA sequencers. Sequence data was assembled and edited using Genetic Center Group (GCG, Madison, Wis.) programs GelAssemble and Seqed or the ABI model 670 Inherit Sequence Analysis system and the AutoAssembler and SeqEd programs.

Polypeptides corresponding to a domain, a synthase unit, or a multi-functional polypeptide can be produced by expression of the cDNA sequence in a bacteria, for example, using known expression vectors. Alternatively, the polypeptides mentioned above can be extracted from tylactone-producing bacteria such as Streptomyces fradiae. In addition, the techniques of synthetic chemistry can be employed to synthesize the polypeptides mentioned above. The procedures and techniques for isolation and purification of homogenous protein or polypeptides are well known in the art.

Since the genetic organization of the tylactone synthase gene cluster appears to correspond to the order of the reactions required to complete synthesis of tylactone, knowledge of the tylactone synthase DNA sequence, its genetic organization, and the activities associated with particular open reading frames, modules, and submodules of the gene enables production of novel polyketides having a predicted structure that are not otherwise available. Modifications may be made to the DNA sequence that either alter the initial carboxylic acid building block used or the building block added at any of the condensation steps. The tylactone synthase gene may also be modified to alter the actual number of condensation steps done, thereby changing the size of the carbon backbone. Modifications to portions of the DNA sequence that encode the post-condensation processing activities will alter the functional groups appearing at the various condensation sites on the carbon chain backbone.

These modifications can be accomplished by substituting submodules derived from the tylactone synthase gene and having known activities for corresponding submodules from another polyketide synthase gene having different activities. Submodules from tylactone synthase may also be combined with submodules from other polyketide synthase genes to effect additional catalytic steps. Accordingly, a DNA molecule wherein at least one submodule from the tylactone synthase gene has been combined with, or substituted for, submodules from the DNA sequence of other polyketide synthase genes is also provided by the present invention. Further, submodules that are a part of the present invention may be selectively inactivated thereby giving rise to predictable novel polyketide structures.

For example, a submodule encoding a KS' activity, an AT activity, and an ACP activity, all derived from the first open reading frame of the tylactone synthase gene (ORF1), were exchanged for the corresponding submodule in the platenolide synthase gene (see Example 2). Platenolide is the polyketide backbone of the antibiotic spiramycin.

The submodule from the tylactone synthase gene encodes a domain that catalyzes the incorporation of a propionate as the initial building block whereas the corresponding submodule of the platenolide synthase gene encodes a domain that catalyzes the incorporation of an acetate building block. When the resulting DNA molecule was placed into a bacterial strain and grown under conditions promoting polyketide synthesis, a hybrid molecule having the structure that would be predicted by incorporation of an additional methyl side-chain at the start of the growing polyketide chain was synthesized, in particular, 16-methyl platenolide.

One skilled in the art is fully familiar with the degeneracy of the genetic code. Consequently, the skilled artisan can modify the specific DNA sequences provided by this disclosure to provide proteins having the same or improved characteristics compared to those polypeptides specifically provided herein. Also, one skilled in the art can modify the DNA sequences to express an identical protein to those provided, albeit expressed at higher levels. Furthermore, one skilled in the art is familiar with means to prepare synthetically, either partially, or in whole, DNA sequences which would be useful in preparing recombinant DNA vectors or coding sequences which are encompassed by the current invention. Additionally, recombinant means for modifying the DNA sequences provided may include for example site-directed deletion or site-directed mutagenesis. These techniques are well known to those skilled in the art and require no further elaboration here. Consequently, as used herein, DNA which is isolated from natural sources, prepared synthetically or semi-synthetically, or which are modified by recombinant DNA methods, are within the scope of the present invention.

Likewise, those skilled in the art will recognize that the polypeptides of the invention may be expressed recombinantly. Alternatively, these polypeptides may be synthesized as well, either in whole or in part, by conventional known non-recombinant techniques; for example, solid-phase synthesis. Thus, the present invention should not be construed as necessarily limited to any specific vector constructions or means for production of the specific polyketide synthase molecules exemplified. These alternate means for preparing the present polypeptides are meant to be encompassed by the present invention.

Many cyclized polyketides undergo glycosylation at one or more sites. Tylosin is a 16-membered cyclic lactone, tylactone, with three attached sugar residues. The process of converting tylactone to tylosin is will known in the art. The present invention also provides the information needed to synthesize novel tylosin-related polyketides based on tylactone. The principles have already been described above. In addition, any product resulting from post-transcriptional or post-translational modification in vivo or in vitro based on the DNA sequence information disclosed herein are meant to be encompassed by the present invention.

The following examples are provided for exemplification purposes only and are not intended to limit the scope of the invention which has been described in broad terms above.

EXAMPLE 1

The DNA sequence of the *Streptomyces fradiae* tylactone synthase gene, tylG, was obtained by sequencing the inserts of recombinant DNA subclones containing contiguous or overlapping DNA segments, which when considered cumulatively span the entire region of tylG. All sequences representing tylG are fully contained in the overlapping cosmid subclones pSET506 and pSET507.

In accord with the current invention, the sequence may now be obtained by subcloning and sequencing the DNA fragment designated by EcORI restriction sites at 3.0 and 4.0 kb on the map presented in FIG. 3, the fragment bounded by the EcoRI site at 4.0 kb and the BamHI site at 7.5 kb, the fragments bounded by BamHI sites at 7.5, 12.0, 23.4, 27.3, 34.6, 39.5, and 50.5 kb.

In order to obtain the tylG gene on a single DNA fragment, the 31.6 kb DNA fragment bounded by the EcoRI site at 3.0 kb and the BamHI site at 34.6 kb is isolated from a partial digestion of pSET506 with the restriction enzymes EcoRI and BamHI. The 15.9 kb DNA fragment bounded by the BamHI sites at 34.6 and 50.5 kb is isolated from a partial digestion of pSET507 with the restriction enzyme BamHI. The resulting fragments are ligated and cloned in an appropriate recombinant DNA vector. Clones containing the correct orientation of the two ligated fragments are identified by restriction enzyme site mapping.

EXAMPLE 2

Production of a Polyketide Hybrid of Platenolide and Tylactone

The lactone rings of the polyketides platenolide and tylactone undergo an identical set of post-condensation processing steps. However, these two polyketides are synthesized by condensation of more than one type of carboxylic acid and the specific building blocks chosen for incorporation in the two pathways differ. The organization of the platenolide gene cluster is shown in FIG. 4 along with the accompanying synthetic pathway in FIG. 5. The specific carboxylic acid substrates that are used for each condensation reaction and the post-condensation activities of platenolide synthesis are indicated.

The DNA sequence of the *Streptomyces ambofaciens* platenolide synthase (srmG) genes was obtained by sequencing inserts of recombinant DNA subclones containing contiguous or overlapping DNA segments, which when considered together span the entire srmG region. All sequences representing srmG are fully contained in the overlapping cosmid clones pKC1080 and pKC1306 (FIG. 6). The sequence can be obtained by subcloning and sequencing the fragments bounded by NruI sites at position 1, 0.3 kb, 8.2 kb, 14.1 kb, 20.2 kb, 29.5 kb, 31.4 kb, 41.1 kb, and 42.0 kb. The DNA sequence of the platenolide synthase gene cluster isolated from *Streptomyces ambofaciens* is represented by SEQ ID NO:7.

In order to obtain the srmG region on a single fragment, the 25.0 kb fragment bounded by the NruI site at position 1 and the SfuI site at 25.0 kb is isolated from a partial digestion of pKC1080 with restriction enzymes NruI and SfuI. The 17.8 kb DNA fragment bounded by the SfuI sites at 25.0 kb and 42.8 kb is isolated by digestion of pKC1306 with the restriction enzyme SfuI. The resulting fragments are ligated and cloned in an appropriate recombinant DNA vector. Clones containing the correct orientation of the two ligated fragments are identified by restriction enzyme mapping.

An exchange of tylactone polyketide synthase DNA with corresponding platenolide DNA was effected as follows in order to generate a novel polyketide structure.

A strain of *Streptomyces ambofaciens*, the organism that produces platenolide, was constructed with most of ORF1 deleted. This ORF1-deficient strain produced no detectable platenolide. To confirm that the lack of ORF1 was the only deficiency in platenolide production, a construct containing ORF1, and not any functional activities of ORFs 2-5, was introduced into the ORF1-deficient strain on a vector that contains the site-specific integration function from the streptomycete phage φC31. Integration of ORF1 at the φC31 att site restored spiramycin production to parental levels, confirming that ORF1 codes for a functional protein and that ORFs 2–5 are expressed in the ORF1-deficient strain.

ORF1 of srmG is organized like tylG ORF1. DNA coding for a KS', an AT, and an ACP from tyl ORF1 was exchanged with the corresponding region from srm ORF1. Specifically, an EcoRI-ApaI fragment of srm ORF1 (nucleotides 450–3462 of SEQ ID NO:7) was replaced with an EcoRI-SfuI fragment excised from tyl ORF1 (nucleotides 1000–3982 of SEQ ID NO:1). The tylG fragment was inserted into the srmG sequence using a linker (SEQ ID NO:15) to join the SfuI and ApaI sites.

When the hybrid ORF1 sequence was introduced into the ORF1-deficient strain, polyketide synthesis was restored. The products produced by this restored strain were indistinguishable from those produced by the parental strain of *Streptomyces ambofaciens* when analyzed by thin-layer chromatography and HPLC.

The DNA sequence containing the hybrid ORF1 is SEQ ID NO:13 and the amino acid sequence of the ORF1-encoded polypeptide is SEQ ID NO:14. The rest of the DNA sequence of the hybrid molecule is identical to original srmg sequence and the polypeptides encoded by this remaining portion are therefore identical as well.

In order to simplify physical analysis of the putative novel polyketide, an XhoI fragment encoding sugar synthesis or addition was deleted from the restored sequence. Deletion of this fragment led to a strain that produced only the lactone without any sugar residues added. When analyzed by NMR and mass spectroscopy, the isolated product made by this sugar-deficient strain was confirmed as 16-methyl-platenolide, which is the structure that would be predicted from the incorporation of a propionate in place of the acetate normally utilized in platenolide synthesis. 16-methyl-platenolide is, therefore, the intermediate to the sugar-modified analog (16-methyl-spiramycin), which was predicted to have antibiotic activity.

We claim:

1. An isolated DNA molecule comprising a DNA sequence that encodes a tylactone synthase domain.

2. The DNA molecule as claimed in claim 1 wherein the DNA sequence is selected from the group consisting of:

nucleotides 942 to 2156, 2571 to 3557, 3675 to 3929, 3993 to 5264, 5631 to 6617, 7410 to 7949, 8220 to 8471, 8541 to 9812, 10260 to 11246, 11319 to 11876, 12861 to 13415, 13719 to 13970, 14411 to 15697, 16055 to 17122, 17198 to 17794, 18584 to 19138, 19415 to 19666, 20136 to 21404, 21771 to 22757, 23541 to 24077, 24360 to 24611, 24675 to 25949, 26292 to 27284, 27360 to 27917, 28767 to 29813, 29829 to 30368, 30651 to 30902, 31337 to 32608, 32975 to 33961, 34694 to 35236, 35492 to 35743, 36360 to 37631, 37989 to 38987, 39759 to 40313, 40575 to 40826, and 41235 to 41333 all in SEQ ID NO:1.

3. The DNA molecule as claimed in claim 1 wherein the DNA sequence is selected from the group consisting of:

nucleotides 942 to 8471, 8541 to 13970, 14411 to 19666, 20136 to 24611, 24675 to 30902, 31337 to 35743, and 36360 to 40826 all in SEQ ID NO:1.

4. The DNA molecule as claimed in claim 1 wherein the DNA sequence is selected from the group consisting of:

nucleotides 816 to 14234, 14351 to 19945, 20010 to 31199, 31232 to 36067, and 36249 to 41774 all in SEQ ID NO:1.

5. The DNA molecule as claimed in claim 1 wherein the isolated DNA sequence is SEQ ID NO:1.

6. An isolated polypeptide comprising an amino acid sequence that consists of a tylactone synthase domain.

7. The polypeptide of claim 6 wherein the amino acid sequence is selected from the group consisting of:

(a) amino acids 43 to 447, 586 to 914, 954 to 1038, 1060 to 1483, 1606 to 1934, 2199 to 2378, 2469 to 2552, 2576 to 2999, 3149 to 3477, 3502 to 3687, 4016 to 4200, and 4302 to 4385 in SEQ ID NO:2;

(b) amino acids 21 to 449, 569 to 924, 950 to 1148, 1412 to 1596, and 1689 to 1772 in SEQ ID NO:3;

(c) amino acids 43 to 465, 588 to 916, 1178 to 1356, and 1451 to 1534, 1556 to 1980, 2095 to 2425, 2451 to 2636, 3274 to 3453, and 3548 to 3631 in SEQ ID NO:4;

(d) amino acids 36 to 459, 582 to 910, 1155 to 1335, and 1421 to 1504 in SEQ ID NO:5; and (e) amino acids 38 to 461, 581 to 913, 1171 to 1355, 1443 to 1526, and 1663 to 1695 in SEQ ID NO:6.

8. The polypeptide of claim 6 wherein the amino acid sequence is selected from the group consisting of:

(a) amino acids 1060 to 2552 and 2576 to 4385 in SEQ ID NO:2;

(b) amino acids 21 to 1772 in SEQ ID NO:3;

(c) amino acids 43 to 1534 and 1556 to 3631 in SEQ ID NO:4;

(d) amino acids 36 to 1504 in SEQ ID NO:5; and (e) amino acids 38 to 1526 in SEQ ID NO:6.

9. The polypeptide of claim 6 wherein the amino acid sequence is selected from the group consisting of SEQ ID NO:2, SEQ ID NO:3, SEQ ID NO:4, SEQ ID NO:5, and SEQ ID NO:6.

10. A recombinant DNA vector comprising a DNA molecule of claim 1.

11. A recombinant DNA vector comprising a DNA molecule of claim 2.

12. A recombinant DNA vector comprising a DNA molecule of claim 3.

13. A recombinant DNA vector comprising a DNA molecule of claim 4.

14. A recombinant DNA vector comprising a DNA molecule of claim 5.

15. A recombinant DNA vector of claim 10 which is NRRL B-18688.

16. A recombinant DNA vector of claim 10 which is NRRL B-18689.

17. A host cell transformed with a recombinant DNA vector of claim 10.

18. A host cell transformed with a recombinant DNA vector of claim 11.

19. A host cell transformed with a recombinant DNA vector of claim 12.

20. A host cell transformed with a recombinant DNA vector of claim 13.

21. A host cell transformed with a recombinant DNA vector of claim 14.

22. The DNA molecule as claimed in claim 1 wherein the isolated DNA sequence is SEQ ID NO:13.

23. The polypeptide of SEQ ID NO:14.

* * * * *